(12) United States Patent
Zurcher et al.

(10) Patent No.: US 9,751,818 B2
(45) Date of Patent: Sep. 5, 2017

(54) NANOWIRE CATALYSTS AND METHODS FOR THEIR USE AND PREPARATION

(71) Applicant: Siluria Technologies, Inc., San Francisco, CA (US)

(72) Inventors: Fabio R. Zurcher, Brisbane, CA (US); Erik C. Scher, San Francisco, CA (US); Joel M. Cizeron, Redwood City, CA (US); Wayne P. Schammel, Brisbane, CA (US); Alex Tkachenko, San Francisco, CA (US); Joel Gamoras, Vallejo, CA (US); Dmitry Karshtedt, San Francisco, CA (US); Greg Nyce, Pleasanton, CA (US); Anja Rumplecker, San Francisco, CA (US); Jarod McCormick, San Carlos, CA (US); Anna Merzlyak, San Francisco, CA (US); Marian Alcid, Sunnyvale, CA (US); Daniel Rosenberg, San Francisco, CA (US); Erik-Jan Ras, Amsterdam (NL)

(73) Assignee: Siluria Technologies, Inc., San Francisco, CA (US)

( * ) Notice: Subject to any disclaimer, the term of this patent is extended or adjusted under 35 U.S.C. 154(b) by 0 days.

(21) Appl. No.: 14/557,225

(22) Filed: Dec. 1, 2014

(65) Prior Publication Data
US 2015/0087875 A1 Mar. 26, 2015

Related U.S. Application Data

(63) Continuation of application No. 13/689,611, filed on Nov. 29, 2012, now Pat. No. 8,962,517.
(Continued)

(51) Int. Cl.
*C07C 2/84* (2006.01)
*B01J 23/30* (2006.01)
(Continued)

(52) U.S. Cl.
CPC ............... *C07C 2/84* (2013.01); *B01J 21/066* (2013.01); *B01J 21/10* (2013.01); *B01J 23/02* (2013.01);
(Continued)

(58) Field of Classification Search
CPC ...................................................... B01J 21/00
See application file for complete search history.

(56) References Cited

U.S. PATENT DOCUMENTS

| 3,413,817 A | 12/1968 | Kniel |
| 3,596,473 A | 8/1971 | Streich |

(Continued)

FOREIGN PATENT DOCUMENTS

| CN | 1073891 A | 7/1993 |
| CN | 1087291 A | 6/1994 |

(Continued)

OTHER PUBLICATIONS

Nanostructured Ceria-Basedcatalysts for Oxydehydrogenation of Ethane With CO2. Valenzuela et al. Topics in Catalysts vol. 15, No. 2-4 2001.*

(Continued)

*Primary Examiner* — Melvin C Mayes
*Assistant Examiner* — Colette Nguyen
(74) *Attorney, Agent, or Firm* — Seed IP Law Group LLP

(57) ABSTRACT

Nanowires useful as heterogeneous catalysts are provided. The nanowire catalysts are useful in a variety of catalytic reactions, for example, the oxidative coupling of methane to (Continued)

C2 hydrocarbons. Related methods for use and manufacture of the same are also disclosed.

41 Claims, 24 Drawing Sheets

Related U.S. Application Data

(60) Provisional application No. 61/651,399, filed on May 24, 2012, provisional application No. 61/564,834, filed on Nov. 29, 2011, provisional application No. 61/564,836, filed on Nov. 29, 2011.

(51) Int. Cl.

| | | |
|---|---|---|
| *B01J 23/02* | (2006.01) | |
| *B01J 23/04* | (2006.01) | |
| *B01J 37/03* | (2006.01) | |
| *B01J 37/08* | (2006.01) | |
| *B01J 37/10* | (2006.01) | |
| *B01J 21/06* | (2006.01) | |
| *B01J 21/10* | (2006.01) | |
| *B01J 23/10* | (2006.01) | |
| *B01J 23/22* | (2006.01) | |
| *B01J 23/34* | (2006.01) | |
| *B01J 35/00* | (2006.01) | |
| *B01J 35/06* | (2006.01) | |
| *B01J 37/00* | (2006.01) | |
| *C01F 5/02* | (2006.01) | |
| *C01F 5/08* | (2006.01) | |
| *C01F 5/14* | (2006.01) | |
| *C01F 17/00* | (2006.01) | |
| *C01G 25/02* | (2006.01) | |
| *C01G 31/02* | (2006.01) | |
| *C01G 45/02* | (2006.01) | |
| *C01G 45/12* | (2006.01) | |
| *B82Y 30/00* | (2011.01) | |

(52) U.S. Cl.
CPC ............... *B01J 23/04* (2013.01); *B01J 23/10* (2013.01); *B01J 23/22* (2013.01); *B01J 23/30* (2013.01); *B01J 23/34* (2013.01); *B01J 35/0013* (2013.01); *B01J 35/06* (2013.01); *B01J 37/0018* (2013.01); *B01J 37/031* (2013.01); *B01J 37/08* (2013.01); *B01J 37/10* (2013.01); *B82Y 30/00* (2013.01); *C01F 5/02* (2013.01); *C01F 5/08* (2013.01); *C01F 5/14* (2013.01); *C01F 17/0043* (2013.01); *C01G 25/02* (2013.01); *C01G 31/02* (2013.01); *C01G 45/02* (2013.01); *C01G 45/1221* (2013.01); *C01P 2002/52* (2013.01); *C01P 2002/72* (2013.01); *C01P 2004/04* (2013.01); *C01P 2004/16* (2013.01); *C01P 2004/54* (2013.01); *C01P 2004/80* (2013.01); *C01P 2006/12* (2013.01); *C07C 2521/06* (2013.01); *C07C 2521/10* (2013.01); *C07C 2523/02* (2013.01); *C07C 2523/04* (2013.01); *C07C 2523/10* (2013.01); *C07C 2523/22* (2013.01); *C07C 2523/30* (2013.01); *C07C 2523/34* (2013.01)

(56) References Cited

U.S. PATENT DOCUMENTS

| | | |
|---|---|---|
| 4,105,641 A | 8/1978 | Buysch et al. |
| 4,126,580 A | 11/1978 | Lauder |
| 4,140,504 A | 2/1979 | Campbell et al. |
| 4,375,566 A | 3/1983 | Kawamata et al. |
| 4,554,395 A | 11/1985 | Jones et al. |
| 4,629,718 A | 12/1986 | Jones et al. |
| 4,636,378 A | 1/1987 | Pastor et al. |
| 4,751,336 A | 6/1988 | Jezl et al. |
| 4,754,091 A | 6/1988 | Jezl et al. |
| 4,754,093 A | 6/1988 | Jezl et al. |
| 4,777,313 A | 10/1988 | Sofranko et al. |
| 4,780,449 A | 10/1988 | Hicks |
| 4,814,539 A | 3/1989 | Jezl et al. |
| 4,826,796 A | 5/1989 | Erekson et al. |
| 4,844,803 A | 7/1989 | Urech et al. |
| 4,849,571 A | 7/1989 | Gaffney |
| 4,895,823 A | 1/1990 | Kolts et al. |
| 4,900,347 A | 2/1990 | McCue, Jr. et al. |
| 4,939,311 A | 7/1990 | Washecheck et al. |
| 4,939,312 A | 7/1990 | Baerns et al. |
| 4,962,252 A | 10/1990 | Wade |
| 5,012,028 A | 4/1991 | Gupta et al. |
| 5,024,984 A | 6/1991 | Kaminsky et al. |
| 5,041,405 A | 8/1991 | Lunsford et al. |
| 5,057,478 A | 10/1991 | Abe et al. |
| 5,073,662 A | 12/1991 | Olbrich |
| 5,080,872 A | 1/1992 | Jezl et al. |
| 5,118,898 A | 6/1992 | Tyler et al. |
| 5,132,472 A | 7/1992 | Durante et al. |
| 5,134,103 A | 7/1992 | Lowery et al. |
| 5,137,862 A | 8/1992 | Mackrodt et al. |
| 5,149,516 A | 9/1992 | Han et al. |
| 5,179,056 A | 1/1993 | Bartley |
| 5,196,634 A | 3/1993 | Washecheck et al. |
| 5,198,596 A | 3/1993 | Kaminsky et al. |
| 5,263,998 A | 11/1993 | Mackrodt et al. |
| 5,306,854 A | 4/1994 | Choudhary et al. |
| 5,312,795 A | 5/1994 | Kaminsky et al. |
| 5,316,995 A | 5/1994 | Kaminsky et al. |
| 5,328,883 A | 7/1994 | Washecheck et al. |
| 5,336,825 A | 8/1994 | Choudhary et al. |
| 5,336,826 A | 8/1994 | Brophy et al. |
| 5,371,306 A | 12/1994 | Woo et al. |
| 5,414,157 A | 5/1995 | Durante et al. |
| 5,500,149 A | 3/1996 | Green et al. |
| 5,523,493 A | 6/1996 | Cameron et al. |
| 5,599,510 A | 2/1997 | Kaminsky et al. |
| 5,659,090 A | 8/1997 | Cameron et al. |
| 5,670,442 A | 9/1997 | Fornasari et al. |
| RE35,632 E | 10/1997 | Leyshon |
| RE35,633 E | 10/1997 | Leyshon |
| 5,712,217 A | 1/1998 | Choudhary et al. |
| 5,714,657 A | 2/1998 | deVries |
| 5,736,107 A | 4/1998 | Inomata et al. |
| 5,744,015 A | 4/1998 | Mazanec et al. |
| 5,749,937 A | 5/1998 | Detering et al. |
| 5,750,821 A | 5/1998 | Inomata et al. |
| 5,763,722 A | 6/1998 | Vic et al. |
| 5,789,339 A | 8/1998 | Ziebarth et al. |
| 5,817,904 A | 10/1998 | Vic et al. |
| 5,830,822 A | 11/1998 | Euzen |
| 5,849,973 A | 12/1998 | Van Der Vaart |
| 5,866,737 A | 2/1999 | Hagemeyer et al. |
| 5,897,945 A | 4/1999 | Lieber et al. |
| 5,917,136 A | 6/1999 | Gaffney et al. |
| 5,935,293 A | 8/1999 | Detering et al. |
| 5,935,897 A | 8/1999 | Trubenbach et al. |
| 5,935,898 A | 8/1999 | Trubenbach et al. |
| 5,936,135 A | 8/1999 | Choudhary et al. |
| 5,959,170 A | 9/1999 | Withers |
| 5,968,866 A | 10/1999 | Wu |
| 6,020,533 A | 2/2000 | Lewis et al. |
| 6,037,298 A | 3/2000 | Hagen et al. |
| 6,087,545 A | 7/2000 | Choudhary et al. |
| 6,096,934 A | 8/2000 | Rekoske |
| 6,110,979 A | 8/2000 | Nataraj et al. |
| 6,114,400 A | 9/2000 | Nataraj et al. |
| 6,143,203 A | 11/2000 | Zeng et al. |
| 6,146,549 A | 11/2000 | Mackay et al. |
| 6,153,149 A | 11/2000 | Rabitz et al. |
| 6,262,325 B1 | 7/2001 | Narbeshuber et al. |
| 6,316,377 B1 | 11/2001 | Fulton et al. |

(56) References Cited

U.S. PATENT DOCUMENTS

| | | |
|---|---|---|
| 6,355,093 B1 | 3/2002 | Schwartz et al. |
| 6,403,523 B1 | 6/2002 | Cantrell et al. |
| RE37,853 E | 9/2002 | Detering et al. |
| 6,447,745 B1 | 9/2002 | Feeley et al. |
| 6,518,218 B1 | 2/2003 | Sun et al. |
| 6,518,476 B1 | 2/2003 | Culp et al. |
| 6,521,806 B1 | 2/2003 | Tamura et al. |
| 6,521,808 B1 | 2/2003 | Ozkan et al. |
| 6,576,200 B1 | 6/2003 | Yamamoto et al. |
| 6,576,803 B2 | 6/2003 | Cantrell et al. |
| 6,596,912 B1 | 7/2003 | Lunsford et al. |
| 6,610,124 B1 | 8/2003 | Dolan et al. |
| 6,696,388 B2 | 2/2004 | Kourtakis et al. |
| 6,726,850 B1 | 4/2004 | Reyes et al. |
| 6,730,808 B2 | 5/2004 | Bitterlich et al. |
| 6,747,066 B2 | 6/2004 | Wang et al. |
| 6,761,838 B2 | 7/2004 | Zeng et al. |
| 6,764,602 B2 | 7/2004 | Shutt et al. |
| 6,800,702 B2 | 10/2004 | Wass |
| 6,821,500 B2 | 11/2004 | Fincke et al. |
| 7,116,546 B2 | 10/2006 | Chow et al. |
| 7,166,267 B2 | 1/2007 | Villa |
| 7,176,342 B2 | 2/2007 | Bellussi et al. |
| 7,183,451 B2 | 2/2007 | Gattis et al. |
| 7,199,273 B2 | 4/2007 | Molinier et al. |
| 7,208,647 B2 | 4/2007 | Peterson et al. |
| 7,250,543 B2 | 7/2007 | Bagherzadeh et al. |
| 7,291,321 B2 | 11/2007 | Bagherzadeh et al. |
| 7,332,108 B2 | 2/2008 | Chartier et al. |
| 7,361,622 B2 | 4/2008 | Benderly et al. |
| 7,396,798 B2 | 7/2008 | Ma et al. |
| 7,414,006 B2 | 8/2008 | McConville et al. |
| 7,438,887 B2 | 10/2008 | Suib et al. |
| 7,452,844 B2 | 11/2008 | Hu et al. |
| 7,473,814 B2 | 1/2009 | Basset et al. |
| 7,566,440 B2 | 7/2009 | Lim et al. |
| 7,576,030 B2 | 8/2009 | Benderly |
| 7,576,296 B2 | 8/2009 | Fincke et al. |
| 7,585,812 B2 | 9/2009 | Hu et al. |
| 7,589,246 B2 | 9/2009 | Iaccino et al. |
| 7,619,290 B2 | 11/2009 | Lieber et al. |
| 7,659,437 B2 | 2/2010 | Iaccino et al. |
| 7,667,085 B2 | 2/2010 | Gattis et al. |
| 7,683,227 B2 | 3/2010 | Iaccino et al. |
| 7,687,041 B2 | 3/2010 | Singh |
| 7,700,816 B2 | 4/2010 | Xu et al. |
| 7,728,186 B2 | 6/2010 | Iaccino et al. |
| 7,781,636 B2 | 8/2010 | Iaccino et al. |
| 7,795,490 B2 | 9/2010 | Iaccino et al. |
| 7,829,749 B2 | 11/2010 | Gao et al. |
| 7,867,938 B2 | 1/2011 | De et al. |
| 7,868,243 B2 | 1/2011 | Plissonnier et al. |
| 7,879,119 B2 | 2/2011 | Abughazaleh et al. |
| 7,902,113 B2 | 3/2011 | Zarrinpashne et al. |
| 7,910,670 B2 | 3/2011 | Knudsen et al. |
| 7,915,461 B2 | 3/2011 | Gattis et al. |
| 7,915,462 B2 | 3/2011 | Gattis et al. |
| 7,915,463 B2 | 3/2011 | Gattis et al. |
| 7,915,464 B2 | 3/2011 | Gattis et al. |
| 7,915,465 B2 | 3/2011 | Gattis et al. |
| 7,915,466 B2 | 3/2011 | Gattis et al. |
| 7,932,296 B2 | 4/2011 | Malhotra et al. |
| 7,932,311 B2 | 4/2011 | Aymonier et al. |
| 7,943,106 B2 | 5/2011 | Robinson |
| 7,968,020 B2 | 6/2011 | Behelfer et al. |
| 7,968,759 B2 | 6/2011 | Iaccino et al. |
| 7,977,519 B2 | 7/2011 | Iaccino et al. |
| 8,039,681 B2 | 10/2011 | Krusic et al. |
| 8,071,498 B2 | 12/2011 | Aono et al. |
| 8,071,836 B2 | 12/2011 | Butler |
| 8,129,305 B2 | 3/2012 | Bagherzadeh et al. |
| 8,277,525 B2 | 10/2012 | Dalton |
| 8,293,805 B2 | 10/2012 | Khan et al. |
| 8,361,925 B2 | 1/2013 | Matsueda et al. |
| 8,399,527 B1 | 3/2013 | Brown et al. |
| 8,399,726 B2 | 3/2013 | Chinga et al. |
| 8,414,798 B2 | 4/2013 | Costello et al. |
| 8,435,920 B2 | 5/2013 | White et al. |
| 8,450,546 B2 | 5/2013 | Chinta et al. |
| 8,552,236 B2 | 10/2013 | Iaccino |
| 8,647,999 B2 | 2/2014 | Hayashi et al. |
| 8,669,171 B2 | 3/2014 | Perraud et al. |
| 8,710,286 B2 | 4/2014 | Butler |
| 8,729,328 B2 | 5/2014 | Chinta et al. |
| 8,759,598 B2 | 6/2014 | Hayashi et al. |
| 8,796,497 B2 | 8/2014 | Chinta et al. |
| 8,911,834 B2 | 12/2014 | Aktas et al. |
| 8,912,381 B2 | 12/2014 | Chinta et al. |
| 8,921,256 B2 | 12/2014 | Cizeron et al. |
| 8,932,781 B2 | 1/2015 | Yang et al. |
| 8,962,517 B2 | 2/2015 | Zurcher et al. |
| 9,133,079 B2 | 9/2015 | Weinberger et al. |
| 9,446,397 B2 | 9/2016 | Gamoras et al. |
| 9,469,577 B2 | 10/2016 | Schammel et al. |
| 2001/0044520 A1 | 11/2001 | Suzuki et al. |
| 2003/0135971 A1* | 7/2003 | Liberman ......... B01D 67/0041 29/419.1 |
| 2003/0189202 A1 | 10/2003 | Li et al. |
| 2003/0207984 A1 | 11/2003 | Ding et al. |
| 2003/0233019 A1 | 12/2003 | Sherwood |
| 2004/0005723 A1 | 1/2004 | Empedocles et al. |
| 2004/0187963 A1 | 9/2004 | Tayu et al. |
| 2004/0220053 A1 | 11/2004 | Bagherzadeh et al. |
| 2005/0009686 A1 | 1/2005 | Julsrud et al. |
| 2005/0065391 A1 | 3/2005 | Gattis et al. |
| 2005/0199559 A1 | 9/2005 | Duby |
| 2005/0221083 A1 | 10/2005 | Belcher et al. |
| 2005/0255993 A1 | 11/2005 | Tanaka et al. |
| 2006/0083970 A1 | 4/2006 | Shibutani et al. |
| 2006/0125025 A1 | 6/2006 | Kawashima et al. |
| 2006/0135838 A1 | 6/2006 | Bagherzadeh et al. |
| 2006/0155157 A1 | 7/2006 | Zarrinpashne et al. |
| 2006/0177629 A1 | 8/2006 | Kunieda |
| 2006/0283780 A1 | 12/2006 | Spivey et al. |
| 2006/0284162 A1* | 12/2006 | Kurt ............... G03F 7/70291 257/14 |
| 2007/0027030 A1 | 2/2007 | Cheung et al. |
| 2007/0043181 A1 | 2/2007 | Knudsen et al. |
| 2007/0073083 A1 | 3/2007 | Sunley |
| 2007/0083073 A1 | 4/2007 | Bagherzadeh et al. |
| 2007/0095445 A1 | 5/2007 | Gangopadhyay et al. |
| 2007/0138082 A1 | 6/2007 | Connors et al. |
| 2007/0158611 A1 | 7/2007 | Oldenburg |
| 2008/0051279 A1 | 2/2008 | Klett et al. |
| 2008/0141713 A1 | 6/2008 | Verma |
| 2008/0262114 A1 | 10/2008 | Reynhout |
| 2008/0267852 A1 | 10/2008 | Schumacher et al. |
| 2008/0275143 A1 | 11/2008 | Malhotra et al. |
| 2008/0279744 A1* | 11/2008 | Robinson ............... B82Y 30/00 423/263 |
| 2008/0281136 A1 | 11/2008 | Bagherzadeh et al. |
| 2008/0293980 A1 | 11/2008 | Kiesslich et al. |
| 2008/0318044 A1 | 12/2008 | Tian et al. |
| 2009/0043141 A1 | 2/2009 | Mazanec et al. |
| 2009/0087496 A1 | 4/2009 | Katusic et al. |
| 2009/0202427 A1 | 8/2009 | Katusic et al. |
| 2009/0259076 A1 | 10/2009 | Simmons et al. |
| 2009/0267852 A1 | 10/2009 | Tahmisian et al. |
| 2009/0324470 A1 | 12/2009 | Alamdari et al. |
| 2010/0000153 A1 | 1/2010 | Kurkjian et al. |
| 2010/0003179 A1 | 1/2010 | Katusic et al. |
| 2010/0173070 A1 | 7/2010 | Niu |
| 2010/0183937 A1 | 7/2010 | Halloran et al. |
| 2010/0185034 A1 | 7/2010 | Nishimura et al. |
| 2010/0191031 A1 | 7/2010 | Sundaram |
| 2010/0197482 A1 | 8/2010 | Basset et al. |
| 2010/0200501 A1 | 8/2010 | Hoag et al. |
| 2010/0249473 A1 | 9/2010 | Butler |
| 2010/0331174 A1 | 12/2010 | Chinta et al. |
| 2010/0331593 A1 | 12/2010 | Chinta et al. |
| 2010/0331595 A1 | 12/2010 | Chinta et al. |
| 2011/0070139 A1 | 3/2011 | Kim et al. |
| 2011/0104588 A1 | 5/2011 | Kwon et al. |
| 2011/0124488 A1 | 5/2011 | Neltner et al. |

(56) References Cited

U.S. PATENT DOCUMENTS

| | | |
|---|---|---|
| 2011/0160508 A1 | 6/2011 | Ma et al. |
| 2011/0171629 A1 | 7/2011 | Swager et al. |
| 2011/0189559 A1 | 8/2011 | De Miranda et al. |
| 2011/0217544 A1 | 9/2011 | Young et al. |
| 2011/0240926 A1 | 10/2011 | Schellen et al. |
| 2011/0257453 A1 | 10/2011 | Chinta et al. |
| 2011/0275011 A1 | 11/2011 | Zhu et al. |
| 2012/0029218 A1 | 2/2012 | Kim et al. |
| 2012/0041246 A1 | 2/2012 | Scher et al. |
| 2012/0065412 A1 | 3/2012 | Abdallah et al. |
| 2012/0116094 A1 | 5/2012 | Swager et al. |
| 2012/0129690 A1 | 5/2012 | Larcher et al. |
| 2012/0136164 A1 | 5/2012 | Ying et al. |
| 2012/0172648 A1 | 7/2012 | Seebauer |
| 2012/0183770 A1 | 7/2012 | Bosnyak et al. |
| 2012/0198769 A1 | 8/2012 | Schirrmeister et al. |
| 2012/0204716 A1 | 8/2012 | Schirrmeister et al. |
| 2012/0215045 A1 | 8/2012 | Butler |
| 2012/0222422 A1 | 9/2012 | Nunley et al. |
| 2013/0025201 A1 | 1/2013 | Dalton |
| 2013/0039806 A1 | 2/2013 | Blinn et al. |
| 2013/0040806 A1 | 2/2013 | Dismukes et al. |
| 2013/0089739 A1 | 4/2013 | Polshettiwar et al. |
| 2013/0105305 A1 | 5/2013 | Yang et al. |
| 2013/0142707 A1 | 6/2013 | Chinta et al. |
| 2013/0158322 A1 | 6/2013 | Nyce et al. |
| 2013/0165728 A1 | 6/2013 | Zurcher et al. |
| 2013/0178680 A1 | 7/2013 | Ha et al. |
| 2013/0225884 A1 | 8/2013 | Weinberger et al. |
| 2013/0252808 A1 | 9/2013 | Yamazaki et al. |
| 2013/0253248 A1 | 9/2013 | Gamoras et al. |
| 2013/0266809 A1 | 10/2013 | Nueraji et al. |
| 2013/0270180 A1 | 10/2013 | Zhang et al. |
| 2014/0050629 A1 | 2/2014 | Masuda et al. |
| 2014/0054516 A1 | 2/2014 | Moon et al. |
| 2014/0080699 A1 | 3/2014 | Ghose et al. |
| 2014/0107385 A1 | 4/2014 | Schammel et al. |
| 2014/0121433 A1 | 5/2014 | Cizeron et al. |
| 2014/0128484 A1 | 5/2014 | Hassan et al. |
| 2014/0128485 A1 | 5/2014 | Hassan et al. |
| 2014/0171707 A1 | 6/2014 | Nyce et al. |
| 2014/0178788 A1 | 6/2014 | Ha et al. |
| 2014/0194663 A1 | 7/2014 | Butler |
| 2014/0249339 A1 | 9/2014 | Simanzhenkov et al. |
| 2014/0274671 A1 | 9/2014 | Schammel et al. |
| 2014/0332733 A1 | 11/2014 | Joo et al. |
| 2014/0378728 A1 | 12/2014 | Davis et al. |
| 2015/0010467 A1 | 1/2015 | Ito et al. |
| 2015/0073192 A1 | 3/2015 | Cizeron et al. |
| 2015/0125383 A1 | 5/2015 | Yamazaki et al. |
| 2015/0314267 A1 | 11/2015 | Schammel et al. |
| 2016/0074844 A1 | 3/2016 | Freer et al. |
| 2016/0107143 A1 | 4/2016 | Schammel et al. |
| 2016/0122261 A1 | 5/2016 | Schammel et al. |
| 2016/0340272 A1 | 11/2016 | Cizeron et al. |

FOREIGN PATENT DOCUMENTS

| | | | |
|---|---|---|---|
| CN | 1100669 | A | 3/1995 |
| CN | 1321728 | A | 11/2001 |
| CN | 1389293 | A | 1/2003 |
| CN | 1403375 | A | 3/2003 |
| CN | 101 224 432 | A | 7/2008 |
| CN | 101 387 019 | A | 3/2009 |
| CN | 102 125 825 | A | 7/2011 |
| DE | 3406751 | A1 | 8/1985 |
| EP | 0 253 522 | A2 | 1/1988 |
| EP | 0595425 | A1 | 5/1994 |
| EP | 0761307 | B1 | 2/2003 |
| EP | 0764467 | B1 | 2/2003 |
| EP | 1 632 467 | A1 | 3/2006 |
| EP | 1 749 807 | A1 | 2/2007 |
| EP | 2287142 | A1 | 2/2011 |
| EP | 2374526 | A1 | 10/2011 |
| FR | 649429 | A | 12/1928 |
| GB | 2191212 | A | 12/1987 |
| JP | S6363626 | A | 3/1988 |
| JP | H02218623 | A | 8/1990 |
| JP | H03262535 | A | 11/1991 |
| JP | H05238961 | A | 9/1993 |
| JP | 2005-161225 | A | 6/2005 |
| JP | 2011032257 | A | 2/2011 |
| WO | 8607351 | A1 | 12/1986 |
| WO | 0016901 | A1 | 3/2000 |
| WO | 2004/033488 | A2 | 4/2004 |
| WO | 2005/067683 | A2 | 7/2005 |
| WO | 2007/130515 | A2 | 11/2007 |
| WO | 2008/005055 | A2 | 1/2008 |
| WO | 2008/014841 | A1 | 2/2008 |
| WO | 2008/022147 | A1 | 2/2008 |
| WO | 2008/073143 | A2 | 6/2008 |
| WO | 2009/071463 | A2 | 6/2009 |
| WO | 2009/115805 | A1 | 9/2009 |
| WO | 2010005453 | A2 | 1/2010 |
| WO | 2011/050359 | A1 | 4/2011 |
| WO | 2011/149996 | A2 | 12/2011 |
| WO | 2012/162526 | A2 | 11/2012 |
| WO | 2013186789 | A1 | 12/2013 |
| WO | 2014043603 | A1 | 3/2014 |
| WO | 2014049445 | A2 | 4/2014 |

OTHER PUBLICATIONS

Oxidative Coupling of Methane Over SrO Deposited on Different Commercial Supports Precoated With La2O3. Choudhary et al. Ind Eng. Chem. Res 1998, 37, 2142-2147.*

Preparation of Porous LaFeO3 Nanowires Using AAO Template and Their Catalytic Properties. Kwang-Hyeon Ryu et al. Bulletin Koreaa Chem Soc. 2011.*

Freer et al., "Catalysts for Natural Gas Processes" U.S. Appl. No. 14/856,177, filed Sep. 16, 2015, 183 pages.

Schammel et al., "Catalysts for Petrochemical Catalysis," U.S. Appl. No. 14/777,333, filed Sep. 15, 2015, 259 pages.

Dedov, A.G. et al. "Oxidative coupling of methane catalyzed by rare earth oxides. Unexpected synergistic effect of the oxide mixtures" Applied Catalysis (2003) 245:209-220.

Fallah, B. et al. "A New Nano-(2Li2O/MgO) Catalyst/Porous Alpha-Alumina Composite for the Oxidative Coupling of Methane Reaction" AIChE Journal (2010) 56(3):717-728.

Krishnadas, K.R. et al. "Pristine and Hybrid Nickel Nanowires: Template-, Magnetic Field-, and Surfactant-Free Wet Chemical Synthesis and Raman Studies" J Phys Chem (Feb. 25, 2011) 115:4483-4490.

Park, J-M et al. "Fabrication of metallic nano wires and nano ribbons using laser interference lithography and shadow lithography" Nanotechnology (2010) 21:1-6.

Cizeron et al., "Catalysts for Petrochemical Catalysis," U.S. Appl. No. 14/692,495, filed Apr. 21, 2015, 211 pages.

"Autothermal Partial Oxidative Coupling of Methane," An IP.com Prior Art Database Technical Disclosure, IP.com No. IPCOM000173290D, Jul. 29, 2008.

Cavani et al., "Oxidative dehydrogenation of ethane and propane: How far from commercial implementation?" *Catalysis Today* 127:113-131, 2007.

Choudhary, et al., "Aromatization of dilute ethylene over Ga-modified ZSM-5 type zeolite catalysts," *Microporous and Mesoporous Materials* 47:253-267, 2001.

Choudhary et al., "Oxidative conversion of methane/natural gas into higher hydrocarbons," *Catalysis Surveys from Asia* 8(1):15-25, Feb. 2004.

Choudhary et al., "Surface Basicity and Acidity of Alkaline Earth-Promoted $La_2O_3$ Catalysts and Their Performance in Oxidative Coupling of Methane," *J. Chem. Technol. Biotechnol.* 72:125-130, 1998.

Christopher et al., "Engineering Selectivity in Heterogeneous Catalysis: Ag Nanowires as Selective Ethylene Epoxidation Catalysts," *J. Am. Chem. Soc.* 130:11264-11265, 2008.

Cizeron et al., "Catalysts for Petrochemical Catalysis," filed May 24, 2011, for U.S. Appl. No. 61/489,651, 86 pages.

(56) References Cited

OTHER PUBLICATIONS

Débart et al., "α-MnO2 Nanowires: A Catalyst for the O2 Electrode in Rechargeable Lithium Batteries," *Angew. Chem. Int. Ed.* 47:4521-4524, 2008.
Enger et al., "A review of catalytic partial oxidation of methane to synthesis gas with emphasis on reaction mechanisms over transition metal catalysts," *Applied Catalysis A: General* 346:1-27, Aug. 2008.
Guo et al., "Current Status and Some Perspectives of Rare Earth Catalytic Materials," *Journal of The Chinese Rare Earth Society* 25(1):1-15, Feb. 2007.
Gao et al., "The direct decomposition of NO over the $La_2CuO_4$ nanofiber catalyst," *Journal of Solid State Chemistry* 181:2804-2807, 2008.
Gao et al., "A study on methanol steam reforming to $CO_2$ and $H_2$ over the $La_2CuO_4$ nanofiber catalyst," *Journal of Solid State Chemistry* 181:7-13, 2008.
Huang et al., "Exploiting Shape Effects of $La_2O_3$ Nanocatalysts for Oxidative Coupling of Methane Reaction," The Royal Society of Chemistry 2013, 5 pages.
Huang et al., "Exploiting Shape Effects of $La_2O_3$ Nanocatalysts for Oxidative Coupling of Methane Reaction," The Royal Society of Chemistry 2013, 7 pages (Electronic Supplementary Information).
Ling et al., "Preparation of $Ag_{core}Au_{core}$ Nanowires and Their Surface Enhanced Raman Spectroscopic Studies," *Acta Chimica Sinica* 65(9):779-784, 2007.
Liu et al., "A novel $Na_2WO_4$-Mn/SiC monolithic foam catalyst with improved thermal properties for the oxidative coupling of methane," *Catalysis Communications* 9(6):1302-1306, 2007.
Jiangrong et al., "Preparation and Characterization of $La_2O_2CO_3$ Nanowires with High Surface Areas," *Journal of the Chinese Rare Earth Society* 23(Spec. Issue):33-36, Dec. 2005.
Keller et al., "Synthesis of Ethylene via Oxidative Coupling of Methane." *Journal of Catalysis* 73:9-19, 1982.
Kuang et al., "Grafting of PEG onto lanthanum hydroxide nanowires," *Materials Letters* 62:4078-4080, 2008.
Labinger, "Oxidative Coupling of Methane: An Inherent Limit to Selectivity?" *Catalysis Letters* 1:371-376, 1988.
Lunsford, "The Catalytic Oxidative Coupling of Methane," *Angew. Chem. Int. Ed. Engl.* 34:970-980, 1995.
Mleczko et al., "Catalytic oxidative coupling of methane—reaction engineering aspects and process schemes," *Fuel Processing Technology* 42:217-248, 1995.
Neltner, "Hybrid Bio-templated Catalysts," Doctoral Thesis, Massachusetts Institute of Technology, Jun. 2010, 156 pages.
Neither et al., "Production of Hydrogen Using Nanocrystalline Protein-Templated Catalysts on M13 Phage," *ACSNano* 4(6):3227-3235, 2010.
Niu et al., "Preparation and Characterization of $La_2O_2CO_3$ Nanowires with High Surface Areas," *Journal of the Chinese Rare Earth Society* 23(Spec. Issue):33-36, Dec. 2005.
Nyce et al., "Polymer Templated Nanowire Catalysts," filed Nov. 29, 2011 for U.S. Appl. No. 61/564,836, 317 pages.
Pak et al., "Elementary Reactions in the Oxidative Coupling of Methane over $Mn/Na_2WO_4/SiO_2$ and $Mn/Na_2WO_4/MgO$ Catalysts," *Journal of Catalysis* 179:222-230, 1998.
Qiu et al., "Steady-state conversion of methane to aromatics in high yields using an integrated recycle reaction system," *Catalysis Letters* 48:11-15, 1997.
Schweer et al., "OCM in a fixed-bed reactor: limits and perspectives," *Catalysis Today* 21:357-369, 1994.
Somorjai et al., "High technology catalysts towards 100% selectivity Fabrication, characterization and reaction studies," *Catalysis Today* 100:201-215, Jan. 2005.
Takanabe et al., "Mechanistic Aspects and Reaction Pathways for Oxidative Coupling of Methane on $Mn/Na_2WO_4/SiO_2$ Catalysts," *J. Phys. Chem. C* 113:10131-10145, 2009.
Takanabe et al., "Rate and Selectivity Enhancements Mediated by OH Radicals in the Oxidative Coupling of Methane Catalyzed by $Mn/Na_2WO_4/SiO_2$," *Angew. Chem. Int. Ed.* 47:7689-7693, 2008.
Taylor et al., "Lanthanum Catalysts for $CH_4$ Oxidative Coupling: A Comparison of the Reactivity of Phases," *Ind. Eng. Chem. Res* 30:1016-1023, 1991.
Tong et al., "Development Strategy Research of Downstream Products of Ethene in Tianjin," *Tianjin Economy*, pp. 37-40, 1996.
Trautmann et al., "Cyrogenic Technology for Nitrogen Rejection from Variable Content Natural Gas," XIV Convencion Internacional de Gas, Caracas, Venezuela, May 10-12, 2000.
Wang et al., "Autothermal oxidative coupling of methane on the $SrCO_3/Sm_2O_3$ catalysts," *Catalysis Communications* 10:807-810, 2009.
Wang et al., "Comparative study on oxidation of methane to ethane and ethylene over $Na_2WO_4$-Mn/$SiO_2$ catalysts prepared by different methods," *Journal of Molecular Catalysis A: Chemical* 245:272-277, 2006.
Wang et al., "Low-temperature selective oxidation of methane to ethane and ethylene over $BaCO_3/La_2O_3$ catalysts prepared by urea combustion method," *Catalysis Communications* 7:59-63, 2006.
Wong et al., "Oxidative Coupling of Methane Over Alkali Metal Oxide Promoted $LA_2O_3/BACO_3$ Catalysts," *Journal of Chemical Technology and Biotechnology* 65(4):351-354, 1996.
Yang et al., "Anisotropic syntheses of boat-shaped core-shell Au-Ag nanocrystals and nanowires," *Nanotechnology* 17(9):2304-2310, 2006.
Yu et al., "Oxidative Coupling of Methane over Acceptor-doped $SrTiO_3$: Correlation between p-type Conductivity and $C_2$ Yield," *Journal of Catalysis* 13(5):338-344, 1992.
Zhao, "Technologies and Catalysts for Catalytic Preparation of Ethene," *Industrial Catalysis* 12(Supp.):285-289, 2004.
Zhou et al., "Functionalization of lanthanum hydroxide nanowires by atom transfer radical polymerization," *Nanotechnology* 18(40):1-7, 2007.
Zimmermann et al., "Ethylene," Ullmann's Encyclopedia of Industrial Chemistry, Wiley-VCH Verlag GmbH & Co. KGaA, Weinheim, Germany, 2009, 66 pages.
Zurcher et al., "Nanowire Catalysts," U.S. Appl. No. 61/564,834, filed Nov. 29, 2011, 367 pages.
Zurcher et al., "Nanowire Catalysts," U.S. Appl. No. 61/651,399, filed May 24, 2012, 406 pages.
Agapie, T "Selective ethylene oligomerization: recent advances in chromium catalysis and mechanistic investigations" Coord Chem Rev (2011) 255:861-880.
Bergh, S. et al. "Combinatorial Heterogeneous Catalysis: Oxidative Dehydrogenation of Ethane to Ethylene, Selective Oxidation of Ethane to Acetic Acid, and Selective Ammoxidation of Propane to Acrylonitrile" Topics in Catalysis (2003) 23(1-4):65-79.
Carter, et al. "High activity ethylene trimerisation catalysts based on diphosphine ligands." Chem Commun (Camb). (Apr. 21, 2002) (8):858-9.
Dixon, J.T. et al. "Advances in selective ethylene trimerisation—a critical overview" J. Organometallic Chem. (2004) 689(23):3641-3668.
Dulai, A. et al. "N,N'-Bis(diphenylphosphino)diaminophenylphosphine Ligands for Chromium-Catalyzed Selective Ethylene Oligomerization Reactions" Organometallics (2011) 30(5):935-941.
Guo, X. et al. "Direct, Nonoxidative Conversion of Methane to Ethylene, Aromatics, and Hydrogen" Science (2014) 344:616-619.
Hinson, P.G. Et al. "The oxidative coupling of methane on chlorinated Lithium-doped magnesium oxide" J Chem Soc, Chem Comm (1991) 20:1430-1432.
Jaramillo, P. et al. "Comparative analysis of the production costs and life-cycle GHG emissions of FT liquid fuels from coal and natural gas" Env. Sci. Tech (2008) 42:7559-7565.
Kaminsky, M.P. et al. "Deactivation of Li-Based Catalysts for Methane Oxidative Coupling" Poster ACS Symposium on Natural Gas Upgrading II (Apr. 5-10, 1992).
Kaminsky, M.P. et al. "Oxygen X-Ray Absorption Near-Edge Structure Characterization of the Ba-Doped Yttria Oxidative Coupling Catalyst" J Catalysis (1992) 136:16-23.
O'Connor, C.T. et al. "Alkene oligomerization" Catalysis Today (1990) 6(3):329-349.

(56) References Cited

OTHER PUBLICATIONS

Peitz, S. et al. "An Alternative Mechanistic Concept for Homogeneous Selective Ethylene Oligomerization of Chromium-Based Catalysts: Binuclear Metallacycles as a Reason for 1-Octene Selectivity?" Chemistry—A European Journal (2010) 16(26):7670-7676.
Ren, T. et al. "Basic petrochemicals from natural gas, coal and biomass: Energy use and CO2 emissions" Res Consery Recycl (2009) 53(9):513-528.
Schaarschmidt, D. et al. "Ferrocenyl phosphane nickel carbonyls: Synthesis, solid state structure, and their use as catalysts in the oligomerization of ethylene" J. Organometallic Chem. (2010) 695(10-11):1541-1549.
Song, S. et al. "Synthesis, characterization and ethylene oligomerization behaviour of 8-(1-aryliminoethylidene) quinaldinylnickel dihalides" Catal. Sci. Technol. (2011) 1(1):69-75.
Van Santen, R.A. et al. "An introduction to molecular heterogeneous catalysis" New Trends in Material Chemistry (1997) pp. 345-363.
Wang, X. et al. "Synthesis and Characterization of Lanthanide Hydroxide Single-Crystal Nanowires" Angew Chem Int Ed (2002) 41(24):4790-4793.
Zhang, Q. Journal of Natural Gas Chem., (2003) 12:81.
Zhu, F. et al. "Recent Research Progress in Preparation of Ethylene Oligomers with Chromium-Based Catalytic Systems" Designed Monomers & Polymers (2011) 14(1):1-23.
Nagamoto et al., "Methane Oxidation over Perovskite-type Oxide Containing Alkaline-earth Metal," Chemistry Letters, pp. 237-240, 1988.
Miller et al., "Oxidation reactions of ethane over Ba—Ce—O based perovskites," Applied Catalysis A: General 201:45-54, 2000.
Natural Gas Spec Sheet, prepared by Florida Power and Light Company, 2003.
Choudhary, V.R. et al. "Oxidative Coupling of Methane over SrO Deposited on Different Commercial Supports Precoated with La2O3" Ind Eng Chem Res (1998) 37:2142-2147.
Galadima, a. et al. "Revisiting the oxidative coupling of methane to ethylene in the golden period of shale gas: A review" J Ind Eng Chem (Mar. 2016) http://dx.doi.org/10.1016/jliec.2016.03.027.
Au et al., "A Comparison of BaF2/La2O3 and BaBr/La2O3 Cetalysts for the the Oxidative Coupling of Methane" J Catalysis (Apr. 1996) 159(2):280-287.
Choudhary et al. "Oxidative Coupling of Methane and Owidiant Dehydrogenation of Ethane over Strontium-Promoted Rare Earth Oxide Catalysts" J Chem Tech and Biotech (Feb. 1998) 71(2):167-172
Devi et al. "College Inorganic Chemistry" Devi, K.V.S. Laxmi, Patel, N. C., and Venkatachalam, A.. College Inorganic Chemistry. Mumbai, IND: Himalaya Publishing House, 2010. Jan. 1, 2010 (Jan. 1, 2010), XP055242276, Retrieved from the Internet: URL:http://site.ebrary.com/lib/epo/reader.action?docID=10415159 [retried on Jan. 18, 2016] 1 page.
Ferreira et al., "Effect of Mg, Ca, and Sr on CeO2 Based Catalysts for the Oxidative Coupling of Methane: Investigation on the Oxygen Species Responsible for Catalytic Performance" Indus and Eng Chem Res (Jul. 2012) 51 (32):10535-10541.
Gong et al., "Preparation of Carbon Nanotubes (CNTs)-Cordierite Monoliths by Catalytic Chemical Vapor Deposition as Catalyst Supports for Ammonia Synthesis" Catalysis Letts (May 2008) 122(3):287-294.

Istadi et al., "Synergistic effect of catalyst basicity and reducibility on performance of ternary Ce-O2-based catalyst for CO2 OCM to C2 hydrocarbons" J Mol Catalysis A: Chem (Nov. 2006) 259(1-2):61-66.
Ma, et al. "Processing and properties of carbon nanotubes-non-SiC ceramic" J Mat Sci (Nov. 1998) 33 (21):5245-5246/
Ryu, K-H et al. "Preparation of Porous LaFeO3 Nanowires using AAO Template and Their Catalytic Properties" Bull. Korean Chem Soc. (2011) 32(7):2457-2460.
Tana et al., "Morphology-dependent redox and catalytic properties of CeO2 nanostructures: Nanowires, nano rods and nanoparticles" Catalysis Today (Oct. 2009) 148(1-2):179-183.
Theuerkauf et al. "Analysis of particle porosity distribution in fixed beds using the discrete element method" Powder Tech (Jul. 2006) 165(2):92-99.
Tian et al., "Catalytic reduction of NOx with NH3 over different-shaped MnO2 at low temperature" J Hazardous Mats (Jan. 2011) 188(1-3):105-109.
Valenzuela et al., "Nanostructured ceria-based catalysts for oxydehydrogenation of ethane with CO2" Topics in Catalysis (Jun. 2001) 15(2-4):181-188.
Wang et al., "Nanostructured Sheets of Ti-O Nanobelts for Gas Sensing and Antibacterial Applications" Adv Functional Mats (Apr. 2008) 18(7):1131-1137.
Zhang et al., "Relationship between packing structure and porosity in fixed beds of equilateral cylindrical particles" Chem Eng Sci (Dec. 2006) 61(24):8060-8074.
Zhang, X. et al. "Single-Walled Carbon Nanotube-Based Coaxial Nanowires: Synthesis, Characterization, and Electrical properties" J Phys Chem (2005) 109(3):1101-1107.
Dai, "Study on low temperature catalytic activation of methane," Thesis of graduate student for Master's Degree in Physical Chemistry, East China Normal University, May 2005, 8 pages. (with English Translation).
Eskendirov et al., "Methane oxidative coupling on the Au/La2O3/CaO catalyst in the presence of hydrogen peroxide," Catalysis Letters 35:33-37, 1995.
Hess et al. (eds.) "Kirk-Othmer encyclopedia of chemical technology" New York, John Wiley & Sons Ltd. 1998, p. 171.
Li, Y. et al. "Color control and white light generation of upconversion luminescence by operating dopant concentrations and pump densities in Yb3+, ER3+ and Tm3+ trip doped Lu2O3 nanocrystal" J Mater Chem (2011) 21:2895-2900.
Nam et al. "Virus-Enabled Synthesis and Assembly of Nanowires for Lithium Ion Battery Electrodes" Science (2006) 312(5775):885-888.
Spinicci, R. et al. "Oxidative coupling of methane on LaAlO3 perovskites partially substituted with alkali or alkali-earth ions" J Molecular Catalysts (2001) 176:253-265.
Teymouri, M. et al. "Reactivity of perovskites on oxidative coupling of methane" J Mat Sci (1995) 30(11):3005-3009.
Tomishige, K. et al. "Reactivity and characterization of absorbed oxygen on SrTi1-xMgxO3-δ catalysts for oxidative ,coupling of methane," Physical Chemistry Chemical Physics, Royal Society of Chemistry (1999) 1(12):3039-3045.
Tullo "Ethylene from Methane" Chemical and Engineering News (2011) 89(3):2021.
Matskevich, N.I. et al. "Synthesis and thermochemistry of new phase BaCe0.7Nd0.2In0.1O2.85" J Alloys and Compounds (2013) 577:148-151.

\* cited by examiner

SEQUENCE LISTING

```
<160> NUMBER OF SEQ ID NOS: 31

<210> SEQ ID NO 1
<211> LENGTH: 52
<212> TYPE: PRT
<213> ORGANISM: Artificial Sequence
<220> FEATURE:
<223> OTHER INFORMATION: M13 bacteriophage pVIII protein tailored for
      surface affinity to metal ions

<400> SEQUENCE: 1

Ala Glu Glu Gly Ser Glu Asp Pro Ala Lys Ala Ala Phe Asn Ser Leu
1               5                   10                  15

Gln Ala Ser Ala Thr Glu Tyr Ile Gly Tyr Ala Trp Ala Met Val Val
            20                  25                  30

Val Ile Val Gly Ala Thr Ile Gly Ile Lys Leu Phe Lys Lys Phe Thr
        35                  40                  45

Ser Lys Ala Ser
    50

<210> SEQ ID NO 2
<211> LENGTH: 51
<212> TYPE: PRT
<213> ORGANISM: Artificial Sequence
<220> FEATURE:
<223> OTHER INFORMATION: M13 bacteriophage pVIII protein tailored for
      surface affinity to metal ions

<400> SEQUENCE: 2

Glu Glu Gly Ser Asp Asp Pro Ala Lys Ala Ala Phe Asn Ser Leu Gln
1               5                   10                  15

Ala Ser Ala Thr Glu Tyr Ile Gly Tyr Ala Trp Ala Met Val Val Val
            20                  25                  30

Ile Val Gly Ala Thr Ile Gly Ile Lys Leu Phe Lys Lys Phe Thr Ser
        35                  40                  45

Lys Ala Ser
    50

<210> SEQ ID NO 3
<211> LENGTH: 50
<212> TYPE: PRT
<213> ORGANISM: Artificial Sequence
<220> FEATURE:
<223> OTHER INFORMATION: M13 bacteriophage pVIII protein tailored for
      surface affinity to metal ions

<400> SEQUENCE: 3

Ala Glu Glu Glu Asp Pro Ala Lys Ala Ala Phe Asn Ser Leu Gln Ala
1               5                   10                  15

Ser Ala Thr Glu Tyr Ile Gly Tyr Ala Trp Ala Met Val Val Val Ile
            20                  25                  30

Val Gly Ala Thr Ile Gly Ile Lys Leu Phe Lys Lys Phe Thr Ser Lys
        35                  40                  45
```

Ala Ser
    50

<210> SEQ ID NO 4
<211> LENGTH: 49
<212> TYPE: PRT
<213> ORGANISM: Artificial Sequence
<220> FEATURE:
<223> OTHER INFORMATION: M13 bacteriophage pVIII protein tailored for
      surface affinity to metal ions

<400> SEQUENCE: 4

Glu Glu Glu Asp Pro Ala Lys Ala Ala Phe Asn Ser Leu Gln Ala Ser
1               5                   10                  15

Ala Thr Glu Tyr Ile Gly Tyr Ala Trp Ala Met Val Val Ile Val
            20                  25                  30

Gly Ala Thr Ile Gly Ile Lys Leu Phe Lys Lys Phe Thr Ser Lys Ala
        35                  40                  45

Ser

<210> SEQ ID NO 5
<211> LENGTH: 51
<212> TYPE: PRT
<213> ORGANISM: Artificial Sequence
<220> FEATURE:
<223> OTHER INFORMATION: M13 bacteriophage pVIII protein tailored for
      surface affinity to metal ions

<400> SEQUENCE: 5

Ala Glu Glu Glu Glu Asp Pro Ala Lys Ala Ala Phe Asn Ser Leu Gln
1               5                   10                  15

Ala Ser Ala Thr Glu Tyr Ile Gly Tyr Ala Trp Ala Met Val Val Val
            20                  25                  30

Ile Val Gly Ala Thr Ile Gly Ile Lys Leu Phe Lys Lys Phe Thr Ser
        35                  40                  45

Lys Ala Ser
    50

<210> SEQ ID NO 6
<211> LENGTH: 51
<212> TYPE: PRT
<213> ORGANISM: Artificial Sequence
<220> FEATURE:
<223> OTHER INFORMATION: M13 bacteriophage pVIII protein tailored for
      surface affinity to metal ions

<400> SEQUENCE: 6

Ala Glu Glu Ala Glu Asp Pro Ala Lys Ala Ala Phe Asn Ser Leu Gln
1               5                   10                  15

Ala Ser Ala Thr Glu Tyr Ile Gly Tyr Ala Trp Ala Met Val Val Val
            20                  25                  30

Ile Val Gly Ala Thr Ile Gly Ile Lys Leu Phe Lys Lys Phe Thr Ser
        35                  40                  45

Lys Ala Ser
    50

<210> SEQ ID NO 7
<211> LENGTH: 50
<212> TYPE: PRT
<213> ORGANISM: Artificial Sequence
<220> FEATURE:
<223> OTHER INFORMATION: M13 bacteriophage pVIII protein tailored for -continued surface affinity to metal ions
<220> FEATURE:
<221> NAME/KEY: misc_feature
<222> LOCATION: (3)..(3)
<223> OTHER INFORMATION: X = E or G

<400> SEQUENCE: 7

Glu Glu Xaa Glu Asp Pro Ala Lys Ala Ala Phe Asn Ser Leu Gln Ala
1               5                   10                  15

Ser Ala Thr Glu Tyr Ile Gly Tyr Ala Trp Ala Met Val Val Val Ile
            20                  25                  30

Val Gly Ala Thr Ile Gly Ile Lys Leu Phe Lys Lys Phe Thr Ser Lys
        35                  40                  45

Ala Ser
    50

<210> SEQ ID NO 8
<211> LENGTH: 50
<212> TYPE: PRT
<213> ORGANISM: Artificial Sequence
<220> FEATURE:
<223> OTHER INFORMATION: M13 bacteriophage pVIII protein tailored for
      surface affinity to metal ions

<400> SEQUENCE: 8

Ala Glu Asp Asp Asp Pro Ala Lys Ala Ala Phe Asn Ser Leu Gln Ala
1               5                   10                  15

Ser Ala Thr Glu Tyr Ile Gly Tyr Ala Trp Ala Met Val Val Val Ile
            20                  25                  30

Val Gly Ala Thr Ile Gly Ile Lys Leu Phe Lys Lys Phe Thr Ser Lys
        35                  40                  45

Ala Ser
    50

<210> SEQ ID NO 9
<211> LENGTH: 55
<212> TYPE: PRT
<213> ORGANISM: Artificial Sequence
<220> FEATURE:
<223> OTHER INFORMATION: M13 bacteriophage pVIII protein tailored for
      surface affinity to metal ions

<400> SEQUENCE: 9

Ala Val Ser Gly Ser Ser Pro Gly Asp Asp Pro Ala Lys Ala Ala Phe
1               5                   10                  15

Asn Ser Leu Gln Ala Ser Ala Thr Glu Tyr Ile Gly Tyr Ala Trp Ala
            20                  25                  30

Met Val Val Val Ile Val Gly Ala Thr Ile Gly Ile Lys Leu Phe Lys
        35                  40                  45

Lys Phe Thr Ser Lys Ala Ser
    50                  55

<210> SEQ ID NO 10
<211> LENGTH: 55
<212> TYPE: PRT
<213> ORGANISM: Artificial Sequence
<220> FEATURE:
<223> OTHER INFORMATION: M13 bacteriophage pVIII protein tailored for
      surface affinity to metal ions

<400> SEQUENCE: 10

Ala Val Ser Gly Ser Ser Pro Asp Ser Asp Pro Ala Lys Ala Ala Phe
1               5                   10                  15

```
Asn Ser Leu Gln Ala Ser Ala Thr Glu Tyr Ile Gly Tyr Ala Trp Ala
            20                  25                  30

Met Val Val Val Ile Val Gly Ala Thr Ile Gly Ile Lys Leu Phe Lys
        35                  40                  45

Lys Phe Thr Ser Lys Ala Ser
    50                  55

<210> SEQ ID NO 11
<211> LENGTH: 55
<212> TYPE: PRT
<213> ORGANISM: Artificial Sequence
<220> FEATURE:
<223> OTHER INFORMATION: M13 bacteriophage pVIII protein tailored for
      surface affinity to metal ions

<400> SEQUENCE: 11

Ala Gly Glu Thr Gln Gln Ala Met Glu Asp Pro Ala Lys Ala Ala Phe
1               5                   10                  15

Asn Ser Leu Gln Ala Ser Ala Thr Glu Tyr Ile Gly Tyr Ala Trp Ala
            20                  25                  30

Met Val Val Val Ile Val Gly Ala Thr Ile Gly Ile Lys Leu Phe Lys
        35                  40                  45

Lys Phe Thr Ser Lys Ala Ser
    50                  55

<210> SEQ ID NO 12
<211> LENGTH: 55
<212> TYPE: PRT
<213> ORGANISM: Artificial Sequence
<220> FEATURE:
<223> OTHER INFORMATION: M13 bacteriophage pVIII protein tailored for
      surface affinity to metal ions

<400> SEQUENCE: 12

Ala Ala Gly Glu Thr Gln Gln Ala Met Asp Pro Ala Lys Ala Ala Phe
1               5                   10                  15

Asn Ser Leu Gln Ala Ser Ala Thr Glu Tyr Ile Gly Tyr Ala Trp Ala
            20                  25                  30

Met Val Val Val Ile Val Gly Ala Thr Ile Gly Ile Lys Leu Phe Lys
        35                  40                  45

Lys Phe Thr Ser Lys Ala Ser
    50                  55

<210> SEQ ID NO 13
<211> LENGTH: 56
<212> TYPE: PRT
<213> ORGANISM: Artificial Sequence
<220> FEATURE:
<223> OTHER INFORMATION: M13 bacteriophage pVIII protein tailored for
      surface affinity to metal ions

<400> SEQUENCE: 13

Ala Glu Pro Gly His Asp Ala Val Pro Glu Asp Pro Ala Lys Ala Ala
1               5                   10                  15

Phe Asn Ser Leu Gln Ala Ser Ala Thr Glu Tyr Ile Gly Tyr Ala Trp
            20                  25                  30

Ala Met Val Val Val Ile Val Gly Ala Thr Ile Gly Ile Lys Leu Phe
        35                  40                  45

Lys Lys Phe Thr Ser Lys Ala Ser
    50                  55
```

<210> SEQ ID NO 14
<211> LENGTH: 52
<212> TYPE: PRT
<213> ORGANISM: Artificial Sequence
<220> FEATURE:
<223> OTHER INFORMATION: M13 bacteriophage pVIII protein tailored for
      surface affinity to metal ions

<400> SEQUENCE: 14

Ala Glu Asp Pro Ala Glu Asp Pro Ala Lys Ala Ala Phe Asn Ser Leu
1               5                   10                  15

Gln Ala Ser Ala Thr Glu Tyr Ile Gly Tyr Ala Trp Ala Met Val Val
            20                  25                  30

Val Ile Val Gly Ala Thr Ile Gly Ile Lys Leu Phe Lys Lys Phe Thr
        35                  40                  45

Ser Lys Ala Ser
    50

<210> SEQ ID NO 15
<211> LENGTH: 52
<212> TYPE: PRT
<213> ORGANISM: Artificial Sequence
<220> FEATURE:
<223> OTHER INFORMATION: M13 bacteriophage pVIII protein tailored for
      surface affinity to metal ions

<400> SEQUENCE: 15

Ala Glu Asp Pro Ala Lys Asp Pro Ala Lys Ala Ala Phe Asn Ser Leu
1               5                   10                  15

Gln Ala Ser Ala Thr Glu Tyr Ile Gly Tyr Ala Trp Ala Met Val Val
            20                  25                  30

Val Ile Val Gly Ala Thr Ile Gly Ile Lys Leu Phe Lys Lys Phe Thr
        35                  40                  45

Ser Lys Ala Ser
    50

<210> SEQ ID NO 16
<211> LENGTH: 53
<212> TYPE: PRT
<213> ORGANISM: Artificial Sequence
<220> FEATURE:
<223> OTHER INFORMATION: M13 bacteriophage pVIII protein tailored for
      surface affinity to metal ions

<400> SEQUENCE: 16

Ala Glu Phe Glu Val Glu Ala Asp Pro Ala Lys Ala Ala Phe Asn Ser
1               5                   10                  15

Leu Gln Ala Ser Ala Thr Glu Tyr Ile Gly Tyr Ala Trp Ala Met Val
            20                  25                  30

Val Val Ile Val Gly Ala Thr Ile Gly Ile Lys Leu Phe Lys Lys Phe
        35                  40                  45

Thr Ser Lys Ala Ser
    50

<210> SEQ ID NO 17
<211> LENGTH: 53
<212> TYPE: PRT
<213> ORGANISM: Artificial Sequence
<220> FEATURE:
<223> OTHER INFORMATION: M13 bacteriophage pVIII protein tailored for
      surface affinity to metal ions

<400> SEQUENCE: 17

Ala Glu His Glu Ala Glu Glu Asp Pro Ala Lys Ala Ala Phe Asn Ser
1               5                   10                  15

Leu Gln Ala Ser Ala Thr Glu Tyr Ile Gly Tyr Ala Trp Ala Met Val
            20                  25                  30

Val Val Ile Val Gly Ala Thr Ile Gly Ile Lys Leu Phe Lys Lys Phe
        35                  40                  45

Thr Ser Lys Ala Ser
    50

<210> SEQ ID NO 18
<211> LENGTH: 53
<212> TYPE: PRT
<213> ORGANISM: Artificial Sequence
<220> FEATURE:
<223> OTHER INFORMATION: M13 bacteriophage pVIII protein tailored for
      surface affinity to metal ions

<400> SEQUENCE: 18

Ala Glu Ser Glu Phe Glu Leu Asp Pro Ala Lys Ala Ala Phe Asn Ser
1               5                   10                  15

Leu Gln Ala Ser Ala Thr Glu Tyr Ile Gly Tyr Ala Trp Ala Met Val
            20                  25                  30

Val Val Ile Val Gly Ala Thr Ile Gly Ile Lys Leu Phe Lys Lys Phe
        35                  40                  45

Thr Ser Lys Ala Ser
    50

<210> SEQ ID NO 19
<211> LENGTH: 53
<212> TYPE: PRT
<213> ORGANISM: Artificial Sequence
<220> FEATURE:
<223> OTHER INFORMATION: M13 bacteriophage pVIII protein tailored for
      surface affinity to metal ions

<400> SEQUENCE: 19

Ala Asp Asn Asp Val Asp Leu Asp Pro Ala Lys Ala Ala Phe Asn Ser
1               5                   10                  15

Leu Gln Ala Ser Ala Thr Glu Tyr Ile Gly Tyr Ala Trp Ala Met Val
            20                  25                  30

Val Val Ile Val Gly Ala Thr Ile Gly Ile Lys Leu Phe Lys Lys Phe
        35                  40                  45

Thr Ser Lys Ala Ser
    50

<210> SEQ ID NO 20
<211> LENGTH: 53
<212> TYPE: PRT
<213> ORGANISM: Artificial Sequence
<220> FEATURE:
<223> OTHER INFORMATION: M13 bacteriophage pVIII protein tailored for
      surface affinity to metal ions

<400> SEQUENCE: 20

Ala Asp Ser Asp Tyr Asp Gly Asp Pro Ala Lys Ala Ala Phe Asn Ser
1               5                   10                  15

Leu Gln Ala Ser Ala Thr Glu Tyr Ile Gly Tyr Ala Trp Ala Met Val
            20                  25                  30

Val Val Ile Val Gly Ala Thr Ile Gly Ile Lys Leu Phe Lys Lys Phe
        35                  40                  45

<210> SEQ ID NO 21
<211> LENGTH: 53
<212> TYPE: PRT
<213> ORGANISM: Artificial Sequence
<220> FEATURE:
<223> OTHER INFORMATION: M13 bacteriophage pVIII protein tailored for
      surface affinity to metal ions

<400> SEQUENCE: 21

```
Ala Asp Ala Asp Arg Asp Gly Asp Pro Ala Lys Ala Ala Phe Asn Ser
1               5                   10                  15

Leu Gln Ala Ser Ala Thr Glu Tyr Ile Gly Tyr Ala Trp Ala Met Val
            20                  25                  30

Val Val Ile Val Gly Ala Thr Ile Gly Ile Lys Leu Phe Lys Lys Phe
        35                  40                  45

Thr Ser Lys Ala Ser
    50
```

<210> SEQ ID NO 22
<211> LENGTH: 53
<212> TYPE: PRT
<213> ORGANISM: Artificial Sequence
<220> FEATURE:
<223> OTHER INFORMATION: M13 bacteriophage pVIII protein tailored for
      surface affinity to metal ions

<400> SEQUENCE: 22

```
Ala Asp Ser Asp Pro Asp Gly Asp Pro Ala Lys Ala Ala Phe Asn Ser
1               5                   10                  15

Leu Gln Ala Ser Ala Thr Glu Tyr Ile Gly Tyr Ala Trp Ala Met Val
            20                  25                  30

Val Val Ile Val Gly Ala Thr Ile Gly Ile Lys Leu Phe Lys Lys Phe
        35                  40                  45

Thr Ser Lys Ala Ser
    50
```

<210> SEQ ID NO 23
<211> LENGTH: 53
<212> TYPE: PRT
<213> ORGANISM: Artificial Sequence
<220> FEATURE:
<223> OTHER INFORMATION: M13 bacteriophage pVIII protein tailored for
      surface affinity to metal ions

<400> SEQUENCE: 23

```
Ala Asp Ser Asp Thr Asp Ser Asp Pro Ala Lys Ala Ala Phe Asn Ser
1               5                   10                  15

Leu Gln Ala Ser Ala Thr Glu Tyr Ile Gly Tyr Ala Trp Ala Met Val
            20                  25                  30

Val Val Ile Val Gly Ala Thr Ile Gly Ile Lys Leu Phe Lys Lys Phe
        35                  40                  45

Thr Ser Lys Ala Ser
    50
```

<210> SEQ ID NO 24
<211> LENGTH: 53
<212> TYPE: PRT
<213> ORGANISM: Artificial Sequence
<220> FEATURE:
<223> OTHER INFORMATION: M13 bacteriophage pVIII protein tailored for surface affinity to metal ions

<400> SEQUENCE: 24

Ala Asp Lys Asp Tyr Asp Leu Asp Pro Ala Lys Ala Ala Phe Asn Ser
1               5                   10                  15

Leu Gln Ala Ser Ala Thr Glu Tyr Ile Gly Tyr Ala Trp Ala Met Val
            20                  25                  30

Val Val Ile Val Gly Ala Thr Ile Gly Ile Lys Leu Phe Lys Lys Phe
        35                  40                  45

Thr Ser Lys Ala Ser
    50

<210> SEQ ID NO 25
<211> LENGTH: 53
<212> TYPE: PRT
<213> ORGANISM: Artificial Sequence
<220> FEATURE:
<223> OTHER INFORMATION: M13 bacteriophage pVIII protein tailored for
      surface affinity to metal ions

<400> SEQUENCE: 25

Ala Glu Phe Glu Val Gly Ala Asp Pro Ala Lys Ala Ala Phe Asn Ser
1               5                   10                  15

Leu Gln Ala Ser Ala Thr Glu Tyr Ile Gly Tyr Ala Trp Ala Met Val
            20                  25                  30

Val Val Ile Val Gly Ala Thr Ile Gly Ile Lys Leu Phe Lys Lys Phe
        35                  40                  45

Thr Ser Lys Ala Ser
    50

<210> SEQ ID NO 26
<211> LENGTH: 53
<212> TYPE: PRT
<213> ORGANISM: Artificial Sequence
<220> FEATURE:
<223> OTHER INFORMATION: M13 bacteriophage pVIII protein tailored for
      surface affinity to metal ions

<400> SEQUENCE: 26

Ala Gly Phe Glu Gly Glu Ala Asp Pro Ala Lys Ala Ala Phe Asn Ser
1               5                   10                  15

Leu Gln Ala Ser Ala Thr Glu Tyr Ile Gly Tyr Ala Trp Ala Met Val
            20                  25                  30

Val Val Ile Val Gly Ala Thr Ile Gly Ile Lys Leu Phe Lys Lys Phe
        35                  40                  45

Thr Ser Lys Ala Ser
    50

<210> SEQ ID NO 27
<211> LENGTH: 53
<212> TYPE: PRT
<213> ORGANISM: Artificial Sequence
<220> FEATURE:
<223> OTHER INFORMATION: M13 bacteriophage pVIII protein tailored for
      surface affinity to metal ions

<400> SEQUENCE: 27

Ala Asp Gly Asp Leu Asp Gln Asp Pro Ala Lys Ala Ala Phe Asn Ser
1               5                   10                  15

Leu Gln Ala Ser Ala Thr Glu Tyr Ile Gly Tyr Ala Trp Ala Met Val
            20                  25                  30

```
Val Val Ile Val Gly Ala Thr Ile Gly Ile Lys Leu Phe Lys Lys Phe
            35                  40                  45

Thr Ser Lys Ala Ser
    50

<210> SEQ ID NO 28
<211> LENGTH: 53
<212> TYPE: PRT
<213> ORGANISM: Artificial Sequence
<220> FEATURE:
<223> OTHER INFORMATION: M13 bacteriophage pVIII protein tailored for
      surface affinity to metal ions

<400> SEQUENCE: 28

Ala Glu Phe Glu Ala Glu Ala Asp Pro Ala Lys Ala Ala Phe Asn Ser
1               5                   10                  15

Leu Gln Ala Ser Ala Thr Glu Tyr Ile Gly Tyr Ala Trp Ala Met Val
            20                  25                  30

Val Val Ile Val Gly Ala Thr Ile Gly Ile Lys Leu Phe Lys Lys Phe
            35                  40                  45

Thr Ser Lys Ala Ser
    50

<210> SEQ ID NO 29
<211> LENGTH: 53
<212> TYPE: PRT
<213> ORGANISM: Artificial Sequence
<220> FEATURE:
<223> OTHER INFORMATION: M13 bacteriophage pVIII protein tailored for
      surface affinity to metal ions

<400> SEQUENCE: 29

Ala Gly Phe Glu Val Glu Ala Asp Pro Ala Lys Ala Ala Phe Asn Ser
1               5                   10                  15

Leu Gln Ala Ser Ala Thr Glu Tyr Ile Gly Tyr Ala Trp Ala Met Val
            20                  25                  30

Val Val Ile Val Gly Ala Thr Ile Gly Ile Lys Leu Phe Lys Lys Phe
            35                  40                  45

Thr Ser Lys Ala Ser
    50

<210> SEQ ID NO 30
<211> LENGTH: 51
<212> TYPE: PRT
<213> ORGANISM: M13 Bacteriophage

<400> SEQUENCE: 30

Ala Glu Gly Asp Asp Pro Ala Lys Ala Ala Phe Asn Ser Leu Gln
1               5                   10                  15

Ala Ser Ala Thr Glu Tyr Ile Gly Tyr Ala Trp Ala Met Val Val Val
            20                  25                  30

Ile Val Gly Ala Thr Ile Gly Ile Lys Leu Phe Lys Lys Phe Thr Ser
            35                  40                  45

Lys Ala Ser
    50

<210> SEQ ID NO 31
<211> LENGTH: 74
<212> TYPE: PRT
<213> ORGANISM: M13 Bacteriophage

<400> SEQUENCE: 31
```

-continued

```
Met Lys Lys Ser Leu Val Leu Lys Ala Ser Val Ala Val Ala Thr Leu
1               5                   10                  15
Val Pro Met Leu Ser Phe Ala Ala Glu Gly Asp Asp Asp Pro Ala Lys
            20                  25              30
Ala Ala Phe Asn Ser Leu Gln Ala Ser Ala Thr Glu Tyr Ile Gly Tyr
        35                  40                  45
Ala Trp Ala Met Val Val Val Ile Val Gly Ala Thr Ile Gly Ile Lys
    50                  55                  60
Leu Phe Lys Lys Phe Thr Ser Lys Ala Ser
65                  70
```

NANOWIRE CATALYSTS AND METHODS FOR THEIR USE AND PREPARATION

CROSS-REFERENCES TO RELATED APPLICATIONS

This application is a continuation of U.S. patent application Ser. No. 13/689,611, filed on Nov. 29, 2012, now U.S. Pat. No. 8,962,517, which claims the benefit under 35 U.S.C. §119(e) of U.S. Provisional Patent Application No. 61/564,834, filed on Nov. 29, 2011; Provisional Patent Application No. 61/564,836, filed on Nov. 29, 2011; and U.S. Provisional Patent Application No. 61/651,399, filed on May 24, 2012; each of which are incorporated herein by reference in their entireties.

STATEMENT REGARDING SEQUENCE LISTING

The Sequence Listing associated with this application is provided in text format in lieu of a paper copy, and is hereby incorporated by reference into the specification. The name of the text file containing the Sequence Listing 860158_420C1_SEQUENCE_LISTING.txt. The text file is 19 KB, was created on Dec. 1, 2014, and is being submitted electronically via EFS-Web.

BACKGROUND

1. Technical Field

This invention is generally related to novel nanowire catalysts and, more specifically, to nanowires useful as heterogeneous catalysts in a variety of catalytic reactions, such as the oxidative coupling of methane to C2 hydrocarbons.

2. Description of the Related Art

Catalysis is the process in which the rate of a chemical reaction is either increased or decreased by means of a catalyst. Positive catalysts increase the speed of a chemical reaction, while negative catalysts slow it down. Substances that increase the activity of a catalyst are referred to as promoters or activators, and substances that deactivate a catalyst are referred to as catalytic poisons or deactivators. Unlike other reagents, a catalyst is not consumed by the chemical reaction, but instead participates in multiple chemical transformations. In the case of positive catalysts, the catalytic reaction generally has a lower rate-limiting free energy change to the transition state than the corresponding uncatalyzed reaction, resulting in an increased reaction rate at the same temperature. Thus, at a given temperature, a positive catalyst tends to increase the yield of desired product while decreasing the yield of undesired side products. Although catalysts are not consumed by the reaction itself, they may be inhibited, deactivated or destroyed by secondary processes, resulting in loss of catalytic activity.

Catalysts are generally characterized as either heterogeneous or homogeneous. Heterogeneous catalysts exist in a different phase than the reactants (e.g. a solid metal catalyst and gas phase reactants), and the catalytic reaction generally occurs on the surface of the heterogeneous catalyst. Thus, for the catalytic reaction to occur, the reactants must diffuse to and/or adsorb onto the catalyst surface. This transport and adsorption of reactants is often the rate limiting step in a heterogeneous catalysis reaction. Heterogeneous catalysts are also generally easily separable from the reaction mixture by common techniques such as filtration or distillation.

In contrast to a heterogeneous catalyst, a homogenous catalyst exists in the same phase as the reactants (e.g., a soluble organometallic catalyst and solvent-dissolved reactants). Accordingly, reactions catalyzed by a homogeneous catalyst are controlled by different kinetics than a heterogeneously catalyzed reaction. In addition, homogeneous catalysts can be difficult to separate from the reaction mixture.

While catalysis is involved in any number of technologies, one particular area of importance is the petrochemical industry. At the foundation of the modern petrochemical industry is the energy-intensive endothermic steam cracking of crude oil. Cracking is used to produce nearly all the fundamental chemical intermediates in use today. The amount of oil used for cracking and the volume of green house gases (GHG) emitted in the process are quite large: cracking consumes nearly 10% of the total oil extracted globally and produces 200M metric tons of $CO_2$ equivalent every year (Ren, T, Patel, M. *Res. Conserv. Recycl.* 53:513, 2009). There remains a significant need in this field for new technology directed to the conversion of unreactive petrochemical feedstocks (e.g. paraffins, methane, ethane, etc.) into reactive chemical intermediates (e.g. olefins), particularly with regard to highly selective heterogeneous catalysts for the direct oxidation of hydrocarbons.

While there are multistep paths to convert methane to certain specific chemicals using first; high temperature steam reforming to syngas (a mixture of $H_2$ and CO), followed by stochiometry adjustment and conversion to either methanol or, via the Fischer-Tropsch (F-T) synthesis, to liquid hydrocarbon fuels such as diesel or gasoline, this does not allow for the formation of certain high value chemical intermediates. This multi-step indirect method also requires a large capital investment in facilities and is expensive to operate, in part due to the energy intensive endothermic reforming step. (For instance, in methane reforming, nearly 40% of methane is consumed as fuel for the reaction.) It is also inefficient in that a substantial part of the carbon fed into the process ends up as the GHG $CO_2$, both directly from the reaction and indirectly by burning fossil fuels to heat the reaction. Thus, to better exploit the natural gas resource, direct methods that are more efficient, economical and environmentally responsible are required.

One of the reactions for direct natural gas activation and its conversion into a useful high value chemical, is the oxidative coupling of methane ("OCM") to ethylene: $2CH_4 + O_2 \rightarrow C_2H_4 + 2H_2O$. See, e.g., Zhang, Q., *Journal of Natural Gas Chem.*, 12:81, 2003; Olah, G. "Hydrocarbon Chemistry", Ed. 2, John Wiley & Sons (2003). This reaction is exothermic ($\Delta H = -67$ kcals/mole) and has typically been shown to occur at very high temperatures (>700° C.). Although the detailed reaction mechanism is not fully characterized, experimental evidence suggests that free radical chemistry is involved. (Lunsford, *J. Chem. Soc., Chem. Comm.*, 1991; H. Lunsford, *Angew. Chem., Int. Ed. Engl.*, 34:970, 1995). In the reaction, methane ($CH_4$) is activated on the catalyst surface, forming methyl radicals which then couple in the gas phase to form ethane ($C_2H_6$), followed by dehydrogenation to ethylene ($C_2H_4$). Several catalysts have shown activity for OCM, including various forms of iron oxide, $V_2O_5$, $MoO_3$, $Co_3O_4$, Pt—Rh, $Li/ZrO_2$, Ag—Au, $Au/Co_3O_4$, Co/Mn, $CeO_2$, MgO, $La_2O_3$, $Mn_3O_4$, $Na_2WO_4$, MnO, ZnO, and combinations thereof, on various supports. A number of doping elements have also proven to be useful in combination with the above catalysts.

Since the OCM reaction was first reported over thirty years ago, it has been the target of intense scientific and commercial interest, but the fundamental limitations of the conventional approach to C—H bond activation appear to limit the yield of this attractive reaction. Specifically, numerous publications from industrial and academic labs have consistently demonstrated characteristic performance of high selectivity at low conversion of methane, or low selectivity at high conversion (J. A. Labinger, *Cat. Lett.*, 1:371, 1988). Limited by this conversion/selectivity threshold, no OCM catalyst has been able to exceed 20-25% combined $C_2$ yield (i.e. ethane and ethylene), and more importantly, all such reported yields operate at extremely high temperatures (>800 C).

In this regard, it is believed that the low yield of desired products (i.e. $C_2H_4$ and $C_2H_6$) is caused by the unique homogeneous/heterogeneous nature of the reaction. Specifically, due to the high reaction temperature, a majority of methyl radicals escape the catalyst surface and enter the gas phase. There, in the presence of oxygen and hydrogen, multiple side reactions are known to take place (J. A. Labinger, *Cat. Lett.*, 1:371, 1988). The non-selective over-oxidation of hydrocarbons to CO and $CO_2$ (e.g., complete oxidation) is the principal competing fast side reaction. Other undesirable products (e.g. methanol, formaldehyde) have also been observed and rapidly react to form CO and $CO_2$.

In order to result in a commercially viable OCM process, a catalyst optimized for the activation of the C—H bond of methane at lower temperatures (e.g. 500-700° C.), higher activities and higher pressures are required. While the above discussion has focused on the OCM reaction, numerous other catalytic reactions (as discussed in greater detail below) would significantly benefit from catalytic optimization. Accordingly, there remains a need in the art for improved catalysts and, more specifically, a need for novel approaches to catalyst design for improving the yield of, for example, the OCM reaction and other catalyzed reactions. The present invention fulfills these needs and provides further related advantages.

BRIEF SUMMARY

In brief, nanowires and related methods are disclosed. The nanowires find utility in any number of applications, including use as heterogeneous catalysts in petrochemical processes, such as OCM. In one embodiment, the disclosure provides a catalytic nanowire comprising a combination of at least four different doping elements, wherein the doping elements are selected from a metal element, a semi-metal element and a non-metal element In other embodiments, the present disclosure is directed to a catalytic nanowire comprising at least two different doping elements, wherein the doping elements are selected from a metal element, a semi-metal element and a non-metal element, and wherein at least one of the doping elements is K, Sc, Ti, V, Nb, Ru, Os, Ir, Cd, In, Tl, S, Se, Po, Pr, Tb, Dy, Ho, Er, Tm, Lu or an element selected from any of groups 6, 7, 10, 11, 14, 15 or 17.

In yet another aspect, the present disclosure provides a catalytic nanowire comprising at least one of the following dopant combinations: Eu/Na, Sr/Na, Na/Zr/Eu/Ca, Mg/Na, Sr/Sm/Ho/Tm, Sr/W, Mg/La/K, Na/K/Mg/Tm, Na/Dy/K, Na/La/Dy, Sr/Hf/K, Na/La/Eu, Na/La/Eu/In, Na/La/K, Na/La/Li/Cs, K/La, K/La/S, K/Na, Li/Cs, Li/Cs/La, Li/Cs/La/Tm, Li/Cs/Sr/Tm, Li/Sr/Cs, Li/Sr/Zn/K, Li/Ga/Cs, Li/K/Sr/La, Li/Na, Li/Na/Rb/Ga, Li/Na/Sr, Li/Na/Sr/La, Sr/Zr, Li/Sm/Cs, Ba/Sm/Yb/S, Ba/Tm/K/La, Ba/Tm/Zn/K, Sr/Zr/K, Cs/K/La, Cs/La/Tm/Na, Cs/Li/K/La, Sm/Li/Sr/Cs, Sr/Cs/La, Sr/Tm/Li/Cs, Zn/K, Zr/Cs/K/La, Rb/Ca/In/Ni, Sr/Ho/ Tm, La/Nd/S, Li/Rb/Ca, Li/K, Tm/Lu/Ta/P, Rb/Ca/Dy/P, Mg/La/Yb/Zn, Rb/Sr/Lu, Na/Sr/Lu/Nb, Na/Eu/Hf, Dy/Rb/Gd, Sr/Ce, Na/Pt/Bi, Rb/Hf, Ca/Cs, Ca/Mg/Na, Hf/Bi, Sr/Sn, Sr/W, Sr/Nb, Sr/Ce/K, Zr/W, Y/W, Na/W, Bi/W, Bi/Cs, Bi/Ca, Bi/Sn, Bi/Sb, Ge/Hf, Hf/Sm, Sb/Ag, Sb/Bi, Sb/Au, Sb/Sm, Sb/Sr, Sb/W, Sb/Hf, Sb/Yb, Sb/Sn, Yb/Au, Yb/Ta, Yb/W, Yb/Sr, Yb/Pb, Yb/W, Yb/Ag, Au/Sr, W/Ge, Sr/Tb, Ta/Hf, W/Au, Ca/W, Au/Re, Sm/Li, La/K, Zn/Cs, Na/K/Mg, Zr/Cs, Ca/Ce, Na/Li/Cs, Li/Sr, Cs/Zn, La/Dy/K, Dy/K, La/Mg, Na/Nd/In/K, In/Sr, Sr/Cs, Rb/Ga/Tm/Cs, Ga/Cs, K/La/Zr/Ag, Lu/Fe, Sr/Tb/K, Sr/Tm, La/Dy, Sm/Li/ Sr, Mg/K, Sr/Pr, Li/Rb/Ga, Li/Cs/Tm, Zr/K, Li/Cs, Li/K/La, Ce/Zr/La, Ca/Al/La, Sr/Zn/La, Sr/Cs/Zn, Sm/Cs, In/K, Ho/Cs/Li/La, Sr/Pr/K, Cs/La/Na, La/S/Sr, K/La/Zr/Ag, Lu/Tl, Pr/Zn, Rb/Sr/La, Na/Sr/Eu/Ca, K/Cs/Sr/La, Na/Sr/ Lu, Sr/Eu/Dy, Lu/Nb, La/Dy/Gd, Na/Mg/Tl/P, Na/Pt, Gd/Li/ K, Rb/K/Lu, Sr/La/Dy/S, Na/Ce/Co, Na/Ce, Na/Ga/Gd/Al, Ba/Rh/Ta, Ba/Ta, Na/Al/Bi, Sr/Hf/Rb, Cs/Eu/S, Sm/Tm/Yb/ Fe, Sm/Tm/Yb, Hf/Zr/Ta, Rb/Gd/Li/K, Gd/Ho/Al/P, Na/Ca/ Lu, Cu/Sn, Ag/Au, Al/Bi, Al/Mo, Al/Nb, Au/Pt, Ga/Bi, Mg/W, Pb/Au, Sn/Mg, Sr/B, Zn/Bi, Gd/Ho, Zr/Bi, Ho/Sr, Gd/Ho/Sr, Ca/Sr, Ca/Sr/W, Sr/Ho/Tm/Na, Na/Zr/Eu/Tm, Sr/Ho/Tm/Na, Sr/Pb, Sr/W/Li, Ca/Sr/W or Sr/Hf.

In still other embodiments, the disclosure provides a catalytic nanowire comprising $Ln1_{4-x}Ln2_xO_6$ and a dopant comprising a metal element, a semi-metal element, a non-metal element or combinations thereof, wherein Ln1 and Ln2 are each independently a lanthanide element, wherein Ln1 and Ln2 are not the same and x is a number ranging from greater than 0 to less than 4.

In other embodiments, the disclosure provides a nanowire comprising a mixed oxide of Y—La, Zr—La, Pr—La, Ce—La or combinations thereof and at least one dopant selected from a metal element, a semi-metal element and a non-metal element.

In still other embodiments, the invention provides a catalytic nanowire comprising a mixed oxide of a rare earth element and a Group 13 element, wherein the catalytic nanowire further comprises one or more Group 2 elements.

The disclosure is also directed to a catalytic nanowire, wherein the single pass methane conversion in an OCM reaction catalyzed by the nanowire is greater than 20%.

In still other embodiments the disclosure provides a catalytic nanowire having a C2 selectivity of greater than 10% in the OCM reaction when the OCM reaction is performed with an oxygen source other than air or $O_2$. For example the catalytic nanowire may have activity in the OCM reaction in the presence of $CO_2$, $H_2O$, $SO_2$, $SO_3$ or combinations thereof. In some embodiments of the foregoing, the catalytic nanowire comprises $La_2O_3/ZnO$, $CeO_2/ZnO$, $CaO/ZnO$, $CaO/CeO_2$, $CaO/Cr_2O_3$, $CaO/MnO_2$, $SrO/ZnO$, $SrO/CeO_2$, $SrO/Cr_2O_3$, $SrO/MnO_2$, $SrCO_3/MnO_2$, $BaO/ZnO$, $BaO/CeO_2$, $BaO/Cr_2O_3$, $BaO/MnO_2$, $CaO/MnO/CeO_2$, $Na_2WO_4/Mn/SiO_2$, $Pr_2O_3$, $Tb_2O_3$ or combinations thereof.

In yet other embodiments of any of the foregoing catalytic nanowires, the catalytic nanowire is polycrystalline and has a ratio of effective length to actual length of less than one and an aspect ratio of greater than ten as measured by TEM in bright field mode at 5 keV, wherein the catalytic nanowire comprises one or more elements from any of Groups 1 through 7, lanthanides, actinides or combinations thereof.

In yet other embodiments of any of the foregoing catalytic nanowires, the catalytic nanowire has a bent morphology, and in other embodiments the catalytic nanowire has a straight morphology. In yet other embodiments of any of the foregoing catalytic nanowires, the catalytic nanowire comprises a metal oxide, metal oxy-hydroxide, a metal oxycarbonate, a metal carbonate or combinations thereof, for example in some embodiments the catalytic nanowire comprises a metal oxide.

The present disclosure also provides a catalytic material comprising a plurality of catalytic nanowires in combination with a diluent or support, wherein the diluent or support comprises an alkaline earth metal compound. In some embodiments, the alkaline earth metal compound is MgO, $MgCO_3$, $MgSO_4$, $Mg_3(PO_4)_2$, $MgAl_2O_4$, CaO, $CaCO_3$, $CaSO_4$, $Ca_3(PO_4)_2$, $CaAl_2O_4$, SrO, $SrCO_3$, $SrSO_4$, $Sr_3(PO_4)_2$, $SrAl_2O_4$, BaO, $BaCO_3$, $BaSO_4$, $Ba_3(PO_4)_2$, $BaAl_2O_4$ or combinations thereof. For example, in some embodiments the alkaline earth metal compound is MgO, CaO, SrO, $MgCO_3$, $CaCO_3$, $SrCO_3$ or combinations thereof. In other embodiments, the catalytic material is in the form of a pressed pellet, extrudate or monolith structure.

In other embodiments, the disclosure relates to a catalytic material comprising a plurality of catalytic nanowires and a sacrificial binder, and in other embodiments the disclosure is directed to a catalytic material in the form of a pressed pellet (e.g., pressure treated), wherein the catalytic material comprises a plurality of catalytic nanowires and substantially no binder material.

In other embodiments, the disclosure provides a catalytic material in the form of a pressed pellet or extrudate, wherein the catalytic material comprises a plurality of catalytic nanowires and pores greater than 20 nm in diameter. For example, in some embodiments the catalytic material is in the form of a pellet, and in other embodiments, the catalytic material is in the form of an extrudate.

In still other embodiments of the present disclosure, a catalytic material comprising a plurality of catalytic nanowires supported on a structured support is provided. For example, the structured support may comprise a foam, foil or honeycomb structure. In other embodiments, the structured support comprises silicon carbide or alumina, and in still other embodiments the structured support comprises a metal foam, silicon carbide or alumina foams, corrugated metal foil arranged to form channel arrays or extruded ceramic honeycomb.

Other embodiments provide a catalytic material comprising a catalytic nanowire, wherein the catalytic material is in contact with a reactor. For example, in some embodiments the reactor is used for performing OCM, and in other embodiments the catalytic material comprises silicon carbide. In further embodiments the reactor is a fixed bed reactor, and in other examples the reactor comprises an inner diameter of at least 1 inch.

In another embodiment, the disclosure provides a catalytic material comprising at least one $O_2$-OCM catalyst and at least one $CO_2$-OCM catalyst. For example in some aspects at least one of the $O_2$-OCM catalyst or the $CO_2$-OCM catalyst is a catalytic nanowire.

In another embodiment, the disclosure provides a catalytic material comprising at least one $O_2$-OCM catalyst and at least one $CO_2$-ODH catalyst. For example in some aspects at least one of the $O_2$-OCM catalyst or the $CO_2$-ODH catalyst is a catalytic nanowire.

In other embodiments of any of the foregoing catalytic materials, the catalytic material comprises any of the catalytic nanowires disclosed herein.

Other embodiments of the present disclosure include a method for preparing a catalytic material, the method comprising admixing a plurality of catalytic nanowires with a sacrificial binder and removing the sacrificial binder to obtain a catalytic material comprising substantially no binder material and having an increased microporosity compared a to catalytic material prepared without the sacrificial binder. For example, the catalytic material may be any of the foregoing catalytic materials.

In still other embodiments, the disclosure is directed to a method for purifying a phage solution, the method comprising:

a) a microfiltration step comprising filtering a phage solution through a membrane comprising pores ranging from 0.1 to 3 µm to obtain a microfiltration retentate and a microfiltration permeate; and b) an ultrafiltration step comprising filtering the microfiltration permeate through a membrane comprising pores ranging from 1 to 1000 kDa and recovering an ultrafiltration retentate comprising a purified phage solution.

In some embodiments, the ultrafiltration step is performed using tangential flow filtration. In other embodiments, the method further comprises diafiltrating the purified phage solution to exchange media for buffer solution.

In some embodiments, the microfiltration step and the ultrafiltration step are performed using tangential flow filtration, while in other embodiments the microfiltration step is performed using depth filtration.

In other embodiments, the disclosure provides a method for preparing a catalytic nanowire comprising a metal oxide, a metal oxy-hydroxide, a metal oxycarbonate or a metal carbonate, the method comprising:

a) providing a solution comprising a plurality of biological templates;

(b) introducing at least one metal ion and at least one anion to the solution under conditions and for a time sufficient to allow for nucleation and growth of a nanowire comprising a plurality of metal salts $(M_mX_nZ_p)$ on the template; and (c) converting the nanowire $(M_mX_nZ_p)$ to a metal oxide nanowire comprising a plurality of metal oxides $(M_xO_y)$, metal oxy-hydroxides $(M_xO_yOH_z)$, metal oxycarbonates $(M_xO_y(CO_3)_z)$, metal carbonate $(M_x(CO_3)_y)$ or combinations thereof wherein:

M is, at each occurrence, independently a metal element from any of Groups 1 through 7, lanthanides or actinides;

X is, at each occurrence, independently hydroxides, carbonates, bicarbonates, phosphates, hydrogenphosphates, dihydrogenphosphates, sulfates, nitrates or oxalates;

Z is O;

n, m, x and y are each independently a number from 1 to 100; and p is a number from 0 to 100.

In yet other embodiments, the disclosure provides a method for preparing metal oxide, metal oxy-hydroxide, metal oxycarbonate or metal carbonate catalytic nanowires in a core/shell structure, the method comprising:

(a) providing a solution that includes a plurality of biological templates;

(b) introducing a first metal ion and a first anion to the solution under conditions and for a time sufficient to allow for nucleation and growth of a first nanowire $(M1_{m1}X1_{n1}Z_{p1})$ on the template; and (c) introducing a second metal ion and optionally a second anion to the solution under conditions and for a time sufficient to allow for nucleation and growth of a second nanowire $(M2_{m2}X2_{n2}Z_{p2})$ on the first nanowire $(M1_{m1}X1_{n1}Z_{p1})$;

(d) converting the first nanowire $(M1_{m1}X1_{n1}Z_{p1})$ and the second nanowire $(M2_{m2}X2_{n2}Z_{p2})$ to the respective metal oxide nanowires $(M1_{x1}O_{y1})$ and $(M2_{x2}O_{y2})$, the respective metal oxy-hydroxide nanowires ($M1_{x1}O_{y1}OH_{z1}$) and ($M2_{x2}O_{y2}OH_{z2}$) the respective metal oxycarbonate nanowires ($M1_{x1}O_{y1}(CO_3)_{z1}$) and ($M2_{x2}O_{y2}(CO_3)_{z2}$) or the respective metal carbonate nanowires ($M1_{x1}(CO_3)_{y1}$) and ($M2_{x2}(CO_3)_{y2}$), wherein:

M1 and M2 are the same or different and independently selected from a metal element;

X1 and X2 are the same or different and independently hydroxides, carbonates, bicarbonates, phosphates, hydrogenphosphates, dihydrogenphosphates, sulfates, nitrates or oxalates;

Z is O;

n1, m1n2, m2, x1, y1, z1, x2, y2 and z2 are each independently a number from 1 to 100; and p1 and p2 are independently a number from 0 to 100.

In still other embodiments, the disclosure provides a method for preparing a catalytic nanowire, the method comprising treating at least one metal compound with an ammonium salt having the formula $NR_4X$, wherein each R is independently H, alkyl, alkenyl, alkynyl or aryl, and X is an anion. For example, in some embodiments X is phosphate, hydrogenphosphage, dihydrogenphosphate, metatungstate, tungstate, molybdate, bicarbonate sulfate, nitrate or acetate.

In other embodiments of the foregoing method, the method comprises treating two or more different metal compounds with the ammonium salt and the nanowire comprises two or more different metals. In other embodiments, the nanowire comprises a mixed metal oxide, metal oxyhalide, metal oxynitrate or metal sulfate, and in other aspects the ammonium salt is contacted with the metal compound in solution or in the solid state.

In still other embodiments of the foregoing method, the method further comprises treating the at least one metal compound with the ammonium salt in the presence of at least one doping element, and the nanowire comprises the least one doping element. In other embodiments, the at least one metal compound is an oxide of a lanthanide element. In still other embodiments, R is methyl, ethyl, propyl, isopropyl, butyl, tert-butyl, pentenyl, cyclohexyl, phenyl, tolyl, benzyl, hexynyl, octyl, octenyl, octynyl, dodecyl, cetyl, oleyl or stearyl.

In other embodiments of the foregoing method, the ammonium salt is ammonium chloride, dimethylammonium chloride, methylammonium chloride, ammonium acetate, ammonium nitrate, dimethylammonium nitrate, methylammonium nitrate or cetyl trimethylammonium bromide (CTAB), while in other embodiments the method further comprises treating the metal oxide and ammonium salt at temperatures ranging from 0° C. to reflux temperature in an aqueous solvent for a time sufficient to produce the nanowires. Other examples comprise heating the metal oxide and ammonium salt under hydrothermal conditions at temperatures ranging from reflux temperature to 300° C. at atmospheric pressure.

In another embodiment, the disclosure provides a method for the oxidative coupling of methane, the method comprising converting methane to one or more C2 hydrocarbons in the presence of a catalytic material, wherein the catalytic material comprises at least one $O_2$-OCM catalyst and at least one $CO_2$-OCM catalyst. In some embodiments, at least one of the $O_2$-OCM catalyst or the $CO_2$-OCM catalyst is a catalytic nanowire, for example any of the nanowires disclosed herein. In some embodiments, the catalytic material comprises a bed of alternating layers of $O_2$-OCM catalysts and $CO_2$-OCM catalysts, while in other embodiments the catalytic material comprises a homogeneous mixture of $O_2$-OCM catalysts and $CO_2$-OCM catalysts.

In yet more embodiments, the disclosure provides a method for the preparation of ethane, ethylene or combinations thereof, the method comprising converting methane to ethane, ethylene or combinations thereof in the presence of a catalytic material, wherein the catalytic material comprises at least one $O_2$-OCM catalyst and at least one $CO_2$-ODH catalyst. For example, in some embodiments at least one of the $O_2$-OCM catalyst or the $CO_2$-OCM catalyst is a catalytic nanowire, for example any of the catalytic nanowires disclosed herein, such as a metal oxide, metal oxy-hydroxide, a metal oxycarbonate or a metal carbonate nanowire or combinations thereof.

These and other aspects of the invention will be apparent upon reference to the following detailed description. To this end, various references are set forth herein which describe in more detail certain background information, procedures, compounds and/or compositions, and are each hereby incorporated by reference in their entirety.

BRIEF DESCRIPTION OF THE SEVERAL VIEWS OF THE DRAWINGS

In the drawings, the sizes and relative positions of elements in the drawings are not necessarily drawn to scale. For example, the various elements and angles are not drawn to scale, and some of these elements are arbitrarily enlarged and positioned to improve drawing legibility. Further, the particular shapes of the elements as drawn are not intended to convey any information regarding the actual shape of the particular elements, and have been selected solely for ease of recognition in the drawings.

DETAILED DESCRIPTION OF THE INVENTION

In the following description, certain specific details are set forth in order to provide a thorough understanding of various embodiments. However, one skilled in the art will understand that the invention may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed invention.

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments. Also, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

As discussed above, heterogeneous catalysis takes place between several phases. Generally, the catalyst is a solid, the reactants are gases or liquids and the products are gases or liquids. Thus, a heterogeneous catalyst provides a surface that has multiple active sites for adsorption of one more gas or liquid reactants. Once adsorbed, certain bonds within the reactant molecules are weakened and dissociate, creating reactive fragments of the reactants, e.g., in free radical forms. One or more products are generated as new bonds between the resulting reactive fragments form, in part, due to their proximity to each other on the catalytic surface.

Figure 1:
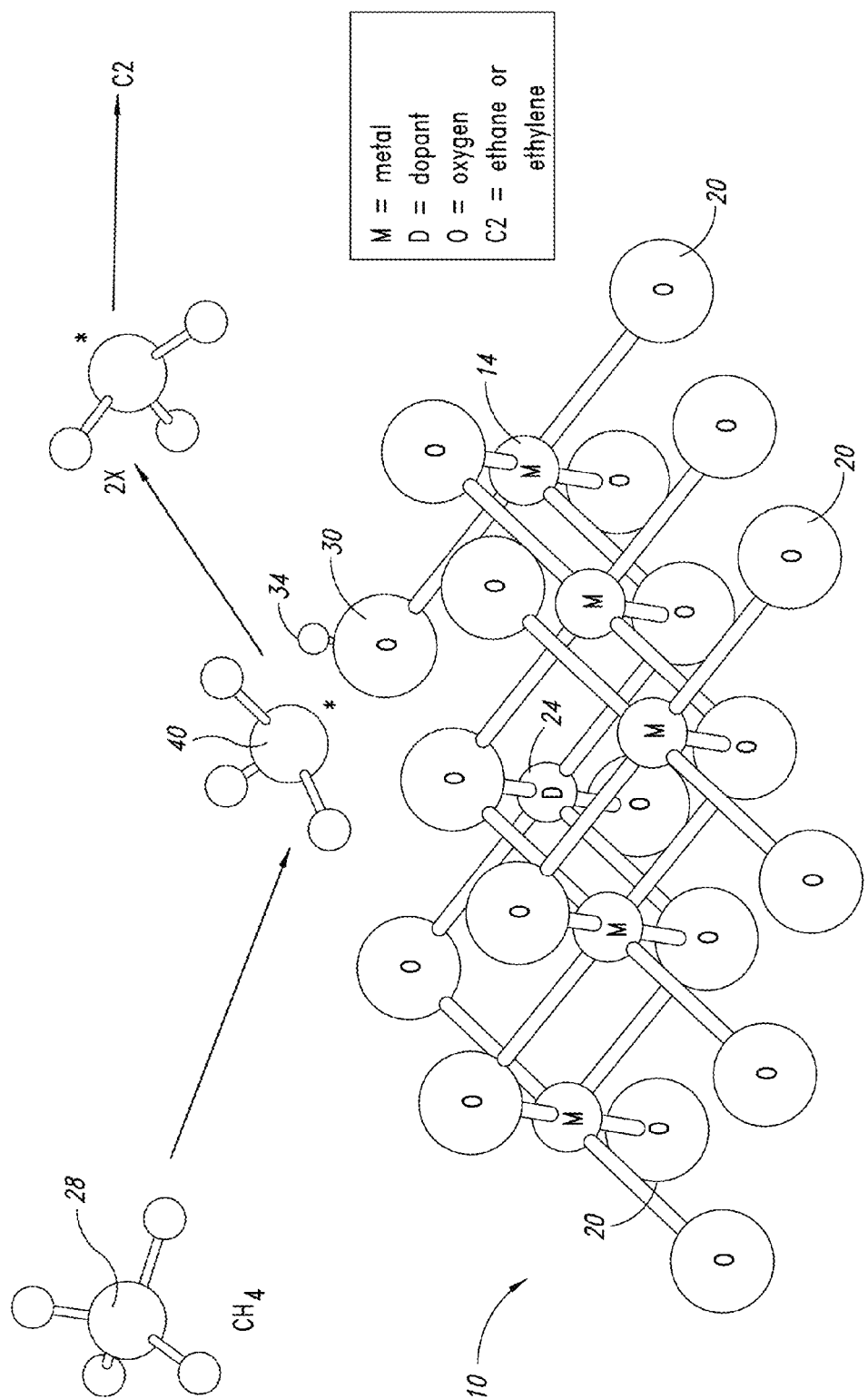
FIG. 1 schematically depicts a first part of an OCM reaction at the surface of a metal oxide catalyst.

As an example, FIG. 1 shows schematically the first part of an OCM reaction that takes place on the surface of a metal oxide catalyst 10 which is followed by methyl radical coupling in the gas phase. A crystal lattice structure of metal atoms 14 and oxygen atoms 20 are shown, with an optional dopant 24 incorporated into the lattice structure. In this reaction, a methane molecule 28 comes into contact with an active site (e.g., surface oxygen 30) and becomes activated when a hydrogen atom 34 dissociates from the methane molecule 28. As a result, a methyl radical 40 is generated on or near the catalytic surface. Two methyl radicals thus generated can couple in the gas phase to create ethane and/or ethylene, which are collectively referred to as the "C2" coupling products.

It is generally recognized that the catalytic properties of a catalyst strongly correlate to its surface morphology. Typically, the surface morphology can be defined by geometric parameters such as: (1) the number of surface atoms (e.g., the surface oxygen of FIG. 1) that coordinate to the reactant; and (2) the degree of coordinative unsaturation of the surface atoms, which is the coordination number of the surface atoms with their neighboring atoms. For example, the reactivity of a surface atom decreases with decreasing coordinative unsaturation. For example, for the dense surfaces of a face-centered crystal, a surface atom with 9 surface atom neighbors will have a different reactivity than one with 8 neighbors. Additional surface characteristics that may contribute to the catalytic properties include, for example, crystal dimensions, lattice distortion, surface reconstructions, defects, grain boundaries, and the like. See, e.g., Van Santen R. A. et al *New Trends in Materials Chemistry* 345-363 (1997).

Catalysts in nano-size dimensions have substantially increased surface areas compared to their counterpart bulk materials. The catalytic properties are expected to be enhanced as more surface active sites are exposed to the reactants. Typically in traditional preparations, a top-down approach (e.g., milling) is adopted to reduce the size of the bulk material. However, the surface morphologies of such catalysts remain largely the same as those of the parent bulk material.

Various embodiments described herein are directed to nanowires with controllable or tunable surface morphologies. In particular, nanowires synthesized by a "bottom up" approach, by which inorganic polycrystalline nanowires are nucleated from solution phase in the presence of a template, e.g., a linear or anisotropic shaped biological template. By varying the synthetic conditions, nanowires having different compositions and/or different surface morphologies are generated.

In contrast to a bulk catalyst of a given elemental composition, which is likely to have a particular corresponding surface morphology, diverse nanowires with different surface morphologies can be generated despite having the same elemental composition. In this way, morphologically diverse nanowires can be created and screened according to their catalytic activity and performance parameters in any given catalytic reaction. Advantageously, the nanowires disclosed herein and methods of producing the same have general applicability to a wide variety of heterogeneous catalyses, including without limitation: oxidative coupling of methane (e.g., FIG. 1), oxidative dehydrogenation of alkanes to their corresponding alkenes, selective oxidation of alkanes to alkenes and alkynes, oxidation of carbon monoxide, dry reforming of methane, selective oxidation of aromatics, Fischer-Tropsch reaction, hydrocarbon cracking and the like.

Figure 2:
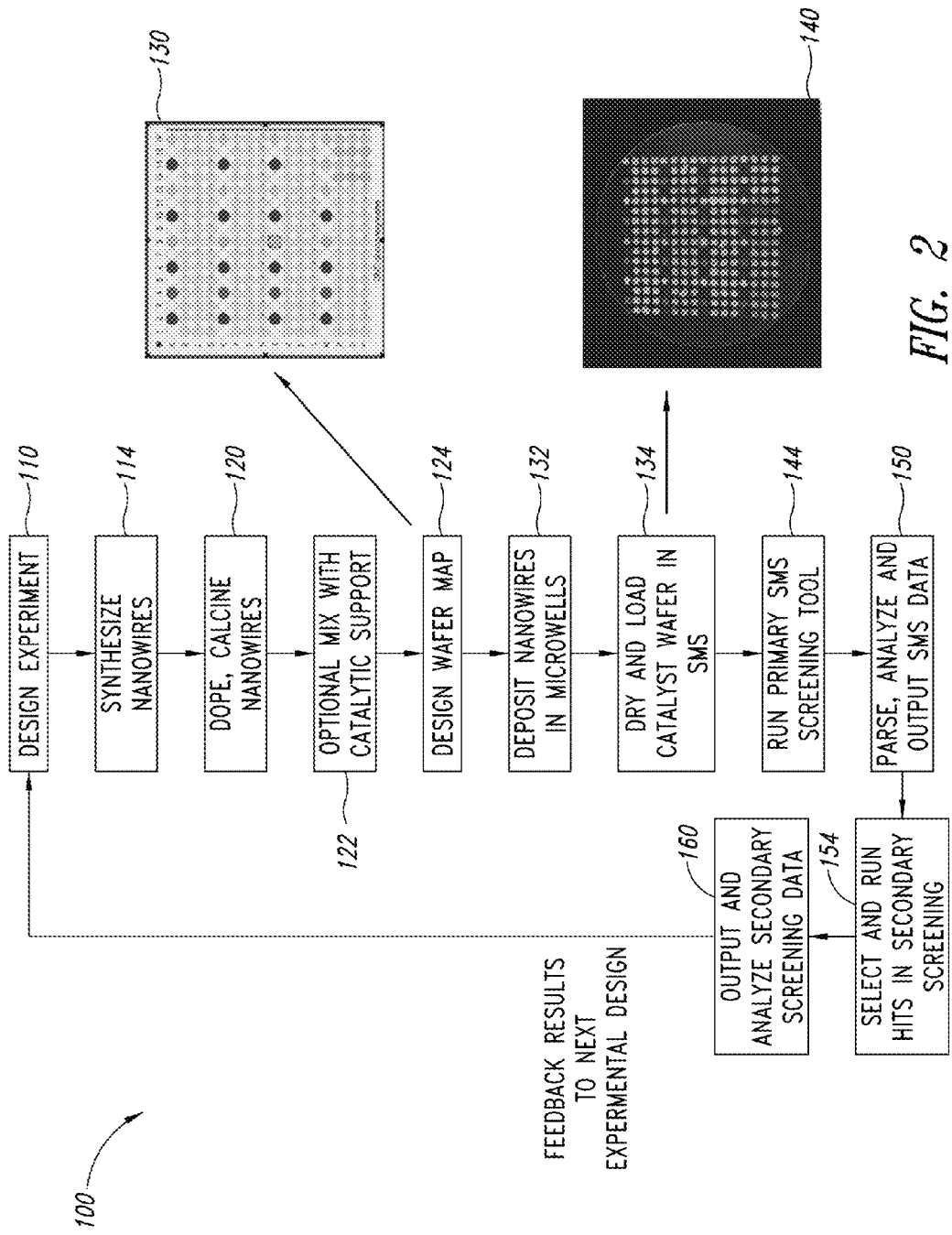
FIG. 2 shows a high throughput work flow for synthetically generating and testing libraries of nanowires.

FIG. 2 schematically shows a high throughput work flow for synthetically generating libraries of morphologically or compositionally diverse nanowires and screening for their catalytic properties. An initial phase of the work flow involves a primary screening, which is designed to broadly and efficiently screen a large and diverse set of nanowires that logically could perform the desired catalytic transformation. For example, certain doped bulk metal oxides (e.g., Li/MgO and Sr/La$_2$O$_3$) are known catalysts for the OCM reaction. Therefore, nanowires of various metal oxide compositions and/or surface morphologies can be prepared and evaluated for their catalytic performances in an OCM reaction.

More specifically, the work flow 100 begins with designing synthetic experiments based on solution phase template formations (block 110). The synthesis, subsequent treatments and screenings can be manual or automated. As will be discussed in more detail herein, by varying the synthetic conditions, nanowires can be prepared with various surface morphologies and/or compositions in respective microwells (block 114). The nanowires are subsequently calcined and then optionally doped (block 120). Optionally, the doped and calcined nanowires are further mixed with a catalyst support (block 122). Beyond the optional support step, all subsequent steps are carried out in a "wafer" format, in which nanowire catalysts are deposited in a quartz wafer that has been etched to create an ordered array of microwells. Each microwell is a self-contained reactor, in which independently variable processing conditions can be designed to include, without limitation, respective choices of elemental compositions, catalyst support, reaction precursors, templates, reaction durations, pH values, temperatures, ratio between reactants, gas flows, and calcining conditions (block 124). Due to design constraints of some wafers, in some embodiments calcining and other temperature variables are identical in all microwells. A wafer map 130 can be created to correlate the processing conditions to the nanowire in each microwell. A library of diverse nanowires can be generated in which each library member corresponds to a particular set of processing conditions and corresponding compositional and/or morphological characteristics.

Nanowires obtained under various synthetic conditions are thereafter deposited in respective microwells of a wafer (140) for evaluating their respective catalytic properties in a given reaction (blocks 132 and 134). The catalytic performance of each library member can be screened serially by several known primary screening technologies, including scanning mass spectroscopy (SMS) (Symyx Technologies Inc., Santa Clara, Calif.). The screening process is fully automated, and the SMS tool can determine if a nanowire is catalytically active or not, as well as its relative strength as a catalyst at a particular temperature. Typically, the wafer is placed on a motion control stage capable of positioning a single well below a probe that flows the feed of the starting material over the nanowire surface and removes reaction products to a mass spectrometer and/or other detector technologies (blocks 134 and 140). The individual nanowire is heated to a preset reaction temperature, e.g., using a CO$_2$ IR laser from the backside of the quartz wafer and an IR camera to monitor temperature and a preset mixture of reactant gases. The SMS tool collects data with regard to the consumption of the reactant(s) and the generation of the product(s) of the catalytic reaction in each well (block 144), and at each temperature and flow rate.

The SMS data obtained as described above provide information on relative catalytic properties among all the library members (block 150). In order to obtain more quantitative data on the catalytic properties of the nanowires, possible hits that meet certain criteria are subjected to a secondary screening (block 154). Typically, secondary screening technologies include a single, or alternatively multiple channel fixed-bed or fluidized bed reactors (as described in more detail herein). In parallel reactor systems or multi-channel fixed-bed reactor system, a single feed system supplies reactants to a set of flow restrictors. The flow restrictors divide the flows evenly among parallel reactors. Care is taken to achieve uniform reaction temperature between the reactors such that the various nanowires can be differentiated solely based on their catalytic performances. The secondary screening allows for accurate determination of catalytic properties such as selectivity, yield and conversion (block 160). These results serve as a feedback for designing further nanowire libraries.

Figure 10:
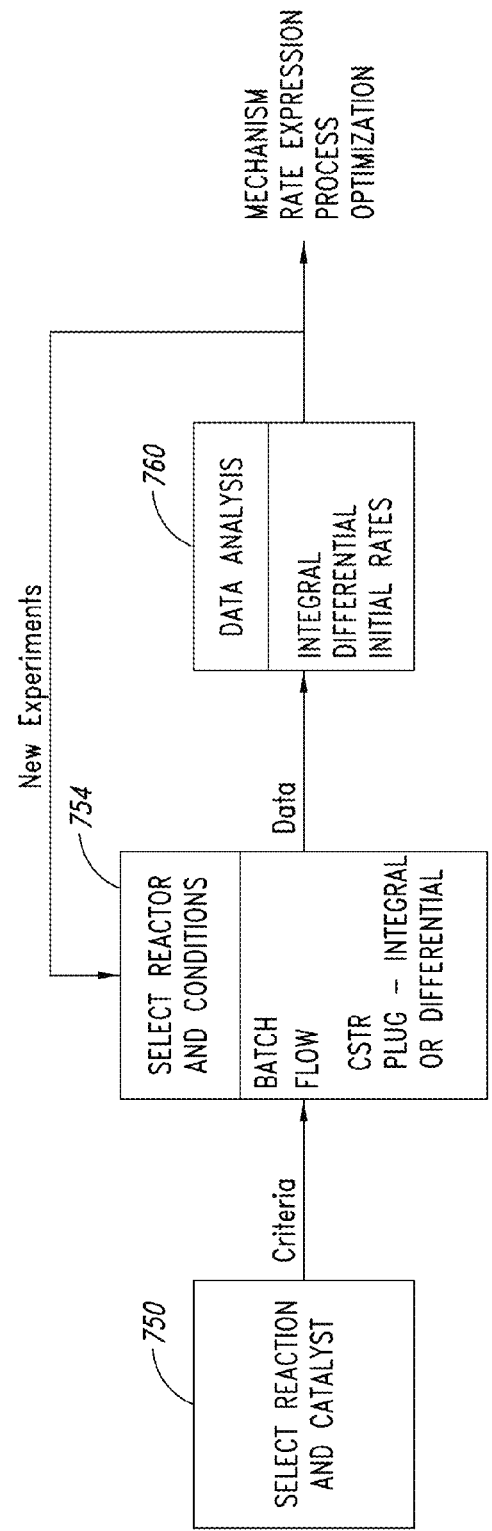
FIG. 10 is a flow chart for data collection and processing in evaluating catalytic performance.

Secondary screening is also schematically depicted in FIG. 10, which depicts a flow chart for data collection and processing in evaluating catalytic performance of catalysts according to the invention. Additional description of SMS tools in a combinatorial approach for discovering catalysts can be found in, e.g., Bergh, S. et al. *Topics in Catalysts* 23:1-4, 2003.

Thus, in accordance with various embodiments described herein, compositional and morphologically diverse nanowires can be rationally synthesized to meet catalytic performance criteria. These and other aspects of the present disclosure are described in more detail below.

DEFINITIONS

As used herein, and unless the context dictates otherwise, the following terms have the meanings as specified below.

"Catalyst" means a substance that alters the rate of a chemical reaction. A catalyst may either increase the chemical reaction rate (i.e. a "positive catalyst") or decrease the reaction rate (i.e. a "negative catalyst"). Catalysts participate in a reaction in a cyclic fashion such that the catalyst is cyclically regenerated. "Catalytic" means having the properties of a catalyst.

"Nanoparticle" means a particle having at least one diameter on the order of nanometers (e.g. between about 1 and 100 nanometers).

"Nanowire" means a nanowire structure having at least one diameter on the order of nanometers (e.g. between about 1 and 100 nanometers) and an aspect ratio greater than 10:1. The "aspect ratio" of a nanowire is the ratio of the actual length (L) of the nanowire to the diameter (D) of the nanowire. Aspect ratio is expressed as L:D.

"Polycrystalline nanowire" means a nanowire having multiple crystal domains. Polycrystalline nanowires generally have different morphologies (e.g. bent vs. straight) as compared to the corresponding "single-crystalline" nanowires.

"Effective length" of a nanowire means the shortest distance between the two distal ends of a nanowire as measured by transmission electron microscopy (TEM) in bright field mode at 5 keV. "Average effective length" refers to the average of the effective lengths of individual nanowires within a plurality of nanowires.

"Actual length" of a nanowire means the distance between the two distal ends of a nanowire as traced through the backbone of the nanowire as measured by TEM in bright field mode at 5 keV. "Average actual length" refers to the average of the actual lengths of individual nanowires within a plurality of nanowires.

The "diameter" of a nanowire is measured in an axis perpendicular to the axis of the nanowire's actual length (i.e. perpendicular to the nanowires backbone). The diameter of a nanowire will vary from narrow to wide as measured at different points along the nanowire backbone. As used herein, the diameter of a nanowire is the most prevalent (i.e. the mode) diameter.

The "ratio of effective length to actual length" is determined by dividing the effective length by the actual length. A nanowire having a "bent morphology" will have a ratio of effective length to actual length of less than one as described in more detail herein. A straight nanowire will have a ratio of effective length to actual length equal to one as described in more detail herein.

"Inorganic" means a substance comprising a metal element or semi-metal element. In certain embodiments, inorganic refers to a substance comprising a metal element. An inorganic compound can contain one or more metals in its elemental state, or more typically, a compound formed by a metal ion ($M^{n+}$, wherein n 1, 2, 3, 4, 5, 6 or 7) and an anion ($X^{m-}$, m is 1, 2, 3 or 4), which balance and neutralize the positive charges of the metal ion through electrostatic interactions. Non-limiting examples of inorganic compounds include oxides, hydroxides, halides, nitrates, sulfates, carbonates, phosphates, acetates, oxalates, and combinations thereof, of metal elements. Other non-limiting examples of inorganic compounds include $Li_2CO_3$, $Li_2PO_4$, $LiOH$, $Li_2O$, $LiCl$, $LiBr$, $LiI$, $Li_2C_2O_4$, $Li_2SO_4$, $Na_2CO_3$, $Na_2PO_4$, $NaOH$, $Na_2O$, $NaCl$, $NaBr$, $NaI$, $Na_2C_2O_4$, $Na_2SO_4$, $K_2CO_3$, $K_2PO_4$, $KOH$, $K_2O$, $KCl$, $KBr$, $K_1$, $K_2C_2O_4$, $K_2SO_4$, $Cs_2CO_3$, $CsPO_4$, $CsOH$, $Cs_2O$, $CsCl$, $CsBr$, $CsI$, $CsC_2O_4$, $CsSO_4$, $Be(OH)_2$, $BeCO_3$, $BePO_4$, $BeO$, $BeCl_2$, $BeBr_2$, $BeI_2$, $BeC_2O_4$. $BeSO_4$, $Mg(OH)_2$, $MgCO_3$, $MgPO_4$, $MgO$, $MgCl_2$, $MgBr_2$, $MgI_2$, $MgC_2O_4$. $MgSO_4$, $Ca(OH)_2$, $CaO$, $CaCO_3$, $CaPO_4$, $CaCl_2$, $CaBr_2$, $CaI_2$, $Ca(OH)_2$, $CaC_2O_4$, $CaSO_4$, $Y_2O_3$, $Y_2(CO_3)_3$, $Y_2(PO_4)_3$, $Y(OH)_3$, $YCl_3$, $YBr_3$, $YI_3$, $Y_2(C_2O_4)_3$, $Y_2(SO_4)_3$, $Zr(OH)_4$, $Zr(CO_3)_2$, $Zr(PO_4)_2$, $ZrO(OH)_2$, $ZrO2$, $ZrCl_4$, $ZrBr_4$, $ZrI_4$, $Zr(C_2O_4)_2$, $Zr(SO_4)_2$, $Ti(OH)_4$, $TiO(OH)_2$, $Ti(CO_3)_2$, $Ti(PO_4)_2$, $TiO2$, $TiCl_4$, $TiBr_4$, $TiI_4$, $Ti(C_2O_4)_2$, $Ti(SO_4)_2$, $BaO$, $Ba(OH)_2$, $BaCO_3$, $BaPO_4$, $BaCl_2$, $BaBr_2$, $BaI_2$, $BaC_2O_4$, $BaSO_4$, $La(OH)_3$, $La_2(CO_3)_3$, $La_2(PO_4)_3$, $La_2O_3$, $LaCl_3$, $LaBr_3$, $LaI_3$, $La_2(C_2O_4)_3$, $La_2(SO_4)_3$, $Ce(OH)_4$, $Ce(CO_3)_2$, $Ce(PO_4)_2$, $CeO_2$, $Ce_2O_3$, $CeCl_4$, $CeBr_4$, $CeI_4$, $Ce(C_2O_4)_2$, $Ce(SO_4)_2$, $ThO_2$, $Th(CO_3)_2$, $Th(PO_4)_2$, $ThCl_4$, $ThBr_4$, $ThI_4$, $Th(OH)_4$, $Th(C_2O_4)_2$, $Th(SO_4)_2$, $Sr(OH)_2$, $SrCO_3$, $SrPO_4$, $SrO$, $SrCl_2$, $SrBr_2$, $SrI_2$, $SrC_2O_4$, $SrSO_4$, $Sm_2O_3$, $Sm_2(CO_3)_3$, $Sm_2(PO_4)_3$, $SmCl_3$, $SmBr_3$, $SmI_3$, $Sm(OH)_3$, $Sm_2(CO_3)_3$, $Sm_2(OC_2O_3)_3$, $Sm_2(SO_4)_3$, $LiCa_2Bi_3O_4Cl_6$, $Na_2WO_4$, K/Sr-$CoO_3$, K/Na/$SrCoO_3$, Li/$SrCoO_3$, $SrCoO_3$, molybdenum oxides, molybdenum hydroxides, molybdenum carbonates, molybdenum phosphates, molybdenum chlorides, molybdenum bromides, molybdenum iodides, molybdenum oxalates, molybdenum sulfates, manganese oxides, manganese chlorides, manganese bromides, manganese iodides, manganese hydroxides, manganese oxalates, manganese sulfates, manganese tugstates, vanadium oxides, vanadium carbonates, vanadium phosphates, vanadium chlorides, vanadium bromides, vanadium iodides, vanadium hydroxides, vanadium oxalates, vanadium sulfates, tungsten oxides, tungsten carbonates, tungsten phosphates, tungsten chlorides, tungsten bromides, tungsten iodides, tungsten hydroxides, tungsten oxalates, tungsten sulfates, neodymium oxides, neodymium carbonates, neodymium phosphates, neodymium chlorides, neodymium bromides, neodymium iodides, neodymium hydroxides, neodymium oxalates, neodymium sulfates, europium oxides, europium carbonates, europium phosphates, europium chlorides, europium bromides, europium iodides, europium hydroxides, europium oxalates, europium sulfates rhenium oxides, rhenium carbonates, rhenium phosphates, rhenium chlorides, rhenium bromides, rhenium iodides, rhenium hydroxides, rhenium oxalates, rhenium sulfates, chromium oxides, chromium carbonates, chromium phosphates, chromium chlorides, chromium bromides, chromium iodides, chromium hydroxides, chromium oxalates, chromium sulfates, potassium molybdenum oxides and the like.

"Salt" means a compound comprising negative and positive ions. Salts are generally comprised of cations and counter ions. Under appropriate conditions, e.g., the solution also comprises a template, the metal ion ($M^{n+}$) and the anion ($X^{m-}$) bind to the template to induce nucleation and growth of a nanowire of $M_mX_n$ on the template. "Anion precursor" thus is a compound that comprises an anion and a cationic counter ion, which allows the anion ($X^{m-}$) to dissociate from the cationic counter ion in a solution. Specific examples of the metal salt and anion precursors are described in further detail herein.

"Oxide" refers to a metal compound comprising oxygen. Examples of oxides include, but are not limited to, metal oxides ($M_xO_y$), metal oxyhalides ($M_xO_yX_z$), metal oxynitrates ($M_xO_y(NO_3)_z$), metal phosphates ($M_x(PO_4)_y$), metal oxycarbonates ($M_xO_y(CO_3)_z$), metal carbonates, metal oxyhydroxides ($M_xO_y(OH)_z$) and the like, wherein X is independently, at each occurrence, fluoro, chloro, bromo or iodo, and x, y and z are numbers from 1 to 100.

"Mixed oxide" or "mixed metal oxide" refers to a compound comprising two or more oxidized metals and oxygen (i.e., $M1_xM2_yO_z$, wherein M1 and M2 are the same or different metal elements, O is oxygen and x, y and z are numbers from 1 to 100). A mixed oxide may comprise metal elements in various oxidation states and may comprise more than one type of metal element. For example, a mixed oxide of manganese and magnesium comprises oxidized forms of magnesium and manganese. Each individual manganese and magnesium atom may or may not have the same oxidation state. Mixed oxides comprising 2, 3, 4, 5, 6 or more metal elements can be represented in an analogous manner. Mixed oxides also include oxy-hydroxides (e.g., $M_xO_yOH_z$, wherein M is a metal element, O is oxygen, x, y and z are numbers from 1 to 100 and OH is hydroxy). Mixed oxides may be represented herein as M1-M2, wherein M1 and M2 are each independently a metal element.

"Rare earth oxide" refers to an oxide of an element from group 3, lanthanides or actinides. Rare earth oxides include mixed oxides containing a rare earth element. Examples of rare earth oxides include, but are not limited to, $La_2O_3$, $Nd_2O_3$, $Yb_2O_3$, $Eu_2O_3$, $Sm_2O_3$, $Y_2O_3$, $Ce_2O_3$, $Pr_2O_3$, $Ln1_{4-x}Ln2_xO_6$, $La_{4-x}Ln1_xO_6$, $La_{4-x}Nd_xO_6$, wherein Ln1 and Ln2 are each independently a lanthanide element, wherein Ln1 and Ln2 are not the same and x is a number ranging from greater than 0 to less than 4, $La_3NdO_6$, $LaNd_3O_6$, $La_{1.5}Nd_{2.5}O_6$, $La_{2.5}Nd_{1.5}O_6$, $La_{3.2}Nd_{0.8}O_6$, $La_{3.5}Nd_{0.5}O_6$, $La_{3.8}Nd_{0.2}O_6$, Y—La, Zr—La, Pr—La and Ce—La.

"Crystal domain" means a continuous region over which a substance is crystalline.

"Single-crystalline nanowires" means a nanowire having a single crystal domain.

"Template" is any synthetic and/or natural material that provides at least one nucleation site where ions can nucleate and grow to form nanoparticles. In certain embodiments, the templates can be a multi-molecular biological structure comprising one or more biomolecules. Typically, the biological template comprises multiple binding sites that recognize certain ions and allow for the nucleation and growth of the same. Non-limiting examples of biological templates include bacteriophages, amyloid fibers, viruses and capsids.

"Biomolecule" refers to any organic molecule of a biological origin. Biomolecule includes modified and/or degraded molecules of a biological origin. Non-limiting examples of biomolecules include peptides, proteins (including cytokines, growth factors, etc.), nucleic acids, polynucleotides, amino acids, antibodies, enzymes, and single-stranded or double-stranded nucleic acid, including any modified and/or degraded forms thereof.

"Amyloid fibers" refers to proteinaceous filaments of about 1-25 nm in diameter.

A "bacteriophage" or "phage" is any one of a number of viruses that infect bacteria. Typically, bacteriophages consist of an outer protein coat or "major coat protein" enclosing genetic material. A non-limiting example of a bacteriophage is the M13 bacteriophage. Non-limiting examples of bacteriophage coat proteins include the pIII, pV, pVIII, etc. protein as described in more detail below.

A "capsid" is the protein shell of a virus. A capsid comprises several oligomeric structural subunits made of proteins.

"Nucleation" refers to the process of forming a solid from solubilized particles, for example forming a nanowire in situ by converting a soluble precursor (e.g. metal and hydroxide ions) into nanocrystals in the presence of a template.

"Nucleation site" refers to a site on a template, for example a bacteriophage, where nucleation of ions may occur. Nucleation sites include, for example, amino acids having carboxylic acid (—COOH), amino (—$NH_3^+$ or —$NH_2$), hydroxyl (—OH), and/or thiol (—SH) functional groups.

A "peptide" refers to two or more amino acids joined by peptide (amide) bonds. The amino-acid building blocks (subunits) include naturally occurring α-amino acids and/or unnatural amino acids, such asp-amino acids and homoamino acids. An unnatural amino acid can be a chemically modified form of a natural amino acid. Peptides can be comprised of 2 or more, 5 or more, 10 or more, 20 or more, or 40 or more amino acids.

"Peptide sequence" refers to the sequence of amino acids within a peptide or protein.

"Protein" refers to a natural or engineered macromolecule having a primary structure characterized by peptide sequences. In addition to the primary structure, proteins also exhibit secondary and tertiary structures that determine their final geometric shapes.

"Polynucleotide" means a molecule comprised of two or more nucleotides connected via an internucleotide bond (e.g. a phosphate bond). Polynucleotides may be comprised of both ribose and/or deoxy ribose nucleotides. Examples of nucleotides include guanosine, adenosine, thiamine, and cytosine, as well as unnatural analogues thereof.

"Nucleic acid" means a macromolecule comprised of polynucleotides. Nucleic acids may be both single stranded and double stranded, and, like proteins, can exhibit secondary and tertiary structures that determine their final geometric shapes.

"Nucleic acid sequence" of "nucleotide sequence" refers to the sequence of nucleotides within a polynucleotide or nucleic acid.

"Anisotropic" means having an aspect ratio greater than one.

"Anisotropic biomolecule" means a biomolecule, as defined herein, having an aspect ratio greater than 1. Non-limiting examples of anisotropic biomolecules include bacteriophages, amyloid fibers, and capsids.

"Turnover number" is a measure of the number of reactant molecules a catalyst can convert to product molecules per unit time.

"Active" or "catalytically active" refers to a catalyst which has substantial activity in the reaction of interest. For example, in some embodiments a catalyst which is OCM active (i.e., has activity in the OCM reaction) has a C2 selectivity of 5% or more and/or a methane conversion of 5% or more when the catalyst is employed as a heterogenous catalyst in the oxidative coupling of methane at a temperature of 750° C. or less.

"Inactive" or "catalytically inactive" refers to a catalyst which does not have substantial activity in the reaction of interest. For example, in some embodiments a catalyst which is OCM inactive has a C2 selectivity of less than 5% and/or a methane conversion of less than 5% when the catalyst is employed as a heterogenous catalyst in the oxidative coupling of methane at a temperature of 750° C. or less.

"Activation temperature" refers to the temperature at which a catalyst becomes catalytically active.

"OCM activity" refers to the ability of a catalyst to catalyse the OCM reaction.

A catalyst having "high OCM activity" refers to a catalyst having a C2 selectivity of 50% or more and/or a methane conversion of 20% or more when the catalyst is employed as a heterogenous catalyst in the oxidative coupling of methane at a specific temperature, for example 750° C. or less.

A catalyst having "moderate OCM activity" refers to a catalyst having a C2 selectivity of about 20-50% and/or a methane conversion of about 10-20% or more when the catalyst is employed as a heterogenous catalyst in the oxidative coupling of methane at a temperature of 750° C. or less.

A catalyst having "low OCM activity" refers to a catalyst having a C2 selectivity of about 5-20% and/or a methane conversion of about 5-10% or more when the catalyst is employed as a heterogenous catalyst in the oxidative coupling of methane at a temperature of 750° C. or less.

"Dopant" or "doping agent" is an impurity added to or incorporated within a catalyst to optimize catalytic performance (e.g. increase or decrease catalytic activity). As compared to the undoped catalyst, a doped catalyst may increase or decrease the selectivity, conversion, and/or yield of a reaction catalyzed by the catalyst.

"Atomic percent" (at % or at/at) or "atomic ratio" when used in the context of nanowire dopants refers to the ratio of the total number of dopant atoms to the total number of metal atoms in the nanowire. For example, the atomic percent of dopant in a lithium doped $Mg_6MnO_8$ nanowire is determined by calculating the total number of lithium atoms and dividing by the sum of the total number of magnesium and manganese atoms and multiplying by 100 (i.e., atomic percent of dopant=[Li atoms/(Mg atoms+Mn atoms)]×100).

"Weight percent" (wt/wt)" when used in the context of nanowire dopants refers to the ratio of the total weight of dopant to the total combined weight of the dopant and the nanowire. For example, the weight percent of dopant in a lithium doped $Mg_6MnO_8$ nanowire is determined by calculating the total weight of lithium and dividing by the sum of the total combined weight of lithium and $Mg_6MnO_8$ and multiplying by 100 (i.e., weight percent of dopant=[Li weight/(Li weight+$Mg_6MnO_8$ weight)]×100).

An "extrudate" refers to a material (e.g., catalytic material) prepared by forcing a semisolid material comprising a catalyst through a die or opening of appropriate shape. Extrudates can be prepared in a variety of shapes and structures by common means known in the art.

A "pellet" or "pressed pellet" refers to a material (e.g., catalytic material) prepared by applying pressure to (i.e., compressing) a material comprising a catalyst into a desired shape. Pellets having various dimensions and shapes can be prepared according to common techniques in the art.

"Monolith" or "monolith support" is generally a structure formed from a single structural unit preferably having passages disposed through it in either an irregular or regular pattern with porous or non-porous walls separating adjacent passages. Examples of such monolithic supports include, e.g., ceramic or metal foam-like or porous structures. The single structural unit may be used in place of or in addition to conventional particulate or granular catalysts (e.g., pellets or extrudates). Examples of such irregular patterned monolith substrates include filters used for molten metals. Monoliths generally have a porous fraction ranging from about 60% to 90% and a flow resistance substantially less than the flow resistance of a packed bed of similar volume (e.g., about 10% tp 30% of the flow resistance of a packed bed of similar volume). Examples of regular patterned substrates include monolith honeycomb supports used for purifying exhausts from motor vehicles and used in various chemical processes and ceramic foam structures having irregular passages. Many types of monolith support structures made from conventional refractory or ceramic materials such as alumina, zirconia, yttria, silicon carbide, and mixtures thereof, are well known and commercially available from, among others, Corning, lac.; Vesuvius Hi-Tech Ceramics, Inc.; and Porvair Advanced Materials, Inc. and SiCAT (Sicatalyst.com). Monoliths include foams, honeycombs, foils, mesh, guaze and the like.

"Group 1" elements include lithium (Li), sodium (Na), potassium (K), rubidium (Rb), cesium (Cs), and francium (Fr).

"Group 2" elements include beryllium (Be), magnesium (Mg), calcium (Ca), strontium (Sr), barium (Ba), and radium (Ra).

"Group 3" elements include scandium (Sc) and yttrium (Y).

"Group 4" elements include titanium (Ti), zirconium (Zr), halfnium (Hf), and rutherfordium (Rf).

"Group 5" elements include vanadium (V), niobium (Nb), tantalum (Ta), and dubnium (Db).

"Group 6" elements include chromium (Cr), molybdenum (Mo), tungsten (W), and seaborgium (Sg).

"Group 7" elements include manganese (Mn), technetium (Tc), rhenium (Re), and bohrium (Bh).

"Group 8" elements include iron (Fe), ruthenium (Ru), osmium (Os), and hassium (Hs).

"Group 9" elements include cobalt (Co), rhodium (Rh), iridium (Ir), and meitnerium (Mt).

"Group 10" elements include nickel (Ni), palladium (Pd), platinum (Pt) and darmistadium (Ds).

"Group 11" elements include copper (Cu), silver (Ag), gold (Au), and roentgenium (Rg).

"Group 12" elements include zinc (Zn), cadmium (Cd), mercury (Hg), and copernicium (Cn).

"Lanthanides" include lanthanum (La), cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), yitterbium (Yb), and lutetium (Lu).

"Actinides" include actinium (Ac), thorium (Th), protactinium (Pa), uranium (U), neptunium (Np), plutonium (Pu), americium (Am), curium (Cm), berklelium (Bk), californium (Cf), einsteinium (Es), fermium (Fm), mendelevium (Md), nobelium (No), and lawrencium (Lr).

"Rare earth" elements include Group 3, lanthanides and actinides.

"Metal element" or "metal" is any element, except hydrogen, selected from Groups 1 through 12, lanthanides, actinides, aluminum (Al), gallium (Ga), indium (In), tin (Sn), thallium (Tl), lead (Pb), and bismuth (Bi). Metal elements include metal elements in their elemental form as well as metal elements in an oxidized or reduced state, for example, when a metal element is combined with other elements in the form of compounds comprising metal elements. For example, metal elements can be in the form of hydrates, salts, oxides, as well as various polymorphs thereof, and the like.

"Semi-metal element" refers to an element selected from boron (B), silicon (Si), germanium (Ge), arsenic (As), antimony (Sb), tellurium (Te), and polonium (Po).

"Non-metal element" refers to an element selected from carbon (C), nitrogen (N), oxygen (O), fluorine (F), phosphorus (P), sulfur (S), chlorine (Cl), selenium (Se), bromine (Br), iodine (I), and astatine (At).

"C2" refers to a hydrocarbon (i.e., compound consisting of carbon and hydrogen atoms) having only two carbon atoms, for example ethane and ethylene. Similarily, "C3" refers to a hydrocarbon having only 3 carbon atoms, for example propane and propylene.

"Conversion" means the mole fraction (i.e., percent) of a reactant converted to a product or products.

"Selectivity" refers to the percent of converted reactant that went to a specified product, e.g., C2 selectivity is the % of converted methane that formed ethane and ethylene, C3 selectivity is the % of converted methane that formed propane and propylene, CO selectivity is the % of converted methane that formed CO.

"Yield" is a measure of (e.g. percent) of product obtained relative to the theoretical maximum product obtainable. Yield is calculated by dividing the amount of the obtained product in moles by the theoretical yield in moles. Percent yield is calculated by multiplying this value by 100. C2 yield is defined as the sum of the ethane and ethylene molar flow at the reactor outlet multiplied by two and divided by the inlet methane molar flow. C3 yield is defined as the sum of propane and propylene molar flow at the reactor outlet multiplied by three and divided by the inlet methane molar flow. C2+ yield is the sum of the C2 yield and C3 yield. Yield is also calculable by multiplying the methane conversion by the relevant selectivity, e.g. C2 yield is equal to the methane conversion times the C2 selectivity.

"Bulk catalyst" or "bulk material" means a catalyst prepared by traditional techniques, for example by milling or grinding large catalyst particles to obtain smaller/higher surface area catalyst particles. Bulk materials are prepared with minimal control over the size and/or morphology of the material.

"Alkane" means a straight chain or branched, noncyclic or cyclic, saturated aliphatic hydrocarbon. Alkanes include linear, branched and cyclic structures. Representative straight chain alkanes include methane, ethane, n-propane, n-butane, n-pentane, n-hexane, and the like; while branched alkanes include isopropane, sec-butane, isobutanel, tert-butane, isopentane, and the like. Representative cyclic alkanes include cyclopropane, cyclobutane, cyclopentane, cyclohexane, and the like. "Alkene" means a straight chain or branched, noncyclic or cyclic, unsaturated aliphatic hydrocarbon having at least one carbon-carbon double bond.

Alkenes include linear, branched and cyclic structures. Representative straight chain and branched alkenes include ethylene, propylene, 1-butene, 2-butene, isobutylene, 1-pentene, 2-pentene, 3-methyl-1-butene, 2-methyl-2-butene, 2,3-dimethyl-2-butene, and the like. Cyclic alkenes include cyclohexene and cyclopentene and the like.

"Alkyne" means a straight chain or branched, noncyclic or cyclic, unsaturated aliphatic hydrocarbon having at least one carbon-carbon triple bond. Alkynes include linear, branched and cyclic structures. Representative straight chain and branched alkynes include acetylene, propyne, 1-butyne, 2-butyne, 1-pentyne, 2-pentyne, 3-methyl-1-butyne, and the like. Representative cyclic alkynes include cycloheptyne and the like.

"Alkyl," "alkenyl" and "alkynyl" refers to an alkane, alkene or alkyne radical, respectively.

"Aromatic" means a carbocyclic moiety having a cyclic system of conjugated p orbitals forming a delocalized conjugated π system and a number of π electrons equal to $4n+2$ with $n=0, 1, 2, 3$, etc. Representative examples of aromatics include benzene and naphthalene and toluene. "Aryl" refers to an aromatic radical. Exemplary aryl groups include, but are not limited to, phenyl, napthyl and the like.

"Carbon-containing compounds" are compounds that comprise carbon. Non-limiting examples of carbon-containing compounds include hydrocarbons, CO and $CO_2$.

Nanowires

1. Structure/Physical Characteristics

Figure 3A:
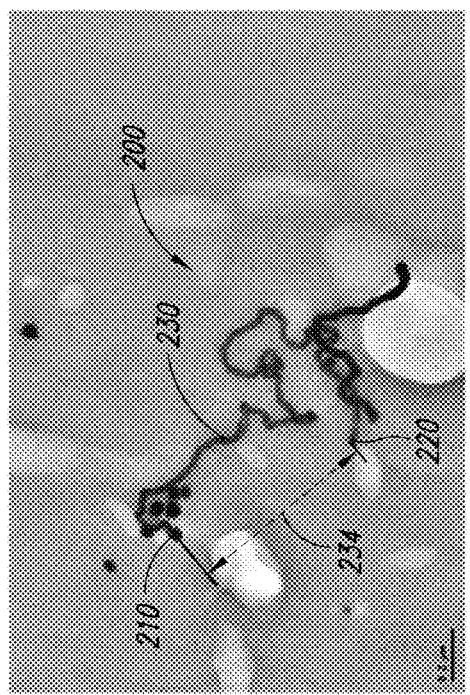
FIGS. 3A and 3B illustrate a nanowire in one embodiment.
Figure 3B:
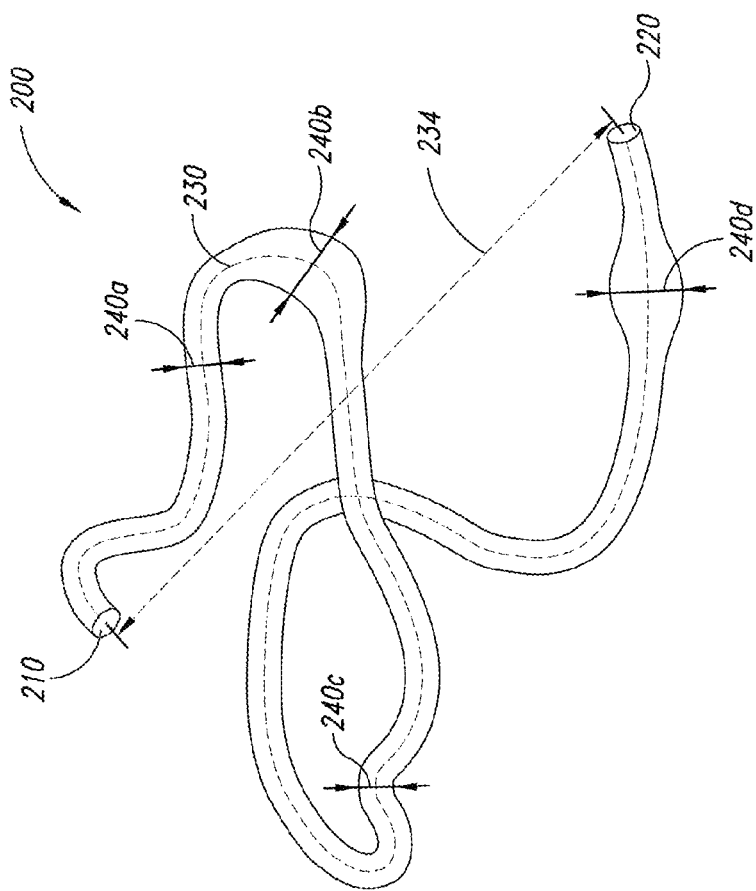

As noted above, disclosed herein are nanowires useful as catalysts. Catalytic nanowires, and methods for preparing the same, are also described in PCT Pub. No. 2011/149996 and U.S. application. Ser. No. 13/689,514, filed on Nov. 29, 2012 and entitled "Polymer Templated Nanowire Catalysts," the full disclosures of which are incorporated herein by reference in their entireties. FIG. 3A is a TEM image of a polycrystalline nanowire 200 having two distal ends 210 and 220. As shown, an actual length 230 essentially traces along the backbone of the nanowire 200, whereas an effective length 234 is the shortest distance between the two distal ends. The ratio of the effective length to the actual length is an indicator of the degrees of twists, bends and/or kinks in the general morphology of the nanowire. FIG. 3B is a schematic representation of the nanowire 200 of FIG. 3A. Typically, the nanowire is not uniform in its thickness or diameter. At any given location along the nanowire backbone, a diameter (240a, 240b, 240c, 240d) is the longest dimension of a cross section of the nanowire, i.e., is perpendicular to the axis of the nanowire backbone).

Figure 4A:
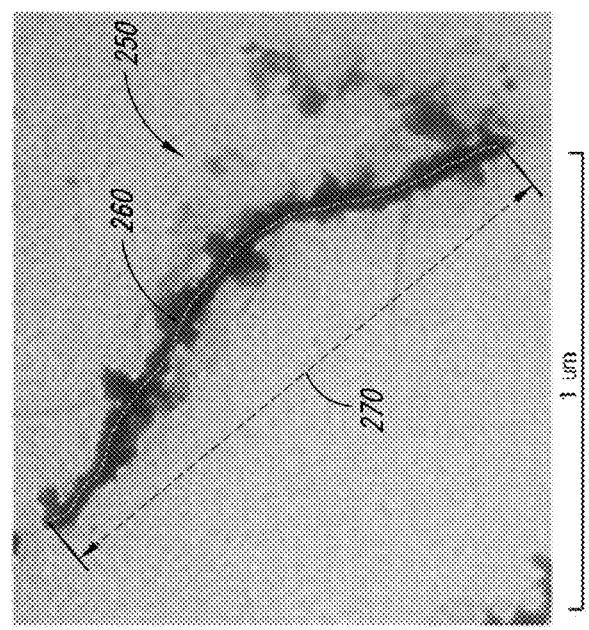
FIGS. 4A and 4B illustrate a nanowire in a different embodiment.
Figure 4B:
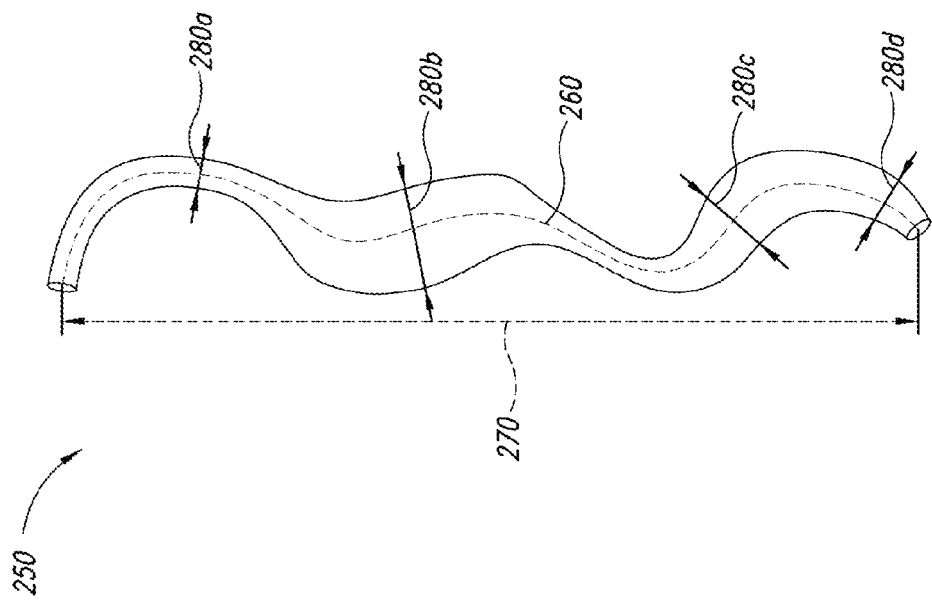

Compared to nanowire 200 of FIG. 3A, nanowire 250 of FIG. 4A has a different morphology and does not exhibit as many twists, bends and kinks, which suggests a different underlying crystal structure and different number of defects and/or stacking faults. As shown, for nanowire 250, the ratio of the effective length 270 and the actual length 260 is greater than the ratio of the effective length 234 and the actual length 240 of nanowire 200 of FIG. 3A. FIG. 4B is a schematic representation of the nanowire 250, which shows non-uniform diameters (280a, 280b, 280c and 280d).

As noted above, in some embodiments nanowires having a "bent" morphology (i.e. "bent nanowires") are provided. A "bent" morphology means that the bent nanowires comprise various twists, bends and/or kinks in their general morphology as illustrated generally in FIGS. 3A and 3B and discussed above. Bent nanowires have a ratio of effective length to actual length of less than one. Accordingly, in some embodiments the present disclosure provides nanowires having a ratio of effective length to actual length of less than one. In other embodiments, the nanowires have a ratio of effective length to actual length of between 0.99 and 0.01, between 0.9 and 0.1, between 0.8 and 0.2, between 0.7 and 0.3, or between 0.6 and 0.4. In other embodiments, the ratio of effective length to actual length is less than 0.99, less than 0.9, less than 0.8, less than 0.7, less than 0.6, less than 0.5, less than 0.4, less than 0.3, less than 0.2 or less than 0.1. In other embodiments, the ratio of effective length to actual length is less than 1.0 and more than 0.9, less than 1.0 and more than 0.8, less than 1.0 and more than 0.7, less than 1.0 and more than 0.6, less than 1.0 and more than 0.5, less than 1.0 and more than 0.4, less than 1.0 and more than 0.3, less than 1.0 and more than 0.2, or less than 1.0 and more than 0.1.

The ratio of effective length to actual length of a nanowire having a bent morphology may vary depending on the angle of observation. For example, one-skilled in the art will recognize that the same nanowire, when observed from different perspectives, can have a different effective length as determined by TEM. In addition, not all nanowires having a bent morphology will have the same ratio of effective length to actual length. Accordingly, in a population (i.e. plurality) of nanowires having a bent morphology, a range of ratios of effective length to actual length is expected. Although the ratio of effective length to actual length may vary from nanowire to nanowire, nanowires having a bent morphology will always have a ratio of effective length to actual length of less than one from any angle of observation.

In various embodiments, a substantially straight nanowire is provided. A substantially straight nanowire has a ratio of effective length to actual length equal to one. Accordingly, in some embodiments, the nanowires of the present disclosure have a ratio of effective length to actual length equal to one.

The actual lengths of the nanowires disclosed herein may vary. For example in some embodiments, the nanowires have an actual length of between 100 nm and 100 μm. In other embodiments, the nanowires have an actual length of between 100 nm and 10 μm. In other embodiments, the nanowires have an actual length of between 200 nm and 10 μm. In other embodiments, the nanowires have an actual length of between 500 nm and 5 μm. In other embodiments, the actual length is greater than 5 μm. In other embodiments, the nanowires have an actual length of between 800 nm and 1000 nm. In other further embodiments, the nanowires have an actual length of 900 nm. As noted below, the actual length of the nanowires may be determined by TEM, for example, in bright field mode at 5 keV.

The diameter of the nanowires may be different at different points along the nanowire backbone. However, the nanowires comprise a mode diameter (i.e. the most frequently occurring diameter). As used herein, the diameter of a nanowire refers to the mode diameter. In some embodiments, the nanowires have a diameter of between 1 nm and 10 μm, between 1 nm and 1 μm, between 1 nm and 500 nm, between 1 nm and 100 nm, between 7 nm and 100 nm, between 7 nm and 50 nm, between 7 nm and 25 nm, or between 7 nm and 15 nm. On other embodiments, the diameter is greater than 500 nm. As noted below, the diameter of the nanowires may be determined by TEM, for example, in bright field mode at 5 keV.

Various embodiments of the present disclosure provide nanowires having different aspect ratios. In some embodiments, the nanowires have an aspect ratio of greater than 10:1. In other embodiments, the nanowires have an aspect ratio greater than 20:1. In other embodiments, the nanowires have an aspect ratio greater than 50:1. In other embodiments, the nanowires have an aspect ratio greater than 100:1.

In some embodiments, the nanowires comprise a solid core while in other embodiments, the nanowires comprise a hollow core.

The morphology of a nanowire (including length, diameter, and other parameters) can be determined by transmission electron microscopy (TEM). Transmission electron microscopy (TEM) is a technique whereby a beam of electrons is transmitted through an ultra thin specimen, interacting with the specimen as it passes through. An image is formed from the interaction of the electrons transmitted through the specimen. The image is magnified and focused onto an imaging device, such as a fluorescent screen, on a layer of photographic film or detected by a sensor such as a CCD camera. TEM techniques are well known to those of skill in the art.

A TEM image of nanowires may be taken, for example, in bright field mode at 5 keV (e.g., as shown in FIGS. 3A and 4A).

The nanowires of the present disclosure can be further characterized by powder x-ray diffraction (XRD). XRD is a technique capable of revealing information about the crystallographic structure, chemical composition, and physical properties of materials, including nanowires. XRD is based on observing the diffracted intensity of an X-ray beam hitting a sample as a function of incident and diffraction angle, polarization, and wavelength or energy.

Crystal structure, composition, and phase, including the crystal domain size of the nanowires, can be determined by XRD. In some embodiments, the nanowires comprise a single crystal domain (i.e. single crystalline). In other embodiments, the nanowires comprise multiple crystal domains (i.e. polycrystalline). In some other embodiments, the average crystal domain of the nanowires is less than 100 nm, less than 50 nm, less than 30 nm, less than 20 nm, less than 10 nm, less than 5 nm, or less than 2 nm.

Figure 5B:
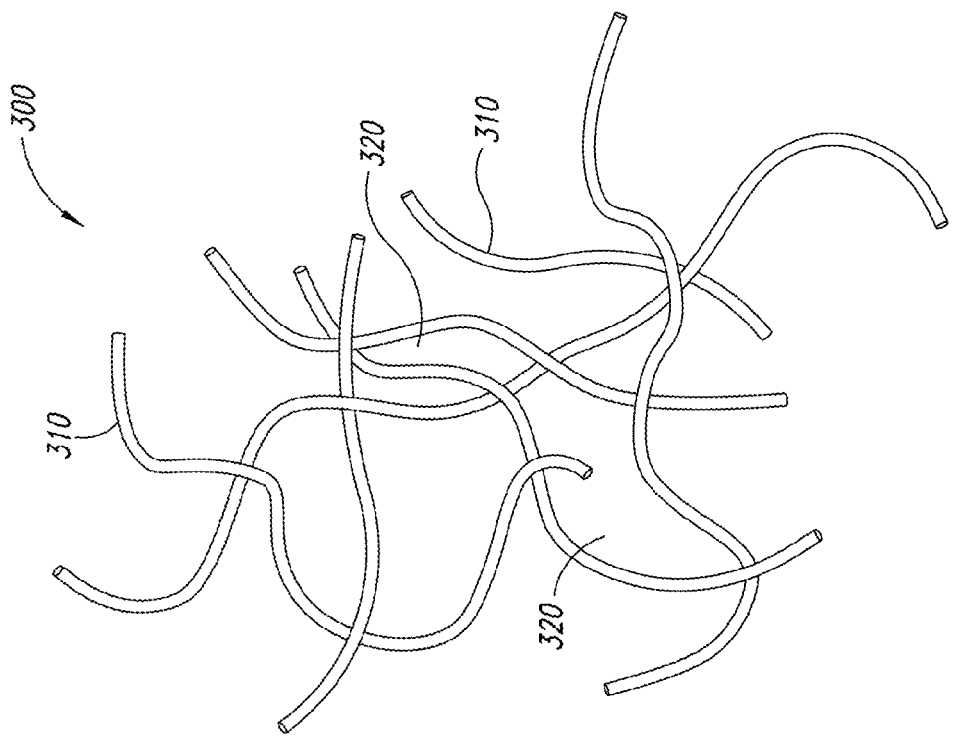
FIGS. 5A and 5B illustrate a plurality of nanowires.
Figure 5A:
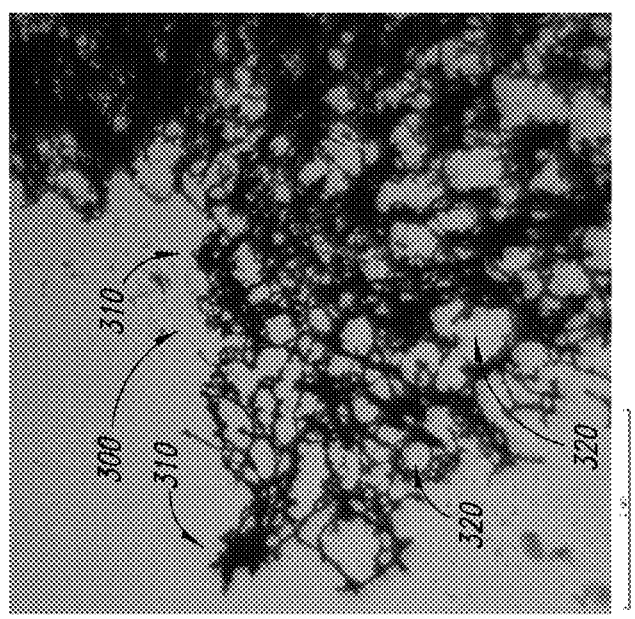

Typically, a catalytic material described herein comprises a plurality of nanowires. In certain embodiments, the plurality of nanowires form a mesh of randomly distributed and, to various degrees, interconnected nanowires. FIG. 5A is a TEM image of a nanowire mesh 300 comprising a plurality of nanowires 310 and a plurality of pores 320. FIG. 5B is a schematic representation of the nanowire mesh 300 of FIG. 5A.

The total surface area per gram of a nanowire or plurality of nanowires may have an effect on the catalytic performance. Pore size distribution may affect the nanowires catalytic performance as well. Surface area and pore size distribution of the nanowires or plurality of nanowires can be determined by BET (Brunauer, Emmett, Teller) measurements. BET techniques utilize nitrogen adsorption at various temperatures and partial pressures to determine the surface area and pore sizes of catalysts. BET techniques for determining surface area and pore size distribution are well known in the art.

In some embodiments the nanowires have a surface area of between 0.0001 and 3000 $m^2/g$, between 0.0001 and 2000 $m^2/g$, between 0.0001 and 1000 $m^2/g$, between 0.0001 and 500 $m^2/g$, between 0.0001 and 100 $m^2/g$, between 0.0001 and 50 $m^2/g$, between 0.0001 and 20 $m^2/g$, between 0.0001 and 10 $m^2/g$ or between 0.0001 and 5 $m^2/g$.

In some embodiments the nanowires have a surface area of between 0.001 and 3000 $m^2/g$, between 0.001 and 2000 $m^2/g$, between 0.001 and 1000 $m^2/g$, between 0.001 and 500 $m^2/g$, between 0.001 and 100 $m^2/g$, between 0.001 and 50 $m^2/g$, between 0.001 and 20 $m^2/g$, between 0.001 and 10 $m^2/g$ or between 0.001 and 5 $m^2/g$.

In some other embodiments the nanowires have a surface area of between 2000 and 3000 $m^2/g$, between 1000 and 2000 $m^2/g$, between 500 and 1000 $m^2/g$, between 100 and 500 $m^2/g$, between 10 and 100 $m^2/g$, between 5 and 50 $m^2/g$, between 2 and 20 $m^2/g$ or between 0.0001 and 10 $m^2/g$.

In other embodiments, the nanowires have a surface area of greater than 2000 $m^2/g$, greater than 1000 $m^2/g$, greater than 500 $m^2/g$, greater than 100 $m^2/g$, greater than 50 $m^2/g$, greater than 20 $m^2/g$, greater than 10 $m^2/g$, greater than 5 $m^2/g$, greater than 1 $m^2/g$, greater than 0.0001 $m^2/g$.

2. Chemical Composition

The catalytic nanowires may have any number of compositions and morphologies. In some embodiments, the nanowires are inorganic. In other embodiments, the nanowires are polycrystalline. In some other embodiments, the nanowires are inorganic and polycrystalline. In yet other embodiments, the nanowires are single-crystalline, or in other embodiments the nanowires are inorganic and single-crystalline. In still other embodiments of any of the foregoing, the nanowires may have a ratio of effective length to actual length of less than one and an aspect ratio of greater than ten as measured by TEM in bright field mode at 5 keV. In still other embodiments of any of the forgoing, the nanowires may comprise one or more elements from any of Groups 1 through 7, lanthanides, actinides or combinations thereof.

In one embodiment, the disclosure provides a catalyst comprising an inorganic catalytic polycrystalline nanowire, the nanowire having a ratio of effective length to actual length of less than one and an aspect ratio of greater than ten as measured by TEM in bright field mode at 5 keV, wherein the nanowire comprises one or more elements from any of Groups 1 through 7, lanthanides, actinides or combinations thereof.

In some embodiments, the nanowires comprise one or more metal elements from any of Groups 1-7, lanthanides, actinides or combinations thereof, for example, the nanowires may be mono-metallic, bi-metallic, tri-metallic, etc (i.e. contain one, two, three, etc. metal elements). In some embodiments, the metal elements are present in the nanowires in elemental form while in other embodiments the metal elements are present in the nanowires in oxidized form. In other embodiments the metal elements are present in the nanowires in the form of a compound comprising a metal element. The metal element or compound comprising the metal element may be in the form of oxides, hydroxides, oxyhydroxides, salts, hydrated oxides, carbonates, oxy-carbonates, sulfates, phosphates, acetates, oxalates and the like. The metal element or compound comprising the metal element may also be in the form of any of a number of different polymorphs or crystal structures.

In certain examples, metal oxides may be hygroscopic and may change forms once exposed to air, may absorb carbon dioxide, may be subjected to incomplete calcination or any combination thereof. Accordingly, although the nanowires are often referred to as metal oxides, in certain embodiments the nanowires also comprise hydrated oxides, oxyhydroxides, hydroxides, oxycarbonates (or oxide carbonates), carbonates or combinations thereof.

In other embodiments, the nanowires comprise one or more metal elements from Group 1. In other embodiments, the nanowires comprise one or more metal elements from Group 2. In other embodiments, the nanowires comprise one or more metal elements from Group 3. In other embodiments, the nanowires comprise one or more metal elements from Group 4. In other embodiments, the nanowires comprise one or more metal elements from Group 5. In other embodiments, the nanowires comprise one or more metal elements from Group 6. In other embodiments, the nanowires comprise one or more metal elements from Group 7. In other embodiments, the nanowires comprise one or more metal elements from the lanthanides. In other embodiments, the nanowires comprise one or more metal elements from the actinides.

In one embodiment, the nanowires comprise one or more metal elements from any of Groups 1-7, lanthanides, actinides or combinations thereof in the form of an oxide. In another embodiment, the nanowires comprise one or more metal elements from Group 1 in the form of an oxide. In another embodiment, the nanowires comprise one or more metal elements from Group 2 in the form of an oxide. In another embodiment, the nanowires comprise one or more metal elements from Group 3 in the form of an oxide. In another embodiment, the nanowires comprise one or more metal elements from Group 4 in the form of an oxide. In another embodiment, the nanowires comprise one or more metal elements from Group 5 in the form of an oxide. In another embodiment, the nanowires comprise one or more metal elements from Group 6 in the form of an oxide. In another embodiment, the nanowires comprise one or more metal elements from Group 7 in the form of an oxide. In another embodiment, the nanowires comprise one or more metal elements from the lanthanides in the form of an oxide. In another embodiment, the nanowires comprise one or more metal elements from the actinides in the form of an oxide.

In other embodiments, the nanowires comprise oxides, hydroxides, sulfates, carbonates, oxide carbonates, acetates, oxalates, phosphates (including hydrogenphosphates and dihydrogenphosphates), oxyhalides, hydroxihalides, oxyhydroxides, oxysulfates or combinations thereof of one or more metal elements from any of Groups 1-7, lanthanides, actinides or combinations thereof. In some other embodiments, the nanowires comprise oxides, hydroxides, sulfates, carbonates, oxide carbonates, oxalates or combinations thereof of one or more metal elements from any of Groups 1-7, lanthanides, actinides or combinations thereof. In other embodiments, the nanowires comprise oxides, and in other embodiments, the nanowires comprise hydroxides. In other embodiments, the nanowires comprise carbonates, and in other embodiments, the nanowires comprise oxy-carbonates. In other embodiments, the nanowires comprise $Li_2CO_3$, $LiOH$, $Li_2O$, $Li_2C_2O_4$, $Li_2SO_4$, $Na_2CO_3$, $NaOH$, $Na_2O$, $Na_2C_2O_4$, $Na_2SO_4$, $K_2CO_3$, $KOH$, $K_2O$, $K_2C_2O_4$, $K_2SO_4$, $Cs_2CO_3$, $CsOH$, $Cs_2O$, $CsC_2O_4$, $CsSO_4$, $Be(OH)_2$, $BeCO_3$, $BeO$, $BeC_2O_4$, $BeSO_4$, $Mg(OH)_2$, $MgCO_3$, $MgO$, $MgC_2O_4$, $MgSO_4$, $Ca(OH)_2$, $CaO$, $CaCO_3$, $CaC_2O_4$, $CaSO_4$, $Y_2O_3$, $Y_3(CO_3)_2$, $Y(OH)_3$, $Y_2(C_2O_4)_3$, $Y_2(SO4)_3$, $Zr(OH)_4$, $ZrO(OH)_2$, $ZrO_2$, $Zr(C_2O_4)_2$, $Zr(SO_4)_2$, $Ti(OH)_4$, $TiO(OH)_2$, $TiO2$, $Ti(C_2O_4)_2$, $Ti(SO_4)_2$, $BaO$, $Ba(OH)_2$, $BaCO_3$, $BaC_2O_4$, $BaSO_4$, $La(OH)_3$, $La_2O_3$, $La_2(C_2O_4)_3$, $La_2(SO_4)_3$, $La_2(CO_3)_3$, $Ce(OH)_4$, $CeO_2$, $Ce_2O_3$, $Ce(C_2O_4)_2$, $Ce(SO_4)_2$, $Ce(CO_3)_2$, $ThO_2$, $Th(OH)_4$, $Th(C_2O_4)_2$, $Th(SO_4)_2$, $Th(CO_3)_2$, $Sr(OH)_2$, $SrCO_3$, $SrO$, $SrC_2O_4$, $SrSO_4$, $Sm_2O_3$, $Sm(OH)_3$, $Sm_2(CO_3)_3$, $Sm_2(C_2O_3)_3$, $Sm_2(SO_4)_3$, $LiCa_2Bi_3O_4Cl_6$, $NaMnO_4$, $Na_2WO_4$, $NaMn/WO_4$, $CoWO_4$, $CuWO_4$, $K/SrCCO_3$, $K/Na/SrCoO_3$, $Na/SrCoO_3$, $Li/SrCoO_3$, $SrCoO_3$, $Mg_6MnO_8$, $LiMn_2O_4$, $Li/Mg_6MnO_8$, $Na_{10}Mn/W_5O_{17}$, $Mg_3Mn_3B_2O_{10}$, $Mg_3(BO_3)_2$, molybdenum oxides, molybdenum hydroxides, molybdenum oxalates, molybdenum sulfates, $Mn_2O_3$, $Mn_3O_4$, manganese oxides, manganese hydroxides, manganese oxalates, manganese sulfates, manganese tungstates, manganese carbonates, vanadium oxides, vanadium hydroxides, vanadium oxalates, vanadium sulfates, tungsten oxides, tungsten hydroxides, tungsten oxalates, tungsten sulfates, neodymium oxides, neodymium hydroxides, neodymium carbonates, neodymium oxalates, neodymium sulfates, europium oxides, europium hydroxides, europium carbonates, europium oxalates, europium sulfates, praseodymium oxides, praseodymium hydroxides, praseodymium carbonates, praseodymium oxalates, praseodymium sulfates, rhenium oxides, rhenium hydroxides, rhenium oxalates, rhenium sulfates, chromium oxides, chromium hydroxides, chromium oxalates, chromium sulfates, potassium molybdenum oxides/silicon oxide or combinations thereof.

In other embodiments, the nanowires comprise $Li_2O$, $Na_2O$, $K_2O$, $Cs_2O$, $BeO$ $MgO$, $CaO$, $ZrO(OH)_2$, $ZrO2$, $TiO_2$, $TiO(OH)_2$, $BaO$, $Y_2O_3$, $La_2O_3$, $CeO_2$, $Ce_2O_3$, $ThO_2$, $SrO$, $Sm_2O_3$, $Nd_2O_3$, $Eu_2O_3$, $Pr_2O_3$, $LiCa_2Bi_3O_4Cl_6$, $NaMnO_4$, $Na_2WO_4$, $Na/Mn/WO_4$, $Na/MnWO_4$, $Mn/WO4$, $K/SrCoO_3$, $K/Na/SrCoO_3$, $K/SrCoO_3$, $Na/SrCoO_3$, $Li/SrCoO_3$, $SrCoO_3$, $Mg_6MnO_8$, $Na/B/Mg_6MnO_8$, $Li/B/Mg_6MnO_8$, $Zr_2Mo_2O_8$, molybdenum oxides, $Mn_2O_3$, $Mn_3O_4$, manganese oxides, vanadium oxides, tungsten oxides, neodymium oxides, rhenium oxides, chromium oxides, or combinations thereof.

In still other aspects, the nanowires comprise lanthanide containing perovskites. A perovskite is any material with the same type of crystal structure as calcium titanium oxide ($CaTiO_3$). Examples of perovskites within the context of the present disclosure include, but are not limited to, $LaCoO_3$ and $La/SrCoO_3$.

In other embodiments, the nanowires comprise $TiO_2$, $Sm_2O_3$, $V_2O_5$, $MoO_3$, $BeO$, $MnO_2$, $MgO$, $La_2O_3$, $Nd_2O_3$, $Eu_2O_3$, $ZrO_2$, $SrO$, $Na_2WO_4$, $Mn/WO_4$, $BaO$, $Mn_2O_3$, $Mn_3O_4$, $Mg_6MnO_8$, $Na/B/Mg_6MnO_8$, $Li/B/Mg_6MnO_8$, $NaMnO_4$, $CaO$ or combinations thereof. In further embodiments, the nanowires comprise $MgO$, $La_2O_3$, $Nd_2O_3$, $Na_2WO_4$, $Mn/WO_4$, $Mn_2O_3$, $Mn_3O_4$, $Mg_6MnO_8$, $Na/B/Mg_6MnO_8$, $Li/B/Mg_6MnO_8$ or combinations thereof.

In some embodiments, the nanowires comprise Mg, Ca, Sr, Ba, Y, La, W, Mn, Mo, Nd, Sm, Eu, Pr, Zr or combinations thereof, and in other embodiments the nanowire comprises $MgO$, $CaO$, $SrO$, $BaO$, $Y_2O_3$, $La_2O_3$, $Na_2WO_4$, $Mn_2O_3$, $Mn_3O_4$, $Nd_2O_3$, $Sm_2O_3$, $Eu_2O_3$, $Pr_2O_3$, $Mg_6MnO_8$, $NaMnO_4$, $Na/Mn/W/O$, $Na/MnWO_4$, $MnWO_4$ or combinations thereof.

In more specific embodiments, the nanowires comprise MgO. In other specific embodiments, the nanowires comprise CaO. In other embodiments, the nanowires comprise SrO. In other specific embodiments, the nanowires comprise $La_2O_3$. In other specific embodiments, the nanowires comprise $Na_2WO_4$ and may optionally further comprise $Mn/WO_4$. In other specific embodiments, the nanowires comprise $Mn_2O_3$. In other specific embodiments, the nanowires comprise $Mn_3O_4$. In other specific embodiments, the nanowires comprise $Mg_6MnO_8$. In other specific embodiments, the nanowires comprise $NaMnO_4$. In other specific embodiments, the nanowires comprise $Nd_2O_3$. In other specific embodiments, the nanowires comprise $Eu_2O_3$. In other specific embodiments, the nanowires comprise $Pr_2O_3$. In some other embodiments, the nanowires comprise $Sm_2O_3$.

In certain embodiments, the nanowires comprise an oxide of a group 2 element. For example, in some embodiments, the nanowires comprise an oxide of magnesium. In other embodiments, the nanowires comprise an oxide of calcium.

In other embodiments, the nanowires comprise an oxide of strontium. In other embodiments, the nanowires comprise an oxide of barium.

In certain other embodiments, the nanowires comprise an oxide of a group 3 element. For example, in some embodiments, the nanowires comprise an oxide of yttrium. In other embodiments, the nanowires comprise an oxide of scandium.

In yet other certain embodiments, the nanowires comprise an oxide of an early lanthanide element. For example, in some embodiments, the nanowires comprise an oxide of lanthanum. In other embodiments, the nanowires comprise an oxide of cerium. In other embodiments, the nanowires comprise an oxide of praseodymium. In other embodiments, the nanowires comprise an oxide of neodymium. In other embodiments, the nanowires comprise an oxide of promethium. In other embodiments, the nanowires comprise an oxide of samarium. In other embodiments, the nanowires comprise an oxide of europium. In other embodiments, the nanowires comprise an oxide of gadolinium.

In certain other embodiments, the nanowires comprise a lanthanide in the form of an oxy-carbonate. For example, the nanowires may comprise $Ln_2O_2(CO_3)$, where Ln represents a lanthanide. Examples in this regard include: La, Ce, Pr, Nd, Pm, Sm, Eu, Gd, Tb, Dy, Ho, Er, Tm, Yb and Lu oxy-carbonates. In other embodiments, the nanowires comprise an oxy-carbonate of one or more elements from any of Groups 1 through 7, lanthanides, actinides or combinations thereof. Accordingly in one embodiment the nanowires comprise Li, Na, K, Rb, Cs, Fr, Be, Mg, Ca, Sr, Ba, Ra, Sc, Y, Ti, Zr, Hf, V, Nb, Ta, Cr, Mo, W, Mn, Tc or Re oxy-carbonate. In other embodiments, the nanowires comprise Ac, Th, U or Pa oxide carbonate. An oxy-carbonate may be represented by the following formula: $M_xO_y(CO_3)_z$, wherein M is a metal element from any of Groups 1 through 7, lanthanides or actinides and x, y and z are integers such that the overall charge of the metal oxy-carbonate is neutral.

In certain other embodiments, the nanowires comprise a carbonate of a group 2 element. For example, the nanowires may comprise $MgCO_3$, $CaCO_3$, $SrCO_3$, $BaCO_3$ or combination thereof. In other embodiments, the nanowires comprise a carbonate of one or more elements from any of the Group 1 through 7, lanthanides and actinides or combination thereof. Accordingly in one embodiment the nanowires comprise a Li, Na, K, Rb, Cs, Fr, Be, Mg, Ca, Sr, Ba, Ra, Sc, Y, Ti, Zr, Hf, V, Nb, Ta, Cr, Mo, W, Mn, Tc, Re, La, Ce, Pr, Nd, Pm, Sm, Eu, Gd, Tb, Dy, Ho, Er, Tm, Yb, Lu, Ac, Th, Pa or U carbonate.

In other embodiments, the nanowires comprise $TiO_2$, $Sm_2O_3$, $V_2O_5$, $MoO_3$, BeO, $MnO_2$, MgO, $La_2O_3$, $ZrO_2$, SrO, $Na_2WO_4$, $BaCO_3$, $Mn_2O_3$, $Mn_3O_4$, $Mg_6MnO_8$, Na/B/$Mg_6MnO_8$, Li/B/$Mg_6MnO_8$, $Zr_2Mo_2O_8$, $NaMnO_4$, CaO or combinations thereof and further comprise one or more dopants comprised of metal elements, semi-metal elements, non-metal elements or combinations thereof. In some further embodiments, the nanowires comprise MgO, $La_2O_3$, $Na_2WO_4$, $Mn_2O_3$, $Mn_3O_4$, $Mg_6MnO_8$, $Zr_2Mo_2O_8$, $NaMnO_4$ or combinations thereof, and the nanowires further comprise Li, Sr, Zr, Ba, Mn or Mn/$WO_4$.

In some embodiments, the nanowires or a catalytic material comprising a plurality of the nanowires comprise a combination of one or more of metal elements from any of Groups 1-7, lanthanides or actinides and one or more of metal elements, semi-metal elements or non-metal elements. For example in one embodiment, the nanowires comprise the combinations of Li/Mg/O, Ba/Mg/O, Zr/La/O, Ba/La/O, Sr/La/O, Zr/V/P/O, Mo/V/Sb/O, $V_2O_5/Al_2O_3$, Mo/V/O, V/Ce/O, V/Ti/P/O, $V_2O_5/TiO_2$, V/P/O/$TiO_2$, V/P/O/$Al_2O_3$, V/Mg/O, $V_2O_5/ZrO_2$, Mo/V/Te/O, V/Mo/O/$Al_2O_3$, Ni/V/Sb/O, Co/V/Sb/O, Sn/V/Sb/O, Bi/V/Sb/O, Mo/V/Te/Nb/O, Mo/V/Nb/O, $V_2O_5$/MgO/$SiO_2$, V/Co, $MoO_3$/$Al_2O_3$, Ni/Nb/O, NiO/$Al_2O_3$, Ga/Cr/Zr/P/O, $MoO_3$/Cl/$SiO_2$/$TiO_2$, Co/Cr/Sn/W/O, Cr/Mo/O, $MoO_3$/Cl/$SiO_2$/$TiO_2$, Co/Ca, NiO/MgO, $MoO_3$/$Al_2O_3$, Nb/P/Mo/O, Mo/V/Te/Sb//Nb/O, La/Na/Al/O, Ni/Ta/Nb/O, Mo/Mn/V/W/O, Li/Dy/Mg/O, Sr/La/Nd/O, Co/Cr/Sn/W/O, $MoO_3$/$SiO_2$/$TiO_2$, Sm/Na/P/O, Sm/Sr/O, Sr/La/Nd/O, Co/P/O/$TiO_2$, La/Sr/Fe/Cl/O, La/Sr/Cu/Cl/O, Y/Ba/Cu/O, Na/Ca/O, $V_2O_5$/$ZrO_2$, V/Mg/O, Mn/V/Cr/W/O/$Al_2O_3$, $V_2O_5$/K/$SiO_2$, $V_2O_5$/Ca/$TiO_2$, $V_2O_5$/K/$TiO_2$, V/Mg/Al/O, V/Zr/O, V/Nb/O, $V_2O_5$/$Ga_2O_3$, V/Mg/Al/O, V/Nb/O, V/Sb/O, V/Mn/O, V/Nb/O/$Sb_2O_4$, V/Sb/O/$TiO_2$, $V_2O_5$/Ca, $V_2O_5$/K/$Al_2O_3$, $V_2O_5$/$TiO_2$, $V_2O_5$/MgO/$TiO_2$, $V_2O_5$/$ZrO_2$, V/Al/F/O, V/Nb/O/$TiO_2$, Ni/V/O, $V_2O_5$/$SmVO_4$, V/W/O, $V_2O_5$/Zn/$Al_2O_3$, $V_2O_5$/$CeO_2$, V/Sm/O, $V_2O_5$/$TiO_2$/$SiO_2$, Mo/Li/O/$Al_2O_3$, Mg/Dy/Li/Cl/O, Mg/Dy/Li/Cl/O, Ce/Ni/O, Ni/Mo/O/V, Ni/Mo/O/V/N, Ni/Mo/O Sb/O/N, $MoO_3$/Cl/$SiO_2$/$TiO_2$, Co/Mo/O, Ni/Ti/O, Ni/Zr/O, Cr/O, $MoO_3$/$Al_2O_3$, Mn/P/O, $MoO_3$/K/$ZrO_2$, Na/W/O, Mn/Na/W/O, Mn/Na//W/O/$SiO_2$, Na/W/O/$SiO_2$, Mn/Mo/O, $Nb_2O_5$/$TiO_2$, Co/W/O, Ni/Mo/O, Ga/Mo/O, Mg/Mo/V/O, $Cr_2O_3$/$Al_2O_3$, Cr/Mo/Cs/O/$Al_2O_3$, Co/Sr/O/Ca, Ag/Mo/P/O, $MoO_3$/$SmVO_4$, Mo/Mg/Al/O, $MoO_3$/K/$SiO_2$/$TiO_2$, Cr/Mo/O/$Al_2O_3$, $MoO_3$/$Al_2O_3$, Ni/Co/Mo/O, Y/Zr/O, Y/Hf, Zr/Mo/Mn/O, Mg/Mn/O, Li/Mn/O, Mg/Mn/B/O, Mg/B/O, Na/B/Mg/Mn/O, Li/B/Mg/Mn/O, Mn/Na/P/O, Na/Mn/Mg/O, Zr/Mo/O, Mn/W/O or Mg/Mn/O.

In a specific embodiment, the nanowires comprise the combinations of Li/Mg/O, Ba/Mg/O, Zr/La/O, Ba/La/O, Sr/La/O, Sr/Nd/O, La/O, Nd/O, Eu/O, Mg/La/O, Mg/Nd/O, Na/La/O, Na/Nd/O, Sm/O, Mn/Na/W/O, Mg/Mn/O, Na/B/Mg/Mn/O, Li/B/Mg/Mn/O, Zr/Mo/O or Na/Mn/Mg/O. For example, in some embodiments the nanowires comprise the combinations of Li/MgO, Ba/MgO, Sr/$La_2O_3$, Ba/$La_2O_3$, Mn/$Na_2WO_4$, Mn/$Na_2WO_4$/$SiO_2$, $Mn_2O_3$/$Na_2WO_4$, $Mn_3O_4$/$Na_2WO_4$, Li/B/$Mg_6MnO_8$, Na/B/$Mg_6MnO_8$ or $NaMnO_4$/MgO. In certain embodiments, the nanowire comprises Li/MgO, Ba/MgO, Sr/$La_2O_3$, Mg/Na/$La_2O_3$, Sr/$Nd_2O_3$, or Mn/$Na_2WO_4$.

In some other specific embodiments, the nanowires comprise the combination of Li/MgO. In other specific embodiments, the nanowires comprise the combination of Ba/MgO. In other specific embodiments, the nanowires comprise the combination of Sr/$La_2O_3$. In other specific embodiments, the nanowires comprise the combination of Ba/$La_2O_3$. In other specific embodiments, the nanowires comprise the combination of Mn/$Na_2WO_4$. In other specific embodiments, the nanowires comprise the combination of Mn/$Na_2WO_4$/$SiO_2$. In other specific embodiments, the nanowires comprise the combination of $Mn_2O_3$/$Na_2WO_4$. In other specific embodiments, the nanowires comprise the combination of $Mn_3O_4$/$Na_2WO_4$. In other specific embodiments, the nanowires comprise the combination of Mn/$WO_4$/$Na_2WO_4$. In other specific embodiments, the nanowires comprise the combination of Li/B/$Mg_6MnO_8$. In other specific embodiments, the nanowires comprise the combination of Na/B/$Mg_6MnO_8$. In other specific embodiments, the nanowires comprise the combination of $NaMnO_4$/MgO.

Polyoxymetalates (POM) are a class of metal oxides that range in structure from the molecular to the micrometer scale. The unique physical and chemical properties of POM clusters, and the ability to tune these properties by synthetic means have attracted significant interest from the scientific community to create "designer" materials. For example, heteropolyanions such as the well-known Keggin

[XM$_{12}$O$_{40}$]$^-$ and Wells-Dawson [X$_2$M1$_8$O$_{62}$]$^-$ anions (where M=W or Mo; and X=a tetrahedral template such as but not limited to Si, Ge, P) and isopolyanions with metal oxide frameworks with general formulas [MO$_x$]$_n$ where M=Mo, W, V, and Nb and x=4-7 are ideal candidates for OCM/ODH catalysts. Accordingly, in one embodiment the nanowires comprise [XM$_{12}$O$_{40}$]$^-$ or [X$_2$M1$_8$O$_{62}$]$^-$ anions (where M=W or Mo; and X=a tetrahedral template such as but not limited to Si, Ge, P) and isopolyanions with metal oxide frameworks with general formulas [MO$_x$]$_n$ where M=Mo, W, V, and Nb and x=4-7. In some embodiments, X is P or Si.

These POM clusters have "lacunary" sites that can accommodate divalent and trivalent first row transition metals, the metal oxide clusters acting as ligands. These lacunary sites are essentially "doping" sites, allowing the dopant to be dispersed at the molecular level instead of in the bulk which can create pockets of unevenly dispersed doped material. Because the POM clusters can be manipulated by standard synthetic techniques, POMs are highly modular and a wide library of materials can be prepared with different compositions, cluster size, and dopant oxidation state. These parameters can be tuned to yield desired OCM/ODH catalytic properties. Accordingly, one embodiment of the present disclosure is a nanowire comprising one or more POM clusters. Such nanowires find utility as catalysts, for example, in the OCM and ODH reactions.

Silica doped sodium manganese tungstate (NaMn/WO$_4$/SiO$_2$) is a promising OCM catalyst. The NaMn/WO$_4$/SiO$_2$ system is attractive due to its high C2 selectivity and yield. Unfortunately, good catalytic activity is only achievable at temperatures greater than 800° C. and although the exact active portion of the catalyst is still subject to debate, it is thought that sodium plays an important role in the catalytic cycle. In addition, the NaMn/WO$_4$/SiO$_2$ catalyst surface area is relatively low <2 m$^2$/g. Manganese tungstate (Mn/WO$_4$) nanorods (i.e., straight nanowires) can be used to model a NaMn/WO$_4$/SiO$_2$ based nanowire OCM catalyst. The Mn/WO$_4$ nanorods are prepared hydro-thermally and the size can be tuned based on reaction conditions with dimensions of 25-75 nm in diameter to 200-800 nm in length. The as-prepared nano-rods have higher surface areas than the NaMn/WO$_4$/SiO$_2$ catalyst systems. In addition, the amount of sodium, or other elements, can be precisely doped into the Mn/WO$_4$ nanorod material to target optimal catalytic activity. Nanorod tungstate based materials can be expanded to, but not limited to, CoWO$_4$ or CuWO$_4$ materials, which may serve as base materials for OCM/ODH catalysis. In addition to straight nanowires, the above discussion applies to the disclosed nanowires having a bent morphology as well. The nanowires of the disclosure may be analyzed by inductively coupled plasma mass spectrometry (ICP-MS) to determine the element content of the nanowires. ICP-MS is a type of mass spectrometry that is highly sensitive and capable of the determination of a range of metals and several non-metals at concentrations below one part in 10$^{12}$. ICP is based on coupling together an inductively coupled plasma as a method of producing ions (ionization) with a mass spectrometer as a method of separating and detecting the ions. ICP-MS methods are well known in the art.

In some embodiments, the nanowire comprises a combination of two or more metal compounds, for example metal oxides. For example, in some embodiments, the nanowire comprises Mn$_2$O$_3$/Na$_2$WO$_4$, Mn$_3$O$_4$/Na$_2$WO$_4$ MnWO$_4$/Na$_2$WO$_4$/Mn$_2$O$_3$, MnWO$_4$/Na$_2$WO$_4$/Mn$_3$O$_4$ or NaMnO$_4$/MgO.

Certain rare earth compositions have been found to be useful catalysts, for example as catalysts in the OCM reaction. Thus, in one embodiment, the nanowire catalysts comprise lanthanide oxides such as La$_2$O$_3$, Nd$_2$O$_3$, Yb$_2$O$_3$, Eu$_2$O$_3$, Sm$_2$O$_3$, Y$_2$O$_3$, Ce$_2$O$_3$ or Pr$_2$O$_3$. In other embodiments, the nanowires comprise mixed oxides of lanthanide metals. Such mixed oxides are represented by Ln1$_{4-x}$Ln2$_x$O$_6$, wherein Ln1 and Ln2 are each independently a lanthanide element and x is a number ranging from greater than 0 to less than 4. In other more specific embodiments, the lanthanide mixed oxides comprise La$_{4-x}$Ln1$_x$O$_6$, wherein Ln1 is a lanthanide element and x is a number ranging from greater than 0 to less than 4. For example, in some embodiments the lanthanide mixed oxides are mixed oxides of lanthanum and neodymium and the nanowires comprise La$_{4-x}$Nd$_x$O$_6$, wherein x is a number ranging from greater than 0 to less than 4 have also been found to be useful in the OCM reaction. For example La$_3$NdO$_6$, LaNd$_3$O$_6$, La$_{1.6}$Nd$_{2.6}$O$_6$, La$_{2.5}$Nd$_{1.5}$O$_6$, La$_{3.2}$Nd$_{0.8}$O$_6$, La$_{3.5}$Nd$_{0.5}$O$_6$, La$_{3.8}$Nd$_{0.2}$O$_6$, or combinations thereof have been found to be useful OCM catalyst compositions.

Any of the foregoing nanowire catalysts may have any morphology (e.g., bent, straight, etc.) and may be prepared via any method described herein or known in the art. For example, these nanowires may be prepared from phage or another biological template, or the nanowires may be prepared in the absence of a template, for example by hydrothermal methods. Also as discussed below, certain dopant combinations with the above lanthanide nanowires have been found to be useful for enhancing the catalytic activity of the nanowires.

In other embodiments the nanowires are in a core/shell arrangement (see below) and the nanowires comprise Eu on a MgO core; La on a MgO core; Nd on a MgO core; Sm on a MgO core; Y—Ce on a Na doped MgO core Na or Na doped Ce—Y on a MgO core.

In an aspect of the invention, nanowires, and materials comprising the same, having the empirical formula M4$_w$M5$_x$M6$_y$O$_z$ are provided, wherein each M4 is independently one or more elements selected from Groups 1 through 4, each M5 is independently one or more elements selected from Group 7 and M6 is independently one or more elements selected from Groups 5 through 8 and Groups 14 through 15 and w, x, y and z are integers such that the overall charge is balanced.

In some embodiments, M4 comprises one or more elements selected from Group 1, such as sodium (Na), while M6 includes one or more elements selected from Group 6, such as tungsten (W) and M5 is Mn. In another embodiment, M4 is Na, M5 is Mn, M6 is W, the ratio of w:x is 10:1, and the ratio of w:y is 2:1. In such a case, the overall empirical formula of the nanowire is Na$_{10}$MnW$_6$O$_z$. When Na is in the +1 oxidation state, W is in the +6 oxidation state, and Mn is in the +4 oxidation state, z must equal 17 so as to fill the valence requirements of Na, W and Mn. As a result, the overall empirical formula of the nanowire in this embodiment is Na$_{10}$MnW$_5$O$_{17}$.

In other embodiments, the ratios of w:x can be 1:1, or 5:1, or 15:1, or 25:1, or 50:1. In yet other embodiments, for any given ratio of w:x, the ratios of w:y can be 1:5, or 1:2, or 1:2, or 5:1. In still other embodiments, any nanowire of the empirical formula M4$_w$M5$_x$M6$_y$O$_z$, including the nanowire of the empirical formula M4$_{10}$MnM6$_5$O$_{17}$ described above, can be supported on an oxide substrate. Oxide substrates can include silica, alumina, and titania. The reaction that anchors nanowire materials onto oxide substrates is analogous to the reaction that anchors bulk materials onto oxide substrates, such as that described in U.S. Pat. No. 4,808,563, which is entirely incorporated herein by reference. Example 18 describes the anchoring of nanowire material $Na_{10}MnW_5O_{17}$ onto a silica substrate. Alternatively, non-oxide support, for example silicon carbide can be used to support nanowires of the present invention, for example $Na_{10}MnW_5O_{17}$ nanowires and others. Silicon carbide has very good high temperature stability and chemical inertness toward OCM reaction intermediates and thus is particularily effective as a support in this reaction.

3. Catalytic Materials

As noted above, the present disclosure provides a catalytic material comprising a plurality of nanowires. In some embodiments, the disclosure provides a catalytic material comprising a plurality of inorganic catalytic polycrystalline nanowires, the plurality of nanowires having a ratio of average effective length to average actual length of less than one and an average aspect ratio of greater than ten as measured by TEM in bright field mode at 5 keV, wherein the plurality of nanowires comprises one or more elements from any of Groups 1 through 7, lanthanides, actinides or combinations thereof.

In certain embodiments, the catalytic material comprises a support or carrier. The support is preferably porous and has a high surface area. In some embodiments the support is active (i.e. has catalytic activity). In other embodiments, the support is inactive (i.e. non-catalytic). In some embodiments, the support comprises an inorganic oxide, $Al_2O_3$, $SiO_2$, $TiO_2$, MgO, CaO, SrO, $ZrO_2$, ZnO, $LiAlO_2$, $MgAl_2O_4$, MnO, $MnO_2$, $Mn_3O_4$, $La_2O_3$, $AlPO_4$, $SiO_2/Al_2O_3$, activated carbon, silica gel, zeolites, activated clays, activated $Al_2O_3$, SiC, diatomaceous earth, magnesia, aluminosilicates, calcium aluminate, support nanowires or combinations thereof. In some embodiments the support comprises silicon, for example $SiO_2$. In other embodiments the support comprises magnesium, for example MgO. In other embodiments the support comprises zirconium, for example $ZrO_2$. In yet other embodiments, the support comprises lanthanum, for example $La_2O_3$. In yet other embodiments, the support comprises lanthanum, for example $Y_2O_3$. In yet other embodiments, the support comprises hafnium, for example $HfO_2$. In yet other embodiments, the support comprises aluminum, for example $Al_2O_3$. In yet other embodiments, the support comprises gallium, for example $Ga_2O_3$.

In still other embodiments, the support material comprises an inorganic oxide, $Al_2O_3$, $SiO_2$, $TiO_2$, MgO, $ZrO_2$, HfO2, CaO, SrO, ZnO, $LiAlO_2$, $MgAl_2O_4$, MnO, $MnO_2$, $Mn_2O_4$, $Mn_3O_4$, $La_2O_3$, activated carbon, silica gel, zeolites, activated clays, activated $Al_2O_3$, diatomaceous earth, magnesia, aluminosilicates, calcium aluminate, support nanowires or combinations thereof. For example, the support material may comprise $SiO_2$, $ZrO_2$, CaO, $La_2O_3$ or MgO.

In still other embodiments, the support material comprises a carbonate. For example, in some embodiments the support material comprises $MgCO_3$, $CaCO_3$, $SrCO_3$, $BaCO_3$, $Y_2(CO_3)_3$, $La_2(CO_3)_3$ or combinations thereof.

In yet other embodiments, a nanowire may serve as a support for another nanowire. For example, a nanowire may be comprised of non-catalytic metal elements and adhered to or incorporated within the support nanowire is a catalytic nanowire. For example, in some embodiments, the support nanowires are comprised of $SiO_2$, MgO, CaO, SrO, $TiO_2$, $ZrO_2$, $Al_2O_3$, ZnO $MgCO_3$, $CaCO_3$, $SrCO_3$ or combinations thereof. Preparation of nanowire supported nanowire catalysts (i.e., core/shell nanowires) is discussed in more detail below. The optimum amount of nanowire present on the support depends, inter alia, on the catalytic activity of the nanowire. In some embodiments, the amount of nanowire present on the support ranges from 1 to 100 parts by weight nanowires per 100 parts by weight of support or from 10 to 50 parts by weight nanowires per 100 parts by weight of support. In other embodiments, the amount of nanowire present on the support ranges from 100-200 parts of nanowires per 100 parts by weight of support, or 200-500 parts of nanowires per 100 parts by weight of support, or 500-1000 parts of nanowires per 100 parts by weight of support. Typically, heterogeneous catalysts are used either in their pure form or blended with inert materials, such as silica, alumina, etc. The blending with inert materials is used in order to reduce and/or control large temperature non-uniformities within the reactor bed often observed in the case of strongly exothermic (or endothermic) reactions. In the case of complex multistep reactions, such as the reaction to convert methane into ethylene (OCM), typical blending materials can selectively slow down or quench one or more of the reactions of the system and promote unwanted side reactions. For example, in the case of the oxidative coupling of methane, silica and alumina can quench the methyl radicals and thus prevent the formation of ethane. In certain aspects, the present disclosure provides a catalytic material which solves these problems typically associated with catalyst support material. Accordingly, in certain embodiments the catalytic activity of the catalytic material can be tuned by blending two or more catalysts and/or catalyst support materials. The blended catalytic material may comprise a catalytic nanowire as described herein and a bulk catalyst material and/or inert support material.

The blended catalytic materials comprise metal oxides, hydroxides, oxy-hydroxides, carbonates, oxalates of the groups 1-16, lanthanides, actinides or combinations thereof. For example, the blended catalytic materials may comprise a plurality of inorganic catalytic polycrystalline nanowires, as disclosed herein, and any one or more of straight nanowires, nanoparticles, bulk materials and inert support materials. Bulk materials are defined as any material in which no attempt to control the size and/or morphology was performed during its synthesis. The catalytic materials may be undoped or may be doped with any of the dopants described herein.

In one embodiment, the catalyst blend comprises at least one type 1 component and at least one type 2 component. Type 1 components comprise catalysts having a high OCM activity at moderately low temperatures and type 2 components comprise catalysts having limited or no OCM activity at these moderately low temperatures, but are OCM active at higher temperatures. For example, in some embodiments the type 1 component is a catalyst (e.g., nanowire) having high OCM activity at moderately low temperatures. For example, the type 1 component may comprise a C2 yield of greater than 5% or greater than 10% at temperatures less than 800° C., less than 700° C. or less than 600° C. The type 2 component may comprise a C2 yield less than 0.1%, less than 1% or less than 5% at temperatures less than 800° C., less than 700° C. or less than 600° C. The type 2 component may comprise a C2 yield of greater than 0.1%, greater than 1%, greater than 5% or greater than 10% at temperatures greater than 800° C., greater than 700° C. or greater than 600° C. Typical type 1 components include nanowires, for example polycrystalline nanowires as described herein, while typical type 2 components include bulk OCM catalysts and nanowire catalysts which only have good OCM activity at higher temperatures, for example greater than 800° C. Examples of type 2 components may include catalysts comprising MgO. The catalyst blend may further comprise inert support materials as described above (e.g., silica, alumina, silicon carbide, etc.).

In certain embodiments, the type 2 component acts as diluent in the same way an inert material does and thus helps reduce and/or control hot spots in the catalyst bed caused by the exothermic nature of the OCM reaction. However, because the type 2 component is an OCM catalyst, albeit not a particularly active one, it may prevent the occurrence of undesired side reactions, e.g. methyl radical quenching. Additionally, controlling the hotspots has the beneficial effect of extending the lifetime of the catalyst.

For example, it has been found that diluting active lanthanide oxide OCM catalysts (e.g., nanowires) with as much as a 10:1 ratio of MgO, which by itself is not an active OCM catalyst at the temperature which the lanthanide oxide operates, is a good way to minimize "hot spots" in the reactor catalyst bed, while maintaining the selectivity and yield performance of the catalyst. On the other hand, doing the same dilution with quartz $SiO_2$ is not effective because it appears to quench the methyl radicals which serves to lower the selectivity to C2s.

In yet another embodiment, the type 2 components are good oxidative dehydrogenation (ODH) catalysts at the same temperature that the type 1 components are good OCM catalysts. In this embodiment, the ethylene/ethane ratio of the resulting gas mixture can be tuned in favor of higher ethylene. In another embodiment, the type 2 components are not only good ODH catalysts at the same temperature the type 1 components are good OCM catalysts, but also have limited to moderate OCM activity at these temperatures.

In related embodiments, the catalytic performance of the catalytic material is tuned by selecting specific type 1 and type 2 components of a catalyst blend. In another embodiment, the catalytic performance is tuned by adjusting the ratio of the type 1 and type 2 components in the catalytic material. For example, the type 1 catalyst may be a catalyst for a specific step in the catalytic reaction, while the type 2 catalyst may be specific for a different step in the catalytic reaction. For example, the type 1 catalyst may be optimized for formation of methyl radicals and the type 2 catalyst may be optimized for formation of ethane or ethylene.

In other embodiments, the catalytic material comprises at least two different components (component 1, component 2, component 3, etc.). The different components may comprise different morphologies, e.g. nanowires, nanoparticles, bulk, etc. The different components in the catalyst material can be, but not necessarily, of the same chemical composition and the only difference is in the morphology and/or the size of the particles. This difference in morphology and particle size may result in a difference in reactivity at a specific temperature. Additionally, the difference in morphology and particle size of the catalytic material components is advantageous for creating a very intimate blending, e.g. very dense packing of the catalysts particles, which can have a beneficial effect on catalyst performance. Also, the difference in morphology and particle size of the blend components would allow for control and tuning of the macro-pore distribution in the reactor bed and thus its catalytic efficiency. An additional level of micro-pore tuning can be attained by blending catalysts with different chemical composition and different morphology and/or particle size. The proximity effect would be advantageous for the reaction selectivity.

Accordingly, in one embodiment the present disclosure provides the use of a catalytic material comprising a first catalytic nanowire and a bulk catalyst and/or a second catalytic nanowire in a catalytic reaction, for example the catalytic reaction may be OCM or ODH. In other embodiments, the first catalytic nanowire and the bulk catalyst and/or second catalytic nanowire are each catalytic with respect to the same reaction, and in other examples the first catalytic nanowire and the bulk catalyst and/or second catalytic nanowire have the same chemical composition.

In some specific embodiments of the foregoing, the catalytic material comprises a first catalytic nanowire and a second catalytic nanowire. Each nanowire can have completely different chemical compositions or they may have the same base composition and differ only by the doping elements. In other embodiments, each nanowire can have the same or a different morphology. For example, each nanowire can differ by the nanowire size (length and/or aspect ratio), by ratio of actual/effective length, by chemical composition or any combination thereof. Furthermore, the first and second nanowires may each be catalytic with respect to the same reaction but may have different activity. Alternatively, each nanowire may catalyze different reactions.

In a related embodiment, the catalytic material comprises a first catalytic nanowire and a bulk catalyst. The first nanowire and the bulk catalyst can have completely different chemical compositions or they may have the same base composition and differ only by the doping elements. Furthermore, the first nanowire and the bulk catalyst may each be catalytic with respect to the same reaction but may have different activity. Alternatively, the first nanowire and the bulk catalyst may catalyze different reactions.

In yet other embodiments of the foregoing, the catalytic nanowire has a catalytic activity in the catalytic reaction, which is greater than a catalytic activity of the bulk catalyst in the catalytic reaction at the same temperature. In still other embodiments, the catalytic activity of the bulk catalyst in the catalytic reaction increases with increasing temperature.

OCM catalysts may be prone to hotspots due to the very exothermic nature of the OCM reaction. Diluting such catalysts helps to manage the hotspots. However, the diluent needs to be carefully chosen so that the overall performance of the catalyst is not degraded. Silicon carbide for example can be used as a diluent with little impact on the OCM selectivity of the blended catalytic material whereas using silica as a diluent significantly reduces OCM selectivity. The good heat conductivity of SiC is also beneficial in minimizing hot spots. As noted above, use of a catalyst diluents or support material that is itself OCM active has significant advantages over more traditional diluents such as silica and alumina, which can quench methyl radicals and thus reduce the OCM performance of the catalyst. An OCM active diluent is not expected to have any adverse impact on the generation and lifetime of methyl radicals and thus the dilution should not have any adverse impact on the catalyst performance. Thus embodiments of the invention include catalyst compositions comprising an OCM catalyst (e.g., any of the disclosed nanowire catalysts) in combination with a diluent or support material that is also OCM active. Methods for use of the same in an OCM reaction are also provided.

In some embodiments, the above diluent comprises alkaline earth metal compounds, for example alkaline metal oxides, carbonates, sulfates or phosphates. Examples of diluents useful in various embodiments include, but are not limited to, MgO, $MgCO_3$, $MgSO_4$, $Mg_3(PO_4)_2$, $MgAl_2O_4$, CaO, $CaCO_3$, $CaSO_4$, $Ca_3(PO_4)_2$, $CaAl_2O_4$, SrO, $SrCO_3$, $SrSO_4$, $Sr_3(PO_4)_2$, $SrAl_2O_4$, BaO, $BaCO_3$, $BaSO_4$, $Ba_3(PO_4)_2$, $BaAl_2O_4$ and the like. Most of these compounds are very cheap, especially MgO, CaO, $MgCO_3$, $CaCO_3$, SrO, $SrCO_3$ and thus very attractive for use as diluents from an economic point of view. Additionally, the magnesium, calcium and strontium compounds are environmentally friendly too. Accordingly, an embodiment of the invention provides a catalytic material comprising a catalytic nanowire in combination with a diluent selected from one or more of MgO, $MgCO_3$, $MgSO_4$, $Mg_3(PO_4)_2$, CaO, $CaCO_3$, $CaSO_4$, $Ca_3(PO_4)_2$, SrO, $SrCO_3$, $SrSO_4$, $Sr_3(PO_4)_2$, BaO, $BaCO_3$, $BaSO_4$, $Ba_3(PO_4)_2$. In some specific embodiments the diluents is MgO, CaO, SrO, $MgCO_3$, $CaCO_3$, $SrCO_3$ or combination thereof. Methods for use of the foregoing catalytic materials in an OCM reaction are also provided. The methods comprise converting methane to ethane and or ethylene in the presence of the catalytic materials.

The above diluents and supports may be employed in any number of methods. For example, in some embodiments a support (e.g., MgO, CaO, $CaCO_3$, $SrCO_3$) may be used in the form of a pellet or monolith (e.g., honeycomb) structure, and the nanowire catalysts may be impregnated or supported thereon. In other embodiments, a core/shell arrangement is provided and the support material may form part of the core or shell. For example, a core of MgO, CaO, $CaCO_3$ or $SrCO_3$ may be coated with a shell of any of the disclosed nanowire compositions.

In some embodiments, the diluent has a morphology selected from bulk (e.g. commercial grade), nano (nanowires, nanorods, nanoparticles, etc.) or combinations thereof.

In some embodiments, the diluent has none to moderate catalytic activity at the temperature the OCM catalyst is operated. In some other embodiments, the diluent has moderate to large catalytic activity at a temperature higher than the temperature the OCM catalyst is operated. In yet some other embodiments, the diluent has none to moderate catalytic activity at the temperature the OCM catalyst is operated and moderate to large catalytic activity at temperatures higher than the temperature the OCM catalyst is operated. Typical temperatures for operating an OCM reaction according to the present disclosure are 800° C. or lower, 750° C. or lower, 700° C. or lower, 650° C. or lower, 600° C. or lower and 550° C. or lower.

For example, $CaCO_3$ is a relatively good OCM catalyst at T>750° C. (50% selectivity, >20% conversion) but has essentially no activity below 700° C. Experiments performed in support of the present invention showed that dilution of $Nd_2O_3$ straight nanowires with $CaCO_3$ or $SrCO_3$ (bulk) showed no degradation of OCM performance and, in some cases, even better performance than the neat catalyst.

In some embodiments, the diluent portion in the catalyst/diluent mixture is 0.01%, 10%, 30%, 50%, 70%, 90% or 99.99% (weight percent) or any other value between 0.01% and 99.9%. In some embodiments, the dilution is performed with the OCM catalyst ready to go, e.g. after calcination. In some other embodiments, the dilution is performed prior to the final calcination of the catalyst, i.e. the catalyst and the diluent are calcined together. In yet some other embodiments, the dilution can be done during the synthesis as well, so that, for example, a mixed oxide is formed.

In some embodiments, the catalyst/diluent mixture comprises more than one catalyst and/or more than one diluent. In some other embodiments, the catalyst/diluent mixture is pelletized and sized, or made into shaped extrudates or deposited on a monolith or foam, or is used as it is. Methods of the invention include taking advantage of the very exothermic nature of OCM by diluting the catalyst with another catalyst that is (almost) inactive in the OCM reaction at the operating temperature of the first catalyst but active at higher temperature. In these methods, the heat generated by the hotspots of the first catalyst will provide the necessary heat for the second catalyst to become active.

For ease of illustration, the above description of catalytic materials often refers to OCM; however, such catalytic materials find utility in other catalytic reactions including but not limited to: oxidative dehydrogenation (ODH) of alkanes to their corresponding alkenes, selective oxidation of alkanes and alkenes and alkynes, oxidation of co, dry reforming of methane, selective oxidation of aromatics, Fischer-Tropsch, combustion of hydrocarbons, etc.

4. Preparation of Catalytic Materials

The catalytic materials can be prepared according to any number of methods known in the art. For example, the catalytic materials can be prepared after preparation of the individual components by mixing the individual components in their dry form, e.g. blend of powders, and optionally, ball milling can be used to reduce particle size and/or increase mixing. Each component can be added together or one after the other to form layered particles. Alternatively, the individual components can be mixed prior to calcination, after calcination or by mixing already calcined components with uncalcined components. The catalytic materials may also be prepared by mixing the individual components in their dry form and optionally pressing them together into a "pill" followed by calcination to above 400° C.

In other examples, the catalytic materials are prepared by mixing the individual components with one or more solvents into a suspension or slurry, and optional mixing and/or ball milling can be used to maximize uniformity and reduce particle size. Examples of slurry solvents useful in this context include, but are not limited to: water, alcohols, ethers, carboxylic acids, ketones, esters, amides, aldehydes, amines, alkanes, alkenes, alkynes, aromatics, etc. In other embodiments, the individual components are deposited on a supporting material such as silica, alumina, magnesia, activated carbon, and the like, or by mixing the individual components using a fluidized bed granulator. Combinations of any of the above methods may also be used.

The catalytic materials may optionally comprise a dopant as described in more detail below. In this respect, doping material(s) may be added during preparation of the individual components, after preparation of the individual components but before drying of the same, after the drying step but before calcinations or after calcination. If more than one doping material is used, each dopant can be added together or one after the other to form layers of dopants.

Doping material(s) may also be added as dry components and optionally ball milling can be used to increase mixing. In other embodiments, doping material(s) are added as a liquid (e.g. solution, suspension, slurry, etc.) to the dry individual catalyst components or to the blended catalytic material. The amount of liquid may optionally be adjusted for optimum wetting of the catalyst, which can result in optimum coverage of catalyst particles by doping material. Mixing and/or ball milling can also be used to maximize doping coverage and uniform distribution. Alternatively, doping material(s) are added as a liquid (e.g. solution, suspension, slurry, etc.) to a suspension or slurry of the catalyst in a solvent. Mixing and/or ball milling can be used to maximize doping coverage and uniform distribution. Incorporation of dopants can also be achieved using any of the methods described elsewhere herein.

As noted below, an optional calcination step usually follows an optional drying step at T<200 C (typically 60-120 C) in a regular oven or in a vacuum oven. Calcination may be performed on the individual components of the catalytic material or on the blended catalytic material. Calcination is generally performed in an oven/furnace at a temperature higher than the minimum temperature at which at least one of the components decomposes or undergoes a phase transformation and can be performed in inert atmosphere (e.g. $N_2$, Ar, He, etc.), oxidizing atmosphere (air, $O_2$, etc.) or reducing atmosphere ($H_2$, $H_2/N_2$, $H_2/Ar$, etc.). The atmosphere may be a static atmosphere or a gas flow and may be performed at ambient pressure, at p<1 atm, in vacuum or at p>1 atm. High pressure treatment (at any temperature) may also be used to induce phase transformation including amorphous to crystalline. Calcinations may also be performed using microwave heating.

Calcination is generally performed in any combination of steps comprising ramp up, dwell and ramp down. For example, ramp to 500° C., dwell at 500° C. for 5 h, ramp down to RT. Another example includes ramp to 100° C., dwell at 100° C. for 2 h, ramp to 300° C., dwell at 300° C. for 4 h, ramp to 550° C., dwell at 550° C. for 4 h, ramp down to RT. Calcination conditions (pressure, atmosphere type, etc.) can be changed during the calcination. In some embodiments, calcination is performed before preparation of the blended catalytic material (i.e., individual components are calcined), after preparation of the blended catalytic material but before doping, after doping of the individual components or blended catalytic material. Calcination may also be performed multiple times, e.g. after catalyst preparation and after doping.

The catalytic materials may be incorporated into a reactor bed for performing any number of catalytic reactions (e.g., OCM, ODH and the like). Accordingly, in one embodiment the present disclosure provides a catalytic material as disclosed herein in contact with a reactor and/or in a reactor bed. For example, the reactor may be for performing an OCM reaction, may be a fixed bed reactor and may have a diameter greater than 1 inch. In this regard, the catalytic material may be packed neat (without diluents) or diluted with an inert material (e.g., sand, silica, alumina, etc.) The catalyst components may be packed uniformly forming a homogeneous reactor bed.

The particle size of the individual components within a catalytic material may also alter the catalytic activity, and other properties, of the same. Accordingly, in one embodiment, the catalyst is milled to a target average particle size or the catalyst powder is sieved to select a particular particle size. In some aspects, the catalyst powder may be pressed into pellets and the catalyst pellets can be optionally milled and or sieved to obtain the desired particle size distribution.

In some embodiments, the catalytic materials, alone or with binders and/or diluents, can be configured into larger aggregate forms, such as pellets, extrudates, or other aggregations of catalyst particles. For ease of discussion, such larger forms are generally referred to herein as "pellets". Such pellets may optionally include a binder and/or support material; however, the present inventors have surprisingly found that the disclosed nanowires are particularly suited to used in the form of a pellet without a binder and/or support material. Accordingly, one embodiment of the disclosure provides a catalytic material in the absence of a binder. In this regard, the morphology of the disclosed nanowires (either bent or straight, etc.) is believed to contribute to the nanowires' ability to be pressed into pellets without the need for a binder. Catalytic materials without binders are simpler, less complex and cheaper than corresponding materials with binders and thus offer certain advantages.

In some instances, catalytic materials may be prepared using a "sacrificial binder" or support. Because of their special properties, the nanowires allow for preparation of catalytic material forms (e.g. pellets) without the use of a binder. A "sacrificial" binder can be used in order to create unique microporosity in pellets or extrudates. After removing the sacrificial binder, the structural integrity of the catalyst is ensured by the special binding properties of the nanowires and the resulting catalytic material has unique microporosity as a result of removing the binder. For example, in some embodiments a catalytic nanowire may be prepared with a binder and then the binder removed by any number of techniques (e.g., combustion, calcinations, acid erosion, etc.). This method allows for design and preparation of catalytic materials having unique microporosity (i.e., the microporosity is a function of size, etc. of the sacrificial binder). The ability to prepare different forms (e.g., pellets) of the nanowires without the use of binder is not only useful for preparation of catalytic materials from the nanowires, but also allows the nanowires to be used as support materials (or both catalytic and support material). Sacrificial binders and techniques useful in this regard include sacrificial cellulosic fibers or other organic polymers that can be easily removed by calcination, non-sacrificial binders and techniques useful in this regard include, colloidal oxide binders such as Ludox Silica or Nyacol colloidal zirconia that can also be added to strengthen the formed aggregate when needed. Sacrificial binders are added to increase macro-porosity (pores larger than 20 nm diameter) of the catalytic materials. Accordingly, in some embodiments the catalytic materials comprise pores greater than 20 nm in diameter, greater than 50 nm in diameter, greater than 75 nm in diameter, greater than 100 nm in diameter or greater than 150 nm in diameter.

Catalytic materials also include any of the disclosed nanowires disposed on or adhered to a solid support. For example, the nanowires may be adhered to the surface of a monolith support. As with the binder-less materials discussed above, in these embodiments the nanowires may be adhered to the surface of the monolith in the absence of a binder due to their unique morphology and packing properties. Monoliths include honeycomb-type structures, foams and other catalytic support structures derivable by one skilled in the art. In one embodiment, the support is a honeycomb matrix formed from silicon carbide, and the support further comprises catalytic nanowires disposed on the surface.

As the OCM reaction is very exothermic, it can be desirable to reduce the rate of conversion per unit volume of reactor in order to avoid run away temperature rise in the catalyst bed that can result in hot spots affecting performance and catalyst life. One way to reduce the OCM reaction rate per unit volume of reactor is to spread the active catalyst onto an inert support with interconnected large pores as in ceramic or metallic foams (including metal alloys having reduced reactivity with hydrocarbons under OCM reaction conditions) or having arrays of channel as in honeycomb structured ceramic or metal assembly.

In one embodiment, a catalytic material comprising a catalytic nanowire as disclosed herein supported on a structured support is provided. Examples of such structure supports include, but are not limited to, metal foams, Silicon Carbide or Alumina foams, corrugated metal foil arranged to form channel arrays, extruded ceramic honeycomb, for example Cordierite (available from Corning or NGK ceramics, USA), Silicon Carbide or Alumina.

Active catalyst loading on the structured support ranges from 1 to 500 mg per ml of support component, for example from 5 to 100 mg per ml of structure support. Cell densities on honeycomb structured support materials may range from 100 to 900 CPSI (cell per square inch), for example 200 to 600 CPSI. Foam densities may range from 10 to 100 PPI (pore per inch), for example 20 to 60 PPI.

In other embodiments, the exotherm of the OCM reaction may be at least partially controlled by blending the active catalytic material with catalytically inert material, and pressing or extruding the mixture into shaped pellets or extrudates. In some embodiments, these mixed particles may then be loaded into a pack-bed reactor. The Extrudates or pellets comprise between 30% to 70% pore volume with 5% to 50% active catalyst weight fraction. Useful inert materials in this regard include, but are not limited to MgO, CaO, $Al_2O_3$, SiC and cordierite.

In addition to reducing the potential for hot spots within the catalytic reactor, another advantage of using a structured ceramic with large pore volume as a catalytic support is reduced flow resistance at the same gas hourly space velocity versus a pack-bed containing the same amount of catalyst.

Yet another advantage of using such supports is that the structured support can be used to provide features difficult to obtain in a pack-bed reactor. For example the support structure can improve mixing or enabling patterning of the active catalyst depositions through the reactor volume. Such patterning can consist of depositing multiple layers of catalytic materials on the support in addition to the OCM active component in order to affect transport to the catalyst or combining catalytic functions as adding O2-ODH activity, CO2-OCM activity or CO2-ODH activity to the system in addition to O2-OCM active material. Another patterning strategy can be to create bypass within the structure catalyst essentially free of active catalyst to limit the overall conversion within a given supported catalyst volume.

Yet another advantage is reduced heat capacity of the bed of the structured catalyst over a pack bed a similar active catalyst loading therefore reducing startup time.

Nanowire shaped catalysts are particularly well suited for incorporation into pellets or extrudates or deposition onto structured supports. Nanowire aggregates forming a mesh type structure can have good adhesion onto rough surfaces.

The mesh like structure can also provide improved cohesion in composite ceramic improving the mechanical properties of pellets or extrudates containing the nanowire shaped catalyst particles.

Alternatively, such nanowire on support or in pellet form approaches can be used for other reactions besides OCM, such as ODH, dry methane reforming, FT, and all other catalytic reactions.

In yet another embodiment, the catalysts are packed in bands forming a layered reactor bed. Each layer is composed by either a catalyst of a particular type, morphology or size or a particular blend of catalysts. In one embodiment, the catalysts blend may have better sintering properties, i.e. lower tendency to sinter, then a material in its pure form. Better sintering resistance is expected to increase the catalyst's lifetime and improve the mechanical properties of the reactor bed.

In yet other embodiments, the disclosure provides a catalytic material comprising one or more different catalysts. The catalysts may be a nanowire as disclosed herein and a different catalyst for example a bulk catalysts. Mixtures of two or more nanowire catalysts are also contemplated. The catalytic material may comprise a catalyst, for example a nanowire catalyst, having good OCM activity and a catalyst having good activity in the ODH reaction. Either one or both of these catalysts may be nanowires as disclosed herein.

On skilled in the art will recognize that various combinations or alternatives of the above methods are possible, and such variations are also included within the scope of the present disclosure.

5. Dopants

In further embodiments, the disclosure provides nanowires comprising a dopant (i.e., doped nanowires). As noted above, dopants or doping agents are impurities added to or incorporated within a catalyst to optimize catalytic performance (e.g., increase or decrease catalytic activity). As compared to the undoped catalyst, a doped catalyst may increase or decrease the selectivity, conversion, and/or yield of a catalytic reaction. In one embodiment, nanowire dopants comprise one or more metal elements, semi-metal elements, non-metal elements or combinations thereof. Although oxygen is included in the group of nonmetal elements, in certain embodiments oxygen is not considered a dopant. For example, certain embodiments are directed to nanowires comprising two, three or even four or more dopants, and the dopants are non-oxygen dopants. Thus in these embodiments, a metal oxide nanowire is not considered to be a metal nanowire doped with oxygen. Analagously, in the case of mixed oxides (i.e., $M1_xM2_yO_z$), both the metal elements and oxygen are considered a part of the base catalyst (nanowire) and are not included in the total number of dopants.

The dopant may be present in any form and may be derived from any suitable source of the element (e.g., chlorides, bromides, iodides, nitrates, oxynitrates, oxyhalides, acetates, formates, hydroxides, carbonates, phosphates, sulfates, alkoxides, and the like.). In some embodiments, the nanowire dopant is in elemental form. In other embodiments, the nanowire dopant is in reduced or oxidized form. In other embodiments, the nanowire dopant comprises an oxide, hydroxide, carbonate, nitrate, acetate, sulfate, formate, oxynitrate, halide, oxyhalide or hydroxyhalide of a metal element, semi-metal element or non-metal element or combinations thereof.

In one embodiment, the nanowires comprise one or more metal elements selected from Groups 1-7, lanthanides, actinides or combinations thereof in the form of an oxide and further comprise one or more dopants, wherein the one or more dopants comprise metal elements, semi-metal elements, non-metal elements or combinations thereof. In another embodiment, the nanowires comprise one or more metal elements selected from group 1 in the form of an oxide and further comprise one or more dopants, wherein the one or more dopants comprise metal elements, semi-metal elements, non-metal elements or combinations thereof. In another embodiment, the nanowires comprise one or more metal elements selected from group 2 in the form of an oxide and further comprise one or more dopants, wherein the one or more dopants comprise metal elements, semi-metal elements, non-metal elements or combinations thereof. In another embodiment, the nanowires comprise one or more metal elements selected from group 3 in the form of an oxide and further comprise one or more dopants, wherein the one or more dopants comprise metal elements, semi-metal elements, non-metal elements or combinations thereof. In another embodiment, the nanowires comprise one or more metal elements selected from group 4 in the form of an oxide and further comprise one or more dopants, wherein the one or more dopants comprise metal elements, semi-metal elements, non-metal elements or combinations thereof. In another embodiment, the nanowires comprise one or more metal elements selected from group 5 in the form of an oxide and further comprise one or more dopants, wherein the one or more dopants comprise metal elements, semi-metal elements, non-metal elements or combinations thereof. In another embodiment, the nanowires comprise one or more metal elements selected from group 6 in the form of an oxide and further comprise one or more dopants, wherein the one or more dopants comprise metal elements, semi-metal elements, non-metal elements or combinations thereof. In another embodiment, the nanowires comprise one or more metal elements selected from group 7 in the form of an oxide and further comprise one or more dopants, wherein the one or more dopants comprise metal elements, semi-metal elements, non-metal elements or combinations thereof. In another embodiment, the nanowires comprise one or more metal elements selected from lanthanides in the form of an oxide and further comprise one or more dopants, wherein the one or more dopants comprise metal elements, semi-metal elements, non-metal elements or combinations thereof. In another embodiment, the nanowires comprise one or more metal elements selected from actinides in the form of an oxide and further comprise one or more dopants, wherein the one or more dopants comprise metal elements, semi-metal elements, non-metal elements or combinations thereof.

For example, in one embodiment, the nanowire dopant comprises Li, $Li_2CO_3$, LiOH, $Li_2O$, LiCl, $LiNO_3$, Na, $Na_2CO_3$, NaOH, $Na_2O$, NaCl, $NaNO_3$, K, $K_2CO_3$, KOH, $K_2O$, KCl, $KNO_3$, Rb, $Rb_2CO_3$, RbOH, $Rb_2O$, RbCl, $RbNO_3$, Cs, $Cs_2CO_3$, CsOH, $Cs_2O$, CsCl, $CsNO_3$, Mg, $MgCO_3$, $Mg(OH)_2$, MgO, $MgCl_2$, $Mg(NO_3)_2$, Ca, CaO, $CaCO_3$, $Ca(OH)_2$, $CaCl_2$, $Ca(NO_3)_2$, Sr, SrO, $SrCO_3$, $Sr(OH)_2$, $SrCl_2$, $Sr(NO_3)_2$, Ba, BaO, $BaCO_3$, $Ba(OH)_2$, $BaCl_2$, $Ba(NO_3)_2$, La, $La_2O_3$, $La_2(CO_3)_3$, $La(OH)_3$, $LaCl_3$, $La(NO_3)_2$, Nd, $Nd_2O_3$, $Nd_2(CO_3)_3$, $Nd(OH)_3$, $NdCl_3$, $Nd(NO_3)_2$, Sm, $Sm_2O_3$, $Sm_2(CO_3)_3$, $Sm(OH)_3$, $SmCl_3$, $Sm(NO_3)_2$, Eu, $Eu_2O_3$, $Eu_2(CO_3)_3$, $Eu(OH)_3$, $EuCl_3$, $Eu(NO_3)_2$, Gd, $Gd_2O_3$, $Gd_2(CO_3)_3$, $Gd(OH)_3$, $GdCl_3$, $Gd(NO_3)_2$, Ce, $Ce(OH)_4$, $CeO_2$, $Ce_2O_3$, $Ce(CO_3)_2$, $CeCl_4$, $Ce(NO_3)_2$, Th, $ThO_2$, $ThCl_4$, $Th(OH)_4$, Zr, $ZrO_2$, $ZrCl_4$, $Zr(OH)_4$, $ZrOCl_2$, $Zr(CO_3)2$, $ZrOCO_3$, $ZrO(NO_3)_2$, P, phosphorous oxides, phosphorous chlorides, phosphorous carbonates, Ni, nickel oxides, nickel chlorides, nickel carbonates, nickel hydroxides, Nb, niobium oxides, niobium chlorides, niobium carbonates, niobium hydroxides, Au, gold oxides, gold chlorides, gold carbonates, gold hydroxides, Mo, molybdenum oxides, molybdenum chlorides, molybdenum carbonates, molybdenum hydroxides, tungsten chlorides, tungsten carbonates, tungsten hydroxides, Cr, chromium oxides, chromium chlorides, chromium hydroxides, Mn, manganese oxides, manganese chlorides, manganese hydroxides, Zn, ZnO, $ZnCl_2$, $Zn(OH)_2$, B, borates, $BCl_3$, N, nitrogen oxides, nitrates, La, Ce, Pr, Nd, Pm, Sm, Eu, Gd, Tb, Dy, Ho, Er, Tm, Yb, Lu, In, Y, Sc, Al, Cu, Cs, Ga, Hf, Fe, Ru, Rh, Be, Co, Sb, V, Ag, Te, Pd, Tb, Ir, Rb or combinations thereof. In other embodiments, the nanowire dopant comprises Li, Na, K, Rb, Cs, Mg, Ca, Sr, Eu, In, Nd, Sm, Ce, Gd, Tb, Er, Tm, Yb, Y, Sc or combinations thereof.

In other embodiments, the nanowire dopant comprises Li, $Li_2O$, Na, $Na_2O$, K, $K_2O$, Mg, MgO, Ca, CaO, Sr, SrO, Ba, BaO, La, $La_2O_3$, Ce, $CeO_2$, $Ce_2O_3$, Th, $ThO_2$, Zr, $ZrO_2$, P, phosphorous oxides, Ni, nickel oxides, Nb, niobium oxides, Au, gold oxides, Mo, molybdenum oxides, Cr, chromium oxides, Mn, manganese oxides, Zn, ZnO, B, borates, N, nitrogen oxides or combinations thereof. In other embodiments, the nanowire dopant comprises Li, Na, K, Mg, Ca, Sr, Ba, La, Ce, Th, Zr, P, Ni, Nb, Au, Mo, Cr, Mn, Zn, B, N or combinations thereof. In other embodiments, the nanowire dopant comprises $Li_2O$, $Na_2O$, $K_2O$, MgO, CaO, SrO, BaO, $La_2O_3$, $CeO_2$, $Ce_2O_3$, $ThO_2$, $ZrO_2$, phosphorous oxides, nickel oxides, niobium oxides, gold oxides, molybdenum oxides, chromium oxides, manganese oxides, ZnO, borates, nitrogen oxides or combinations thereof. In further embodiments, the dopant comprises Sr or Li. In other specific embodiments, the nanowire dopant comprises La, Ce, Pr, Nd, Pm, Sm, Eu, Gd, Tb, Dy, Ho, Er, Tm, Yb, Lu, In, Y, Sc or combinations thereof. In other specific embodiments, the nanowire dopant comprises Li, Na, K, Mg, Ca, Ba, Sr, Eu, Sm, Co or Mn.

In certain embodiments, the dopant comprises an element from group 1. In some embodiments, the dopant comprises lithium. In some embodiments, the dopant comprises sodium. In some embodiments, the dopant comprises potassium. In some embodiments, the dopant comprises rubidium. In some embodiments, the dopant comprises caesium.

In some embodiments the nanowires comprise a lanthanide element and are doped with a dopant from group 1, group 2, or combinations thereof. For example, in some embodiments, the nanowires comprise a lanthanide element and are doped with lithium. In other embodiments, the nanowires comprise a lanthanide element and are doped with sodium. In other embodiments, the nanowires comprise a lanthanide element and are doped with potassium. In other embodiments, the nanowires comprise a lanthanide element and are doped with rubidium. In other embodiments, the nanowires comprise a lanthanide element and are doped with caesium. In other embodiments, the nanowires comprise a lanthanide element and are doped with beryllium. In other embodiments, the nanowires comprise a lanthanide element and are doped with magnesium. In other embodiments, the nanowires comprise a lanthanide element and are doped with calcium. In other embodiments, the nanowires comprise a lanthanide element and are doped with strontium. In other embodiments, the nanowires comprise a lanthanide element and are doped with barium.

In some embodiments the nanowires comprise a transition metal tungstate (e.g., Mn/W and the like) and are doped with a dopant from group 1, group 2, or combinations thereof. For example, in some embodiments, the nanowires comprise a transition metal tungstate and are doped with lithium. In other embodiments, the nanowires comprise a transition metal tungstate and are doped with sodium. In other embodiments, the nanowires comprise a transition metal tungstate and are doped with potassium. In other embodiments, the nanowires comprise a transition metal tungstate and are doped with rubidium. In other embodiments, the nanowires comprise a transition metal tungstate and are doped with caesium. In other embodiments, the nanowires comprise a transition metal tungstate and are doped with beryllium. In other embodiments, the nanowires comprise a transition metal tungstate and are doped with magnesium. In other embodiments, the nanowires comprise a transition metal tungstate and are doped with calcium. In other embodiments, the nanowires comprise a transition metal tungstate and are doped with strontium. In other embodiments, the nanowires comprises a transition metal tungstate and are doped with barium.

In some embodiments the nanowires comprise Mn/Mg/O and are doped with a dopant from group 1, group 2, group 7, group 8, group 9 or group 10 or combinations thereof. For example, in some embodiments, the nanowires comprise Mn/Mg/O and are doped with lithium. In other embodiments, the nanowires comprise Mn/Mg/O and are doped with sodium. In other embodiments, the nanowires comprise Mn/Mg/O and are doped with potassium. In other embodiments, the nanowires comprise Mn/Mg/O and are doped with rubidium. In other embodiments, the nanowires comprise Mn/Mg/O and are doped with caesium. In other embodiments, the nanowires comprise Mn/Mg/O and are doped with beryllium. In other embodiments, the nanowires comprise Mn/Mg/O and are doped with magnesium. In other embodiments, the nanowires comprise Mn/Mg/O and are doped with calcium. In other embodiments, the nanowires comprise Mn/Mg/O and are doped with strontium. In other embodiments, the nanowires comprise Mn/Mg/O and are doped with barium.

In yet some other embodiments, the nanowires comprise Mn/Mg/O and are doped with manganese. In other embodiments, the nanowires comprise Mn/Mg/O and are doped with technetium. In other embodiments, the nanowires comprise Mn/Mg/O and are doped with rhenium. In other embodiments, the nanowires comprise Mn/Mg/O and are doped with iron. In other embodiments, the nanowires comprise Mn/Mg/O and are doped with ruthenium. In other embodiments, the nanowires comprise Mn/Mg/O and are doped with osmium. In other embodiments, the nanowires comprise Mn/Mg/O and are doped with cobalt. In other embodiments, the nanowires comprise Mn/Mg/O and are doped with rhodium. In other embodiments, the nanowires comprise Mn/Mg/O and are doped with iridium. In other embodiments, the nanowires comprise Mn/Mg/O and are doped with nickel. In other embodiments, the nanowires comprise Mn/Mg/O and are doped with palladium. In other embodiments, the nanowires comprise Mn/Mg/O and are doped with platinum.

As noted above, the present inventors have determined that certain nanowire catalysts comprising rare earth elements (e.g., rare earth oxides) are useful as catalysts in a number of reactions, for example the OCM reaction. In certain embodiments the rare earth element is La, Nd, Eu, Sm, Yb, Gd or Y. In some embodiments, the rare earth element is La. In other embodiments, the rare earth element is Nd. In other embodiments, the rare earth element is Eu. In other embodiments, the rare earth element is Sm. In other embodiments, the rare earth element is Yb. In other embodiments, the rare earth element is Gd. In other embodiments, the rare earth element is Y.

In certain embodiments of the nanowire catalysts comprising rare earth elements, the catalyst may further comprise a dopant selected from alkaline earth (Group 2) elements. For example, in some embodiments the dopant is selected from Be, Mg, Ca, Sr and Ba. In other embodiments, the dopant is Be. In other embodiments, the dopant is Ca. In other embodiments, the dopant is Sr. In other embodiments, the dopant is Ba.

In some embodiments, these rare earth compositions comprise $La_2O_3$, $Nd_2O_3$, $Yb_2O_3$, $Eu_2O_3$, $Sm_2O_3$, $Y_2O_3$, $Ce_2O_3$, $Pr_2O_3$, $Ln1_{4-x}Ln2_xO_6$, $La_{4-x}Ln1_xO_6$, $La_{4-x}Nd_xO_6$, $La_3NdO_6$, $LaNd_3O_6$, $La_{1.5}Nd_{2.5}O_6$, $La_{2.5}Nd_{1.5}O_6$, $La_{3.2}Nd_{0.8}O_6$, $La_{3.5}Nd_{0.5}O_6$, $La_{3.8}Nd_{0.2}O_6$, Y—La, Zr—La, Pr—La or Ce—La or combinations thereof, wherein Ln1 and Ln2 are each independently a lanthanide element, wherein Ln1 and Ln2 are not the same and x is a number ranging from greater than 0 to less than 4.

Further, Applicants have discovered that certain doping combinations, when combined with the above rare earth compositions, serve to enhance the catalytic activity of the nanowires in certain catalytic reactions, for example OCM. The dopants may be present in various levels (e.g., w/w), and the nanowires may be prepared by any number of methods. Various aspects of the above nanowires are provided in the following paragraphs and in Tables 9-12.

In certain embodiments, the above rare earth compositions comprise a strontium dopant and at least one more additional dopant selected from group 1, 4-6, 13 and lanthanides. For example, in some embodiments the additional dopant is Hf, K, Zr, Ce, Tb, Pr, W, Rb, Ta, B or combinations thereof. In other embodiments, the dopant comprises Sr/Hf, Sr/Hf/K, Sr/Zr, Sr/Zr/K, Sr/Ce, Sr/Ce/K, Sr/Tb, Sr/Tb/K, Sr/Pr, Sr/Pr/K, Sr/W, Sr/Hf/Rb, Sr/Ta or Sr/B. In some other embodiments, the foregoing rare earth nanowires comprise $La_2O_3$ or $La_3NdO_6$.

In other embodiments, the nanowire catalysts comprise a rare earth oxide and dopants selected from at least one of the following combinations Eu/Na, Sr/Na, Mg/Na, Sr/W, K/La, K/Na, Li/Cs, Li/Na, Zn/K, Li/K, Rb/Hf, Ca/Cs, Hf/Bi, Sr/Sn, Sr/W, Sr/Nb, Zr/W, Y/W, Na/W, Bi/W, Bi/Cs, Bi/Ca, Bi/Sn, Bi/Sb, Ge/Hf, Hf/Sm, Sb/Ag, Sb/Bi, Sb/Au, Sb/Sm, Sb/Sr, Sb/W, Sb/Hf, Sb/Yb, Sb/Sn, Yb/Au, Yb/Ta, Yb/W, Yb/Sr, Yb/Pb, Yb/W, Yb/Ag, Au/Sr, W/Ge, Ta/Hf, W/Au, Ca/W, Au/Re, Sm/Li, La/K, Zn/Cs, Zr/Cs, Ca/Ce, Li/Sr, Cs/Zn, Dy/K, La/Mg, In/Sr, Sr/Cs, Ga/Cs, Lu/Fe, Sr/Tm, La/Dy, Mg/K, Zr/K, Li/Cs, Sm/Cs, In/K, Lu/Tl, Pr/Zn, Lu/Nb, Na/Pt, Na/Ce, Ba/Ta, Cu/Sn, Ag/Au, Al/Bi, Al/Mo, Al/Nb, Au/Pt, Ga/Bi, Mg/W, Pb/Au, Sn/Mg, Zn/Bi, Gd/Ho, Zr/Bi, Ho/Sr, Ca/Sr, Sr/Pb and Sr/Hf.

In still other embodiments, the nanowire catalysts comprise a rare earth oxide and dopants selected from at least one of the following combinations La/Nd, La/Sm, La/Ce, La/Sr, Eu/Na, Eu/Gd, Ca/Na, Eu/Sm, Eu/Sr, Mg/Sr, Ce/Mg, Gd/Sm, Sr/W, Sr/Ta, Au/Re, Au/Pb, Bi/Hf, Sr/Sn or Mg/N, Ca/S, Rb/S, Sr/Nd, Eu/Y, Mg/Nd, Sr/Na, Nd/Mg, La/Mg, Yb/S, Mg/Na, Sr/W, K/La, K/Na, Li/Cs, Li/Na, Zn/K, Li/K, Rb/Hf, Ca/Cs, Hf/Bi, Sr/Sn, Sr/W, Sr/Nb, Zr/W, Y/W, Na/W, Bi/W, Bi/Cs, Bi/Ca, Bi/Sn, Bi/Sb, Ge/Hf, Hf/Sm, Sb/Ag, Sb/Bi, Sb/Au, Sb/Sm, Sb/Sr, Sb/W, Sb/Hf, Sb/Yb, Sb/Sn, Yb/Au, Yb/Ta, Yb/W, Yb/Sr, Yb/Pb, Yb/W, Yb/Ag, Au/Sr, W/Ge, Ta/Hf, W/Au, Ca/W, Au/Re, Sm/Li, La/K, Zn/Cs, Zr/Cs, Ca/Ce, Li/Sr, Cs/Zn, Dy/K, La/Mg, In/Sr, Sr/Cs, Ga/Cs, Lu/Fe, Sr/Tm, La/Dy, Mg/K, Zr/K, Li/Cs, Sm/Cs, In/K, Lu/Tl, Pr/Zn, Lu/Nb, Na/Pt, Na/Ce, Ba/Ta, Cu/Sn, Ag/Au, Al/Bi, Al/Mo, Al/Nb, Au/Pt, Ga/Bi, Mg/W, Pb/Au, Sn/Mg, Zn/Bi, Gd/Ho, Zr/Bi, Ho/Sr, Ca/Sr, Sr/Pb and Sr/Hf.

In other embodiments of the foregoing rare earth oxide nanowire catalysts, the nanowire catalysts comprise a combination of two doping elements. In some embodiments, the combination of two doping elements is La/Nd. In other embodiments, the combination of two doping elements is La/Sm. In other embodiments, the combination of two doping elements is La/Ce. In other embodiments, the combination of two doping elements is La/Sr. In other embodiments, the combination of two doping elements is Eu/Na. In other embodiments, the combination of two doping elements is Eu/Gd. In other embodiments, the combination of two doping elements is Ca/Na. In other embodiments, the combination of two doping elements is Eu/Sm. In other embodiments, the combination of two doping elements is Eu/Sr. In other embodiments, the combination of two doping elements is Mg/Sr. In other embodiments, the combination of two doping elements is Ce/Mg. In other embodiments, the combination of two doping elements is Gd/Sm. In other embodiments, the combination of two doping elements is Sr/W. In other embodiments, the combination of two doping elements is Sr/Ta. In other embodiments, the combination of two doping elements is Au/Re. In other embodiments, the combination of two doping elements is Au/Pb. In other embodiments, the combination of two doping elements is Bi/Hf. In other embodiments, the combination of two doping elements is Sr/Sn. In other embodiments, the combination of two doping elements is Mg/N. In other embodiments, the combination of two doping elements is Ca/S. In other embodiments, the combination of two doping elements is Rb/S. In other embodiments, the combination of two doping elements is Sr/Nd. In other embodiments, the combination of two doping elements is Eu/Y. In other embodiments, the combination of two doping elements is Mg/Nd. In other embodiments, the combination of two doping elements is Sr/Na. In other embodiments, the combination of two doping elements is Nd/Mg. In other embodiments, the combination of two doping elements is La/Mg. In other embodiments, the combination of two doping elements is Yb/S. In other embodiments, the combination of two doping elements is Mg/Na. In other embodiments, the combination of two doping elements is Sr/W. In other embodiments, the combination of two doping elements is K/La. In other embodiments, the combination of two doping elements is K/Na. In other embodiments, the combination of two doping elements is Li/Cs. In other embodiments, the combination of two doping elements is Li/Na. In other embodiments, the combination of two doping elements is Zn/K. In other embodiments, the combination of two doping elements is Li/K. In other embodiments, the combination of two doping elements is Rb/Hf. In other embodiments, the combination of two doping elements is Ca/Cs. In other embodiments, the combination of two doping elements is Hf/Bi. In other embodiments, the combination of two doping elements is Sr/Sn. In other embodiments, the combination of two doping elements is Sr/W. In other embodiments, the combination of two doping elements is Sr/Nb. In other embodiments, the combination of two doping elements is Zr/W. In other embodiments, the combination of two doping elements is Y/W. In other embodiments, the combination of two doping elements is Na/W. In other embodiments, the combination of two doping elements is Bi/W. In other embodiments, the combination of two doping elements is Bi/Cs. In other embodiments, the combination of two doping elements is Bi/Ca. In other embodiments, the combination of two doping elements is Bi/Sn. In other embodiments, the combination of two doping elements is Bi/Sb. In other embodiments, the combination of two doping elements is Ge/Hf. In other embodiments, the combination of two doping elements is Hf/Sm. In other embodiments, the combination of two doping elements is Sb/Ag. In other embodiments, the combination of two doping elements is Sb/Bi. In other embodiments, the combination of two doping elements is Sb/Au. In other embodiments, the combination of two doping elements is Sb/Sm. In other embodiments, the combination of two doping elements is Sb/Sr. In other embodiments, the combination of two doping elements is Sb/W. In other embodiments, the combination of two doping elements is Sb/Hf. In other embodiments, the combination of two doping elements is Sb/Yb. In other embodiments, the combination of two doping elements is Sb/Sn. In other embodiments, the combination of two doping elements is Yb/Au. In other embodiments, the combination of two doping elements is Yb/Ta. In other embodiments, the combination of two doping elements is Yb/W. In other embodiments, the combination of two doping elements is Yb/Sr. In other embodiments, the combination of two doping elements is Yb/Pb. In other embodiments, the combination of two doping elements is Yb/W. In other embodiments, the combination of two doping elements is Yb/Ag. In other embodiments, the combination of two doping elements is Au/Sr. In other embodiments, the combination of two doping elements is W/Ge. In other embodiments, the combination of two doping elements is Ta/Hf. In other embodiments, the combination of two doping elements is W/Au. In other embodiments, the combination of two doping elements is Ca/W. In other embodiments, the combination of two doping elements is Au/Re. In other embodiments, the combination of two doping elements is Sm/Li. In other embodiments, the combination of two doping elements is La/K. In other embodiments, the combination of two doping elements is Zn/Cs. In other embodiments, the combination of two doping elements is Zr/Cs. In other embodiments, the combination of two doping elements is Ca/Ce. In other embodiments, the combination of two doping elements is Li/Sr. In other embodiments, the combination of two doping elements is Cs/Zn. In other embodiments, the combination of two doping elements is Dy/K. In other embodiments, the combination of two doping elements is La/Mg. In other embodiments, the combination of two doping elements is In/Sr. In other embodiments, the combination of two doping elements is Sr/Cs. In other embodiments, the combination of two doping elements is Ga/Cs. In other embodiments, the combination of two doping elements is Lu/Fe. In other embodiments, the combination of two doping elements is Sr/Tm. In other embodiments, the combination of two doping elements is La/Dy. In other embodiments, the combination of two doping elements is Mg/K. In other embodiments, the combination of two doping elements is Zr/K. In other embodiments, the combination of two doping elements is Li/Cs. In other embodiments, the combination of two doping elements is Sm/Cs. In other embodiments, the combination of two doping elements is In/K. In other embodiments, the combination of two doping elements is Lu/Tl. In other embodiments, the combination of two doping elements is Pr/Zn. In other embodiments, the combination of two doping elements is Lu/Nb. In other embodiments, the combination of two doping elements is Na/Pt. In other embodiments, the combination of two doping elements is Na/Ce. In other embodiments, the combination of two doping elements is Ba/Ta. In other embodiments, the combination of two doping elements is Cu/Sn. In other embodiments, the combination of two doping elements is Ag/Au. In other embodiments, the combination of two doping elements is Al/Bi. In other embodiments, the combination of two doping elements is Al/Mo. In other embodiments, the combination of two doping elements is Al/Nb. In other embodiments, the combination of two doping elements is Au/Pt. In other embodiments, the combination of two doping elements is Ga/Bi. In other embodiments, the combination of two doping elements is Mg/W. In other embodiments, the combination of two doping elements is Pb/Au. In other embodiments, the combination of two doping elements is Sn/Mg. In other embodiments, the combination of two doping elements is Zn/Bi. In other embodiments, the combination of two doping elements is Gd/Ho. In other embodiments, the combination of two doping elements is Zr/Bi. In other embodiments, the combination of two doping elements is Ho/Sr. In other embodiments, the combination of two doping elements is Ca/Sr. In other embodiments, the combination of two doping elements is Sr/Pb. In other embodiments, the combination of two doping elements is Sr/Hf.

In still other embodiments, the nanowire catalysts comprise a rare earth oxide and dopants selected from at least one of the following combinations Mg/La/K, Na/Dy/K, Na/La/Dy, Na/La/Eu, Na/La/K, K/La/S, Li/Cs/La, Li/Sr/Cs, Li/Ga/Cs, Li/Na/Sr, Li/Sm/Cs, Cs/K/La, Sr/Cs/La, Sr/Ho/Tm, La/Nd/S, Li/Rb/Ca, Rb/Sr/Lu, Na/Eu/Hf, Dy/Rb/Gd, Na/Pt/Bi, Ca/Mg/Na, Na/K/Mg, Na/Li/Cs, La/Dy/K, Sm/Li/Sr, Li/Rb/Ga, Li/Cs/Tm, Li/K/La, Ce/Zr/La, Ca/Al/La, Sr/Zn/La, Cs/La/Na, La/S/Sr, Rb/Sr/La, Na/Sr/Lu, Sr/Eu/Dy, La/Dy/Gd, Gd/Li/K, Rb/K/Lu, Na/Ce/Co, Ba/Rh/Ta, Na/Al/Bi, Cs/Eu/S, Sm/Tm/Yb, Hf/Zr/Ta, Na/Ca/Lu, Gd/Ho/Sr, Ca/Sr/W, Na/Zr/Eu/Tm, Sr/W/Li, Ca/Sr/W or Mg/Nd/Fe.

In more embodiments, the nanowire catalysts comprise a rare earth oxide and dopants selected from at least one of the following combinations Nd/Sr/CaO, La/Nd/Sr, La/Bi/Sr, Mg/Nd/Fe, Mg/La/K, Na/Dy/K, Na/La/Dy, Na/La/Eu, Na/La/K, K/La/S, Li/Cs/La, Li/Sr/Cs, Li/Ga/Cs, Li/Na/Sr, Li/Sm/Cs, Cs/K/La, Sr/Cs/La, Sr/Ho/Tm, La/Nd/S, Li/Rb/Ca, Rb/Sr/Lu, Na/Eu/Hf, Dy/Rb/Gd, Na/Pt/Bi, Ca/Mg/Na, Na/K/Mg, Na/Li/Cs, La/Dy/K, Sm/Li/Sr, Li/Rb/Ga, Li/Cs/Tm, Li/K/La, Ce/Zr/La, Ca/Al/La, Sr/Zn/La, Cs/La/Na, La/S/Sr, Rb/Sr/La, Na/Sr/Lu, Sr/Eu/Dy, La/Dy/Gd, Gd/Li/K, Rb/K/Lu, Na/Ce/Co, Ba/Rh/Ta, Na/Al/Bi, Cs/Eu/S, Sm/Tm/Yb, Hf/Zr/Ta, Na/Ca/Lu, Gd/Ho/Sr, Ca/Sr/W, Na/Zr/Eu/Tm, Sr/W/Li or Ca/Sr/W.

In other embodiments of the foregoing rare earth oxide nanowire catalysts, the nanowire catalysts comprise a combination of at least three doping elements. In some embodiments, the combination of at least three different doping elements is Nd/Sr/CaO. In other embodiments, the combination of at least three different doping elements is La/Nd/Sr. In other embodiments, the combination of at least three different doping elements is La/Bi/Sr. In other embodiments, the combination of at least three different doping elements is Mg/Nd/Fe. In other embodiments, the combination of at least three different doping elements is Mg/La/K. In other embodiments, the combination of at least three different doping elements is Na/Dy/K. In other embodiments, the combination of at least three different doping elements is Na/La/Dy. In other embodiments, the combination of at least three different doping elements is Na/La/Eu. In other embodiments, the combination of at least three different doping elements is Na/La/K. In other embodiments, the combination of at least three different doping elements is K/La/S. In other embodiments, the combination of at least three different doping elements is Li/Cs/La. In other embodiments, the combination of at least three different doping elements is Li/Sr/Cs. In other embodiments, the combination of at least three different doping elements is Li/Ga/Cs. In other embodiments, the combination of at least three different doping elements is Li/Na/Sr. In other embodiments, the combination of at least three different doping elements is Li/Sm/Cs. In other embodiments, the combination of at least three different doping elements is Cs/K/La. In other embodiments, the combination of at least three different doping elements is Sr/Cs/La. In other embodiments, the combination of at least three different doping elements is Sr/Ho/Tm. In other embodiments, the combination of at least three different doping elements is La/Nd/S. In other embodiments, the combination of at least three different doping elements is Li/Rb/Ca. In other embodiments, the combination of at least three different doping elements is Rb/Sr/Lu. In other embodiments, the combination of at least three different doping elements is Na/Eu/Hf. In other embodiments, the combination of at least three different doping elements is Dy/Rb/Gd. In other embodiments, the combination of at least three different doping elements is Na/Pt/Bi. In other embodiments, the combination of at least three different doping elements is Ca/Mg/Na. In other embodiments, the combination of at least three different doping elements is Na/K/Mg. In other embodiments, the combination of at least three different doping elements is Na/Li/Cs. In other embodiments, the combination of at least three different doping elements is La/Dy/K. In other embodiments, the combination of at least three different doping elements is Sm/Li/Sr. In other embodiments, the combination of at least three different doping elements is Li/Rb/Ga. In other embodiments, the combination of at least three different doping elements is Li/Cs/Tm. In other embodiments, the combination of at least three different doping elements is Li/K/La. In other embodiments, the combination of at least three different doping elements is Ce/Zr/La. In other embodiments, the combination of at least three different doping elements is Ca/Al/La. In other embodiments, the combination of at least three different doping elements is Sr/Zn/La. In other embodiments, the combination of at least three different doping elements is Cs/La/Na. In other embodiments, the combination of at least three different doping elements is La/S/Sr. In other embodiments, the combination of at least three different doping elements is Rb/Sr/La. In other embodiments, the combination of at least three different doping elements is Na/Sr/Lu. In other embodiments, the combination of at least three different doping elements is Sr/Eu/Dy. In other embodiments, the combination of at least three different doping elements is La/Dy/Gd. In other embodiments, the combination of at least three different doping elements is Gd/Li/K. In other embodiments, the combination of at least three different doping elements is Rb/K/Lu. In other embodiments, the combination of at least three different doping elements is Na/Ce/Co. In other embodiments, the combination of at least three different doping elements is Ba/Rh/Ta. In other embodiments, the combination of at least three different doping elements is Na/Al/Bi. In other embodiments, the combination of at least three different doping elements is Cs/Eu/S. In other embodiments, the combination of at least three different doping elements is Sm/Tm/Yb. In other embodiments, the combination of at least three different doping elements is Hf/Zr/Ta. In other embodiments, the combination of at least three different doping elements is Na/Ca/Lu. In other embodiments, the combination of at least three different doping elements is Gd/Ho/Sr. In other embodiments, the combination of at least three different doping elements is Ca/Sr/W. In other embodiments, the combination of at least three different doping elements is Na/Zr/Eu/Tm. In other embodiments, the combination of at least three different doping elements is Sr/W/Li. In other embodiments, the combination of at least three different doping elements is Ca/Sr/W.

As noted above, certain doping combinations have been found useful in various catalytic reactions, such as OCM. Thus, in one embodiment, the catalytic nanowire comprises a combination of at least four different doping elements, wherein the doping elements are selected from a metal element, a semi-metal element and a non-metal element. For example in certain embodiments the catalytic nanowire comprises a metal oxide, and in other embodiments the catalytic nanowire comprises a lanthanide metal. Still other embodiments provide a catalytic nanowire comprising $La_2O_3$, $Nd_2O_3$, $Yb_2O_3$, $Eu_2O_3$, $Sm_2O_3$, $Y_2O_3$, $Ce_2O_3$, $Pr_2O_3$ or combinations thereof. In still other embodiments, the doping elements do not include at least one of Li, B, Na, Co or Ga, and in other embodiments the nanowires do not comprise Mg and/or Mn.

In other embodiments, the catalytic nanowire comprises a lanthanide oxide, for example a lanthanide mixed oxide, for example in some embodiments the catalytic nanowire comprises $Ln1_{4-x}Ln2_xO_6$, wherein Ln1 and Ln2 are each independently a lanthanide element, wherein Ln1 and Ln2 are not the same and x is a number ranging from greater than 0 to less than 4. In other embodiments, the catalytic nanowire comprises $La_{4-x}Nd_xO_6$, wherein x is a number ranging from greater than 0 to less than 4, and in still other embodiments, the catalytic nanowire comprises $La_3NdO_6$, $LaNd_3O_6$, $La_{1.6}Nd_{2.5}O_6$, $La_{2.5}Nd_{1.5}O_6$, $La_{3.2}Nd_{0.8}O_6$, $La_{3.6}Nd_{0.6}O_6$, $La_{3.8}Nd_{0.2}O_6$ or combinations thereof. In certain other embodiments the mixed oxide comprises Y—La, Zr—La, Pr—La, Ce—La or combinations thereof.

In other embodiments, the doping elements are selected from Eu, Na, Sr, Ca, Mg, Sm, Ho, Tm, W, La, K, Dy, In, Li, Cs, S, Zn, Ga, Rb, Ba, Yb, Ni, Lu, Ta, P, Hf, Tb, Gd, Pt, Bi, Sn, Nb, Sb, Ge, Ag, Au, Pb, B, Re, Fe, Al, Zr, Tl, Pr, Co, Ce, Rh, and Mo. For example, in some embodiments, the combination of at least four different doping elements is: Na/Zr/Eu/Ca, Sr/Sm/Ho/Tm, Na/K/Mg/Tm, Na/La/Eu/In, Na/La/Li/Cs, Li/Cs/La/Tm, Li/Cs/Sr/Tm, Li/Sr/Cs, Li/Sr/Zn/K, Li/K/Sr/La, Li/Na/Rb/Ga, Li/Na/Sr/La, Ba/Sm/Yb/S, Ba/Tm/K/La, Ba/Tm/Zn/K, Cs/La/Tm/Na, Cs/Li/K/La, Sm/Li/Sr/Cs, Sr/Tm/Li/Cs, Zr/Cs/K/La, Rb/Ca/In/Ni, Tm/Lu/Ta/P, Rb/Ca/Dy/P, Mg/La/Yb/Zn, Na/Sr/Lu/Nb, Na/Nd/In/K, Rb/Ga/Tm/Cs, K/La/Zr/Ag, Ho/Cs/Li/La, K/La/Zr/Ag, Na/Sr/Eu/Ca, K/Cs/Sr/La, Na/Mg/Tl/P, Sr/La/Dy/S, Na/Ga/Gd/Al, Sm/Tm/Yb/Fe, Rb/Gd/Li/K, Gd/Ho/Al/P, Na/Zr/Eu/Tm Sr/Ho/Tm/Na or Rb/Ga/Tm/Cs or La/Bi/Ce/Nd/Sr.

In other embodiments, the combination of at least four different doping elements is Sr/Sm/Ho/Tm. In other embodiments, the combination of at least four different doping elements is Na/K/Mg/Tm. In other embodiments, the combination of at least four different doping elements is Na/La/Eu/In. In other embodiments, the combination of at least four different doping elements is Na/La/Li/Cs. In other embodiments, the combination of at least four different doping elements is Li/Cs/La/Tm. In other embodiments, the combination of at least four different doping elements is Li/Cs/Sr/Tm. In other embodiments, the combination of at least four different doping elements is Li/Sr/Zn/K. In other embodiments, the combination of at least four different doping elements is Li/Ga/Cs. In other embodiments, the combination of at least four different doping elements is Li/K/Sr/La. In other embodiments, the combination of at least four different doping elements is Li/Na/Rb/Ga. In other embodiments, the combination of at least four different doping elements is Li/Na/Sr/La. In other embodiments, the combination of at least four different doping elements is Ba/Sm/Yb/S. In other embodiments, the combination of at least four different doping elements is Ba/Tm/K/La. In other embodiments, the combination of at least four different doping elements is Ba/Tm/Zn/K. In other embodiments, the combination of at least four different doping elements is Cs/La/Tm/Na. In other embodiments, the combination of at least four different doping elements is Cs/Li/K/La. In other embodiments, the combination of at least four different doping elements is Sm/Li/Sr/Cs. In other embodiments, the combination of at least four different doping elements is Sr/Tm/Li/Cs. In other embodiments, the combination of at least four different doping elements is Zr/Cs/K/La. In other embodiments, the combination of at least four different doping elements is Rb/Ca/In/Ni. In other embodiments, the combination of at least four different doping elements is Tm/Lu/Ta/P. In other embodiments, the combination of at least four different doping elements is Rb/Ca/Dy/P. In other embodiments, the combination of at least four different doping elements is Mg/La/Yb/Zn. In other embodiments, the combination of at least four different doping elements is Na/Sr/Lu/Nb. In other embodiments, the combination of at least four different doping elements is Na/Nd/In/K. In other embodiments, the combination of at least four different doping elements is K/La/Zr/Ag. In other embodiments, the combination of at least four different doping elements is Ho/Cs/Li/La. In other embodiments, the combination of at least four different doping elements is K/La/Zr/Ag. In other embodiments, the combination of at least four different doping elements is Na/Sr/Eu/Ca. In other embodiments, the combination of at least four different doping elements is K/Cs/Sr/La. In other embodiments, the combination of at least four different doping elements is Na/Mg/Tl/P. In other embodiments, the combination of at least four different doping elements is Sr/La/Dy/S. In other embodiments, the combination of at least four different doping elements is Na/Ga/Gd/Al. In other embodiments, the combination of at least four different doping elements is Sm/Tm/Yb/Fe. In other embodiments, the combination of at least four different doping elements is Rb/Gd/Li/K. In other embodiments, the combination of at least four different doping elements is Gd/Ho/Al/P. In other embodiments, the combination of at least four different doping elements is Na/Zr/Eu/T. In other embodiments, the combination of at least four different doping elements is Sr/Ho/Tm/Na. In other embodiments, the combination of at least four different doping elements is Na/Zr/Eu/Ca. In other embodiments, the combination of at least four different doping elements is Rb/Ga/Tm/Cs. In other embodiments, the combination of at least four different doping elements is La/Bi/Ce/Nd/Sr.

In other embodiments, the catalytic nanowire comprises at least two different doping elements, wherein the doping elements are selected from a metal element, a semi-metal element and a non-metal element, and wherein at least one of the doping elements is K, Sc, Ti, V, Nb, Ru, Os, Ir, Cd, In, Tl, S, Se, Po, Pr, Tb, Dy, Ho, Er, Tm, Lu or an element selected from any of groups 6, 7, 10, 11, 14, 15 or 17. In some embodiments, at least one of the doping elements is K, Ti, V, Nb, Ru, Os, Ir, Cd, In, Tl, S, Se, Po, Pr, Tb, Dy, Ho, Er, Tm, Lu or an element selected from any of groups 10, 11, 14, 15 or 17. In certain other embodiments of the foregoing catalytic nanowire, the catalytic nanowire comprises a metal oxide, and in other embodiments the catalytic nanowire comprises a lanthanide metal. In still other embodiments the catalytic nanowire comprises $La_2O_3$, $Nd_2O_3$, $Yb_2O_3$, $Eu_2O_3$, $Sm_2O_3$, $Y_2O_3$, $Ce_2O_3$, $Pr_2O_3$ or combinations thereof.

In other embodiments of the foregoing catalytic nanowire, the catalytic nanowire comprises a lanthanide oxide, for example a lanthanide mixed oxide, for example in some embodiments the catalytic nanowire comprises $Ln1_{4-x}Ln2_xO_6$, wherein Ln1 and Ln2 are each independently a lanthanide element, wherein Ln1 and Ln2 are not the same and x is a number ranging from greater than 0 to less than 4. In other embodiments, the catalytic nanowire comprises $La_{4-x}Nd_xO_6$, wherein x is a number ranging from greater than 0 to less than 4, and in still other embodiments, the catalytic nanowire comprises $La_3NdO_6$, $LaNd_3O_6$, $La_{1.5}Nd_{2.5}O_6$, $La_{2.5}Nd_{1.5}O_6$, $La_{3.2}Nd_{0.8}O_6$, $La_{3.5}Nd_{0.5}O_6$, $La_{3.8}Nd_{0.2}O_6$ or combinations thereof. In certain other embodiments the mixed oxide comprises Y—La, Zr—La, Pr—La, Ce—La or combinations thereof.

In other embodiments of the nanowire comprising at least two doping elements, the doping elements are selected from Eu, Na, Sr, Ca, Mg, Sm, Ho, Tm, W, La, K, Dy, In, Li, Cs, S, Zn, Ga, Rb, Ba, Yb, Ni, Lu, Ta, P, Hf, Tb, Gd, Pt, Bi, Sn, Nb, Sb, Ge, Ag, Au, Pb, B, Re, Fe, Al, Zr, Tl, Pr, Co, Ce, Rh, and Mo.

In yet another aspect, the present disclosure provides a catalytic nanowire comprising at least one of the following dopant combinations: Eu/Na, Sr/Na, Na/Zr/Eu/Ca, Mg/Na, Sr/Sm/Ho/Tm, Sr/W, Mg/La/K, Na/K/Mg/Tm, Na/Dy/K, Na/La/Dy, Sr/Hf/K, Na/La/Eu, Na/La/Eu/In, Na/La/K, Na/La/Li/Cs, K/La, K/La/S, K/Na, Li/Cs, Li/Cs/La, Li/Cs/

La/Tm, Li/Cs/Sr/Tm, Li/Sr/Cs, Li/Sr/Zn/K, Li/Ga/Cs, Li/K/Sr/La, Li/Na, Li/Na/Rb/Ga, Li/Na/Sr, Li/Na/Sr/La, Sr/Zr, Li/Sm/Cs, Ba/Sm/Yb/S, Ba/Tm/K/La, Ba/Tm/Zn/K, Sr/Zr/K, Cs/K/La, Cs/La/Tm/Na, Cs/Li/K/La, Sm/Li/Sr/Cs, Sr/Cs/La, Sr/Tm/Li/Cs, Zn/K, Zr/Cs/K/La, Rb/Ca/In/Ni, Sr/Ho/Tm, La/Nd/S, Li/Rb/Ca, Li/K, Tm/Lu/Ta/P, Rb/Ca/Dy/P, Mg/La/Yb/Zn, Rb/Sr/Lu, Na/Sr/Lu/Nb, Na/Eu/Hf, Dy/Rb/Gd, Sr/Ce, Na/Pt/Bi, Rb/Hf, Ca/Cs, Ca/Mg/Na, Hf/Bi, Sr/Sn, Sr/W, Sr/Nb, Sr/Ce/K, Zr/W, Y/W, Na/W, Bi/W, Bi/Cs, Bi/Ca, Bi/Sn, Bi/Sb, Ge/Hf, Hf/Sm, Sb/Ag, Sb/Bi, Sb/Au, Sb/Sm, Sb/Sr, Sb/W, Sb/Hf, Sb/Yb, Sb/Sn, Yb/Au, Yb/Ta, Yb/W, Yb/Sr, Yb/Pb, Yb/W, Yb/Ag, Au/Sr, W/Ge, Sr/Tb, Ta/Hf, W/Au, Ca/W, Au/Re, Sm/Li, La/K, Zn/Cs, Na/K/Mg, Zr/Cs, Ca/Ce, Na/Li/Cs, Li/Sr, Cs/Zn, La/Dy/K, Dy/K, La/Mg, Na/Nd/In/K, In/Sr, Sr/Cs, Rb/Ga/Tm/Cs, Ga/Cs, K/La/Zr/Ag, Lu/Fe, Sr/Tb/K, Sr/Tm, La/Dy, Sm/Li/Sr, Mg/K, Sr/Pr, Li/Rb/Ga, Li/Cs/Tm, Zr/K, Li/Cs, Li/K/La, Ce/Zr/La, Ca/Al/La, Sr/Zn/La, Sr/Cs/Zn, Sm/Cs, In/K, Ho/Cs/Li/La, Sr/Pr/K, Cs/La/Na, La/S/Sr, K/La/Zr/Ag, Lu/Tl, Pr/Zn, Rb/Sr/La, Na/Sr/Eu/Ca, K/Cs/Sr/La, Na/Sr/Lu, Sr/Eu/Dy, Lu/Nb, La/Dy/Gd, Na/Mg/Tl/P, Na/Pt, Gd/Li/K, Rb/K/Lu, Sr/La/Dy/S, Na/Ce/Co, Na/Ce, Na/Ga/Gd/Al, Ba/Rh/Ta, Ba/Ta, Na/Al/Bi, Sr/Hf/Rb, Cs/Eu/S, Sm/Tm/Yb/Fe, Sm/Tm/Yb, Hf/Zr/Ta, Rb/Gd/Li/K, Gd/Ho/Al/P, Na/Ca/Lu, Cu/Sn, Ag/Au, Al/Bi, Al/Mo, Al/Nb, Au/Pt, Ga/Bi, Mg/W, Pb/Au, Sn/Mg, Sr/B, Zn/Bi, Gd/Ho, Zr/Bi, Ho/Sr, Gd/Ho/Sr, Ca/Sr, Ca/Sr/W, Sr/Ho/Tm/Na, Na/Zr/Eu/Tm, Sr/Ho/Tm/Na, Sr/Pb, Sr/W/Li, Ca/Sr/W or Sr/Hf.

In other embodiments of the foregoing catalytic nanowire, the dopant is selected from Cs/Eu/S, Sm/Tm/Yb/Fe, Sm/Tm/Yb, Hf/Zr/Ta, Rb/Gd/Li/K, Gd/Ho/Al/P, Na/Ca/Lu, Cu/Sn, Ag/Au, Al/Bi, Al/Mo, Al/Nb, Au/Pt, Ga/Bi, Mg/W, Pb/Au, Sn/Mg, Zn/Bi, Gd/Ho, Zr/Bi, Ho/Sr, Gd/Ho/Sr, Ca/Sr, Ca/Sr/W, Na/Zr/Eu/Tm, Sr/Ho/Tm/Na, Sr/Pb, Ca, Sr/W/Li, Ca/Sr/W, Sr/Hf, Eu/Na, Sr/Na, Na/Zr/Eu/Ca, Mg/Na, Sr/Sm/Ho/Tm, Sr/W, Mg/La/K, Na/K/Mg/Tm, Na/Dy/K, Na/La/Dy, Na/La/Eu, Na/La/Eu/In, Na/La/K, Na/La/Li/Cs, K/La, K/La/S, K/Na, Li/Cs, Li/Cs/La, Li/Cs/La/Tm, Li/Cs/Sr/Tm, Li/Sr/Cs, Li/Sr/Zn/K, Li/Ga/Cs, Li/K/Sr/La, Li/Na, Li/Na/Rb/Ga and Li/Na/Sr.

In still other embodiments of the foregoing catalytic nanowire the dopant is selected from Li/Na/Sr/La, Li/Sm/Cs, Ba/Sm/Yb/S, Ba/Tm/K/La, Ba/Tm/Zn/K, Cs/K/La, Cs/La/Tm/Na, Cs/Li/K/La, Sm/Li/Sr/Cs, Sr/Cs/La, Sr/Tm/Li/Cs, Zn/K, Zr/Cs/K/La, Rb/Ca/In/Ni, Sr/Ho/Tm, La/Nd/S, Li/Rb/Ca, Li/K, Tm/Lu/Ta/P, Rb/Ca/Dy/P, Mg/La/Yb/Zn, Rb/Sr/Lu, Na/Sr/Lu/Nb, Na/Eu/Hf, Dy/Rb/Gd, Na/Pt/Bi, Rb/Hf, Ga/Cs, K/La/Zr/Ag, Lu/Fe, Sr/Tm, La/Dy, Sm/Li/Sr, Mg/K, Li/Rb/Ga, Li/Cs/Tm, Zr/K, Li/Cs, Li/K/La, Ce/Zr/La, Ca/Al/La, Sr/Zn/La, Sr/Cs/Zn, Sm/Cs, In/K, Ho/Cs/Li/La, Cs/La/Na, La/S/Sr, K/La/Zr/Ag, Lu/Tl, Pr/Zn, Rb/Sr/La, Na/Sr/Eu/Ca, K/Cs/Sr/La, Na/Sr/Lu, Sr/Eu/Dy, Lu/Nb, La/Dy/Gd, Na/Mg/Tl/P, Na/Pt, Gd/Li/K, Rb/K/Lu, Sr/La/Dy/S, Na/Ce/Co, Na/Ce, Na/Ga/Gd/Al, Ba/Rh/Ta, Ba/Ta, Na/Al/Bi, Cs/Eu/S, Sm/Tm/Yb/Fe, Sm/Tm/Yb, Hf/Zr/Ta, Rb/Gd/Li/K, Gd/Ho/Al/P and Na/Ca/Lu.

In still other embodiments of the foregoing catalytic nanowire, the dopant is selected from Ta/Hf, W/Au, Ca/W, Au/Re, Sm/Li, La/K, Zn/Cs, Na/K/Mg, Zr/Cs, Ca/Ce, Na/Li/Cs, Li/Sr, Cs/Zn, La/Dy/K, Dy/K, La/Mg, Na/Nd/In/K, In/Sr, Sr/Cs, Rb/Ga/Tm/Cs, Ga/Cs, K/La/Zr/Ag, Lu/Fe, Sr/Tm, La/Dy, Sm/Li/Sr, Mg/K, Li/Rb/Ga, Li/Cs/Tm, Zr/K, Li/Cs, Li/K/La, Ce/Zr/La, Ca/Al/La, Sr/Zn/La, Sr/Cs/Zn, Sm/Cs, In/K, Ho/Cs/Li/La, Cs/La/Na, La/S/Sr, K/La/Zr/Ag, Lu/Tl, Pr/Zn, Rb/Sr/La, Na/Sr/Eu/Ca, K/Cs/Sr/La, Na/Sr/Lu, Sr/Eu/Dy, Lu/Nb, La/Dy/Gd, Na/Mg/Tl/P, Na/Pt, Gd/Li/K, Li/Sr/Cs, Li/Sr/Zn/K, Li/Ga/Cs, Li/K/Sr/La, Li/Na, Li/Na/Rb/Ga, Li/Na/Sr, Li/Na/Sr/La, Li/Sm/Cs, Ba/Sm/Yb/S, Ba/Tm/K/La, Ba/Tm/Zn/K, Cs/K/La, Cs/La/Tm/Na, Cs/Li/K/La, Sm/Li/Sr/Cs, Sr/Cs/La, Sr/Tm/Li/Cs, Zn/K, Zr/Cs/K/La, Rb/Ca/In/Ni, Sr/Ho/Tm, La/Nd/S, Li/Rb/Ca, Li/K, Tm/Lu/Ta/P, Rb/Ca/Dy/P, Mg/La/Yb/Zn, Rb/Sr/Lu, Na/Sr/Lu/Nb, Na/Eu/Hf, Dy/Rb/Gd, Na/Pt/Bi, Rb/Hf, Ca/Cs, Ca/Mg/Na, Hf/Bi, Sr/Sn, Sr/W, Sr/Nb, Zr/W, Y/W, Na/W, Bi/W, Bi/Cs, Bi/Ca, Bi/Sn, Bi/Sb, Ge/Hf, Hf/Sm, Sb/Ag, Sb/Bi, Sb/Au, Sb/Sm, Sb/Sr, Sb/W, Sb/Hf, Sb/Yb, Sb/Sn, Yb/Au, Yb/Ta, Yb/W, Yb/Sr, Yb/Pb, Yb/W, Yb/Ag, Au/Sr and W/Ge.

For example in certain embodiments of the foregoing catalytic nanowire, the catalytic nanowire comprises a metal oxide, and in other embodiments the catalytic nanowire comprises a lanthanide metal. In still other embodiments, the catalytic nanowire comprises $La_2O_3$, $Nd_2O_3$, $Yb_2O_3$, $Eu_2O_3$, $Sm_2O_3$, $Y_2O_3$, $Ce_2O_3$, $Pr_2O_3$ or combinations thereof.

In other embodiments of the foregoing nanowire, the catalytic nanowire comprises a lanthanide oxide, for example a lanthanide mixed oxide, for example in some embodiments the catalytic nanowire comprises $Ln1_{4-x}Ln2_xO_6$, wherein Ln1 and Ln2 are each independently a lanthanide element, wherein Ln1 and Ln2 are not the same and x is a number ranging from greater than 0 to less than 4. In other embodiments, the catalytic nanowire comprises $La_{4-x}Nd_xO_6$, wherein x is a number ranging from greater than 0 to less than 4, and in still other embodiments, the catalytic nanowire comprises $La_3NdO_6$, $LaNd_3O_6$, $La_{1.5}Nd_{2.5}O_6$, $La_{2.5}Nd_{1.5}O_6$, $La_{3.2}Nd_{0.8}O_6$, $La_{3.5}Nd_{0.5}O_6$, $La_{3.8}Nd_{0.2}O_6$ or combinations thereof. In certain other embodiments the mixed oxide comprises Y—La, Zr—La, Pr—La, Ce—La or combinations thereof.

In still other embodiments, the disclosure provides a catalytic nanowire comprising $Ln1_{4-x}Ln2_xO_6$ and a dopant comprising a metal element, a semi-metal element, a non-metal element or combinations thereof, wherein Ln1 and Ln2 are each independently a lanthanide element, wherein Ln1 and Ln2 are not the same and x is a number ranging from greater than 0 to less than 4. For example, in certain embodiments the catalytic nanowire comprises $La_{4-x}Ln1_xO_6$, wherein Ln1 is a lanthanide element and x is a number ranging from greater than 0 to less than 4, and in other specific embodiments, the catalytic nanowire comprises $La_{4-x}Nd_xO_6$, wherein x is a number ranging from greater than 0 to less than 4.

Still further embodiments of the foregoing nanowire include embodiments wherein the catalytic nanowire comprises comprises $La_3NdO_6$, $LaNd_3O_6$, $La_{1.5}Nd_{2.5}O_6$, $La_{2.5}Nd_{1.5}O_6$, $La_{3.2}Nd_{0.8}O_6$, $La_{3.5}Nd_{0.5}O_6$, $La_{3.8}Nd_{0.2}O_6$ or combinations thereof.

In other embodiments, the dopant is selected from: Eu, Na, Sr, Ca, Mg, Sm, Ho, Tm, W, La, K, Dy, In, Li, Cs, S, Zn, Ga, Rb, Ba, Yb, Ni, Lu, Ta, P, Hf, Tb, Gd, Pt, Bi, Sn, Nb, Sb, Ge, Ag, Au, Pb, B, Re, Fe, Al, Zr, Tl, Pr, Co, Ce, Rh, and Mo. For example in certain embodiments, the catalytic nanowire comprises at least one of the following dopant combinations: Eu/Na, Sr/Na, Na/Zr/Eu/Ca, Mg/Na, Sr/Sm/Ho/Tm, Sr/W, Mg/La/K, Na/K/Mg/Tm, Na/Dy/K, Na/La/Dy, Sr/Hf/K, Na/La/Eu, Na/La/Eu/In, Na/La/K, Na/La/Li/Cs, K/La, K/La/S, K/Na, Li/Cs, Li/Cs/La, Li/Cs/La/Tm, Li/Cs/Sr/Tm, Li/Sr/Cs, Li/Sr/Zn/K, Li/Ga/Cs, Li/K/Sr/La, Li/Na, Li/Na/Rb/Ga, Li/Na/Sr, Li/Na/Sr/La, Sr/Zr, Li/Sm/Cs, Ba/Sm/Yb/S, Ba/Tm/K/La, Ba/Tm/Zn/K, Sr/Zr/K, Cs/K/La, Cs/La/Tm/Na, Cs/Li/K/La, Sm/Li/Sr/Cs, Sr/Cs/La, Sr/Tm/Li/Cs, Zn/K, Zr/Cs/K/La, Rb/Ca/In/Ni, Sr/Ho/Tm, La/Nd/S, Li/Rb/Ca, Li/K, Tm/Lu/Ta/P, Rb/Ca/Dy/P, Mg/La/Yb/Zn, Rb/Sr/Lu, Na/Sr/Lu/Nb, Na/Eu/Hf, Dy/Rb/Gd, Sr/Ce, Na/Pt/Bi, Rb/Hf, Ca/Cs, Ca/Mg/Na, Hf/Bi, Sr/Sn, Sr/W, Sr/Nb, Sr/Ce/ K, Zr/W, Y/W, Na/W, Bi/W, Bi/Cs, Bi/Ca, Bi/Sn, Bi/Sb, Ge/Hf, Hf/Sm, Sb/Ag, Sb/Bi, Sb/Au, Sb/Sm, Sb/Sr, Sb/W, Sb/Hf, Sb/Yb, Sb/Sn, Yb/Au, Yb/Ta, Yb/W, Yb/Sr, Yb/Pb, Yb/W, Yb/Ag, Au/Sr, W/Ge, Sr/Tb, Ta/Hf, W/Au, Ca/W, Au/Re, Sm/Li, La/K, Zn/Cs, Na/K/Mg, Zr/Cs, Ca/Ce, Na/Li/ Cs, Li/Sr, Cs/Zn, La/Dy/K, Dy/K, La/Mg, Na/Nd/In/K, In/Sr, Sr/Cs, Rb/Ga/Tm/Cs, Ga/Cs, K/La/Zr/Ag, Lu/Fe, Sr/Tb/K, Sr/Tm, La/Dy, Sm/Li/Sr, Mg/K, Sr/Pr, Li/Rb/Ga, Li/Cs/Tm, Zr/K, Li/Cs, Li/K/La, Ce/Zr/La, Ca/Al/La, Sr/Zn/ La, Sr/Cs/Zn, Sm/Cs, In/K, Ho/Cs/Li/La, Sr/Pr/K, Cs/La/ Na, La/S/Sr, K/La/Zr/Ag, Lu/Tl, Pr/Zn, Rb/Sr/La, Na/Sr/Eu/ Ca, K/Cs/Sr/La, Na/Sr/Lu, Sr/Eu/Dy, Lu/Nb, La/Dy/Gd, Na/Mg/Tl/P, Na/Pt, Gd/Li/K, Rb/K/Lu, Sr/La/Dy/S, Na/Ce/ Co, Na/Ce, Na/Ga/Gd/Al, Ba/Rh/Ta, Ba/Ta, Na/Al/Bi, Sr/Hf/Rb, Cs/Eu/S, Sm/Tm/Yb/Fe, Sm/Tm/Yb, Hf/Zr/Ta, Rb/Gd/Li/K, Gd/Ho/Al/P, Na/Ca/Lu, Cu/Sn, Ag/Au, Al/Bi, Al/Mo, Al/Nb, Au/Pt, Ga/Bi, Mg/W, Pb/Au, Sn/Mg, Sr/B, Zn/Bi, Gd/Ho, Zr/Bi, Ho/Sr, Gd/Ho/Sr, Ca/Sr, Ca/Sr/W, Sr/Ho/Tm/Na, Na/Zr/Eu/Tm, Sr/Ho/Tm/Na, Sr/Pb, Sr/W/Li, Ca/Sr/W or Sr/Hf.

In other embodiments, the disclosure provides a nanowire comprising a mixed oxide of Y—La, Zr—La, Pr—La, Ce—La or combinations thereof and at least one dopant selected from a metal element, a semi-metal element and a non-metal element. For example, in some embodiments the at least one dopant is selected from Eu, Na, Sr, Ca, Mg, Sm, Ho, Tm, W, La, K, Dy, In, Li, Cs, S, Zn, Ga, Rb, Ba, Yb, Ni, Lu, Ta, P, Hf, Tb, Gd, Pt, Bi, Sn, Nb, Sb, Ge, Ag, Au, Pb, B, Re, Fe, Al, Zr, Tl, Pr, Co, Ce, Rh, and Mo, and in even other embodiments, the catalytic nanowire comprises at least one of the following dopant combinations: Eu/Na, Sr/Na, Na/Zr/ Eu/Ca, Mg/Na, Sr/Sm/Ho/Tm, Sr/W, Mg/La/K, Na/K/Mg/ Tm, Na/Dy/K, Na/La/Dy, Sr/Hf/K, Na/La/Eu, Na/La/Eu/In, Na/La/K, Na/La/Li/Cs, K/La, K/La/S, K/Na, Li/Cs, Li/Cs/ La, Li/Cs/La/Tm, Li/Cs/Sr/Tm, Li/Sr/Cs, Li/Sr/Zn/K, Li/Ga/Cs, Li/K/Sr/La, Li/Na, Li/Na/Rb/Ga, Li/Na/Sr, Li/Na/ Sr/La, Sr/Zr, Li/Sm/Cs, Ba/Sm/Yb/S, Ba/Tm/K/La, Ba/Tm/ Zn/K, Sr/Zr/K, Cs/K/La, Cs/La/Tm/Na, Cs/Li/K/La, Sm/Li/ Sr/Cs, Sr/Cs/La, Sr/Tm/Li/Cs, Zn/K, Zr/Cs/K/La, Rb/Ca/In/ Ni, Sr/Ho/Tm, La/Nd/S, Li/Rb/Ca, Li/K, Tm/Lu/Ta/P, Rb/Ca/Dy/P, Mg/La/Yb/Zn, Rb/Sr/Lu, Na/Sr/Lu/Nb, Na/Eu/ Hf, Dy/Rb/Gd, Sr/Ce, Na/Pt/Bi, Rb/Hf, Ca/Cs, Ca/Mg/Na, Hf/Bi, Sr/Sn, Sr/W, Sr/Nb, Sr/Ce/K, Zr/W, Y/W, Na/W, Bi/W, Bi/Cs, Bi/Ca, Bi/Sn, Bi/Sb, Ge/Hf, Hf/Sm, Sb/Ag, Sb/Bi, Sb/Au, Sb/Sm, Sb/Sr, Sb/W, Sb/Hf, Sb/Yb, Sb/Sn, Yb/Au, Yb/Ta, Yb/W, Yb/Sr, Yb/Pb, Yb/W, Yb/Ag, Au/Sr, W/Ge, Sr/Tb, Ta/Hf, W/Au, Ca/W, Au/Re, Sm/Li, La/K, Zn/Cs, Na/K/Mg, Zr/Cs, Ca/Ce, Na/Li/Cs, Li/Sr, Cs/Zn, La/Dy/K, Dy/K, La/Mg, Na/Nd/In/K, In/Sr, Sr/Cs, Rb/Ga/ Tm/Cs, Ga/Cs, K/La/Zr/Ag, Lu/Fe, Sr/Tb/K, Sr/Tm, La/Dy, Sm/Li/Sr, Mg/K, Sr/Pr, Li/Rb/Ga, Li/Cs/Tm, Zr/K, Li/Cs, Li/K/La, Ce/Zr/La, Ca/Al/La, Sr/Zn/La, Sr/Cs/Zn, Sm/Cs, In/K, Ho/Cs/Li/La, Sr/Pr/K, Cs/La/Na, La/S/Sr, K/La/Zr/ Ag, Lu/Tl, Pr/Zn, Rb/Sr/La, Na/Sr/Eu/Ca, K/Cs/Sr/La, Na/Sr/Lu, Sr/Eu/Dy, Lu/Nb, La/Dy/Gd, Na/Mg/Tl/P, Na/Pt, Gd/Li/K, Rb/K/Lu, Sr/La/Dy/S, Na/Ce/Co, Na/Ce, Na/Ga/ Gd/Al, Ba/Rh/Ta, Ba/Ta, Na/Al/Bi, Sr/Hf/Rb, Cs/Eu/S, Sm/Tm/Yb/Fe, Sm/Tm/Yb, Hf/Zr/Ta, Rb/Gd/Li/K, Gd/Ho/ Al/P, Na/Ca/Lu, Cu/Sn, Ag/Au, Al/Bi, Al/Mo, Al/Nb, Au/Pt, Ga/Bi, Mg/W, Pb/Au, Sn/Mg, Sr/B, Zn/Bi, Gd/Ho, Zr/Bi, Ho/Sr, Gd/Ho/Sr, Ca/Sr, Ca/Sr/W, Sr/Ho/Tm/Na, Na/Zr/Eu/ Tm, Sr/Ho/Tm/Na, Sr/Pb, Sr/W/Li, Ca/Sr/W or Sr/Hf.

In still other embodiments, the invention provides a catalytic nanowire comprising a mixed oxide of a rare earth element and a Group 13 element, wherein the catalytic nanowire further comprises one or more Group 2 elements.

In some embodiments, the Group 13 element is B, Al, Ga or In. In other embodiments, the Group 2 element is Ca or Sr. In still other embodiments, the rare earth element is La, Y, Nd, Yb, Sm, Pr, Ce or Eu.

Examples of the foregoing catalytic nanowires include catalytic nanowires comprising $CaLnBO_x$, $CaLnAlO_x$, $CaLnGaO_x$, $CaLnInO_x$, $CaLnAlSrO_x$ and $CaLnAlSrO_x$, wherein Ln is a lanthanide or yttrium and x is number such that all charges are balanced. For example, in some embodiments, the catalytic nanowire comprises $CaLaBO_4$, $CaLaAlO_4$, $CaLaGaO_4$, $CaLaInO_4$, $CaLaAlSrO_5$, $CaLaAlSrO_5$, $CaNdBO_4$, $CaNdAlO_4$, $CaNdGaO_4$, $CaNdInO_4$, $CaNdAlSrO_4$, $CaNdAlSrO_4$, $CaYbBO_4$, $CaYbAlO_4$, $CaYbGaO_4$, $CaYbInO_4$, $CaYbAlSrO_5$, $CaYbAlSrO_5$, $CaEuBO_4$, $CaEuAlO_4$, $CaEuGaO_4$, $CaEuInO_4$, $CaEuAlSrO_5$, $CaEuAlSrO_5$, $CaSmBO_4$, $CaSmAlO_4$, $CaSmGaO_4$, $CaSmInO_4$, $CaSmAlSrO_5$, $CaSmAlSrO_5$, $CaYBO_4$, $CaYAlO_4$, $CaYGaO_4$, $CaYInO_4$, $CaYAlSrO_5$, $CaYAlSrO_5$, $CaCeBO_4$, $CaCeAlO_4$, $CaCeGaO_4$, $CaCeInO_4$, $CaCeAlSrO_5$, $CaCeAlSrO_5$, $CaPrBO_4$, $CaPrAlO_4$, $CaPrGaO_4$, $CaPrInO_4$, $CaPrAlSrO_5$ or $CaPrAlSrO_5$.

In still other embodiments, the invention is directed to a catalytic nanowire comprising a rare earth oxide, wherein the nanowires are doped with a dopant (or dopants) selected from Eu/Na, Sr/Na, Na/Zr/Eu/Ca, Mg/Na, Sr/Sm/Ho/Tm, Sr/W, Mg/La/K, Na/K/Mg/Tm, Na/Dy/K, Na/La/Dy, Sr/Hf/ K, Na/La/Eu, Na/La/Eu/In, Na/La/K, Na/La/Li/Cs, K/La, K/La/S, K/Na, Li/Cs, Li/Cs/La, Li/Cs/La/Tm, Li/Cs/Sr/Tm, Li/Sr/Cs, Li/Sr/Zn/K, Li/Ga/Cs, Li/K/Sr/La, Li/Na, Li/Na/ Rb/Ga, Li/Na/Sr, Li/Na/Sr/La, Sr/Zr, Li/Sm/Cs, Ba/Sm/Yb/ S, Ba/Tm/K/La, Ba/Tm/Zn/K, Sr/Zr/K, Cs/K/La, Cs/La/Tm/ Na, Cs/Li/K/La, Sm/Li/Sr/Cs, Sr/Cs/La, Sr/Tm/Li/Cs, Zn/K, Zr/Cs/K/La, Rb/Ca/In/Ni, Sr/Ho/Tm, La/Nd/S, Li/Rb/Ca, Li/K, Tm/Lu/Ta/P, Rb/Ca/Dy/P, Mg/La/Yb/Zn, Rb/Sr/Lu, Na/Sr/Lu/Nb, Na/Eu/Hf, Dy/Rb/Gd, Sr/Ce, Na/Pt/Bi, Rb/Hf, Ca/Cs, Ca/Mg/Na, Hf/Bi, Sr/Sn, Sr/W, Sr/Nb, Sr/Ce/ K, Zr/W, Y/W, Na/W, Bi/W, Bi/Cs, Bi/Ca, Bi/Sn, Bi/Sb, Ge/Hf, Hf/Sm, Sb/Ag, Sb/Bi, Sb/Au, Sb/Sm, Sb/Sr, Sb/W, Sb/Hf, Sb/Yb, Sb/Sn, Yb/Au, Yb/Ta, Yb/W, Yb/Sr, Yb/Pb, Yb/W, Yb/Ag, Au/Sr, W/Ge, Sr/Tb, Ta/Hf, W/Au, Ca/W, Au/Re, Sm/Li, La/K, Zn/Cs, Na/K/Mg, Zr/Cs, Ca/Ce, Na/Li/ Cs, Li/Sr, Cs/Zn, La/Dy/K, Dy/K, La/Mg, Na/Nd/In/K, In/Sr, Sr/Cs, Rb/Ga/Tm/Cs, Ga/Cs, K/La/Zr/Ag, Lu/Fe, Sr/Tb/K, Sr/Tm, La/Dy, Sm/Li/Sr, Mg/K, Li/Rb/Ga, Li/Cs/ Tm, Zr/K, Li/Cs, Li/K/La, Ce/Zr/La, Ca/Al/La, Sr/Zn/La, Sr/Cs/Zn, Sm/Cs, In/K, Ho/Cs/Li/La, Sr/Pr/K, Cs/La/Na, La/S/Sr, K/La/Zr/Ag, Lu/Tl, Pr/Zn, Rb/Sr/La, Na/Sr/Eu/Ca, K/Cs/Sr/La, Na/Sr/Lu, Sr/Eu/Dy, Lu/Nb, La/Dy/Gd, Na/Mg/Tl/P, Na/Pt, Gd/Li/K, Rb/K/Lu, Sr/La/Dy/S, Na/Ce/ Co, Na/Ce, Na/Ga/Gd/Al, Ba/Rh/Ta, Ba/Ta, Na/Al/Bi, Sr/Hf/Rb, Cs/Eu/S, Sm/Tm/Yb/Fe, Sm/Tm/Yb, Hf/Zr/Ta, Rb/Gd/Li/K, Gd/Ho/Al/P, Na/Ca/Lu, Cu/Sn, Ag/Au, Al/Bi, Al/Mo, Al/Nb, Au/Pt, Ga/Bi, Mg/W, Pb/Au, Sn/Mg, Sr/B, Zn/Bi, Gd/Ho, Zr/Bi, Ho/Sr, Gd/Ho/Sr, Ca/Sr, Ca/Sr/W, Sr/Ho/Tm/Na, Na/Zr/Eu/Tm, Sr/Pb, Sr/W/Li, Ca/Sr/W or Sr/Hf. In one embodiment of the foregoing, nanowires comprise $La_2O_3$, $Nd_2O_3$, $Yb_2O_3$, $Eu_2O_3$, $Sm_2O_3$, $Ln1_{4-x}Ln2_xO_6$, $La_{4-x}Ln1_xO_6$, $La_{4-x}Nd_xO_6$, wherein Ln1 and Ln2 are each independently a lanthanide element, wherein Ln1 and Ln2 are not the same and x is a number ranging from greater than 0 to less than 4, $La_3NdO_6$, $LaNd_3O_6$, $La_{1.5}Nd_{2.5}O_6$, $La_{2.5}Nd_{1.5}O_6$, $La_{3.2}Nd_{0.8}O_6$, $La_{3.5}Nd_{0.5}O_6$, $La_{3.8}Nd_{0.2}O_6$, Y—La, Zr—La, Pr—La or Ce—La or combinations thereof.

In other embodiments, the nanowires comprise $La_2O_3$, $Yb_2O_3$, $Eu_2O_3$, $Sm_2O_3$, $Y_2O_3$, $Ce_2O_3$, $Pr_2O_3$, $Ln1_{4-x}Ln2_xO_6$, $La_{4-x}Ln1_xO_6$, $La_{4-x}Nd_xO_6$, wherein $L_n1$ and $L_n2$ are each independently a lanthanide element, wherein $L_n1$ and $L_n2$ are not the same and x is a number ranging from greater than 0 to less than 4, $La_3NdO_6$, $LaNd_3O_6$, $La_{1.5}Nd_{2.5}O_6$, $La_{2.5}Nd_{1.5}O_6$, $La_{3.2}Nd_{0.8}O_6$, $La_{3.5}Nd_{0.5}O_6$, $La_{3.8}Nd_{0.2}O_6$, Y—La, Zr—La, Pr—La or Ce—La doped with Sr/Ta, for example in some embodiments the nanowires comprise $Sr/Ta/La_2O_3$, $Sr/Ta/Yb_2O_3$, $Sr/Ta/Eu_2O_3$, $Sr/Ta/Sm_2O_3$, $Sr/Ta/La_3NdO_6$, $Sr/Ta/LaNd_3O_6$, $Sr/Ta/La_{1.5}Nd_{2.5}O_6$, $Sr/Ta/La_{2.5}Nd_{1.5}O_6$, $Sr/Ta/La_{3.2}Nd_{0.8}O_6$, $Sr/Ta/La_{3.5}Nd_{0.5}O_6$, $Sr/Ta/La_{3.8}Nd_{0.2}O_6$, Sr/Ta/Y—La, Sr/Ta/Zr—La, Sr/Ta/Pr—La or Sr/Ta/Ce—La or combinations thereof. In other embodiments, the nanowires comprise $Ln1_{4-x}Ln2_xO_6$, $La_{4-x}Ln1_xO_6$, $La_{4-x}Nd_xO_6$, wherein Ln1 and Ln2 are each independently a lanthanide element, wherein Ln1 and Ln2 are not the same and x is a number ranging from greater than 0 to less than 4, $La_3NdO_6$, $LaNd_3O_6$, $La_{1.5}Nd_{2.5}O_6$, $La_{2.5}Nd_{1.5}O_6$, $La_{3.2}Nd_{0.8}O_6$, $La_{3.5}Nd_{0.5}O_6$, $La_{3.8}Nd_{0.2}O_6$, Y—La, Zr—La, Pr—La or Ce—La doped with Na, Sr, Ca, Yb, Cs or Sb, for example the nanowires may comprise $Na/Ln1_{4-x}Ln2_xO_6$, $Sr/Ln1_{4-x}Ln2_xO_6$, $Ca/Ln1_{4-x}Ln2_xO_6$, $Yb/Ln1_{4-x}Ln2_xO_6$, $Cs/Ln1_{4-x}Ln2_xO_6$, $Sb/Ln1_{4-x}Ln2_xO_6$, $Na/La_{4-x}Ln1_xO_6$, $Na/La_3NdO_6$, $Sr/La_{4-x}Ln1_xO_6$, $Ca/La_{4-x}Ln1_xO_6$, $Yb/La_{4-x}Ln1_xO_6$, $Cs/La_{4-x}Ln1_xO_6$, $Sb/La_{4-x}Ln1_xO_6$, $Na/La_{4-x}Nd_xO_6$, $Sr/La_{4-x}Nd_xO_6$, $Ca/La_{4-x}Nd_xO_6$, $Yb/La_{4-x}Nd_xO_6$, Cs $La_{4-x}Nd_xO_6$, $Sb/La_{4-x}Nd_xO_6$, $Na/LaNd_3O_6$, $Na/La_{1.5}Nd_{2.5}O_6$, $Na/La_{2.5}Nd_{1.5}O_6$, $Na/La_{3.2}Nd_{0.8}O_6$, $Na/La_{3.5}Nd_{0.5}O_6$, $Na/La_{3.8}Nd_{0.2}O_6$, Na/Y—La, Na/Zr—La, Na/Pr—La, Na/Ce—La, $Sr/La_3NdO_6$, $Sr/LaNd_3O_6$, $Sr/La_{1.5}Nd_{2.5}O_6$, $Sr/La_{2.5}Nd_{1.5}O_6$, $Sr/La_{3.2}Nd_{0.8}O_6$, $Sr/La_{3.5}Nd_{0.5}O_6$, $Sr/La_{3.8}Nd_{0.2}O_6$, Sr/Y—La, Sr/Zr—La, Sr/Pr—La, Sr/Ce—La, $Ca/La_3NdO_6$, $Ca/LaNd_3O_6$, $Ca/La_{1.5}Nd_{2.5}O_6$, $Ca/La_{2.5}Nd_{1.5}O_6$, $Ca/La_{3.2}Nd_{0.8}O_6$, $Ca/La_{3.5}Nd_{0.5}O_6$, $Ca/La_{3.8}Nd_{0.2}O_6$, Ca/Y—La, Ca/Zr—La, Ca/Pr—La, Ca/Ce—La, $Yb/La_3NdO_6$, $Yb/LaNd_3O_6$, $Yb/La_{1.5}Nd_{2.5}O_6$, $Yb/La_{2.5}Nd_{1.5}O_6$, $Yb/La_{3.2}Nd_{0.8}O_6$, $Yb/La_{3.5}Nd_{0.5}O_6$, $Yb/La_{3.8}Nd_{0.2}O_6$, Yb/Y—La, Yb/Zr—La, Yb/Pr—La, Yb/Ce—La, $Cs/La_3NdO_6$ $LaNd_3O_6$, $Cs/La_{1.5}Nd_{2.5}O_6$, $Cs/La_{2.5}Nd_{1.5}O_6$, $Cs/La_{3.2}Nd_{0.8}O_6$, $Cs/La_{3.5}Nd_{0.5}O_6$, $Cs/La_{3.8}Nd_{0.2}O_6$, Cs/Y—La, Cs/Zr—La, Cs/Pr—La, Cs/Ce—La, $Sb/La_3NdO_6$, $Sb/LaNd_3O_6$, $Sb/La_{1.5}Nd_{2.5}O_6$, $Sb/La_{2.5}Nd_{1.5}O_6$, $Sb/La_{3.2}Nd_{0.8}O_6$, $Sb/La_{3.5}Nd_{0.5}O_6$, $Sb/La_{3.8}Nd_{0.2}O_6$, Sb/Y—La, Sb/Zr—La, Sb/Pr—La, Sb/Ce—La or combinations thereof.

Furthermore, the present inventors have discovered that lanthanide oxides doped with alkali metals and/or alkaline earth metals and at least one other dopant selected from Groups 3-16 have desirable catalytic properties and are useful in a variety of catalytic reactions, such as OCM. Accordingly, in one embodiment the nanowire catalysts comprise a lanthanide oxide doped with an alkali metal, an alkaline earth metal or combinations thereof, and at least one other dopant from groups 3-16. In some embodiments, the nanowire catalyst comprises a lanthanide oxide, an alkali metal dopant and at least one other dopant selected from Groups 3-16. In other embodiments, the nanowire catalyst comprises a lanthanide oxide, an alkaline earth metal dopant and at least one other dopant selected from Groups 3-16.

In some more specific embodiments of the foregoing, the nanowire catalyst comprises a lanthanide oxide, a lithium dopant and at least one other dopant selected from Groups 3-16. In still other embodiments, the nanowire catalyst comprises a lanthanide oxide, a sodium dopant and at least one other dopant selected from Groups 3-16. In other embodiments, the nanowire catalyst comprises a lanthanide oxide, a potassium dopant and at least one other dopant selected from Groups 3-16. In other embodiments, the nanowire catalyst comprises a lanthanide oxide, a rubidium dopant and at least one other dopant selected from Groups 3-16. In more embodiments, the nanowire catalyst comprises a lanthanide oxide, a caesium dopant and at least one other dopant selected from Groups 3-16.

In still other embodiments of the foregoing, the nanowire catalyst comprises a lanthanide oxide, a beryllium dopant and at least one other dopant selected from Groups 3-16. In other embodiments, the nanowire catalyst comprises a lanthanide oxide, a magnesium dopant and at least one other dopant selected from Groups 3-16. In still other embodiments, the nanowire catalyst comprises a lanthanide oxide, a calcium dopant and at least one other dopant selected from Groups 3-16. In more embodiments, the nanowire catalyst comprises a lanthanide oxide, a strontium dopant and at least one other dopant selected from Groups 3-16. In more embodiments, the nanowire catalyst comprises a lanthanide oxide, a barium dopant and at least one other dopant selected from Groups 3-16.

In some embodiments of the foregoing lanthanide oxide nanowire catalysts, the catalysts comprise $La_2O_3$, $Nd_2O_3$, $Yb_2O_3$, $Eu_2O_3$, $Sm_2O_3$, $Ln1_{4-x}Ln2_xO_6$, $La_{4-x}Ln1_xO_6$, $La_{4-x}Nd_xO_6$, wherein Ln1 and Ln2 are each independently a lanthanide element, wherein Ln1 and Ln2 are not the same and x is a number ranging from greater than 0 to less than 4, $La_3NdO_6$, $LaNd_3O_6$, $La_{1.5}Nd_{2.5}O_6$, $La_{2.5}Nd_{1.5}O_6$, $La_{3.2}Nd_{0.8}O_6$, $La_{3.5}Nd_{0.5}O_6$, $La_{3.8}Nd_{0.2}O_6$, Y—La, Zr—La, Pr—La or Ce—La or combinations thereof. In other various embodiments, the lanthanide oxide nanowire catalyst comprises a $C_2$ selectivity of greater than 50% and a methane conversion of greater than 20% when the lanthanide oxide nanowire catalyst is employed as a heterogenous catalyst in the oxidative coupling of methane at a temperature of 750° C. or less.

In various embodiments, of any of the above nanowire catalysts, the nanowire catalyst comprises a $C_2$ selectivity of greater than 50% and a methane conversion of greater than 20% when the nanowire catalyst is employed as a heterogenous catalyst in the oxidative coupling of methane at a temperature of 750° C. or less, 700° C. or less, 650° C. or less or even 600° C. or less.

In more embodiments, of any of the above nanowire catalysts, the nanowire catalyst comprises a $C_2$ selectivity of greater than 50%, greater than 55%, greater than 60%, greater than 65%, greater than 70%, or even greater than 75%, and a methane conversion of greater than 20% when the nanowire catalyst is employed as a heterogenous catalyst in the oxidative coupling of methane at a temperature of 750° C. or less.

In other embodiments, of any of the above catalysts, the catalyst comprises a $C_2$ selectivity of greater than 50%, and a methane conversion of greater than 20%, greater than 25%, greater than 30%, greater than 35%, greater than 40%, greater than 45%, or even greater than 50% when the rare earth oxide catalyst is employed as a heterogenous catalyst in the oxidative coupling of methane at a temperature of 750° C. or less. In some embodiments of the foregoing, the methan conversion and C2 selectivity are calculated based on a single pass basis (i.e., the percent of methane converted or C2 selectivity upon a single pass over the catalyst or catalytic bed, etc.)

In some embodiments, the foregoing doped nanowires comprise 1, 2, 3 or four doping elements. In other embodiments, the nanowires comprise more than four doping elements, for example, 5, 6, 7, 8, 9, 10 or even more doping elements. In this regard, each dopant may be present in the nanowires (for example any of the nanowires disclosed in Tables 9-12) in up to 75% by weight. For example, in one embodiment the concentration of a first doping element ranges from 0.01% to 1% w/w, 1%-5% w/w, 5%-10% w/w, 10%-20% ww, 20%-30% w/w, 30%-40% w/w or 40%-50% w/w, for example about 1% w/w, about 2% w/w, about 3% w/w, about 4% w/w, about 5% w/w, about 6% w/w, about 7% w/w, about 8% w/w, about 9% w/w, about 10% w/w, about 11% w/w, about 12% w/w, about 13% w/w, about 14% w/w, about 15% w/w, about 16% w/w, about 17% w/w, about 18% w/w, about 19% w/w or about 20% w/w.

In other embodiments, the concentration of a second doping element (when present) ranges from 0.01% to 1% w/w, 1%-5% w/w, 5%-10% w/w. 10%-20% ww, 20%-30% w/w, 30%-40% w/w or 40%-50% w/w, for example about 1% w/w, about 2% w/w, about 3% w/w, about 4% w/w, about 5% w/w, about 6% w/w, about 7% w/w, about 8% w/w, about 9% w/w, about 10% w/w, about 11% w/w, about 12% w/w, about 13% w/w, about 14% w/w, about 15% w/w, about 16% w/w, about 17% w/w, about 18% w/w, about 19% w/w or about 20% w/w.

In other embodiments, the concentration of a third doping element (when present) ranges from 0.01% to 1% w/w, 1%-5% w/w, 5%-10% w/w. 10%-20% ww, 20%-30% w/w, 30%-40% w/w or 40%-50% w/w, for example about 1% w/w, about 2% w/w, about 3% w/w, about 4% w/w, about 5% w/w, about 6% w/w, about 7% w/w, about 8% w/w, about 9% w/w, about 10% w/w, about 11% w/w, about 12% w/w, about 13% w/w, about 14% w/w, about 15% w/w, about 16% w/w, about 17% w/w, about 18% w/w, about 19% w/w or about 20% w/w.

In other embodiments, the concentration of a fourth doping element (when present) ranges from 0.01% to 1% w/w, 1%-5% w/w, 5%-10% w/w. 10%-20% ww, 20%-30% w/w, 30%-40% w/w or 40%-50% w/w, for example about 1% w/w, about 2% w/w, about 3% w/w, about 4% w/w, about 5% w/w, about 6% w/w, about 7% w/w, about 8% w/w, about 9% w/w, about 10% w/w, about 11% w/w, about 12% w/w, about 13% w/w, about 14% w/w, about 15% w/w, about 16% w/w, about 17% w/w, about 18% w/w, about 19% w/w or about 20% w/w.

In other embodiments, the concentration of the dopant is measured in terms of atomic percent (at/at). In some of these embodiments, each dopant may be present in the nanowires (for example any of the nanowires disclosed in Tables 1-12) in up to 75% at/at. For example, in one embodiment the concentration of a first doping element ranges from 0.01% to 1% at/at, 1%-5% at/at, 5%-10% at/at. 10%-20% at/at, 20%-30% at/at, 30%-40% at/at or 40%-50% at/at, for example about 1% at/at, about 2% at/at, about 3% at/at, about 4% at/at, about 5% at/at, about 6% at/at, about 7% at/at, about 8% at/at, about 9% at/at, about 10% at/at, about 11% at/at, about 12% at/at, about 13% at/at, about 14% at/at, about 15% at/at, about 16% at/at, about 17% at/at, about 18% at/at, about 19% at/at or about 20% at/at.

In other embodiments, the concentration of a second doping element (when present) ranges from 0.01% to 1% at/at, 1%-5% at/at, 5%-10% at/at. 10%-20% ww, 20%-30% at/at, 30%-40% at/at or 40%-50% at/at, for example about 1% at/at, about 2% at/at, about 3% at/at, about 4% at/at, about 5% at/at, about 6% at/at, about 7% at/at, about 8% at/at, about 9% at/at, about 10% at/at, about 11% at/at, about 12% at/at, about 13% at/at, about 14% at/at, about 15% at/at, about 16% at/at, about 17% at/at, about 18% at/at, about 19% at/at or about 20% at/at.

In other embodiments, the concentration of a third doping element (when present) ranges from 0.01% to 1% at/at, 1%-5% at/at, 5%-10% at/at. 10%-20% ww, 20%-30% at/at, 30%-40% at/at or 40%-50% at/at, for example about 1% at/at, about 2% at/at, about 3% at/at, about 4% at/at, about 5% at/at, about 6% at/at, about 7% at/at, about 8% at/at, about 9% at/at, about 10% at/at, about 11% at/at, about 12% at/at, about 13% at/at, about 14% at/at, about 15% at/at, about 16% at/at, about 17% at/at, about 18% at/at, about 19% at/at or about 20% at/at.

In other embodiments, the concentration of a fourth doping element (when present) ranges from 0.01% to 1% at/at, 1%-5% at/at, 5%-10% at/at. 10%-20% ww, 20%-30% at/at, 30%-40% at/at or 40%-50% at/at, for example about 1% at/at, about 2% at/at, about 3% at/at, about 4% at/at, about 5% at/at, about 6% at/at, about 7% at/at, about 8% at/at, about 9% at/at, about 10% at/at, about 11% at/at, about 12% at/at, about 13% at/at, about 14% at/at, about 15% at/at, about 16% at/at, about 17% at/at, about 18% at/at, about 19% at/at or about 20% at/at.

Accordingly, any of the doped nanowires described above or in Tables 1-12, may comprise any of the foregoing doping concentrations.

Furthermore, different catalytic characteristics of the above doped nanowires can be varied or "tuned" based on the method used to prepare them. For example, in one embodiment the above nanowires (and the nanowires of Tables 1-12) are prepared using a biological templating approach, for example phage. In other embodiments, the nanowires are prepared via a hydrothermal or sol gel approach (i.e., a non-templated approach). Some embodiments for preparing the nanowires (e.g., rare earth nanowires) comprise preparing the nanowires directly from the corresponding oxide or via a metal hydroxide gel approach. Such methods are described in more detail herein and other methods are known in the art. In addition, the above dopants may be incorporated either before or after (or combinations thereof) an optional calcination step as described herein.

In other embodiments, the nanowires comprise a mixed oxide selected from a Y—La mixed oxide doped with Na. (Y ranges from 5 to 20% of La mol/mol); a Zr—La mixed oxide doped with Na (Zr ranges from 1 to 5% of La mo/mol); a Pr—La mixed oxide doped with a group 1 element (Pr ranges from 2 to 6% of La mol/mol); and a Ce—La mixed oxide doped with a group 1 element (Ce ranges from 5 to 20% of La mol/mol). As used herein, the notation "M1-M2", wherein M1 and M2 are each independently metals refers to a mixed metal oxide comprising the two metals. M1 and M2 may be present in equal or different amounts (at/at).

Some embodiments of the metal oxides disclosed herein can be in the form of oxides, oxyhydroxides, hydroxides, oxycarbonates or combination thereof after being exposed to moisture, carbon dioxide, undergoing incomplete calcination or combination thereof.

It is contemplated that any one or more of the dopants disclosed herein can be combined with any one of the nanowires disclosed herein to form a doped nanowire comprising one, two, three or more dopants. Tables 1-12 below show exemplary doped nanowires in accordance with various specific embodiments. Dopants (Dop) are shown in the horizontal rows and base nanowire catalyst (NW) in the vertical columns for Tables 1-8, and dopants are shown in the vertical columns and base nanowire catalyst in the horizontal rows for Tables 9-12. The resulting doped catalysts are shown in the intersecting cells in all tables. In some embodiments, the doped nanowires shown in tables 1-12 are doped with one, two, three or more additional dopants.

TABLE 1

NANOWIRES (NW) DOPED WITH SPECIFIC DOPANTS (DOP)

| NW\Dop | Li | Na | K | Rb | Cs | Be | Mg | Ca |
|---|---|---|---|---|---|---|---|---|
| $Li_2O$ | Li/$Li_2O$ | Na/$Li_2O$ | K/$Li_2O$ | Rb/$Li_2O$ | Cs/$Li_2O$ | Be/$Li_2O$ | Mg/$Li_2O$ | Ca/$Li_2O$ |
| $Na_2O$ | Li/$Na_2O$ | Na/$Na_2O$ | K/$Na_2O$ | Rb/$Na_2O$ | Cs/$Na_2O$ | Be/$Na_2O$ | Mg/$Na_2O$ | Ca/$Na_2O$ |
| $K_2O$ | Li/$K_2O$ | Na/$K_2O$ | K/$K_2O$ | Rb/$K_2O$ | Cs/$K_2O$ | Be/$K_2O$ | Mg/$K_2O$ | Ca/$K_2O$ |
| $Rb_2O$ | Li/$Rb_2O$ | Na/$Rb_2O$ | K/$Rb_2O$ | Rb/$Rb_2O$ | Cs/$Rb_2O$ | Be/$Rb_2O$ | Mg/$Rb_2O$ | Ca/$Rb_2O$ |
| $Cs_2O$ | Li/$Cs_2O$ | Na/$Cs_2O$ | K/$Cs_2O$ | Rb/$Cs_2O$ | Cs/$Cs_2O$ | Be/$Cs_2O$ | Mg/$Cs_2O$ | Ca/$Cs_2O$ |
| BeO | Li/BeO | Na/BeO | K/BeO | Rb/BeO | Cs/BeO | Be/BeO | Mg/BeO | Ca/BeO |
| MgO | Li/MgO | Na/MgO | K/MgO | Rb/MgO | Cs/MgO | Be/MgO | Mg/MgO | Ca/MgO |
| CaO | Li/CaO | Na/CaO | K/CaO | Rb/CaO | Cs/CaO | Be/CaO | Mg/CaO | Ca/CaO |
| SrO | Li/SrO | Na/SrO | K/SrO | Rb/SrO | Cs/SrO | Be/SrO | Mg/SrO | Ca/SrO |
| BaO | Li/BaO | Na/BaO | K/BaO | Rb/BaO | Cs/BaO | Be/BaO | Mg/BaO | Ca/BaO |
| $Sc_2O_3$ | Li/$Sc_2O_3$ | Na/$Sc_2O_3$ | K/$Sc_2O_3$ | Rb/$Sc_2O_3$ | Cs/$Sc_2O_3$ | Be/$Sc_2O_3$ | Mg/$Sc_2O_3$ | Ca/$Sc_2O_3$ |
| $Y_2O_3$ | Li/$Y_2O_3$ | Na/$Y_2O_3$ | K/$Y_2O_3$ | Rb/$Y_2O_3$ | Cs/$Y_2O_3$ | Be/$Y_2O_3$ | Mg/$Y_2O_3$ | Ca/$Y_2O_3$ |
| $La_2O_3$ | Li/$La_2O_3$ | Na/$La_2O_3$ | K/$La_2O_3$ | Rb/$La_2O_3$ | Cs/$La_2O_3$ | Be/$La_2O_3$ | Mg/$La_2O_3$ | Ca/$La_2O_3$ |
| $CeO_2$ | Li/$CeO_2$ | Na/$CeO_2$ | K/$CeO_2$ | Rb/$CeO_2$ | Cs/$CeO_2$ | Be/$CeO_2$ | Mg/$CeO_2$ | Ca/$CeO_2$ |
| $Ce_2O_3$ | Li/$Ce_2O_3$ | Na/$Ce_2O_3$ | K/$Ce_2O_3$ | Rb/$Ce_2O_3$ | Cs/$Ce_2O_3$ | Be/$Ce_2O_3$ | Mg/$Ce_2O_3$ | Ca/$Ce_2O_3$ |
| $Pr_2O_3$ | Li/$Pr_2O_3$ | Na/$Pr_2O_3$ | K/$Pr_2O_3$ | Rb/$Pr_2O_3$ | Cs/$Pr_2O_3$ | Be/$Pr_2O_3$ | Mg/$Pr_2O_3$ | Ca/$Pr_2O_3$ |
| $Nd_2O_3$ | Li/$Nd_2O_3$ | Na/$Nd_2O_3$ | K/$Nd_2O_3$ | Rb/$Nd_2O_3$ | Cs/$Nd_2O_3$ | Be/$Nd_2O_3$ | Mg/$Nd_2O_3$ | Ca/$Nd_2O_3$ |
| $Sm_2O_3$ | Li/$Sm_2O_3$ | Na/$Sm_2O_3$ | K/$Sm_2O_3$ | Rb/$Sm_2O_3$ | Cs/$Sm_2O_3$ | Be/$Sm_2O_3$ | Mg/$Sm_2O_3$ | Ca/$Sm_2O_3$ |
| $Eu_2O_3$ | Li/$Eu_2O_3$ | Na/$Eu_2O_3$ | K/$Eu_2O_3$ | Rb/$Eu_2O_3$ | Cs/$Eu_2O_3$ | Be/$Eu_2O_3$ | Mg/$Eu_2O_3$ | Ca/$Eu_2O_3$ |
| $Gd_2O_3$ | Li/$Gd_2O_3$ | Na/$Gd_2O_3$ | K/$Gd_2O_3$ | Rb/$Gd_2O_3$ | Cs/$Gd_2O_3$ | Be/$Gd_2O_3$ | Mg/$Gd_2O_3$ | Ca/$Gd_2O_3$ |
| $Tb_2O_3$ | Li/$Tb_2O_3$ | Na/$Tb_2O_3$ | K/$Tb_2O_3$ | Rb/$Tb_2O_3$ | Cs/$Tb_2O_3$ | Be/$Tb_2O_3$ | Mg/$Tb_2O_3$ | Ca/$Tb_2O_3$ |
| $TbO_2$ | Li/$TbO_2$ | Na/$TbO_2$ | K/$TbO_2$ | Rb/$TbO_2$ | Cs/$TbO_2$ | Be/$TbO_2$ | Mg/$TbO_2$ | Ca/$TbO_2$ |
| $Tb_6O_{11}$ | Li/$Tb_6O_{11}$ | Na/$Tb_6O_{11}$ | K/$Tb_6O_{11}$ | Rb/$Tb_6O_{11}$ | Cs/$Tb_6O_{11}$ | Be/$Tb_6O_{11}$ | Mg/$Tb_6O_{11}$ | Ca/$Tb_6O_{11}$ |
| $Dy_2O_3$ | Li/$Dy_2O_3$ | Na/$Dy_2O_3$ | K/$Dy_2O_3$ | Rb/$Dy_2O_3$ | Cs/$Dy_2O_3$ | Be/$Dy_2O_3$ | Mg/$Dy_2O_3$ | Ca/$Dy_2O_3$ |
| $Ho_2O_3$ | Li/$Ho_2O_3$ | Na/$Ho_2O_3$ | K/$Ho_2O_3$ | Rb/$Ho_2O_3$ | Cs/$Ho_2O_3$ | Be/$Ho_2O_3$ | Mg/$Ho_2O_3$ | Ca/$Ho_2O_3$ |
| $Er_2O_3$ | Li/$Er_2O_3$ | Na/$Er_2O_3$ | K/$Er_2O_3$ | Rb/$Er_2O_3$ | Cs/$Er_2O_3$ | Be/$Er_2O_3$ | Mg/$Er_2O_3$ | Ca/$Er_2O_3$ |
| $Tm_2O_3$ | Li/$Tm_2O_3$ | Na/$Tm_2O_3$ | K/$Tm_2O_3$ | Rb/$Tm_2O_3$ | Cs/$Tm_2O_3$ | Be/$Tm_2O_3$ | Mg/$Tm_2O_3$ | Ca/$Tm_2O_3$ |
| $Yb_2O_3$ | Li/$Yb_2O_3$ | Na/$Yb_2O_3$ | K/$Yb_2O_3$ | Rb/$Yb_2O_3$ | Cs/$Yb_2O_3$ | Be/$Yb_2O_3$ | Mg/$Yb_2O_3$ | Ca/$Yb_2O_3$ |
| $Lu_2O_3$ | Li/$Lu_2O_3$ | Na/$Lu_2O_3$ | K/$Lu_2O_3$ | Rb/$Lu_2O_3$ | Cs/$Lu_2O_3$ | Be/$Lu_2O_3$ | Mg/$Lu_2O_3$ | Ca/$Lu_2O_3$ |
| $Ac_2O_3$ | Li/$Ac_2O_3$ | Na/$Ac_2O_3$ | K/$Ac_2O_3$ | Rb/$Ac_2O_3$ | Cs/$Ac_2O_3$ | Be/$Ac_2O_3$ | Mg/$Ac_2O_3$ | Ca/$Ac_2O_3$ |
| $Th_2O_3$ | Li/$Th_2O_3$ | Na/$Th_2O_3$ | K/$Th_2O_3$ | Rb/$Th_2O_3$ | Cs/$Th_2O_3$ | Be/$Th_2O_3$ | Mg/$Th_2O_3$ | Ca/$Th_2O_3$ |
| $ThO_2$ | Li/$ThO_2$ | Na/$ThO_2$ | K/$ThO_2$ | Rb/$ThO_2$ | Cs/$ThO_2$ | Be/$ThO_2$ | Mg/$ThO_2$ | Ca/$ThO_2$ |
| $Pa_2O_3$ | Li/$Pa_2O_3$ | Na/$Pa_2O_3$ | K/$Pa_2O_3$ | Rb/$Pa_2O_3$ | Cs/$Pa_2O_3$ | Be/$Pa_2O_3$ | Mg/$Pa_2O_3$ | Ca/$Pa_2O_3$ |
| $PaO_2$ | Li/$PaO_2$ | Na/$PaO_2$ | K/$PaO_2$ | Rb/$PaO_2$ | Cs/$PaO_2$ | Be/$PaO_2$ | Mg/$PaO_2$ | Ca/$PaO_2$ |
| $TiO_2$ | Li/$TiO_2$ | Na/$TiO_2$ | K/$TiO_2$ | Rb/$TiO_2$ | Cs/$TiO_2$ | Be/$TiO_2$ | Mg/$TiO_2$ | Ca/$TiO_2$ |
| TiO | Li/TiO | Na/TiO | K/TiO | Rb/TiO | Cs/TiO | Be/TiO | Mg/TiO | Ca/TiO |
| $Ti_2O_3$ | Li/$Ti_2O_3$ | Na/$Ti_2O_3$ | K/$Ti_2O_3$ | Rb/$Ti_2O_3$ | Cs/$Ti_2O_3$ | Be/$Ti_2O_3$ | Mg/$Ti_2O_3$ | Ca/$Ti_2O_3$ |
| $Ti_3O$ | Li/$Ti_3O$ | Na/$Ti_3O$ | K/$Ti_3O$ | Rb/$Ti_3O$ | Cs/$Ti_3O$ | Be/$Ti_3O$ | Mg/$Ti_3O$ | Ca/$Ti_3O$ |

TABLE 1-continued

NANOWIRES (NW) DOPED WITH SPECIFIC DOPANTS (DOP)

| NW\Dop | Li | Na | K | Rb | Cs | Be | Mg | Ca |
|---|---|---|---|---|---|---|---|---|
| $Ti_2O$ | Li/$Ti_2O$ | Na/$Ti_2O$ | K/$Ti_2O$ | Rb/$Ti_2O$ | Cs/$Ti_2O$ | Be/$Ti_2O$ | Mg/$Ti_2O$ | Ca/$Ti_2O$ |
| $Ti_3O_5$ | Li/$Ti_3O_5$ | Na/$Ti_3O_5$ | K/$Ti_3O_5$ | Rb/$Ti_3O_5$ | Cs/$Ti_3O_5$ | Be/$Ti_3O_5$ | Mg/$Ti_3O_5$ | Ca/$Ti_3O_5$ |
| $Ti_4O_7$ | Li/$Ti_4O_7$ | Na/$Ti_4O_7$ | K/$Ti_4O_7$ | Rb/$Ti_4O_7$ | Cs/$Ti_4O_7$ | Be/$Ti_4O_7$ | Mg/$Ti_4O_7$ | Ca/$Ti_4O_7$ |
| $ZrO_2$ | Li/$ZrO_2$ | Na/$ZrO_2$ | K/$ZrO_2$ | Rb/$ZrO_2$ | Cs/$ZrO_2$ | Be/$ZrO_2$ | Mg/$ZrO_2$ | Ca/$ZrO_2$ |
| $HfO_2$ | Li/$HfO_2$ | Na/$HfO_2$ | K/$HfO_2$ | Rb/$HfO_2$ | Cs/$HfO_2$ | Be/$HfO_2$ | Mg/$HfO_2$ | Ca/$HfO_2$ |
| VO | Li/VO | Na/VO | K/VO | Rb/VO | Cs/VO | Be/VO | Mg/VO | Ca/VO |
| $V_2O_3$ | Li/$V_2O_3$ | Na/$V_2O_3$ | K/$V_2O_3$ | Rb/$V_2O_3$ | Cs/$V_2O_3$ | Be/$V_2O_3$ | Mg/$V_2O_3$ | Ca/$V_2O_3$ |
| $VO_2$ | Li/$VO_2$ | Na/$VO_2$ | K/$VO_2$ | Rb/$VO_2$ | Cs/$VO_2$ | Be/$VO_2$ | Mg/$VO_2$ | Ca/$VO_2$ |
| $V_2O_5$ | Li/$V_2O_5$ | Na/$V_2O_5$ | K/$V_2O_5$ | Rb/$V_2O_5$ | Cs/$V_2O_5$ | Be/$V_2O_5$ | Mg/$V_2O_5$ | Ca/$V_2O_5$ |
| $V_3O_7$ | Li/$V_3O_7$ | Na/$V_3O_7$ | K/$V_3O_7$ | Rb/$V_3O_7$ | Cs/$V_3O_7$ | Be/$V_3O_7$ | Mg/$V_3O_7$ | Ca/$V_3O_7$ |
| $V_4O_9$ | Li/$V_4O_9$ | Na/$V_4O_9$ | K/$V_4O_9$ | Rb/$V_4O_9$ | Cs/$V_4O_9$ | Be/$V_4O_9$ | Mg/$V_4O_9$ | Ca/$V_4O_9$ |
| $V_6O_{13}$ | Li/$V_6O_{13}$ | Na/$V_6O_{13}$ | K/$V_6O_{13}$ | Rb/$V_6O_{13}$ | Cs/$V_6O_{13}$ | Be/$V_6O_{13}$ | Mg/$V_6O_{13}$ | Ca/$V_6O_{13}$ |
| NbO | Li/NbO | Na/NbO | K/NbO | Rb/NbO | Cs/NbO | Be/NbO | Mg/NbO | Ca/NbO |
| $NbO_2$ | Li/$NbO_2$ | Na/$NbO_2$ | K/$NbO_2$ | Rb/$NbO_2$ | Cs/$NbO_2$ | Be/$NbO_2$ | Mg/$NbO_2$ | Ca/$NbO_2$ |
| $Nb_2O_5$ | Li/$Nb_2O_5$ | Na/$Nb_2O_5$ | K/$Nb_2O_5$ | Rb/$Nb_2O_5$ | Cs/$Nb_2O_5$ | Be/$Nb_2O_5$ | Mg/$Nb_2O_5$ | Ca/$Nb_2O_5$ |
| $Nb_8O_{19}$ | Li/$Nb_8O_{19}$ | Na/$Nb_8O_{19}$ | K/$Nb_8O_{19}$ | Rb/$Nb_8O_{19}$ | Cs/$Nb_8O_{19}$ | Be/$Nb_8O_{19}$ | Mg/$Nb_8O_{19}$ | Ca/$Nb_8O_{19}$ |
| $Nb_{16}O_{38}$ | Li/$Nb_{16}O_{38}$ | Na/$Nb_{16}O_{38}$ | K/$Nb_{16}O_{38}$ | Rb/$Nb_{16}O_{38}$ | Cs/$Nb_{16}O_{38}$ | Be/$Nb_{16}O_{38}$ | Mg/$Nb_{16}O_{38}$ | Ca/$Nb_{16}O_{38}$ |
| $Nb_{12}O_{29}$ | Li/$Nb_{12}O_{29}$ | Na/$Nb_{12}O_{29}$ | K/$Nb_{12}O_{29}$ | Rb/$Nb_{12}O_{29}$ | Cs/$Nb_{12}O_{29}$ | Be/$Nb_{12}O_{29}$ | Mg/$Nb_{12}O_{29}$ | Ca/$Nb_{12}O_{29}$ |
| $Nb_{47}O_{116}$ | Li/$Nb_{47}O_{116}$ | Na/$Nb_{47}O_{116}$ | K/$Nb_{47}O_{116}$ | Rb/$Nb_{47}O_{116}$ | Cs/$Nb_{47}O_{116}$ | Be/$Nb_{47}O_{116}$ | Mg/$Nb_{47}O_{116}$ | Ca/$Nb_{47}O_{116}$ |
| $Ta_2O_5$ | Li/$Ta_2O_5$ | Na/$Ta_2O_5$ | K/$Ta_2O_5$ | Rb/$Ta_2O_5$ | Cs/$Ta_2O_5$ | Be/$Ta_2O_5$ | Mg/$Ta_2O_5$ | Ca/$Ta_2O_5$ |
| CrO | Li/CrO | Na/CrO | K/CrO | Rb/CrO | Cs/CrO | Be/CrO | Mg/CrO | Ca/CrO |
| $Cr_2O_3$ | Li/$Cr_2O_3$ | Na/$Cr_2O_3$ | K/$Cr_2O_3$ | Rb/$Cr_2O_3$ | Cs/$Cr_2O_3$ | Be/$Cr_2O_3$ | Mg/$Cr_2O_3$ | Ca/$Cr_2O_3$ |
| $CrO_2$ | Li/$CrO_2$ | Na/$CrO_2$ | K/$CrO_2$ | Rb/$CrO_2$ | Cs/$CrO_2$ | Be/$CrO_2$ | Mg/$CrO_2$ | Ca/$CrO_2$ |
| $CrO_3$ | Li/$CrO_3$ | Na/$CrO_3$ | K/$CrO_3$ | Rb/$CrO_3$ | Cs/$CrO_3$ | Be/$CrO_3$ | Mg/$CrO_3$ | Ca/$CrO_3$ |
| $Cr_8O_{21}$ | Li/$Cr_8O_{21}$ | Na/$Cr_8O_{21}$ | K/$Cr_8O_{21}$ | Rb/$Cr_8O_{21}$ | Cs/$Cr_8O_{21}$ | Be/$Cr_8O_{21}$ | Mg/$Cr_8O_{21}$ | Ca/$Cr_8O_{21}$ |
| $MoO_2$ | Li/$MoO_2$ | Na/$MoO_2$ | K/$MoO_2$ | Rb/$MoO_2$ | Cs/$MoO_2$ | Be/$MoO_2$ | Mg/$MoO_2$ | Ca/$MoO_2$ |
| $MoO_3$ | Li/$MoO_3$ | Na/$MoO_3$ | K/$MoO_3$ | Rb/$MoO_3$ | Cs/$MoO_3$ | Be/$MoO_3$ | Mg/$MoO_3$ | Ca/$MoO_3$ |
| $W_2O_3$ | Li/$W_2O_3$ | Na/$W_2O_3$ | K/$W_2O_3$ | Rb/$W_2O_3$ | Cs/$W_2O_3$ | Be/$W_2O_3$ | Mg/$W_2O_3$ | Ca/$W_2O_3$ |
| $WoO_2$ | Li/$WoO_2$ | Na/$WoO_2$ | K/$WoO_2$ | Rb/$WoO_2$ | Cs/$WoO_2$ | Be/$WoO_2$ | Mg/$WoO_2$ | Ca/$WoO_2$ |
| $WoO_3$ | Li/$WoO_3$ | Na/$WoO_3$ | K/$WoO_3$ | Rb/$WoO_3$ | Cs/$WoO_3$ | Be/$WoO_3$ | Mg/$WoO_3$ | Ca/$WoO_3$ |
| MnO | Li/MnO | Na/MnO | K/MnO | Rb/MnO | Cs/MnO | Be/MnO | Mg/MnO | Ca/MnO |
| Mn/Mg/O | Li/Mn/Mg/O | Na/Mn/Mg/O | K/Mn/Mg/O | Rb/Mn/Mg/O | Cs/Mn/Mg/O | Be/Mn/Mg/O | Mg/Mn/Mg/O | Ca/Mn/Mg/O |
| $Mn_3O_4$ | Li/$Mn_3O_4$ | Na/$Mn_3O_4$ | K/$Mn_3O_4$ | Rb/$Mn_3O_4$ | Cs/$Mn_3O_4$ | Be/$Mn_3O_4$ | Mg/$Mn_3O_4$ | Ca/$Mn_3O_4$ |
| $Mn_2O_3$ | Li/$Mn_2O_3$ | Na/$Mn_2O_3$ | K/$Mn_2O_3$ | Rb/$Mn_2O_3$ | Cs/$Mn_2O_3$ | Be/$Mn_2O_3$ | Mg/$Mn_2O_3$ | Ca/$Mn_2O_3$ |
| $MnO_2$ | Li/$MnO_2$ | Na/$MnO_2$ | K/$MnO_2$ | Rb/$MnO_2$ | Cs/$MnO_2$ | Be/$MnO_2$ | Mg/$MnO_2$ | Ca/$MnO_2$ |
| $Mn_2O_7$ | Li/$Mn_2O_7$ | Na/$Mn_2O_7$ | K/$Mn_2O_7$ | Rb/$Mn_2O_7$ | Cs/$Mn_2O_7$ | Be/$Mn_2O_7$ | Mg/$Mn_2O_7$ | Ca/$Mn_2O_7$ |
| $ReO_2$ | Li/$ReO_2$ | Na/$ReO_2$ | K/$ReO_2$ | Rb/$ReO_2$ | Cs/$ReO_2$ | Be/$ReO_2$ | Mg/$ReO_2$ | Ca/$ReO_2$ |
| $ReO_3$ | Li/$ReO_3$ | Na/$ReO_3$ | K/$ReO_3$ | Rb/$ReO_3$ | Cs/$ReO_3$ | Be/$ReO_3$ | Mg/$ReO_3$ | Ca/$ReO_3$ |

TABLE 1-continued

NANOWIRES (NW) DOPED WITH SPECIFIC DOPANTS (DOP)

| NW\Dop | Li | Na | K | Rb | Cs | Be | Mg | Ca |
|---|---|---|---|---|---|---|---|---|
| $Re_2O_7$ | $Li/Re_2O_7$ | $Na/Re_2O_7$ | $K/Re_2O_7$ | $Rb/Re_2O_7$ | $Cs/Re_2O_7$ | $Be/Re_2O_7$ | $Mg/Re_2O_7$ | $Ca/Re_2O_7$ |
| $Mg_3Mn_3$—$B_2O_{10}$ | $Li/Mg_3Mn_3$—$B_2O_{10}$ | $Na/Mg_3Mn_3$—$B_2O_{10}$ | $K/Mg_3Mn_3$—$B_2O_{10}$ | $Rb/Mg_3Mn_3$—$B_2O_{10}$ | $Cs/Mg_3Mn_3$—$B_2O_{10}$ | $Be/Mg_3Mn_3$—$B_2O_{10}$ | $Mg/Mg_3Mn_3$—$B_2O_{10}$ | $Ca/Mg_3Mn_3$—$B_2O_{10}$ |
| $Mg_3(BO_3)_2$ | $Li/Mg_3(BO_3)_2$ | $Na/Mg_3(BO_3)_2$ | $K/Mg_3(BO_3)_2$ | $Rb/Mg_3(BO_3)_2$ | $Cs/Mg_3(BO_3)_2$ | $Be/Mg_3(BO_3)_2$ | $Mg/Mg_3(BO_3)_2$ | $Ca/Mg_3(BO_3)_2$ |
| $NaWO_4$ | $Li/NaWO_4$ | $Na/NaWO_4$ | $K/NaWO_4$ | $Rb/NaWO_4$ | $Cs/NaWO_4$ | $Be/NaWO_4$ | $Mg/NaWO_4$ | $Ca/NaWO_4$ |
| $Mg_6MnO_8$ | $Li/Mg_6MnO_8$ | $Na/Mg_6MnO_8$ | $K/Mg_6MnO_8$ | $Rb/Mg_6MnO_8$ | $Cs/Mg_6MnO_8$ | $Be/Mg_6MnO_8$ | $Mg/Mg_6MnO_8$ | $Ca/Mg_6MnO_8$ |
| $(Li,Mg)_6$—$MnO_8$ | $Li/(Li,Mg)_6$—$MnO_8$ | $Na/(Li,Mg)_6$—$MnO_8$ | $K/(Li,Mg)_6$—$MnO_8$ | $Rb/(Li,Mg)_6$—$MnO_8$ | $Cs/(Li,Mg)_6$—$MnO_8$ | $Be/(Li,Mg)_6$—$MnO_8$ | $Mg/(Li,Mg)_6$—$MnO_8$ | $Ca/(Li,Mg)_6$—$MnO_8$ |
| $Mn_2O_4$ | $Li/Mn_2O_4$ | $Na/Mn_2O_4$ | $K/Mn_2O_4$ | $Rb/Mn_2O_4$ | $Cs/Mn_2O_4$ | $Be/Mn_2O_4$ | $Mg/Mn_2O_4$ | $Ca/Mn_2O_4$ |
| $Na_4P_2O_7$ | $Li/Na_4P_2O_7$ | $Na/Na_4P_2O_7$ | $K/Na_4P_2O_7$ | $Rb/Na_4P_2O_7$ | $Cs/Na_4P_2O_7$ | $Be/Na_4P_2O_7$ | $Mg/Na_4P_2O_7$ | $Ca/Na_4P_2O_7$ |
| $Mo_2O_8$ | $Li/Mo_2O_8$ | $Na/Mo_2O_8$ | $K/Mo_2O_8$ | $Rb/Mo_2O_8$ | $Cs/Mo_2O_8$ | $Be/Mo_2O_8$ | $Mg/Mo_2O_8$ | $Ca/Mo_2O_8$ |
| $Mn_3O_4/WO_4$ | $Li/Mn_3O_4/WO_4$ | $Na/Mn_3O_4/WO_4$ | $K/Mn_3O_4/WO_4$ | $Rb/Mn_3O_4/WO_4$ | $Cs/Mn_3O_4/WO_4$ | $Be/Mn_3O_4/WO_4$ | $Mg/Mn_3O_4/WO_4$ | $Ca/Mn_3O_4/WO_4$ |
| $Na_2WO_4$ | $Li/Na_2WO_4$ | $Na/Na_2WO_4$ | $K/Na_2WO_4$ | $Rb/Na_2WO_4$ | $Cs/Na_2WO_4$ | $Be/Na_2WO_4$ | $Mg/Na_2WO_4$ | $Ca/Na_2WO_4$ |
| $Zr_2Mo_2O_8$ | $Li/Zr_2Mo_2O_8$ | $Na/Zr_2Mo_2O_8$ | $K/Zr_2Mo_2O_8$ | $Rb/Zr_2Mo_2O_8$ | $Cs/Zr_2Mo_2O_8$ | $Be/Zr_2Mo_2O_8$ | $Mg/Zr_2Mo_2O_8$ | $Ca/Zr_2Mo_2O_8$ |
| $NaMnO_4$—/$MgO$ | $Li/NaMnO_4$—/$MgO$ | $Na/NaMnO_4$—/$MgO$ | $K/NaMnO_4$—/$MgO$ | $Rb/NaMnO_4$—/$MgO$ | $Cs/NaMnO_4$—/$MgO$ | $Be/NaMnO_4$—/$MgO$ | $Mg/NaMnO_4$—/$MgO$ | $Ca/NaMnO_4$—/$MgO$ |
| $Na_{10}Mn$—$W_5O_{17}$ | $Li/Na_{10}Mn$—$W_5O_{17}$ | $Na/Na_{10}Mn$—$W_5O_{17}$ | $K/Na_{10}Mn$—$W_5O_{17}$ | $Rb/Na_{10}Mn$—$W_5O_{17}$ | $Cs/Na_{10}Mn$—$W_5O_{17}$ | $Be/Na_{10}Mn$—$W_5O_{17}$ | $Mg/Na_{10}Mn$—$W_5O_{17}$ | $Ca/Na_{10}Mn$—$W_5O_{17}$ |
| $La_3NdO_6$ | $Li/La_3NdO_6$ | $Na/La_3NdO_6$ | $K/La_3NdO_6$ | $Rb/La_3NdO_6$ | $Cs/La_3NdO_6$ | $Be/La_3NdO_6$ | $Mg/La_3NdO_6$ | $Ca/La_3NdO_6$ |
| $LaNd_3O_6$ | $Li/LaNd_3O_6$ | $Na/LaNd_3O_6$ | $K/LaNd_3O_6$ | $Rb/LaNd_3O_6$ | $Cs/LaNd_3O_6$ | $Be/LaNd_3O_6$ | $Mg/LaNd_3O_6$ | $Ca/LaNd_3O_6$ |
| $La_{1.5}Nd_{2.5}O_6$ | $Li/La_{1.5}Nd_{2.5}O_6$ | $Na/La_{1.5}Nd_{2.5}O_6$ | $K/La_{1.5}Nd_{2.5}O_6$ | $Rb/La_{1.5}Nd_{2.5}O_6$ | $Cs/La_{1.5}Nd_{2.5}O_6$ | $Be/La_{1.5}Nd_{2.5}O_6$ | $Mg/La_{1.5}Nd_{2.5}O_6$ | $Ca/La_{1.5}Nd_{2.5}O_6$ |
| $La_{2.5}Nd_{1.5}O_6$ | $Li/La_{2.5}Nd_{1.5}O_6$ | $Na/La_{2.5}Nd_{1.5}O_6$ | $K/La_{2.5}Nd_{1.5}O_6$ | $Rb/La_{2.5}Nd_{1.5}O_6$ | $Cs/La_{2.5}Nd_{1.5}O_6$ | $Be/La_{2.5}Nd_{1.5}O_6$ | $Mg/La_{2.5}Nd_{1.5}O_6$ | $Ca/La_{2.5}Nd_{1.5}O_6$ |
| $La_{3.2}Nd_{0.8}O_6$ | $Li/La_{3.2}Nd_{0.8}O_6$ | $Na/La_{3.2}Nd_{0.8}O_6$ | $K/La_{3.2}Nd_{0.8}O_6$ | $Rb/La_{3.2}Nd_{0.8}O_6$ | $Cs/La_{3.2}Nd_{0.8}O_6$ | $Be/La_{3.2}Nd_{0.8}O_6$ | $Mg/La_{3.2}Nd_{0.8}O_6$ | $Ca/La_{3.2}Nd_{0.8}O_6$ |
| $La_{3.5}Nd_{0.5}O_6$ | $Li/La_{3.5}Nd_{0.5}O_6$ | $Na/La_{3.5}Nd_{0.5}O_6$ | $K/La_{3.5}Nd_{0.5}O_6$ | $Rb/La_{3.5}Nd_{0.5}O_6$ | $Cs/La_{3.5}Nd_{0.5}O_6$ | $Be/La_{3.5}Nd_{0.5}O_6$ | $Mg/La_{3.5}Nd_{0.5}O_6$ | $Ca/La_{3.5}Nd_{0.5}O_6$ |
| $La_{3.8}Nd_{0.2}O_6$ | $Li/La_{3.8}Nd_{0.2}O_6$ | $Na/La_{3.8}Nd_{0.2}O_6$ | $K/La_{3.8}Nd_{0.2}O_6$ | $Rb/La_{3.8}Nd_{0.2}O_6$ | $Cs/La_{3.8}Nd_{0.2}O_6$ | $Be/La_{3.8}Nd_{0.2}O_6$ | $Mg/La_{3.8}Nd_{0.2}O_6$ | $Ca/La_{3.8}Nd_{0.2}O_6$ |
| Y—La | Li/Y—La | Na/Y—La | K/Y—La | Rb/Y—La | Cs/Y—La | Be/Y—La | Mg/Y—La | Ca/Y—La |
| Zr—La | Li/Zr—La | Na/Zr—La | K/Zr—La | Rb/Zr—La | Cs/Zr—La | Be/Zr—La | Mg/Zr—La | Ca/Zr—La |
| Pr—La | Li/Pr—La | Na/Pr—La | K/Pr—La | Rb/Pr—La | Cs/Pr—La | Be/Pr—La | Mg/Pr—La | Ca/Pr—La |
| Ce—La | Li/Ce—La | Na/Ce—La | K/Ce—La | Rb/Ce—La | Cs/Ce—La | Be/Ce—La | Mg/Ce—La | Ca/Ce—La |

TABLE 2

NANOWIRES (NW) DOPED WITH SPECIFIC DOPANTS (DOP)

| NW\Dop | Sr | Ba | B | P | S | F | Cl |
|---|---|---|---|---|---|---|---|
| $Li_2O$ | $Sr/Li_2O$ | $Ba/Li_2O$ | $B/Li_2O$ | $P/Li_2O$ | $S/Li_2O$ | $F/Li_2O$ | $Cl/Li_2O$ |
| $Na_2O$ | $Sr/Na_2O$ | $Ba/Na_2O$ | $B/Na_2O$ | $P/Na_2O$ | $S/Na_2O$ | $F/Na_2O$ | $Cl/Na_2O$ |
| $K_2O$ | $Sr/K_2O$ | $Ba/K_2O$ | $B/K_2O$ | $P/K_2O$ | $S/K_2O$ | $F/K_2O$ | $Cl/K_2O$ |
| $Rb_2O$ | $Sr/Rb_2O$ | $Ba/Rb_2O$ | $B/Rb_2O$ | $P/Rb_2O$ | $S/Rb_2O$ | $F/Rb_2O$ | $Cl/Rb_2O$ |
| $Cs_2O$ | $Sr/Cs_2O$ | $Ba/Cs_2O$ | $B/Cs_2O$ | $P/Cs_2O$ | $S/Cs_2O$ | $F/Cs_2O$ | $Cl/Cs_2O$ |

TABLE 2-continued

NANOWIRES (NW) DOPED WITH SPECIFIC DOPANTS (DOP)

| NW\Dop | Sr | Ba | B | P | S | F | Cl |
|---|---|---|---|---|---|---|---|
| BeO | Sr/BeO | Ba/BeO | B/BeO | P/BeO | S/BeO | F/BeO | Cl/BeO |
| MgO | Sr/MgO | Ba/MgO | B/MgO | P/MgO | S/MgO | F/MgO | Cl/MgO |
| CaO | Sr/CaO | Ba/CaO | B/CaO | P/CaO | S/CaO | F/CaO | Cl/CaO |
| SrO | Sr/SrO | Ba/SrO | B/SrO | P/SrO | S/SrO | F/SrO | Cl/SrO |
| BaO | Sr/BaO | Ba/BaO | B/BaO | P/BaO | S/BaO | F/BaO | Cl/BaO |
| $Sc_2O_3$ | Sr/$Sc_2O_3$ | Ba/$Sc_2O_3$ | B/$Sc_2O_3$ | P/$Sc_2O_3$ | S/$Sc_2O_3$ | F/$Sc_2O_3$ | Cl/$Sc_2O_3$ |
| $Y_2O_3$ | Sr/$Y_2O_3$ | Ba/$Y_2O_3$ | B/$Y_2O_3$ | P/$Y_2O_3$ | S/$Y_2O_3$ | F/$Y_2O_3$ | Cl/$Y_2O_3$ |
| $La_2O_3$ | Sr/$La_2O_3$ | Ba/$La_2O_3$ | B/$La_2O_3$ | P/$La_2O_3$ | S/$La_2O_3$ | F/$La_2O_3$ | Cl/$La_2O_3$ |
| $CeO_2$ | Sr/$CeO_2$ | Ba/$CeO_2$ | B/$CeO_2$ | P/$CeO_2$ | S/$CeO_2$ | F/$CeO_2$ | Cl/$CeO_2$ |
| $Ce_2O_3$ | Sr/$Ce_2O_3$ | Ba/$Ce_2O_3$ | B/$Ce_2O_3$ | P/$Ce_2O_3$ | S/$Ce_2O_3$ | F/$Ce_2O_3$ | Cl/$Ce_2O_3$ |
| $Pr_2O_3$ | Sr/$Pr_2O_3$ | Ba/$Pr_2O_3$ | B/$Pr_2O_3$ | P/$Pr_2O_3$ | S/$Pr_2O_3$ | F/$Pr_2O_3$ | Cl/$Pr_2O_3$ |
| $Nd_2O_3$ | Sr/$Nd_2O_3$ | Ba/$Nd_2O_3$ | B/$Nd_2O_3$ | P/$Nd_2O_3$ | S/$Nd_2O_3$ | F/$Nd_2O_3$ | Cl/$Nd_2O_3$ |
| $Sm_2O_3$ | Sr/$Sm_2O_3$ | Ba/$Sm_2O_3$ | B/$Sm_2O_3$ | P/$Sm_2O_3$ | S/$Sm_2O_3$ | F/$Sm_2O_3$ | Cl/$Sm_2O_3$ |
| $Eu_2O_3$ | Sr/$Eu_2O_3$ | Ba/$Eu_2O_3$ | B/$Eu_2O_3$ | P/$Eu_2O_3$ | S/$Eu_2O_3$ | F/$Eu_2O_3$ | Cl/$Eu_2O_3$ |
| $Gd_2O_3$ | Sr/$Gd_2O_3$ | Ba/$Gd_2O_3$ | B/$Gd_2O_3$ | P/$Gd_2O_3$ | S/$Gd_2O_3$ | F/$Gd_2O_3$ | Cl/$Gd_2O_3$ |
| $Tb_2O_3$ | Sr/$Tb_2O_3$ | Ba/$Tb_2O_3$ | B/$Tb_2O_3$ | P/$Tb_2O_3$ | S/$Tb_2O_3$ | F/$Tb_2O_3$ | Cl/$Tb_2O_3$ |
| $TbO_2$ | Sr/$TbO_2$ | Ba/$TbO_2$ | B/$TbO_2$ | P/$TbO_2$ | S/$TbO_2$ | F/$TbO_2$ | Cl/$TbO_2$ |
| $Tb_6O_{11}$ | Sr/$Tb_6O_{11}$ | Ba/$Tb_6O_{11}$ | B/$Tb_6O_{11}$ | P/$Tb_6O_{11}$ | S/$Tb_6O_{11}$ | F/$Tb_6O_{11}$ | Cl/$Tb_6O_{11}$ |
| $Dy_2O_3$ | Sr/$Dy_2O_3$ | Ba/$Dy_2O_3$ | B/$Dy_2O_3$ | P/$Dy_2O_3$ | S/$Dy_2O_3$ | F/$Dy_2O_3$ | Cl/$Dy_2O_3$ |
| $Ho_2O_3$ | Sr/$Ho_2O_3$ | Ba/$Ho_2O_3$ | B/$Ho_2O_3$ | P/$Ho_2O_3$ | S/$Ho_2O_3$ | F/$Ho_2O_3$ | Cl/$Ho_2O_3$ |
| $Er_2O_3$ | Sr/$Er_2O_3$ | Ba/$Er_2O_3$ | B/$Er_2O_3$ | P/$Er_2O_3$ | S/$Er_2O_3$ | F/$Er_2O_3$ | Cl/$Er_2O_3$ |
| $Tm_2O_3$ | Sr/$Tm_2O_3$ | Ba/$Tm_2O_3$ | B/$Tm_2O_3$ | P/$Tm_2O_3$ | S/$Tm_2O_3$ | F/$Tm_2O_3$ | Cl/$Tm_2O_3$ |
| $Yb_2O_3$ | Sr/$Yb_2O_3$ | Ba/$Yb_2O_3$ | B/$Yb_2O_3$ | P/$Yb_2O_3$ | S/$Yb_2O_3$ | F/$Yb_2O_3$ | Cl/$Yb_2O_3$ |
| $Lu_2O_3$ | Sr/$Lu_2O_3$ | Ba/$Lu_2O_3$ | B/$Lu_2O_3$ | P/$Lu_2O_3$ | S/$Lu_2O_3$ | F/$Lu_2O_3$ | Cl/$Lu_2O_3$ |
| $Ac_2O_3$ | Sr/$Ac_2O_3$ | Ba/$Ac_2O_3$ | B/$Ac_2O_3$ | P/$Ac_2O_3$ | S/$Ac_2O_3$ | F/$Ac_2O_3$ | Cl/$Ac_2O_3$ |
| $Th_2O_3$ | Sr/$Th_2O_3$ | Ba/$Th_2O_3$ | B/$Th_2O_3$ | P/$Th_2O_3$ | S/$Th_2O_3$ | F/$Th_2O_3$ | Cl/$Th_2O_3$ |
| $ThO_2$ | Sr/$ThO_2$ | Ba/$ThO_2$ | B/$ThO_2$ | P/$ThO_2$ | S/$ThO_2$ | F/$ThO_2$ | Cl/$ThO_2$ |
| $Pa_2O_3$ | Sr/$Pa_2O_3$ | Ba/$Pa_2O_3$ | B/$Pa_2O_3$ | P/$Pa_2O_3$ | S/$Pa_2O_3$ | F/$Pa_2O_3$ | Cl/$Pa_2O_3$ |
| $PaO_2$ | Sr/$PaO_2$ | Ba/$PaO_2$ | B/$PaO_2$ | P/$PaO_2$ | S/$PaO_2$ | F/$PaO_2$ | Cl/$PaO_2$ |
| $TiO_2$ | Sr/$TiO_2$ | Ba/$TiO_2$ | B/$TiO_2$ | P/$TiO_2$ | S/$TiO_2$ | F/$TiO_2$ | Cl/$TiO_2$ |
| TiO | Sr/TiO | Ba/TiO | B/TiO | P/TiO | S/TiO | F/TiO | Cl/TiO |
| $Ti_2O_3$ | Sr/$Ti_2O_3$ | Ba/$Ti_2O_3$ | B/$Ti_2O_3$ | P/$Ti_2O_3$ | S/$Ti_2O_3$ | F/$Ti_2O_3$ | Cl/$Ti_2O_3$ |
| $Ti_3O$ | Sr/$Ti_3O$ | Ba/$Ti_3O$ | B/$Ti_3O$ | P/$Ti_3O$ | S/$Ti_3O$ | F/$Ti_3O$ | Cl/$Ti_3O$ |
| $Ti_2O$ | Sr/$Ti_2O$ | Ba/$Ti_2O$ | B/$Ti_2O$ | P/$Ti_2O$ | S/$Ti_2O$ | F/$Ti_2O$ | Cl/$Ti_2O$ |
| $Ti_3O_5$ | Sr/$Ti_3O_5$ | Ba/$Ti_3O_5$ | B/$Ti_3O_5$ | P/$Ti_3O_5$ | S/$Ti_3O_5$ | F/$Ti_3O_5$ | Cl/$Ti_3O_5$ |
| $Ti_4O_7$ | Sr/$Ti_4O_7$ | Ba/$Ti_4O_7$ | B/$Ti_4O_7$ | P/$Ti_4O_7$ | S/$Ti_4O_7$ | F/$Ti_4O_7$ | Cl/$Ti_4O_7$ |
| $ZrO_2$ | Sr/$ZrO_2$ | Ba/$ZrO_2$ | B/$ZrO_2$ | P/$ZrO_2$ | S/$ZrO_2$ | F/$ZrO_2$ | Cl/$ZrO_2$ |
| $HfO_2$ | Sr/$HfO_2$ | Ba/$HfO_2$ | B/$HfO_2$ | P/$HfO_2$ | S/$HfO_2$ | F/$HfO_2$ | Cl/$HfO_2$ |

TABLE 2-continued

NANOWIRES (NW) DOPED WITH SPECIFIC DOPANTS (DOP)

| NW\Dop | Sr | Ba | B | P | S | F | Cl |
|---|---|---|---|---|---|---|---|
| VO | Sr/VO | Ba/VO | B/VO | P/VO | S/VO | F/VO | Cl/VO |
| $V_2O_3$ | Sr/$V_2O_3$ | Ba/$V_2O_3$ | B/$V_2O_3$ | P/$V_2O_3$ | S/$V_2O_3$ | F/$V_2O_3$ | Cl/$V_2O_3$ |
| $VO_2$ | Sr/$VO_2$ | Ba/$VO_2$ | B/$VO_2$ | P/$VO_2$ | S/$VO_2$ | F/$VO_2$ | Cl/$VO_2$ |
| $V_2O_5$ | Sr/$V_2O_5$ | Ba/$V_2O_5$ | B/$V_2O_5$ | P/$V_2O_5$ | S/$V_2O_5$ | F/$V_2O_5$ | Cl/$V_2O_5$ |
| $V_3O_7$ | Sr/$V_3O_7$ | Ba/$V_3O_7$ | B/$V_3O_7$ | P/$V_3O_7$ | S/$V_3O_7$ | F/$V_3O_7$ | Cl/$V_3O_7$ |
| $V_4O_9$ | Sr/$V_4O_9$ | Ba/$V_4O_9$ | B/$V_4O_9$ | P/$V_4O_9$ | S/$V_4O_9$ | F/$V_4O_9$ | Cl/$V_4O_9$ |
| $V_6O_{13}$ | Sr/$V_6O_{13}$ | Ba/$V_6O_{13}$ | B/$V_6O_{13}$ | P/$V_6O_{13}$ | S/$V_6O_{13}$ | F/$V_6O_{13}$ | Cl/$V_6O_{13}$ |
| NbO | Sr/NbO | Ba/NbO | B/NbO | P/NbO | S/NbO | F/NbO | Cl/NbO |
| $NbO_2$ | Sr/$NbO_2$ | Ba/$NbO_2$ | B/$NbO_2$ | P/$NbO_2$ | S/$NbO_2$ | F/$NbO_2$ | Cl/$NbO_2$ |
| $Nb_2O_5$ | Sr/$Nb_2O_5$ | Ba/$Nb_2O_5$ | B/$Nb_2O_5$ | P/$Nb_2O_5$ | S/$Nb_2O_5$ | F/$Nb_2O_5$ | Cl/$Nb_2O_5$ |
| $Nb_8O_{19}$ | Sr/$Nb_8O_{19}$ | Ba/$Nb_8O_{19}$ | B/$Nb_8O_{19}$ | P/$Nb_8O_{19}$ | S/$Nb_8O_{19}$ | F/$Nb_8O_{19}$ | Cl/$Nb_8O_{19}$ |
| $Nb_{16}O_{38}$ | Sr/$Nb_{16}O_{38}$ | Ba/$Nb_{16}O_{38}$ | B/$Nb_{16}O_{38}$ | P/$Nb_{16}O_{38}$ | S/$Nb_{16}O_{38}$ | F/$Nb_{16}O_{38}$ | Cl/$Nb_{16}O_{38}$ |
| $Nb_{12}O_{29}$ | Sr/$Nb_{12}O_{29}$ | Ba/$Nb_{12}O_{29}$ | B/$Nb_{12}O_{29}$ | P/$Nb_{12}O_{29}$ | S/$Nb_{12}O_{29}$ | F/$Nb_{12}O_{29}$ | Cl/$Nb_{12}O_{29}$ |
| $Nb_{47}O_{116}$ | Sr/$Nb_{47}O_{116}$ | Ba/$Nb_{47}O_{116}$ | B/$Nb_{47}O_{116}$ | P/$Nb_{47}O_{116}$ | S/$Nb_{47}O_{116}$ | F/$Nb_{47}O_{116}$ | Cl/$Nb_{47}O_{116}$ |
| $Ta_2O_5$ | Sr/$Ta_2O_5$ | Ba/$Ta_2O_5$ | B/$Ta_2O_5$ | P/$Ta_2O_5$ | S/$Ta_2O_5$ | F/$Ta_2O_5$ | Cl/$Ta_2O_5$ |
| CrO | Sr/CrO | Ba/CrO | B/CrO | P/CrO | S/CrO | F/CrO | Cl/CrO |
| $Cr_2O_3$ | Sr/$Cr_2O_3$ | Ba/$Cr_2O_3$ | B/$Cr_2O_3$ | P/$Cr_2O_3$ | S/$Cr_2O_3$ | F/$Cr_2O_3$ | Cl/$Cr_2O_3$ |
| $CrO_2$ | Sr/$CrO_2$ | Ba/$CrO_2$ | B/$CrO_2$ | P/$CrO_2$ | S/$CrO_2$ | F/$CrO_2$ | Cl/$CrO_2$ |
| $CrO_3$ | Sr/$CrO_3$ | Ba/$CrO_3$ | B/$CrO_3$ | P/$CrO_3$ | S/$CrO_3$ | F/$CrO_3$ | Cl/$CrO_3$ |
| $Cr_8O_{21}$ | Sr/$Cr_8O_{21}$ | Ba/$Cr_8O_{21}$ | B/$Cr_8O_{21}$ | P/$Cr_8O_{21}$ | S/$Cr_8O_{21}$ | F/$Cr_8O_{21}$ | Cl/$Cr_8O_{21}$ |
| $MoO_2$ | Sr/$MoO_2$ | Ba/$MoO_2$ | B/$MoO_2$ | P/$MoO_2$ | S/$MoO_2$ | F/$MoO_2$ | Cl/$MoO_2$ |
| $MoO_3$ | Sr/$MoO_3$ | Ba/$MoO_3$ | B/$MoO_3$ | P/$MoO_3$ | S/$MoO_3$ | F/$MoO_3$ | Cl/$MoO_3$ |
| $W_2O_3$ | Sr/$W_2O_3$ | Ba/$W_2O_3$ | B/$W_2O_3$ | P/$W_2O_3$ | S/$W_2O_3$ | F/$W_2O_3$ | Cl/$W_2O_3$ |
| $WoO_2$ | Sr/$WoO_2$ | Ba/$WoO_2$ | B/$WoO_2$ | P/$WoO_2$ | S/$WoO_2$ | F/$WoO_2$ | Cl/$WoO_2$ |
| $WoO_3$ | Sr/$WoO_3$ | Ba/$WoO_3$ | B/$WoO_3$ | P/$WoO_3$ | S/$WoO_3$ | F/$WoO_3$ | Cl/$WoO_3$ |
| MnO | Sr/MnO | Ba/MnO | B/MnO | P/MnO | S/MnO | F/MnO | Cl/MnO |
| Mn/Mg/O | Sr/Mn/Mg/O | Ba/Mn/Mg/O | B/Mn/Mg/O | P/Mn/Mg/O | S/Mn/Mg/O | F/Mn/Mg/O | Cl/Mn/Mg/O |
| $Mn_3O_4$ | Sr/$Mn_3O_4$ | Ba/$Mn_3O_4$ | B/$Mn_3O_4$ | P/$Mn_3O_4$ | S/$Mn_3O_4$ | F/$Mn_3O_4$ | Cl/$Mn_3O_4$ |
| $Mn_2O_3$ | Sr/$Mn_2O_3$ | Ba/$Mn_2O_3$ | B/$Mn_2O_3$ | P/$Mn_2O_3$ | S/$Mn_2O_3$ | F/$Mn_2O_3$ | Cl/$Mn_2O_3$ |
| $MnO_2$ | Sr/$MnO_2$ | Ba/$MnO_2$ | B/$MnO_2$ | P/$MnO_2$ | S/$MnO_2$ | F/$MnO_2$ | Cl/$MnO_2$ |
| $Mn_2O_7$ | Sr/$Mn_2O_7$ | Ba/$Mn_2O_7$ | B/$Mn_2O_7$ | P/$Mn_2O_7$ | S/$Mn_2O_7$ | F/$Mn_2O_7$ | Cl/$Mn_2O_7$ |
| $ReO_2$ | Sr/$ReO_2$ | Ba/$ReO_2$ | B/$ReO_2$ | P/$ReO_2$ | S/$ReO_2$ | F/$ReO_2$ | Cl/$ReO_2$ |
| $ReO_3$ | Sr/$ReO_3$ | Ba/$ReO_3$ | B/$ReO_3$ | P/$ReO_3$ | S/$ReO_3$ | F/$ReO_3$ | Cl/$ReO_3$ |
| $Re_2O_7$ | Sr/$Re_2O_7$ | Ba/$Re_2O_7$ | B/$Re_2O_7$ | P/$Re_2O_7$ | S/$Re_2O_7$ | F/$Re_2O_7$ | Cl/$Re_2O_7$ |
| $Mg_3Mn_3$—$B_2O_{10}$ | Sr/$Mg_3Mn_3$—$B_2O_{10}$ | Ba/$Mg_3Mn_3$—$B_2O_{10}$ | B/$Mg_3Mn_3$—$B_2O_{10}$ | P/$Mg_3Mn_3$—$B_2O_{10}$ | S/$Mg_3Mn_3$—$B_2O_{10}$ | F/$Mg_3Mn_3$—$B_2O_{10}$ | Cl/$Mg_3Mn_3$—$B_2O_{10}$ |
| $Mg_3(BO_3)_2$ | Sr/$Mg_3(BO_3)_2$ | Ba/$Mg_3(BO_3)_2$ | B/$Mg_3(BO_3)_2$ | P/$Mg_3(BO_3)_2$ | S/$Mg_3(BO_3)_2$ | F/$Mg_3(BO_3)_2$ | Cl/$Mg_3(BO_3)_2$ |
| $NaWO_4$ | Sr/$NaWO_4$ | Ba/$NaWO_4$ | B/$NaWO_4$ | P/$NaWO_4$ | S/$NaWO_4$ | F/$NaWO_4$ | Cl/$NaWO_4$ |

TABLE 2-continued

NANOWIRES (NW) DOPED WITH SPECIFIC DOPANTS (DOP)

| NW\Dop | Sr | Ba | B | P | S | F | Cl |
|---|---|---|---|---|---|---|---|
| $Mg_6MnO_8$ | Sr/$Mg_6MnO_8$ | Ba/$Mg_6MnO_8$ | B/$Mg_6MnO_8$ | P/$Mg_6MnO_8$ | S/$Mg_6MnO_8$ | F/$Mg_6MnO_8$ | Cl/$Mg_6MnO_8$ |
| $(Li,Mg)_6MnO_8$ | Sr/$(Li,Mg)_6MnO_8$ | Ba/$(Li,Mg)_6MnO_8$ | B/$(Li,Mg)_6MnO_8$ | P/$(Li,Mg)_6MnO_8$ | S/$(Li,Mg)_6MnO_8$ | F/$(Li,Mg)_6MnO_8$ | Cl/$(Li,Mg)_6MnO_8$ |
| $Mn_2O_4$ | Sr/$Mn_2O_4$ | Ba/$Mn_2O_4$ | B/$Mn_2O_4$ | P/$Mn_2O_4$ | S/$Mn_2O_4$ | F/$Mn_2O_4$ | Cl/$Mn_2O_4$ |
| $Na_4P_2O_7$ | Sr/$Na_4P_2O_7$ | Ba/$Na_4P_2O_7$ | B/$Na_4P_2O_7$ | P/$Na_4P_2O_7$ | S/$Na_4P_2O_7$ | F/$Na_4P_2O_7$ | Cl/$Na_4P_2O_7$ |
| $Mo_2O_8$ | Sr/$Mo_2O_8$ | Ba/$Mo_2O_8$ | B/$Mo_2O_8$ | P/$Mo_2O_8$ | S/$Mo_2O_8$ | F/$Mo_2O_8$ | Cl/$Mo_2O_8$ |
| $Mn_3O_4/WO_4$ | Sr/$Mn_3O_4/WO_4$ | Ba/$Mn_3O_4/WO_4$ | B/$Mn_3O_4/WO_4$ | P/$Mn_3O_4/WO_4$ | S/$Mn_3O_4/WO_4$ | F/$Mn_3O_4/WO_4$ | Cl/$Mn_3O_4/WO_4$ |
| $Na_2WO_4$ | Sr/$Na_2WO_4$ | Ba/$Na_2WO_4$ | B/$Na_2WO_4$ | P/$Na_2WO_4$ | S/$Na_2WO_4$ | F/$Na_2WO_4$ | Cl/$Na_2WO_4$ |
| $Zr_2Mo_2O_8$ | Sr/$Zr_2Mo_2O_8$ | Ba/$Zr_2Mo_2O_8$ | B/$Zr_2Mo_2O_8$ | P/$Zr_2Mo_2O_8$ | S/$Zr_2Mo_2O_8$ | F/$Zr_2Mo_2O_8$ | Cl/$Zr_2Mo_2O_8$ |
| $NaMnO_4/MgO$ | Sr/$NaMnO_4/MgO$ | Ba/$NaMnO_4/MgO$ | B/$NaMnO_4/MgO$ | P/$NaMnO_4/MgO$ | S/$NaMnO_4/MgO$ | F/$NaMnO_4/MgO$ | Cl/$NaMnO_4/MgO$ |
| $Na_{10}Mn$—$W_5O_{17}$ | Sr/$Na_{10}Mn$—$W_5O_{17}$ | Ba/$Na_{10}Mn$—$W_5O_{17}$ | B/$Na_{10}Mn$—$W_5O_{17}$ | P/$Na_{10}Mn$—$W_5O_{17}$ | S/$Na_{10}Mn$—$W_5O_{17}$ | F/$Na_{10}Mn$—$W_5O_{17}$ | Cl/$Na_{10}Mn$—$W_5O_{17}$ |
| $La_3NdO_6$ | Sr/$La_3NdO_6$ | Ba/$La_3NdO_6$ | B/$La_3NdO_6$ | P/$La_3NdO_6$ | S/$La_3NdO_6$ | F/$La_3NdO_6$ | Cl/$La_3NdO_6$ |
| $LaNd_3O_6$ | Sr/$LaNd_3O_6$ | Ba/$LaNd_3O_6$ | B/$LaNd_3O_6$ | P/$LaNd_3O_6$ | S/$LaNd_3O_6$ | F/$LaNd_3O_6$ | Cl/$LaNd_3O_6$ |
| $La_{1.5}Nd_{2.5}O_6$ | Sr/$La_{1.5}Nd_{2.5}O_6$ | Ba/$La_{1.5}Nd_{2.5}O_6$ | B/$La_{1.5}Nd_{2.5}O_6$ | P/$La_{1.5}Nd_{2.5}O_6$ | S/$La_{1.5}Nd_{2.5}O_6$ | F/$La_{1.5}Nd_{2.5}O_6$ | Cl/$La_{1.5}Nd_{2.5}O_6$ |
| $La_{2.5}Nd_{1.5}O_6$ | Sr/$La_{2.5}Nd_{1.5}O_6$ | Ba/$La_{2.5}Nd_{1.5}O_6$ | B/$La_{2.5}Nd_{1.5}O_6$ | P/$La_{2.5}Nd_{1.5}O_6$ | S/$La_{2.5}Nd_{1.5}O_6$ | F/$La_{2.5}Nd_{1.5}O_6$ | Cl/$La_{2.5}Nd_{1.5}O_6$ |
| $La_{3.2}Nd_{0.8}O_6$ | Sr/$La_{3.2}Nd_{0.8}O_6$ | Ba/$La_{3.2}Nd_{0.8}O_6$ | B/$La_{3.2}Nd_{0.8}O_6$ | P/$La_{3.2}Nd_{0.8}O_6$ | S/$La_{3.2}Nd_{0.8}O_6$ | F/$La_{3.2}Nd_{0.8}O_6$ | Cl/$La_{3.2}Nd_{0.8}O_6$ |
| $La_{3.5}Nd_{0.5}O_6$ | Sr/$La_{3.5}Nd_{0.5}O_6$ | Ba/$La_{3.5}Nd_{0.5}O_6$ | B/$La_{3.5}Nd_{0.5}O_6$ | P/$La_{3.5}Nd_{0.5}O_6$ | S/$La_{3.5}Nd_{0.5}O_6$ | F/$La_{3.5}Nd_{0.5}O_6$ | Cl/$La_{3.5}Nd_{0.5}O_6$ |
| $La_{3.8}Nd_{0.2}O_6$ | Sr/$La_{3.8}Nd_{0.2}O_6$ | Ba/$La_{3.8}Nd_{0.2}O_6$ | B/$La_{3.8}Nd_{0.2}O_6$ | P/$La_{3.8}Nd_{0.2}O_6$ | S/$La_{3.8}Nd_{0.2}O_6$ | F/$La_{3.8}Nd_{0.2}O_6$ | Cl/$La_{3.8}Nd_{0.2}O_6$ |
| Y—La | Sr/Y—La | Ba/Y—La | B/Y—La | P/Y—La | S/Y—La | F/Y—La | Cl/Y—La |
| Zr—La | Sr/Zr—La | Ba/Zr—La | B/Zr—La | P/Zr—La | S/Zr—La | F/Zr—La | Cl/Zr—La |
| Pr—La | Sr/Pr—La | Ba/Pr—La | B/Pr—La | P/Pr—La | S/Pr—La | F/Pr—La | Cl/Pr—La |
| Ce—La | Sr/Ce—La | Ba/Ce—La | B/Ce—La | P/Ce—La | S/Ce—La | F/Ce—La | Cl/Ce—La |

TABLE 3

NANOWIRES (NW) DOPED WITH SPECIFIC DOPANTS (DOP)

| NW\Dop | La | Ce | Pr | Nd | Pm | Sm | Eu | Gd |
|---|---|---|---|---|---|---|---|---|
| $Li_2O$ | La/$Li_2O$ | Ce/$Li_2O$ | Pr/$Li_2O$ | Nd/$Li_2O$ | Pm/$Li_2O$ | Sm/$Li_2O$ | Eu/$Li_2O$ | Gd/$Li_2O$ |
| $Na_2O$ | La/$Na_2O$ | Ce/$Na_2O$ | Pr/$Na_2O$ | Nd/$Na_2O$ | Pm/$Na_2O$ | Sm/$Na_2O$ | Eu/$Na_2O$ | Gd/$Na_2O$ |
| $K_2O$ | La/$K_2O$ | Ce/$K_2O$ | Pr/$K_2O$ | Nd/$K_2O$ | Pm/$K_2O$ | Sm/$K_2O$ | Eu/$K_2O$ | Gd/$K_2O$ |
| $Rb_2O$ | La/$Rb_2O$ | Ce/$Rb_2O$ | Pr/$Rb_2O$ | Nd/$Rb_2O$ | Pm/$Rb_2O$ | Sm/$Rb_2O$ | Eu/$Rb_2O$ | Gd/$Rb_2O$ |
| $Cs_2O$ | La/$Cs_2O$ | Ce/$Cs_2O$ | Pr/$Cs_2O$ | Nd/$Cs_2O$ | Pm/$Cs_2O$ | Sm/$Cs_2O$ | Eu/$Cs_2O$ | Gd/$Cs_2O$ |
| BeO | La/BeO | Ce/BeO | Pr/BeO | Nd/BeO | Pm/BeO | Sm/BeO | Eu/BeO | Gd/BeO |
| MgO | La/MgO | Ce/MgO | Pr/MgO | Nd/MgO | Pm/MgO | Sm/MgO | Eu/MgO | Gd/MgO |
| CaO | La/CaO | Ce/CaO | Pr/CaO | Nd/CaO | Pm/CaO | Sm/CaO | Eu/CaO | Gd/CaO |
| SrO | La/SrO | Ce/SrO | Pr/SrO | Nd/SrO | Pm/SrO | Sm/SrO | Eu/SrO | Gd/SrO |
| BaO | La/BaO | Ce/BaO | Pr/BaO | Nd/BaO | Pm/BaO | Sm/BaO | Eu/BaO | Gd/BaO |
| $Sc_2O_3$ | La/$Sc_2O_3$ | Ce/$Sc_2O_3$ | Pr/$Sc_2O_3$ | Nd/$Sc_2O_3$ | Pm/$Sc_2O_3$ | Sm/$Sc_2O_3$ | Eu/$Sc_2O_3$ | Gd/$Sc_2O_3$ |

TABLE 3-continued

NANOWIRES (NW) DOPED WITH SPECIFIC DOPANTS (DOP)

| NW\Dop | La | Ce | Pr | Nd | Pm | Sm | Eu | Gd |
|---|---|---|---|---|---|---|---|---|
| $Y_2O_3$ | La/$Y_2O_3$ | Ce/$Y_2O_3$ | Pr/$Y_2O_3$ | Nd/$Y_2O_3$ | Pm/$Y_2O_3$ | Sm/$Y_2O_3$ | Eu/$Y_2O_3$ | Gd/$Y_2O_3$ |
| $La_2O_3$ | La/$La_2O_3$ | Ce/$La_2O_3$ | Pr/$La_2O_3$ | Nd/$La_2O_3$ | Pm/$La_2O_3$ | Sm/$La_2O_3$ | Eu/$La_2O_3$ | Gd/$La_2O_3$ |
| $CeO_2$ | La/$CeO_2$ | Ce/$CeO_2$ | Pr/$CeO_2$ | Nd/$CeO_2$ | Pm/$CeO_2$ | Sm/$CeO_2$ | Eu/$CeO_2$ | Gd/$CeO_2$ |
| $Ce_2O_3$ | La/$Ce_2O_3$ | Ce/$Ce_2O_3$ | Pr/$Ce_2O_3$ | Nd/$Ce_2O_3$ | Pm/$Ce_2O_3$ | Sm/$Ce_2O_3$ | Eu/$Ce_2O_3$ | Gd/$Ce_2O_3$ |
| $Pr_2O_3$ | La/$Pr_2O_3$ | Ce/$Pr_2O_3$ | Pr/$Pr_2O_3$ | Nd/$Pr_2O_3$ | Pm/$Pr_2O_3$ | Sm/$Pr_2O_3$ | Eu/$Pr_2O_3$ | Gd/$Pr_2O_3$ |
| $Nd_2O_3$ | La/$Nd_2O_3$ | Ce/$Nd_2O_3$ | Pr/$Nd_2O_3$ | Nd/$Nd_2O_3$ | Pm/$Nd_2O_3$ | Sm/$Nd_2O_3$ | Eu/$Nd_2O_3$ | Gd/$Nd_2O_3$ |
| $Sm_2O_3$ | La/$Sm_2O_3$ | Ce/$Sm_2O_3$ | Pr/$Sm_2O_3$ | Nd/$Sm_2O_3$ | Pm/$Sm_2O_3$ | Sm/$Sm_2O_3$ | Eu/$Sm_2O_3$ | Gd/$Sm_2O_3$ |
| $Eu_2O_3$ | La/$Eu_2O_3$ | Ce/$Eu_2O_3$ | Pr/$Eu_2O_3$ | Nd/$Eu_2O_3$ | Pm/$Eu_2O_3$ | Sm/$Eu_2O_3$ | Eu/$Eu_2O_3$ | Gd/$Eu_2O_3$ |
| $Gd_2O_3$ | La/$Gd_2O_3$ | Ce/$Gd_2O_3$ | Pr/$Gd_2O_3$ | Nd/$Gd_2O_3$ | Pm/$Gd_2O_3$ | Sm/$Gd_2O_3$ | Eu/$Gd_2O_3$ | Gd/$Gd_2O_3$ |
| $Tb_2O_3$ | La/$Tb_2O_3$ | Ce/$Tb_2O_3$ | Pr/$Tb_2O_3$ | Nd/$Tb_2O_3$ | Pm/$Tb_2O_3$ | Sm/$Tb_2O_3$ | Eu/$Tb_2O_3$ | Gd/$Tb_2O_3$ |
| $TbO_2$ | La/$TbO_2$ | Ce/$TbO_2$ | Pr/$TbO_2$ | Nd/$TbO_2$ | Pm/$TbO_2$ | Sm/$TbO_2$ | Eu/$TbO_2$ | Gd/$TbO_2$ |
| $Tb_6O_{11}$ | La/$Tb_6O_{11}$ | Ce/$Tb_6O_{11}$ | Pr/$Tb_6O_{11}$ | Nd/$Tb_6O_{11}$ | Pm/$Tb_6O_{11}$ | Sm/$Tb_6O_{11}$ | Eu/$Tb_6O_{11}$ | Gd/$Tb_6O_{11}$ |
| $Dy_2O_3$ | La/$Dy_2O_3$ | Ce/$Dy_2O_3$ | Pr/$Dy_2O_3$ | Nd/$Dy_2O_3$ | Pm/$Dy_2O_3$ | Sm/$Dy_2O_3$ | Eu/$Dy_2O_3$ | Gd/$Dy_2O_3$ |
| $Ho_2O_3$ | La/$Ho_2O_3$ | Ce/$Ho_2O_3$ | Pr/$Ho_2O_3$ | Nd/$Ho_2O_3$ | Pm/$Ho_2O_3$ | Sm/$Ho_2O_3$ | Eu/$Ho_2O_3$ | Gd/$Ho_2O_3$ |
| $Er_2O_3$ | La/$Er_2O_3$ | Ce/$Er_2O_3$ | Pr/$Er_2O_3$ | Nd/$Er_2O_3$ | Pm/$Er_2O_3$ | Sm/$Er_2O_3$ | Eu/$Er_2O_3$ | Gd/$Er_2O_3$ |
| $Tm_2O_3$ | La/$Tm_2O_3$ | Ce/$Tm_2O_3$ | Pr/$Tm_2O_3$ | Nd/$Tm_2O_3$ | Pm/$Tm_2O_3$ | Sm/$Tm_2O_3$ | Eu/$Tm_2O_3$ | Gd/$Tm_2O_3$ |
| $Yb_2O_3$ | La/$Yb_2O_3$ | Ce/$Yb_2O_3$ | Pr/$Yb_2O_3$ | Nd/$Yb_2O_3$ | Pm/$Yb_2O_3$ | Sm/$Yb_2O_3$ | Eu/$Yb_2O_3$ | Gd/$Yb_2O_3$ |
| $Lu_2O_3$ | La/$Lu_2O_3$ | Ce/$Lu_2O_3$ | Pr/$Lu_2O_3$ | Nd/$Lu_2O_3$ | Pm/$Lu_2O_3$ | Sm/$Lu_2O_3$ | Eu/$Lu_2O_3$ | Gd/$Lu_2O_3$ |
| $Ac_2O_3$ | La/$Ac_2O_3$ | Ce/$Ac_2O_3$ | Pr/$Ac_2O_3$ | Nd/$Ac_2O_3$ | Pm/$Ac_2O_3$ | Sm/$Ac_2O_3$ | Eu/$Ac_2O_3$ | Gd/$Ac_2O_3$ |
| $Th_2O_3$ | La/$Th_2O_3$ | Ce/$Th_2O_3$ | Pr/$Th_2O_3$ | Nd/$Th_2O_3$ | Pm/$Th_2O_3$ | Sm/$Th_2O_3$ | Eu/$Th_2O_3$ | Gd/$Th_2O_3$ |
| $ThO_2$ | La/$ThO_2$ | Ce/$ThO_2$ | Pr/$ThO_2$ | Nd/$ThO_2$ | Pm/$ThO_2$ | Sm/$ThO_2$ | Eu/$ThO_2$ | Gd/$ThO_2$ |
| $Pa_2O_3$ | La/$Pa_2O_3$ | Ce/$Pa_2O_3$ | Pr/$Pa_2O_3$ | Nd/$Pa_2O_3$ | Pm/$Pa_2O_3$ | Sm/$Pa_2O_3$ | Eu/$Pa_2O_3$ | Gd/$Pa_2O_3$ |
| $PaO_2$ | La/$PaO_2$ | Ce/$PaO_2$ | Pr/$PaO_2$ | Nd/$PaO_2$ | Pm/$PaO_2$ | Sm/$PaO_2$ | Eu/$PaO_2$ | Gd/$PaO_2$ |
| $TiO_2$ | La/$TiO_2$ | Ce/$TiO_2$ | Pr/$TiO_2$ | Nd/$TiO_2$ | Pm/$TiO_2$ | Sm/$TiO_2$ | Eu/$TiO_2$ | Gd/$TiO_2$ |
| TiO | La/TiO | Ce/TiO | Pr/TiO | Nd/TiO | Pm/TiO | Sm/TiO | Eu/TiO | Gd/TiO |
| $Ti_2O_3$ | La/$Ti_2O_3$ | Ce/$Ti_2O_3$ | Pr/$Ti_2O_3$ | Nd/$Ti_2O_3$ | Pm/$Ti_2O_3$ | Sm/$Ti_2O_3$ | Eu/$Ti_2O_3$ | Gd/$Ti_2O_3$ |
| $Ti_3O$ | La/$Ti_3O$ | Ce/$Ti_3O$ | Pr/$Ti_3O$ | Nd/$Ti_3O$ | Pm/$Ti_3O$ | Sm/$Ti_3O$ | Eu/$Ti_3O$ | Gd/$Ti_3O$ |
| $Ti_2O$ | La/$Ti_2O$ | Ce/$Ti_2O$ | Pr/$Ti_2O$ | Nd/$Ti_2O$ | Pm/$Ti_2O$ | Sm/$Ti_2O$ | Eu/$Ti_2O$ | Gd/$Ti_2O$ |
| $Ti_3O_5$ | La/$Ti_3O_5$ | Ce/$Ti_3O_5$ | Pr/$Ti_3O_5$ | Nd/$Ti_3O_5$ | Pm/$Ti_3O_5$ | Sm/$Ti_3O_5$ | Eu/$Ti_3O_5$ | Gd/$Ti_3O_5$ |
| $Ti_4O_7$ | La/$Ti_4O_7$ | Ce/$Ti_4O_7$ | Pr/$Ti_4O_7$ | Nd/$Ti_4O_7$ | Pm/$Ti_4O_7$ | Sm/$Ti_4O_7$ | Eu/$Ti_4O_7$ | Gd/$Ti_4O_7$ |
| $ZrO_2$ | La/$ZrO_2$ | Ce/$ZrO_2$ | Pr/$ZrO_2$ | Nd/$ZrO_2$ | Pm/$ZrO_2$ | Sm/$ZrO_2$ | Eu/$ZrO_2$ | Gd/$ZrO_2$ |
| $HfO_2$ | La/$HfO_2$ | Ce/$HfO_2$ | Pr/$HfO_2$ | Nd/$HfO_2$ | Pm/$HfO_2$ | Sm/$HfO_2$ | Eu/$HfO_2$ | Gd/$HfO_2$ |
| VO | La/VO | Ce/VO | Pr/VO | Nd/VO | Pm/VO | Sm/VO | Eu/VO | Gd/VO |
| $V_2O_3$ | La/$V_2O_3$ | Ce/$V_2O_3$ | Pr/$V_2O_3$ | Nd/$V_2O_3$ | Pm/$V_2O_3$ | Sm/$V_2O_3$ | Eu/$V_2O_3$ | Gd/$V_2O_3$ |
| $VO_2$ | La/$VO_2$ | Ce/$VO_2$ | Pr/$VO_2$ | Nd/$VO_2$ | Pm/$VO_2$ | Sm/$VO_2$ | Eu/$VO_2$ | Gd/$VO_2$ |
| $V_2O_5$ | La/$V_2O_5$ | Ce/$V_2O_5$ | Pr/$V_2O_5$ | Nd/$V_2O_5$ | Pm/$V_2O_5$ | Sm/$V_2O_5$ | Eu/$V_2O_5$ | Gd/$V_2O_5$ |
| $V_3O_7$ | La/$V_3O_7$ | Ce/$V_3O_7$ | Pr/$V_3O_7$ | Nd/$V_3O_7$ | Pm/$V_3O_7$ | Sm/$V_3O_7$ | Eu/$V_3O_7$ | Gd/$V_3O_7$ |
| $V_4O_9$ | La/$V_4O_9$ | Ce/$V_4O_9$ | Pr/$V_4O_9$ | Nd/$V_4O_9$ | Pm/$V_4O_9$ | Sm/$V_4O_9$ | Eu/$V_4O_9$ | Gd/$V_4O_9$ |

TABLE 3-continued

NANOWIRES (NW) DOPED WITH SPECIFIC DOPANTS (DOP)

| NW\Dop | La | Ce | Pr | Nd | Pm | Sm | Eu | Gd |
|---|---|---|---|---|---|---|---|---|
| $V_6O_{13}$ | La/$V_6O_{13}$ | Ce/$V_6O_{13}$ | Pr/$V_6O_{13}$ | Nd/$V_6O_{13}$ | Pm/$V_6O_{13}$ | Sm/$V_6O_{13}$ | Eu/$V_6O_{13}$ | Gd/$V_6O_{13}$ |
| NbO | La/NbO | Ce/NbO | Pr/NbO | Nd/NbO | Pm/NbO | Sm/NbO | Eu/NbO | Gd/NbO |
| $NbO_2$ | La/$NbO_2$ | Ce/$NbO_2$ | Pr/$NbO_2$ | Nd/$NbO_2$ | Pm/$NbO_2$ | Sm/$NbO_2$ | Eu/$NbO_2$ | Gd/$NbO_2$ |
| $Nb_2O_5$ | La/$Nb_2O_5$ | Ce/$Nb_2O_5$ | Pr/$Nb_2O_5$ | Nd/$Nb_2O_5$ | Pm/$Nb_2O_5$ | Sm/$Nb_2O_5$ | Eu/$Nb_2O_5$ | Gd/$Nb_2O_5$ |
| $Nb_8O_{19}$ | La/$Nb_8O_{19}$ | Ce/$Nb_8O_{19}$ | Pr/$Nb_8O_{19}$ | Nd/$Nb_8O_{19}$ | Pm/$Nb_8O_{19}$ | Sm/$Nb_8O_{19}$ | Eu/$Nb_8O_{19}$ | Gd/$Nb_8O_{19}$ |
| $Nb_{16}O_{38}$ | La/$Nb_{16}O_{38}$ | Ce/$Nb_{16}O_{38}$ | Pr/$Nb_{16}O_{38}$ | Nd/$Nb_{16}O_{38}$ | Pm/$Nb_{16}O_{38}$ | Sm/$Nb_{16}O_{38}$ | Eu/$Nb_{16}O_{38}$ | Gd/$Nb_{16}O_{38}$ |
| $Nb_{12}O_{29}$ | La/$Nb_{12}O_{29}$ | Ce/$Nb_{12}O_{29}$ | Pr/$Nb_{12}O_{29}$ | Nd/$Nb_{12}O_{29}$ | Pm/$Nb_{12}O_{29}$ | Sm/$Nb_{12}O_{29}$ | Eu/$Nb_{12}O_{29}$ | Gd/$Nb_{12}O_{29}$ |
| $Nb_{47}O_{116}$ | La/$Nb_{47}O_{116}$ | Ce/$Nb_{47}O_{116}$ | Pr/$Nb_{47}O_{116}$ | Nd/$Nb_{47}O_{116}$ | Pm/$Nb_{47}O_{116}$ | Sm/$Nb_{47}O_{116}$ | Eu/$Nb_{47}O_{116}$ | Gd/$Nb_{47}O_{116}$ |
| $Ta_2O_5$ | La/$Ta_2O_5$ | Ce/$Ta_2O_5$ | Pr/$Ta_2O_5$ | Nd/$Ta_2O_5$ | Pm/$Ta_2O_5$ | Sm/$Ta_2O_5$ | Eu/$Ta_2O_5$ | Gd/$Ta_2O_5$ |
| CrO | La/CrO | Ce/CrO | Pr/CrO | Nd/CrO | Pm/CrO | Sm/CrO | Eu/CrO | Gd/CrO |
| $Cr_2O_3$ | La/$Cr_2O_3$ | Ce/$Cr_2O_3$ | Pr/$Cr_2O_3$ | Nd/$Cr_2O_3$ | Pm/$Cr_2O_3$ | Sm/$Cr_2O_3$ | Eu/$Cr_2O_3$ | Gd/$Cr_2O_3$ |
| $CrO_2$ | La/$CrO_2$ | Ce/$CrO_2$ | Pr/$CrO_2$ | Nd/$CrO_2$ | Pm/$CrO_2$ | Sm/$CrO_2$ | Eu/$CrO_2$ | Gd/$CrO_2$ |
| $CrO_3$ | La/$CrO_3$ | Ce/$CrO_3$ | Pr/$CrO_3$ | Nd/$CrO_3$ | Pm/$CrO_3$ | Sm/$CrO_3$ | Eu/$CrO_3$ | Gd/$CrO_3$ |
| $Cr_8O_{21}$ | La/$Cr_8O_{21}$ | Ce/$Cr_8O_{21}$ | Pr/$Cr_8O_{21}$ | Nd/$Cr_8O_{21}$ | Pm/$Cr_8O_{21}$ | Sm/$Cr_8O_{21}$ | Eu/$Cr_8O_{21}$ | Gd/$Cr_8O_{21}$ |
| $MoO_2$ | La/$MoO_2$ | Ce/$MoO_2$ | Pr/$MoO_2$ | Nd/$MoO_2$ | Pm/$MoO_2$ | Sm/$MoO_2$ | Eu/$MoO_2$ | Gd/$MoO_2$ |
| $MoO_3$ | La/$MoO_3$ | Ce/$MoO_3$ | Pr/$MoO_3$ | Nd/$MoO_3$ | Pm/$MoO_3$ | Sm/$MoO_3$ | Eu/$MoO_3$ | Gd/$MoO_3$ |
| $W_2O_3$ | La/$W_2O_3$ | Ce/$W_2O_3$ | Pr/$W_2O_3$ | Nd/$W_2O_3$ | Pm/$W_2O_3$ | Sm/$W_2O_3$ | Eu/$W_2O_3$ | Gd/$W_2O_3$ |
| $WoO_2$ | La/$WoO_2$ | Ce/$WoO_2$ | Pr/$WoO_2$ | Nd/$WoO_2$ | Pm/$WoO_2$ | Sm/$WoO_2$ | Eu/$WoO_2$ | Gd/$WoO_2$ |
| $WoO_3$ | La/$WoO_3$ | Ce/$WoO_3$ | Pr/$WoO_3$ | Nd/$WoO_3$ | Pm/$WoO_3$ | Sm/$WoO_3$ | Eu/$WoO_3$ | Gd/$WoO_3$ |
| MnO | La/MnO | Ce/MnO | Pr/MnO | Nd/MnO | Pm/MnO | Sm/MnO | Eu/MnO | Gd/MnO |
| Mn/Mg/O | La/Mn/Mg/O | Ce/Mn/Mg/O | Pr/Mn/Mg/O | Nd/Mn/Mg/O | Pm/Mn/Mg/O | Sm/Mn/Mg/O | Eu/Mn/Mg/O | Gd/Mn/Mg/O |
| $Mn_3O_4$ | La/$Mn_3O_4$ | Ce/$Mn_3O_4$ | Pr/$Mn_3O_4$ | Nd/$Mn_3O_4$ | Pm/$Mn_3O_4$ | Sm/$Mn_3O_4$ | Eu/$Mn_3O_4$ | Gd/$Mn_3O_4$ |
| $Mn_2O_3$ | La/$Mn_2O_3$ | Ce/$Mn_2O_3$ | Pr/$Mn_2O_3$ | Nd/$Mn_2O_3$ | Pm/$Mn_2O_3$ | Sm/$Mn_2O_3$ | Eu/$Mn_2O_3$ | Gd/$Mn_2O_3$ |
| $MnO_2$ | La/$MnO_2$ | Ce/$MnO_2$ | Pr/$MnO_2$ | Nd/$MnO_2$ | Pm/$MnO_2$ | Sm/$MnO_2$ | Eu/$MnO_2$ | Gd/$MnO_2$ |
| $Mn_2O_7$ | La/$Mn_2O_7$ | Ce/$Mn_2O_7$ | Pr/$Mn_2O_7$ | Nd/$Mn_2O_7$ | Pm/$Mn_2O_7$ | Sm/$Mn_2O_7$ | Eu/$Mn_2O_7$ | Gd/$Mn_2O_7$ |
| $ReO_2$ | La/$ReO_2$ | Ce/$ReO_2$ | Pr/$ReO_2$ | Nd/$ReO_2$ | Pm/$ReO_2$ | Sm/$ReO_2$ | Eu/$ReO_2$ | Gd/$ReO_2$ |
| $ReO_3$ | La/$ReO_3$ | Ce/$ReO_3$ | Pr/$ReO_3$ | Nd/$ReO_3$ | Pm/$ReO_3$ | Sm/$ReO_3$ | Eu/$ReO_3$ | Gd/$ReO_3$ |
| $Re_2O_7$ | La/$Re_2O_7$ | Ce/$Re_2O_7$ | Pr/$Re_2O_7$ | Nd/$Re_2O_7$ | Pm/$Re_2O_7$ | Sm/$Re_2O_7$ | Eu/$Re_2O_7$ | Gd/$Re_2O_7$ |
| $Mg_3Mn-B_2O_{10}$ | La/$Mg_3Mn-B_2O_{10}$ | Ce/$Mg_3Mn-B_2O_{10}$ | Pr/$Mg_3Mn-B_2O_{10}$ | Nd/$Mg_3Mn-B_2O_{10}$ | Pm/$Mg_3Mn-B_2O_{10}$ | Sm/$Mg_3Mn-B_2O_{10}$ | Eu/$Mg_3Mn-B_2O_{10}$ | Gd/$Mg_3Mn-B_2O_{10}$ |
| $Mg_3(BO_3)_2$ | La/$Mg_3(BO_3)_2$ | Ce/$Mg_3(BO_3)_2$ | Pr/$Mg_3(BO_3)_2$ | Nd/$Mg_3(BO_3)_2$ | Pm/$Mg_3(BO_3)_2$ | Sm/$Mg_3(BO_3)_2$ | Eu/$Mg_3(BO_3)_2$ | Gd/$Mg_3(BO_3)_2$ |
| $NaWO_4$ | La/$NaWO_4$ | Ce/$NaWO_4$ | Pr/$NaWO_4$ | Nd/$NaWO_4$ | Pm/$NaWO_4$ | Sm/$NaWO_4$ | Eu/$NaWO_4$ | Gd/$NaWO_4$ |
| $Mg_6MnO_8$ | La/$Mg_6MnO_8$ | Ce/$Mg_6MnO_8$ | Pr/$Mg_6MnO_8$ | Nd/$Mg_6MnO_8$ | Pm/$Mg_6MnO_8$ | Sm/$Mg_6MnO_8$ | Eu/$Mg_6MnO_8$ | Gd/$Mg_6MnO_8$ |
| $(Li,Mg)_6MnO_8$ | La/$(Li,Mg)_6MnO_8$ | Ce/$(Li,Mg)_6MnO_8$ | Pr/$(Li,Mg)_6MnO_8$ | Nd/$(Li,Mg)_6MnO_8$ | Pm/$(Li,Mg)_6MnO_8$ | Sm/$(Li,Mg)_6MnO_8$ | Eu/$(Li,Mg)_6MnO_8$ | Gd/$(Li,Mg)_6MnO_8$ |
| $Mn_2O_4$ | La/$Mn_2O_4$ | Ce/$Mn_2O_4$ | Pr/$Mn_2O_4$ | Nd/$Mn_2O_4$ | Pm/$Mn_2O_4$ | Sm/$Mn_2O_4$ | Eu/$Mn_2O_4$ | Gd/$Mn_2O_4$ |
| $Na_4P_2O_7$ | La/$Na_4P_2O_7$ | Ce/$Na_4P_2O_7$ | Pr/$Na_4P_2O_7$ | Nd/$Na_4P_2O_7$ | Pm/$Na_4P_2O_7$ | Sm/$Na_4P_2O_7$ | Eu/$Na_4P_2O_7$ | Gd/$Na_4P_2O_7$ |
| $Mo_2O_8$ | La/$Mo_2O_8$ | Ce/$Mo_2O_8$ | Pr/$Mo_2O_8$ | Nd/$Mo_2O_8$ | Pm/$Mo_2O_8$ | Sm/$Mo_2O_8$ | Eu/$Mo_2O_8$ | Gd/$Mo_2O_8$ |
| $Mn_3O_4/WO_4$ | La/$Mn_3O_4/WO_4$ | Ce/$Mn_3O_4/WO_4$ | Pr/$Mn_3O_4/WO_4$ | Nd/$Mn_3O_4/WO_4$ | Pm/$Mn_3O_4/WO_4$ | Sm/$Mn_3O_4/WO_4$ | Eu/$Mn_3O_4/WO_4$ | Gd/$Mn_3O_4/WO_4$ |

TABLE 3-continued

NANOWIRES (NW) DOPED WITH SPECIFIC DOPANTS (DOP)

| NW\Dop | La | Ce | Pr | Nd | Pm | Sm | Eu | Gd |
|---|---|---|---|---|---|---|---|---|
| $Na_2WO_4$ | La/$Na_2WO_4$ | Ce/$Na_2WO_4$ | Pr/$Na_2WO_4$ | Nd/$Na_2WO_4$ | Pm/$Na_2WO_4$ | Sm/$Na_2WO_4$ | Eu/$Na_2WO_4$ | Gd/$Na_2WO_4$ |
| $Zr_2Mo_2O_8$ | La/$Zr_2Mo_2O_8$ | Ce/$Zr_2Mo_2O_8$ | Pr/$Zr_2Mo_2O_8$ | Nd/$Zr_2Mo_2O_8$ | Pm/$Zr_2Mo_2O_8$ | Sm/$Zr_2Mo_2O_8$ | Eu/$Zr_2Mo_2O_8$ | Gd/$Zr_2Mo_2O_8$ |
| $NaMnO_4$—MgO | La/$NaMnO_4$—/MgO | Ce/$NaMnO_4$—/MgO | Pr/$NaMnO_4$—/MgO | Nd/$NaMnO_4$—/MgO | Pm/$NaMnO_4$—/MgO | Sm/$NaMnO_4$—/MgO | Eu/$NaMnO_4$—/MgO | Gd/$NaMnO_4$—/MgO |
| $Na_{10}Mn$—$W_5O_{17}$ | La/$Na_{10}Mn$—$W_5O_{17}$ | Ce/$Na_{10}Mn$—$W_5O_{17}$ | Pr/$Na_{10}Mn$—$W_5O_{17}$ | Nd/$Na_{10}Mn$—$W_5O_{17}$ | Pm/$Na_{10}Mn$—$W_5O_{17}$ | Sm/$Na_{10}Mn$—$W_5O_{17}$ | Eu/$Na_{10}Mn$—$W_5O_{17}$ | Gd/$Na_{10}Mn$—$W_5O_{17}$ |
| $La_3NdO_6$ | La/$La_3NdO_6$ | Ce/$La_3NdO_6$ | Pr/$La_3NdO_6$ | Nd/$La_3NdO_6$ | Pm/$La_3NdO_6$ | Sm/$La_3NdO_6$ | Eu/$La_3NdO_6$ | Gd/$La_3NdO_6$ |
| $LaNd_3O_6$ | La/$LaNd_3O_6$ | Ce/$LaNd_3O_6$ | Pr/$LaNd_3O_6$ | Nd/$LaNd_3O_6$ | Pm/$LaNd_3O_6$ | Sm/$LaNd_3O_6$ | Eu/$LaNd_3O_6$ | Gd/$LaNd_3O_6$ |
| $La_{1.5}Nd_{2.5}O_6$ | La/$La_{1.5}Nd_{2.5}O_6$ | Ce/$La_{1.5}Nd_{2.5}O_6$ | Pr/$La_{1.5}Nd_{2.5}O_6$ | Nd/$La_{1.5}Nd_{2.5}O_6$ | Pm/$La_{1.5}Nd_{2.5}O_6$ | Sm/$La_{1.5}Nd_{2.5}O_6$ | Eu/$La_{1.5}Nd_{2.5}O_6$ | Gd/$La_{1.5}Nd_{2.5}O_6$ |
| $La_{2.5}Nd_{1.5}O_6$ | La/$La_{2.5}Nd_{1.5}O_6$ | Ce/$La_{2.5}Nd_{1.5}O_6$ | Pr/$La_{2.5}Nd_{1.5}O_6$ | Nd/$La_{2.5}Nd_{1.5}O_6$ | Pm/$La_{2.5}Nd_{1.5}O_6$ | Sm/$La_{2.5}Nd_{1.5}O_6$ | Eu/$La_{2.5}Nd_{1.5}O_6$ | Gd/$La_{2.5}Nd_{1.5}O_6$ |
| $La_{3.2}Nd_{0.8}O_6$ | La/$La_{3.2}Nd_{0.8}O_6$ | Ce/$La_{3.2}Nd_{0.8}O_6$ | Pr/$La_{3.2}Nd_{0.8}O_6$ | Nd/$La_{3.2}Nd_{0.8}O_6$ | Pm/$La_{3.2}Nd_{0.8}O_6$ | Sm/$La_{3.2}Nd_{0.8}O_6$ | Eu/$La_{3.2}Nd_{0.8}O_6$ | Gd/$La_{3.2}Nd_{0.8}O_6$ |
| $La_{3.5}Nd_{0.5}O_6$ | La/$La_{3.5}Nd_{0.5}O_6$ | Ce/$La_{3.5}Nd_{0.5}O_6$ | Pr/$La_{3.5}Nd_{0.5}O_6$ | Nd/$La_{3.5}Nd_{0.5}O_6$ | Pm/$La_{3.5}Nd_{0.5}O_6$ | Sm/$La_{3.5}Nd_{0.5}O_6$ | Eu/$La_{3.5}Nd_{0.5}O_6$ | Gd/$La_{3.5}Nd_{0.5}O_6$ |
| $La_{3.8}Nd_{0.2}O_6$ | La/$La_{3.8}Nd_{0.2}O_6$ | Ce/$La_{3.8}Nd_{0.2}O_6$ | Pr/$La_{3.8}Nd_{0.2}O_6$ | Nd/$La_{3.8}Nd_{0.2}O_6$ | Pm/$La_{3.8}Nd_{0.2}O_6$ | Sm/$La_{3.8}Nd_{0.2}O_6$ | Eu/$La_{3.8}Nd_{0.2}O_6$ | Gd/$La_{3.8}Nd_{0.2}O_6$ |
| Y—La | La/Y—La | Ce/Y—La | Pr/Y—La | Nd/Y—La | Pm/Y—La | Sm/Y—La | Eu/Y—La | Gd/Y—La |
| Zr—La | La/Zr—La | Ce/Zr—La | Pr/Zr—La | Nd/Zr—La | Pm/Zr—La | Sm/Zr—La | Eu/Zr—La | Gd/Zr—La |
| Pr—La | La/Pr—La | Ce/Pr—La | Pr/Pr—La | Nd/Pr—La | Pm/Pr—La | Sm/Pr—La | Eu/Pr—La | Gd/Pr—La |
| Ce—La | La/Ce—La | Ce/Ce—La | Pr/Ce—La | Nd/Ce—La | Pm/Ce—La | Sm/Ce—La | Eu/Ce—La | Gd/Ce—La |

TABLE 4

NANOWIRES (NW) DOPED WITH SPECIFIC DOPANTS (DOP)

| NW\Dop | Tb | Dy | Ho | Er | Tm | Yb | Lu | In |
|---|---|---|---|---|---|---|---|---|
| Li$_2$O | Tb/Li$_2$O | Dy/Li$_2$O | Ho/Li$_2$O | Er/Li$_2$O | Tm/Li$_2$O | Yb/Li$_2$O | Lu/Li$_2$O | In/Li$_2$O |
| Na$_2$O | Tb/Na$_2$O | Dy/Na$_2$O | Ho/Na$_2$O | Er/Na$_2$O | Tm/Na$_2$O | Yb/Na$_2$O | Lu/Na$_2$O | In/Na$_2$O |
| K$_2$O | Tb/K$_2$O | Dy/K$_2$O | Ho/K$_2$O | Er/K$_2$O | Tm/K$_2$O | Yb/K$_2$O | Lu/K$_2$O | In/K$_2$O |
| Rb$_2$O | Tb/Rb$_2$O | Dy/Rb$_2$O | Ho/Rb$_2$O | Er/Rb$_2$O | Tm/Rb$_2$O | Yb/Rb$_2$O | Lu/Rb$_2$O | In/Rb$_2$O |
| Cs$_2$O | Tb/Cs$_2$O | Dy/Cs$_2$O | Ho/Cs$_2$O | Er/Cs$_2$O | Tm/Cs$_2$O | Yb/Cs$_2$O | Lu/Cs$_2$O | In/Cs$_2$O |
| BeO | Tb/BeO | Dy/BeO | Ho/BeO | Er/BeO | Tm/BeO | Yb/BeO | Lu/BeO | In/BeO |
| MgO | Tb/MgO | Dy/MgO | Ho/MgO | Er/MgO | Tm/MgO | Yb/MgO | Lu/MgO | In/MgO |
| CaO | Tb/CaO | Dy/CaO | Ho/CaO | Er/CaO | Tm/CaO | Yb/CaO | Lu/CaO | In/CaO |
| SrO | Tb/SrO | Dy/SrO | Ho/SrO | Er/SrO | Tm/SrO | Yb/SrO | Lu/SrO | In/SrO |
| BaO | Tb/BaO | Dy/BaO | Ho/BaO | Er/BaO | Tm/BaO | Yb/BaO | Lu/BaO | In/BaO |
| Sc$_2$O$_3$ | Tb/Sc$_2$O$_3$ | Dy/Sc$_2$O$_3$ | Ho/Sc$_2$O$_3$ | Er/Sc$_2$O$_3$ | Tm/Sc$_2$O$_3$ | Yb/Sc$_2$O$_3$ | Lu/Sc$_2$O$_3$ | In/Sc$_2$O$_3$ |
| Y$_2$O$_3$ | Tb/Y$_2$O$_3$ | Dy/Y$_2$O$_3$ | Ho/Y$_2$O$_3$ | Er/Y$_2$O$_3$ | Tm/Y$_2$O$_3$ | Yb/Y$_2$O$_3$ | Lu/Y$_2$O$_3$ | In/Y$_2$O$_3$ |
| La$_2$O$_3$ | Tb/La$_2$O$_3$ | Dy/La$_2$O$_3$ | Ho/La$_2$O$_3$ | Er/La$_2$O$_3$ | Tm/La$_2$O$_3$ | Yb/La$_2$O$_3$ | Lu/La$_2$O$_3$ | In/La$_2$O$_3$ |
| CeO$_2$ | Tb/CeO$_2$ | Dy/CeO$_2$ | Ho/CeO$_2$ | Er/CeO$_2$ | Tm/CeO$_2$ | Yb/CeO$_2$ | Lu/CeO$_2$ | In/CeO$_2$ |
| Ce$_2$O$_3$ | Tb/Ce$_2$O$_3$ | Dy/Ce$_2$O$_3$ | Ho/Ce$_2$O$_3$ | Er/Ce$_2$O$_3$ | Tm/Ce$_2$O$_3$ | Yb/Ce$_2$O$_3$ | Lu/Ce$_2$O$_3$ | In/Ce$_2$O$_3$ |
| Pr$_2$O$_3$ | Tb/Pr$_2$O$_3$ | Dy/Pr$_2$O$_3$ | Ho/Pr$_2$O$_3$ | Er/Pr$_2$O$_3$ | Tm/Pr$_2$O$_3$ | Yb/Pr$_2$O$_3$ | Lu/Pr$_2$O$_3$ | In/Pr$_2$O$_3$ |
| Nd$_2$O$_3$ | Tb/Nd$_2$O$_3$ | Dy/Nd$_2$O$_3$ | Ho/Nd$_2$O$_3$ | Er/Nd$_2$O$_3$ | Tm/Nd$_2$O$_3$ | Yb/Nd$_2$O$_3$ | Lu/Nd$_2$O$_3$ | In/Nd$_2$O$_3$ |
| Sm$_2$O$_3$ | Tb/Sm$_2$O$_3$ | Dy/Sm$_2$O$_3$ | Ho/Sm$_2$O$_3$ | Er/Sm$_2$O$_3$ | Tm/Sm$_2$O$_3$ | Yb/Sm$_2$O$_3$ | Lu/Sm$_2$O$_3$ | In/Sm$_2$O$_3$ |
| Eu$_2$O$_3$ | Tb/Eu$_2$O$_3$ | Dy/Eu$_2$O$_3$ | Ho/Eu$_2$O$_3$ | Er/Eu$_2$O$_3$ | Tm/Eu$_2$O$_3$ | Yb/Eu$_2$O$_3$ | Lu/Eu$_2$O$_3$ | In/Eu$_2$O$_3$ |
| Gd$_2$O$_3$ | Tb/Gd$_2$O$_3$ | Dy/Gd$_2$O$_3$ | Ho/Gd$_2$O$_3$ | Er/Gd$_2$O$_3$ | Tm/Gd$_2$O$_3$ | Yb/Gd$_2$O$_3$ | Lu/Gd$_2$O$_3$ | In/Gd$_2$O$_3$ |
| Tb$_2$O$_3$ | Tb/Tb$_2$O$_3$ | Dy/Tb$_2$O$_3$ | Ho/Tb$_2$O$_3$ | Er/Tb$_2$O$_3$ | Tm/Tb$_2$O$_3$ | Yb/Tb$_2$O$_3$ | Lu/Tb$_2$O$_3$ | In/Tb$_2$O$_3$ |
| TbO$_2$ | Tb/TbO$_2$ | Dy/TbO$_2$ | Ho/TbO$_2$ | Er/TbO$_2$ | Tm/TbO$_2$ | Yb/TbO$_2$ | Lu/TbO$_2$ | In/TbO$_2$ |
| Tb$_6$O$_{11}$ | Tb/Tb$_6$O$_{11}$ | Dy/Tb$_6$O$_{11}$ | Ho/Tb$_6$O$_{11}$ | Er/Tb$_6$O$_{11}$ | Tm/Tb$_6$O$_{11}$ | Yb/Tb$_6$O$_{11}$ | Lu/Tb$_6$O$_{11}$ | In/Tb$_6$O$_{11}$ |
| Dy$_2$O$_3$ | Tb/Dy$_2$O$_3$ | Dy/Dy$_2$O$_3$ | Ho/Dy$_2$O$_3$ | Er/Dy$_2$O$_3$ | Tm/Dy$_2$O$_3$ | Yb/Dy$_2$O$_3$ | Lu/Dy$_2$O$_3$ | In/Dy$_2$O$_3$ |
| Ho$_2$O$_3$ | Tb/Ho$_2$O$_3$ | Dy/Ho$_2$O$_3$ | Ho/Ho$_2$O$_3$ | Er/Ho$_2$O$_3$ | Tm/Ho$_2$O$_3$ | Yb/Ho$_2$O$_3$ | Lu/Ho$_2$O$_3$ | In/Ho$_2$O$_3$ |
| Er$_2$O$_3$ | Tb/Er$_2$O$_3$ | Dy/Er$_2$O$_3$ | Ho/Er$_2$O$_3$ | Er/Er$_2$O$_3$ | Tm/Er$_2$O$_3$ | Yb/Er$_2$O$_3$ | Lu/Er$_2$O$_3$ | In/Er$_2$O$_3$ |
| Tm$_2$O$_3$ | Tb/Tm$_2$O$_3$ | Dy/Tm$_2$O$_3$ | Ho/Tm$_2$O$_3$ | Er/Tm$_2$O$_3$ | Tm/Tm$_2$O$_3$ | Yb/Tm$_2$O$_3$ | Lu/Tm$_2$O$_3$ | In/Tm$_2$O$_3$ |
| Yb$_2$O$_3$ | Tb/Yb$_2$O$_3$ | Dy/Yb$_2$O$_3$ | Ho/Yb$_2$O$_3$ | Er/Yb$_2$O$_3$ | Tm/Yb$_2$O$_3$ | Yb/Yb$_2$O$_3$ | Lu/Yb$_2$O$_3$ | In/Yb$_2$O$_3$ |
| Lu$_2$O$_3$ | Tb/Lu$_2$O$_3$ | Dy/Lu$_2$O$_3$ | Ho/Lu$_2$O$_3$ | Er/Lu$_2$O$_3$ | Tm/Lu$_2$O$_3$ | Yb/Lu$_2$O$_3$ | Lu/Lu$_2$O$_3$ | In/Lu$_2$O$_3$ |
| Ac$_2$O$_3$ | Tb/Ac$_2$O$_3$ | Dy/Ac$_2$O$_3$ | Ho/Ac$_2$O$_3$ | Er/Ac$_2$O$_3$ | Tm/Ac$_2$O$_3$ | Yb/Ac$_2$O$_3$ | Lu/Ac$_2$O$_3$ | In/Ac$_2$O$_3$ |
| Th$_2$O$_3$ | Tb/Th$_2$O$_3$ | Dy/Th$_2$O$_3$ | Ho/Th$_2$O$_3$ | Er/Th$_2$O$_3$ | Tm/Th$_2$O$_3$ | Yb/Th$_2$O$_3$ | Lu/Th$_2$O$_3$ | In/Th$_2$O$_3$ |
| ThO$_2$ | Tb/ThO$_2$ | Dy/ThO$_2$ | Ho/ThO$_2$ | Er/ThO$_2$ | Tm/ThO$_2$ | Yb/ThO$_2$ | Lu/ThO$_2$ | In/ThO$_2$ |
| Pa$_2$O$_3$ | Tb/Pa$_2$O$_3$ | Dy/Pa$_2$O$_3$ | Ho/Pa$_2$O$_3$ | Er/Pa$_2$O$_3$ | Tm/Pa$_2$O$_3$ | Yb/Pa$_2$O$_3$ | Lu/Pa$_2$O$_3$ | In/Pa$_2$O$_3$ |
| PaO$_2$ | Tb/PaO$_2$ | Dy/PaO$_2$ | Ho/PaO$_2$ | Er/PaO$_2$ | Tm/PaO$_2$ | Yb/PaO$_2$ | Lu/PaO$_2$ | In/PaO$_2$ |
| TiO$_2$ | Tb/TiO$_2$ | Dy/TiO$_2$ | Ho/TiO$_2$ | Er/TiO$_2$ | Tm/TiO$_2$ | Yb/TiO$_2$ | Lu/TiO$_2$ | In/TiO$_2$ |
| TiO | Tb/TiO | Dy/TiO | Ho/TiO | Er/TiO | Tm/TiO | Yb/TiO | Lu/TiO | In/TiO |
| Ti$_2$O$_3$ | Tb/Ti$_2$O$_3$ | Dy/Ti$_2$O$_3$ | Ho/Ti$_2$O$_3$ | Er/Ti$_2$O$_3$ | Tm/Ti$_2$O$_3$ | Yb/Ti$_2$O$_3$ | Lu/Ti$_2$O$_3$ | In/Ti$_2$O$_3$ |
| Ti$_3$O | Tb/Ti$_3$O | Dy/Ti$_3$O | Ho/Ti$_3$O | Er/Ti$_3$O | Tm/Ti$_3$O | Yb/Ti$_3$O | Lu/Ti$_3$O | In/Ti$_3$O |
| Ti$_2$O | Tb/Ti$_2$O | Dy/Ti$_2$O | Ho/Ti$_2$O | Er/Ti$_2$O | Tm/Ti$_2$O | Yb/Ti$_2$O | Lu/Ti$_2$O | In/Ti$_2$O |
| Ti$_3$O$_5$ | Tb/Ti$_3$O$_5$ | Dy/Ti$_3$O$_5$ | Ho/Ti$_3$O$_5$ | Er/Ti$_3$O$_5$ | Tm/Ti$_3$O$_5$ | Yb/Ti$_3$O$_5$ | Lu/Ti$_3$O$_5$ | In/Ti$_3$O$_5$ |
| Ti$_4$O$_7$ | Tb/Ti$_4$O$_7$ | Dy/Ti$_4$O$_7$ | Ho/Ti$_4$O$_7$ | Er/Ti$_4$O$_7$ | Tm/Ti$_4$O$_7$ | Yb/Ti$_4$O$_7$ | Lu/Ti$_4$O$_7$ | In/Ti$_4$O$_7$ |
| ZrO$_2$ | Tb/ZrO$_2$ | Dy/ZrO$_2$ | Ho/ZrO$_2$ | Er/ZrO$_2$ | Tm/ZrO$_2$ | Yb/ZrO$_2$ | Lu/ZrO$_2$ | In/ZrO$_2$ |
| HfO$_2$ | Tb/HfO$_2$ | Dy/HfO$_2$ | Ho/HfO$_2$ | Er/HfO$_2$ | Tm/HfO$_2$ | Yb/HfO$_2$ | Lu/HfO$_2$ | In/HfO$_2$ |
| VO | Tb/VO | Dy/VO | Ho/VO | Er/VO | Tm/VO | Yb/VO | Lu/VO | In/VO |
| V$_2$O$_3$ | Tb/V$_2$O$_3$ | Dy/V$_2$O$_3$ | Ho/V$_2$O$_3$ | Er/V$_2$O$_3$ | Tm/V$_2$O$_3$ | Yb/V$_2$O$_3$ | Lu/V$_2$O$_3$ | In/V$_2$O$_3$ |
| VO$_2$ | Tb/VO$_2$ | Dy/VO$_2$ | Ho/VO$_2$ | Er/VO$_2$ | Tm/VO$_2$ | Yb/VO$_2$ | Lu/VO$_2$ | In/VO$_2$ |
| V$_2$O$_5$ | Tb/V$_2$O$_5$ | Dy/V$_2$O$_5$ | Ho/V$_2$O$_5$ | Er/V$_2$O$_5$ | Tm/V$_2$O$_5$ | Yb/V$_2$O$_5$ | Lu/V$_2$O$_5$ | In/V$_2$O$_5$ |

TABLE 4-continued

NANOWIRES (NW) DOPED WITH SPECIFIC DOPANTS (DOP)

| NW\Dop | Tb | Dy | Ho | Er | Tm | Yb | Lu | In |
|---|---|---|---|---|---|---|---|---|
| $V_3O_7$ | $Tb/V_3O_7$ | $Dy/V_3O_7$ | $Ho/V_3O_7$ | $Er/V_3O_7$ | $Tm/V_3O_7$ | $Yb/V_3O_7$ | $Lu/V_3O_7$ | $In/V_3O_7$ |
| $V_4O_9$ | $Tb/V_4O_9$ | $Dy/V_4O_9$ | $Ho/V_4O_9$ | $Er/V_4O_9$ | $Tm/V_4O_9$ | $Yb/V_4O_9$ | $Lu/V_4O_9$ | $In/V_4O_9$ |
| $V_6O_{13}$ | $Tb/V_6O_{13}$ | $Dy/V_6O_{13}$ | $Ho/V_6O_{13}$ | $Er/V_6O_{13}$ | $Tm/V_6O_{13}$ | $Yb/V_6O_{13}$ | $Lu/V_6O_{13}$ | $In/V_6O_{13}$ |
| NbO | Tb/NbO | Dy/NbO | Ho/NbO | Er/NbO | Tm/NbO | Yb/NbO | Lu/NbO | In/NbO |
| $NbO_2$ | $Tb/NbO_2$ | $Dy/NbO_2$ | $Ho/NbO_2$ | $Er/NbO_2$ | $Tm/NbO_2$ | $Yb/NbO_2$ | $Lu/NbO_2$ | $In/NbO_2$ |
| $Nb_2O_5$ | $Tb/Nb_2O_5$ | $Dy/Nb_2O_5$ | $Ho/Nb_2O_5$ | $Er/Nb_2O_5$ | $Tm/Nb_2O_5$ | $Yb/Nb_2O_5$ | $Lu/Nb_2O_5$ | $In/Nb_2O_5$ |
| $Nb_8O_{19}$ | $Tb/Nb_8O_{19}$ | $Dy/Nb_8O_{19}$ | $Ho/Nb_8O_{19}$ | $Er/Nb_8O_{19}$ | $Tm/Nb_8O_{19}$ | $Yb/Nb_8O_{19}$ | $Lu/Nb_8O_{19}$ | $In/Nb_8O_{19}$ |
| $Nb_{16}O_{38}$ | $Tb/Nb_{16}O_{38}$ | $Dy/Nb_{16}O_{38}$ | $Ho/Nb_{16}O_{38}$ | $Er/Nb_{16}O_{38}$ | $Tm/Nb_{16}O_{38}$ | $Yb/Nb_{16}O_{38}$ | $Lu/Nb_{16}O_{38}$ | $In/Nb_{16}O_{38}$ |
| $Nb_{12}O_{29}$ | $Tb/Nb_{12}O_{29}$ | $Dy/Nb_{12}O_{29}$ | $Ho/Nb_{12}O_{29}$ | $Er/Nb_{12}O_{29}$ | $Tm/Nb_{12}O_{29}$ | $Yb/Nb_{12}O_{29}$ | $Lu/Nb_{12}O_{29}$ | $In/Nb_{12}O_{29}$ |
| $Nb_{47}O_{116}$ | $Tb/Nb_{47}O_{116}$ | $Dy/Nb_{47}O_{116}$ | $Ho/Nb_{47}O_{116}$ | $Er/Nb_{47}O_{116}$ | $Tm/Nb_{47}O_{116}$ | $Yb/Nb_{47}O_{116}$ | $Lu/Nb_{47}O_{116}$ | $In/Nb_{47}O_{116}$ |
| $Ta_2O_5$ | $Tb/Ta_2O_5$ | $Dy/Ta_2O_5$ | $Ho/Ta_2O_5$ | $Er/Ta_2O_5$ | $Tm/Ta_2O_5$ | $Yb/Ta_2O_5$ | $Lu/Ta_2O_5$ | $In/Ta_2O_5$ |
| CrO | Tb/CrO | Dy/CrO | Ho/CrO | Er/CrO | Tm/CrO | Yb/CrO | Lu/CrO | In/CrO |
| $Cr_2O_3$ | $Tb/Cr_2O_3$ | $Dy/Cr_2O_3$ | $Ho/Cr_2O_3$ | $Er/Cr_2O_3$ | $Tm/Cr_2O_3$ | $Yb/Cr_2O_3$ | $Lu/Cr_2O_3$ | $In/Cr_2O_3$ |
| $CrO_2$ | $Tb/CrO_2$ | $Dy/CrO_2$ | $Ho/CrO_2$ | $Er/CrO_2$ | $Tm/CrO_2$ | $Yb/CrO_2$ | $Lu/CrO_2$ | $In/CrO_2$ |
| $CrO_3$ | $Tb/CrO_3$ | $Dy/CrO_3$ | $Ho/CrO_3$ | $Er/CrO_3$ | $Tm/CrO_3$ | $Yb/CrO_3$ | $Lu/CrO_3$ | $In/CrO_3$ |
| $C_8O_{21}$ | $Tb/C_8O_{21}$ | $Dy/C_8O_{21}$ | $Ho/C_8O_{21}$ | $Er/C_8O_{21}$ | $Tm/C_8O_{21}$ | $Yb/C_8O_{21}$ | $Lu/C_8O_{21}$ | $In/C_8O_{21}$ |
| $MoO_2$ | $Tb/MoO_2$ | $Dy/MoO_2$ | $Ho/MoO_2$ | $Er/MoO_2$ | $Tm/MoO_2$ | $Yb/MoO_2$ | $Lu/MoO_2$ | $In/MoO_2$ |
| $MoO_3$ | $Tb/MoO_3$ | $Dy/MoO_3$ | $Ho/MoO_3$ | $Er/MoO_3$ | $Tm/MoO_3$ | $Yb/MoO_3$ | $Lu/MoO_3$ | $In/MoO_3$ |
| $W_2O_3$ | $Tb/W_2O_3$ | $Dy/W_2O_3$ | $Ho/W_2O_3$ | $Er/W_2O_3$ | $Tm/W_2O_3$ | $Yb/W_2O_3$ | $Lu/W_2O_3$ | $In/W_2O_3$ |
| $WoO_2$ | $Tb/WoO_2$ | $Dy/WoO_2$ | $Ho/WoO_2$ | $Er/WoO_2$ | $Tm/WoO_2$ | $Yb/WoO_2$ | $Lu/WoO_2$ | $In/WoO_2$ |
| $WoO_3$ | $Tb/WoO_3$ | $Dy/WoO_3$ | $Ho/WoO_3$ | $Er/WoO_3$ | $Tm/WoO_3$ | $Yb/WoO_3$ | $Lu/WoO_3$ | $In/WoO_3$ |
| MnO | Tb/MnO | Dy/MnO | Ho/MnO | Er/MnO | Tm/MnO | Yb/MnO | Lu/MnO | In/MnO |
| $Mn/Mg/O$ | $Tb/Mn/Mg/O$ | $Dy/Mn/Mg/O$ | $Ho/Mn/Mg/O$ | $Er/Mn/Mg/O$ | $Tm/Mn/Mg/O$ | $Yb/Mn/Mg/O$ | $Lu/Mn/Mg/O$ | $In/Mn/Mg/O$ |
| $Mn_3O_4$ | $Tb/Mn_3O_4$ | $Dy/Mn_3O_4$ | $Ho/Mn_3O_4$ | $Er/Mn_3O_4$ | $Tm/Mn_3O_4$ | $Yb/Mn_3O_4$ | $Lu/Mn_3O_4$ | $In/Mn_3O_4$ |
| $Mn_2O_3$ | $Tb/Mn_2O_3$ | $Dy/Mn_2O_3$ | $Ho/Mn_2O_3$ | $Er/Mn_2O_3$ | $Tm/Mn_2O_3$ | $Yb/Mn_2O_3$ | $Lu/Mn_2O_3$ | $In/Mn_2O_3$ |
| $MnO_2$ | $Tb/MnO_2$ | $Dy/MnO_2$ | $Ho/MnO_2$ | $Er/MnO_2$ | $Tm/MnO_2$ | $Yb/MnO_2$ | $Lu/MnO_2$ | $In/MnO_2$ |
| $Mn_2O_7$ | $Tb/Mn_2O_7$ | $Dy/Mn_2O_7$ | $Ho/Mn_2O_7$ | $Er/Mn_2O_7$ | $Tm/Mn_2O_7$ | $Yb/Mn_2O_7$ | $Lu/Mn_2O_7$ | $In/Mn_2O_7$ |
| $ReO_2$ | $Tb/ReO_2$ | $Dy/ReO_2$ | $Ho/ReO_2$ | $Er/ReO_2$ | $Tm/ReO_2$ | $Yb/ReO_2$ | $Lu/ReO_2$ | $In/ReO_2$ |
| $ReO_3$ | $Tb/ReO_3$ | $Dy/ReO_3$ | $Ho/ReO_3$ | $Er/ReO_3$ | $Tm/ReO_3$ | $Yb/ReO_3$ | $Lu/ReO_3$ | $In/ReO_3$ |
| $Re_2O_7$ | $Tb/Re_2O_7$ | $Dy/Re_2O_7$ | $Ho/Re_2O_7$ | $Er/Re_2O_7$ | $Tm/Re_2O_7$ | $Yb/Re_2O_7$ | $Lu/Re_2O_7$ | $In/Re_2O_7$ |
| $Mg_3Mn_3-B_2O_{10}$ | $Tb/Mg_3Mn_3-B_2O_{10}$ | $Dy/Mg_3Mn_3-B_2O_{10}$ | $Ho/Mg_3Mn_3-B_2O_{10}$ | $Er/Mg_3Mn_3-B_2O_{10}$ | $Tm/Mg_3Mn_3-B_2O_{10}$ | $Yb/Mg_3Mn_3-B_2O_{10}$ | $Lu/Mg_3Mn_3-B_2O_{10}$ | $In/Mg_3Mn_3-B_2O_{10}$ |
| $Mg_3(BO_3)_2$ | $Tb/Mg_3(BO_3)_2$ | $Dy/Mg_3(BO_3)_2$ | $Ho/Mg_3(BO_3)_2$ | $Er/Mg_3(BO_3)_2$ | $Tm/Mg_3(BO_3)_2$ | $Yb/Mg_3(BO_3)_2$ | $Lu/Mg_3(BO_3)_2$ | $In/Mg_3(BO_3)_2$ |
| $NaWO_4$ | $Tb/NaWO_4$ | $Dy/NaWO_4$ | $Ho/NaWO_4$ | $Er/NaWO_4$ | $Tm/NaWO_4$ | $Yb/NaWO_4$ | $Lu/NaWO_4$ | $In/NaWO_4$ |
| $Mg_6MnO_8$ | $Tb/Mg_6MnO_8$ | $Dy/Mg_6MnO_8$ | $Ho/Mg_6MnO_8$ | $Er/Mg_6MnO_8$ | $Tm/Mg_6MnO_8$ | $Yb/Mg_6MnO_8$ | $Lu/Mg_6MnO_8$ | $In/Mg_6MnO_8$ |
| $Mn_3O_4$ | $Tb/Mn_2O_4$ | $Dy/Mn_2O_4$ | $Ho/Mn_2O_4$ | $Er/Mn_2O_4$ | $Tm/Mn_2O_4$ | $Yb/Mn_2O_4$ | $Lu/Mn_2O_4$ | $In/Mn_2O_4$ |
| $(Li,Mg)_6MnO_8$ | $Tb/(Li,Mg)_6MnO_8$ | $Dy/(Li,Mg)_6MnO_8$ | $Ho/(Li,Mg)_6MnO_8$ | $Er/(Li,Mg)_6MnO_8$ | $Tm/(Li,Mg)_6MnO_8$ | $Yb/(Li,Mg)_6MnO_8$ | $Lu/(Li,Mg)_6MnO_8$ | $In/(Li,Mg)_6MnO_8$ |
| $Na_4P_2O_7$ | $Tb/Na_4P_2O_7$ | $Dy/Na_4P_2O_7$ | $Ho/Na_4P_2O_7$ | $Er/Na_4P_2O_7$ | $Tm/Na_4P_2O_7$ | $Yb/Na_4P_2O_7$ | $Lu/Na_4P_2O_7$ | $In/Na_4P_2O_7$ |
| $Mo_2O_8$ | $Tb/Mo_2O_8$ | $Dy/Mo_2O_8$ | $Ho/Mo_2O_8$ | $Er/Mo_2O_8$ | $Tm/Mo_2O_8$ | $Yb/Mo_2O_8$ | $Lu/Mo_2O_8$ | $In/Mo_2O_8$ |
| $Mn_3O_4/WO_4$ | $Tb/Mn_3O_4/WO_4$ | $Dy/MnO_4/WO_4$ | $Ho/Mn_3O_4/WO_4$ | $Er/Mn_3O_4/WO_4$ | $Tm/Mn_3O_4/WO_4$ | $Yb/Mn_3O_4/WO_4$ | $Lu/Mn_3O_4/WO_4$ | $In/Mn_3O_4/WO_4$ |
| $Na_3WO_4$ | $Tb/Na_3WO_4$ | $Dy/Na_3WO_4$ | $Ho/Na_3WO_4$ | $Er/Na_3WO_4$ | $Tm/Na_3WO_4$ | $Yb/Na_3WO_4$ | $Lu/Na_3WO_4$ | $In/Na_3WO_4$ |
| $Zr_2Mo_2O_8$ | $Tb/Zr_2Mo_2O_8$ | $Dy/Zr_2Mo_2O_8$ | $Ho/Zr_2Mo_2O_8$ | $Er/Zr_2Mo_2O_8$ | $Tm/Zr_2Mo_2O_8$ | $Yb/Zr_2Mo_2O_8$ | $Lu/Zr_2Mo_2O_8$ | $In/Zr_2Mo_2O_8$ |
| $NaMnO_4/MgO$ | $Tb/NaMnO_4/MgO$ | $Dy/NaMnO_4/MgO$ | $Ho/NaMnO_4/MgO$ | $Er/NaMnO_4/MgO$ | $Tm/NaMnO_4/MgO$ | $Yb/NaMnO_4/MgO$ | $Lu/NaMnO_4/MgO$ | $In/NaMnO_4/MgO$ |
| $Na_{10}Mn-W_5O_{17}$ | $Tb/Na_{10}Mn-W_5O_{17}$ | $Dy/Na_{10}Mn-W_5O_{17}$ | $Ho/Na_{10}Mn-W_5O_{17}$ | $Er/Na_{10}Mn-W_5O_{17}$ | $Tm/Na_{10}Mn-W_5O_{17}$ | $Yb/Na_{10}Mn-W_5O_{17}$ | $Lu/Na_{10}Mn-W_5O_{17}$ | $In/Na_{10}Mn-W_5O_{17}$ |
| $La_3NdO_6$ | $Tb/La_3NdO_6$ | $Dy/La_3NdO_6$ | $Ho/La_3NdO_6$ | $Er/La_3NdO_6$ | $Tm/La_3NdO_6$ | $Yb/La_3NdO_6$ | $Lu/La_3NdO_6$ | $In/La_3NdO_6$ |
| $LaNd_3O_6$ | $Tb/LaNd_3O_6$ | $Dy/LaNd_3O_6$ | $Ho/LaNd_3O_6$ | $Er/LaNd_3O_6$ | $Tm/LaNd_3O_6$ | $Yb/LaNd_3O_6$ | $Lu/LaNd_3O_6$ | $In/LaNd_3O_6$ |
| $La_{1.5}Nd_{2.5}O_6$ | $Tb/La_{1.5}Nd_{2.5}O_6$ | $Dy/La_{1.5}Nd_{2.5}O_6$ | $Ho/La_{1.5}Nd_{2.5}O_6$ | $Er/La_{1.5}Nd_{2.5}O_6$ | $Tm/La_{1.5}Nd_{2.5}O_6$ | $Yb/La_{1.5}Nd_{2.5}O_6$ | $Lu/La_{1.5}Nd_{2.5}O_6$ | $In/La_{1.5}Nd_{2.5}O_6$ |
| $La_{2.5}Nd_{1.5}O_6$ | $Tb/La_{2.5}Nd_{1.5}O_6$ | $Dy/La_{2.5}Nd_{1.5}O_6$ | $Ho/La_{2.5}Nd_{1.5}O_6$ | $Er/La_{2.5}Nd_{1.5}O_6$ | $Tm/La_{2.5}Nd_{1.5}O_6$ | $Yb/La_{2.5}Nd_{1.5}O_6$ | $Lu/La_{2.5}Nd_{1.5}O_6$ | $In/La_{2.5}Nd_{1.5}O_6$ |
| $La_{3.2}Nd_{0.8}O_6$ | $Tb/La_{3.2}Nd_{0.8}O_6$ | $Dy/La_{3.2}Nd_{0.8}O_6$ | $Ho/La_{3.2}Nd_{0.8}O_6$ | $Er/La_{3.2}Nd_{0.8}O_6$ | $Tm/La_{3.2}Nd_{0.8}O_6$ | $Yb/La_{3.2}Nd_{0.8}O_6$ | $Lu/La_{3.2}Nd_{0.8}O_6$ | $In/La_{3.2}Nd_{0.8}O_6$ |
| $La_{3.5}Nd_{0.5}O_6$ | $Tb/La_{3.5}Nd_{0.5}O_6$ | $Dy/La_{3.5}Nd_{0.5}O_6$ | $Ho/La_{3.5}Nd_{0.5}O_6$ | $Er/La_{3.5}Nd_{0.5}O_6$ | $Tm/La_{3.5}Nd_{0.5}O_6$ | $Yb/La_{3.5}Nd_{0.5}O_6$ | $Lu/La_{3.5}Nd_{0.5}O_6$ | $In/La_{3.5}Nd_{0.5}O_6$ |

TABLE 4-continued

NANOWIRES (NW) DOPED WITH SPECIFIC DOPANTS (DOP)

| NW\Dop | Tb | Dy | Ho | Er | Tm | Yb | Lu | In |
|---|---|---|---|---|---|---|---|---|
| La$_{3.8}$Nd$_{0.2}$O$_6$ | Tb/La$_{3.8}$Nd$_{0.2}$O$_6$ | Dy/La$_{3.8}$Nd$_{0.2}$O$_6$ | Ho/La$_{3.8}$Nd$_{0.2}$O$_6$ | Er/La$_{3.8}$Nd$_{0.2}$O$_6$ | Tm/La$_{3.8}$Nd$_{0.2}$O$_6$ | Yb/La$_{3.8}$Nd$_{0.2}$O$_6$ | Lu/La$_{3.8}$Nd$_{0.2}$O$_6$ | In/La$_{3.8}$Nd$_{0.2}$O$_6$ |
| Y—La | Tb/Y—La | Dy/Y—La | Ho/Y—La | Er/Y—La | Tm/Y—La | Yb/Y—La | Lu/Y—La | In/Y—La |
| Zr—La | Tb/Zr—La | Dy/Zr—La | Ho/Zr—La | Er/Zr—La | Tm/Zr—La | Yb/Zr—La | Lu/Zr—La | In/Zr—La |
| Pr—La | Tb/Pr—La | Dy/Pr—La | Ho/Pr—La | Er/Pr—La | Tm/Pr—La | Yb/Pr—La | Lu/Pr—La | In/Pr—La |
| Ce—La | Tb/Ce—La | Dy/Ce—La | Ho/Ce—La | Er/Ce—La | Tm/Ce—La | Yb/Ce—La | Lu/Ce—La | In/Ce—La |

TABLE 5

NANOWIRES (NW) DOPED WITH SPECIFIC DOPANTS (DOP)

| NW\Dop | Y | Sc | Al | Cu | Ga | Hf | Fe | Cr |
|---|---|---|---|---|---|---|---|---|
| $Li_2O$ | $Y/Li_2O$ | $Sc/Li_2O$ | $Al/Li_2O$ | $Cu/Li_2O$ | $Ga/Li_2O$ | $Hf/Li_2O$ | $Fe/Li_2O$ | $Cr/Li_2O$ |
| $Na_2O$ | $Y/Na_2O$ | $Sc/Na_2O$ | $Al/Na_2O$ | $Cu/Na_2O$ | $Ga/Na_2O$ | $Hf/Na_2O$ | $Fe/Na_2O$ | $Cr/Na_2O$ |
| $K_2O$ | $Y/K_2O$ | $Sc/K_2O$ | $Al/K_2O$ | $Cu/K_2O$ | $Ga/K_2O$ | $Hf/K_2O$ | $Fe/K_2O$ | $Cr/K_2O$ |
| $Rb_2O$ | $Y/Rb_2O$ | $Sc/Rb_2O$ | $Al/Rb_2O$ | $Cu/Rb_2O$ | $Ga/Rb_2O$ | $Hf/Rb_2O$ | $Fe/Rb_2O$ | $Cr/Rb_2O$ |
| $Cs_2O$ | $Y/Cs_2O$ | $Sc/Cs_2O$ | $Al/Cs_2O$ | $Cu/Cs_2O$ | $Ga/Cs_2O$ | $Hf/Cs_2O$ | $Fe/Cs_2O$ | $Cr/Cs_2O$ |
| BeO | Y/BeO | Sc/BeO | Al/BeO | Cu/BeO | Ga/BeO | Hf/BeO | Fe/BeO | Cr/BeO |
| MgO | Y/MgO | Sc/MgO | Al/MgO | Cu/MgO | Ga/MgO | Hf/MgO | Fe/MgO | Cr/MgO |
| CaO | Y/CaO | Sc/CaO | Al/CaO | Cu/CaO | Ga/CaO | Hf/CaO | Fe/CaO | Cr/CaO |
| SrO | Y/SrO | Sc/SrO | Al/SrO | Cu/SrO | Ga/SrO | Hf/SrO | Fe/SrO | Cr/SrO |
| BaO | Y/BaO | Sc/BaO | Al/BaO | Cu/BaO | Ga/BaO | Hf/BaO | Fe/BaO | Cr/BaO |
| $Sc_2O_3$ | $Y/Sc_2O_3$ | $Sc/Sc_2O_3$ | $Al/Sc_2O_3$ | $Cu/Sc_2O_3$ | $Ga/Sc_2O_3$ | $Hf/Sc_2O_3$ | $Fe/Sc_2O_3$ | $Cr/Sc_2O_3$ |
| $Y_2O_3$ | $Y/Y_2O_3$ | $Sc/Y_2O_3$ | $Al/Y_2O_3$ | $Cu/Y_2O_3$ | $Ga/Y_2O_3$ | $Hf/Y_2O_3$ | $Fe/Y_2O_3$ | $Cr/Y_2O_3$ |
| $La_2O_3$ | $Y/La_2O_3$ | $Sc/La_2O_3$ | $Al/La_2O_3$ | $Cu/La_2O_3$ | $Ga/La_2O_3$ | $Hf/La_2O_3$ | $Fe/La_2O_3$ | $Cr/La_2O_3$ |
| $CeO_2$ | $Y/CeO_2$ | $Sc/CeO_2$ | $Al/CeO_2$ | $Cu/CeO_2$ | $Ga/CeO_2$ | $Hf/CeO_2$ | $Fe/CeO_2$ | $Cr/CeO_2$ |
| $Ce_2O_3$ | $Y/Ce_2O_3$ | $Sc/Ce_2O_3$ | $Al/Ce_2O_3$ | $Cu/Ce_2O_3$ | $Ga/Ce_2O_3$ | $Hf/Ce_2O_3$ | $Fe/Ce_2O_3$ | $Cr/Ce_2O_3$ |
| $Pr_2O_3$ | $Y/Pr_2O_3$ | $Sc/Pr_2O_3$ | $Al/Pr_2O_3$ | $Cu/Pr_2O_3$ | $Ga/Pr_2O_3$ | $Hf/Pr_2O_3$ | $Fe/Pr_2O_3$ | $Cr/Pr_2O_3$ |
| $Nd_2O_3$ | $Y/Nd_2O_3$ | $Sc/Nd_2O_3$ | $Al/Nd_2O_3$ | $Cu/Nd_2O_3$ | $Ga/Nd_2O_3$ | $Hf/Nd_2O_3$ | $Fe/Nd_2O_3$ | $Cr/Nd_2O_3$ |
| $Sm_2O_3$ | $Y/Sm_2O_3$ | $Sc/Sm_2O_3$ | $Al/Sm_2O_3$ | $Cu/Sm_2O_3$ | $Ga/Sm_2O_3$ | $Hf/Sm_2O_3$ | $Fe/Sm_2O_3$ | $Cr/Sm_2O_3$ |
| $Eu_2O_3$ | $Y/Eu_2O_3$ | $Sc/Eu_2O_3$ | $Al/Eu_2O_3$ | $Cu/Eu_2O_3$ | $Ga/Eu_2O_3$ | $Hf/Eu_2O_3$ | $Fe/Eu_2O_3$ | $Cr/Eu_2O_3$ |
| $Gd_2O_3$ | $Y/Gd_2O_3$ | $Sc/Gd_2O_3$ | $Al/Gd_2O_3$ | $Cu/Gd_2O_3$ | $Ga/Gd_2O_3$ | $Hf/Gd_2O_3$ | $Fe/Gd_2O_3$ | $Cr/Gd_2O_3$ |
| $Tb_2O_3$ | $Y/Tb_2O_3$ | $Sc/Tb_2O_3$ | $Al/Tb_2O_3$ | $Cu/Tb_2O_3$ | $Ga/Tb_2O_3$ | $Hf/Tb_2O_3$ | $Fe/Tb_2O_3$ | $Cr/Tb_2O_3$ |
| $TbO_2$ | $Y/TbO_2$ | $Sc/TbO_2$ | $Al/TbO_2$ | $Cu/TbO_2$ | $Ga/TbO_2$ | $Hf/TbO_2$ | $Fe/TbO_2$ | $Cr/TbO_2$ |
| $Tb_6O_{11}$ | $Y/Tb_6O_{11}$ | $Sc/Tb_6O_{11}$ | $Al/Tb_6O_{11}$ | $Cu/Tb_6O_{11}$ | $Ga/Tb_6O_{11}$ | $Hf/Tb_6O_{11}$ | $Fe/Tb_6O_{11}$ | $Cr/Tb_6O_{11}$ |
| $Dy_2O_3$ | $Y/Dy_2O_3$ | $Sc/Dy_2O_3$ | $Al/Dy_2O_3$ | $Cu/Dy_2O_3$ | $Ga/Dy_2O_3$ | $Hf/Dy_2O_3$ | $Fe/Dy_2O_3$ | $Cr/Dy_2O_3$ |
| $Ho_2O_3$ | $Y/Ho_2O_3$ | $Sc/Ho_2O_3$ | $Al/Ho_2O_3$ | $Cu/Ho_2O_3$ | $Ga/Ho_2O_3$ | $Hf/Ho_2O_3$ | $Fe/Ho_2O_3$ | $Cr/Ho_2O_3$ |
| $Er_2O_3$ | $Y/Er_2O_3$ | $Sc/Er_2O_3$ | $Al/Er_2O_3$ | $Cu/Er_2O_3$ | $Ga/Er_2O_3$ | $Hf/Er_2O_3$ | $Fe/Er_2O_3$ | $Cr/Er_2O_3$ |
| $Tm_2O_3$ | $Y/Tm_2O_3$ | $Sc/Tm_2O_3$ | $Al/Tm_2O_3$ | $Cu/Tm_2O_3$ | $Ga/Tm_2O_3$ | $Hf/Tm_2O_3$ | $Fe/Tm_2O_3$ | $Cr/Tm_2O_3$ |
| $Yb_2O_3$ | $Y/Yb_2O_3$ | $Sc/Yb_2O_3$ | $Al/Yb_2O_3$ | $Cu/Yb_2O_3$ | $Ga/Yb_2O_3$ | $Hf/Yb_2O_3$ | $Fe/Yb_2O_3$ | $Cr/Yb_2O_3$ |
| $Lu_2O_3$ | $Y/Lu_2O_3$ | $Sc/Lu_2O_3$ | $Al/Lu_2O_3$ | $Cu/Lu_2O_3$ | $Ga/Lu_2O_3$ | $Hf/Lu_2O_3$ | $Fe/Lu_2O_3$ | $Cr/Lu_2O_3$ |
| $Ac_2O_3$ | $Y/Ac_2O_3$ | $Sc/Ac_2O_3$ | $Al/Ac_2O_3$ | $Cu/Ac_2O_3$ | $Ga/Ac_2O_3$ | $Hf/Ac_2O_3$ | $Fe/Ac_2O_3$ | $Cr/Ac_2O_3$ |
| $Th_2O_3$ | $Y/Th_2O_3$ | $Sc/Th_2O_3$ | $Al/Th_2O_3$ | $Cu/Th_2O_3$ | $Ga/Th_2O_3$ | $Hf/Th_2O_3$ | $Fe/Th_2O_3$ | $Cr/Th_2O_3$ |
| $ThO_2$ | $Y/ThO_2$ | $Sc/ThO_2$ | $Al/ThO_2$ | $Cu/ThO_2$ | $Ga/ThO_2$ | $Hf/ThO_2$ | $Fe/ThO_2$ | $Cr/ThO_2$ |
| $Pa_2O_3$ | $Y/Pa_2O_3$ | $Sc/Pa_2O_3$ | $Al/Pa_2O_3$ | $Cu/Pa_2O_3$ | $Ga/Pa_2O_3$ | $Hf/Pa_2O_3$ | $Fe/Pa_2O_3$ | $Cr/Pa_2O_3$ |
| $PaO_2$ | $Y/PaO_2$ | $Sc/PaO_2$ | $Al/PaO_2$ | $Cu/PaO_2$ | $Ga/PaO_2$ | $Hf/PaO_2$ | $Fe/PaO_2$ | $Cr/PaO_2$ |
| $TiO_2$ | $Y/TiO_2$ | $Sc/TiO_2$ | $Al/TiO_2$ | $Cu/TiO_2$ | $Ga/TiO_2$ | $Hf/TiO_2$ | $Fe/TiO_2$ | $Cr/TiO_2$ |
| TiO | Y/TiO | Sc/TiO | Al/TiO | Cu/TiO | Ga/TiO | Hf/TiO | Fe/TiO | Cr/TiO |
| $Ti_2O_3$ | $Y/Ti_2O_3$ | $Sc/Ti_2O_3$ | $Al/Ti_2O_3$ | $Cu/Ti_2O_3$ | $Ga/Ti_2O_3$ | $Hf/Ti_2O_3$ | $Fe/Ti_2O_3$ | $Cr/Ti_2O_3$ |
| $Ti_3O$ | $Y/Ti_3O$ | $Sc/Ti_3O$ | $Al/Ti_3O$ | $Cu/Ti_3O$ | $Ga/Ti_3O$ | $Hf/Ti_3O$ | $Fe/Ti_3O$ | $Cr/Ti_3O$ |
| $Ti_2O$ | $Y/Ti_2O$ | $Sc/Ti_2O$ | $Al/Ti_2O$ | $Cu/Ti_2O$ | $Ga/Ti_2O$ | $Hf/Ti_2O$ | $Fe/Ti_2O$ | $Cr/Ti_2O$ |
| $Ti_3O_5$ | $Y/Ti_3O_5$ | $Sc/Ti_3O_5$ | $Al/Ti_3O_5$ | $Cu/Ti_3O_5$ | $Ga/Ti_3O_5$ | $Hf/Ti_3O_5$ | $Fe/Ti_3O_5$ | $Cr/Ti_3O_5$ |
| $Ti_4O_7$ | $Y/Ti_4O_7$ | $Sc/Ti_4O_7$ | $Al/Ti_4O_7$ | $Cu/Ti_4O_7$ | $Ga/Ti_4O_7$ | $Hf/Ti_4O_7$ | $Fe/Ti_4O_7$ | $Cr/Ti_4O_7$ |
| $ZrO_2$ | $Y/ZrO_2$ | $Sc/ZrO_2$ | $Al/ZrO_2$ | $Cu/ZrO_2$ | $Ga/ZrO_2$ | $Hf/ZrO_2$ | $Fe/ZrO_2$ | $Cr/ZrO_2$ |
| $HfO_2$ | $Y/HfO_2$ | $Sc/HfO_2$ | $Al/HfO_2$ | $Cu/HfO_2$ | $Ga/HfO_2$ | $Hf/HfO_2$ | $Fe/HfO_2$ | $Cr/HfO_2$ |
| VO | Y/VO | Sc/VO | Al/VO | Cu/VO | Ga/VO | Hf/VO | Fe/VO | Cr/VO |
| $V_2O_3$ | $Y/V_2O_3$ | $Sc/V_2O_3$ | $Al/V_2O_3$ | $Cu/V_2O_3$ | $Ga/V_2O_3$ | $Hf/V_2O_3$ | $Fe/V_2O_3$ | $Cr/V_2O_3$ |
| $VO_2$ | $Y/VO_2$ | $Sc/VO_2$ | $Al/VO_2$ | $Cu/VO_2$ | $Ga/VO_2$ | $Hf/VO_2$ | $Fe/VO_2$ | $Cr/VO_2$ |
| $V_2O_5$ | $Y/V_2O_5$ | $Sc/V_2O_5$ | $Al/V_2O_5$ | $Cu/V_2O_5$ | $Ga/V_2O_5$ | $Hf/V_2O_5$ | $Fe/V_2O_5$ | $Cr/V_2O_5$ |

TABLE 5-continued

NANOWIRES (NW) DOPED WITH SPECIFIC DOPANTS (DOP)

| NW\Dop | Y | Sc | Al | Cu | Ga | Hf | Fe | Cr |
|---|---|---|---|---|---|---|---|---|
| $V_3O_7$ | $Y/V_3O_7$ | $Sc/V_3O_7$ | $Al/V_3O_7$ | $Cu/V_3O_7$ | $Ga/V_3O_7$ | $Hf/V_3O_7$ | $Fe/V_3O_7$ | $Cr/V_3O_7$ |
| $V_4O_9$ | $Y/V_4O_9$ | $Sc/V_4O_9$ | $Al/V_4O_9$ | $Cu/V_4O_9$ | $Ga/V_4O_9$ | $Hf/V_4O_9$ | $Fe/V_4O_9$ | $Cr/V_4O_9$ |
| $V_6O_{13}$ | $Y/V_6O_{13}$ | $Sc/V_6O_{13}$ | $Al/V_6O_{13}$ | $Cu/V_6O_{13}$ | $Ga/V_6O_{13}$ | $Hf/V_6O_{13}$ | $Fe/V_6O_{13}$ | $Cr/V_6O_{13}$ |
| $NbO$ | $Y/NbO$ | $Sc/NbO$ | $Al/NbO$ | $Cu/NbO$ | $Ga/NbO$ | $Hf/NbO$ | $Fe/NbO$ | $Cr/NbO$ |
| $NbO_2$ | $Y/NbO_2$ | $Sc/NbO_2$ | $Al/NbO_2$ | $Cu/NbO_2$ | $Ga/NbO_2$ | $Hf/NbO_2$ | $Fe/NbO_2$ | $Cr/NbO_2$ |
| $Nb_2O_5$ | $Y/Nb_2O_5$ | $Sc/Nb_2O_5$ | $Al/Nb_2O_5$ | $Cu/Nb_2O_5$ | $Ga/Nb_2O_5$ | $Hf/Nb_2O_5$ | $Fe/Nb_2O_5$ | $Cr/Nb_2O_5$ |
| $Nb_8O_{19}$ | $Y/Nb_8O_{19}$ | $Sc/Nb_8O_{19}$ | $Al/Nb_8O_{19}$ | $Cu/Nb_8O_{19}$ | $Ga/Nb_8O_{19}$ | $Hf/Nb_8O_{19}$ | $Fe/Nb_8O_{19}$ | $Cr/Nb_8O_{19}$ |
| $Nb_{16}O_{38}$ | $Y/Nb_{16}O_{38}$ | $Sc/Nb_{16}O_{38}$ | $Al/Nb_{16}O_{38}$ | $Cu/Nb_{16}O_{38}$ | $Ga/Nb_{16}O_{38}$ | $Hf/Nb_{16}O_{38}$ | $Fe/Nb_{16}O_{38}$ | $Cr/Nb_{16}O_{38}$ |
| $Nb_{12}O_{29}$ | $Y/Nb_{12}O_{29}$ | $Sc/Nb_{12}O_{29}$ | $Al/Nb_{12}O_{29}$ | $Cu/Nb_{12}O_{29}$ | $Ga/Nb_{12}O_{29}$ | $Hf/Nb_{12}O_{29}$ | $Fe/Nb_{12}O_{29}$ | $Cr/Nb_{12}O_{29}$ |
| $Nb_{47}O_{116}$ | $Y/Nb_{47}O_{116}$ | $Sc/Nb_{47}O_{116}$ | $Al/Nb_{47}O_{116}$ | $Cu/Nb_{47}O_{116}$ | $Ga/Nb_{47}O_{116}$ | $Hf/Nb_{47}O_{116}$ | $Fe/Nb_{47}O_{116}$ | $Cr/Nb_{47}O_{116}$ |
| $Ta_2O_5$ | $Y/Ta_2O_5$ | $Sc/Ta_2O_5$ | $Al/Ta_2O_5$ | $Cu/Ta_2O_5$ | $Ga/Ta_2O_5$ | $Hf/Ta_2O_5$ | $Fe/Ta_2O_5$ | $Cr/Ta_2O_5$ |
| $CrO$ | $Y/CrO$ | $Sc/CrO$ | $Al/CrO$ | $Cu/CrO$ | $Ga/CrO$ | $Hf/CrO$ | $Fe/CrO$ | $Cr/CrO$ |
| $Cr_2O_3$ | $Y/Cr_2O_3$ | $Sc/Cr_2O_3$ | $Al/Cr_2O_3$ | $Cu/Cr_2O_3$ | $Ga/Cr_2O_3$ | $Hf/Cr_2O_3$ | $Fe/Cr_2O_3$ | $Cr/Cr_2O_3$ |
| $CrO_2$ | $Y/CrO_2$ | $Sc/CrO_2$ | $Al/CrO_2$ | $Cu/CrO_2$ | $Ga/CrO_2$ | $Hf/CrO_2$ | $Fe/CrO_2$ | $Cr/CrO_2$ |
| $CrO_3$ | $Y/CrO_3$ | $Sc/CrO_3$ | $Al/CrO_3$ | $Cu/CrO_3$ | $Ga/CrO_3$ | $Hf/CrO_3$ | $Fe/CrO_3$ | $Cr/CrO_3$ |
| $C_8O_{21}$ | $Y/C_8O_{21}$ | $Sc/C_8O_{21}$ | $Al/C_8O_{21}$ | $Cu/C_8O_{21}$ | $Ga/C_8O_{21}$ | $Hf/C_8O_{21}$ | $Fe/C_8O_{21}$ | $Cr/C_8O_{21}$ |
| $MoO_2$ | $Y/MoO_2$ | $Sc/MoO_2$ | $Al/MoO_2$ | $Cu/MoO_2$ | $Ga/MoO_2$ | $Hf/MoO_2$ | $Fe/MoO_2$ | $Cr/MoO_2$ |
| $MoO_3$ | $Y/MoO_3$ | $Sc/MoO_3$ | $Al/MoO_3$ | $Cu/MoO_3$ | $Ga/MoO_3$ | $Hf/MoO_3$ | $Fe/MoO_3$ | $Cr/MoO_3$ |
| $W_2O_3$ | $Y/W_2O_3$ | $Sc/W_2O_3$ | $Al/W_2O_3$ | $Cu/W_2O_3$ | $Ga/W_2O_3$ | $Hf/W_2O_3$ | $Fe/W_2O_3$ | $Cr/W_2O_3$ |
| $WoO_2$ | $Y/WoO_2$ | $Sc/WoO_2$ | $Al/WoO_2$ | $Cu/WoO_2$ | $Ga/WoO_2$ | $Hf/WoO_2$ | $Fe/WoO_2$ | $Cr/WoO_2$ |
| $WoO_3$ | $Y/WoO_3$ | $Sc/WoO_3$ | $Al/WoO_3$ | $Cu/WoO_3$ | $Ga/WoO_3$ | $Hf/WoO_3$ | $Fe/WoO_3$ | $Cr/WoO_3$ |
| $MnO$ | $Y/MnO$ | $Sc/MnO$ | $Al/MnO$ | $Cu/MnO$ | $Ga/MnO$ | $Hf/MnO$ | $Fe/MnO$ | $Cr/MnO$ |
| $Mn/Mg/O$ | $Y/Mn/Mg/O$ | $Sc/Mn/Mg/O$ | $Al/Mn/Mg/O$ | $Cu/Mn/Mg/O$ | $Ga/Mn/Mg/O$ | $Hf/Mn/Mg/O$ | $Fe/Mn/Mg/O$ | $Cr/Mn/Mg/O$ |
| $Mn_3O_4$ | $Y/Mn_3O_4$ | $Sc/Mn_3O_4$ | $Al/Mn_3O_4$ | $Cu/Mn_3O_4$ | $Ga/Mn_3O_4$ | $Hf/Mn_3O_4$ | $Fe/Mn_3O_4$ | $Cr/Mn_3O_4$ |
| $Mn_2O_3$ | $Y/Mn_2O_3$ | $Sc/Mn_2O_3$ | $Al/Mn_2O_3$ | $Cu/Mn_2O_3$ | $Ga/Mn_2O_3$ | $Hf/Mn_2O_3$ | $Fe/Mn_2O_3$ | $Cr/Mn_2O_3$ |
| $MnO_2$ | $Y/MnO_2$ | $Sc/MnO_2$ | $Al/MnO_2$ | $Cu/MnO_2$ | $Ga/MnO_2$ | $Hf/MnO_2$ | $Fe/MnO_2$ | $Cr/MnO_2$ |
| $Mn_2O_7$ | $Y/Mn_2O_7$ | $Sc/Mn_2O_7$ | $Al/Mn_2O_7$ | $Cu/Mn_2O_7$ | $Ga/Mn_2O_7$ | $Hf/Mn_2O_7$ | $Fe/Mn_2O_7$ | $Cr/Mn_2O_7$ |
| $ReO_2$ | $Y/ReO_2$ | $Sc/ReO_2$ | $Al/ReO_2$ | $Cu/ReO_2$ | $Ga/ReO_2$ | $Hf/ReO_2$ | $Fe/ReO_2$ | $Cr/ReO_2$ |
| $ReO_3$ | $Y/ReO_3$ | $Sc/ReO_3$ | $Al/ReO_3$ | $Cu/ReO_3$ | $Ga/ReO_3$ | $Hf/ReO_3$ | $Fe/ReO_3$ | $Cr/ReO_3$ |
| $Re_2O_7$ | $Y/Re_2O_7$ | $Sc/Re_2O_7$ | $Al/Re_2O_7$ | $Cu/Re_2O_7$ | $Ga/Re_2O_7$ | $Hf/Re_2O_7$ | $Fe/Re_2O_7$ | $Cr/Re_2O_7$ |
| $Mg_3Mn_3$—$B_2O_{10}$ | $Y/Mg_3Mn_3$—$B_2O_{10}$ | $Sc/Mg_3Mn_3$—$B_2O_{10}$ | $Al/Mg_3Mn_3$—$B_2O_{10}$ | $Cu/Mg_3Mn_3$—$B_2O_{10}$ | $Ga/Mg_3Mn_3$—$B_2O_{10}$ | $Hf/Mg_3Mn_3$—$B_2O_{10}$ | $Fe/Mg_3Mn_3$—$B_2O_{10}$ | $Cr/Mg_3Mn_3$—$B_2O_{10}$ |
| $Mg_3(BO_3)_2$ | $Y/Mg_3(BO_3)_2$ | $Sc/Mg_3(BO_3)_2$ | $Al/Mg_3(BO_3)_2$ | $Cu/Mg_3(BO_3)_2$ | $Ga/Mg_3(BO_3)_2$ | $Hf/Mg_3(BO_3)_2$ | $Fe/Mg_3(BO_3)_2$ | $Cr/Mg_3(BO_3)_2$ |
| $NaWO_4$ | $Y/NaWO_4$ | $Sc/NaWO_4$ | $Al/NaWO_4$ | $Cu/NaWO_4$ | $Ga/NaWO_4$ | $Hf/NaWO_4$ | $Fe/NaWO_4$ | $Cr/NaWO_4$ |
| $Mg_6MnO_8$ | $Y/Mg_6MnO_8$ | $Sc/Mg_6MnO_8$ | $Al/Mg_6MnO_8$ | $Cu/Mg_6MnO_8$ | $Ga/Mg_6MnO_8$ | $Hf/Mg_6MnO_8$ | $Fe/Mg_6MnO_8$ | $Cr/Mg_6MnO_8$ |
| $Mn_2O_4$ | $Y/Mn_2O_4$ | $Sc/Mn_2O_4$ | $Al/Mn_2O_4$ | $Cu/Mn_2O_4$ | $Ga/Mn_2O_4$ | $Hf/Mn_2O_4$ | $Fe/Mn_2O_4$ | $Cr/Mn_2O_4$ |
| $(Li,Mg)_6MnO_8$ | $Y/(Li,Mg)_6MnO_8$ | $Sc/(Li,Mg)_6MnO_8$ | $Al/(Li,Mg)_6MnO_8$ | $Cu/(Li,Mg)_6MnO_8$ | $Ga/(Li,Mg)_6MnO_8$ | $Hf/(Li,Mg)_6MnO_8$ | $Fe/(Li,Mg)_6MnO_8$ | $Cr/(Li,Mg)_6MnO_8$ |
| $Na_4P_2O_7$ | $Y/Na_4P_2O_7$ | $Sc/Na_4P_2O_7$ | $Al/Na_4P_2O_7$ | $Cu/Na_4P_2O_7$ | $Ga/Na_4P_2O_7$ | $Hf/Na_4P_2O_7$ | $Fe/Na_4P_2O_7$ | $Cr/Na_4P_2O_7$ |
| $Mo_2O_8$ | $Y/Mo_2O_8$ | $Sc/Mo_2O_8$ | $Al/Mo_2O_8$ | $Cu/Mo_2O_8$ | $Ga/Mo_2O_8$ | $Hf/Mo_2O_8$ | $Fe/Mo_2O_8$ | $Cr/Mo_2O_8$ |
| $Mn_3O_4/WO_4$ | $Y/Mn_3O_4/WO_4$ | $Sc/Mn_3O_4/WO_4$ | $Al/Mn_3O_4/WO_4$ | $Cu/Mn_3O_4/WO_4$ | $Ga/Mn_3O_4/WO_4$ | $Hf/Mn_3O_4/WO_4$ | $Fe/Mn_3O_4/WO_4$ | $Cr/Mn_3O_4/WO_4$ |
| $Na_3WO_4$ | $Y/Na_3WO_4$ | $Sc/Na_3WO_4$ | $Al/Na_3WO_4$ | $Cu/Na_3WO_4$ | $Ga/Na_3WO_4$ | $Hf/Na_3WO_4$ | $Fe/Na_3WO_4$ | $Cr/Na_3WO_4$ |
| $Zr_2Mo_2O_8$ | $Y/Zr_2Mo_2O_8$ | $Sc/Zr_2Mo_2O_8$ | $Al/Zr_2Mo_2O_8$ | $Cu/Zr_2Mo_2O_8$ | $Ga/Zr_2Mo_2O_8$ | $Hf/Zr_2Mo_2O_8$ | $Fe/Zr_2Mo_2O_8$ | $Cr/Zr_2Mo_2O_8$ |
| $NaMnO_4$—$/MgO$ | $Y/NaMnO_4$—$/MgO$ | $Sc/NaMnO_4$—$/MgO$ | $Al/NaMnO_4$—$/MgO$ | $Cu/NaMnO_4$—$/MgO$ | $Ga/NaMnO_4$—$/MgO$ | $Hf/NaMnO_4$—$/MgO$ | $Fe/NaMnO_4$—$/MgO$ | $Cr/NaMnO_4$—$/MgO$ |
| $Na_{10}Mn$—$W_5O_{17}$ | $Y/Na_{10}Mn$—$W_5O_{17}$ | $Sc/Na_{10}Mn$—$W_5O_{17}$ | $Al/Na_{10}Mn$—$W_5O_{17}$ | $Cu/Na_{10}Mn$—$W_5O_{17}$ | $Ga/Na_{10}Mn$—$W_5O_{17}$ | $Hf/Na_{10}Mn$—$W_5O_{17}$ | $Fe/Na_{10}Mn$—$W_5O_{17}$ | $Cr/Na_{10}Mn$—$W_5O_{17}$ |
| $La_3NdO_6$ | $Y/La_3NdO_6$ | $Sc/La_3NdO_6$ | $Al/La_3NdO_6$ | $Cu/La_3NdO_6$ | $Ga/La_3NdO_6$ | $Hf/La_3NdO_6$ | $Fe/La_3NdO_6$ | $Cr/La_3NdO_6$ |
| $LaNdO_6$ | $Y/LaNd_3O_6$ | $Sc/LaNd_3O_6$ | $Al/LaNd_3O_6$ | $Cu/LaNd_3O_6$ | $Ga/LaNd_3O_6$ | $Hf/LaNd_3O_6$ | $Fe/LaNd_3O_6$ | $Cr/LaNd_3O_6$ |
| $La_{1.5}Nd_{2.5}O_6$ | $Y/La_{1.5}Nd_{2.5}O_6$ | $Sc/La_{1.5}Nd_{2.5}O_6$ | $Al/La_{1.5}Nd_{2.5}O_6$ | $Cu/La_{1.5}Nd_{2.5}O_6$ | $Ga/La_{1.5}Nd_{2.5}O_6$ | $Hf/La_{1.5}Nd_{2.5}O_6$ | $Fe/La_{1.5}Nd_{2.5}O_6$ | $Cr/La_{1.5}Nd_{2.5}O_6$ |
| $La_{2.5}Nd_{1.5}O_6$ | $Y/La_{2.5}Nd_{1.5}O_6$ | $Sc/La_{2.5}Nd_{1.5}O_6$ | $Al/La_{2.5}Nd_{1.5}O_6$ | $Cu/La_{2.5}Nd_{1.5}O_6$ | $Ga/La_{2.5}Nd_{1.5}O_6$ | $Hf/La_{2.5}Nd_{1.5}O_6$ | $Fe/La_{2.5}Nd_{1.5}O_6$ | $Cr/La_{2.5}Nd_{1.5}O_6$ |
| $La_{3.2}Nd_{0.8}O_6$ | $Y/La_{3.2}Nd_{0.8}O_6$ | $Sc/La_{3.2}Nd_{0.8}O_6$ | $Al/La_{3.2}Nd_{0.8}O_6$ | $Cu/La_{3.2}Nd_{0.8}O_6$ | $Ga/La_{3.2}Nd_{0.8}O_6$ | $Hf/La_{3.2}Nd_{0.8}O_6$ | $Fe/La_{3.2}Nd_{0.8}O_6$ | $Cr/La_{3.2}Nd_{0.8}O_6$ |
| $La_{3.5}Nd_{0.5}O_6$ | $Y/La_{3.5}Nd_{0.5}O_6$ | $Sc/La_{3.5}Nd_{0.5}O_6$ | $Al/La_{3.5}Nd_{0.5}O_6$ | $Cu/La_{3.5}Nd_{0.5}O_6$ | $Ga/La_{3.5}Nd_{0.5}O_6$ | $Hf/La_{3.5}Nd_{0.5}O_6$ | $Fe/La_{3.5}Nd_{0.5}O_6$ | $Cr/La_{3.5}Nd_{0.5}O_6$ |

TABLE 5-continued

| NW\Dop | Y | Sc | Al | Cu | Ga | Hf | Fe | Cr |
|---|---|---|---|---|---|---|---|---|
| La$_{3.8}$Nd$_{0.2}$O$_6$ | Y/La$_{3.8}$Nd$_{0.2}$O$_6$ | Sc/La$_{3.8}$Nd$_{0.2}$O$_6$ | Al/La$_{3.8}$Nd$_{0.2}$O$_6$ | Cu/La$_{3.8}$Nd$_{0.2}$O$_6$ | Ga/La$_{3.8}$Nd$_{0.2}$O$_6$ | Hf/La$_{3.8}$Nd$_{0.2}$O$_6$ | Fe/La$_{3.8}$Nd$_{0.2}$O$_6$ | Cr/La$_{3.8}$Nd$_{0.2}$O$_6$ |
| Y—La | Y/Y—La | Sc/Y—La | Al/Y—La | Cu/Y—La | Ga/Y—La | Hf/Y—La | Fe/Y—La | Cr/Y—La |
| Zr—La | Y/Zr—La | Sc/Zr—La | Al/Zr—La | Cu/Zr—La | Ga/Zr—La | Hf/Zr—La | Fe/Zr—La | Cr/Zr—La |
| Pr—La | Y/Pr—La | Sc/Pr—La | Al/Pr—La | Cu/Pr—La | Ga/Pr—La | Hf/Pr—La | Fe/Pr—La | Cr/Pr—La |
| Ce—La | Y/Ce—La | Sc/Ce—La | Al/Ce—La | Cu/Ce—La | Ga/Ce—La | Hf/Ce—La | Fe/Ce—La | Cr/Ce—La |

TABLE 6

NANOWIRES (NW) DOPED WITH SPECIFIC DOPANTS (DOP)

| NW\Dop | Ru | Zr | Ta | Rh |
|---|---|---|---|---|
| $Li_2O$ | $Ru/Li_2O$ | $Zr/Li_2O$ | $Ta/Li_2O$ | $Rh/Li_2O$ |
| $Na_2O$ | $Ru/Na_2O$ | $Zr/Na_2O$ | $Ta/Na_2O$ | $Rh/Na_2O$ |
| $K_2O$ | $Ru/K_2O$ | $Zr/K_2O$ | $Ta/K_2O$ | $Rh/K_2O$ |
| $Rb_2O$ | $Ru/Rb_2O$ | $Zr/Rb_2O$ | $Ta/Rb_2O$ | $Rh/Rb_2O$ |
| $Cs_2O$ | $Ru/Cs_2O$ | $Zr/Cs_2O$ | $Ta/Cs_2O$ | $Rh/Cs_2O$ |
| $BeO$ | $Ru/BeO$ | $Zr/BeO$ | $Ta/BeO$ | $Rh/BeO$ |
| $MgO$ | $Ru/MgO$ | $Zr/MgO$ | $Ta/MgO$ | $Rh/MgO$ |
| $CaO$ | $Ru/CaO$ | $Zr/CaO$ | $Ta/CaO$ | $Rh/CaO$ |
| $SrO$ | $Ru/SrO$ | $Zr/SrO$ | $Ta/SrO$ | $Rh/SrO$ |
| $BaO$ | $Ru/BaO$ | $Zr/BaO$ | $Ta/BaO$ | $Rh/BaO$ |
| $Sc_2O_3$ | $Ru/Sc_2O_3$ | $Zr/Sc_2O_3$ | $Ta/Sc_2O_3$ | $Rh/Sc_2O_3$ |
| $Y_2O_3$ | $Ru/Y_2O_3$ | $Zr/Y_2O_3$ | $Ta/Y_2O_3$ | $Rh/Y_2O_3$ |
| $La_2O_3$ | $Ru/La_2O_3$ | $Zr/La_2O_3$ | $Ta/La_2O_3$ | $Rh/La_2O_3$ |
| $CeO_2$ | $Ru/CeO_2$ | $Zr/CeO_2$ | $Ta/CeO_2$ | $Rh/CeO_2$ |
| $Ce_2O_3$ | $Ru/Ce_2O_3$ | $Zr/Ce_2O_3$ | $Ta/Ce_2O_3$ | $Rh/Ce_2O_3$ |
| $Pr_2O_3$ | $Ru/Pr_2O_3$ | $Zr/Pr_2O_3$ | $Ta/Pr_2O_3$ | $Rh/Pr_2O_3$ |
| $Nd_2O_3$ | $Ru/Nd_2O_3$ | $Zr/Nd_2O_3$ | $Ta/Nd_2O_3$ | $Rh/Nd_2O_3$ |
| $Sm_2O_3$ | $Ru/Sm_2O_3$ | $Zr/Sm_2O_3$ | $Ta/Sm_2O_3$ | $Rh/Sm_2O_3$ |
| $Eu_2O_3$ | $Ru/Eu_2O_3$ | $Zr/Eu_2O_3$ | $Ta/Eu_2O_3$ | $Rh/Eu_2O_3$ |
| $Gd_2O_3$ | $Ru/Gd_2O_3$ | $Zr/Gd_2O_3$ | $Ta/Gd_2O_3$ | $Rh/Gd_2O_3$ |
| $Tb_2O_3$ | $Ru/Tb_2O_3$ | $Zr/Tb_2O_3$ | $Ta/Tb_2O_3$ | $Rh/Tb_2O_3$ |
| $TbO_2$ | $Ru/TbO_2$ | $Zr/TbO_2$ | $Ta/TbO_2$ | $Rh/TbO_2$ |
| $Tb_6O_{11}$ | $Ru/Tb_6O_{11}$ | $Zr/Tb_6O_{11}$ | $Ta/Tb_6O_{11}$ | $Rh/Tb_6O_{11}$ |
| $Dy_2O_3$ | $Ru/Dy_2O_3$ | $Zr/Dy_2O_3$ | $Ta/Dy_2O_3$ | $Rh/Dy_2O_3$ |
| $Ho_2O_3$ | $Ru/Ho_2O_3$ | $Zr/Ho_2O_3$ | $Ta/Ho_2O_3$ | $Rh/Ho_2O_3$ |
| $Er_2O_3$ | $Ru/Er_2O_3$ | $Zr/Er_2O_3$ | $Ta/Er_2O_3$ | $Rh/Er_2O_3$ |
| $Tm_2O_3$ | $Ru/Tm_2O_3$ | $Zr/Tm_2O_3$ | $Ta/Tm_2O_3$ | $Rh/Tm_2O_3$ |
| $Yb_2O_3$ | $Ru/Yb_2O_3$ | $Zr/Yb_2O_3$ | $Ta/Yb_2O_3$ | $Rh/Yb_2O_3$ |
| $Lu_2O_3$ | $Ru/Lu_2O_3$ | $Zr/Lu_2O_3$ | $Ta/Lu_2O_3$ | $Rh/Lu_2O_3$ |
| $Ac_2O_3$ | $Ru/Ac_2O_3$ | $Zr/Ac_2O_3$ | $Ta/Ac_2O_3$ | $Rh/Ac_2O_3$ |
| $Th_2O_3$ | $Ru/Th_2O_3$ | $Zr/Th_2O_3$ | $Ta/Th_2O_3$ | $Rh/Th_2O_3$ |
| $ThO_2$ | $Ru/ThO_2$ | $Zr/ThO_2$ | $Ta/ThO_2$ | $Rh/ThO_2$ |
| $Pa_2O_3$ | $Ru/Pa_2O_3$ | $Zr/Pa_2O_3$ | $Ta/Pa_2O_3$ | $Rh/Pa_2O_3$ |
| $PaO_2$ | $Ru/PaO_2$ | $Zr/PaO_2$ | $Ta/PaO_2$ | $Rh/PaO_2$ |
| $TiO_2$ | $Ru/TiO_2$ | $Zr/TiO_2$ | $Ta/TiO_2$ | $Rh/TiO_2$ |
| $TiO$ | $Ru/TiO$ | $Zr/TiO$ | $Ta/TiO$ | $Rh/TiO$ |
| $Ti_2O_3$ | $Ru/Ti_2O_3$ | $Zr/Ti_2O_3$ | $Ta/Ti_2O_3$ | $Rh/Ti_2O_3$ |
| $Ti_3O$ | $Ru/Ti_3O$ | $Zr/Ti_3O$ | $Ta/Ti_3O$ | $Rh/Ti_3O$ |
| $Ti_2O$ | $Ru/Ti_2O$ | $Zr/Ti_2O$ | $Ta/Ti_2O$ | $Rh/Ti_2O$ |
| $Ti_3O_5$ | $Ru/Ti_3O_5$ | $Zr/Ti_3O_5$ | $Ta/Ti_3O_5$ | $Rh/Ti_3O_5$ |
| $Ti_4O_7$ | $Ru/Ti_4O_7$ | $Zr/Ti_4O_7$ | $Ta/Ti_4O_7$ | $Rh/Ti_4O_7$ |
| $ZrO_2$ | $Ru/ZrO_2$ | $Zr/ZrO_2$ | $Ta/ZrO_2$ | $Rh/ZrO_2$ |
| $HfO_2$ | $Ru/HfO_2$ | $Zr/HfO_2$ | $Ta/HfO_2$ | $Rh/HfO_2$ |
| $VO$ | $Ru/VO$ | $Zr/VO$ | $Ta/VO$ | $Rh/VO$ |
| $V_2O_3$ | $Ru/V_2O_3$ | $Zr/V_2O_3$ | $Ta/V_2O_3$ | $Rh/V_2O_3$ |
| $VO_2$ | $Ru/VO_2$ | $Zr/VO_2$ | $Ta/VO_2$ | $Rh/VO_2$ |
| $V_2O_5$ | $Ru/V_2O_5$ | $Zr/V_2O_5$ | $Ta/V_2O_5$ | $Rh/V_2O_5$ |
| $V_3O_7$ | $Ru/V_3O_7$ | $Zr/V_3O_7$ | $Ta/V_3O_7$ | $Rh/V_3O_7$ |
| $V_4O_9$ | $Ru/V_4O_9$ | $Zr/V_4O_9$ | $Ta/V_4O_9$ | $Rh/V_4O_9$ |
| $V_6O_{13}$ | $Ru/V_6O_{13}$ | $Zr/V_6O_{13}$ | $Ta/V_6O_{13}$ | $Rh/V_6O_{13}$ |
| $NbO$ | $Ru/NbO$ | $Zr/NbO$ | $Ta/NbO$ | $Rh/NbO$ |
| $NbO_2$ | $Ru/NbO_2$ | $Zr/NbO_2$ | $Ta/NbO_2$ | $Rh/NbO_2$ |
| $Nb_2O_5$ | $Ru/Nb_2O_5$ | $Zr/Nb_2O_5$ | $Ta/Nb_2O_5$ | $Rh/Nb_2O_5$ |
| $Nb_8O_{19}$ | $Ru/Nb_8O_{19}$ | $Zr/Nb_8O_{19}$ | $Ta/Nb_8O_{19}$ | $Rh/Nb_8O_{19}$ |
| $Nb_{16}O_{38}$ | $Ru/Nb_{16}O_{38}$ | $Zr/Nb_{16}O_{38}$ | $Ta/Nb_{16}O_{38}$ | $Rh/Nb_{16}O_{38}$ |
| $Nb_{12}O_{29}$ | $Ru/Nb_{12}O_{29}$ | $Zr/Nb_{12}O_{29}$ | $Ta/Nb_{12}O_{29}$ | $Rh/Nb_{12}O_{29}$ |
| $Nb_{47}O_{116}$ | $Ru/Nb_{47}O_{116}$ | $Zr/Nb_{47}O_{116}$ | $Ta/Nb_{47}O_{116}$ | $Rh/Nb_{47}O_{116}$ |
| $Ta_2O_5$ | $Ru/Ta_2O_5$ | $Zr/Ta_2O_5$ | $Ta/Ta_2O_5$ | $Rh/Ta_2O_5$ |
| $CrO$ | $Ru/CrO$ | $Zr/CrO$ | $Ta/CrO$ | $Rh/CrO$ |
| $Cr_2O_3$ | $Ru/Cr_2O_3$ | $Zr/Cr_2O_3$ | $Ta/Cr_2O_3$ | $Rh/Cr_2O_3$ |
| $CrO_2$ | $Ru/CrO_2$ | $Zr/CrO_2$ | $Ta/CrO_2$ | $Rh/CrO_2$ |
| $CrO_3$ | $Ru/CrO_3$ | $Zr/CrO_3$ | $Ta/CrO_3$ | $Rh/CrO_3$ |
| $Cr_8O_{21}$ | $Ru/Cr_8O_{21}$ | $Zr/Cr_8O_{21}$ | $Ta/Cr_8O_{21}$ | $Rh/Cr_8O_{21}$ |
| $MoO_2$ | $Ru/MoO_2$ | $Zr/MoO_2$ | $Ta/MoO_2$ | $Rh/MoO_2$ |
| $MoO_3$ | $Ru/MoO_3$ | $Zr/MoO_3$ | $Ta/MoO_3$ | $Rh/MoO_3$ |
| $W_2O_3$ | $Ru/W_2O_3$ | $Zr/W_2O_3$ | $Ta/W_2O_3$ | $Rh/W_2O_3$ |
| $WoO_2$ | $Ru/WoO_2$ | $Zr/WoO_2$ | $Ta/WoO_2$ | $Rh/WoO_2$ |
| $WoO_3$ | $Ru/WoO_3$ | $Zr/WoO_3$ | $Ta/WoO_3$ | $Rh/WoO_3$ |
| $MnO$ | $Ru/MnO$ | $Zr/MnO$ | $Ta/MnO$ | $Rh/MnO$ |
| $Mn/Mg/O$ | $Ru/Mn/Mg/O$ | $Zr/Mn/Mg/O$ | $Ta/Mn/Mg/O$ | $Rh/Mn/Mg/O$ |
| $Mn_3O_4$ | $Ru/Mn_3O_4$ | $Zr/Mn_3O_4$ | $Ta/Mn_3O_4$ | $Rh/Mn_3O_4$ |
| $Mn_2O_3$ | $Ru/Mn_2O_3$ | $Zr/Mn_2O_3$ | $Ta/Mn_2O_3$ | $Rh/Mn_2O_3$ |
| $MnO_2$ | $Ru/MnO_2$ | $Zr/MnO_2$ | $Ta/MnO_2$ | $Rh/MnO_2$ |
| $Mn_2O_7$ | $Ru/Mn_2O_7$ | $Zr/Mn_2O_7$ | $Ta/Mn_2O_7$ | $Rh/Mn_2O_7$ |
| $ReO_2$ | $Ru/ReO_2$ | $Zr/ReO_2$ | $Ta/ReO_2$ | $Rh/ReO_2$ |
| $ReO_3$ | $Ru/ReO_3$ | $Zr/ReO_3$ | $Ta/ReO_3$ | $Rh/ReO_3$ |

TABLE 6-continued

NANOWIRES (NW) DOPED WITH SPECIFIC DOPANTS (DOP)

| | | | | |
|---|---|---|---|---|
| $Re_2O_7$ | $Ru/Re_2O_7$ | $Zr/Re_2O_7$ | $Ta/Re_2O_7$ | $Rh/Re_2O_7$ |
| $Mg_3Mn_3$—$B_2O_{10}$ | $Ru/Mg_3Mn_3$—$B_2O_{10}$ | $Zr/Mg_3Mn_3$—$B_2O_{10}$ | $Ta/Mg_3Mn_3$—$B_2O_{10}$ | $Rh/Mg_3Mn_3$—$B_2O_{10}$ |
| $Mg_3(BO_3)_2$ | $Ru/Mg_3(BO_3)_2$ | $Zr/Mg_3(BO_3)_2$ | $Ta/Mg_3(BO_3)_2$ | $Rh/Mg_3(BO_3)_2$ |
| $NaWO_4$ | $Ru/NaWO_4$ | $Zr/NaWO_4$ | $Ta/NaWO_4$ | $Rh/NaWO_4$ |
| $Mg_6MnO_8$ | $Ru/Mg_6MnO_8$ | $Zr/Mg_6MnO_8$ | $Ta/Mg_6MnO_8$ | $Rh/Mg_6MnO_8$ |
| $Mn_2O_4$ | $Ru/Mn_2O_4$ | $Zr/Mn_2O_4$ | $Ta/Mn_2O_4$ | $Rh/Mn_2O_4$ |
| $(Li,Mg)_6$—$MnO_8$ | $Ru/(Li,Mg)_6$—$MnO_8$ | $Zr/(Li,Mg)_6$—$MnO_8$ | $Ta/(Li,Mg)_6$—$MnO_8$ | $Rh/(Li,Mg)_6$—$MnO_8$ |
| $Na_4P_2O_7$ | $Ru/Na_4P_2O_7$ | $Zr/Na_4P_2O_7$ | $Ta/Na_4P_2O_7$ | $Rh/Na_4P_2O_7$ |
| $Mo_2O_8$ | $Ru/Mo_2O_8$ | $Zr/Mo_2O_8$ | $Ta/Mo_2O_8$ | $Rh/Mo_2O_8$ |
| $Mn_3O_4/WO_4$ | $Ru/Mn_3O_4/WO_4$ | $Zr/Mn_3O_4/WO_4$ | $Ta/Mn_3O_4/WO_4$ | $Rh/Mn_3O_4/WO_4$ |
| $Na_2WO_4$ | $Ru/Na_2WO_4$ | $Zr/Na_2WO_4$ | $Ta/Na_2WO_4$ | $Rh/Na_2WO_4$ |
| $Zr_2Mo_2O_8$ | $Ru/Zr_2Mo_2O_8$ | $Zr/Zr_2Mo_2O_8$ | $Ta/Zr_2Mo_2O_8$ | $Rh/Zr_2Mo_2O_8$ |
| $NaMnO_4$—/MgO | $Ru/NaMnO_4$—/MgO | $Zr/NaMnO_4$—/MgO | $Ta/NaMnO_4$—/MgO | $Rh/NaMnO_4$—/MgO |
| $Na_{10}Mn$—$W_5O_{17}$ | $Ru/Na_{10}Mn$—$W_5O_{17}$ | $Zr/Na_{10}Mn$—$W_5O_{17}$ | $Ta/Na_{10}Mn$—$W_5O_{17}$ | $Rh/Na_{10}Mn$—$W_5O_{17}$ |
| $La_3NdO_6$ | $Ru/La_3NdO_6$ | $Zr/La_3NdO_6$ | $Ta/La_3NdO_6$ | $Rh/La_3NdO_6$ |
| $LaNd_3O_6$ | $Ru/LaNd_3O_6$ | $Zr/LaNd_3O_6$ | $Ta/LaNd_3O_6$ | $Rh/LaNd_3O_6$ |
| $La_{1.5}Nd_{2.5}O_6$ | $Ru/La_{1.5}Nd_{2.5}O_6$ | $Zr/La_{1.5}Nd_{2.5}O_6$ | $Ta/La_{1.5}Nd_{2.5}O_6$ | $Rh/La_{1.5}Nd_{2.5}O_6$ |
| $La_{2.5}Nd_{1.5}O_6$ | $Ru/La_{2.5}Nd_{1.5}O_6$ | $Zr/La_{2.5}Nd_{1.5}O_6$ | $Ta/La_{2.5}Nd_{1.5}O_6$ | $Rh/La_{2.5}Nd_{1.5}O_6$ |
| $La_{3.2}Nd_{0.8}O_6$ | $Ru/La_{3.2}Nd_{0.8}O_6$ | $Zr/La_{3.2}Nd_{0.8}O_6$ | $Ta/La_{3.2}Nd_{0.8}O_6$ | $Rh/La_{3.2}Nd_{0.8}O_6$ |
| $La_{3.5}Nd_{0.5}O_6$ | $Ru/La_{3.5}Nd_{0.5}O_6$ | $Zr/La_{3.5}Nd_{0.5}O_6$ | $Ta/La_{3.5}Nd_{0.5}O_6$ | $Rh/La_{3.5}Nd_{0.5}O_6$ |
| $La_{3.8}Nd_{0.2}O_6$ | $Ru/La_{3.8}Nd_{0.2}O_6$ | $Zr/La_{3.8}Nd_{0.2}O_6$ | $Ta/La_{3.8}Nd_{0.2}O_6$ | $Rh/La_{3.8}Nd_{0.2}O_6$ |
| Y—La | Ru/Y—La | Zr/Y—La | Ta/Y—La | Rh/Y—La |
| Zr—La | Ru/Zr—La | Zr/Zr—La | Ta/Zr—La | Rh/Zr—La |
| Pr—La | Ru/Pr—La | Zr/Pr—La | Ta/Pr—La | Rh/Pr—La |
| Ce—La | Ru/Ce—La | Zr/Ce—La | Ta/Ce—La | Rh/Ce—La |

| NW\Dop | Au | Mo | Ni |
|---|---|---|---|
| $Li_2O$ | $Au/Li_2O$ | $Mo/Li_2O$ | $Ni/Li_2O$ |
| $Na_2O$ | $Au/Na_2O$ | $Mo/Na_2O$ | $Ni/Na_2O$ |
| $K_2O$ | $Au/K_2O$ | $Mo/K_2O$ | $Ni/K_2O$ |
| $Rb_2O$ | $Au/Rb_2O$ | $Mo/Rb_2O$ | $Ni/Rb_2O$ |
| $Cs_2O$ | $Au/Cs_2O$ | $Mo/Cs_2O$ | $Ni/Cs_2O$ |
| $BeO$ | $Au/BeO$ | $Mo/BeO$ | $Ni/BeO$ |
| $MgO$ | $Au/MgO$ | $Mo/MgO$ | $Ni/MgO$ |
| $CaO$ | $Au/CaO$ | $Mo/CaO$ | $Ni/CaO$ |
| $SrO$ | $Au/SrO$ | $Mo/SrO$ | $Ni/SrO$ |
| $BaO$ | $Au/BaO$ | $Mo/BaO$ | $Ni/BaO$ |
| $Sc_2O_3$ | $Au/Sc_2O_3$ | $Mo/Sc_2O_3$ | $Ni/Sc_2O_3$ |
| $Y_2O_3$ | $Au/Y_2O_3$ | $Mo/Y_2O_3$ | $Ni/Y_2O_3$ |
| $La_2O_3$ | $Au/La_2O_3$ | $Mo/La_2O_3$ | $Ni/La_2O_3$ |
| $CeO_2$ | $Au/CeO_2$ | $Mo/CeO_2$ | $Ni/CeO_2$ |
| $Ce_2O_3$ | $Au/Ce_2O_3$ | $Mo/Ce_2O_3$ | $Ni/Ce_2O_3$ |
| $Pr_2O_3$ | $Au/Pr_2O_3$ | $Mo/Pr_2O_3$ | $Ni/Pr_2O_3$ |
| $Nd_2O_3$ | $Au/Nd_2O_3$ | $Mo/Nd_2O_3$ | $Ni/Nd_2O_3$ |
| $Sm_2O_3$ | $Au/Sm_2O_3$ | $Mo/Sm_2O_3$ | $Ni/Sm_2O_3$ |
| $Eu_2O_3$ | $Au/Eu_2O_3$ | $Mo/Eu_2O_3$ | $Ni/Eu_2O_3$ |
| $Gd_2O_3$ | $Au/Gd_2O_3$ | $Mo/Gd_2O_3$ | $Ni/Gd_2O_3$ |
| $Tb_2O_3$ | $Au/Tb_2O_3$ | $Mo/Tb_2O_3$ | $Ni/Tb_2O_3$ |
| $TbO_2$ | $Au/TbO_2$ | $Mo/TbO_2$ | $Ni/TbO_2$ |
| $Tb_6O_{11}$ | $Au/Tb_6O_{11}$ | $Mo/Tb_6O_{11}$ | $Ni/Tb_6O_{11}$ |
| $Dy_2O_3$ | $Au/Dy_2O_3$ | $Mo/Dy_2O_3$ | $Ni/Dy_2O_3$ |
| $Ho_2O_3$ | $Au/Ho_2O_3$ | $Mo/Ho_2O_3$ | $Ni/Ho_2O_3$ |
| $Er_2O_3$ | $Au/Er_2O_3$ | $Mo/Er_2O_3$ | $Ni/Er_2O_3$ |
| $Tm_2O_3$ | $Au/Tm_2O_3$ | $Mo/Tm_2O_3$ | $Ni/Tm_2O_3$ |
| $Yb_2O_3$ | $Au/Yb_2O_3$ | $Mo/Yb_2O_3$ | $Ni/Yb_2O_3$ |
| $Lu_2O_3$ | $Au/Lu_2O_3$ | $Mo/Lu_2O_3$ | $Ni/Lu_2O_3$ |
| $Ac_2O_3$ | $Au/Ac_2O_3$ | $Mo/Ac_2O_3$ | $Ni/Ac_2O_3$ |
| $Th_2O_3$ | $Au/Th_2O_3$ | $Mo/Th_2O_3$ | $Ni/Th_2O_3$ |
| $ThO_2$ | $Au/ThO_2$ | $Mo/ThO_2$ | $Ni/ThO_2$ |
| $Pa_2O_3$ | $Au/Pa_2O_3$ | $Mo/Pa_2O_3$ | $Ni/Pa_2O_3$ |
| $PaO_2$ | $Au/PaO_2$ | $Mo/PaO_2$ | $Ni/PaO_2$ |
| $TiO_2$ | $Au/TiO_2$ | $Mo/TiO_2$ | $Ni/TiO_2$ |
| $TiO$ | $Au/TiO$ | $Mo/TiO$ | $Ni/TiO$ |
| $Ti_2O_3$ | $Au/Ti_2O_3$ | $Mo/Ti_2O_3$ | $Ni/Ti_2O_3$ |
| $Ti_3O$ | $Au/Ti_3O$ | $Mo/Ti_3O$ | $Ni/Ti_3O$ |
| $Ti_2O$ | $Au/Ti_2O$ | $Mo/Ti_2O$ | $Ni/Ti_2O$ |
| $Ti_3O_5$ | $Au/Ti_3O_5$ | $Mo/Ti_3O_5$ | $Ni/Ti_3O_5$ |
| $Ti_4O_7$ | $Au/Ti_4O_7$ | $Mo/Ti_4O_7$ | $Ni/Ti_4O_7$ |
| $ZrO_2$ | $Au/ZrO_2$ | $Mo/ZrO_2$ | $Ni/ZrO_2$ |
| $HfO_2$ | $Au/HfO_2$ | $Mo/HfO_2$ | $Ni/HfO_2$ |
| $VO$ | $Au/VO$ | $Mo/VO$ | $Ni/VO$ |
| $V_2O_3$ | $Au/V_2O_3$ | $Mo/V_2O_3$ | $Ni/V_2O_3$ |
| $VO_2$ | $Au/VO_2$ | $Mo/VO_2$ | $Ni/VO_2$ |
| $V_2O_5$ | $Au/V_2O_5$ | $Mo/V_2O_5$ | $Ni/V_2O_5$ |
| $V_3O_7$ | $Au/V_3O_7$ | $Mo/V_3O_7$ | $Ni/V_3O_7$ |
| $V_4O_9$ | $Au/V_4O_9$ | $Mo/V_4O_9$ | $Ni/V_4O_9$ |
| $V_6O_{13}$ | $Au/V_6O_{13}$ | $Mo/V_6O_{13}$ | $Ni/V_6O_{13}$ |

TABLE 6-continued

NANOWIRES (NW) DOPED WITH SPECIFIC DOPANTS (DOP)

| | | | |
|---|---|---|---|
| NbO | Au/NbO | Mo/NbO | Ni/NbO |
| $NbO_2$ | $Au/NbO_2$ | $Mo/NbO_2$ | $Ni/NbO_2$ |
| $Nb_2O_5$ | $Au/Nb_2O_5$ | $Mo/Nb_2O_5$ | $Ni/Nb_2O_5$ |
| $Nb_8O_{19}$ | $Au/Nb_8O_{19}$ | $Mo/Nb_8O_{19}$ | $Ni/Nb_8O_{19}$ |
| $Nb_{16}O_{38}$ | $Au/Nb_{16}O_{38}$ | $Mo/Nb_{16}O_{38}$ | $Ni/Nb_{16}O_{38}$ |
| $Nb_{12}O_{29}$ | $Au/Nb_{12}O_{29}$ | $Mo/Nb_{12}O_{29}$ | $Ni/Nb_{12}O_{29}$ |
| $Nb_{47}O_{116}$ | $Au/Nb_{47}O_{116}$ | $Mo/Nb_{47}O_{116}$ | $Ni/Nb_{47}O_{116}$ |
| $Ta_2O_5$ | $Au/Ta_2O_5$ | $Mo/Ta_2O_5$ | $Ni/Ta_2O_5$ |
| CrO | Au/CrO | Mo/CrO | Ni/CrO |
| $Cr_2O_3$ | $Au/Cr_2O_3$ | $Mo/Cr_2O_3$ | $Ni/Cr_2O_3$ |
| $CrO_2$ | $Au/CrO_2$ | $Mo/CrO_2$ | $Ni/CrO_2$ |
| $CrO_3$ | $Au/CrO_3$ | $Mo/CrO_3$ | $Ni/CrO_3$ |
| $Cr_8O_{21}$ | $Au/Cr_8O_{21}$ | $Mo/Cr_8O_{21}$ | $Ni/Cr_8O_{21}$ |
| $MoO_2$ | $Au/MoO_2$ | $Mo/MoO_2$ | $Ni/MoO_2$ |
| $MoO_3$ | $Au/MoO_3$ | $Mo/MoO_3$ | $Ni/MoO_3$ |
| $W_2O_3$ | $Au/W_2O_3$ | $Mo/W_2O_3$ | $Ni/W_2O_3$ |
| $WoO_2$ | $Au/WoO_2$ | $Mo/WoO_2$ | $Ni/WoO_2$ |
| $WoO_3$ | $Au/WoO_3$ | $Mo/WoO_3$ | $Ni/WoO_3$ |
| MnO | Au/MnO | Mo/MnO | Ni/MnO |
| Mn/Mg/O | Au/Mn/Mg/O | Mo/Mn/Mg/O | Ni/Mn/Mg/O |
| $Mn_3O_4$ | $Au/Mn_3O_4$ | $Mo/Mn_3O_4$ | $Ni/Mn_3O_4$ |
| $Mn_2O_3$ | $Au/Mn_2O_3$ | $Mo/Mn_2O_3$ | $Ni/Mn_2O_3$ |
| $MnO_2$ | $Au/MnO_2$ | $Mo/MnO_2$ | $Ni/MnO_2$ |
| $Mn_2O_7$ | $Au/Mn_2O_7$ | $Mo/Mn_2O_7$ | $Ni/Mn_2O_7$ |
| $ReO_2$ | $Au/ReO_2$ | $Mo/ReO_2$ | $Ni/ReO_2$ |
| $ReO_3$ | $Au/ReO_3$ | $Mo/ReO_3$ | $Ni/ReO_3$ |
| $Re_2O_7$ | $Au/Re_2O_7$ | $Mo/Re_2O_7$ | $Ni/Re_2O_7$ |
| $Mg_3Mn_3-B_2O_{10}$ | $Au/Mg_3Mn_3-B_2O_{10}$ | $Mo/Mg_3Mn_3-B_2O_{10}$ | $Ni/Mg_3Mn_3-B_2O_{10}$ |
| $Mg_3(BO_3)_2$ | $Au/Mg_3(BO_3)_2$ | $Mo/Mg_3(BO_3)_2$ | $Ni/Mg_3(BO_3)_2$ |
| $NaWO_4$ | $Au/NaWO_4$ | $Mo/NaWO_4$ | $Ni/NaWO_4$ |
| $Mg_6MnO_8$ | $Au/Mg_6MnO_8$ | $Mo/Mg_6MnO_8$ | $Ni/Mg_6MnO_8$ |
| $Mn_2O_4$ | $Au/Mn_2O_4$ | $Mo/Mn_2O_4$ | $Ni/Mn_2O_4$ |
| $(Li,Mg)_6-MnO_8$ | $Au/(Li,Mg)_6-MnO_8$ | $Mo/(Li,Mg)_6-MnO_8$ | $Ni/(Li,Mg)_6-MnO_8$ |
| $Na_4P_2O_7$ | $Au/Na_4P_2O_7$ | $Mo/Na_4P_2O_7$ | $Ni/Na_4P_2O_7$ |
| $Mo_2O_8$ | $Au/Mo_2O_8$ | $Mo/Mo_2O_8$ | $Ni/Mo_2O_8$ |
| $Mn_3O_4/WO_4$ | $Au/Mn_3O_4/WO_4$ | $Mo/Mn_3O_4/WO_4$ | $Ni/Mn_3O_4/WO_4$ |
| $Na_2WO_4$ | $Au/Na_2WO_4$ | $Mo/Na_2WO_4$ | $Ni/Na_2WO_4$ |
| $Zr_2Mo_2O_8$ | $Au/Zr_2Mo_2O_8$ | $Mo/Zr_2Mo_2O_8$ | $Ni/Zr_2Mo_2O_8$ |
| $NaMnO_4-/MgO$ | $Au/NaMnO_4-/MgO$ | $Mo/NaMnO_4-/MgO$ | $Ni/NaMnO_4-/MgO$ |
| $Na_{10}Mn-W_5O_{17}$ | $Au/Na_{10}Mn-W_5O_{17}$ | $Mo/Na_{10}Mn-W_5O_{17}$ | $Ni/Na_{10}Mn-W_5O_{17}$ |
| $La_3NdO_6$ | $Au/La_3NdO_6$ | $Mo/La_3NdO_6$ | $Ni/La_3NdO_6$ |
| $LaNd_3O_6$ | $Au/LaNd_3O_6$ | $Mo/LaNd_3O_6$ | $Ni/LaNd_3O_6$ |
| $La_{1.5}Nd_{2.5}O_6$ | $Au/La_{1.5}Nd_{2.5}O_6$ | $Mo/La_{1.5}Nd_{2.5}O_6$ | $Ni/La_{1.5}Nd_{2.5}O_6$ |
| $La_{2.5}Nd_{1.5}O_6$ | $Au/La_{2.5}Nd_{1.5}O_6$ | $Mo/La_{2.5}Nd_{1.5}O_6$ | $Ni/La_{2.5}Nd_{1.5}O_6$ |
| $La_{3.2}Nd_{0.8}O_6$ | $Au/La_{3.2}Nd_{0.8}O_6$ | $Mo/La_{3.2}Nd_{0.8}O_6$ | $Ni/La_{3.2}Nd_{0.8}O_6$ |
| $La_{3.5}Nd_{0.5}O_6$ | $Au/La_{3.5}Nd_{0.5}O_6$ | $Mo/La_{3.5}Nd_{0.5}O_6$ | $Ni/La_{3.5}Nd_{0.5}O_6$ |
| $La_{3.8}Nd_{0.2}O_6$ | $Au/La_{3.8}Nd_{0.2}O_6$ | $Mo/La_{3.8}Nd_{0.2}O_6$ | $Ni/La_{3.8}Nd_{0.2}O_6$ |
| Y—La | Au/Y—La | Mo/Y—La | Ni/Y—La |
| Zr—La | Au/Zr—La | Mo/Zr—La | Ni/Zr—La |
| Pr—La | Au/Pr—La | Mo/Pr—La | Ni/Pr—La |
| Ce—La | Au/Ce—La | Mo/Ce—La | Ni/Ce—La |

TABLE 7

NANOWIRES (NW) DOPED WITH SPECIFIC DOPANTS (DOP)

| NW\Dop | Co | Sb | W | V | Ag | Te | Pd | Ir |
|---|---|---|---|---|---|---|---|---|
| $Li_2O$ | $Co/Li_2O$ | $Sb/Li_2O$ | $W/Li_2O$ | $V/Li_2O$ | $Ag/Li_2O$ | $Te/Li_2O$ | $Pd/Li_2O$ | $Ir/Li_2O$ |
| $Na_2O$ | $Co/Na_2O$ | $Sb/Na_2O$ | $W/Na_2O$ | $V/Na_2O$ | $Ag/Na_2O$ | $Te/Na_2O$ | $Pd/Na_2O$ | $Ir/Na_2O$ |
| $K_2O$ | $Co/K_2O$ | $Sb/K_2O$ | $W/K_2O$ | $V/K_2O$ | $Ag/K_2O$ | $Te/K_2O$ | $Pd/K_2O$ | $Ir/K_2O$ |
| $Rb_2O$ | $Co/Rb_2O$ | $Sb/Rb_2O$ | $W/Rb_2O$ | $V/Rb_2O$ | $Ag/Rb_2O$ | $Te/Rb_2O$ | $Pd/Rb_2O$ | $Ir/Rb_2O$ |
| $Cs_2O$ | $Co/Cs_2O$ | $Sb/Cs_2O$ | $W/Cs_2O$ | $V/Cs_2O$ | $Ag/Cs_2O$ | $Te/Cs_2O$ | $Pd/Cs_2O$ | $Ir/Cs_2O$ |
| $BeO$ | $Co/BeO$ | $Sb/BeO$ | $W/BeO$ | $V/BeO$ | $Ag/BeO$ | $Te/BeO$ | $Pd/BeO$ | $Ir/BeO$ |
| $MgO$ | $Co/MgO$ | $Sb/MgO$ | $W/MgO$ | $V/MgO$ | $Ag/MgO$ | $Te/MgO$ | $Pd/MgO$ | $Ir/MgO$ |
| $CaO$ | $Co/CaO$ | $Sb/CaO$ | $W/CaO$ | $V/CaO$ | $Ag/CaO$ | $Te/CaO$ | $Pd/CaO$ | $Ir/CaO$ |
| $SrO$ | $Co/SrO$ | $Sb/SrO$ | $W/SrO$ | $V/SrO$ | $Ag/SrO$ | $Te/SrO$ | $Pd/SrO$ | $Ir/SrO$ |
| $BaO$ | $Co/BaO$ | $Sb/BaO$ | $W/BaO$ | $V/BaO$ | $Ag/BaO$ | $Te/BaO$ | $Pd/BaO$ | $Ir/BaO$ |
| $Sc_2O_3$ | $Co/Sc_2O_3$ | $Sb/Sc_2O_3$ | $W/Sc_2O_3$ | $V/Sc_2O_3$ | $Ag/Sc_2O_3$ | $Te/Sc_2O_3$ | $Pd/Sc_2O_3$ | $Ir/Sc_2O_3$ |
| $Y_2O_3$ | $Co/Y_2O_3$ | $Sb/Y_2O_3$ | $W/Y_2O_3$ | $V/Y_2O_3$ | $Ag/Y_2O_3$ | $Te/Y_2O_3$ | $Pd/Y_2O_3$ | $Ir/Y_2O_3$ |
| $La_2O_3$ | $Co/La_2O_3$ | $Sb/La_2O_3$ | $W/La_2O_3$ | $V/La_2O_3$ | $Ag/La_2O_3$ | $Te/La_2O_3$ | $Pd/La_2O_3$ | $Ir/La_2O_3$ |
| $CeO_2$ | $Co/CeO_2$ | $Sb/CeO_2$ | $W/CeO_2$ | $V/CeO_2$ | $Ag/CeO_2$ | $Te/CeO_2$ | $Pd/CeO_2$ | $Ir/CeO_2$ |
| $Ce_2O_3$ | $Co/Ce_2O_3$ | $Sb/Ce_2O_3$ | $W/Ce_2O_3$ | $V/Ce_2O_3$ | $Ag/Ce_2O_3$ | $Te/Ce_2O_3$ | $Pd/Ce_2O_3$ | $Ir/Ce_2O_3$ |
| $Pr_2O_3$ | $Co/Pr_2O_3$ | $Sb/Pr_2O_3$ | $W/Pr_2O_3$ | $V/Pr_2O_3$ | $Ag/Pr_2O_3$ | $Te/Pr_2O_3$ | $Pd/Pr_2O_3$ | $Ir/Pr_2O_3$ |
| $Nd_2O_3$ | $Co/Nd_2O_3$ | $Sb/Nd_2O_3$ | $W/Nd_2O_3$ | $V/Nd_2O_3$ | $Ag/Nd_2O_3$ | $Te/Nd_2O_3$ | $Pd/Nd_2O_3$ | $Ir/Nd_2O_3$ |
| $Sm_2O_3$ | $Co/Sm_2O_3$ | $Sb/Sm_2O_3$ | $W/Sm_2O_3$ | $V/Sm_2O_3$ | $Ag/Sm_2O_3$ | $Te/Sm_2O_3$ | $Pd/Sm_2O_3$ | $Ir/Sm_2O_3$ |
| $Eu_2O_3$ | $Co/Eu_2O_3$ | $Sb/Eu_2O_3$ | $W/Eu_2O_3$ | $V/Eu_2O_3$ | $Ag/Eu_2O_3$ | $Te/Eu_2O_3$ | $Pd/Eu_2O_3$ | $Ir/Eu_2O_3$ |
| $Gd_2O_3$ | $Co/Gd_2O_3$ | $Sb/Gd_2O_3$ | $W/Gd_2O_3$ | $V/Gd_2O_3$ | $Ag/Gd_2O_3$ | $Te/Gd_2O_3$ | $Pd/Gd_2O_3$ | $Ir/Gd_2O_3$ |
| $Tb_2O_3$ | $Co/Tb_2O_3$ | $Sb/Tb_2O_3$ | $W/Tb_2O_3$ | $V/Tb_2O_3$ | $Ag/Tb_2O_3$ | $Te/Tb_2O_3$ | $Pd/Tb_2O_3$ | $Ir/Tb_2O_3$ |
| $TbO_2$ | $Co/TbO_2$ | $Sb/TbO_2$ | $W/TbO_2$ | $V/TbO_2$ | $Ag/TbO_2$ | $Te/TbO_2$ | $Pd/TbO_2$ | $Ir/TbO_2$ |
| $Tb_6O_{11}$ | $Co/Tb_6O_{11}$ | $Sb/Tb_6O_{11}$ | $W/Tb_6O_{11}$ | $V/Tb_6O_{11}$ | $Ag/Tb_6O_{11}$ | $Te/Tb_6O_{11}$ | $Pd/Tb_6O_{11}$ | $Ir/Tb_6O_{11}$ |
| $Dy_2O_3$ | $Co/Dy_2O_3$ | $Sb/Dy_2O_3$ | $W/Dy_2O_3$ | $V/Dy_2O_3$ | $Ag/Dy_2O_3$ | $Te/Dy_2O_3$ | $Pd/Dy_2O_3$ | $Ir/Dy_2O_3$ |
| $Ho_2O_3$ | $Co/Ho_2O_3$ | $Sb/Ho_2O_3$ | $W/Ho_2O_3$ | $V/Ho_2O_3$ | $Ag/Ho_2O_3$ | $Te/Ho_2O_3$ | $Pd/Ho_2O_3$ | $Ir/Ho_2O_3$ |
| $Er_2O_3$ | $Co/Er_2O_3$ | $Sb/Er_2O_3$ | $W/Er_2O_3$ | $V/Er_2O_3$ | $Ag/Er_2O_3$ | $Te/Er_2O_3$ | $Pd/Er_2O_3$ | $Ir/Er_2O_3$ |
| $Tm_2O_3$ | $Co/Tm_2O_3$ | $Sb/Tm_2O_3$ | $W/Tm_2O_3$ | $V/Tm_2O_3$ | $Ag/Tm_2O_3$ | $Te/Tm_2O_3$ | $Pd/Tm_2O_3$ | $Ir/Tm_2O_3$ |
| $Yb_2O_3$ | $Co/Yb_2O_3$ | $Sb/Yb_2O_3$ | $W/Yb_2O_3$ | $V/Yb_2O_3$ | $Ag/Yb_2O_3$ | $Te/Yb_2O_3$ | $Pd/Yb_2O_3$ | $Ir/Yb_2O_3$ |
| $Lu_2O_3$ | $Co/Lu_2O_3$ | $Sb/Lu_2O_3$ | $W/Lu_2O_3$ | $V/Lu_2O_3$ | $Ag/Lu_2O_3$ | $Te/Lu_2O_3$ | $Pd/Lu_2O_3$ | $Ir/Lu_2O_3$ |
| $Ac_2O_3$ | $Co/Ac_2O_3$ | $Sb/Ac_2O_3$ | $W/Ac_2O_3$ | $V/Ac_2O_3$ | $Ag/Ac_2O_3$ | $Te/Ac_2O_3$ | $Pd/Ac_2O_3$ | $Ir/Ac_2O_3$ |
| $Th_2O_3$ | $Co/Th_2O_3$ | $Sb/Th_2O_3$ | $W/Th_2O_3$ | $V/Th_2O_3$ | $Ag/Th_2O_3$ | $Te/Th_2O_3$ | $Pd/Th_2O_3$ | $Ir/Th_2O_3$ |
| $ThO_2$ | $Co/ThO_2$ | $Sb/ThO_2$ | $W/ThO_2$ | $V/ThO_2$ | $Ag/ThO_2$ | $Te/ThO_2$ | $Pd/ThO_2$ | $Ir/ThO_2$ |
| $Pa_2O_3$ | $Co/Pa_2O_3$ | $Sb/Pa_2O_3$ | $W/Pa_2O_3$ | $V/Pa_2O_3$ | $Ag/Pa_2O_3$ | $Te/Pa_2O_3$ | $Pd/Pa_2O_3$ | $Ir/Pa_2O_3$ |
| $PaO_2$ | $Co/PaO_2$ | $Sb/PaO_2$ | $W/PaO_2$ | $V/PaO_2$ | $Ag/PaO_2$ | $Te/PaO_2$ | $Pd/PaO_2$ | $Ir/PaO_2$ |
| $TiO_2$ | $Co/TiO_2$ | $Sb/TiO_2$ | $W/TiO_2$ | $V/TiO_2$ | $Ag/TiO_2$ | $Te/TiO_2$ | $Pd/TiO_2$ | $Ir/TiO_2$ |
| $TiO$ | $Co/TiO$ | $Sb/TiO$ | $W/TiO$ | $V/TiO$ | $Ag/TiO$ | $Te/TiO$ | $Pd/TiO$ | $Ir/TiO$ |
| $Ti_2O_3$ | $Co/Ti_2O_3$ | $Sb/Ti_2O_3$ | $W/Ti_2O_3$ | $V/Ti_2O_3$ | $Ag/Ti_2O_3$ | $Te/Ti_2O_3$ | $Pd/Ti_2O_3$ | $Ir/Ti_2O_3$ |
| $Ti_3O$ | $Co/Ti_3O$ | $Sb/Ti_3O$ | $W/Ti_3O$ | $V/Ti_3O$ | $Ag/Ti_3O$ | $Te/Ti_3O$ | $Pd/Ti_3O$ | $Ir/Ti_3O$ |
| $Ti_2O$ | $Co/Ti_2O$ | $Sb/Ti_2O$ | $W/Ti_2O$ | $V/Ti_2O$ | $Ag/Ti_2O$ | $Te/Ti_2O$ | $Pd/Ti_2O$ | $Ir/Ti_2O$ |
| $Ti_3O_5$ | $Co/Ti_3O_5$ | $Sb/Ti_3O_5$ | $W/Ti_3O_5$ | $V/Ti_3O_5$ | $Ag/Ti_3O_5$ | $Te/Ti_3O_5$ | $Pd/Ti_3O_5$ | $Ir/Ti_3O_5$ |
| $Ti_4O_7$ | $Co/Ti_4O_7$ | $Sb/Ti_4O_7$ | $W/Ti_4O_7$ | $V/Ti_4O_7$ | $Ag/Ti_4O_7$ | $Te/Ti_4O_7$ | $Pd/Ti_4O_7$ | $Ir/Ti_4O_7$ |
| $ZrO_2$ | $Co/ZrO_2$ | $Sb/ZrO_2$ | $W/ZrO_2$ | $V/ZrO_2$ | $Ag/ZrO_2$ | $Te/ZrO_2$ | $Pd/ZrO_2$ | $Ir/ZrO_2$ |
| $HfO_2$ | $Co/HfO_2$ | $Sb/HfO_2$ | $W/HfO_2$ | $V/HfO_2$ | $Ag/HfO_2$ | $Te/HfO_2$ | $Pd/HfO_2$ | $Ir/HfO_2$ |
| $VO$ | $Co/VO$ | $Sb/VO$ | $W/VO$ | $V/VO$ | $Ag/VO$ | $Te/VO$ | $Pd/VO$ | $Ir/VO$ |
| $V_2O_3$ | $Co/V_2O_3$ | $Sb/V_2O_3$ | $W/V_2O_3$ | $V/V_2O_3$ | $Ag/V_2O_3$ | $Te/V_2O_3$ | $Pd/V_2O_3$ | $Ir/V_2O_3$ |
| $VO_2$ | $Co/VO_2$ | $Sb/VO_2$ | $W/VO_2$ | $V/VO_2$ | $Ag/VO_2$ | $Te/VO_2$ | $Pd/VO_2$ | $Ir/VO_2$ |
| $V_2O_5$ | $Co/V_2O_5$ | $Sb/V_2O_5$ | $W/V_2O_5$ | $V/V_2O_5$ | $Ag/V_2O_5$ | $Te/V_2O_5$ | $Pd/V_2O_5$ | $Ir/V_2O_5$ |

TABLE 7-continued

NANOWIRES (NW) DOPED WITH SPECIFIC DOPANTS (DOP)

| NW\Dop | Co | Sb | W | V | Ag | Te | Pd | Ir |
|---|---|---|---|---|---|---|---|---|
| $V_3O_7$ | $Co/V_3O_7$ | $Sb/V_3O_7$ | $W/V_3O_7$ | $V/V_3O_7$ | $Ag/V_3O_7$ | $Te/V_3O_7$ | $Pd/V_3O_7$ | $Ir/V_3O_7$ |
| $V_4O_9$ | $Co/V_4O_9$ | $Sb/V_4O_9$ | $W/V_4O_9$ | $V/V_4O_9$ | $Ag/V_4O_9$ | $Te/V_4O_9$ | $Pd/V_4O_9$ | $Ir/V_4O_9$ |
| $V_6O_{13}$ | $Co/V_6O_{13}$ | $Sb/V_6O_{13}$ | $W/V_6O_{13}$ | $V/V_6O_{13}$ | $Ag/V_6O_{13}$ | $Te/V_6O_{13}$ | $Pd/V_6O_{13}$ | $Ir/V_6O_{13}$ |
| $NbO$ | $Co/NbO$ | $Sb/NbO$ | $W/NbO$ | $V/NbO$ | $Ag/NbO$ | $Te/NbO$ | $Pd/NbO$ | $Ir/NbO$ |
| $NbO_2$ | $Co/NbO_2$ | $Sb/NbO_2$ | $W/NbO_2$ | $V/NbO_2$ | $Ag/NbO_2$ | $Te/NbO_2$ | $Pd/NbO_2$ | $Ir/NbO_2$ |
| $Nb_2O_5$ | $Co/Nb_2O_5$ | $Sb/Nb_2O_5$ | $W/Nb_2O_5$ | $V/Nb_2O_5$ | $Ag/Nb_2O_5$ | $Te/Nb_2O_5$ | $Pd/Nb_2O_5$ | $Ir/Nb_2O_5$ |
| $Nb_8O_{19}$ | $Co/Nb_8O_{19}$ | $Sb/Nb_8O_{19}$ | $W/Nb_8O_{19}$ | $V/Nb_8O_{19}$ | $Ag/Nb_8O_{19}$ | $Te/Nb_8O_{19}$ | $Pd/Nb_8O_{19}$ | $Ir/Nb_8O_{19}$ |
| $Nb_{16}O_{38}$ | $Co/Nb_{16}O_{38}$ | $Sb/Nb_{16}O_{38}$ | $W/Nb_{16}O_{38}$ | $V/Nb_{16}O_{38}$ | $Ag/Nb_{16}O_{38}$ | $Te/Nb_{16}O_{38}$ | $Pd/Nb_{16}O_{38}$ | $Ir/Nb_{16}O_{38}$ |
| $Nb_{12}O_{29}$ | $Co/Nb_{12}O_{29}$ | $Sb/Nb_{12}O_{29}$ | $W/Nb_{12}O_{29}$ | $V/Nb_{12}O_{29}$ | $Ag/Nb_{12}O_{29}$ | $Te/Nb_{12}O_{29}$ | $Pd/Nb_{12}O_{29}$ | $Ir/Nb_{12}O_{29}$ |
| $Nb_{47}O_{116}$ | $Co/Nb_{47}O_{116}$ | $Sb/Nb_{47}O_{116}$ | $W/Nb_{47}O_{116}$ | $V/Nb_{47}O_{116}$ | $Ag/Nb_{47}O_{116}$ | $Te/Nb_{47}O_{116}$ | $Pd/Nb_{47}O_{116}$ | $Ir/Nb_{47}O_{116}$ |
| $Ta_3O_5$ | $Co/Ta_3O_5$ | $Sb/Ta_3O_5$ | $W/Ta_3O_5$ | $V/Ta_3O_5$ | $Ag/Ta_3O_5$ | $Te/Ta_3O_5$ | $Pd/Ta_3O_5$ | $Ir/Ta_3O_5$ |
| $CrO$ | $Co/CrO$ | $Sb/CrO$ | $W/CrO$ | $V/CrO$ | $Ag/CrO$ | $Te/CrO$ | $Pd/CrO$ | $Ir/CrO$ |
| $Cr_2O_3$ | $Co/Cr_2O_3$ | $Sb/Cr_2O_3$ | $W/Cr_2O_3$ | $V/Cr_2O_3$ | $Ag/Cr_2O_3$ | $Te/Cr_2O_3$ | $Pd/Cr_2O_3$ | $Ir/Cr_2O_3$ |
| $CrO_2$ | $Co/CrO_2$ | $Sb/CrO_2$ | $W/CrO_2$ | $V/CrO_2$ | $Ag/CrO_2$ | $Te/CrO_2$ | $Pd/CrO_2$ | $Ir/CrO_2$ |
| $CrO_3$ | $Co/CrO_3$ | $Sb/CrO_3$ | $W/CrO_3$ | $V/CrO_3$ | $Ag/CrO_3$ | $Te/CrO_3$ | $Pd/CrO_3$ | $Ir/CrO_3$ |
| $C_8O_{21}$ | $Co/C_8O_{21}$ | $Sb/C_8O_{21}$ | $W/C_8O_{21}$ | $V/C_8O_{21}$ | $Ag/C_8O_{21}$ | $Te/C_8O_{21}$ | $Pd/C_8O_{21}$ | $Ir/C_8O_{21}$ |
| $MoO_2$ | $Co/MoO_2$ | $Sb/MoO_2$ | $W/MoO_2$ | $V/MoO_2$ | $Ag/MoO_2$ | $Te/MoO_2$ | $Pd/MoO_2$ | $Ir/MoO_2$ |
| $MoO_3$ | $Co/MoO_3$ | $Sb/MoO_3$ | $W/MoO_3$ | $V/MoO_3$ | $Ag/MoO_3$ | $Te/MoO_3$ | $Pd/MoO_3$ | $Ir/MoO_3$ |
| $W_2O_3$ | $Co/W_2O_3$ | $Sb/W_2O_3$ | $W/W_2O_3$ | $V/W_2O_3$ | $Ag/W_2O_3$ | $Te/W_2O_3$ | $Pd/W_2O_3$ | $Ir/W_2O_3$ |
| $WoO_2$ | $Co/WoO_2$ | $Sb/WoO_2$ | $W/WoO_2$ | $V/WoO_2$ | $Ag/WoO_2$ | $Te/WoO_2$ | $Pd/WoO_2$ | $Ir/WoO_2$ |
| $WoO_3$ | $Co/WoO_3$ | $Sb/WoO_3$ | $W/WoO_3$ | $V/WoO_3$ | $Ag/WoO_3$ | $Te/WoO_3$ | $Pd/WoO_3$ | $Ir/WoO_3$ |
| $MnO$ | $Co/MnO$ | $Sb/MnO$ | $W/MnO$ | $V/MnO$ | $Ag/MnO$ | $Te/MnO$ | $Pd/MnO$ | $Ir/MnO$ |
| $Mn/Mg/O$ | $Co/Mn/Mg/O$ | $Sb/Mn/Mg/O$ | $W/Mn/Mg/O$ | $V/Mn/Mg/O$ | $Ag/Mn/Mg/O$ | $Te/Mn/Mg/O$ | $Pd/Mn/Mg/O$ | $Ir/Mn/Mg/O$ |
| $Mn_3O_4$ | $Co/Mn_3O_4$ | $Sb/Mn_3O_4$ | $W/Mn_3O_4$ | $V/Mn_3O_4$ | $Ag/Mn_3O_4$ | $Te/Mn_3O_4$ | $Pd/Mn_3O_4$ | $Ir/Mn_3O_4$ |
| $Mn_2O_3$ | $Co/Mn_2O_3$ | $Sb/Mn_2O_3$ | $W/Mn_2O_3$ | $V/Mn_2O_3$ | $Ag/Mn_2O_3$ | $Te/Mn_2O_3$ | $Pd/Mn_2O_3$ | $Ir/Mn_2O_3$ |
| $MnO_2$ | $Co/MnO_2$ | $Sb/MnO_2$ | $W/MnO_2$ | $V/MnO_2$ | $Ag/MnO_2$ | $Te/MnO_2$ | $Pd/MnO_2$ | $Ir/MnO_2$ |
| $Mn_2O_7$ | $Co/Mn_2O_7$ | $Sb/Mn_2O_7$ | $W/Mn_2O_7$ | $V/Mn_2O_7$ | $Ag/Mn_2O_7$ | $Te/Mn_2O_7$ | $Pd/Mn_2O_7$ | $Ir/Mn_2O_7$ |
| $ReO_2$ | $Co/ReO_2$ | $Sb/ReO_2$ | $W/ReO_2$ | $V/ReO_2$ | $Ag/ReO_2$ | $Te/ReO_2$ | $Pd/ReO_2$ | $Ir/ReO_2$ |
| $ReO_3$ | $Co/ReO_3$ | $Sb/ReO_3$ | $W/ReO_3$ | $V/ReO_3$ | $Ag/ReO_3$ | $Te/ReO_3$ | $Pd/ReO_3$ | $Ir/ReO_3$ |
| $Re_2O_7$ | $Co/Re_2O_7$ | $Sb/Re_2O_7$ | $W/Re_2O_7$ | $V/Re_2O_7$ | $Ag/Re_2O_7$ | $Te/Re_2O_7$ | $Pd/Re_2O_7$ | $Ir/Re_2O_7$ |
| $Mg_3Mn_3-B_2O_{10}$ | $Co/Mg_3Mn_3-B_2O_{10}$ | $Sb/Mg_3Mn_3-B_2O_{10}$ | $W/Mg_3Mn_3-B_2O_{10}$ | $V/Mg_3Mn_3-B_2O_{10}$ | $Ag/Mg_3Mn_3-B_2O_{10}$ | $Te/Mg_3Mn_3-B_2O_{10}$ | $Pd/Mg_3Mn_3-B_2O_{10}$ | $Ir/Mg_3Mn_3-B_2O_{10}$ |
| $Mg_3(BO_3)_2$ | $Co/Mg_3(BO_3)_2$ | $Sb/Mg_3(BO_3)_2$ | $W/Mg_3(BO_3)_2$ | $V/Mg_3(BO_3)_2$ | $Ag/Mg_3(BO_3)_2$ | $Te/Mg_3(BO_3)_2$ | $Pd/Mg_3(BO_3)_2$ | $Ir/Mg_3(BO_3)_2$ |
| $NaWO_4$ | $Co/NaWO_4$ | $Sb/NaWO_4$ | $W/NaWO_4$ | $V/NaWO_4$ | $Ag/NaWO_4$ | $Te/NaWO_4$ | $Pd/NaWO_4$ | $Ir/NaWO_4$ |
| $Mg_6MnO_8$ | $Co/Mg_6MnO_8$ | $Sb/Mg_6MnO_8$ | $W/Mg_6MnO_8$ | $V/Mg_6MnO_8$ | $Ag/Mg_6MnO_8$ | $Te/Mg_6MnO_8$ | $Pd/Mg_6MnO_8$ | $Ir/Mg_6MnO_8$ |
| $Mn_2O_4$ | $Co/Mn_2O_4$ | $Sb/Mn_2O_4$ | $W/Mn_2O_4$ | $V/Mn_2O_4$ | $Ag/Mn_2O_4$ | $Te/Mn_2O_4$ | $Pd/Mn_2O_4$ | $Ir/Mn_2O_4$ |
| $(Li,Mg)_6-MnO_8$ | $Co/(Li,Mg)_6-MnO_8$ | $Sb/(Li,Mg)_6-MnO_8$ | $W/(Li,Mg)_6-MnO_8$ | $V/(Li,Mg)_6-MnO_8$ | $Ag/(Li,Mg)_6-MnO_8$ | $Te/(Li,Mg)_6-MnO_8$ | $Pd/(Li,Mg)_6-MnO_8$ | $Ir/(Li,Mg)_6-MnO_8$ |
| $Na_4P_2O_7$ | $Co/Na_4P_2O_7$ | $Sb/Na_4P_2O_7$ | $W/Na_4P_2O_7$ | $V/Na_4P_2O_7$ | $Ag/Na_4P_2O_7$ | $Te/Na_4P_2O_7$ | $Pd/Na_4P_2O_7$ | $Ir/Na_4P_2O_7$ |
| $Mo_2O_8$ | $Co/Mo_2O_8$ | $Sb/Mo_2O_8$ | $W/Mo_2O_8$ | $V/Mo_2O_8$ | $Ag/Mo_2O_8$ | $Te/Mo_2O_8$ | $Pd/Mo_2O_8$ | $Ir/Mo_2O_8$ |
| $Mn_3O_4/WO_4$ | $Co/Mn_3O_4/WO_4$ | $Sb/Mn_3O_4/WO_4$ | $W/Mn_3O_4/WO_4$ | $V/Mn_3O_4/WO_4$ | $Ag/Mn_3O_4/WO_4$ | $Te/Mn_3O_4/WO_4$ | $Pd/Mn_3O_4/WO_4$ | $Ir/Mn_3O_4/WO_4$ |
| $Na_3WO_4$ | $Co/Na_3WO_4$ | $Sb/Na_3WO_4$ | $W/Na_3WO_4$ | $V/Na_3WO_4$ | $Ag/Na_3WO_4$ | $Te/Na_3WO_4$ | $Pd/Na_3WO_4$ | $Ir/Na_3WO_4$ |
| $Zr_2Mo_2O_8$ | $Co/Zr_2Mo_2O_8$ | $Sb/Zr_2Mo_2O_8$ | $W/Zr_2Mo_2O_8$ | $V/Zr_2Mo_2O_8$ | $Ag/Zr_2Mo_2O_8$ | $Te/Zr_2Mo_2O_8$ | $Pd/Zr_2Mo_2O_8$ | $Ir/Zr_2Mo_2O_8$ |
| $NaMnO_4-/MgO$ | $Co/NaMnO_4-/MgO$ | $Sb/NaMnO_4-/MgO$ | $W/NaMnO_4-/MgO$ | $V/NaMnO_4-/MgO$ | $Ag/NaMnO_4-/MgO$ | $Te/NaMnO_4-/MgO$ | $Pd/NaMnO_4-/MgO$ | $Ir/NaMnO_4-/MgO$ |
| $Na_{10}Mn-W_5O_{17}$ | $Co/Na_{10}Mn-W_5O_{17}$ | $Sb/Na_{10}Mn-W_5O_{17}$ | $W/Na_{10}Mn-W_5O_{17}$ | $V/Na_{10}Mn-W_5O_{17}$ | $Ag/Na_{10}Mn-W_5O_{17}$ | $Te/Na_{10}Mn-W_5O_{17}$ | $Pd/Na_{10}Mn-W_5O_{17}$ | $Ir/Na_{10}Mn-W_5O_{17}$ |
| $La_3NdO_6$ | $Co/La_3NdO_6$ | $Sb/La_3NdO_6$ | $W/La_3NdO_6$ | $V/La_3NdO_6$ | $Ag/La_3NdO_6$ | $Te/La_3NdO_6$ | $Pd/La_3NdO_6$ | $Ir/La_3NdO_6$ |
| $LaNd_3O_6$ | $Co/LaNd_3O_6$ | $Sb/LaNd_3O_6$ | $W/LaNd_3O_6$ | $V/LaNd_3O_6$ | $Ag/LaNd_3O_6$ | $Te/LaNd_3O_6$ | $Pd/LaNd_3O_6$ | $Ir/LaNd_3O_6$ |
| $La_{1.5}Nd_{2.5}O_6$ | $Co/La_{1.5}Nd_{2.5}O_6$ | $Sb/La_{1.5}Nd_{2.5}O_6$ | $W/La_{1.5}Nd_{2.5}O_6$ | $V/La_{1.5}Nd_{2.5}O_6$ | $Ag/La_{1.5}Nd_{2.5}O_6$ | $Te/La_{1.5}Nd_{2.5}O_6$ | $Pd/La_{1.5}Nd_{2.5}O_6$ | $Ir/La_{1.5}Nd_{2.5}O_6$ |
| $La_{2.5}Nd_{1.5}O_6$ | $Co/La_{2.5}Nd_{1.5}O_6$ | $Sb/La_{2.5}Nd_{1.5}O_6$ | $W/La_{2.5}Nd_{1.5}O_6$ | $V/La_{2.5}Nd_{1.5}O_6$ | $Ag/La_{2.5}Nd_{1.5}O_6$ | $Te/La_{2.5}Nd_{1.5}O_6$ | $Pd/La_{2.5}Nd_{1.5}O_6$ | $Ir/La_{2.5}Nd_{1.5}O_6$ |
| $La_{3.2}Nd_{0.8}O_6$ | $Co/La_{3.2}Nd_{0.8}O_6$ | $Sb/La_{3.2}Nd_{0.8}O_6$ | $W/La_{3.2}Nd_{0.8}O_6$ | $V/La_{3.2}Nd_{0.8}O_6$ | $Ag/La_{3.2}Nd_{0.8}O_6$ | $Te/La_{3.2}Nd_{0.8}O_6$ | $Pd/La_{3.2}Nd_{0.8}O_6$ | $Ir/La_{3.2}Nd_{0.8}O_6$ |
| $La_{3.5}Nd_{0.5}O_6$ | $Co/La_{3.5}Nd_{0.5}O_6$ | $Sb/La_{3.5}Nd_{0.5}O_6$ | $W/La_{3.5}Nd_{0.5}O_6$ | $V/La_{3.5}Nd_{0.5}O_6$ | $Ag/La_{3.5}Nd_{0.5}O_6$ | $Te/La_{3.5}Nd_{0.5}O_6$ | $Pd/La_{3.5}Nd_{0.5}O_6$ | $Ir/La_{3.5}Nd_{0.5}O_6$ |

TABLE 7-continued

NANOWIRES (NW) DOPED WITH SPECIFIC DOPANTS (DOP)

| NW\Dop | Co | Sb | W | V | Ag | Te | Pd | Ir |
|---|---|---|---|---|---|---|---|---|
| $La_{3.8}Nd_{0.2}O_6$ | $Co/La_{3.8}Nd_{0.2}O_6$ | $Sb/La_{3.8}Nd_{0.2}O_6$ | $W/La_{3.8}Nd_{0.2}O_6$ | $V/La_{3.8}Nd_{0.2}O_6$ | $Ag/La_{3.8}Nd_{0.2}O_6$ | $Te/La_{3.8}Nd_{0.2}O_6$ | $Pd/La_{3.8}Nd_{0.2}O_6$ | $Ir/La_{3.8}Nd_{0.2}O_6$ |
| Y—La | Co/Y—La | Sb/Y—La | W/Y—La | V/Y—La | Ag/Y—La | Te/Y—La | Pd/Y—La | Ir/Y—La |
| Zr—La | Co/Zr—La | Sb/Zr—La | W/Zr—La | V/Zr—La | Ag/Zr—La | Te/Zr—La | Pd/Zr—La | Ir/Zr—La |
| Pr—La | Co/Pr—La | Sb/Pr—La | W/Pr—La | V/Pr—La | Ag/Pr—La | Te/Pr—La | Pd/Pr—La | Ir/Pr—La |
| Ce—La | Co/Ce—La | Sb/Ce—La | W/Ce—La | V/Ce—La | Ag/Ce—La | Te/Ce—La | Pd/Ce—La | Ir/Ce—La |

TABLE 8

NANOWIRES (NW) DOPED WITH SPECIFIC DOPANTS (DOP)

| NW\Dop | Mn | Ti |
|---|---|---|
| $Li_2O$ | $Mn/Li_2O$ | $Ti/Li_2O$ |
| $Na_2O$ | $Mn/Na_2O$ | $Ti/Na_2O$ |
| $K_2O$ | $Mn/K_2O$ | $Ti/K_2O$ |
| $Rb_2O$ | $Mn/Rb_2O$ | $Ti/Rb_2O$ |
| $Cs_2O$ | $Mn/Cs_2O$ | $Ti/Cs_2O$ |
| BeO | Mn/BeO | Ti/BeO |
| MgO | Mn/MgO | Ti/MgO |
| CaO | Mn/CaO | Ti/CaO |
| SrO | Mn/SrO | Ti/SrO |
| BaO | Mn/BaO | Ti/BaO |
| $Sc_2O_3$ | $Mn/Sc_2O_3$ | $Ti/Sc_2O_3$ |
| $Y_2O_3$ | $Mn/Y_2O_3$ | $Ti/Y_2O_3$ |
| $La_2O_3$ | $Mn/La_2O_3$ | $Ti/La_2O_3$ |
| $CeO_2$ | $Mn/CeO_2$ | $Ti/CeO_2$ |
| $Ce_2O_3$ | $Mn/Ce_2O_3$ | $Ti/Ce_2O_3$ |
| $Pr_2O_3$ | $Mn/Pr_2O_3$ | $Ti/Pr_2O_3$ |
| $Nd_2O_3$ | $Mn/Nd_2O_3$ | $Ti/Nd_2O_3$ |
| $Sm_2O_3$ | $Mn/Sm_2O_3$ | $Ti/Sm_2O_3$ |
| $Eu_2O_3$ | $Mn/Eu_2O_3$ | $Ti/Eu_2O_3$ |
| $Gd_2O_3$ | $Mn/Gd_2O_3$ | $Ti/Gd_2O_3$ |
| $Tb_2O_3$ | $Mn/Tb_2O_3$ | $Ti/Tb_2O_3$ |
| $TbO_2$ | $Mn/TbO_2$ | $Ti/TbO_2$ |
| $Tb_6O_{11}$ | $Mn/Tb_6O_{11}$ | $Ti/Tb_6O_{11}$ |
| $Dy_2O_3$ | $Mn/Dy_2O_3$ | $Ti/Dy_2O_3$ |
| $Ho_2O_3$ | $Mn/Ho_2O_3$ | $Ti/Ho_2O_3$ |
| $Er_2O_3$ | $Mn/Er_2O_3$ | $Ti/Er_2O_3$ |
| $Tm_2O_3$ | $Mn/Tm_2O_3$ | $Ti/Tm_2O_3$ |
| $Yb_2O_3$ | $Mn/Yb_2O_3$ | $Ti/Yb_2O_3$ |
| $Lu_2O_3$ | $Mn/Lu_2O_3$ | $Ti/Lu_2O_3$ |
| $Ac_2O_3$ | $Mn/Ac_2O_3$ | $Ti/Ac_2O_3$ |
| $Th_2O_3$ | $Mn/Th_2O_3$ | $Ti/Th_2O_3$ |
| $ThO_2$ | $Mn/ThO_2$ | $Ti/ThO_2$ |
| $Pa_2O_3$ | $Mn/Pa_2O_3$ | $Ti/Pa_2O_3$ |
| $PaO_2$ | $Mn/PaO_2$ | $Ti/PaO_2$ |
| $TiO_2$ | $Mn/TiO_2$ | $Ti/TiO_2$ |
| TiO | Mn/TiO | Ti/TiO |
| $Ti_2O_3$ | $Mn/Ti_2O_3$ | $Ti/Ti_2O_3$ |
| $Ti_3O$ | $Mn/Ti_3O$ | $Ti/Ti_3O$ |
| $Ti_2O$ | $Mn/Ti_2O$ | $Ti/Ti_2O$ |
| $Ti_3O_5$ | $Mn/Ti_3O_5$ | $Ti/Ti_3O_5$ |
| $Ti_4O_7$ | $Mn/Ti_4O_7$ | $Ti/Ti_4O_7$ |
| $ZrO_2$ | $Mn/ZrO_2$ | $Ti/ZrO_2$ |
| $HfO_2$ | $Mn/HfO_2$ | $Ti/HfO_2$ |
| VO | Mn/VO | Ti/VO |
| $V_2O_3$ | $Mn/V_2O_3$ | $Ti/V_2O_3$ |
| $VO_2$ | $Mn/VO_2$ | $Ti/VO_2$ |
| $V_2O_5$ | $Mn/V_2O_5$ | $Ti/V_2O_5$ |
| $V_3O_7$ | $Mn/V_3O_7$ | $Ti/V_3O_7$ |
| $V_4O_9$ | $Mn/V_4O_9$ | $Ti/V_4O_9$ |
| $V_6O_{13}$ | $Mn/V_6O_{13}$ | $Ti/V_6O_{13}$ |
| NbO | Mn/NbO | Ti/NbO |
| $NbO_2$ | $Mn/NbO_2$ | $Ti/NbO_2$ |
| $Nb_2O_5$ | $Mn/Nb_2O_5$ | $Ti/Nb_2O_5$ |
| $Nb_8O_{19}$ | $Mn/Nb_8O_{19}$ | $Ti/Nb_8O_{19}$ |
| $Nb_{16}O_{38}$ | $Mn/Nb_{16}O_{38}$ | $Ti/Nb_{16}O_{38}$ |
| $Nb_{12}O_{29}$ | $Mn/Nb_{12}O_{29}$ | $Ti/Nb_{12}O_{29}$ |
| $Nb_{47}O_{116}$ | $Mn/Nb_{47}O_{116}$ | $Ti/Nb_{47}O_{116}$ |
| $Ta_2O_5$ | $Mn/Ta_2O_5$ | $Ti/Ta_2O_5$ |
| CrO | Mn/CrO | Ti/CrO |
| $Cr_2O_3$ | $Mn/Cr_2O_3$ | $Ti/Cr_2O_3$ |
| $CrO_2$ | $Mn/CrO_2$ | $Ti/CrO_2$ |
| $CrO_3$ | $Mn/CrO_3$ | $Ti/CrO_3$ |
| $Cr_8O_{21}$ | $Mn/Cr_8O_{21}$ | $Ti/Cr_8O_{21}$ |
| $MoO_2$ | $Mn/MoO_2$ | $Ti/MoO_2$ |
| $MoO_3$ | $Mn/MoO_3$ | $Ti/MoO_3$ |
| $W_2O_3$ | $Mn/W_2O_3$ | $Ti/W_2O_3$ |
| $WoO_2$ | $Mn/WoO_2$ | $Ti/WoO_2$ |
| $WoO_3$ | $Mn/WoO_3$ | $Ti/WoO_3$ |
| MnO | Mn/MnO | Ti/MnO |
| Mn/Mg/O | Mn/Mn/Mg/O | Ti/Mn/Mg/O |
| $Mn_3O_4$ | $Mn/Mn_3O_4$ | $Ti/Mn_3O_4$ |
| $Mn_2O_3$ | $Mn/Mn_2O_3$ | $Ti/Mn_2O_3$ |
| $MnO_2$ | $Mn/MnO_2$ | $Ti/MnO_2$ |
| $Mn_2O_7$ | $Mn/Mn_2O_7$ | $Ti/Mn_2O_7$ |

TABLE 8-continued

NANOWIRES (NW) DOPED WITH SPECIFIC DOPANTS (DOP)

| NW\Dop | Mn | Ti |
|---|---|---|
| ReO$_2$ | Mn/ReO$_2$ | Ti/ReO$_2$ |
| ReO$_3$ | Mn/ReO$_3$ | Ti/ReO$_3$ |
| Re$_2$O$_7$ | Mn/Re$_2$O$_7$ | Ti/Re$_2$O$_7$ |
| Mg$_3$Mn$_3$—B$_2$O$_{10}$ | Mn/Mg$_3$Mn$_3$—B$_2$O$_{10}$ | Ti/Mg$_3$Mn$_3$—B$_2$O$_{10}$ |
| Mg$_3$(BO$_3$)$_2$ | Mn/Mg$_3$(BO$_3$)$_2$ | Ti/Mg$_3$(BO$_3$)$_2$ |
| NaWO$_4$ | Mn/NaWO$_4$ | Ti/NaWO$_4$ |
| Mg$_6$MnO$_8$ | Mn/Mg$_6$MnO$_8$ | Ti/Mg$_6$MnO$_8$ |
| Mn$_2$O$_4$ | Mn/Mn$_2$O$_4$ | Ti/Mn$_2$O$_4$ |
| (Li,Mg)$_6$—MnO$_8$ | Mn/(Li,Mg)$_6$—MnO$_8$ | Mn/(Li,Mg)$_6$—MnO$_8$ |
| Na$_4$P$_2$O$_7$ | Mn/Na$_4$P$_2$O$_7$ | Ti/Na$_4$P$_2$O$_7$ |
| Mo$_2$O$_8$ | Mn/Mo$_2$O$_8$ | Ti/Mo$_2$O$_8$ |
| Mn$_3$O$_4$/WO$_4$ | Mn/Mn$_3$O$_4$/WO$_4$ | Ti/Mn$_3$O$_4$/WO$_4$ |
| Na$_2$WO$_4$ | Mn/Na$_2$WO$_4$ | Ti/Na$_2$WO$_4$ |
| Zr$_2$Mo$_2$O$_8$ | Mn/Zr$_2$Mo$_2$O$_8$ | Ti/Zr$_2$Mo$_2$O$_8$ |
| NaMnO$_4$—/MgO | Mn/NaMnO$_4$—/MgO | Ti/NaMnO$_4$—/MgO |
| Na$_{10}$Mn—W$_5$O$_{17}$ | Mn/Na$_{10}$Mn—W$_5$O$_{17}$ | Ti/Na$_{10}$Mn—W$_5$O$_{17}$ |
| La$_3$NdO$_6$ | Mn/La$_3$NdO$_6$ | Ti/La$_3$NdO$_6$ |
| LaNd$_3$O$_6$ | Mn/LaNd$_3$O$_6$ | Ti/LaNd$_3$O$_6$ |
| La$_{1.5}$Nd$_{2.5}$O$_6$ | Mn/La$_{1.5}$Nd$_{2.5}$O$_6$ | Ti/La$_{1.5}$Nd$_{2.5}$O$_6$ |
| La$_{2.5}$Nd$_{1.5}$O$_6$ | Mn/La$_{2.5}$Nd$_{1.5}$O$_6$ | Ti/La$_{2.5}$Nd$_{1.5}$O$_6$ |
| La$_{3.2}$Nd$_{0.8}$O$_6$ | Mn/La$_{3.2}$Nd$_{0.8}$O$_6$ | Ti/La$_{3.2}$Nd$_{0.8}$O$_6$ |
| La$_{3.5}$Nd$_{0.5}$O$_6$ | Mn/La$_{3.5}$Nd$_{0.5}$O$_6$ | Ti/La$_{3.5}$Nd$_{0.5}$O$_6$ |
| La$_{3.8}$Nd$_{0.2}$O$_6$ | Mn/La$_{3.8}$Nd$_{0.2}$O$_6$ | Ti/La$_{3.8}$Nd$_{0.2}$O$_6$ |
| Y—La | Mn/Y—La | Ti/Y—La |
| Zr—La | Mn/Zr—La | Ti/Zr—La |
| Pr—La | Mn/Pr—La | Ti/Pr—La |
| Ce—La | Mn/Ce—La | Ti/Ce—La |

TABLE 9

Nanowires (NW) Doped With Specific Dopants (Dop)

| Dop\NW | La$_2$O$_3$ | Nd$_2$O$_3$ | Yb$_2$O$_3$ | Eu$_2$O$_3$ | Sm$_2$O$_3$ | La$_3$NdO$_6$ |
|---|---|---|---|---|---|---|
| Eu/Na | Eu/Na/La$_2$O$_3$ | Eu/Na/Nd$_2$O$_3$ | Eu/Na/Yb$_2$O$_3$ | Eu/Na/Eu$_2$O$_3$ | Eu/Na/Sm$_2$O$_3$ | Eu/Na/La$_3$NdO$_6$ |
| Sr/Na | Sr/Na/La$_2$O$_3$ | Sr/Na/Nd$_2$O$_3$ | Sr/Na/Yb$_2$O$_3$ | Sr/Na/Eu$_2$O$_3$ | Sr/Na/Sm$_2$O$_3$ | Sr/Na/La$_3$NdO$_6$ |
| Na/Zr/Eu/Ca | Na/Zr/Eu/Ca/La$_2$O$_3$ | Na/Zr/Eu/Ca/Nd$_2$O$_3$ | Na/Zr/Eu/Ca/Yb$_2$O$_3$ | Na/Zr/Eu/Ca/Eu$_2$O$_3$ | Na/Zr/Eu/Ca/Sm$_2$O$_3$ | Na/Zr/Eu/Ca/La$_3$NdO$_6$ |
| Mg/Na | Mg/Na/La$_2$O$_3$ | Mg/Na/Nd$_2$O$_3$ | Mg/Na/Yb$_2$O$_3$ | Mg/Na/Eu$_2$O$_3$ | Mg/Na/Sm$_2$O$_3$ | Mg/Na/La$_3$NdO$_6$ |
| Sr/Sm/Ho/Tm | Sr/Sm/Ho/Tm/La$_2$O$_3$ | Sr/Sm/Ho/Tm/Nd$_2$O$_3$ | Sr/Sm/Ho/Tm/Yb$_2$O$_3$ | Sr/Sm/Ho/Tm/Eu$_2$O$_3$ | Sr/Sm/Ho/Tm/Sm$_2$O$_3$ | Sr/Sm/Ho/Tm/La$_3$NdO$_6$ |
| Sr/W | Sr/W/La$_2$O$_3$ | Sr/W/Nd$_2$O$_3$ | Sr/W/Yb$_2$O$_3$ | Sr/W/Eu$_2$O$_3$ | Sr/W/Sm$_2$O$_3$ | Sr/W/La$_3$NdO$_6$ |
| Sr/Zr | Sr/Zr/La$_2$O$_3$ | Sr/Zr/Nd$_2$O$_3$ | Sr/Zr/Yb$_2$O$_3$ | Sr/Zr/Eu$_2$O$_3$ | Sr/Zr/Sm$_2$O$_3$ | Rb/Sr/La$_3$NdO$_6$ |
| Mg/La/K | Mg/La/K/La$_2$O$_3$ | Mg/La/K/Nd$_2$O$_3$ | Mg/La/K/Yb$_2$O$_3$ | Mg/La/K/Eu$_2$O$_3$ | Mg/La/K/Sm$_2$O$_3$ | Mg/La/K/La$_3$NdO$_6$ |
| Na/K/Mg/Tm | Na/K/Mg/Tm/La$_2$O$_3$ | Na/K/Mg/Tm/Nd$_2$O$_3$ | Na/K/Mg/Tm/Yb$_2$O$_3$ | Na/K/Mg/Tm/Eu$_2$O$_3$ | Na/K/Mg/Tm/Sm$_2$O$_3$ | Na/K/Mg/Tm/La$_3$NdO$_6$ |
| Na/Dy/K | Na/Dy/K/La$_2$O$_3$ | Na/Dy/K/Nd$_2$O$_3$ | Na/Dy/K/Yb$_2$O$_3$ | Na/Dy/K/Eu$_2$O$_3$ | Na/Dy/K/Sm$_2$O$_3$ | Na/Dy/K/La$_3$NdO$_6$ |
| Na/La/Dy | Na/La/Dy/La$_2$O$_3$ | Na/La/Dy/Nd$_2$O$_3$ | Na/La/Dy/Yb$_2$O$_3$ | Na/La/Dy/Eu$_2$O$_3$ | Na/La/Dy/Sm$_2$O$_3$ | Na/La/Dy/La$_3$NdO$_6$ |
| Na/La/Eu | Na/La/Eu/La$_2$O$_3$ | Na/La/Eu/Nd$_2$O$_3$ | Na/La/Eu/Yb$_2$O$_3$ | Na/La/Eu/Eu$_2$O$_3$ | Na/La/Eu/Sm$_2$O$_3$ | Na/La/Eu/La$_3$NdO$_6$ |
| Na/La/Eu/In | Na/La/Eu/In/La$_2$O$_3$ | Na/La/Eu/In/Nd$_2$O$_3$ | Na/La/Eu/In/Yb$_2$O$_3$ | Na/La/Eu/In/Eu$_2$O$_3$ | Na/La/Eu/In/Sm$_2$O$_3$ | Na/La/Eu/In/La$_3$NdO$_6$ |
| Sr/Ce | Sr/Ce/La$_2$O$_3$ | Sr/Ce/Nd$_2$O$_3$ | Sr/Ce/Yb$_2$O$_3$ | Sr/Ce/Eu$_2$O$_3$ | Sr/Ce/Sm$_2$O$_3$ | Rb/Sr/La$_3$NdO$_6$ |
| Na/La/K | Na/La/K/La$_2$O$_3$ | Na/La/K/Nd$_2$O$_3$ | Na/La/K/Yb$_2$O$_3$ | Na/La/K/Eu$_2$O$_3$ | Na/La/K/Sm$_2$O$_3$ | Na/La/K/La$_3$NdO$_6$ |
| Na/La/Li/Cs | Na/La/Li/Cs/La$_2$O$_3$ | Na/La/Li/Cs/Nd$_2$O$_3$ | Na/La/Li/Cs/Yb$_2$O$_3$ | Na/La/Li/Cs/Eu$_2$O$_3$ | Na/La/Li/Cs/Sm$_2$O$_3$ | Na/La/Li/Cs/La$_3$NdO$_6$ |
| K/La | K/La/La$_2$O$_3$ | K/La/Nd$_2$O$_3$ | K/La/Yb$_2$O$_3$ | K/La/Eu$_2$O$_3$ | K/La/Sm$_2$O$_3$ | K/La/La$_3$NdO$_6$ |
| K/La/S | K/La/S/La$_2$O$_3$ | K/La/S/Nd$_2$O$_3$ | K/La/S/Yb$_2$O$_3$ | K/La/S/Eu$_2$O$_3$ | K/La/S/Sm$_2$O$_3$ | K/La/S/La$_3$NdO$_6$ |

TABLE 9-continued

Nanowires (NW) Doped With Specific Dopants (Dop)

| Dop\NW | La$_2$O$_3$ | Nd$_2$O$_3$ | Yb$_2$O$_3$ | Eu$_2$O$_3$ | Sm$_2$O$_3$ | La$_3$NdO$_6$ |
|---|---|---|---|---|---|---|
| K/Na | K/Na/La$_2$O$_3$ | K/Na/Nd$_2$O$_3$ | K/Na/Yb$_2$O$_3$ | K/Na/Eu$_2$O$_3$ | K/Na/Sm$_2$O$_3$ | K/Na/La$_3$NdO$_6$ |
| Li/Cs | Li/Cs/La$_2$O$_3$ | Li/Cs/Nd$_2$O$_3$ | Li/Cs/Yb$_2$O$_3$ | Li/Cs/Eu$_2$O$_3$ | Li/Cs/Sm$_2$O$_3$ | Li/Cs/La$_3$NdO$_6$ |
| Li/Cs/La | Li/Cs/La/La$_2$O$_3$ | Li/Cs/La/Nd$_2$O$_3$ | Li/Cs/La/Yb$_2$O$_3$ | Li/Cs/La/Eu$_2$O$_3$ | Li/Cs/La/Sm$_2$O$_3$ | Li/Cs/La/La$_3$NdO$_6$ |
| Li/Cs/La/Tm | Li/Cs/La/Tm/La$_2$O$_3$ | Li/Cs/La/Tm/Nd$_2$O$_3$ | Li/Cs/La/Tm/Yb$_2$O$_3$ | Li/Cs/La/Tm/Eu$_2$O$_3$ | Li/Cs/La/Tm/Sm$_2$O$_3$ | Li/Cs/La/Tm/La$_3$NdO$_6$ |
| Sr/Tb | Sr/Tb/La$_2$O$_3$ | Sr/Tb/Nd$_2$O$_3$ | Sr/Tb/Yb$_2$O$_3$ | Sr/Tb/Eu$_2$O$_3$ | Sr/Tb/Sm$_2$O$_3$ | Rb/Sr/ |
| Li/Cs/Sr/Tm | Li/Cs/Sr/Tm/La$_2$O$_3$ | Li/Cs/Sr/Tm/Nd$_2$O$_3$ | Li/Cs/Sr/Tm/Yb$_2$O$_3$ | Li/Cs/Sr/Tm/Eu$_2$O$_3$ | Li/Cs/Sr/Tm/Sm$_2$O$_3$ | Li/Cs/Sr/Tm/La$_3$NdO$_6$ |
| Li/Sr/Cs | Li/Sr/Cs/La$_2$O$_3$ | Li/Sr/Cs/Nd$_2$O$_3$ | Li/Sr/Cs/Yb$_2$O$_3$ | Li/Sr/Cs/Eu$_2$O$_3$ | Li/Sr/Cs/Sm$_2$O$_3$ | Li/Sr/Cs/La$_3$NdO$_6$ |
| Li/Sr/Zn/K | Li/Sr/Zn/K/La$_2$O$_3$ | Li/Sr/Zn/K/Nd$_2$O$_3$ | Li/Sr/Zn/K/Yb$_2$O$_3$ | Li/Sr/Zn/K/Eu$_2$O$_3$ | Li/Sr/Zn/K/Sm$_2$O$_3$ | Li/Sr/Zn/K/La$_3$NdO$_6$ |
| Li/Ga/Cs | Li/Ga/Cs/La$_2$O$_3$ | Li/Ga/Cs/Nd$_2$O$_3$ | Li/Ga/Cs/Yb$_2$O$_3$ | Li/Ga/Cs/Eu$_2$O$_3$ | Li/Ga/Cs/Sm$_2$O$_3$ | Li/Ga/Cs/La$_3$NdO$_6$ |
| Li/K/Sr/La | Li/K/Sr/La/La$_2$O$_3$ | Li/K/Sr/La/Nd$_2$O$_3$ | Li/K/Sr/La/Yb$_2$O$_3$ | Li/K/Sr/La/Eu$_2$O$_3$ | Li/K/Sr/La/Sm$_2$O$_3$ | Li/K/Sr/La/La$_3$NdO$_6$ |
| Li/Na | Li/Na/La$_2$O$_3$ | Li/Na/Nd$_2$O$_3$ | Li/Na/Yb$_2$O$_3$ | Li/Na/Eu$_2$O$_3$ | Li/Na/Sm$_2$O$_3$ | Li/Na/La$_3$NdO$_6$ |
| Li/Na/Rb/Ga | Li/Na/Rb/Ga/La$_2$O$_3$ | Li/Na/Rb/Ga/Nd$_2$O$_3$ | Li/Na/Rb/Ga/Yb$_2$O$_3$ | Li/Na/Rb/Ga/Eu$_2$O$_3$ | Li/Na/Rb/Ga/Sm$_2$O$_3$ | Li/Na/Rb/Ga/La$_3$NdO$_6$ |
| Li/Na/Sr | Li/Na/Sr/La$_2$O$_3$ | Li/Na/Sr/Nd$_2$O$_3$ | Li/Na/Sr/Yb$_2$O$_3$ | Li/Na/Sr/Eu$_2$O$_3$ | Li/Na/Sr/Sm$_2$O$_3$ | Li/Na/Sr/La$_3$NdO$_6$ |
| Li/Na/Sr/La | Li/Na/Sr/La/La$_2$O$_3$ | Li/Na/Sr/La/Nd$_2$O$_3$ | Li/Na/Sr/La/Yb$_2$O$_3$ | Li/Na/Sr/La/Eu$_2$O$_3$ | Li/Na/Sr/La/Sm$_2$O$_3$ | Li/Na/Sr/La/La$_3$NdO$_6$ |
| Li/Sm/Cs | Li/Sm/Cs/La$_2$O$_3$ | Li/Sm/Cs/Nd$_2$O$_3$ | Li/Sm/Cs/Yb$_2$O$_3$ | Li/Sm/Cs/Eu$_2$O$_3$ | Li/Sm/Cs/Sm$_2$O$_3$ | Li/Sm/Cs/La$_3$NdO$_6$ |
| Ba/Sm/Yb/S | Ba/Sm/Yb/S/La$_2$O$_3$ | Ba/Sm/Yb/S/Nd$_2$O$_3$ | Ba/Sm/Yb/S/Yb$_2$O$_3$ | Ba/Sm/Yb/S/Eu$_2$O$_3$ | Ba/Sm/Yb/S/Sm$_2$O$_3$ | Ba/Sm/Yb/S/La$_3$NdO$_6$ |
| Sr/Ce/K | Sr/Ce/K/La$_2$O$_3$ | Sr/Ce/K/Nd$_2$O$_3$ | Sr/Ce/K/Yb$_2$O$_3$ | Sr/Ce/K/Eu$_2$O$_3$ | Sr/Ce/K/Sm$_2$O$_3$ | Rb/Sr/ |
| Ba/Tm/K/La | Ba/Tm/K/La/La$_2$O$_3$ | Ba/Tm/K/La/Nd$_2$O$_3$ | Ba/Tm/K/La/Yb$_2$O$_3$ | Ba/Tm/K/La/Eu$_2$O$_3$ | Ba/Tm/K/La/Sm$_2$O$_3$ | Ba/Tm/K/La/La$_3$NdO$_6$ |
| Ba/Tm/Zn/K | Ba/Tm/Zn/K/La$_2$O$_3$ | Ba/Tm/Zn/K/Nd$_2$O$_3$ | Ba/Tm/Zn/K/Yb$_2$O$_3$ | Ba/Tm/Zn/K/Eu$_2$O$_3$ | Ba/Tm/Zn/K/Sm$_2$O$_3$ | Ba/Tm/Zn/K/La$_3$NdO$_6$ |
| Cs/K/La | Cs/K/La/La$_2$O$_3$ | Cs/K/La/Nd$_2$O$_3$ | Cs/K/La/Yb$_2$O$_3$ | Cs/K/La/Eu$_2$O$_3$ | Cs/K/La/Sm$_2$O$_3$ | Cs/K/La/La$_3$NdO$_6$ |
| Cs/La/Tm/Na | Cs/La/Tm/Na/La$_2$O$_3$ | Cs/La/Tm/Na/Nd$_2$O$_3$ | Cs/La/Tm/Na/Yb$_2$O$_3$ | Cs/La/Tm/Na/Eu$_2$O$_3$ | Cs/La/Tm/Na/Sm$_2$O$_3$ | Cs/La/Tm/Na/La$_3$NdO$_6$ |
| Cs/Li/K/La | Cs/Li/K/La/La$_2$O$_3$ | Cs/Li/K/La/Nd$_2$O$_3$ | Cs/Li/K/La/Yb$_2$O$_3$ | Cs/Li/K/La/Eu$_2$O$_3$ | Cs/Li/K/La/Sm$_2$O$_3$ | Cs/Li/K/La/La$_3$NdO$_6$ |
| Sm/Li/Sr/Cs | Sm/Li/Sr/Cs/La$_2$O$_3$ | Sm/Li/Sr/Cs/Nd$_2$O$_3$ | Sm/Li/Sr/Cs/Yb$_2$O$_3$ | Sm/Li/Sr/Cs/Eu$_2$O$_3$ | Sm/Li/Sr/Cs/Sm$_2$O$_3$ | Sm/Li/Sr/Cs/La$_3$NdO$_6$ |
| Sr/Cs/La | Sr/Cs/La/La$_2$O$_3$ | Sr/Cs/La/Nd$_2$O$_3$ | Sr/Cs/La/Yb$_2$O$_3$ | Sr/Cs/La/Eu$_2$O$_3$ | Sr/Cs/La/Sm$_2$O$_3$ | Sr/Cs/La/La$_3$NdO$_6$ |
| Sr/Tm/Li/Cs | Sr/Tm/Li/Cs/La$_2$O$_3$ | Sr/Tm/Li/Cs/Nd$_2$O$_3$ | Sr/Tm/Li/Cs/Yb$_2$O$_3$ | Sr/Tm/Li/Cs/Eu$_2$O$_3$ | Sr/Tm/Li/Cs/Sm$_2$O$_3$ | Sr/Tm/Li/Cs/La$_3$NdO$_6$ |
| Zn/K | Zn/K/La$_2$O$_3$ | Zn/K/Nd$_2$O$_3$ | Zn/K/Yb$_2$O$_3$ | Zn/K/Eu$_2$O$_3$ | Zn/K/Sm$_2$O$_3$ | Zn/K/La$_3$NdO$_6$ |
| Zr/Cs/K/La | Zr/Cs/K/La/La$_2$O$_3$ | Zr/Cs/K/La/Nd$_2$O$_3$ | Zr/Cs/K/La/Yb$_2$O$_3$ | Zr/Cs/K/La/Eu$_2$O$_3$ | Zr/Cs/K/La/Sm$_2$O$_3$ | Zr/Cs/K/La/La$_3$NdO$_6$ |
| Rb/Ca/In/Ni | Rb/Ca/In/Ni/La$_2$O$_3$ | Rb/Ca/In/Ni/Nd$_2$O$_3$ | Rb/Ca/In/Ni/Yb$_2$O$_3$ | Rb/Ca/In/Ni/Eu$_2$O$_3$ | Rb/Ca/In/Ni/Sm$_2$O$_3$ | Rb/Ca/In/Ni/La$_3$NdO$_6$ |
| Sr/Ho/Tm | Sr/Ho/Tm/La$_2$O$_3$ | Sr/Ho/Tm/Nd$_2$O$_3$ | Sr/Ho/Tm/Yb$_2$O$_3$ | Sr/Ho/Tm/Eu$_2$O$_3$ | Sr/Ho/Tm/Sm$_2$O$_3$ | Sr/Ho/Tm/La$_3$NdO$_6$ |
| La/Nd/S | La/Nd/S/La$_2$O$_3$ | La/Nd/S/Nd$_2$O$_3$ | La/Nd/S/Yb$_2$O$_3$ | La/Nd/S/Eu$_2$O$_3$ | La/Nd/S/Sm$_2$O$_3$ | La/Nd/S/La$_3$NdO$_6$ |
| Li/Rb/Ca | Li/Rb/Ca/La$_2$O$_3$ | Li/Rb/Ca/Nd$_2$O$_3$ | Li/Rb/Ca/Yb$_2$O$_3$ | Li/Rb/Ca/Eu$_2$O$_3$ | Li/Rb/Ca/Sm$_2$O$_3$ | Li/Rb/Ca/La$_3$NdO$_6$ |
| Li/K | Li/K/La$_2$O$_3$ | Li/K/Nd$_2$O$_3$ | Li/K/Yb$_2$O$_3$ | Li/K/Eu$_2$O$_3$ | Li/K/Sm$_2$O$_3$ | Li/K/La$_3$NdO$_6$ |
| Tm/Lu/Ta/P | Tm/Lu/Ta/P/La$_2$O$_3$ | Tm/Lu/Ta/P/Nd$_2$O$_3$ | Tm/Lu/Ta/P/Yb$_2$O$_3$ | Tm/Lu/Ta/P/Eu$_2$O$_3$ | Tm/Lu/Ta/P/Sm$_2$O$_3$ | Tm/Lu/Ta/P/La$_3$NdO$_6$ |
| Rb/Ca/Dy/P | Rb/Ca/Dy/P/La$_2$O$_3$ | Rb/Ca/Dy/P/Nd$_2$O$_3$ | Rb/Ca/Dy/P/Yb$_2$O$_3$ | Rb/Ca/Dy/P/Eu$_2$O$_3$ | Rb/Ca/Dy/P/Sm$_2$O$_3$ | Rb/Ca/Dy/P/La$_3$NdO$_6$ |
| Mg/La/Yb/Zn | Mg/La/Yb/Zn/La$_2$O$_3$ | Mg/La/Yb/Zn/Nd$_2$O$_3$ | Mg/La/Yb/Zn/Yb$_2$O$_3$ | Mg/La/Yb/Zn/Eu$_2$O$_3$ | Mg/La/Yb/Zn/Sm$_2$O$_3$ | Mg/La/Yb/Zn/La$_3$NdO$_6$ |
| Sr/Zr/K | Sr/Zr/K/La$_2$O$_3$ | Sr/Zr/K/Nd$_2$O$_3$ | Sr/Zr/K/Yb$_2$O$_3$ | Sr/Zr/K/Eu$_2$O$_3$ | Sr/Zr/K/Sm$_2$O$_3$ | Rb/Sr/ |
| Rb/Sr/Lu | Rb/Sr/Lu/La$_2$O$_3$ | Rb/Sr/Lu/Nd$_2$O$_3$ | Rb/Sr/Lu/Yb$_2$O$_3$ | Rb/Sr/Lu/Eu$_2$O$_3$ | Rb/Sr/Lu/Sm$_2$O$_3$ | Rb/Sr/Lu/La$_3$NdO$_6$ |
| Na/Sr/Lu/Nb | Na/Sr/Lu/Nb/La$_2$O$_3$ | Na/Sr/Lu/Nb/Nd$_2$O$_3$ | Na/Sr/Lu/Nb/Yb$_2$O$_3$ | Na/Sr/Lu/Nb/Eu$_2$O$_3$ | Na/Sr/Lu/Nb/Sm$_2$O$_3$ | Na/Sr/Lu/Nb/La$_3$NdO$_6$ |

TABLE 9-continued

Nanowires (NW) Doped With Specific Dopants (Dop)

| Dop\NW | La$_2$O$_3$ | Nd$_2$O$_3$ | Yb$_2$O$_3$ | Eu$_2$O$_3$ | Sm$_2$O$_3$ | La$_3$NdO$_6$ |
|---|---|---|---|---|---|---|
| Na/Eu/Hf | Na/Eu/Hf/ La$_2$O$_3$ | Na/Eu/Hf/ Nd$_2$O$_3$ | Na/Eu/Hf/ Yb$_2$O$_3$ | Na/Eu/Hf/ Eu$_2$O$_3$ | Na/Eu/Hf/ Sm$_2$O$_3$ | Na/Eu/Hf/ La$_3$NdO$_6$ |
| Dy/Rb/Gd | Dy/Rb/Gd/ La$_2$O$_3$ | Dy/Rb/Gd/ Nd$_2$O$_3$ | Dy/Rb/Gd/ Yb$_2$O$_3$ | Dy/Rb/Gd/ Eu$_2$O$_3$ | Dy/Rb/Gd/ Sm$_2$O$_3$ | Dy/Rb/Gd/ La$_3$NdO$_6$ |
| Na/Pt/Bi | Na/Pt/Bi/ La$_2$O$_3$ | Na/Pt/Bi/ Nd$_2$O$_3$ | Na/Pt/Bi/ Yb$_2$O$_3$ | Na/Pt/Bi/ Eu$_2$O$_3$ | Na/Pt/Bi/ Sm$_2$O$_3$ | Na/Pt/Bi/ La$_3$NdO$_6$ |
| Rb/Hf | Rb/Hf/ La$_2$O$_3$ | Rb/Hf/ Nd$_2$O$_3$ | Rb/Hf/ Yb$_2$O$_3$ | Rb/Hf/ Eu$_2$O$_3$ | Rb/Hf/ Sm$_2$O$_3$ | Rb/Hf/ La$_3$NdO$_6$ |
| Ca/Cs | Ca/Cs/ La$_2$O$_3$ | Ca/Cs/ Nd$_2$O$_3$ | Ca/Cs/ Yb$_2$O$_3$ | Ca/Cs/ Eu$_2$O$_3$ | Ca/Cs/ Sm$_2$O$_3$ | Ca/Cs/ La$_3$NdO$_6$ |
| Ca/Mg/Na | Ca/Mg/Na/ La$_2$O$_3$ | Ca/Mg/Na/ Nd$_2$O$_3$ | Ca/Mg/Na/ Yb$_2$O$_3$ | Ca/Mg/Na/ Eu$_2$O$_3$ | Ca/Mg/Na/ Sm$_2$O$_3$ | Ca/Mg/Na/ La$_3$NdO$_6$ |
| Hf/Bi | Hf/Bi/ La$_2$O$_3$ | Hf/Bi/ Nd$_2$O$_3$ | Hf/Bi/ Yb$_2$O$_3$ | Hf/Bi/ Eu$_2$O$_3$ | Hf/Bi/ Sm$_2$O$_3$ | Hf/Bi/ La$_3$NdO$_6$ |
| Sr/Sn | Sr/Sn/ La$_2$O$_3$ | Sr/Sn/ Nd$_2$O$_3$ | Sr/Sn/ Yb$_2$O$_3$ | Sr/Sn/ Eu$_2$O$_3$ | Sr/Sn/ Sm$_2$O$_3$ | Sr/Sn/ La$_3$NdO$_6$ |
| Sr/Pr/K | Sr/Pr/K/ La$_2$O$_3$ | Sr/Pr/K/ Nd$_2$O$_3$ | Sr/Pr/K/ Yb$_2$O$_3$ | Sr/Pr/K/ Eu$_2$O$_3$ | Sr/Pr/K/ Sm$_2$O$_3$ | Sr/Pr/K/ Rb/Sr/ |
| Sr/W | Sr/W/ La$_2$O$_3$ | Sr/W/ Nd$_2$O$_3$ | Sr/W/ Yb$_2$O$_3$ | Sr/W/ Eu$_2$O$_3$ | Sr/W/ Sm$_2$O$_3$ | Sr/W/ La$_3$NdO$_6$ |
| Sr/Nb | Sr/Nb/ La$_2$O$_3$ | Sr/Nb/ Nd$_2$O$_3$ | Sr/Nb/ Yb$_2$O$_3$ | Sr/Nb/ Eu$_2$O$_3$ | Sr/Nb/ Sm$_2$O$_3$ | Sr/Nb/ La$_3$NdO$_6$ |
| Zr/W | Zr/W/ La$_2$O$_3$ | Zr/W/ Nd$_2$O$_3$ | Zr/W/ Yb$_2$O$_3$ | Zr/W/ Eu$_2$O$_3$ | Zr/W/ Sm$_2$O$_3$ | Zr/W/ La$_3$NdO$_6$ |
| Y/W | Y/W/ La$_2$O$_3$ | Y/W/ Nd$_2$O$_3$ | Y/W/ Yb$_2$O$_3$ | Y/W/ Eu$_2$O$_3$ | Y/W/ Sm$_2$O$_3$ | Y/W/ La$_3$NdO$_6$ |
| Na/W | Na/W/ La$_2$O$_3$ | Na/W/ Nd$_2$O$_3$ | Na/W/ Yb$_2$O$_3$ | Na/W/ Eu$_2$O$_3$ | Na/W/ Sm$_2$O$_3$ | Na/W/ La$_3$NdO$_6$ |
| Bi/W | Bi/W/ La$_2$O$_3$ | Bi/W/ Nd$_2$O$_3$ | Bi/W/ Yb$_2$O$_3$ | Bi/W/ Eu$_2$O$_3$ | Bi/W/ Sm$_2$O$_3$ | Bi/W/ La$_3$NdO$_6$ |
| Bi/Cs | Bi/Cs/ La$_2$O$_3$ | Bi/Cs/ Nd$_2$O$_3$ | Bi/Cs/ Yb$_2$O$_3$ | Bi/Cs/ Eu$_2$O$_3$ | Bi/Cs/ Sm$_2$O$_3$ | Bi/Cs/ La$_3$NdO$_6$ |
| Bi/Ca | Bi/Ca/ La$_2$O$_3$ | Bi/Ca/ Nd$_2$O$_3$ | Bi/Ca/ Yb$_2$O$_3$ | Bi/Ca/ Eu$_2$O$_3$ | Bi/Ca/ Sm$_2$O$_3$ | Bi/Ca/ La$_3$NdO$_6$ |
| Bi/Sn | Bi/Sn/ La$_2$O$_3$ | Bi/Sn/ Nd$_2$O$_3$ | Bi/Sn/ Yb$_2$O$_3$ | Bi/Sn/ Eu$_2$O$_3$ | Bi/Sn/ Sm$_2$O$_3$ | Bi/Sn/ La$_3$NdO$_6$ |
| Bi/Sb | Bi/Sb/ La$_2$O$_3$ | Bi/Sb/ Nd$_2$O$_3$ | Bi/Sb/ Yb$_2$O$_3$ | Bi/Sb/ Eu$_2$O$_3$ | Bi/Sb/ Sm$_2$O$_3$ | Bi/Sb/ La$_3$NdO$_6$ |
| Ge/Hf | Ge/Hf/ La$_2$O$_3$ | Ge/Hf/ Nd$_2$O$_3$ | Ge/Hf/ Yb$_2$O$_3$ | Ge/Hf/ Eu$_2$O$_3$ | Ge/Hf/ Sm$_2$O$_3$ | Ge/Hf/ La$_3$NdO$_6$ |
| Hf/Sm | Hf/Sm/ La$_2$O$_3$ | Hf/Sm/ Nd$_2$O$_3$ | Hf/Sm/ Yb$_2$O$_3$ | Hf/Sm/ Eu$_2$O$_3$ | Hf/Sm/ Sm$_2$O$_3$ | Hf/Sm/ La$_3$NdO$_6$ |
| Sb/Ag | Sb/Ag/ La$_2$O$_3$ | Sb/Ag/ Nd$_2$O$_3$ | Sb/Ag/ Yb$_2$O$_3$ | Sb/Ag/ Eu$_2$O$_3$ | Sb/Ag/ Sm$_2$O$_3$ | Sb/Ag/ La$_3$NdO$_6$ |
| Sb/Bi | Sb/Bi/ La$_2$O$_3$ | Sb/Bi/ Nd$_2$O$_3$ | Sb/Bi/ Yb$_2$O$_3$ | Sb/Bi/ Eu$_2$O$_3$ | Sb/Bi/ Sm$_2$O$_3$ | Sb/Bi/ La$_3$NdO$_6$ |
| Sb/Au | Sb/Au/ La$_2$O$_3$ | Sb/Au/ Nd$_2$O$_3$ | Sb/Au/ Yb$_2$O$_3$ | Sb/Au/ Eu$_2$O$_3$ | Sb/Au/ Sm$_2$O$_3$ | Sb/Au/ La$_3$NdO$_6$ |
| Sb/Sm | Sb/Sm/ La$_2$O$_3$ | Sb/Sm/ Nd$_2$O$_3$ | Sb/Sm/ Yb$_2$O$_3$ | Sb/Sm/ Eu$_2$O$_3$ | Sb/Sm/ Sm$_2$O$_3$ | Sb/Sm/ La$_3$NdO$_6$ |
| Sr/Tb/K | Sr/Tb/K/ La$_2$O$_3$ | Sr/Tb/K/ Nd$_2$O$_3$ | Sr/Tb/K/ Yb$_2$O$_3$ | Sr/Tb/K/ Eu$_2$O$_3$ | Sr/Tb/K/ Sm$_2$O$_3$ | Sr/Tb/K/ Rb/Sr/ |
| Sb/Sr | Sb/Sr/ La$_2$O$_3$ | Sb/Sr/ Nd$_2$O$_3$ | Sb/Sr/ Yb$_2$O$_3$ | Sb/Sr/ Eu$_2$O$_3$ | Sb/Sr/ Sm$_2$O$_3$ | Sb/Sr/ La$_3$NdO$_6$ |
| Sb/W | Sb/W/ La$_2$O$_3$ | Sb/W/ Nd$_2$O$_3$ | Sb/W/ Yb$_2$O$_3$ | Sb/W/ Eu$_2$O$_3$ | Sb/W/ Sm$_2$O$_3$ | Sb/W/ La$_3$NdO$_6$ |
| Sb/Hf | Sb/Hf/ La$_2$O$_3$ | Sb/Hf/ Nd$_2$O$_3$ | Sb/Hf/ Yb$_2$O$_3$ | Sb/Hf/ Eu$_2$O$_3$ | Sb/Hf/ Sm$_2$O$_3$ | Sb/Hf/ La$_3$NdO$_6$ |
| Sb/Yb | Sb/Yb/ La$_2$O$_3$ | Sb/Yb/ Nd$_2$O$_3$ | Sb/Yb/ Yb$_2$O$_3$ | Sb/Yb/ Eu$_2$O$_3$ | Sb/Yb/ Sm$_2$O$_3$ | Sb/Yb/ La$_3$NdO$_6$ |
| Sb/Sn | Sb/Sn/ La$_2$O$_3$ | Sb/Sn/ Nd$_2$O$_3$ | Sb/Sn/ Yb$_2$O$_3$ | Sb/Sn/ Eu$_2$O$_3$ | Sb/Sn/ Sm$_2$O$_3$ | Sb/Sn/ La$_3$NdO$_6$ |
| Yb/Au | Yb/Au/ La$_2$O$_3$ | Yb/Au/ Nd$_2$O$_3$ | Yb/Au/ Yb$_2$O$_3$ | Yb/Au/ Eu$_2$O$_3$ | Yb/Au/ Sm$_2$O$_3$ | Yb/Au/ La$_3$NdO$_6$ |
| Yb/Ta | Yb/Ta/ La$_2$O$_3$ | Yb/Ta/ Nd$_2$O$_3$ | Yb/Ta/ Yb$_2$O$_3$ | Yb/Ta/ Eu$_2$O$_3$ | Yb/Ta/ Sm$_2$O$_3$ | Yb/Ta/ La$_3$NdO$_6$ |
| Yb/W | Yb/W/ La$_2$O$_3$ | Yb/W/ Nd$_2$O$_3$ | Yb/W/ Yb$_2$O$_3$ | Yb/W/ Eu$_2$O$_3$ | Yb/W/ Sm$_2$O$_3$ | Yb/W/ La$_3$NdO$_6$ |
| Yb/Sr | Yb/Sr/ La$_2$O$_3$ | Yb/Sr/ Nd$_2$O$_3$ | Yb/Sr/ Yb$_2$O$_3$ | Yb/Sr/ Eu$_2$O$_3$ | Yb/Sr/ Sm$_2$O$_3$ | Yb/Sr/ La$_3$NdO$_6$ |
| Yb/Pb | Yb/Pb/ La$_2$O$_3$ | Yb/Pb/ Nd$_2$O$_3$ | Yb/Pb/ Yb$_2$O$_3$ | Yb/Pb/ Eu$_2$O$_3$ | Yb/Pb/ Sm$_2$O$_3$ | Yb/Pb/ La$_3$NdO$_6$ |
| Yb/W | Yb/W/ La$_2$O$_3$ | Yb/W/ Nd$_2$O$_3$ | Yb/W/ Yb$_2$O$_3$ | Yb/W/ Eu$_2$O$_3$ | Yb/W/ Sm$_2$O$_3$ | Yb/W/ La$_3$NdO$_6$ |
| Yb/Ag | Yb/Ag/ La$_2$O$_3$ | Yb/Ag/ Nd$_2$O$_3$ | Yb/Ag/ Yb$_2$O$_3$ | Yb/Ag/ Eu$_2$O$_3$ | Yb/Ag/ Sm$_2$O$_3$ | Yb/Ag/ La$_3$NdO$_6$ |

TABLE 9-continued

Nanowires (NW) Doped With Specific Dopants (Dop)

| Dop\NW | La$_2$O$_3$ | Nd$_2$O$_3$ | Yb$_2$O$_3$ | Eu$_2$O$_3$ | Sm$_2$O$_3$ | La$_3$NdO$_6$ |
|---|---|---|---|---|---|---|
| Au/Sr | Au/Sr/La$_2$O$_3$ | Au/Sr/Nd$_2$O$_3$ | Au/Sr/Yb$_2$O$_3$ | Au/Sr/Eu$_2$O$_3$ | Au/Sr/Sm$_2$O$_3$ | Au/Sr/La$_3$NdO$_6$ |
| Sr/Hf/K | Sr/Hf/K/La$_2$O$_3$ | Sr/Hf/K/Nd$_2$O$_3$ | Sr/Hf/K/Yb$_2$O$_3$ | Sr/Hf/K/Eu$_2$O$_3$ | Sr/Hf/K/Sm$_2$O$_3$ | Sr/Hf/K/Rb/Sr/ |
| W/Ge | W/Ge/La$_2$O$_3$ | W/Ge/Nd$_2$O$_3$ | W/Ge/Yb$_2$O$_3$ | W/Ge/Eu$_2$O$_3$ | W/Ge/Sm$_2$O$_3$ | W/Ge/La$_3$NdO$_6$ |
| Ta/Sr | Ta/Sr/La$_2$O$_3$ | Ta/Sr/Nd$_2$O$_3$ | Ta/Sr/Yb$_2$O$_3$ | Ta/Sr/Eu$_2$O$_3$ | Ta/Sr/Sm$_2$O$_3$ | Ta/Sr/La$_3$NdO$_6$ |
| Ta/Hf | Ta/Hf/La$_2$O$_3$ | Ta/Hf/Nd$_2$O$_3$ | Ta/Hf/Yb$_2$O$_3$ | Ta/Hf/Eu$_2$O$_3$ | Ta/Hf/Sm$_2$O$_3$ | Ta/Hf/La$_3$NdO$_6$ |
| W/Au | W/Au/La$_2$O$_3$ | W/Au/Nd$_2$O$_3$ | W/Au/Yb$_2$O$_3$ | W/Au/Eu$_2$O$_3$ | W/Au/Sm$_2$O$_3$ | W/Au/La$_3$NdO$_6$ |
| Ca/W | Ca/W/La$_2$O$_3$ | Ca/W/Nd$_2$O$_3$ | Ca/W/Yb$_2$O$_3$ | Ca/W/Eu$_2$O$_3$ | Ca/W/Sm$_2$O$_3$ | Ca/W/La$_3$NdO$_6$ |
| Au/Re | Au/Re/La$_2$O$_3$ | Au/Re/Nd$_2$O$_3$ | Au/Re/Yb$_2$O$_3$ | Au/Re/Eu$_2$O$_3$ | Au/Re/Sm$_2$O$_3$ | Au/Re/La$_3$NdO$_6$ |
| Sm/Li | Sm/Li/La$_2$O$_3$ | Sm/Li/Nd$_2$O$_3$ | Sm/Li/Yb$_2$O$_3$ | Sm/Li/Eu$_2$O$_3$ | Sm/Li/Sm$_2$O$_3$ | Sm/Li/La$_3$NdO$_6$ |
| La/K | La/K/La$_2$O$_3$ | La/K/Nd$_2$O$_3$ | La/K/Yb$_2$O$_3$ | La/K/Eu$_2$O$_3$ | La/K/Sm$_2$O$_3$ | La/K/La$_3$NdO$_6$ |
| Zn/Cs | Zn/Cs/La$_2$O$_3$ | Zn/Cs/Nd$_2$O$_3$ | Zn/Cs/Yb$_2$O$_3$ | Zn/Cs/Eu$_2$O$_3$ | Zn/Cs/Sm$_2$O$_3$ | Zn/Cs/La$_3$NdO$_6$ |
| Na/K/Mg | Na/K/Mg/La$_2$O$_3$ | Na/K/Mg/Nd$_2$O$_3$ | Na/K/Mg/Yb$_2$O$_3$ | Na/K/Mg/Eu$_2$O$_3$ | Na/K/Mg/Sm$_2$O$_3$ | Na/K/Mg/La$_3$NdO$_6$ |
| Zr/Cs | Zr/Cs/La$_2$O$_3$ | Zr/Cs/Nd$_2$O$_3$ | Zr/Cs/Yb$_2$O$_3$ | Zr/Cs/Eu$_2$O$_3$ | Zr/Cs/Sm$_2$O$_3$ | Zr/Cs/La$_3$NdO$_6$ |
| Ca/Ce | Ca/Ce/La$_2$O$_3$ | Ca/Ce/Nd$_2$O$_3$ | Ca/Ce/Yb$_2$O$_3$ | Ca/Ce/Eu$_2$O$_3$ | Ca/Ce/Sm$_2$O$_3$ | Ca/Ce/La$_3$NdO$_6$ |
| Na/Li/Cs | Na/Li/Cs/La$_2$O$_3$ | Na/Li/Cs/Nd$_2$O$_3$ | Na/Li/Cs/Yb$_2$O$_3$ | Na/Li/Cs/Eu$_2$O$_3$ | Na/Li/Cs/Sm$_2$O$_3$ | Na/Li/Cs/La$_3$NdO$_6$ |
| Li/Sr | Li/Sr/La$_2$O$_3$ | Li/Sr/Nd$_2$O$_3$ | Li/Sr/Yb$_2$O$_3$ | Li/Sr/Eu$_2$O$_3$ | Li/Sr/Sm$_2$O$_3$ | Li/Sr/La$_3$NdO$_6$ |
| La/Dy/K | La/Dy/K/La$_2$O$_3$ | La/Dy/K/Nd$_2$O$_3$ | La/Dy/K/Yb$_2$O$_3$ | La/Dy/K/Eu$_2$O$_3$ | La/Dy/K/Sm$_2$O$_3$ | La/Dy/K/La$_3$NdO$_6$ |
| Sr/Pr | Sr/Pr/La$_2$O$_3$ | Sr/Pr/Nd$_2$O$_3$ | Sr/Pr/Yb$_2$O$_3$ | Sr/Pr/Eu$_2$O$_3$ | Sr/Pr/Sm$_2$O$_3$ | Sr/Pr/Rb/Sr/ |
| Dy/K | Dy/K/La$_2$O$_3$ | Dy/K/Nd$_2$O$_3$ | Dy/K/Yb$_2$O$_3$ | Dy/K/Eu$_2$O$_3$ | Dy/K/Sm$_2$O$_3$ | Dy/K/La$_3$NdO$_6$ |
| La/Mg | La/Mg/La$_2$O$_3$ | La/Mg/Nd$_2$O$_3$ | La/Mg/Yb$_2$O$_3$ | La/Mg/Eu$_2$O$_3$ | La/Mg/Sm$_2$O$_3$ | La/Mg/La$_3$NdO$_6$ |
| Na/Nd/In/K | Na/Nd/In/K/La$_2$O$_3$ | Na/Nd/In/K/Nd$_2$O$_3$ | Na/Nd/In/K/Yb$_2$O$_3$ | Na/Nd/In/K/Eu$_2$O$_3$ | Na/Nd/In/K/Sm$_2$O$_3$ | Na/Nd/In/K/La$_3$NdO$_6$ |
| In/Sr | In/Sr/La$_2$O$_3$ | In/Sr/Nd$_2$O$_3$ | In/Sr/Yb$_2$O$_3$ | In/Sr/Eu$_2$O$_3$ | In/Sr/Sm$_2$O$_3$ | In/Sr/La$_3$NdO$_6$ |
| Sr/Cs | Sr/Cs/La$_2$O$_3$ | Sr/Cs/Nd$_2$O$_3$ | Sr/Cs/Yb$_2$O$_3$ | Sr/Cs/Eu$_2$O$_3$ | Sr/Cs/Sm$_2$O$_3$ | Sr/Cs/La$_3$NdO$_6$ |
| Rb/Ga/Tm/Cs | Rb/Ga/Tm/Cs/La$_2$O$_3$ | Rb/Ga/Tm/Cs/Nd$_2$O$_3$ | Rb/Ga/Tm/Cs/Yb$_2$O$_3$ | Rb/Ga/Tm/Cs/Eu$_2$O$_3$ | Rb/Ga/Tm/Cs/Sm$_2$O$_3$ | Rb/Ga/Tm/Cs/La$_3$NdO$_6$ |
| Ga/Cs | Ga/Cs/La$_2$O$_3$ | Ga/Cs/Nd$_2$O$_3$ | Ga/Cs/Yb$_2$O$_3$ | Ga/Cs/Eu$_2$O$_3$ | Ga/Cs/Sm$_2$O$_3$ | Ga/Cs/La$_3$NdO$_6$ |
| K/La/Zr/Ag | K/La/Zr/Ag/La$_2$O$_3$ | K/La/Zr/Ag/Nd$_2$O$_3$ | K/La/Zr/Ag/Yb$_2$O$_3$ | K/La/Zr/Ag/Eu$_2$O$_3$ | K/La/Zr/Ag/Sm$_2$O$_3$ | K/La/Zr/Ag/La$_3$NdO$_6$ |
| Lu/Fe | Lu/Fe/La$_2$O$_3$ | Lu/Fe/Nd$_2$O$_3$ | Lu/Fe/Yb$_2$O$_3$ | Lu/Fe/Eu$_2$O$_3$ | Lu/Fe/Sm$_2$O$_3$ | Lu/Fe/La$_3$NdO$_6$ |
| Sr/Tm | Sr/Tm/La$_2$O$_3$ | Sr/Tm/Nd$_2$O$_3$ | Sr/Tm/Yb$_2$O$_3$ | Sr/Tm/Eu$_2$O$_3$ | Sr/Tm/Sm$_2$O$_3$ | Sr/Tm/La$_3$NdO$_6$ |
| La/Dy | La/Dy/La$_2$O$_3$ | La/Dy/Nd$_2$O$_3$ | La/Dy/Yb$_2$O$_3$ | La/Dy/Eu$_2$O$_3$ | La/Dy/Sm$_2$O$_3$ | La/Dy/La$_3$NdO$_6$ |
| Sm/Li/Sr | Sm/Li/Sr/La$_2$O$_3$ | Sm/Li/Sr/Nd$_2$O$_3$ | Sm/Li/Sr/Yb$_2$O$_3$ | Sm/Li/Sr/Eu$_2$O$_3$ | Sm/Li/Sr/Sm$_2$O$_3$ | Sm/Li/Sr/La$_3$NdO$_6$ |
| Mg/K | Mg/K/La$_2$O$_3$ | Mg/K/Nd$_2$O$_3$ | Mg/K/Yb$_2$O$_3$ | Mg/K/Eu$_2$O$_3$ | Mg/K/Sm$_2$O$_3$ | Mg/K/La$_3$NdO$_6$ |
| Li/Rb/Ga | Li/Rb/Ga/La$_2$O$_3$ | Li/Rb/Ga/Nd$_2$O$_3$ | Li/Rb/Ga/Yb$_2$O$_3$ | Li/Rb/Ga/Eu$_2$O$_3$ | Li/Rb/Ga/Sm$_2$O$_3$ | Li/Rb/Ga/La$_3$NdO$_6$ |
| Li/Cs/Tm | Li/Cs/Tm/La$_2$O$_3$ | Li/Cs/Tm/Nd$_2$O$_3$ | Li/Cs/Tm/Yb$_2$O$_3$ | Li/Cs/Tm/Eu$_2$O$_3$ | Li/Cs/Tm/Sm$_2$O$_3$ | Li/Cs/Tm/La$_3$NdO$_6$ |
| Zr/K | Zr/K/La$_2$O$_3$ | Zr/K/Nd$_2$O$_3$ | Zr/K/Yb$_2$O$_3$ | Zr/K/Eu$_2$O$_3$ | Zr/K/Sm$_2$O$_3$ | Zr/K/La$_3$NdO$_6$ |
| Sr/Hf/Rb | Sr/Hf/Rb/La$_2$O$_3$ | Sr/Hf/Rb/Nd$_2$O$_3$ | Sr/Hf/Rb/Yb$_2$O$_3$ | Sr/Hf/Rb/Eu$_2$O$_3$ | Sr/Hf/Rb/Sm$_2$O$_3$ | Sr/Hf/Rb/Rb/Sr/ |
| Li/Cs | Li/Cs/La$_2$O$_3$ | Li/Cs/Nd$_2$O$_3$ | Li/Cs/Yb$_2$O$_3$ | Li/Cs/Eu$_2$O$_3$ | Li/Cs/Sm$_2$O$_3$ | Li/Cs/La$_3$NdO$_6$ |
| Li/K/La | Li/K/La/La$_2$O$_3$ | Li/K/La/Nd$_2$O$_3$ | Li/K/La/Yb$_2$O$_3$ | Li/K/La/Eu$_2$O$_3$ | Li/K/La/Sm$_2$O$_3$ | Li/K/La/La$_3$NdO$_6$ |
| Ce/Zr/La | Ce/Zr/La/La$_2$O$_3$ | Ce/Zr/La/Nd$_2$O$_3$ | Ce/Zr/La/Yb$_2$O$_3$ | Ce/Zr/La/Eu$_2$O$_3$ | Ce/Zr/La/Sm$_2$O$_3$ | Ce/Zr/La/La$_3$NdO$_6$ |

TABLE 9-continued

Nanowires (NW) Doped With Specific Dopants (Dop)

| Dop\NW | $La_2O_3$ | $Nd_2O_3$ | $Yb_2O_3$ | $Eu_2O_3$ | $Sm_2O_3$ | $La_3NdO_6$ |
|---|---|---|---|---|---|---|
| Ca/Al/La | Ca/Al/La/$La_2O_3$ | Ca/Al/La/$Nd_2O_3$ | Ca/Al/La/$Yb_2O_3$ | Ca/Al/La/$Eu_2O_3$ | Ca/Al/La/$Sm_2O_3$ | Ca/Al/La/$La_3NdO_6$ |
| Sr/Zn/La | Sr/Zn/La/$La_2O_3$ | Sr/Zn/La/$Nd_2O_3$ | Sr/Zn/La/$Yb_2O_3$ | Sr/Zn/La/$Eu_2O_3$ | Sr/Zn/La/$Sm_2O_3$ | Sr/Zn/La/$La_3NdO_6$ |
| Sr/Cs/Zn | Sr/Cs/Zn/$La_2O_3$ | Sr/Cs/Zn/$Nd_2O_3$ | Sr/Cs/Zn/$Yb_2O_3$ | Sr/Cs/Zn/$Eu_2O_3$ | Sr/Cs/Zn/$Sm_2O_3$ | Sr/Cs/Zn/$La_3NdO_6$ |
| Sm/Cs | Sm/Cs/$La_2O_3$ | Sm/Cs/$Nd_2O_3$ | Sm/Cs/$Yb_2O_3$ | Sm/Cs/$Eu_2O_3$ | Sm/Cs/$Sm_2O_3$ | Sm/Cs/$La_3NdO_6$ |
| In/K | In/K/$La_2O_3$ | In/K/$Nd_2O_3$ | In/K/$Yb_2O_3$ | In/K/$Eu_2O_3$ | In/K/$Sm_2O_3$ | In/K/$La_3NdO_6$ |
| Ho/Cs/Li/La | Ho/Cs/Li/La/$La_2O_3$ | Ho/Cs/Li/La/$Nd_2O_3$ | Ho/Cs/Li/La/$Yb_2O_3$ | Ho/Cs/Li/La/$Eu_2O_3$ | Ho/Cs/Li/La/$Sm_2O_3$ | Ho/Cs/Li/La/$La_3NdO_6$ |
| Cs/La/Na | Cs/La/Na/$La_2O_3$ | Cs/La/Na/$Nd_2O_3$ | Cs/La/Na/$Yb_2O_3$ | Cs/La/Na/$Eu_2O_3$ | Cs/La/Na/$Sm_2O_3$ | Cs/La/Na/$La_3NdO_6$ |
| La/S/Sr | La/S/Sr/$La_2O_3$ | La/S/Sr/$Nd_2O_3$ | La/S/Sr/$Yb_2O_3$ | La/S/Sr/$Eu_2O_3$ | La/S/Sr/$Sm_2O_3$ | La/S/Sr/$La_3NdO_6$ |
| K/La/Zr/Ag | K/La/Zr/Ag/$La_2O_3$ | K/La/Zr/Ag/$Nd_2O_3$ | K/La/Zr/Ag/$Yb_2O_3$ | K/La/Zr/Ag/$Eu_2O_3$ | K/La/Zr/Ag/$Sm_2O_3$ | K/La/Zr/Ag/$La_3NdO_6$ |
| Lu/Tl | Lu/Tl/$La_2O_3$ | Lu/Tl/$Nd_2O_3$ | Lu/Tl/$Yb_2O_3$ | Lu/Tl/$Eu_2O_3$ | Lu/Tl/$Sm_2O_3$ | Lu/Tl/$La_3NdO_6$ |
| Pr/Zn | Pr/Zn/$La_2O_3$ | Pr/Zn/$Nd_2O_3$ | Pr/Zn/$Yb_2O_3$ | Pr/Zn/$Eu_2O_3$ | Pr/Zn/$Sm_2O_3$ | Pr/Zn/$La_3NdO_6$ |
| Rb/Sr/La | Rb/Sr/La/$La_2O_3$ | Rb/Sr/La/$Nd_2O_3$ | Rb/Sr/La/$Yb_2O_3$ | Rb/Sr/La/$Eu_2O_3$ | Rb/Sr/La/$Sm_2O_3$ | Rb/Sr/La/$La_3NdO_6$ |
| Na/Sr/Eu/Ca | Na/Sr/Eu/Ca/$La_2O_3$ | Na/Sr/Eu/Ca/$Nd_2O_3$ | Na/Sr/Eu/Ca/$Yb_2O_3$ | Na/Sr/Eu/Ca/$Eu_2O_3$ | Na/Sr/Eu/Ca/$Sm_2O_3$ | Na/Sr/Eu/Ca/$La_3NdO_6$ |
| Sr/B | Sr/B/$La_2O_3$ | Sr/B/$Nd_2O_3$ | Sr/B/$Yb_2O_3$ | Sr/B/$Eu_2O_3$ | Sr/B/$Sm_2O_3$ | Rb/Sr/$La_3NdO_6$ |
| K/Cs/Sr/La | K/Cs/Sr/La/$La_2O_3$ | K/Cs/Sr/La/$Nd_2O_3$ | K/Cs/Sr/La/$Yb_2O_3$ | K/Cs/Sr/La/$Eu_2O_3$ | K/Cs/Sr/La/$Sm_2O_3$ | K/Cs/Sr/La/$La_3NdO_6$ |
| Na/Sr/Lu | Na/Sr/Lu/$La_2O_3$ | Na/Sr/Lu/$Nd_2O_3$ | Na/Sr/Lu/$Yb_2O_3$ | Na/Sr/Lu/$Eu_2O_3$ | Na/Sr/Lu/$Sm_2O_3$ | Na/Sr/Lu/$La_3NdO_6$ |
| Sr/Eu/Dy | Sr/Eu/Dy/$La_2O_3$ | Sr/Eu/Dy/$Nd_2O_3$ | Sr/Eu/Dy/$Yb_2O_3$ | Sr/Eu/Dy/$Eu_2O_3$ | Sr/Eu/Dy/$Sm_2O_3$ | Sr/Eu/Dy/$La_3NdO_6$ |
| Lu/Nb | Lu/Nb/$La_2O_3$ | Lu/Nb/$Nd_2O_3$ | Lu/Nb/$Yb_2O_3$ | Lu/Nb/$Eu_2O_3$ | Lu/Nb/$Sm_2O_3$ | Lu/Nb/$La_3NdO_6$ |
| La/Dy/Gd | La/Dy/Gd/$La_2O_3$ | La/Dy/Gd/$Nd_2O_3$ | La/Dy/Gd/$Yb_2O_3$ | La/Dy/Gd/$Eu_2O_3$ | La/Dy/Gd/$Sm_2O_3$ | La/Dy/Gd/$La_3NdO_6$ |
| Na/Mg/Tl/P | Na/Mg/Tl/P/$La_2O_3$ | Na/Mg/Tl/P/$Nd_2O_3$ | Na/Mg/Tl/P/$Yb_2O_3$ | Na/Mg/Tl/P/$Eu_2O_3$ | Na/Mg/Tl/P/$Sm_2O_3$ | Na/Mg/Tl/P/$La_3NdO_6$ |
| Na/Pt | Na/Pt/$La_2O_3$ | Na/Pt/$Nd_2O_3$ | Na/Pt/$Yb_2O_3$ | Na/Pt/$Eu_2O_3$ | Na/Pt/$Sm_2O_3$ | Na/Pt/$La_3NdO_6$ |
| Gd/Li/K | Gd/Li/K/$La_2O_3$ | Gd/Li/K/$Nd_2O_3$ | Gd/Li/K/$Yb_2O_3$ | Gd/Li/K/$Eu_2O_3$ | Gd/Li/K/$Sm_2O_3$ | Gd/Li/K/$La_3NdO_6$ |
| Rb/K/Lu | Rb/K/Lu/$La_2O_3$ | Rb/K/Lu/$Nd_2O_3$ | Rb/K/Lu/$Yb_2O_3$ | Rb/K/Lu/$Eu_2O_3$ | Rb/K/Lu/$Sm_2O_3$ | Rb/K/Lu/$La_3NdO_6$ |
| Sr/La/Dy/S | Sr/La/Dy/S/$La_2O_3$ | Sr/La/Dy/S/$Nd_2O_3$ | Sr/La/Dy/S/$Yb_2O_3$ | Sr/La/Dy/S/$Eu_2O_3$ | Sr/La/Dy/S/$Sm_2O_3$ | Sr/La/Dy/S/$La_3NdO_6$ |
| Na/Ce/Co | Na/Ce/Co/$La_2O_3$ | Na/Ce/Co/$Nd_2O_3$ | Na/Ce/Co/$Yb_2O_3$ | Na/Ce/Co/$Eu_2O_3$ | Na/Ce/Co/$Sm_2O_3$ | Na/Ce/Co/$La_3NdO_6$ |
| Na/Ce | Na/Ce/$La_2O_3$ | Na/Ce/$Nd_2O_3$ | Na/Ce/$Yb_2O_3$ | Na/Ce/$Eu_2O_3$ | Na/Ce/$Sm_2O_3$ | Na/Ce/$La_3NdO_6$ |
| Na/Ga/Gd/Al | Na/Ga/Gd/Al/$La_2O_3$ | Na/Ga/Gd/Al/$Nd_2O_3$ | Na/Ga/Gd/Al/$Yb_2O_3$ | Na/Ga/Gd/Al/$Eu_2O_3$ | Na/Ga/Gd/Al/$Sm_2O_3$ | Na/Ga/Gd/Al/$La_3NdO_6$ |
| Ba/Rh/Ta | Ba/Rh/Ta/$La_2O_3$ | Ba/Rh/Ta/$Nd_2O_3$ | Ba/Rh/Ta/$Yb_2O_3$ | Ba/Rh/Ta/$Eu_2O_3$ | Ba/Rh/Ta/$Sm_2O_3$ | Ba/Rh/Ta/$La_3NdO_6$ |
| Ba/Ta | Ba/Ta/$La_2O_3$ | Ba/Ta/$Nd_2O_3$ | Ba/Ta/$Yb_2O_3$ | Ba/Ta/$Eu_2O_3$ | Ba/Ta/$Sm_2O_3$ | Ba/Ta/$La_3NdO_6$ |
| Na/Al/Bi | Na/Al/Bi/$La_2O_3$ | Na/Al/Bi/$Nd_2O_3$ | Na/Al/Bi/$Yb_2O_3$ | Na/Al/Bi/$Eu_2O_3$ | Na/Al/Bi/$Sm_2O_3$ | Na/Al/Bi/$La_3NdO_6$ |
| Cs/Eu/S | Cs/Eu/S/$La_2O_3$ | Cs/Eu/S/$Nd_2O_3$ | Cs/Eu/S/$Yb_2O_3$ | Cs/Eu/S/$Eu_2O_3$ | Cs/Eu/S/$Sm_2O_3$ | Cs/Eu/S/$La_3NdO_6$ |
| Sm/Tm/Yb/Fe | Sm/Tm/Yb/Fe/$La_2O_3$ | Sm/Tm/Yb/Fe/$Nd_2O_3$ | Sm/Tm/Yb/Fe/$Yb_2O_3$ | Sm/Tm/Yb/Fe/$Eu_2O_3$ | Sm/Tm/Yb/Fe/$Sm_2O_3$ | Sm/Tm/Yb/Fe/$La_3NdO_6$ |
| Sm/Tm/Yb | Sm/Tm/Yb/$La_2O_3$ | Sm/Tm/Yb/$Nd_2O_3$ | Sm/Tm/Yb/$Yb_2O_3$ | Sm/Tm/Yb/$Eu_2O_3$ | Sm/Tm/Yb/$Sm_2O_3$ | Sm/Tm/Yb/$La_3NdO_6$ |
| Hf/Zr/Ta | Hf/Zr/Ta/$La_2O_3$ | Hf/Zr/Ta/$Nd_2O_3$ | Hf/Zr/Ta/$Yb_2O_3$ | Hf/Zr/Ta/$Eu_2O_3$ | Hf/Zr/Ta/$Sm_2O_3$ | Hf/Zr/Ta/$La_3NdO_6$ |
| Rb/Gd/Li/K | Rb/Gd/Li/K/$La_2O_3$ | Rb/Gd/Li/K/$Nd_2O_3$ | Rb/Gd/Li/K/$Yb_2O_3$ | Rb/Gd/Li/K/$Eu_2O_3$ | Rb/Gd/Li/K/$Sm_2O_3$ | Rb/Gd/Li/K/$La_3NdO_6$ |
| Gd/Ho/Al/P | Gd/Ho/Al/P/$La_2O_3$ | Gd/Ho/Al/P/$Nd_2O_3$ | Gd/Ho/Al/P/$Yb_2O_3$ | Gd/Ho/Al/P/$Eu_2O_3$ | Gd/Ho/Al/P/$Sm_2O_3$ | Gd/Ho/Al/P/$La_3NdO_6$ |
| Na/Ca/Lu | Na/Ca/Lu/$La_2O_3$ | Na/Ca/Lu/$Nd_2O_3$ | Na/Ca/Lu/$Yb_2O_3$ | Na/Ca/Lu/$Eu_2O_3$ | Na/Ca/Lu/$Sm_2O_3$ | Na/Ca/Lu/$La_3NdO_6$ |
| Cu/Sn | Cu/Sn/$La_2O_3$ | Cu/Sn/$Nd_2O_3$ | Cu/Sn/$Yb_2O_3$ | Cu/Sn/$Eu_2O_3$ | Cu/Sn/$Sm_2O_3$ | Cu/Sn/$La_3NdO_6$ |

TABLE 9-continued

Nanowires (NW) Doped With Specific Dopants (Dop)

| Dop\NW | $La_2O_3$ | $Nd_2O_3$ | $Yb_2O_3$ | $Eu_2O_3$ | $Sm_2O_3$ | $La_3NdO_6$ |
|---|---|---|---|---|---|---|
| Ag/Au | Ag/Au/$La_2O_3$ | Ag/Au/$Nd_2O_3$ | Ag/Au/$Yb_2O_3$ | Ag/Au/$Eu_2O_3$ | Ag/Au/$Sm_2O_3$ | Ag/Au/$La_3NdO_6$ |
| Al/Bi | Al/Bi/$La_2O_3$ | Al/Bi/$Nd_2O_3$ | Al/Bi/$Yb_2O_3$ | Al/Bi/$Eu_2O_3$ | Al/Bi/$Sm_2O_3$ | Al/Bi/$La_3NdO_6$ |
| Al/Mo | Al/Mo/$La_2O_3$ | Al/Mo/$Nd_2O_3$ | Al/Mo/$Yb_2O_3$ | Al/Mo/$Eu_2O_3$ | Al/Mo/$Sm_2O_3$ | Al/Mo/$La_3NdO_6$ |
| Al/Nb | Al/Nb/$La_2O_3$ | Al/Nb/$Nd_2O_3$ | Al/Nb/$Yb_2O_3$ | Al/Nb/$Eu_2O_3$ | Al/Nb/$Sm_2O_3$ | Al/Nb/$La_3NdO_6$ |
| Au/Pt | Au/Pt/$La_2O_3$ | Au/Pt/$Nd_2O_3$ | Au/Pt/$Yb_2O_3$ | Au/Pt/$Eu_2O_3$ | Au/Pt/$Sm_2O_3$ | Au/Pt/$La_3NdO_6$ |
| Ga/Bi | Ga/Bi/$La_2O_3$ | Ga/Bi/$Nd_2O_3$ | Ga/Bi/$Yb_2O_3$ | Ga/Bi/$Eu_2O_3$ | Ga/Bi/$Sm_2O_3$ | Ga/Bi/$La_3NdO_6$ |
| Mg/W | Mg/W/$La_2O_3$ | Mg/W/$Nd_2O_3$ | Mg/W/$Yb_2O_3$ | Mg/W/$Eu_2O_3$ | Mg/W/$Sm_2O_3$ | Mg/W/$La_3NdO_6$ |
| Pb/Au | Pb/Au/$La_2O_3$ | Pb/Au/$Nd_2O_3$ | Pb/Au/$Yb_2O_3$ | Pb/Au/$Eu_2O_3$ | Pb/Au/$Sm_2O_3$ | Pb/Au/$La_3NdO_6$ |
| Sn/Mg | Sn/Mg/$La_2O_3$ | Sn/Mg/$Nd_2O_3$ | Sn/Mg/$Yb_2O_3$ | Sn/Mg/$Eu_2O_3$ | Sn/Mg/$Sm_2O_3$ | Sn/Mg/$La_3NdO_6$ |
| Zn/Bi | Zn/Bi/$La_2O_3$ | Zn/Bi/$Nd_2O_3$ | Zn/Bi/$Yb_2O_3$ | Zn/Bi/$Eu_2O_3$ | Zn/Bi/$Sm_2O_3$ | Zn/Bi/$La_3NdO_6$ |
| Sr/Ta | Sr/Ta/$La_2O_3$ | Sr/Ta/$Nd_2O_3$ | Sr/Ta/$Yb_2O_3$ | Sr/Ta/$Eu_2O_3$ | Sr/Ta/$Sm_2O_3$ | Sr/Ta/$La_3NdO_6$ |
| Na | Na/$La_2O_3$ | Na/$Nd_2O_3$ | Na/$Yb_2O_3$ | Na/$Eu_2O_3$ | Na/$Sm_2O_3$ | Na/$La_3NdO_6$ |
| Sr | Sr/$La_2O_3$ | Sr/$Nd_2O_3$ | Sr/$Yb_2O_3$ | Sr/$Eu_2O_3$ | Sr/$Sm_2O_3$ | Sr/$La_3NdO_6$ |
| Ca | Ca/$La_2O_3$ | Ca/$Nd_2O_3$ | Ca/$Yb_2O_3$ | Ca/$Eu_2O_3$ | Ca/$Sm_2O_3$ | Ca/$La_3NdO_6$ |
| Yb | Yb/$La_2O_3$ | Yb/$Nd_2O_3$ | Yb/$Yb_2O_3$ | Yb/$Eu_2O_3$ | Yb/$Sm_2O_3$ | Yb/$La_3NdO_6$ |
| Cs | Cs/$La_2O_3$ | Cs/$Nd_2O_3$ | Cs/$Yb_2O_3$ | Cs/$Eu_2O_3$ | Cs/$Sm_2O_3$ | Cs/$La_3NdO_6$ |
| Sb | Sb/$La_2O_3$ | Sb/$Nd_2O_3$ | Sb/$Yb_2O_3$ | Sb/$Eu_2O_3$ | Sb/$Sm_2O_3$ | Sb/$La_3NdO_6$ |
| Gd/Ho | Gd/Ho/$La_2O_3$ | Gd/Ho/$Nd_2O_3$ | Gd/Ho/$Yb_2O_3$ | Gd/Ho/$Eu_2O_3$ | Gd/Ho/$Sm_2O_3$ | Gd/Ho/$La_3NdO_6$ |
| Zr/Bi | Zr/Bi/$La_2O_3$ | Zr/Bi/$Nd_2O_3$ | Zr/Bi/$Yb_2O_3$ | Zr/Bi/$Eu_2O_3$ | Zr/Bi/$Sm_2O_3$ | Zr/Bi/$La_3NdO_6$ |
| Ho/Sr | Ho/Sr/$La_2O_3$ | Ho/Sr/$Nd_2O_3$ | Ho/Sr/$Yb_2O_3$ | Ho/Sr/$Eu_2O_3$ | Ho/Sr/$Sm_2O_3$ | Ho/Sr/$La_3NdO_6$ |
| Gd/Ho/Sr | Gd/Ho/Sr/$La_2O_3$ | Gd/Ho/Sr/$Nd_2O_3$ | Gd/Ho/Sr/$Yb_2O_3$ | Gd/Ho/Sr/$Eu_2O_3$ | Gd/Ho/Sr/$Sm_2O_3$ | Gd/Ho/Sr/$La_3NdO_6$ |
| Ca/Sr | Ca/Sr/$La_2O_3$ | Ca/Sr/$Nd_2O_3$ | Ca/Sr/$Yb_2O_3$ | Ca/Sr/$Eu_2O_3$ | Ca/Sr/$Sm_2O_3$ | Ca/Sr/$La_3NdO_6$ |
| Ca/Sr/W | Ca/Sr/W/$La_2O_3$ | Ca/Sr/W/$Nd_2O_3$ | Ca/Sr/W/$Yb_2O_3$ | Ca/Sr/W/$Eu_2O_3$ | Ca/Sr/W/$Sm_2O_3$ | Ca/Sr/W/$La_3NdO_6$ |
| Na/Zr/Eu/Tm | Na/Zr/Eu/Tm/$La_2O_3$ | Na/Zr/Eu/Tm/$Nd_2O_3$ | Na/Zr/Eu/Tm/$Yb_2O_3$ | Na/Zr/Eu/Tm/$Eu_2O_3$ | Na/Zr/Eu/Tm/$Sm_2O_3$ | Na/Zr/Eu/Tm/$La_3NdO_6$ |
| Sr/Ho/Tm/Na | Sr/Ho/Tm/Na/$La_2O_3$ | Sr/Ho/Tm/Na/$Nd_2O_3$ | Sr/Ho/Tm/Na/$Yb_2O_3$ | Sr/Ho/Tm/Na/$Eu_2O_3$ | Sr/Ho/Tm/Na/$Sm_2O_3$ | Sr/Ho/Tm/Na/$La_3NdO_6$ |
| Sr/Pb | Sr/Pb/$La_2O_3$ | Sr/Pb/$Nd_2O_3$ | Sr/Pb/$Yb_2O_3$ | Sr/Pb/$Eu_2O_3$ | Sr/Pb/$Sm_2O_3$ | Sr/Pb/$La_3NdO_6$ |
| Sr/W/Li | Sr/W/Li/$La_2O_3$ | Sr/W/Li/$Nd_2O_3$ | Sr/W/Li/$Yb_2O_3$ | Sr/W/Li/$Eu_2O_3$ | Sr/W/Li/$Sm_2O_3$ | Sr/W/Li/$La_3NdO_6$ |
| Ca/Sr/W | Ca/Sr/W/$La_2O_3$ | Ca/Sr/W/$Nd_2O_3$ | Ca/Sr/W/$Yb_2O_3$ | Ca/Sr/W/$Eu_2O_3$ | Ca/Sr/W/$Sm_2O_3$ | Ca/Sr/W/$La_3NdO_6$ |
| Sr/Hf | Sr/Hf/$La_2O_3$ | Sr/Hf/$Nd_2O_3$ | Sr/Hf/$Yb_2O_3$ | Sr/Hf/$Eu_2O_3$ | Sr/Hf/$Sm_2O_3$ | Sr/Hf/$La_3NdO_6$ |
| Au/Re | Au/Re/$La_2O_3$ | Au/Re/$Nd_2O_3$ | Au/Re/$Yb_2O_3$ | Au/Re/$Eu_2O_3$ | Au/Re/$Sm_2O_3$ | Au/Re/$La_3NdO_6$ |
| Sr/W | Sr/W/$La_2O_3$ | Sr/W/$Nd_2O_3$ | Sr/W/$Yb_2O_3$ | Sr/W/$Eu_2O_3$ | Sr/W/$Sm_2O_3$ | Sr/W/$La_3NdO_6$ |
| La/Nd | La/Nd/$La_2O_3$ | La/Nd/$Nd_2O_3$ | La/Nd/$Yb_2O_3$ | La/Nd/$Eu_2O_3$ | La/Nd/$Sm_2O_3$ | La/Nd/$La_3NdO_6$ |
| La/Sm | La/Sm/$La_2O_3$ | La/Sm/$Nd_2O_3$ | La/Sm/$Yb_2O_3$ | La/Sm/$Eu_2O_3$ | La/Sm/$Sm_2O_3$ | La/Sm/$La_3NdO_6$ |
| La/Ce | La/Ce/$La_2O_3$ | La/Ce/$Nd_2O_3$ | La/Ce/$Yb_2O_3$ | La/Ce/$Eu_2O_3$ | La/Ce/$Sm_2O_3$ | La/Ce/$La_3NdO_6$ |
| La/Sr | La/Sr/$La_2O_3$ | La/Sr/$Nd_2O_3$ | La/Sr/$Yb_2O_3$ | La/Sr/$Eu_2O_3$ | La/Sr/$Sm_2O_3$ | La/Sr/$La_3NdO_6$ |
| La/Nd/Sr | La/Nd/Sr/$La_2O_3$ | La/Nd/Sr/$Nd_2O_3$ | La/Nd/Sr/$Yb_2O_3$ | La/Nd/Sr/$Eu_2O_3$ | La/Nd/Sr/$Sm_2O_3$ | La/Nd/Sr/$La_3NdO_6$ |
| La/Bi/Sr | La/Bi/Sr/$La_2O_3$ | La/Bi/Sr/$Nd_2O_3$ | La/Bi/Sr/$Yb_2O_3$ | La/Bi/Sr/$Eu_2O_3$ | La/Bi/Sr/$Sm_2O_3$ | La/Bi/Sr/$La_3NdO_6$ |
| La/Ce/Nd/Sr | La/Ce/Nd/Sr/$La_2O_3$ | La/Ce/Nd/Sr/$Nd_2O_3$ | La/Ce/Nd/Sr/$Yb_2O_3$ | La/Ce/Nd/Sr/$Eu_2O_3$ | La/Ce/Nd/Sr/$Sm_2O_3$ | La/Ce/Nd/Sr/$La_3NdO_6$ |

TABLE 9-continued

Nanowires (NW) Doped With Specific Dopants (Dop)

| Dop\NW | $La_2O_3$ | $Nd_2O_3$ | $Yb_2O_3$ | $Eu_2O_3$ | $Sm_2O_3$ | $La_3NdO_6$ |
|---|---|---|---|---|---|---|
| La/Bi/Ce/Nd/Sr | La/Bi/Ce/Nd/Sr/ $La_2O_3$ | La/Bi/Ce/Nd/Sr/ $Nd_2O_3$ | La/Bi/Ce/Nd/Sr/ $Yb_2O_3$ | La/Bi/Ce/Nd/Sr/ $Eu_2O_3$ | La/Bi/Ce/Nd/Sr/ $Sm_2O_3$ | La/Bi/Ce/Nd/Sr/ $La_3NdO_6$ |
| Eu/Gd | Eu/Gd/ $La_2O_3$ | Eu/Gd/ $Nd_2O_3$ | Eu/Gd/ $Yb_2O_3$ | Eu/Gd/ $Eu_2O_3$ | Eu/Gd/ $Sm_2O_3$ | Eu/Gd/ $La_3NdO_6$ |
| Ca/Na | Ca/Na/ $La_2O_3$ | Ca/Na/ $Nd_2O_3$ | Ca/Na/ $Yb_2O_3$ | Ca/Na/ $Eu_2O_3$ | Ca/Na/ $Sm_2O_3$ | Ca/Na/ $La_3NdO_6$ |
| Eu/Sm | Eu/Sm/ $La_2O_3$ | Eu/Sm/ $Nd_2O_3$ | Eu/Sm/ $Yb_2O_3$ | Eu/Sm/ $Eu_2O_3$ | Eu/Sm/ $Sm_2O_3$ | Eu/Sm/ $La_3NdO_6$ |
| Eu/Sr | Eu/Sr/ $La_2O_3$ | Eu/Sr/ $Nd_2O_3$ | Eu/Sr/ $Yb_2O_3$ | Eu/Sr/ $Eu_2O_3$ | Eu/Sr/ $Sm_2O_3$ | Eu/Sr/ $La_3NdO_6$ |
| Mg/Sr | Mg/Sr/ $La_2O_3$ | Mg/Sr/ $Nd_2O_3$ | Mg/Sr/ $Yb_2O_3$ | Mg/Sr/ $Eu_2O_3$ | Mg/Sr/ $Sm_2O_3$ | Mg/Sr/ $La_3NdO_6$ |
| Ce/Mg | Ce/Mg/ $La_2O_3$ | Ce/Mg/ $Nd_2O_3$ | Ce/Mg/ $Yb_2O_3$ | Ce/Mg/ $Eu_2O_3$ | Ce/Mg/ $Sm_2O_3$ | Ce/Mg/ $La_3NdO_6$ |
| Gd/Sm | Gd/Sm/ $La_2O_3$ | Gd/Sm/ $Nd_2O_3$ | Gd/Sm/ $Yb_2O_3$ | Gd/Sm/ $Eu_2O_3$ | Gd/Sm/ $Sm_2O_3$ | Gd/Sm/ $La_3NdO_6$ |
| Au/Pb | Au/Pb/ $La_2O_3$ | Au/Pb/ $Nd_2O_3$ | Au/Pb/ $Yb_2O_3$ | Au/Pb/ $Eu_2O_3$ | Au/Pb/ $Sm_2O_3$ | Au/Pb/ $La_3NdO_6$ |
| Bi/Hf | Bi/Hf/ $La_2O_3$ | Bi/Hf/ $Nd_2O_3$ | Bi/Hf/ $Yb_2O_3$ | Bi/Hf/ $Eu_2O_3$ | Bi/Hf/ $Sm_2O_3$ | Bi/Hf/ $La_3NdO_6$ |
| Rb/S | Rb/S/ $La_2O_3$ | Rb/S/ $Nd_2O_3$ | Rb/S/ $Yb_2O_3$ | Rb/S/ $Eu_2O_3$ | Rb/S/ $Sm_2O_3$ | Rb/S/ $La_3NdO_6$ |
| Sr/Nd | Sr/Nd/ $La_2O_3$ | Sr/Nd/ $Nd_2O_3$ | Sr/Nd/ $Yb_2O_3$ | Sr/Nd/ $Eu_2O_3$ | Sr/Nd/ $Sm_2O_3$ | Sr/Nd/ $La_3NdO_6$ |
| Eu/Y | Eu/Y/ $La_2O_3$ | Eu/Y/ $Nd_2O_3$ | Eu/Y/ $Yb_2O_3$ | Eu/Y/ $Eu_2O_3$ | Eu/Y/ $Sm_2O_3$ | Eu/Y/ $La_3NdO_6$ |
| Mg/Nd | Mg/Nd/ $La_2O_3$ | Mg/Nd/ $Nd_2O_3$ | Mg/Nd/ $Yb_2O_3$ | Mg/Nd/ $Eu_2O_3$ | Mg/Nd/ $Sm_2O_3$ | Mg/Nd/ $La_3NdO_6$ |
| La/Mg | La/Mg/ $La_2O_3$ | La/Mg/ $Nd_2O_3$ | La/Mg/ $Yb_2O_3$ | La/Mg/ $Eu_2O_3$ | La/Mg/ $Sm_2O_3$ | La/Mg/ $La_3NdO_6$ |
| Mg/Nd/Fe | Mg/Nd/Fe/ $La_2O_3$ | Mg/Nd/Fe/ $Nd_2O_3$ | Mg/Nd/Fe/ $Yb_2O_3$ | Mg/Nd/Fe/ $Eu_2O_3$ | Mg/Nd/Fe/ $Sm_2O_3$ | Mg/Nd/Fe/ $La_3NdO_6$ |
| Rb/Sr | Rb/Sr/ $La_2O_3$ | Rb/Sr/ $Nd_2O_3$ | Rb/Sr/ $Yb_2O_3$ | Rb/Sr/ $Eu_2O_3$ | Rb/Sr/ $Sm_2O_3$ | Rb/Sr/ Rb/Sr/ |

TABLE 10

Nanowires (NW) Doped With Specific Dopants (Dop)

| Dop\NW | $La_{4-x}Nd_xO_6$* | $LaNd_3O_6$ | $La_{1.5}Nd_{2.5}O_6$ | $La_{2.5}Nd_{1.5}O_6$ | $La_{3.2}Nd_{0.8}O_6$ | $La_{3.5}Nd_{0.5}O_6$ |
|---|---|---|---|---|---|---|
| Eu/Na | Eu/Na/ $La_{4-x}Nd_xO_6$ | Eu/Na/ $LaNd_3O_6$ | Eu/Na/ $La_{1.5}Nd_{2.5}O_6$ | Eu/Na/ $La_{2.5}Nd_{1.5}O_6$ | Eu/Na/ $La_{3.2}Nd_{0.8}O_6$ | Eu/Na/ $La_{3.5}Nd_{0.5}O_6$ |
| Sr/Na | Sr/Na/ $La_{4-x}Nd_xO_6$ | Sr/Na/ $LaNd_3O_6$ | Sr/Na/ $La_{1.5}Nd_{2.5}O_6$ | Sr/Na/ $La_{2.5}Nd_{1.5}O_6$ | Sr/Na/ $La_{3.2}Nd_{0.8}O_6$ | Sr/Na/ $La_{3.5}Nd_{0.5}O_6$ |
| Na/Zr/Eu/Ca | Na/Zr/Eu/Ca/ $La_{4-x}Nd_xO_6$ | Na/Zr/Eu/Ca/ $LaNd_3O_6$ | Na/Zr/Eu/Ca/ $La_{1.5}Nd_{2.5}O_6$ | Na/Zr/Eu/Ca/ $La_{2.5}Nd_{1.5}O_6$ | Na/Zr/Eu/Ca/ $La_{3.2}Nd_{0.8}O_6$ | Na/Zr/Eu/Ca/ $La_{3.5}Nd_{0.5}O_6$ |
| Mg/Na | Mg/Na/ $La_{4-x}Nd_xO_6$ | Mg/Na/ $LaNd_3O_6$ | Mg/Na/ $La_{1.5}Nd_{2.5}O_6$ | Mg/Na/ $La_{2.5}Nd_{1.5}O_6$ | Mg/Na/ $La_{3.2}Nd_{0.8}O_6$ | Mg/Na/ $La_{3.5}Nd_{0.5}O_6$ |
| Sr/Sm/Ho/Tm | Sr/Sm/Ho/Tm/ $La_{4-x}Nd_xXO_6$ | Sr/Sm/Ho/Tm/ $LaNd_3O_6$ | Sr/Sm/Ho/Tm/ $La_{1.5}Nd_{2.5}O_6$ | Sr/Sm/Ho/Tm/ $La_{2.5}Nd_{1.5}O_6$ | Sr/Sm/Ho/Tm/ $La_{3.2}Nd_{0.8}O_6$ | Sr/Sm/Ho/Tm/ $La_{3.5}Nd_{0.5}O_6$ |
| Sr/W | Sr/W/ $La_{4-x}Nd_xO_6$ | Sr/W/ $LaNd_3O_6$ | Sr/W/ $La_{1.5}Nd_{2.5}O_6$ | Sr/W/ $La_{2.5}Nd_{1.5}O_6$ | Sr/W/ $La_{3.2}Nd_{0.8}O_6$ | Sr/W/ $La_{3.5}Nd_{0.5}O_6$ |
| Mg/La/K | Mg/La/K/ $La_{4-x}Nd_xO_6$ | Mg/La/K/ $LaNd_3O_6$ | Mg/La/K/ $La_{1.5}Nd_{2.5}O_6$ | Mg/La/K/ $La_{2.5}Nd_{1.5}O_6$ | Mg/La/K/ $La_{3.2}Nd_{0.8}O_6$ | Mg/La/K/ $La_{3.5}Nd_{0.5}O_6$ |
| Na/K/Mg/Tm | Na/K/Mg/Tm/ $La_{4-x}Nd_xO_6$ | Na/K/Mg/Tm/ $LaNd_3O_6$ | Na/K/Mg/Tm/ $La_{1.5}Nd_{2.5}O_6$ | Na/K/Mg/Tm/ $La_{2.5}Nd_{1.5}O_6$ | Na/K/Mg/Tm/ $La_{3.2}Nd_{0.8}O_6$ | Na/K/Mg/Tm/ $La_{3.5}Nd_{0.5}O_6$ |
| Na/Dy/K | Na/Dy/K/ $La_{4-x}Nd_xO_6$ | Na/Dy/K/ $LaNd_3O_6$ | Na/Dy/K/ $La_{1.5}Nd_{2.5}O_6$ | Na/Dy/K/ $La_{2.5}Nd_{1.5}O_6$ | Na/Dy/K/ $La_{3.2}Nd_{0.8}O_6$ | Na/Dy/K/ $La_{3.5}Nd_{0.5}O_6$ |
| Sr/B | Sr/B/ $La_{4-x}Nd_xO_6$ | Sr/B/ $LaNd_3O_6$ | Sr/B/ $La_{1.5}Nd_{2.5}O_6$ | Sr/B/ $La_{2.5}Nd_{1.5}O_6$ | Sr/B/ $La_{3.2}Nd_{0.8}O_6$ | Sr/B/ $La_{3.5}Nd_{0.5}O_6$ |
| Na/La/Dy | Na/La/Dy/ $La_{4-x}Nd_xO_6$ | Na/La/Dy/ $LaNd_3O_6$ | Na/La/Dy/ $La_{1.5}Nd_{2.5}O_6$ | Na/La/Dy/ $La_{2.5}Nd_{1.5}O_6$ | Na/La/Dy/ $La_{3.2}Nd_{0.8}O_6$ | Na/La/Dy/ $La_{3.5}Nd_{0.5}O_6$ |
| Na/La/Eu | Na/La/Eu/ $La_{4-x}Nd_xO_6$ | Na/La/Eu/ $LaNd_3O_6$ | Na/La/Eu/ $La_{1.5}Nd_{2.5}O_6$ | Na/La/Eu/ $La_{2.5}Nd_{1.5}O_6$ | Na/La/Eu/ $La_{3.2}Nd_{0.8}O_6$ | Na/La/Eu/ $La_{3.5}Nd_{0.5}O_6$ |
| Na/La/Eu/In | Na/La/Eu/In/ $La_{4-x}Nd_xO_6$ | Na/La/Eu/In/ $LaNd_3O_6$ | Na/La/Eu/In/ $La_{1.5}Nd_{2.5}O_6$ | Na/La/Eu/In/ $La_{2.5}Nd_{1.5}O_6$ | Na/La/Eu/In/ $La_{3.2}Nd_{0.8}O_6$ | Na/La/Eu/In/ $La_{3.5}Nd_{0.5}O_6$ |
| Na/La/K | Na/La/K/ $La_{4-x}Nd_xO_6$ | Na/La/K/ $LaNd_3O_6$ | Na/La/K/ $La_{1.5}Nd_{2.5}O_6$ | Na/La/K/ $La_{2.5}Nd_{1.5}O_6$ | Na/La/K/ $La_{3.2}Nd_{0.8}O_6$ | Na/La/K/ $La_{3.5}Nd_{0.5}O_6$ |
| Na/La/Li/Cs | Na/La/Li/Cs/ $La_{4-x}Nd_xO_6$ | Na/La/Li/Cs/ $LaNd_3O_6$ | Na/La/Li/Cs/ $La_{1.5}Nd_{2.5}O_6$ | Na/La/Li/Cs/ $La_{2.5}Nd_{1.5}O_6$ | Na/La/Li/Cs/ $La_{3.2}Nd_{0.8}O_6$ | Na/La/Li/Cs/ $La_{3.5}Nd_{0.5}O_6$ |
| K/La | K/La/ $La_{4-x}Nd_xO_6$ | K/La/ $LaNd_3O_6$ | K/La/ $La_{1.5}Nd_{2.5}O_6$ | K/La/ $La_{2.5}Nd_{1.5}O_6$ | K/La/ $La_{3.2}Nd_{0.8}O_6$ | K/La/ $La_{3.5}Nd_{0.5}O_6$ |

TABLE 10-continued

Nanowires (NW) Doped With Specific Dopants (Dop)

| Dop\NW | $La_{4-x}Nd_xO_6$* | $LaNd_3O_6$ | $La_{1.5}Nd_{2.5}O_6$ | $La_{2.5}Nd_{1.5}O_6$ | $La_{3.2}Nd_{0.8}O_6$ | $La_{3.5}Nd_{0.5}O_6$ |
|---|---|---|---|---|---|---|
| K/La/S | K/La/S/ $La_{4-x}Nd_xO_6$ | K/La/S/ $LaNd_3O_6$ | K/La/S/ $La_{1.5}Nd_{2.5}O_6$ | K/La/S/ $La_{2.5}Nd_{1.5}O_6$ | K/La/S/ $La_{3.2}Nd_{0.8}O_6$ | K/La/S/ $La_{3.5}Nd_{0.5}O_6$ |
| K/Na | K/Na/ $La_{4-x}Nd_xO_6$ | K/Na/ $LaNd_3O_6$ | K/Na/ $La_{1.5}Nd_{2.5}O_6$ | K/Na/ $La_{2.5}Nd_{1.5}O_6$ | K/Na/ $La_{3.2}Nd_{0.8}O_6$ | K/Na/ $La_{3.5}Nd_{0.5}O_6$ |
| Li/Cs | Li/Cs/ $La_{4-x}Nd_xO_6$ | Li/Cs/ $LaNd_3O_6$ | Li/Cs/ $La_{1.5}Nd_{2.5}O_6$ | Li/Cs/ $La_{2.5}Nd_{1.5}O_6$ | Li/Cs/ $La_{3.2}Nd_{0.8}O_6$ | Li/Cs/ $La_{3.5}Nd_{0.5}O_6$ |
| Li/Cs/La | Li/Cs/La/ $La_{4-x}Nd_xO_6$ | Li/Cs/La/ $LaNd_3O_6$ | Li/Cs/La/ $La_{1.5}Nd_{2.5}O_6$ | Li/Cs/La/ $La_{2.5}Nd_{1.5}O_6$ | Li/Cs/La/ $La_{3.2}Nd_{0.8}O_6$ | Li/Cs/La/ $La_{3.5}Nd_{0.5}O_6$ |
| Li/Cs/La/Tm | Li/Cs/La/Tm/ $La_{4-x}Nd_xO_6$ | Li/Cs/La/Tm/ $LaNd_3O_6$ | Li/Cs/La/Tm/ $La_{1.5}Nd_{2.5}O_6$ | Li/Cs/La/Tm/ $La_{2.5}Nd_{1.5}O_6$ | Li/Cs/La/Tm/ $La_{3.2}Nd_{0.8}O_6$ | Li/Cs/La/Tm/ $La_{3.5}Nd_{0.5}O_6$ |
| Li/Cs/Sr/Tm | Li/Cs/Sr/Tm/ $La_{4-x}Nd_xO_6$ | Li/Cs/Sr/Tm/ $LaNd_3O_6$ | Li/Cs/Sr/Tm/ $La_{1.5}Nd_{2.5}O_6$ | Li/Cs/Sr/Tm/ $La_{2.5}Nd_{1.5}O_6$ | Li/Cs/Sr/Tm/ $La_{3.2}Nd_{0.8}O_6$ | Li/Cs/Sr/Tm/ $La_{3.5}Nd_{0.5}O_6$ |
| Li/Sr/Cs | Li/Sr/Cs/ $La_{4-x}Nd_xO_6$ | Li/Sr/Cs/ $LaNd_3O_6$ | Li/Sr/Cs/ $La_{1.5}Nd_{2.5}O_6$ | Li/Sr/Cs/ $La_{2.5}Nd_{1.5}O_6$ | Li/Sr/Cs/ $La_{3.2}Nd_{0.8}O_6$ | Li/Sr/Cs/ $La_{3.5}Nd_{0.5}O_6$ |
| Li/Sr/Zn/K | Li/Sr/Zn/K/ $La_{4-x}Nd_xO_6$ | Li/Sr/Zn/K/ $LaNd_3O_6$ | Li/Sr/Zn/K/ $La_{1.5}Nd_{2.5}O_6$ | Li/Sr/Zn/K/ $La_{2.5}Nd_{1.5}O_6$ | Li/Sr/Zn/K/ $La_{3.2}Nd_{0.8}O_6$ | Li/Sr/Zn/K/ $La_{3.5}Nd_{0.5}O_6$ |
| Sr/Pr | Sr/Pr/ $La_{4-x}Nd_xO_6$ | Sr/Pr/ $LaNd_3O_6$ | Sr/Pr/ $La_{1.5}Nd_{2.5}O_6$ | Sr/Pr/ $La_{2.5}Nd_{1.5}O_6$ | Sr/Pr/ $La_{3.2}Nd_{0.8}O_6$ | Sr/Pr/ $La_{3.5}Nd_{0.5}O_6$ |
| Li/Ga/Cs | Li/Ga/Cs/ $La_{4-x}Nd_xO_6$ | Li/Ga/Cs/ $LaNd_3O_6$ | Li/Ga/Cs/ $La_{1.5}Nd_{2.5}O_6$ | Li/Ga/Cs/ $La_{2.5}Nd_{1.5}O_6$ | Li/Ga/Cs/ $La_{3.2}Nd_{0.8}O_6$ | Li/Ga/Cs/ $La_{3.5}Nd_{0.5}O_6$ |
| Li/K/Sr/La | Li/K/Sr/La/ $La_{4-x}Nd_xO_6$ | Li/K/Sr/La/ $LaNd_3O_6$ | Li/K/Sr/La/ $La_{1.5}Nd_{2.5}O_6$ | Li/K/Sr/La/ $La_{2.5}Nd_{1.5}O_6$ | Li/K/Sr/La/ $La_{3.2}Nd_{0.8}O_6$ | Li/K/Sr/La/ $La_{3.5}Nd_{0.5}O_6$ |
| Li/Na | Li/Na/ $La_{4-x}Nd_xO_6$ | Li/Na/ $LaNd_3O_6$ | Li/Na/ $La_{1.5}Nd_{2.5}O_6$ | Li/Na/ $La_{2.5}Nd_{1.5}O_6$ | Li/Na/ $La_{3.2}Nd_{0.8}O_6$ | Li/Na/ $La_{3.5}Nd_{0.5}O_6$ |
| Li/Na/Rb/Ga | Li/Na/Rb/Ga/ $La_{4-x}Nd_xO_6$ | Li/Na/Rb/Ga/ $LaNd_3O_6$ | Li/Na/Rb/Ga/ $La_{1.5}Nd_{2.5}O_6$ | Li/Na/Rb/Ga/ $La_{2.5}Nd_{1.5}O_6$ | Li/Na/Rb/Ga/ $La_{3.2}Nd_{0.8}O_6$ | Li/Na/Rb/Ga/ $La_{3.5}Nd_{0.5}O_6$ |
| Li/Na/Sr | Li/Na/Sr/ $La_{4-x}Nd_xO_6$ | Li/Na/Sr/ $LaNd_3O_6$ | Li/Na/Sr/ $La_{1.5}Nd_{2.5}O_6$ | Li/Na/Sr/ $La_{2.5}Nd_{1.5}O_6$ | Li/Na/Sr/ $La_{3.2}Nd_{0.8}O_6$ | Li/Na/Sr/ $La_{3.5}Nd_{0.5}O_6$ |
| Li/Na/Sr/La | Li/Na/Sr/La/ $La_{4-x}Nd_xO_6$ | Li/Na/Sr/La/ $LaNd_3O_6$ | Li/Na/Sr/La/ $La_{1.5}Nd_{2.5}O_6$ | Li/Na/Sr/La/ $La_{2.5}Nd_{1.5}O_6$ | Li/Na/Sr/La/ $La_{3.2}Nd_{0.8}O_6$ | Li/Na/Sr/La/ $La_{3.5}Nd_{0.5}O_6$ |
| Li/Sm/Cs | Li/Sm/Cs/ $La_{4-x}Nd_xO_6$ | Li/Sm/Cs/ $LaNd_3O_6$ | Li/Sm/Cs/ $La_{1.5}Nd_{2.5}O_6$ | Li/Sm/Cs/ $La_{2.5}Nd_{1.5}O_6$ | Li/Sm/Cs/ $La_{3.2}Nd_{0.8}O_6$ | Li/Sm/Cs/ $La_{3.5}Nd_{0.5}O_6$ |
| Ba/Sm/Yb/S | Ba/Sm/Yb/S/ $La_{4-x}Nd_xO_6$ | Ba/Sm/Yb/S/ $LaNd_3O_6$ | Ba/Sm/Yb/S/ $La_{1.5}Nd_{2.5}O_6$ | Ba/Sm/Yb/S/ $La_{2.5}Nd_{1.5}O_6$ | Ba/Sm/Yb/S/ $La_{3.2}Nd_{0.8}O_6$ | Ba/Sm/Yb/S/ $La_{3.5}Nd_{0.5}O_6$ |
| Ba/Tm/K/La | Ba/Tm/K/La/ $La_{4-x}Nd_xO_6$ | Ba/Tm/K/La/ $LaNd_3O_6$ | Ba/Tm/K/La/ $La_{1.5}Nd_{2.5}O_6$ | Ba/Tm/K/La/ $La_{2.5}Nd_{1.5}O_6$ | Ba/Tm/K/La/ $La_{3.2}Nd_{0.8}O_6$ | Ba/Tm/K/La/ $La_{3.5}Nd_{0.5}O_6$ |
| Ba/Tm/Zn/K | Ba/Tm/Zn/K/ $La_{4-x}Nd_xO_6$ | Ba/Tm/Zn/K/ $LaNd_3O_6$ | Ba/Tm/Zn/K/ $La_{1.5}Nd_{2.5}O_6$ | Ba/Tm/Zn/K/ $La_{2.5}Nd_{1.5}O_6$ | Ba/Tm/Zn/K/ $La_{3.2}Nd_{0.8}O_6$ | Ba/Tm/Zn/K/ $La_{3.5}Nd_{0.5}O_6$ |
| Cs/K/La | Cs/K/La/ $La_{4-x}Nd_xO_6$ | Cs/K/La/ $LaNd_3O_6$ | Cs/K/La/ $La_{1.5}Nd_{2.5}O_6$ | Cs/K/La/ $La_{2.5}Nd_{1.5}O_6$ | Cs/K/La/ $La_{3.2}Nd_{0.8}O_6$ | Cs/K/La/ $La_{3.5}Nd_{0.5}O_6$ |
| Sr/Pr/K | Sr/Pr/K/ $La_{4-x}Nd_xO_6$ | Sr/Pr/K/ $LaNd_3O_6$ | Sr/Pr/K/ $La_{1.5}Nd_{2.5}O_6$ | Sr/Pr/K/ $La_{2.5}Nd_{1.5}O_6$ | Sr/Pr/K/ $La_{3.2}Nd_{0.8}O_6$ | Sr/Pr/K/ $La_{3.5}Nd_{0.5}O_6$ |
| Cs/La/Tm/Na | Cs/La/Tm/Na/ $La_{4-x}Nd_xO_6$ | Cs/La/Tm/Na/ $LaNd_3O_6$ | Cs/La/Tm/Na/ $La_{1.5}Nd_{2.5}O_6$ | Cs/La/Tm/Na/ $La_{2.5}Nd_{1.5}O_6$ | Cs/La/Tm/Na/ $La_{3.2}Nd_{0.8}O_6$ | Cs/La/Tm/Na/ $La_{3.5}Nd_{0.5}O_6$ |
| Cs/Li/K/La | Cs/Li/K/La/ $La_{4-x}Nd_xO_6$ | Cs/Li/K/La/ $LaNd_3O_6$ | Cs/Li/K/La/ $La_{1.5}Nd_{2.5}O_6$ | Cs/Li/K/La/ $La_{2.5}Nd_{1.5}O_6$ | Cs/Li/K/La/ $La_{3.2}Nd_{0.8}O_6$ | Cs/Li/K/La/ $La_{3.5}Nd_{0.5}O_6$ |
| Sm/Li/Sr/Cs | Sm/Li/Sr/Cs/ $La_{4-x}Nd_xO_6$ | Sm/Li/Sr/Cs/ $LaNd_3O_6$ | Sm/Li/Sr/Cs/ $La_{1.5}Nd_{2.5}O_6$ | Sm/Li/Sr/Cs/ $La_{2.5}Nd_{1.5}O_6$ | Sm/Li/Sr/Cs/ $La_{3.2}Nd_{0.8}O_6$ | Sm/Li/Sr/Cs/ $La_{3.5}Nd_{0.5}O_6$ |
| Sr/Cs/La | Sr/Cs/La/ $La_{4-x}Nd_xO_6$ | Sr/Cs/La/ $LaNd_3O_6$ | Sr/Cs/La/ $La_{1.5}Nd_{2.5}O_6$ | Sr/Cs/La/ $La_{2.5}Nd_{1.5}O_6$ | Sr/Cs/La/ $La_{3.2}Nd_{0.8}O_6$ | Sr/Cs/La/ $La_{3.5}Nd_{0.5}O_6$ |
| Sr/Tm/Li/Cs | Sr/Tm/Li/Cs/ $La_{4-x}Nd_xO_6$ | Sr/Tm/Li/Cs/ $LaNd_3O_6$ | Sr/Tm/Li/Cs/ $La_{1.5}Nd_{2.5}O_6$ | Sr/Tm/Li/Cs/ $La_{2.5}Nd_{1.5}O_6$ | Sr/Tm/Li/Cs/ $La_{3.2}Nd_{0.8}O_6$ | Sr/Tm/Li/Cs/ $La_{3.5}Nd_{0.5}O_6$ |
| Zn/K | Zn/K/ $La_{4-x}Nd_xO_6$ | Zn/K/ $LaNd_3O_6$ | Zn/K/ $La_{1.5}Nd_{2.5}O_6$ | Zn/K/ $La_{2.5}Nd_{1.5}O_6$ | Zn/K/ $La_{3.2}Nd_{0.8}O_6$ | Zn/K/ $La_{3.5}Nd_{0.5}O_6$ |
| Zr/Cs/K/La | Zr/Cs/K/La/ $La_{4-x}Nd_xO_6$ | Zr/Cs/K/La/ $LaNd_3O_6$ | Zr/Cs/K/La/ $La_{1.5}Nd_{2.5}O_6$ | Zr/Cs/K/La/ $La_{2.5}Nd_{1.5}O_6$ | Zr/Cs/K/La/ $La_{3.2}Nd_{0.8}O_6$ | Zr/Cs/K/La/ $La_{3.5}Nd_{0.5}O_6$ |
| Rb/Ca/In/Ni | Rb/Ca/In/Ni/ $La_{4-x}Nd_xO_6$ | Rb/Ca/In/Ni/ $LaNd_3O_6$ | Rb/Ca/In/Ni/ $La_{1.5}Nd_{2.5}O_6$ | Rb/Ca/In/Ni/ $La_{2.5}Nd_{1.5}O_6$ | Rb/Ca/In/Ni/ $La_{3.2}Nd_{0.8}O_6$ | Rb/Ca/In/Ni/ $La_{3.5}Nd_{0.5}O_6$ |
| Sr/Ho/Tm | Sr/Ho/Tm/ $La_{4-x}Nd_xO_6$ | Sr/Ho/Tm/ $LaNd_3O_6$ | Sr/Ho/Tm/ $La_{1.5}Nd_{2.5}O_6$ | Sr/Ho/Tm/ $La_{2.5}Nd_{1.5}O_6$ | Sr/Ho/Tm/ $La_{3.2}Nd_{0.8}O_6$ | Sr/Ho/Tm/ $La_{3.5}Nd_{0.5}O_6$ |
| La/Nd/S | La/Nd/S/ $La_{4-x}Nd_xO_6$ | La/Nd/S/ $LaNd_3O_6$ | La/Nd/S/ $La_{1.5}Nd_{2.5}O_6$ | La/Nd/S/ $La_{2.5}Nd_{1.5}O_6$ | La/Nd/S/ $La_{3.2}Nd_{0.8}O_6$ | La/Nd/S/ $La_{3.5}Nd_{0.5}O_6$ |
| Sr/Hf/Rb | Sr/Hf/Rb/ $La_{4-x}Nd_xO_6$ | Sr/Hf/Rb/ $LaNd_3O_6$ | Sr/Hf/Rb/ $La_{1.5}Nd_{2.5}O_6$ | Sr/Hf/Rb/ $La_{2.5}Nd_{1.5}O_6$ | Sr/Hf/Rb/ $La_{3.2}Nd_{0.8}O_6$ | Sr/Hf/Rb/ $La_{3.5}Nd_{0.5}O_6$ |
| Li/Rb/Ca | Li/Rb/Ca/ $La_{4-x}Nd_xO_6$ | Li/Rb/Ca/ $LaNd_3O_6$ | Li/Rb/Ca/ $La_{1.5}Nd_{2.5}O_6$ | Li/Rb/Ca/ $La_{2.5}Nd_{1.5}O_6$ | Li/Rb/Ca/ $La_{3.2}Nd_{0.8}O_6$ | Li/Rb/Ca/ $La_{3.5}Nd_{0.5}O_6$ |
| Li/K | Li/K/ $La_{4-x}Nd_xO_6$ | Li/K/ $LaNd_3O_6$ | Li/K/ $La_{1.5}Nd_{2.5}O_6$ | Li/K/ $La_{2.5}Nd_{1.5}O_6$ | Li/K/ $La_{3.2}Nd_{0.8}O_6$ | Li/K/ $La_{3.5}Nd_{0.5}O_6$ |
| Tm/Lu/Ta/P | Tm/Lu/Ta/P/ $La_{4-x}Nd_xO_6$ | Tm/Lu/Ta/P/ $LaNd_3O_6$ | Tm/Lu/Ta/P/ $La_{1.5}Nd_{2.5}O_6$ | Tm/Lu/Ta/P/ $La_{2.5}Nd_{1.5}O_6$ | Tm/Lu/Ta/P/ $La_{3.2}Nd_{0.8}O_6$ | Tm/Lu/Ta/P/ $La_{3.5}Nd_{0.5}O_6$ |
| Rb/Ca/Dy/P | Rb/Ca/Dy/P/ $La_{4-x}Nd_xO_6$ | Rb/Ca/Dy/P/ $LaNd_3O_6$ | Rb/Ca/Dy/P/ $La_{1.5}Nd_{2.5}O_6$ | Rb/Ca/Dy/P/ $La_{2.5}Nd_{1.5}O_6$ | Rb/Ca/Dy/P/ $La_{3.2}Nd_{0.8}O_6$ | Rb/Ca/Dy/P/ $La_{3.5}Nd_{0.5}O_6$ |
| Mg/La/Yb/Zn | Mg/La/Yb/Zn/ $La_{4-x}Nd_xO_6$ | Mg/La/Yb/Zn/ $LaNd_3O_6$ | Mg/La/Yb/Zn/ $La_{1.5}Nd_{2.5}O_6$ | Mg/La/Yb/Zn/ $La_{2.5}Nd_{1.5}O_6$ | Mg/La/Yb/Zn/ $La_{3.2}Nd_{0.8}O_6$ | Mg/La/Yb/Zn/ $La_{3.5}Nd_{0.5}O_6$ |
| Rb/Sr/Lu | Rb/Sr/Lu/ $La_{4-x}Nd_xO_6$ | Rb/Sr/Lu/ $LaNd_3O_6$ | Rb/Sr/Lu/ $La_{1.5}Nd_{2.5}O_6$ | Rb/Sr/Lu/ $La_{2.5}Nd_{1.5}O_6$ | Rb/Sr/Lu/ $La_{3.2}Nd_{0.8}O_6$ | Rb/Sr/Lu/ $La_{3.5}Nd_{0.5}O_6$ |

TABLE 10-continued

Nanowires (NW) Doped With Specific Dopants (Dop)

| Dop\NW | $La_{4-x}Nd_xO_6$* | $LaNd_3O_6$ | $La_{1.5}Nd_{2.5}O_6$ | $La_{2.5}Nd_{1.5}O_6$ | $La_{3.2}Nd_{0.8}O_6$ | $La_{3.5}Nd_{0.5}O_6$ |
|---|---|---|---|---|---|---|
| Na/Sr/Lu/Nb | Na/Sr/Lu/Nb/$La_{4-x}Nd_xO_6$ | Na/Sr/Lu/Nb/$LaNd_3O_6$ | Na/Sr/Lu/Nb/$La_{1.5}Nd_{2.5}O_6$ | Na/Sr/Lu/Nb/$La_{2.5}Nd_{1.5}O_6$ | Na/Sr/Lu/Nb/$La_{3.2}Nd_{0.8}O_6$ | Na/Sr/Lu/Nb/$La_{3.5}Nd_{0.5}O_6$ |
| Na/Eu/Hf | Na/Eu/Hf/$La_{4-x}Nd_xO_6$ | Na/Eu/Hf/$LaNd_3O_6$ | Na/Eu/Hf/$La_{1.5}Nd_{2.5}O_6$ | Na/Eu/Hf/$La_{2.5}Nd_{1.5}O_6$ | Na/Eu/Hf/$La_{3.2}Nd_{0.8}O_6$ | Na/Eu/Hf/$La_{3.5}Nd_{0.5}O_6$ |
| Dy/Rb/Gd | Dy/Rb/Gd/$La_{4-x}Nd_xO_6$ | Dy/Rb/Gd/$LaNd_3O_6$ | Dy/Rb/Gd/$La_{1.5}Nd_{2.5}O_6$ | Dy/Rb/Gd/$La_{2.5}Nd_{1.5}O_6$ | Dy/Rb/Gd/$La_{3.2}Nd_{0.8}O_6$ | Dy/Rb/Gd/$La_{3.5}Nd_{0.5}O_6$ |
| Na/Pt/Bi | Na/Pt/Bi/$La_{4-x}Nd_xO_6$ | Na/Pt/Bi/$LaNd_3O_6$ | Na/Pt/Bi/$La_{1.5}Nd_{2.5}O_6$ | Na/Pt/Bi/$La_{2.5}Nd_{1.5}O_6$ | Na/Pt/Bi/$La_{3.2}Nd_{0.8}O_6$ | Na/Pt/Bi/$La_{3.5}Nd_{0.5}O_6$ |
| Rb/Hf | Rb/Hf/$La_{4-x}Nd_xO_6$ | Rb/Hf/$LaNd_3O_6$ | Rb/Hf/$La_{1.5}Nd_{2.5}O_6$ | Rb/Hf/$La_{2.5}Nd_{1.5}O_6$ | Rb/Hf/$La_{3.2}Nd_{0.8}O_6$ | Rb/Hf/$La_{3.5}Nd_{0.5}O_6$ |
| Ca/Cs | Ca/Cs/$La_{4-x}Nd_xO_6$ | Ca/Cs/$LaNd_3O_6$ | Ca/Cs/$La_{1.5}Nd_{2.5}O_6$ | Ca/Cs/$La_{2.5}Nd_{1.5}O_6$ | Ca/Cs/$La_{3.2}Nd_{0.8}O_6$ | Ca/Cs/$La_{3.5}Nd_{0.5}O_6$ |
| Ca/Mg/Na | Ca/Mg/Na/$La_{4-x}Nd_xO_6$ | Ca/Mg/Na/$LaNd_3O_6$ | Ca/Mg/Na/$La_{1.5}Nd_{2.5}O_6$ | Ca/Mg/Na/$La_{2.5}Nd_{1.5}O_6$ | Ca/Mg/Na/$La_{3.2}Nd_{0.8}O_6$ | Ca/Mg/Na/$La_{3.5}Nd_{0.5}O_6$ |
| Hf/Bi | Hf/Bi/$La_{4-x}Nd_xO_6$ | Hf/Bi/$LaNd_3O_6$ | Hf/Bi/$La_{1.5}Nd_{2.5}O_6$ | Hf/Bi/$La_{2.5}Nd_{1.5}O_6$ | Hf/Bi/$La_{3.2}Nd_{0.8}O_6$ | Hf/Bi/$La_{3.5}Nd_{0.5}O_6$ |
| Sr/Sn | Sr/Sn/$La_{4-x}Nd_xO_6$ | Sr/Sn/$LaNd_3O_6$ | Sr/Sn/$La_{1.5}Nd_{2.5}O_6$ | Sr/Sn/$La_{2.5}Nd_{1.5}O_6$ | Sr/Sn/$La_{3.2}Nd_{0.8}O_6$ | Sr/Sn/$La_{3.5}Nd_{0.5}O_6$ |
| Sr/W | Sr/W/$La_{4-x}Nd_xO_6$ | Sr/W/$LaNd_3O_6$ | Sr/W/$La_{1.5}Nd_{2.5}O_6$ | Sr/W/$La_{2.5}Nd_{1.5}O_6$ | Sr/W/$La_{3.2}Nd_{0.8}O_6$ | Sr/W/$La_{3.5}Nd_{0.5}O_6$ |
| Sr/Nb | Sr/Nb/$La_{4-x}Nd_xO_6$ | Sr/Nb/$LaNd_3O_6$ | Sr/Nb/$La_{1.5}Nd_{2.5}O_6$ | Sr/Nb/$La_{2.5}Nd_{1.5}O_6$ | Sr/Nb/$La_{3.2}Nd_{0.8}O_6$ | Sr/Nb/$La_{3.5}Nd_{0.5}O_6$ |
| Zr/W | Zr/W/$La_{4-x}Nd_xO_6$ | Zr/W/$LaNd_3O_6$ | Zr/W/$La_{1.5}Nd_{2.5}O_6$ | Zr/W/$La_{2.5}Nd_{1.5}O_6$ | Zr/W/$La_{3.2}Nd_{0.8}O_6$ | Zr/W/$La_{3.5}Nd_{0.5}O_6$ |
| Sr/Hf/K | Sr/Hf/K/$La_{4-x}Nd_xO_6$ | Sr/Hf/K/$LaNd_3O_6$ | Sr/Hf/K/$La_{1.5}Nd_{2.5}O_6$ | Sr/Hf/K/$La_{2.5}Nd_{1.5}O_6$ | Sr/Hf/K/$La_{3.2}Nd_{0.8}O_6$ | Sr/Hf/K/$La_{3.5}Nd_{0.5}O_6$ |
| Y/W | Y/W/$La_{4-x}Nd_xO_6$ | Y/W/$LaNd_3O_6$ | Y/W/$La_{1.5}Nd_{2.5}O_6$ | Y/W/$La_{2.5}Nd_{1.5}O_6$ | Y/W/$La_{3.2}Nd_{0.8}O_6$ | Y/W/$La_{3.5}Nd_{0.5}O_6$ |
| Na/W | Na/W/$La_{4-x}Nd_xO_6$ | Na/W/$LaNd_3O_6$ | Na/W/$La_{1.5}Nd_{2.5}O_6$ | Na/W/$La_{2.5}Nd_{1.5}O_6$ | Na/W/$La_{3.2}Nd_{0.8}O_6$ | Na/W/$La_{3.5}Nd_{0.5}O_6$ |
| Bi/W | Bi/W/$La_{4-x}Nd_xO_6$ | Bi/W/$LaNd_3O_6$ | Bi/W/$La_{1.5}Nd_{2.5}O_6$ | Bi/W/$La_{2.5}Nd_{1.5}O_6$ | Bi/W/$La_{3.2}Nd_{0.8}O_6$ | Bi/W/$La_{3.5}Nd_{0.5}O_6$ |
| Bi/Cs | Bi/Cs/$La_{4-x}Nd_xO_6$ | Bi/Cs/$LaNd_3O_6$ | Bi/Cs/$La_{1.5}Nd_{2.5}O_6$ | Bi/Cs/$La_{2.5}Nd_{1.5}O_6$ | Bi/Cs/$La_{3.2}Nd_{0.8}O_6$ | Bi/Cs/$La_{3.5}Nd_{0.5}O_6$ |
| Bi/Ca | Bi/Ca/$La_{4-x}Nd_xO_6$ | Bi/Ca/$LaNd_3O_6$ | Bi/Ca/$La_{1.5}Nd_{2.5}O_6$ | Bi/Ca/$La_{2.5}Nd_{1.5}O_6$ | Bi/Ca/$La_{3.2}Nd_{0.8}O_6$ | Bi/Ca/$La_{3.5}Nd_{0.5}O_6$ |
| Bi/Sn | Bi/Sn/$La_{4-x}Nd_xO_6$ | Bi/Sn/$LaNd_3O_6$ | Bi/Sn/$La_{1.5}Nd_{2.5}O_6$ | Bi/Sn/$La_{2.5}Nd_{1.5}O_6$ | Bi/Sn/$La_{3.2}Nd_{0.8}O_6$ | Bi/Sn/$La_{3.5}Nd_{0.5}O_6$ |
| Bi/Sb | Bi/Sb/$La_{4-x}Nd_xO_6$ | Bi/Sb/$LaNd_3O_6$ | Bi/Sb/$La_{1.5}Nd_{2.5}O_6$ | Bi/Sb/$La_{2.5}Nd_{1.5}O_6$ | Bi/Sb/$La_{3.2}Nd_{0.8}O_6$ | Bi/Sb/$La_{3.5}Nd_{0.5}O_6$ |
| Ge/Hf | Ge/Hf/$La_{4-x}Nd_xO_6$ | Ge/Hf/$LaNd_3O_6$ | Ge/Hf/$La_{1.5}Nd_{2.5}O_6$ | Ge/Hf/$La_{2.5}Nd_{1.5}O_6$ | Ge/Hf/$La_{3.2}Nd_{0.8}O_6$ | Ge/Hf/$La_{3.5}Nd_{0.5}O_6$ |
| Hf/Sm | Hf/Sm/$La_{4-x}Nd_xO_6$ | Hf/Sm/$LaNd_3O_6$ | Hf/Sm/$La_{1.5}Nd_{2.5}O_6$ | Hf/Sm/$La_{2.5}Nd_{1.5}O_6$ | Hf/Sm/$La_{3.2}Nd_{0.8}O_6$ | Hf/Sm/$La_{3.5}Nd_{0.5}O_6$ |
| Sb/Ag | Sb/Ag/$La_{4-x}Nd_xO_6$ | Sb/Ag/$LaNd_3O_6$ | Sb/Ag/$La_{1.5}Nd_{2.5}O_6$ | Sb/Ag/$La_{2.5}Nd_{1.5}O_6$ | Sb/Ag/$La_{3.2}Nd_{0.8}O_6$ | Sb/Ag/$La_{3.5}Nd_{0.5}O_6$ |
| Sb/Bi | Sb/Bi/$La_{4-x}Nd_xO_6$ | Sb/Bi/$LaNd_3O_6$ | Sb/Bi/$La_{1.5}Nd_{2.5}O_6$ | Sb/Bi/$La_{2.5}Nd_{1.5}O_6$ | Sb/Bi/$La_{3.2}Nd_{0.8}O_6$ | Sb/Bi/$La_{3.5}Nd_{0.5}O_6$ |
| Sb/Au | Sb/Au/$La_{4-x}Nd_xO_6$ | Sb/Au/$LaNd_3O_6$ | Sb/Au/$La_{1.5}Nd_{2.5}O_6$ | Sb/Au/$La_{2.5}Nd_{1.5}O_6$ | Sb/Au/$La_{3.2}Nd_{0.8}O_6$ | Sb/Au/$La_{3.5}Nd_{0.5}O_6$ |
| Sr/Zr | Sr/Zr/$La_{4-x}Nd_xO_6$ | Sr/Zr/$LaNd_3O_6$ | Sr/Zr/$La_{1.5}Nd_{2.5}O_6$ | Sr/Zr/$La_{2.5}Nd_{1.5}O_6$ | Sr/Zr/$La_{3.2}Nd_{0.8}O_6$ | Sr/Zr/$La_{3.5}Nd_{0.5}O_6$ |
| Sb/Sm | Sb/Sm/$La_{4-x}Nd_xO_6$ | Sb/Sm/$LaNd_3O_6$ | Sb/Sm/$La_{1.5}Nd_{2.5}O_6$ | Sb/Sm/$La_{2.5}Nd_{1.5}O_6$ | Sb/Sm/$La_{3.2}Nd_{0.8}O_6$ | Sb/Sm/$La_{3.5}Nd_{0.5}O_6$ |
| Sb/Sr | Sb/Sr/$La_{4-x}Nd_xO_6$ | Sb/Sr/$LaNd_3O_6$ | Sb/Sr/$La_{1.5}Nd_{2.5}O_6$ | Sb/Sr/$La_{2.5}Nd_{1.5}O_6$ | Sb/Sr/$La_{3.2}Nd_{0.8}O_6$ | Sb/Sr/$La_{3.5}Nd_{0.5}O_6$ |
| Sb/W | Sb/W/$La_{4-x}Nd_xO_6$ | Sb/W/$LaNd_3O_6$ | Sb/W/$La_{1.5}Nd_{2.5}O_6$ | Sb/W/$La_{2.5}Nd_{1.5}O_6$ | Sb/W/$La_{3.2}Nd_{0.8}O_6$ | Sb/W/$La_{3.5}Nd_{0.5}O_6$ |
| Sb/Hf | Sb/Hf/$La_{4-x}Nd_xO_6$ | Sb/Hf/$LaNd_3O_6$ | Sb/Hf/$La_{1.5}Nd_{2.5}O_6$ | Sb/Hf/$La_{2.5}Nd_{1.5}O_6$ | Sb/Hf/$La_{3.2}Nd_{0.8}O_6$ | Sb/Hf/$La_{3.5}Nd_{0.5}O_6$ |
| Sb/Yb | Sb/Yb/$La_{4-x}Nd_xO_6$ | Sb/Yb/$LaNd_3O_6$ | Sb/Yb/$La_{1.5}Nd_{2.5}O_6$ | Sb/Yb/$La_{2.5}Nd_{1.5}O_6$ | Sb/Yb/$La_{3.2}Nd_{0.8}O_6$ | Sb/Yb/$La_{3.5}Nd_{0.5}O_6$ |
| Sb/Sn | Sb/Sn/$La_{4-x}Nd_xO_6$ | Sb/Sn/$LaNd_3O_6$ | Sb/Sn/$La_{1.5}Nd_{2.5}O_6$ | Sb/Sn/$La_{2.5}Nd_{1.5}O_6$ | Sb/Sn/$La_{3.2}Nd_{0.8}O_6$ | Sb/Sn/$La_{3.5}Nd_{0.5}O_6$ |
| Yb/Au | Yb/Au/$La_{4-x}Nd_xO_6$ | Yb/Au/$LaNd_3O_6$ | Yb/Au/$La_{1.5}Nd_{2.5}O_6$ | Yb/Au/$La_{2.5}Nd_{1.5}O_6$ | Yb/Au/$La_{3.2}Nd_{0.8}O_6$ | Yb/Au/$La_{3.5}Nd_{0.5}O_6$ |
| Yb/Ta | Yb/Ta/$La_{4-x}Nd_xO_6$ | Yb/Ta/$LaNd_3O_6$ | Yb/Ta/$La_{1.5}Nd_{2.5}O_6$ | Yb/Ta/$La_{2.5}Nd_{1.5}O_6$ | Yb/Ta/$La_{3.2}Nd_{0.8}O_6$ | Yb/Ta/$La_{3.5}Nd_{0.5}O_6$ |
| Yb/W | Yb/W/$La_{4-x}Nd_xO_6$ | Yb/W/$LaNd_3O_6$ | Yb/W/$La_{1.5}Nd_{2.5}O_6$ | Yb/W/$La_{2.5}Nd_{1.5}O_6$ | Yb/W/$La_{3.2}Nd_{0.8}O_6$ | Yb/W/$La_{3.5}Nd_{0.5}O_6$ |
| Yb/Sr | Yb/Sr/$La_{4-x}Nd_xO_6$ | Yb/Sr/$LaNd_3O_6$ | Yb/Sr/$La_{1.5}Nd_{2.5}O_6$ | Yb/Sr/$La_{2.5}Nd_{1.5}O_6$ | Yb/Sr/$La_{3.2}Nd_{0.8}O_6$ | Yb/Sr/$La_{3.5}Nd_{0.5}O_6$ |
| Yb/Pb | Yb/Pb/$La_{4-x}Nd_xO_6$ | Yb/Pb/$LaNd_3O_6$ | Yb/Pb/$La_{1.5}Nd_{2.5}O_6$ | Yb/Pb/$La_{2.5}Nd_{1.5}O_6$ | Yb/Pb/$La_{3.2}Nd_{0.8}O_6$ | Yb/Pb/$La_{3.5}Nd_{0.5}O_6$ |
| Yb/W | Yb/W/$La_{4-x}Nd_xO_6$ | Yb/W/$LaNd_3O_6$ | Yb/W/$La_{1.5}Nd_{2.5}O_6$ | Yb/W/$La_{2.5}Nd_{1.5}O_6$ | Yb/W/$La_{3.2}Nd_{0.8}O_6$ | Yb/W/$La_{3.5}Nd_{0.5}O_6$ |

TABLE 10-continued

Nanowires (NW) Doped With Specific Dopants (Dop)

| Dop\NW | $La_{4-x}Nd_xO_6$* | $LaNd_3O_6$ | $La_{1.5}Nd_{2.5}O_6$ | $La_{2.5}Nd_{1.5}O_6$ | $La_{3.2}Nd_{0.8}O_6$ | $La_{3.5}Nd_{0.5}O_6$ |
|---|---|---|---|---|---|---|
| Yb/Ag | Yb/Ag/ $La_{4-x}Nd_xO_6$ | Yb/Ag/ $LaNd_3O_6$ | Yb/Ag/ $La_{1.5}Nd_{2.5}O_6$ | Yb/Ag/ $La_{2.5}Nd_{1.5}O_6$ | Yb/Ag/ $La_{3.2}Nd_{0.8}O_6$ | Yb/Ag/ $La_{3.5}Nd_{0.5}O_6$ |
| Au/Sr | Au/Sr/ $La_{4-x}Nd_xO_6$ | Au/Sr/ $LaNd_3O_6$ | Au/Sr/ $La_{1.5}Nd_{2.5}O_6$ | Au/Sr/ $La_{2.5}Nd_{1.5}O_6$ | Au/Sr/ $La_{3.2}Nd_{0.8}O_6$ | Au/Sr/ $La_{3.5}Nd_{0.5}O_6$ |
| W/Ge | W/Ge/ $La_{4-x}Nd_xO_6$ | W/Ge/ $LaNd_3O_6$ | W/Ge/ $La_{1.5}Nd_{2.5}O_6$ | W/Ge/ $La_{2.5}Nd_{1.5}O_6$ | W/Ge/ $La_{3.2}Nd_{0.8}O_6$ | W/Ge/ $La_{3.5}Nd_{0.5}O_6$ |
| Ta/Sr | Ta/Sr/ $La_{4-x}Nd_xO_6$ | Ta/Sr/ $LaNd_3O_6$ | Ta/Sr/ $La_{1.5}Nd_{2.5}O_6$ | Ta/Sr/ $La_{2.5}Nd_{1.5}O_6$ | Ta/Sr/ $La_{3.2}Nd_{0.8}O_6$ | Ta/Sr/ $La_{3.5}Nd_{0.5}O_6$ |
| Ta/Hf | Ta/Hf/ $La_{4-x}Nd_xO_6$ | Ta/Hf/ $LaNd_3O_6$ | Ta/Hf/ $La_{1.5}Nd_{2.5}O_6$ | Ta/Hf/ $La_{2.5}Nd_{1.5}O_6$ | Ta/Hf/ $La_{3.2}Nd_{0.8}O_6$ | Ta/Hf/ $La_{3.5}Nd_{0.5}O_6$ |
| W/Au | W/Au/ $La_{4-x}Nd_xO_6$ | W/Au/ $LaNd_3O_6$ | W/Au/ $La_{1.5}Nd_{2.5}O_6$ | W/Au/ $La_{2.5}Nd_{1.5}O_6$ | W/Au/ $La_{3.2}Nd_{0.8}O_6$ | W/Au/ $La_{3.5}Nd_{0.5}O_6$ |
| Sr/Tb | Sr/Tb/ $La_{4-x}Nd_xO_6$ | Sr/Tb/ $LaNd_3O_6$ | Sr/Tb/ $La_{1.5}Nd_{2.5}O_6$ | Sr/Tb/ $La_{2.5}Nd_{1.5}O_6$ | Sr/Tb/ $La_{3.2}Nd_{0.8}O_6$ | Sr/Tb/ $La_{3.5}Nd_{0.5}O_6$ |
| Ca/W | Ca/W/ $La_{4-x}Nd_xO_6$ | Ca/W/ $LaNd_3O_6$ | Ca/W/ $La_{1.5}Nd_{2.5}O_6$ | Ca/W/ $La_{2.5}Nd_{1.5}O_6$ | Ca/W/ $La_{3.2}Nd_{0.8}O_6$ | Ca/W/ $La_{3.5}Nd_{0.5}O_6$ |
| Au/Re | Au/Re/ $La_{4-x}Nd_xO_6$ | Au/Re/ $LaNd_3O_6$ | Au/Re/ $La_{1.5}Nd_{2.5}O_6$ | Au/Re/ $La_{2.5}Nd_{1.5}O_6$ | Au/Re/ $La_{3.2}Nd_{0.8}O_6$ | Au/Re/ $La_{3.5}Nd_{0.5}O_6$ |
| Sm/Li | Sm/Li/ $La_{4-x}Nd_xO_6$ | Sm/Li/ $LaNd_3O_6$ | Sm/Li/ $La_{1.5}Nd_{2.5}O_6$ | Sm/Li/ $La_{2.5}Nd_{1.5}O_6$ | Sm/Li/ $La_{3.2}Nd_{0.8}O_6$ | Sm/Li/ $La_{3.5}Nd_{0.5}O_6$ |
| La/K | La/K/ $La_{4-x}Nd_xO_6$ | La/K/ $LaNd_3O_6$ | La/K/ $La_{1.5}Nd_{2.5}O_6$ | La/K/ $La_{2.5}Nd_{1.5}O_6$ | La/K/ $La_{3.2}Nd_{0.8}O_6$ | La/K/ $La_{3.5}Nd_{0.5}O_6$ |
| Zn/Cs | Zn/Cs/ $La_{4-x}Nd_xO_6$ | Zn/Cs/ $LaNd_3O_6$ | Zn/Cs/ $La_{1.5}Nd_{2.5}O_6$ | Zn/Cs/ $La_{2.5}Nd_{1.5}O_6$ | Zn/Cs/ $La_{3.2}Nd_{0.8}O_6$ | Zn/Cs/ $La_{3.5}Nd_{0.5}O_6$ |
| Na/K/Mg | Na/K/Mg/ $La_{4-x}Nd_xO_6$ | Na/K/Mg/ $LaNd_3O_6$ | Na/K/Mg/ $La_{1.5}Nd_{2.5}O_6$ | Na/K/Mg/ $La_{2.5}Nd_{1.5}O_6$ | Na/K/Mg/ $La_{3.2}Nd_{0.8}O_6$ | Na/K/Mg/ $La_{3.5}Nd_{0.5}O_6$ |
| Zr/Cs | Zr/Cs/ $La_{4-x}Nd_xO_6$ | Zr/Cs/ $LaNd_3O_6$ | Zr/Cs/ $La_{1.5}Nd_{2.5}O_6$ | Zr/Cs/ $La_{2.5}Nd_{1.5}O_6$ | Zr/Cs/ $La_{3.2}Nd_{0.8}O_6$ | Zr/Cs/ $La_{3.5}Nd_{0.5}O_6$ |
| Ca/Ce | Ca/Ce/ $La_{4-x}Nd_xO_6$ | Ca/Ce/ $LaNd_3O_6$ | Ca/Ce/ $La_{1.5}Nd_{2.5}O_6$ | Ca/Ce/ $La_{2.5}Nd_{1.5}O_6$ | Ca/Ce/ $La_{3.2}Nd_{0.8}O_6$ | Ca/Ce/ $La_{3.5}Nd_{0.5}O_6$ |
| Na/Li/Cs | Na/Li/Cs/ $La_{4-x}Nd_xO_6$ | Na/Li/Cs/ $LaNd_3O_6$ | Na/Li/Cs/ $La_{1.5}Nd_{2.5}O_6$ | Na/Li/Cs/ $La_{2.5}Nd_{1.5}O_6$ | Na/Li/Cs/ $La_{3.2}Nd_{0.8}O_6$ | Na/Li/Cs/ $La_{3.5}Nd_{0.5}O_6$ |
| Li/Sr | Li/Sr/ $La_{4-x}Nd_xO_6$ | Li/Sr/ $LaNd_3O_6$ | Li/Sr/ $La_{1.5}Nd_{2.5}O_6$ | Li/Sr/ $La_{2.5}Nd_{1.5}O_6$ | Li/Sr/ $La_{3.2}Nd_{0.8}O_6$ | Li/Sr/ $La_{3.5}Nd_{0.5}O_6$ |
| La/Dy/K | La/Dy/K/ $La_{4-x}Nd_xO_6$ | La/Dy/K/ $LaNd_3O_6$ | La/Dy/K/ $La_{1.5}Nd_{2.5}O_6$ | La/Dy/K/ $La_{2.5}Nd_{1.5}O_6$ | La/Dy/K/ $La_{3.2}Nd_{0.8}O_6$ | La/Dy/K/ $La_{3.5}Nd_{0.5}O_6$ |
| Dy/K | Dy/K/ $La_{4-x}Nd_xO_6$ | Dy/K/ $LaNd_3O_6$ | Dy/K/ $La_{1.5}Nd_{2.5}O_6$ | Dy/K/ $La_{2.5}Nd_{1.5}O_6$ | Dy/K/ $La_{3.2}Nd_{0.8}O_6$ | Dy/K/ $La_{3.5}Nd_{0.5}O_6$ |
| La/Mg | La/Mg/ $La_{4-x}Nd_xO_6$ | La/Mg/ $LaNd_3O_6$ | La/Mg/ $La_{1.5}Nd_{2.5}O_6$ | La/Mg/ $La_{2.5}Nd_{1.5}O_6$ | La/Mg/ $La_{3.2}Nd_{0.8}O_6$ | La/Mg/ $La_{3.5}Nd_{0.5}O_6$ |
| Na/Nd/In/K | Na/Nd/In/K/ $La_{4-x}Nd_xO_6$ | Na/Nd/In/K/ $LaNd_3O_6$ | Na/Nd/In/K/ $La_{1.5}Nd_{2.5}O_6$ | Na/Nd/In/K/ $La_{2.5}Nd_{1.5}O_6$ | Na/Nd/In/K/ $La_{3.2}Nd_{0.8}O_6$ | Na/Nd/In/K/ $La_{3.5}Nd_{0.5}O_6$ |
| In/Sr | In/Sr/ $La_{4-x}Nd_xO_6$ | In/Sr/ $LaNd_3O_6$ | In/Sr/ $La_{1.5}Nd_{2.5}O_6$ | In/Sr/ $La_{2.5}Nd_{1.5}O_6$ | In/Sr/ $La_{3.2}Nd_{0.8}O_6$ | In/Sr/ $La_{3.5}Nd_{0.5}O_6$ |
| Sr/Cs | Sr/Cs/ $La_{4-x}Nd_xO_6$ | Sr/Cs/ $LaNd_3O_6$ | Sr/Cs/ $La_{1.5}Nd_{2.5}O_6$ | Sr/Cs/ $La_{2.5}Nd_{1.5}O_6$ | Sr/Cs/ $La_{3.2}Nd_{0.8}O_6$ | Sr/Cs/ $La_{3.5}Nd_{0.5}O_6$ |
| Sr/Ce | Sr/Ce/ $La_{4-x}Nd_xO_6$ | Sr/Ce/ $LaNd_3O_6$ | Sr/Ce/ $La_{1.5}Nd_{2.5}O_6$ | Sr/Ce/ $La_{2.5}Nd_{1.5}O_6$ | Sr/Ce/ $La_{3.2}Nd_{0.8}O_6$ | Sr/Ce/ $La_{3.5}Nd_{0.5}O_6$ |
| Rb/Ga/Tm/Cs | Rb/Ga/Tm/Cs/ $La_{4-x}Nd_xO_6$ | Rb/Ga/Tm/Cs/ $LaNd_3O_6$ | Rb/Ga/Tm/Cs/ $La_{1.5}Nd_{2.5}O_6$ | Rb/Ga/Tm/Cs/ $La_{2.5}Nd_{1.5}O_6$ | Rb/Ga/Tm/Cs/ $La_{3.2}Nd_{0.8}O_6$ | Rb/Ga/Tm/Cs/ $La_{3.5}Nd_{0.5}O_6$ |
| Ga/Cs | Ga/Cs/ $La_{4-x}Nd_xO_6$ | Ga/Cs/ $LaNd_3O_6$ | Ga/Cs/ $La_{1.5}Nd_{2.5}O_6$ | Ga/Cs/ $La_{2.5}Nd_{1.5}O_6$ | Ga/Cs/ $La_{3.2}Nd_{0.8}O_6$ | Ga/Cs/ $La_{3.5}Nd_{0.5}O_6$ |
| K/La/Zr/Ag | K/La/Zr/Ag/ $La_{4-x}Nd_xO_6$ | K/La/Zr/Ag/ $LaNd_3O_6$ | K/La/Zr/Ag/ $La_{1.5}Nd_{2.5}O_6$ | K/La/Zr/Ag/ $La_{2.5}Nd_{1.5}O_6$ | K/La/Zr/Ag/ $La_{3.2}Nd_{0.8}O_6$ | K/La/Zr/Ag/ $La_{3.5}Nd_{0.5}O_6$ |
| Lu/Fe | Lu/Fe/ $La_{4-x}Nd_xO_6$ | Lu/Fe/ $LaNd_3O_6$ | Lu/Fe/ $La_{1.5}Nd_{2.5}O_6$ | Lu/Fe/ $La_{2.5}Nd_{1.5}O_6$ | Lu/Fe/ $La_{3.2}Nd_{0.8}O_6$ | Lu/Fe/ $La_{3.5}Nd_{0.5}O_6$ |
| Sr/Tm | Sr/Tm/ $La_{4-x}Nd_xO_6$ | Sr/Tm/ $LaNd_3O_6$ | Sr/Tm/ $La_{1.5}Nd_{2.5}O_6$ | Sr/Tm/ $La_{2.5}Nd_{1.5}O_6$ | Sr/Tm/ $La_{3.2}Nd_{0.8}O_6$ | Sr/Tm/ $La_{3.5}Nd_{0.5}O_6$ |
| La/Dy | La/Dy/ $La_{4-x}Nd_xO_6$ | La/Dy/ $LaNd_3O_6$ | La/Dy/ $La_{1.5}Nd_{2.5}O_6$ | La/Dy/ $La_{2.5}Nd_{1.5}O_6$ | La/Dy/ $La_{3.2}Nd_{0.8}O_6$ | La/Dy/ $La_{3.5}Nd_{0.5}O_6$ |
| Sm/Li/Sr | Sm/Li/Sr/ $La_{4-x}Nd_xO_6$ | Sm/Li/Sr/ $LaNd_3O_6$ | Sm/Li/Sr/ $La_{1.5}Nd_{2.5}O_6$ | Sm/Li/Sr/ $La_{2.5}Nd_{1.5}O_6$ | Sm/Li/Sr/ $La_{3.2}Nd_{0.8}O_6$ | Sm/Li/Sr/ $La_{3.5}Nd_{0.5}O_6$ |
| Sr/Zr/K | Sr/Zr/K/ $La_{4-x}Nd_xO_6$ | Sr/Zr/K/ $LaNd_3O_6$ | Sr/Zr/K/ $La_{1.5}Nd_{2.5}O_6$ | Sr/Zr/K/ $La_{2.5}Nd_{1.5}O_6$ | Sr/Zr/K/ $La_{3.2}Nd_{0.8}O_6$ | Sr/Zr/K/ $La_{3.5}Nd_{0.5}O_6$ |
| Mg/K | Mg/K/ $La_{4-x}Nd_xO_6$ | Mg/K/ $LaNd_3O_6$ | Mg/K/ $La_{1.5}Nd_{2.5}O_6$ | Mg/K/ $La_{2.5}Nd_{1.5}O_6$ | Mg/K/ $La_{3.2}Nd_{0.8}O_6$ | Mg/K/ $La_{3.5}Nd_{0.5}O_6$ |
| Li/Rb/Ga | Li/Rb/Ga/ $La_{4-x}Nd_xO_6$ | Li/Rb/Ga/ $LaNd_3O_6$ | Li/Rb/Ga/ $La_{1.5}Nd_{2.5}O_6$ | Li/Rb/Ga/ $La_{2.5}Nd_{1.5}O_6$ | Li/Rb/Ga/ $La_{3.2}Nd_{0.8}O_6$ | Li/Rb/Ga/ $La_{3.5}Nd_{0.5}O_6$ |
| Li/Cs/Tm | Li/Cs/Tm/ $La_{4-x}Nd_xO_6$ | Li/Cs/Tm/ $LaNd_3O_6$ | Li/Cs/Tm/ $La_{1.5}Nd_{2.5}O_6$ | Li/Cs/Tm/ $La_{2.5}Nd_{1.5}O_6$ | Li/Cs/Tm/ $La_{3.2}Nd_{0.8}O_6$ | Li/Cs/Tm/ $La_{3.5}Nd_{0.5}O_6$ |
| Zr/K | Zr/K/ $La_{4-x}Nd_xO_6$ | Zr/K/ $LaNd_3O_6$ | Zr/K/ $La_{1.5}Nd_{2.5}O_6$ | Zr/K/ $La_{2.5}Nd_{1.5}O_6$ | Zr/K/ $La_{3.2}Nd_{0.8}O_6$ | Zr/K/ $La_{3.5}Nd_{0.5}O_6$ |
| Li/Cs | Li/Cs/ $La_{4-x}Nd_xO_6$ | Li/Cs/ $LaNd_3O_6$ | Li/Cs/ $La_{1.5}Nd_{2.5}O_6$ | Li/Cs/ $La_{2.5}Nd_{1.5}O_6$ | Li/Cs/ $La_{3.2}Nd_{0.8}O_6$ | Li/Cs/ $La_{3.5}Nd_{0.5}O_6$ |
| Li/K/La | Li/K/La/ $La_{4-x}Nd_xO_6$ | Li/K/La/ $LaNd_3O_6$ | Li/K/La/ $La_{1.5}Nd_{2.5}O_6$ | Li/K/La/ $La_{2.5}Nd_{1.5}O_6$ | Li/K/La/ $La_{3.2}Nd_{0.8}O_6$ | Li/K/La/ $La_{3.5}Nd_{0.5}O_6$ |

TABLE 10-continued

Nanowires (NW) Doped With Specific Dopants (Dop)

| Dop\NW | $La_{4-x}Nd_xO_6$* | $LaNd_3O_6$ | $La_{1.5}Nd_{2.5}O_6$ | $La_{2.5}Nd_{1.5}O_6$ | $La_{3.2}Nd_{0.8}O_6$ | $La_{3.5}Nd_{0.5}O_6$ |
|---|---|---|---|---|---|---|
| Ce/Zr/La | Ce/Zr/La/$La_{4-x}Nd_xO_6$ | Ce/Zr/La/$LaNd_3O_6$ | Ce/Zr/La/$La_{1.5}Nd_{2.5}O_6$ | Ce/Zr/La/$La_{2.5}Nd_{1.5}O_6$ | Ce/Zr/La/$La_{3.2}Nd_{0.8}O_6$ | Ce/Zr/La/$La_{3.5}Nd_{0.5}O_6$ |
| Ca/Al/La | Ca/Al/La/$La_{4-x}Nd_xO_6$ | Ca/Al/La/$LaNd_3O_6$ | Ca/Al/La/$La_{1.5}Nd_{2.5}O_6$ | Ca/Al/La/$La_{2.5}Nd_{1.5}O_6$ | Ca/Al/La/$La_{3.2}Nd_{0.8}O_6$ | Ca/Al/La/$La_{3.5}Nd_{0.5}O_6$ |
| Sr/Zn/La | Sr/Zn/La/$La_{4-x}Nd_xO_6$ | Sr/Zn/La/$LaNd_3O_6$ | Sr/Zn/La/$La_{1.5}Nd_{2.5}O_6$ | Sr/Zn/La/$La_{2.5}Nd_{1.5}O_6$ | Sr/Zn/La/$La_{3.2}Nd_{0.8}O_6$ | Sr/Zn/La/$La_{3.5}Nd_{0.5}O_6$ |
| Sr/Cs/Zn | Sr/Cs/Zn/$La_{4-x}Nd_xO_6$ | Sr/Cs/Zn/$LaNd_3O_6$ | Sr/Cs/Zn/$La_{1.5}Nd_{2.5}O_6$ | Sr/Cs/Zn/$La_{2.5}Nd_{1.5}O_6$ | Sr/Cs/Zn/$La_{3.2}Nd_{0.8}O_6$ | Sr/Cs/Zn/$La_{3.5}Nd_{0.5}O_6$ |
| Sm/Cs | Sm/Cs/$La_{4-x}Nd_xO_6$ | Sm/Cs/$LaNd_3O_6$ | Sm/Cs/$La_{1.5}Nd_{2.5}O_6$ | Sm/Cs/$La_{2.5}Nd_{1.5}O_6$ | Sm/Cs/$La_{3.2}Nd_{0.8}O_6$ | Sm/Cs/$La_{3.5}Nd_{0.5}O_6$ |
| In/K | In/K/$La_{4-x}Nd_xO_6$ | In/K/$LaNd_3O_6$ | In/K/$La_{1.5}Nd_{2.5}O_6$ | In/K/$La_{2.5}Nd_{1.5}O_6$ | In/K/$La_{3.2}Nd_{0.8}O_6$ | In/K/$La_{3.5}Nd_{0.5}O_6$ |
| Ho/Cs/Li/La | Ho/Cs/Li/La/$La_{4-x}Nd_xO_6$ | Ho/Cs/Li/La/$LaNd_3O_6$ | Ho/Cs/Li/La/$La_{1.5}Nd_{2.5}O_6$ | Ho/Cs/Li/La/$La_{2.5}Nd_{1.5}O_6$ | Ho/Cs/Li/La/$La_{3.2}Nd_{0.8}O_6$ | Ho/Cs/Li/La/$La_{3.5}Nd_{0.5}O_6$ |
| Cs/La/Na | Cs/La/Na/$La_{4-x}Nd_xO_6$ | Cs/La/Na/$LaNd_3O_6$ | Cs/La/Na/$La_{1.5}Nd_{2.5}O_6$ | Cs/La/Na/$La_{2.5}Nd_{1.5}O_6$ | Cs/La/Na/$La_{3.2}Nd_{0.8}O_6$ | Cs/La/Na/$La_{3.5}Nd_{0.5}O_6$ |
| La/S/Sr | La/S/Sr/$La_{4-x}Nd_xO_6$ | La/S/Sr/$LaNd_3O_6$ | La/S/Sr/$La_{1.5}Nd_{2.5}O_6$ | La/S/Sr/$La_{2.5}Nd_{1.5}O_6$ | La/S/Sr/$La_{3.2}Nd_{0.8}O_6$ | La/S/Sr/$La_{3.5}Nd_{0.5}O_6$ |
| K/La/Zr/Ag | K/La/Zr/Ag/$La_{4-x}Nd_xO_6$ | K/La/Zr/Ag/$LaNd_3O_6$ | K/La/Zr/Ag/$La_{1.5}Nd_{2.5}O_6$ | K/La/Zr/Ag/$La_{2.5}Nd_{1.5}O_6$ | K/La/Zr/Ag/$La_{3.2}Nd_{0.8}O_6$ | K/La/Zr/Ag/$La_{3.5}Nd_{0.5}O_6$ |
| Lu/Tl | Lu/Tl/$La_{4-x}Nd_xO_6$ | Lu/Tl/$LaNd_3O_6$ | Lu/Tl/$La_{1.5}Nd_{2.5}O_6$ | Lu/Tl/$La_{2.5}Nd_{1.5}O_6$ | Lu/Tl/$La_{3.2}Nd_{0.8}O_6$ | Lu/Tl/$La_{3.5}Nd_{0.5}O_6$ |
| Pr/Zn | Pr/Zn/$La_{4-x}Nd_xO_6$ | Pr/Zn/$LaNd_3O_6$ | Pr/Zn/$La_{1.5}Nd_{2.5}O_6$ | Pr/Zn/$La_{2.5}Nd_{1.5}O_6$ | Pr/Zn/$La_{3.2}Nd_{0.8}O_6$ | Pr/Zn/$La_{3.5}Nd_{0.5}O_6$ |
| Rb/Sr/La | Rb/Sr/La/$La_{4-x}Nd_xO_6$ | Rb/Sr/La/$LaNd_3O_6$ | Rb/Sr/La/$La_{1.5}Nd_{2.5}O_6$ | Rb/Sr/La/$La_{2.5}Nd_{1.5}O_6$ | Rb/Sr/La/$La_{3.2}Nd_{0.8}O_6$ | Rb/Sr/La/$La_{3.5}Nd_{0.5}O_6$ |
| Sr/Ce/K | Sr/Ce/K/$La_{4-x}Nd_xO_6$ | Sr/Ce/K/$LaNd_3O_6$ | Sr/Ce/K/$La_{1.5}Nd_{2.5}O_6$ | Sr/Ce/K/$La_{2.5}Nd_{1.5}O_6$ | Sr/Ce/K/$La_{3.2}Nd_{0.8}O_6$ | Sr/Ce/K/$La_{3.5}Nd_{0.5}O_6$ |
| Na/Sr/Eu/Ca | Na/Sr/Eu/Ca/$La_{4-x}Nd_xO_6$ | Na/Sr/Eu/Ca/$LaNd_3O_6$ | Na/Sr/Eu/Ca/$La_{1.5}Nd_{2.5}O_6$ | Na/Sr/Eu/Ca/$La_{2.5}Nd_{1.5}O_6$ | Na/Sr/Eu/Ca/$La_{3.2}Nd_{0.8}O_6$ | Na/Sr/Eu/Ca/$La_{3.5}Nd_{0.5}O_6$ |
| K/Cs/Sr/La | K/Cs/Sr/La/$La_{4-x}Nd_xO_6$ | K/Cs/Sr/La/$LaNd_3O_6$ | K/Cs/Sr/La/$La_{1.5}Nd_{2.5}O_6$ | K/Cs/Sr/La/$La_{2.5}Nd_{1.5}O_6$ | K/Cs/Sr/La/$La_{3.2}Nd_{0.8}O_6$ | K/Cs/Sr/La/$La_{3.5}Nd_{0.5}O_6$ |
| Na/Sr/Lu | Na/Sr/Lu/$La_{4-x}Nd_xO_6$ | Na/Sr/Lu/$LaNd_3O_6$ | Na/Sr/Lu/$La_{1.5}Nd_{2.5}O_6$ | Na/Sr/Lu/$La_{2.5}Nd_{1.5}O_6$ | Na/Sr/Lu/$La_{3.2}Nd_{0.8}O_6$ | Na/Sr/Lu/$La_{3.5}Nd_{0.5}O_6$ |
| Sr/Eu/Dy | Sr/Eu/Dy/$La_{4-x}Nd_xO_6$ | Sr/Eu/Dy/$LaNd_3O_6$ | Sr/Eu/Dy/$La_{1.5}Nd_{2.5}O_6$ | Sr/Eu/Dy/$La_{2.5}Nd_{1.5}O_6$ | Sr/Eu/Dy/$La_{3.2}Nd_{0.8}O_6$ | Sr/Eu/Dy/$La_{3.5}Nd_{0.5}O_6$ |
| Lu/Nb | Lu/Nb/$La_{4-x}Nd_xO_6$ | Lu/Nb/$LaNd_3O_6$ | Lu/Nb/$La_{1.5}Nd_{2.5}O_6$ | Lu/Nb/$La_{2.5}Nd_{1.5}O_6$ | Lu/Nb/$La_{3.2}Nd_{0.8}O_6$ | Lu/Nb/$La_{3.5}Nd_{0.5}O_6$ |
| La/Dy/Gd | La/Dy/Gd/$La_{4-x}Nd_xO_6$ | La/Dy/Gd/$LaNd_3O_6$ | La/Dy/Gd/$La_{1.5}Nd_{2.5}O_6$ | La/Dy/Gd/$La_{2.5}Nd_{1.5}O_6$ | La/Dy/Gd/$La_{3.2}Nd_{0.8}O_6$ | La/Dy/Gd/$La_{3.5}Nd_{0.5}O_6$ |
| Na/Mg/Tl/P | Na/Mg/Tl/P/$La_{4-x}Nd_xO_6$ | Na/Mg/Tl/P/$LaNd_3O_6$ | Na/Mg/Tl/P/$La_{1.5}Nd_{2.5}O_6$ | Na/Mg/Tl/P/$La_{2.5}Nd_{1.5}O_6$ | Na/Mg/Tl/P/$La_{3.2}Nd_{0.8}O_6$ | Na/Mg/Tl/P/$La_{3.5}Nd_{0.5}O_6$ |
| Na/Pt | Na/Pt/$La_{4-x}Nd_xO_6$ | Na/Pt/$LaNd_3O_6$ | Na/Pt/$La_{1.5}Nd_{2.5}O_6$ | Na/Pt/$La_{2.5}Nd_{1.5}O_6$ | Na/Pt/$La_{3.2}Nd_{0.8}O_6$ | Na/Pt/$La_{3.5}Nd_{0.5}O_6$ |
| Gd/Li/K | Gd/Li/K/$La_{4-x}Nd_xO_6$ | Gd/Li/K/$LaNd_3O_6$ | Gd/Li/K/$La_{1.5}Nd_{2.5}O_6$ | Gd/Li/K/$La_{2.5}Nd_{1.5}O_6$ | Gd/Li/K/$La_{3.2}Nd_{0.8}O_6$ | Gd/Li/K/$La_{3.5}Nd_{0.5}O_6$ |
| Rb/K/Lu | Rb/K/Lu/$La_{4-x}Nd_xO_6$ | Rb/K/Lu/$LaNd_3O_6$ | Rb/K/Lu/$La_{1.5}Nd_{2.5}O_6$ | Rb/K/Lu/$La_{2.5}Nd_{1.5}O_6$ | Rb/K/Lu/$La_{3.2}Nd_{0.8}O_6$ | Rb/K/Lu/$La_{3.5}Nd_{0.5}O_6$ |
| Sr/La/Dy/S | Sr/La/Dy/S/$La_{4-x}Nd_xO_6$ | Sr/La/Dy/S/$LaNd_3O_6$ | Sr/La/Dy/S/$La_{1.5}Nd_{2.5}O_6$ | Sr/La/Dy/S/$La_{2.5}Nd_{1.5}O_6$ | Sr/La/Dy/S/$La_{3.2}Nd_{0.8}O_6$ | Sr/La/Dy/S/$La_{3.5}Nd_{0.5}O_6$ |
| Na/Ce/Co | Na/Ce/Co/$La_{4-x}Nd_xO_6$ | Na/Ce/Co/$LaNd_3O_6$ | Na/Ce/Co/$La_{1.5}Nd_{2.5}O_6$ | Na/Ce/Co/$La_{2.5}Nd_{1.5}O_6$ | Na/Ce/Co/$La_{3.2}Nd_{0.8}O_6$ | Na/Ce/Co/$La_{3.5}Nd_{0.5}O_6$ |
| Na/Ce | Na/Ce/$La_{4-x}Nd_xO_6$ | Na/Ce/$LaNd_3O_6$ | Na/Ce/$La_{1.5}Nd_{2.5}O_6$ | Na/Ce/$La_{2.5}Nd_{1.5}O_6$ | Na/Ce/$La_{3.2}Nd_{0.8}O_6$ | Na/Ce/$La_{3.5}Nd_{0.5}O_6$ |
| Na/Ga/Gd/Al | Na/Ga/Gd/Al/$La_{4-x}Nd_xO_6$ | Na/Ga/Gd/Al/$LaNd_3O_6$ | Na/Ga/Gd/Al/$La_{1.5}Nd_{2.5}O_6$ | Na/Ga/Gd/Al/$La_{2.5}Nd_{1.5}O_6$ | Na/Ga/Gd/Al/$La_{3.2}Nd_{0.8}O_6$ | Na/Ga/Gd/Al/$La_{3.5}Nd_{0.5}O_6$ |
| Ba/Rh/Ta | Ba/Rh/Ta/$La_{4-x}Nd_xO_6$ | Ba/Rh/Ta/$LaNd_3O_6$ | Ba/Rh/Ta/$La_{1.5}Nd_{2.5}O_6$ | Ba/Rh/Ta/$La_{2.5}Nd_{1.5}O_6$ | Ba/Rh/Ta/$La_{3.2}Nd_{0.8}O_6$ | Ba/Rh/Ta/$La_{3.5}Nd_{0.5}O_6$ |
| Ba/Ta | Ba/Ta/$La_{4-x}Nd_xO_6$ | Ba/Ta/$LaNd_3O_6$ | Ba/Ta/$La_{1.5}Nd_{2.5}O_6$ | Ba/Ta/$La_{2.5}Nd_{1.5}O_6$ | Ba/Ta/$La_{3.2}Nd_{0.8}O_6$ | Ba/Ta/$La_{3.5}Nd_{0.5}O_6$ |
| Na/Al/Bi | Na/Al/Bi/$La_{4-x}Nd_xO_6$ | Na/Al/Bi/$LaNd_3O_6$ | Na/Al/Bi/$La_{1.5}Nd_{2.5}O_6$ | Na/Al/Bi/$La_{2.5}Nd_{1.5}O_6$ | Na/Al/Bi/$La_{3.2}Nd_{0.8}O_6$ | Na/Al/Bi/$La_{3.5}Nd_{0.5}O_6$ |
| Cs/Eu/S | Cs/Eu/S/$La_{4-x}Nd_xO_6$ | Cs/Eu/S/$LaNd_3O_6$ | Cs/Eu/S/$La_{1.5}Nd_{2.5}O_6$ | Cs/Eu/S/$La_{2.5}Nd_{1.5}O_6$ | Cs/Eu/S/$La_{3.2}Nd_{0.8}O_6$ | Cs/Eu/S/$La_{3.5}Nd_{0.5}O_6$ |
| Sm/Tm/Yb/Fe | Sm/Tm/Yb/Fe/$La_{4-x}Nd_xO_6$ | Sm/Tm/Yb/Fe/$LaNd_3O_6$ | Sm/Tm/Yb/Fe/$La_{1.5}Nd_{2.5}O_6$ | Sm/Tm/Yb/Fe/$La_{2.5}Nd_{1.5}O_6$ | Sm/Tm/Yb/Fe/$La_{3.2}Nd_{0.8}O_6$ | Sm/Tm/Yb/Fe/$La_{3.5}Nd_{0.5}O_6$ |
| Sm/Tm/Yb | Sm/Tm/Yb/$La_{4-x}Nd_xO_6$ | Sm/Tm/Yb/$LaNd_3O_6$ | Sm/Tm/Yb/$La_{1.5}Nd_{2.5}O_6$ | Sm/Tm/Yb/$La_{2.5}Nd_{1.5}O_6$ | Sm/Tm/Yb/$La_{3.2}Nd_{0.8}O_6$ | Sm/Tm/Yb/$La_{3.5}Nd_{0.5}O_6$ |
| Hf/Zr/Ta | Hf/Zr/Ta/$La_{4-x}Nd_xO_6$ | Hf/Zr/Ta/$LaNd_3O_6$ | Hf/Zr/Ta/$La_{1.5}Nd_{2.5}O_6$ | Hf/Zr/Ta/$La_{2.5}Nd_{1.5}O_6$ | Hf/Zr/Ta/$La_{3.2}Nd_{0.8}O_6$ | Hf/Zr/Ta/$La_{3.5}Nd_{0.5}O_6$ |
| Sr/Tb/K | Sr/Tb/K/$La_{4-x}Nd_xO_6$ | Sr/Tb/K/$LaNd_3O_6$ | Sr/Tb/K/$La_{1.5}Nd_{2.5}O_6$ | Sr/Tb/K/$La_{2.5}Nd_{1.5}O_6$ | Sr/Tb/K/$La_{3.2}Nd_{0.8}O_6$ | Sr/Tb/K/$La_{3.5}Nd_{0.5}O_6$ |
| Rb/Gd/Li/K | Rb/Gd/Li/K/$La_{4-x}Nd_xO_6$ | Rb/Gd/Li/K/$LaNd_3O_6$ | Rb/Gd/Li/K/$La_{1.5}Nd_{2.5}O_6$ | Rb/Gd/Li/K/$La_{2.5}Nd_{1.5}O_6$ | Rb/Gd/Li/K/$La_{3.2}Nd_{0.8}O_6$ | Rb/Gd/Li/K/$La_{3.5}Nd_{0.5}O_6$ |
| Gd/Ho/Al/P | Gd/Ho/Al/P/$La_{4-x}Nd_xO_6$ | Gd/Ho/Al/P/$LaNd_3O_6$ | Gd/Ho/Al/P/$La_{1.5}Nd_{2.5}O_6$ | Gd/Ho/Al/P/$La_{2.5}Nd_{1.5}O_6$ | Gd/Ho/Al/P/$La_{3.2}Nd_{0.8}O_6$ | Gd/Ho/Al/P/$La_{3.5}Nd_{0.5}O_6$ |

TABLE 10-continued

Nanowires (NW) Doped With Specific Dopants (Dop)

| Dop\NW | $La_{4-x}Nd_xO_6$* | $LaNd_3O_6$ | $La_{1.5}Nd_{2.5}O_6$ | $La_{2.5}Nd_{1.5}O_6$ | $La_{3.2}Nd_{0.8}O_6$ | $La_{3.5}Nd_{0.5}O_6$ |
|---|---|---|---|---|---|---|
| Na/Ca/Lu | Na/Ca/Lu/$La_{4-x}Nd_xO_6$ | Na/Ca/Lu/$LaNd_3O_6$ | Na/Ca/Lu/$La_{1.5}Nd_{2.5}O_6$ | Na/Ca/Lu/$La_{2.5}Nd_{1.5}O_6$ | Na/Ca/Lu/$La_{3.2}Nd_{0.8}O_6$ | Na/Ca/Lu/$La_{3.5}Nd_{0.5}O_6$ |
| Cu/Sn | Cu/Sn/$La_{4-x}Nd_xO_6$ | Cu/Sn/$LaNd_3O_6$ | Cu/Sn/$La_{1.5}Nd_{2.5}O_6$ | Cu/Sn/$La_{2.5}Nd_{1.5}O_6$ | Cu/Sn/$La_{3.2}Nd_{0.8}O_6$ | Cu/Sn/$La_{3.5}Nd_{0.5}O_6$ |
| Ag/Au | Ag/Au/$La_{4-x}Nd_xO_6$ | Ag/Au/$LaNd_3O_6$ | Ag/Au/$La_{1.5}Nd_{2.5}O_6$ | Ag/Au/$La_{2.5}Nd_{1.5}O_6$ | Ag/Au/$La_{3.2}Nd_{0.8}O_6$ | Ag/Au/$La_{3.5}Nd_{0.5}O_6$ |
| Al/Bi | Al/Bi/$La_{4-x}Nd_xO_6$ | Al/Bi/$LaNd_3O_6$ | Al/Bi/$La_{1.5}Nd_{2.5}O_6$ | Al/Bi/$La_{2.5}Nd_{1.5}O_6$ | Al/Bi/$La_{3.2}Nd_{0.8}O_6$ | Al/Bi/$La_{3.5}Nd_{0.5}O_6$ |
| Al/Mo | Al/Mo/$La_{4-x}Nd_xO_6$ | Al/Mo/$LaNd_3O_6$ | Al/Mo/$La_{1.5}Nd_{2.5}O_6$ | Al/Mo/$La_{2.5}Nd_{1.5}O_6$ | Al/Mo/$La_{3.2}Nd_{0.8}O_6$ | Al/Mo/$La_{3.5}Nd_{0.5}O_6$ |
| Al/Nb | Al/Nb/$La_{4-x}Nd_xO_6$ | Al/Nb/$LaNd_3O_6$ | Al/Nb/$La_{1.5}Nd_{2.5}O_6$ | Al/Nb/$La_{2.5}Nd_{1.5}O_6$ | Al/Nb/$La_{3.2}Nd_{0.8}O_6$ | Al/Nb/$La_{3.5}Nd_{0.5}O_6$ |
| Au/Pt | Au/Pt/$La_{4-x}Nd_xO_6$ | Au/Pt/$LaNd_3O_6$ | Au/Pt/$La_{1.5}Nd_{2.5}O_6$ | Au/Pt/$La_{2.5}Nd_{1.5}O_6$ | Au/Pt/$La_{3.2}Nd_{0.8}O_6$ | Au/Pt/$La_{3.5}Nd_{0.5}O_6$ |
| Ga/Bi | Ga/Bi/$La_{4-x}Nd_xO_6$ | Ga/Bi/$LaNd_3O_6$ | Ga/Bi/$La_{1.5}Nd_{2.5}O_6$ | Ga/Bi/$La_{2.5}Nd_{1.5}O_6$ | Ga/Bi/$La_{3.2}Nd_{0.8}O_6$ | Ga/Bi/$La_{3.5}Nd_{0.5}O_6$ |
| Mg/W | Mg/W/$La_{4-x}Nd_xO_6$ | Mg/W/$LaNd_3O_6$ | Mg/W/$La_{1.5}Nd_{2.5}O_6$ | Mg/W/$La_{2.5}Nd_{1.5}O_6$ | Mg/W/$La_{3.2}Nd_{0.8}O_6$ | Mg/W/$La_{3.5}Nd_{0.5}O_6$ |
| Pb/Au | Pb/Au/$La_{4-x}Nd_xO_6$ | Pb/Au/$LaNd_3O_6$ | Pb/Au/$La_{1.5}Nd_{2.5}O_6$ | Pb/Au/$La_{2.5}Nd_{1.5}O_6$ | Pb/Au/$La_{3.2}Nd_{0.8}O_6$ | Pb/Au/$La_{3.5}Nd_{0.5}O_6$ |
| Sn/Mg | Sn/Mg/$La_{4-x}Nd_xO_6$ | Sn/Mg/$LaNd_3O_6$ | Sn/Mg/$La_{1.5}Nd_{2.5}O_6$ | Sn/Mg/$La_{2.5}Nd_{1.5}O_6$ | Sn/Mg/$La_{3.2}Nd_{0.8}O_6$ | Sn/Mg/$La_{3.5}Nd_{0.5}O_6$ |
| Zn/Bi | Zn/Bi/$La_{4-x}Nd_xO_6$ | Zn/Bi/$LaNd_3O_6$ | Zn/Bi/$La_{1.5}Nd_{2.5}O_6$ | Zn/Bi/$La_{2.5}Nd_{1.5}O_6$ | Zn/Bi/$La_{3.2}Nd_{0.8}O_6$ | Zn/Bi/$La_{3.5}Nd_{0.5}O_6$ |
| Sr/Ta | Sr/Ta/$La_{4-x}Nd_xO_6$ | Sr/Ta/$LaNd_3O_6$ | Sr/Ta/$La_{1.5}Nd_{2.5}O_6$ | Sr/Ta/$La_{2.5}Nd_{1.5}O_6$ | Sr/Ta/$La_{3.2}Nd_{0.8}O_6$ | Sr/Ta/$La_{3.5}Nd_{0.5}O_6$ |
| Na | Na/$La_{4-x}Nd_xO_6$ | Na/$LaNd_3O_6$ | Na/$La_{1.5}Nd_{2.5}O_6$ | Na/$La_{2.5}Nd_{1.5}O_6$ | Na/$La_{3.2}Nd_{0.8}O_6$ | Na/$La_{3.5}Nd_{0.5}O_6$ |
| Sr | Sr/$La_{4-x}Nd_xO_6$ | Sr/$LaNd_3O_6$ | Sr/$La_{1.5}Nd_{2.5}O_6$ | Sr/$La_{2.5}Nd_{1.5}O_6$ | Sr/$La_{3.2}Nd_{0.8}O_6$ | Sr/$La_{3.5}Nd_{0.5}O_6$ |
| Ca | Ca/$La_{4-x}Nd_xO_6$ | Ca/$LaNd_3O_6$ | Ca/$La_{1.5}Nd_{2.5}O_6$ | Ca/$La_{2.5}Nd_{1.5}O_6$ | Ca/$La_{3.2}Nd_{0.8}O_6$ | Ca/$La_{3.5}Nd_{0.5}O_6$ |
| Yb | Yb/$La_{4-x}Nd_xO_6$ | Yb/$LaNd_3O_6$ | Yb/$La_{1.5}Nd_{2.5}O_6$ | Yb/$La_{2.5}Nd_{1.5}O_6$ | Yb/$La_{3.2}Nd_{0.8}O_6$ | Yb/$La_{3.5}Nd_{0.5}O_6$ |
| Cs | Cs/$La_{4-x}Nd_xO_6$ | Cs/$LaNd_3O_6$ | Cs/$La_{1.5}Nd_{2.5}O_6$ | Cs/$La_{2.5}Nd_{1.5}O_6$ | Cs/$La_{3.2}Nd_{0.8}O_6$ | Cs/$La_{3.5}Nd_{0.5}O_6$ |
| Sb | Sb/$La_{4-x}Nd_xO_6$ | Sb/$LaNd_3O_6$ | Sb/$La_{1.5}Nd_{2.5}O_6$ | Sb/$La_{2.5}Nd_{1.5}O_6$ | Sb/$La_{3.2}Nd_{0.8}O_6$ | Sb/$La_{3.5}Nd_{0.5}O_6$ |
| Gd/Ho | Gd/Ho/$La_{4-x}Nd_xO_6$ | Gd/Ho/$LaNd_3O_6$ | Gd/Ho/$La_{1.5}Nd_{2.5}O_6$ | Gd/Ho/$La_{2.5}Nd_{1.5}O_6$ | Gd/Ho/$La_{3.2}Nd_{0.8}O_6$ | Gd/Ho/$La_{3.5}Nd_{0.5}O_6$ |
| Zr/Bi | Zr/Bi/$La_{4-x}Nd_xO_6$ | Zr/Bi/$LaNd_3O_6$ | Zr/Bi/$La_{1.5}Nd_{2.5}O_6$ | Zr/Bi/$La_{2.5}Nd_{1.5}O_6$ | Zr/Bi/$La_{3.2}Nd_{0.8}O_6$ | Zr/Bi/$La_{3.5}Nd_{0.5}O_6$ |
| Ho/Sr | Ho/Sr/$La_{4-x}Nd_xO_6$ | Ho/Sr/$LaNd_3O_6$ | Ho/Sr/$La_{1.5}Nd_{2.5}O_6$ | Ho/Sr/$La_{2.5}Nd_{1.5}O_6$ | Ho/Sr/$La_{3.2}Nd_{0.8}O_6$ | Ho/Sr/$La_{3.5}Nd_{0.5}O_6$ |
| Gd/Ho/Sr | Gd/Ho/Sr/$La_{4-x}Nd_xO_6$ | Gd/Ho/Sr/$LaNd_3O_6$ | Gd/Ho/Sr/$La_{1.5}Nd_{2.5}O_6$ | Gd/Ho/Sr/$La_{2.5}Nd_{1.5}O_6$ | Gd/Ho/Sr/$La_{3.2}Nd_{0.8}O_6$ | Gd/Ho/Sr/$La_{3.5}Nd_{0.5}O_6$ |
| Ca/Sr | Ca/Sr/$La_{4-x}Nd_xO_6$ | Ca/Sr/$LaNd_3O_6$ | Ca/Sr/$La_{1.5}Nd_{2.5}O_6$ | Ca/Sr/$La_{2.5}Nd_{1.5}O_6$ | Ca/Sr/$La_{3.2}Nd_{0.8}O_6$ | Ca/Sr/$La_{3.5}Nd_{0.5}O_6$ |
| Ca/Sr/W | Ca/Sr/W/$La_{4-x}Nd_xO_6$ | Ca/Sr/W/$LaNd_3O_6$ | Ca/Sr/W/$La_{1.5}Nd_{2.5}O_6$ | Ca/Sr/W/$La_{2.5}Nd_{1.5}O_6$ | Ca/Sr/W/$La_{3.2}Nd_{0.8}O_6$ | Ca/Sr/W/$La_{3.5}Nd_{0.5}O_6$ |
| Na/Zr/Eu/Tm | Na/Zr/Eu/Tm/$La_{4-x}Nd_xO_6$ | Na/Zr/Eu/Tm/$LaNd_3O_6$ | Na/Zr/Eu/Tm/$La_{1.5}Nd_{2.5}O_6$ | Na/Zr/Eu/Tm/$La_{2.5}Nd_{1.5}O_6$ | Na/Zr/Eu/Tm/$La_{3.2}Nd_{0.8}O_6$ | Na/Zr/Eu/Tm/$La_{3.5}Nd_{0.5}O_6$ |
| Sr/Ho/Tm/Na | Sr/Ho/Tm/Na/$La_{4-x}Nd_xO_6$ | Sr/Ho/Tm/Na/$LaNd_3O_6$ | Sr/Ho/Tm/Na/$La_{1.5}Nd_{2.5}O_6$ | Sr/Ho/Tm/Na/$La_{2.5}Nd_{1.5}O_6$ | Sr/Ho/Tm/Na/$La_{3.2}Nd_{0.8}O_6$ | Sr/Ho/Tm/Na/$La_{3.5}Nd_{0.5}O_6$ |
| Sr/Pb | Sr/Pb/$La_{4-x}Nd_xO_6$ | Sr/Pb/$LaNd_3O_6$ | Sr/Pb/$La_{1.5}Nd_{2.5}O_6$ | Sr/Pb/$La_{2.5}Nd_{1.5}O_6$ | Sr/Pb/$La_{3.2}Nd_{0.8}O_6$ | Sr/Pb/$La_{3.5}Nd_{0.5}O_6$ |
| Sr/W/Li | Sr/W/Li/$La_{4-x}Nd_xO_6$ | Sr/W/Li/$LaNd_3O_6$ | Sr/W/Li/$La_{1.5}Nd_{2.5}O_6$ | Sr/W/Li/$La_{2.5}Nd_{1.5}O_6$ | Sr/W/Li/$La_{3.2}Nd_{0.8}O_6$ | Sr/W/Li/$La_{3.5}Nd_{0.5}O_6$ |
| Ca/Sr/W | Ca/Sr/W/$La_{4-x}Nd_xO_6$ | Ca/Sr/W/$LaNd_3O_6$ | Ca/Sr/W/$La_{1.5}Nd_{2.5}O_6$ | Ca/Sr/W/$La_{2.5}Nd_{1.5}O_6$ | Ca/Sr/W/$La_{3.2}Nd_{0.8}O_6$ | Ca/Sr/W/$La_{3.5}Nd_{0.5}O_6$ |
| Sr/Hf | Sr/Hf/$La_{4-x}Nd_xO_6$ | Sr/Hf/$LaNd_3O_6$ | Sr/Hf/$La_{1.5}Nd_{2.5}O_6$ | Sr/Hf/$La_{2.5}Nd_{1.5}O_6$ | Sr/Hf/$La_{3.2}Nd_{0.8}O_6$ | Sr/Hf/$La_{3.5}Nd_{0.5}O_6$ |
| Au/Re | Au/Re/$La_{4-x}Nd_xO_6$ | Au/Re/$LaNd_3O_6$ | Au/Re/$La_{1.5}Nd_{2.5}O_6$ | Au/Re/$La_{2.5}Nd_{1.5}O_6$ | Au/Re/$La_{3.2}Nd_{0.8}O_6$ | Au/Re/$La_{3.5}Nd_{0.5}O_6$ |
| Sr/W | Sr/W/$La_{4-x}Nd_xO_6$ | Sr/W/$LaNd_3O_6$ | Sr/W/$La_{1.5}Nd_{2.5}O_6$ | Sr/W/$La_{2.5}Nd_{1.5}O_6$ | Sr/W/$La_{3.2}Nd_{0.8}O_6$ | Sr/W/$La_{3.5}Nd_{0.5}O_6$ |
| La/Nd | La/Nd/$La_{4-x}Nd_xO_6$ | La/Nd/$LaNd_3O_6$ | La/Nd/$La_{1.5}Nd_{2.5}O_6$ | La/Nd/$La_{2.5}Nd_{1.5}O_6$ | La/Nd/$La_{3.2}Nd_{0.8}O_6$ | La/Nd/$La_{3.5}Nd_{0.5}O_6$ |
| La/Sm | La/Sm/$La_{4-x}Nd_xO_6$ | La/Sm/$LaNd_3O_6$ | La/Sm/$La_{1.5}Nd_{2.5}O_6$ | La/Sm/$La_{2.5}Nd_{1.5}O_6$ | La/Sm/$La_{3.2}Nd_{0.8}O_6$ | La/Sm/$La_{3.5}Nd_{0.5}O_6$ |
| La/Ce | La/Ce/$La_{4-x}Nd_xO_6$ | La/Ce/$LaNd_3O_6$ | La/Ce/$La_{1.5}Nd_{2.5}O_6$ | La/Ce/$La_{2.5}Nd_{1.5}O_6$ | La/Ce/$La_{3.2}Nd_{0.8}O_6$ | La/Ce/$La_{3.5}Nd_{0.5}O_6$ |
| La/Sr | La/Sr/$La_{4-x}Nd_xO_6$ | La/Sr/$LaNd_3O_6$ | La/Sr/$La_{1.5}Nd_{2.5}O_6$ | La/Sr/$La_{2.5}Nd_{1.5}O_6$ | La/Sr/$La_{3.2}Nd_{0.8}O_6$ | La/Sr/$La_{3.5}Nd_{0.5}O_6$ |
| La/Nd/Sr | La/Nd/Sr/$La_{4-x}Nd_xO_6$ | La/Nd/Sr/$LaNd_3O_6$ | La/Nd/Sr/$La_{1.5}Nd_{2.5}O_6$ | La/Nd/Sr/$La_{2.5}Nd_{1.5}O_6$ | La/Nd/Sr/$La_{3.2}Nd_{0.8}O_6$ | La/Nd/Sr/$La_{3.5}Nd_{0.5}O_6$ |

TABLE 10-continued

Nanowires (NW) Doped With Specific Dopants (Dop)

| Dop\NW | $La_{4-x}Nd_xO_6$* | $LaNd_3O_6$ | $La_{1.5}Nd_{2.5}O_6$ | $La_{2.5}Nd_{1.5}O_6$ | $La_{3.2}Nd_{0.8}O_6$ | $La_{3.5}Nd_{0.5}O_6$ |
|---|---|---|---|---|---|---|
| La/Bi/Sr | La/Bi/Sr/ $La_{4-x}Nd_xO_6$ | La/Bi/Sr/ $LaNd_3O_6$ | La/Bi/Sr/ $La_{1.5}Nd_{2.5}O_6$ | La/Bi/Sr/ $La_{2.5}Nd_{1.5}O_6$ | La/Bi/Sr/ $La_{3.2}Nd_{0.8}O_6$ | La/Bi/Sr/ $La_{3.5}Nd_{0.5}O_6$ |
| La/Ce/Nd/Sr | La/Ce/Nd/Sr/ $La_{4-x}Nd_xO_6$ | La/Ce/Nd/Sr/ $LaNd_3O_6$ | La/Ce/Nd/Sr/ $La_{1.5}Nd_{2.5}O_6$ | La/Ce/Nd/Sr/ $La_{2.5}Nd_{1.5}O_6$ | La/Ce/Nd/Sr/ $La_{3.2}Nd_{0.8}O_6$ | La/Ce/Nd/Sr/ $La_{3.5}Nd_{0.5}O_6$ |
| La/Bi/Ce/Nd/Sr | La/Bi/Ce/Nd/Sr/ $La_{4-x}Nd_xO_6$ | La/Bi/Ce/Nd/Sr/ $LaNd_3O_6$ | La/Bi/Ce/Nd/Sr/ $La_{1.5}Nd_{2.5}O_6$ | La/Bi/Ce/Nd/Sr/ $La_{2.5}Nd_{1.5}O_6$ | La/Bi/Ce/Nd/Sr/ $La_{3.2}Nd_{0.8}O_6$ | La/Bi/Ce/Nd/Sr/ $La_{3.5}Nd_{0.5}O_6$ |
| Eu/Gd | Eu/Gd/ $La_{4-x}Nd_xO_6$ | Eu/Gd/ $LaNd_3O_6$ | Eu/Gd/ $La_{1.5}Nd_{2.5}O_6$ | Eu/Gd/ $La_{2.5}Nd_{1.5}O_6$ | Eu/Gd/ $La_{3.2}Nd_{0.8}O_6$ | Eu/Gd/ $La_{3.5}Nd_{0.5}O_6$ |
| Ca/Na | Ca/Na/ $La_{4-x}Nd_xO_6$ | Ca/Na/ $LaNd_3O_6$ | Ca/Na/ $La_{1.5}Nd_{2.5}O_6$ | Ca/Na/ $La_{2.5}Nd_{1.5}O_6$ | Ca/Na/ $La_{3.2}Nd_{0.8}O_6$ | Ca/Na/ $La_{3.5}Nd_{0.5}O_6$ |
| Eu/Sm | Eu/Sm/ $La_{4-x}Nd_xO_6$ | Eu/Sm/ $LaNd_3O_6$ | Eu/Sm/ $La_{1.5}Nd_{2.5}O_6$ | Eu/Sm/ $La_{2.5}Nd_{1.5}O_6$ | Eu/Sm/ $La_{3.2}Nd_{0.8}O_6$ | Eu/Sm/ $La_{3.5}Nd_{0.5}O_6$ |
| Eu/Sr | Eu/Sr/ $La_{4-x}Nd_xO_6$ | Eu/Sr/ $LaNd_3O_6$ | Eu/Sr/ $La_{1.5}Nd_{2.5}O_6$ | Eu/Sr/ $La_{2.5}Nd_{1.5}O_6$ | Eu/Sr/ $La_{3.2}Nd_{0.8}O_6$ | Eu/Sr/ $La_{3.5}Nd_{0.5}O_6$ |
| Mg/Sr | Mg/Sr/ $La_{4-x}Nd_xO_6$ | Mg/Sr/ $LaNd_3O_6$ | Mg/Sr/ $La_{1.5}Nd_{2.5}O_6$ | Mg/Sr/ $La_{2.5}Nd_{1.5}O_6$ | Mg/Sr/ $La_{3.2}Nd_{0.8}O_6$ | Mg/Sr/ $La_{3.5}Nd_{0.5}O_6$ |
| Ce/Mg | Ce/Mg/ $La_{4-x}Nd_xO_6$ | Ce/Mg/ $LaNd_3O_6$ | Ce/Mg/ $La_{1.5}Nd_{2.5}O_6$ | Ce/Mg/ $La_{2.5}Nd_{1.5}O_6$ | Ce/Mg/ $La_{3.2}Nd_{0.8}O_6$ | Ce/Mg/ $La_{3.5}Nd_{0.5}O_6$ |
| Gd/Sm | Gd/Sm/ $La_{4-x}Nd_xO_6$ | Gd/Sm/ $LaNd_3O_6$ | Gd/Sm/ $La_{1.5}Nd_{2.5}O_6$ | Gd/Sm/ $La_{2.5}Nd_{1.5}O_6$ | Gd/Sm/ $La_{3.2}Nd_{0.8}O_6$ | Gd/Sm/ $La_{3.5}Nd_{0.5}O_6$ |
| Au/Pb | Au/Pb/ $La_{4-x}Nd_xO_6$ | Au/Pb/ $LaNd_3O_6$ | Au/Pb/ $La_{1.5}Nd_{2.5}O_6$ | Au/Pb/ $La_{2.5}Nd_{1.5}O_6$ | Au/Pb/ $La_{3.2}Nd_{0.8}O_6$ | Au/Pb/ $La_{3.5}Nd_{0.5}O_6$ |
| Bi/Hf | Bi/Hf/ $La_{4-x}Nd_xO_6$ | Bi/Hf/ $LaNd_3O_6$ | Bi/Hf/ $La_{1.5}Nd_{2.5}O_6$ | Bi/Hf/ $La_{2.5}Nd_{1.5}O_6$ | Bi/Hf/ $La_{3.2}Nd_{0.8}O_6$ | Bi/Hf/ $La_{3.5}Nd_{0.5}O_6$ |
| Rb/S | Rb/S/ $La_{4-x}Nd_xO_6$ | Rb/S/ $LaNd_3O_6$ | Rb/S/ $La_{1.5}Nd_{2.5}O_6$ | Rb/S/ $La_{2.5}Nd_{1.5}O_6$ | Rb/S/ $La_{3.2}Nd_{0.8}O_6$ | Rb/S/ $La_{3.5}Nd_{0.5}O_6$ |
| Sr/Nd | Sr/Nd/ $La_{4-x}Nd_xO_6$ | Sr/Nd/ $LaNd_3O_6$ | Sr/Nd/ $La_{1.5}Nd_{2.5}O_6$ | Sr/Nd/ $La_{2.5}Nd_{1.5}O_6$ | Sr/Nd/ $La_{3.2}Nd_{0.8}O_6$ | Sr/Nd/ $La_{3.5}Nd_{0.5}O_6$ |
| Eu/Y | Eu/Y/ $La_{4-x}Nd_xO_6$ | Eu/Y/ $LaNd_3O_6$ | Eu/Y/ $La_{1.5}Nd_{2.5}O_6$ | Eu/Y/ $La_{2.5}Nd_{1.5}O_6$ | Eu/Y/ $La_{3.2}Nd_{0.8}O_6$ | Eu/Y/ $La_{3.5}Nd_{0.5}O_6$ |
| Mg/Nd | Mg/Nd/ $La_{4-x}Nd_xO_6$ | Mg/Nd/ $LaNd_3O_6$ | Mg/Nd/ $La_{1.5}Nd_{2.5}O_6$ | Mg/Nd/ $La_{2.5}Nd_{1.5}O_6$ | Mg/Nd/ $La_{3.2}Nd_{0.8}O_6$ | Mg/Nd/ $La_{3.5}Nd_{0.5}O_6$ |
| La/Mg | La/Mg/ $La_{4-x}Nd_xO_6$ | La/Mg/ $LaNd_3O_6$ | La/Mg/ $La_{1.5}Nd_{2.5}O_6$ | La/Mg/ $La_{2.5}Nd_{1.5}O_6$ | La/Mg/ $La_{3.2}Nd_{0.8}O_6$ | La/Mg/ $La_{3.5}Nd_{0.5}O_6$ |
| Mg/Nd/Fe | Mg/Nd/Fe/ $La_{4-x}Nd_xO_6$ | Mg/Nd/Fe/ $LaNd_3O_6$ | Mg/Nd/Fe/ $La_{1.5}Nd_{2.5}O_6$ | Mg/Nd/Fe/ $La_{2.5}Nd_{1.5}O_6$ | Mg/Nd/Fe/ $La_{3.2}Nd_{0.8}O_6$ | Mg/Nd/Fe/ $La_{3.5}Nd_{0.5}O_6$ |
| Rb/Sr | Rb/Sr/ $La_{4-x}Nd_xO_6$ | Rb/Sr/ $LaNd_3O_6$ | Rb/Sr/ $La_{1.5}Nd_{2.5}O_6$ | Rb/Sr/ $La_{2.5}Nd_{1.5}O_6$ | Rb/Sr/ $La_{3.2}Nd_{0.8}O_6$ | Rb/Sr/ $La_{3.5}Nd_{0.5}O_6$ |

*x is a number ranging from greater than 0 to less than 4

TABLE 11

NANOWIRES (NW) DOPED WITH SPECIFIC DOPANTS (DOP)

| Dop\NW | $La_{3.8}Nd_{0.2}O_6$ | Y—La | Zr—La | Pr—La | Ce—La |
|---|---|---|---|---|---|
| Eu/Na | Eu/Na/ $La_{3.8}Nd_{0.2}O_6$ | Eu/Na/ Y—La | Eu/Na/ Zr—La | Eu/Na/ Pr—La | Eu/Na/ Ce—La |
| Sr/Na | Sr/Na/ $La_{3.8}Nd_{0.2}O_6$ | Sr/Na/ Y—La | Sr/Na/ Zr—La | Sr/Na/ Pr—La | Sr/Na/ Ce—La |
| Na/Zr/Eu/Ca | Na/Zr/Eu/Ca/ $La_{3.8}Nd_{0.2}O_6$ | Na/Zr/Eu/Ca/ Y—La | Na/Zr/Eu/Ca/ Zr—La | Na/Zr/Eu/Ca/ Pr—Laa | Na/Zr/Eu/Ca/ Ce—La |
| Mg/Na | Mg/Na/ $La_{3.8}Nd_{0.2}O_6$ | Mg/Na/ Y—La | Mg/Na/ Zr—La | Mg/Na/ Pr—La | Mg/Na/ Ce—La |
| Sr/Sm/Ho/Tm | Sr/Sm/Ho/Tm/ $La_{3.8}Nd_{0.2}O_6$ | Sr/Sm/Ho/Tm/ Y—La | Sr/Sm/Ho/Tm/ Zr—La | Sr/Sm/Ho/Tm/ Pr—La | Sr/Sm/Ho/Tm/ Ce—La |
| Sr/W | Sr/W/ $La_{3.8}Nd_{0.2}O_6$ | Sr/W/ Y—La | Sr/W/ Zr—La | Sr/W/ Pr—La | Sr/W/ Ce—La |
| Mg/La/K | Mg/La/K/ $La_{3.8}Nd_{0.2}O_6$ | Mg/La/K/ Y—La | Mg/La/K/ Zr—La | Mg/La/K/ Pr—La | Mg/La/K/ Ce—La |
| Na/K/Mg/Tm | Na/K/Mg/Tm/ $La_{3.8}Nd_{0.2}O_6$ | Na/K/Mg/Tm/ Y—La | Na/K/Mg/Tm/ Zr—La | Na/K/Mg/Tm/ Pr—La | Na/K/Mg/Tm/ Ce—La |
| Na/Dy/K | Na/Dy/K/ $La_{3.8}Nd_{0.2}O_6$ | Na/Dy/K/ Y—La | Na/Dy/K/ Zr—La | Na/Dy/K/ Pr—La | Na/Dy/K/ Ce—La |
| Na/La/Dy | Na/La/Dy/ $La_{3.8}Nd_{0.2}O_6$ | Na/La/Dy/ Y—La | Na/La/Dy/ Zr—La | Na/La/Dy/ Pr—La | Na/La/Dy/ Ce—La |
| Na/La/Eu | Na/La/Eu/ $La_{3.8}Nd_{0.2}O_6$ | Na/La/Eu/ Y—La | Na/La/Eu/ Zr—La | Na/La/Eu/ Pr—La | Na/La/Eu/ Ce—La |
| Na/La/Eu/In | Na/La/Eu/In/ $La_{3.8}Nd_{0.2}O_6$ | Na/La/Eu/In/ Y—La | Na/La/Eu/In/ Zr—La | Na/La/Eu/In/ Pr—La | Na/La/Eu/In/ Ce—La |
| Na/La/K | Na/La/K/ $La_{3.8}Nd_{0.2}O_6$ | Na/La/K/ Y—La | Na/La/K/ Zr—La | Na/La/K/ Pr—La | Na/La/K/ Ce—La |

TABLE 11-continued

NANOWIRES (NW) DOPED WITH SPECIFIC DOPANTS (DOP)

| Dop\NW | $La_{3.8}Nd_{0.2}O_6$ | Y—La | Zr—La | Pr—La | Ce—La |
|---|---|---|---|---|---|
| Na/La/Li/Cs | Na/La/Li/Cs/ $La_{3.8}Nd_{0.2}O_6$ | Na/La/Li/Cs/ Y—La | Na/La/Li/Cs/ Zr—La | Na/La/Li/Cs/ Pr—La | Na/La/Li/Cs/ Ce—La |
| K/La | K/La/ $La_{3.8}Nd_{0.2}O_6$ | K/La/ Y—La | K/La/ Zr—La | K/La/ Pr—La | K/La/ Ce—La |
| K/La/S | K/La/S/ $La_{3.8}Nd_{0.2}O_6$ | K/La/S/ Y—La | K/La/S/ Zr—La | K/La/S/ Pr—La | K/La/S/ Ce—La |
| K/Na | K/Na/ $La_{3.8}Nd_{0.2}O_6$ | K/Na/ Y—La | K/Na/ Zr—La | K/Na/ Pr—La | K/Na/ Ce—La |
| Li/Cs | Li/Cs/ $La_{3.8}Nd_{0.2}O_6$ | Li/Cs/ Y—La | Li/Cs/ Zr—La | Li/Cs/ Pr—La | Li/Cs/ Ce—La |
| Li/Cs/La | Li/Cs/La/ $La_{3.8}Nd_{0.2}O_6$ | Li/Cs/La/ Y—La | Li/Cs/La/ Zr—La | Li/Cs/La/ Pr—La | Li/Cs/La/ Ce—La |
| Sr/Pr/K | Sr/Pr/K/ $La_{3.8}Nd_{0.2}O_6$ | Sr/Pr/K/ Y—La | Sr/Pr/K/ Zr—La | Sr/Pr/K/ Pr—La | Sr/Pr/K/ Ce—La |
| Li/Cs/La/Tm | Li/Cs/La/Tm/ $La_{3.8}Nd_{0.2}O_6$ | Li/Cs/La/Tm/ Y—La | Li/Cs/La/Tm/ Zr—La | Li/Cs/La/Tm/ Pr—La | Li/Cs/La/Tm/ Ce—La |
| Li/Cs/Sr/Tm | Li/Cs/Sr/Tm/ $La_{3.8}Nd_{0.2}O_6$ | Li/Cs/Sr/Tm/ Y—La | Li/Cs/Sr/Tm/ Zr—La | Li/Cs/Sr/Tm/ Pr—La | Li/Cs/Sr/Tm/ Ce—La |
| Li/Sr/Cs | Li/Sr/Cs/ $La_{3.8}Nd_{0.2}O_6$ | Li/Sr/Cs/ Y—La | Li/Sr/Cs/ Zr—La | Li/Sr/Cs/ Pr—La | Li/Sr/Cs/ Ce—La |
| Li/Sr/Zn/K | Li/Sr/Zn/K/ $La_{3.8}Nd_{0.2}O_6$ | Li/Sr/Zn/K/ Y—La | Li/Sr/Zn/K/ Zr—La | Li/Sr/Zn/K/ Pr—La | Li/Sr/Zn/K/ Ce—La |
| Li/Ga/Cs | Li/Ga/Cs/ $La_{3.8}Nd_{0.2}O_6$ | Li/Ga/Cs/ Y—La | Li/Ga/Cs/ Zr—La | Li/Ga/Cs/ Pr—La | Li/Ga/Cs/ Ce—La |
| Li/K/Sr/La | Li/K/Sr/La/ $La_{3.8}Nd_{0.2}O_6$ | Li/K/Sr/La/ Y—La | Li/K/Sr/La/ Zr—La | Li/K/Sr/La/ Pr—La | Li/K/Sr/La/ Ce—La |
| Li/Na | Li/Na/ $La_{3.8}Nd_{0.2}O_6$ | Li/Na/ Y—La | Li/Na/ Zr—La | Li/Na/ Pr—La | Li/Na/ Ce—La |
| Li/Na/Rb/Ga | Li/Na/Rb/Ga/ $La_{3.8}Nd_{0.2}O_6$ | Li/Na/Rb/Ga/ Y—La | Li/Na/Rb/Ga/ Zr—La | Li/Na/Rb/Ga/ Pr—La | Li/Na/Rb/Ga/ Ce—La |
| Li/Na/Sr | Li/Na/Sr/ $La_{3.8}Nd_{0.2}O_6$ | Li/Na/Sr/ Y—La | Li/Na/Sr/ Zr—La | Li/Na/Sr/ Pr—La | Li/Na/Sr/ Ce—La |
| Li/Na/Sr/La | Li/Na/Sr/La/ $La_{3.8}Nd_{0.2}O_6$ | Li/Na/Sr/La/ Y—La | Li/Na/Sr/La/ Zr—La | Li/Na/Sr/La/ Pr—La | Li/Na/Sr/La/ Ce—La |
| Li/Sm/Cs | Li/Sm/Cs/ $La_{3.8}Nd_{0.2}O_6$ | Li/Sm/Cs/ Y—La | Li/Sm/Cs/ Zr—La | Li/Sm/Cs/ Pr—La | Li/Sm/Cs/ Ce—La |
| Ba/Sm/Yb/S | Ba/Sm/Yb/S/ $La_{3.8}Nd_{0.2}O_6$ | Ba/Sm/Yb/S/ Y—La | Ba/Sm/Yb/S/ Zr—La | Ba/Sm/Yb/S/ Pr—La | Ba/Sm/Yb/S/ Ce—La |
| Ba/Tm/K/La | Ba/Tm/K/La/ $La_{3.8}Nd_{0.2}O_6$ | Ba/Tm/K/La/ Y—La | Ba/Tm/K/La/ Zr—La | Ba/Tm/K/La/ Pr—La | Ba/Tm/K/La/ Ce—La |
| Ba/Tm/Zn/K | Ba/Tm/Zn/K/ $La_{3.8}Nd_{0.2}O_6$ | Ba/Tm/Zn/K/ Y—La | Ba/Tm/Zn/K/ Zr—La | Ba/Tm/Zn/K/ Pr—La | Ba/Tm/Zn/K/ Ce—La |
| Sr/Tb/K | Sr/Tb/K/ $La_{3.8}Nd_{0.2}O_6$ | Sr/Tb/K/ Y—La | Sr/Tb/K/ Zr—La | Sr/Tb/K/ Pr—La | Sr/Tb/K/ Ce—La |
| C + s/K/La | Cs/K/La/ $La_{3.8}Nd_{0.2}O_6$ | Cs/K/La/ Y—La | Cs/K/La/ Zr—La | Cs/K/La/ Pr—La | Cs/K/La/ Ce—La |
| Cs/La/Tm/Na | Cs/La/Tm/Na/ $La_{3.8}Nd_{0.2}O_6$ | Cs/La/Tm/Na/ Y—La | Cs/La/Tm/Na/ Zr—La | Cs/La/Tm/Na/ Pr—La | Cs/La/Tm/Na/ Ce—La |
| Cs/Li/K/La | Cs/Li/K/La/ $La_{3.8}Nd_{0.2}O_6$ | Cs/Li/K/La/ Y—La | Cs/Li/K/La/ Zr—La | Cs/Li/K/La/ Pr—La | Cs/Li/K/La/ Ce—La |
| Sm/Li/Sr/Cs | Sm/Li/Sr/Cs/ $La_{3.8}Nd_{0.2}O_6$ | Sm/Li/Sr/Cs/ Y—La | Sm/Li/Sr/Cs/ Zr—La | Sm/Li/Sr/Cs/ Pr—La | Sm/Li/Sr/Cs/ Ce—La |
| Sr/Cs/La | Sr/Cs/La/ $La_{3.8}Nd_{0.2}O_6$ | Sr/Cs/La/ Y—La | Sr/Cs/La/ Zr—La | Sr/Cs/La/ Pr—La | Sr/Cs/La/ Ce—La |
| Sr/Tm/Li/Cs | Sr/Tm/Li/Cs/ $La_{3.8}Nd_{0.2}O_6$ | Sr/Tm/Li/Cs/ Y—La | Sr/Tm/Li/Cs/ Zr—La | Sr/Tm/Li/Cs/ Pr—La | Sr/Tm/Li/Cs/ Ce—La |
| Zn/K | Zn/K/ $La_{3.8}Nd_{0.2}O_6$ | Zn/K/ Y—La | Zn/K/ Zr—La | Zn/K/ Pr—La | Zn/K/ Ce—La |
| Zr/Cs/K/La | Zr/Cs/K/La/ $La_{3.8}Nd_{0.2}O_6$ | Zr/Cs/K/La/ Y—La | Zr/Cs/K/La/ Zr—La | Zr/Cs/K/La/ Pr—La | Zr/Cs/K/La/ Ce—La |
| Rb/Ca/In/Ni | Rb/Ca/In/Ni/ $La_{3.8}Nd_{0.2}O_6$ | Rb/Ca/In/Ni/ Y—La | Rb/Ca/In/Ni/ Zr—La | Rb/Ca/In/Ni/ Pr—La | Rb/Ca/In/Ni/ Ce—La |
| Sr/Ho/Tm | Sr/Ho/Tm/ $La_{3.8}Nd_{0.2}O_6$ | Sr/Ho/Tm/ Y—La | Sr/Ho/Tm/ Zr—La | Sr/Ho/Tm/ Pr—La | Sr/Ho/Tm/ Ce—La |
| La/Nd/S | La/Nd/S/ $La_{3.8}Nd_{0.2}O_6$ | La/Nd/S/ Y—La | La/Nd/S/ Zr—La | La/Nd/S/ Pr—La | La/Nd/S/ Ce—La |
| Li/Rb/Ca | Li/Rb/Ca/ $La_{3.8}Nd_{0.2}O_6$ | Li/Rb/Ca/ Y—La | Li/Rb/Ca/ Zr—La | Li/Rb/Ca/ Pr—La | Li/Rb/Ca/ Ce—La |
| Li/K | Li/K/ $La_{3.8}Nd_{0.2}O_6$ | Li/K/ Y—La | Li/K/ Zr—La | Li/K/ Pr—La | Li/K/ Ce—La |
| Tm/Lu/Ta/P | Tm/Lu/Ta/P/ $La_{3.8}Nd_{0.2}O_6$ | Tm/Lu/Ta/P/ Y—La | Tm/Lu/Ta/P/ Zr—La | Tm/Lu/Ta/P/ Pr—La | Tm/Lu/Ta/P/ Ce—La |
| Rb/Ca/Dy/P | Rb/Ca/Dy/P/ $La_{3.8}Nd_{0.2}O_6$ | Rb/Ca/Dy/P/ Y—La | Rb/Ca/Dy/P/ Zr—La | Rb/Ca/Dy/P/ Pr—La | Rb/Ca/Dy/P/ Ce—La |
| Mg/La/Yb/Zn | Mg/La/Yb/Zn/ $La_{3.8}Nd_{0.2}O_6$ | Mg/La/Yb/Zn/ Y—La | Mg/La/Yb/Zn/ Zr—La | Mg/La/Yb/Zn/ Pr—La | Mg/La/Yb/Zn/ Ce—La |

TABLE 11-continued

NANOWIRES (NW) DOPED WITH SPECIFIC DOPANTS (DOP)

| Dop\NW | $La_{3.8}Nd_{0.2}O_6$ | Y—La | Zr—La | Pr—La | Ce—La |
|---|---|---|---|---|---|
| Rb/Sr/Lu | Rb/Sr/Lu/$La_{3.8}Nd_{0.2}O_6$ | Rb/Sr/Lu/Y—La | Rb/Sr/Lu/Zr—La | Rb/Sr/Lu/Pr—La | Rb/Sr/Lu/Ce—La |
| Sr/B | Sr/B/$La_{3.8}Nd_{0.2}O_6$ | Sr/B/Y—La | Sr/B/Zr—La | Sr/B/Pr—La | Sr/B/Ce—La |
| Na/Sr/Lu/Nb | Na/Sr/Lu/Nb/$La_{3.8}Nd_{0.2}O_6$ | Na/Sr/Lu/Nb/Y—La | Na/Sr/Lu/Nb/Zr—La | Na/Sr/Lu/Nb/Pr—La | Na/Sr/Lu/Nb/Ce—La |
| Na/Eu/Hf | Na/Eu/Hf/$La_{3.8}Nd_{0.2}O_6$ | Na/Eu/Hf/Y—La | Na/Eu/Hf/Zr—La | Na/Eu/Hf/Pr—La | Na/Eu/Hf/Ce—La |
| Dy/Rb/Gd | Dy/Rb/Gd/$La_{3.8}Nd_{0.2}O_6$ | Dy/Rb/Gd/Y—La | Dy/Rb/Gd/Zr—La | Dy/Rb/Gd/Pr—La | Dy/Rb/Gd/Ce—La |
| Na/Pt/Bi | Na/Pt/Bi/$La_{3.8}Nd_{0.2}O_6$ | Na/Pt/Bi/Y—La | Na/Pt/Bi/Zr—La | Na/Pt/Bi/Pr—La | Na/Pt/Bi/Ce—La |
| Rb/Hf | Rb/Hf/$La_{3.8}Nd_{0.2}O_6$ | Rb/Hf/Y—La | Rb/Hf/Zr—La | Rb/Hf/Pr—La | Rb/Hf/Ce—La |
| Ca/Cs | Ca/Cs/$La_{3.8}Nd_{0.2}O_6$ | Ca/Cs/Y—La | Ca/Cs/Zr—La | Ca/Cs/Pr—La | Ca/Cs/Ce—La |
| Ca/Mg/Na | Ca/Mg/Na/$La_{3.8}Nd_{0.2}O_6$ | Ca/Mg/Na/Y—La | Ca/Mg/Na/Zr—La | Ca/Mg/Na/Pr—La | Ca/Mg/Na/Ce—La |
| Hf/Bi | Hf/Bi/$La_{3.8}Nd_{0.2}O_6$ | Hf/Bi/Y—La | Hf/Bi/Zr—La | Hf/Bi/Pr—La | Hf/Bi/Ce—La |
| Sr/Sn | Sr/Sn/$La_{3.8}Nd_{0.2}O_6$ | Sr/Sn/Y—La | Sr/Sn/Zr—La | Sr/Sn/Pr—La | Sr/Sn/Ce—La |
| Sr/W | Sr/W/$La_{3.8}Nd_{0.2}O_6$ | Sr/W/Y—La | Sr/W/Zr—La | Sr/W/Pr—La | Sr/W/Ce—La |
| Sr/Nb | Sr/Nb/$La_{3.8}Nd_{0.2}O_6$ | Sr/Nb/Y—La | Sr/Nb/Zr—La | Sr/Nb/Pr—La | Sr/Nb/Ce—La |
| Zr/W | Zr/W/$La_{3.8}Nd_{0.2}O_6$ | Zr/W/Y—La | Zr/W/Zr—La | Zr/W/Pr—La | Zr/W/Ce—La |
| Y/W | Y/W/$La_{3.8}Nd_{0.2}O_6$ | Y/W/Y—La | Y/W/Zr—La | Y/W/Pr—La | Y/W/Ce—La |
| Na/W | Na/W/$La_{3.8}Nd_{0.2}O_6$ | Na/W/Y—La | Na/W/Zr—La | Na/W/Pr—La | Na/W/Ce—La |
| Bi/W | Bi/W/$La_{3.8}Nd_{0.2}O_6$ | Bi/W/Y—La | Bi/W/Zr—La | Bi/W/Pr—La | Bi/W/Ce—La |
| Bi/Cs | Bi/Cs/$La_{3.8}Nd_{0.2}O_6$ | Bi/Cs/Y—La | Bi/Cs/Zr—La | Bi/Cs/Pr—La | Bi/Cs/Ce—La |
| Bi/Ca | Bi/Ca/$La_{3.8}Nd_{0.2}O_6$ | Bi/Ca/Y—La | Bi/Ca/Zr—La | Bi/Ca/Pr—La | Bi/Ca/Ce—La |
| Sr/Pr | Sr/Pr/$La_{3.8}Nd_{0.2}O_6$ | Sr/Pr/Y—La | Sr/Pr/Zr—La | Sr/Pr/Pr—La | Sr/Pr/Ce—La |
| Bi/Sn | Bi/Sn/$La_{3.8}Nd_{0.2}O_6$ | Bi/Sn/Y—La | Bi/Sn/Zr—La | Bi/Sn/Pr—La | Bi/Sn/Ce—La |
| Bi/Sb | Bi/Sb/$La_{3.8}Nd_{0.2}O_6$ | Bi/Sb/Y—La | Bi/Sb/Zr—La | Bi/Sb/Pr—La | Bi/Sb/Ce—La |
| Ge/Hf | Ge/Hf/$La_{3.8}Nd_{0.2}O_6$ | Ge/Hf/Y—La | Ge/Hf/Zr—La | Ge/Hf/Pr—La | Ge/Hf/Ce—La |
| Hf/Sm | Hf/Sm/$La_{3.8}Nd_{0.2}O_6$ | Hf/Sm/Y—La | Hf/Sm/Zr—La | Hf/Sm/Pr—La | Hf/Sm/Ce—La |
| Sb/Ag | Sb/Ag/$La_{3.8}Nd_{0.2}O_6$ | Sb/Ag/Y—La | Sb/Ag/Zr—La | Sb/Ag/Pr—La | Sb/Ag/Ce—La |
| Sb/Bi | Sb/Bi/$La_{3.8}Nd_{0.2}O_6$ | Sb/Bi/Y—La | Sb/Bi/Zr—La | Sb/Bi/Pr—La | Sb/Bi/Ce—La |
| Sb/Au | Sb/Au/$La_{3.8}Nd_{0.2}O_6$ | Sb/Au/Y—La | Sb/Au/Zr—La | Sb/Au/Pr—La | Sb/Au/Ce—La |
| Sb/Sm | Sb/Sm/$La_{3.8}Nd_{0.2}O_6$ | Sb/Sm/Y—La | Sb/Sm/Zr—La | Sb/Sm/Pr—La | Sb/Sm/Ce—La |
| Sb/Sr | Sb/Sr/$La_{3.8}Nd_{0.2}O_6$ | Sb/Sr/Y—La | Sb/Sr/Zr—La | Sb/Sr/Pr—La | Sb/Sr/Ce—La |
| Sb/W | Sb/W/$La_{3.8}Nd_{0.2}O_6$ | Sb/W/Y—La | Sb/W/Zr—La | Sb/W/Pr—La | Sb/W/Ce—La |
| Sb/Hf | Sb/Hf/$La_{3.8}Nd_{0.2}O_6$ | Sb/Hf/Y—La | Sb/Hf/Zr—La | Sb/Hf/Pr—La | Sb/Hf/Ce—La |
| Sb/Yb | Sb/Yb/$La_{3.8}Nd_{0.2}O_6$ | Sb/Yb/Y—La | Sb/Yb/Zr—La | Sb/Yb/Pr—La | Sb/Yb/Ce—La |
| Sr/Hf/K | Sr/Hf/K/$La_{3.8}Nd_{0.2}O_6$ | Sr/Hf/K/Y—La | Sr/Hf/K/Zr—La | Sr/Hf/K/Pr—La | Sr/Hf/K/Ce—La |
| Sb/Sn | Sb/Sn/$La_{3.8}Nd_{0.2}O_6$ | Sb/Sn/Y—La | Sb/Sn/Zr—La | Sb/Sn/Pr—La | Sb/Sn/Ce—La |
| Yb/Au | Yb/Au/$La_{3.8}Nd_{0.2}O_6$ | Yb/Au/Y—La | Yb/Au/Zr—La | Yb/Au/Pr—La | Yb/Au/Ce—La |
| Yb/Ta | Yb/Ta/$La_{3.8}Nd_{0.2}O_6$ | Yb/Ta/Y—La | Yb/Ta/Zr—La | Yb/Ta/Pr—La | Yb/Ta/Ce—La |
| Yb/W | Yb/W/$La_{3.8}Nd_{0.2}O_6$ | Yb/W/Y—La | Yb/W/Zr—La | Yb/W/Pr—La | Yb/W/Ce—La |
| Yb/Sr | Yb/Sr/$La_{3.8}Nd_{0.2}O_6$ | Yb/Sr/Y—La | Yb/Sr/Zr—La | Yb/Sr/Pr—La | Yb/Sr/Ce—La |

TABLE 11-continued

NANOWIRES (NW) DOPED WITH SPECIFIC DOPANTS (DOP)

| Dop\NW | La$_{3.8}$Nd$_{0.2}$O$_6$ | Y—La | Zr—La | Pr—La | Ce—La |
|---|---|---|---|---|---|
| Yb/Pb | Yb/Pb/La$_{3.8}$Nd$_{0.2}$O$_6$ | Yb/Pb/Y—La | Yb/Pb/Zr—La | Yb/Pb/Pr—La | Yb/Pb/Ce—La |
| Yb/W | Yb/W/La$_{3.8}$Nd$_{0.2}$O$_6$ | Yb/W/Y—La | Yb/W/Zr—La | Yb/W/Pr—La | Yb/W/Ce—La |
| Yb/Ag | Yb/Ag/La$_{3.8}$Nd$_{0.2}$O$_6$ | Yb/Ag/Y—La | Yb/Ag/Zr—La | Yb/Ag/Pr—La | Yb/Ag/Ce—La |
| Au/Sr | Au/Sr/La$_{3.8}$Nd$_{0.2}$O$_6$ | Au/Sr/Y—La | Au/Sr/Zr—La | Au/Sr/Pr—La | Au/Sr/Ce—La |
| W/Ge | W/Ge/La$_{3.8}$Nd$_{0.2}$O$_6$ | W/Ge/Y—La | W/Ge/Zr—La | W/Ge/Pr—La | W/Ge/Ce—La |
| Sr/Hf/Rb | Sr/Hf/Rb/La$_{3.8}$Nd$_{0.2}$O$_6$ | Sr/Hf/Rb/Y—La | Sr/Hf/Rb/Zr—La | Sr/Hf/Rb/Pr—La | Sr/Hf/Rb/Ce—La |
| Ta/Sr | Ta/Sr/La$_{3.8}$Nd$_{0.2}$O$_6$ | Ta/Sr/Y—La | Ta/Sr/Zr—La | Ta/Sr/Pr—La | Ta/Sr/Ce—La |
| Ta/Hf | Ta/Hf/La$_{3.8}$Nd$_{0.2}$O$_6$ | Ta/Hf/Y—La | Ta/Hf/Zr—La | Ta/Hf/Pr—La | Ta/Hf/Ce—La |
| W/Au | W/Au/La$_{3.8}$Nd$_{0.2}$O$_6$ | W/Au/Y—La | W/Au/Zr—La | W/Au/Pr—La | W/Au/Ce—La |
| Ca/W | Ca/W/La$_{3.8}$Nd$_{0.2}$O$_6$ | Ca/W/Y—La | Ca/W/Zr—La | Ca/W/Pr—La | Ca/W/Ce—La |
| Au/Re | Au/Re/La$_{3.8}$Nd$_{0.2}$O$_6$ | Au/Re/Y—La | Au/Re/Zr—La | Au/Re/Pr—La | Au/Re/Ce—La |
| Sm/Li | Sm/Li/La$_{3.8}$Nd$_{0.2}$O$_6$ | Sm/Li/Y—La | Sm/Li/Zr—La | Sm/Li/Pr—La | Sm/Li/Ce—La |
| La/K | La/K/La$_{3.8}$Nd$_{0.2}$O$_6$ | La/K/Y—La | La/K/Zr—La | La/K/Pr—La | La/K/Ce—La |
| Zn/Cs | Zn/Cs/La$_{3.8}$Nd$_{0.2}$O$_6$ | Zn/Cs/Y—La | Zn/Cs/Zr—La | Zn/Cs/Pr—La | Zn/Cs/Ce—La |
| Na/K/Mg | Na/K/Mg/La$_{3.8}$Nd$_{0.2}$O$_6$ | Na/K/Mg/Y—La | Na/K/Mg/Zr—La | Na/K/Mg/Pr—La | Na/K/Mg/Ce—La |
| Zr/Cs | Zr/Cs/La$_{3.8}$Nd$_{0.2}$O$_6$ | Zr/Cs/Y—La | Zr/Cs/Zr—La | Zr/Cs/Pr—La | Zr/Cs/Ce—La |
| Ca/Ce | Ca/Ce/La$_{3.8}$Nd$_{0.2}$O$_6$ | Ca/Ce/Y—La | Ca/Ce/Zr—La | Ca/Ce/Pr—La | Ca/Ce/Ce—La |
| Sr/Zr/K | Sr/Zr/K/La$_{3.8}$Nd$_{0.2}$O$_6$ | Sr/Zr/K/Y—La | Sr/Zr/K/Zr—La | Sr/Zr/K/Pr—La | Sr/Zr/K/Ce—La |
| Na/Li/Cs | Na/Li/Cs/La$_{3.8}$Nd$_{0.2}$O$_6$ | Na/Li/Cs/Y—La | Na/Li/Cs/Zr—La | Na/Li/Cs/Pr—La | Na/Li/Cs/Ce—La |
| Li/Sr | Li/Sr/La$_{3.8}$Nd$_{0.2}$O$_6$ | Li/Sr/Y—La | Li/Sr/Zr—La | Li/Sr/Pr—La | Li/Sr/Ce—La |
| La/Dy/K | La/Dy/K/La$_{3.8}$Nd$_{0.2}$O$_6$ | La/Dy/K/Y—La | La/Dy/K/Zr—La | La/Dy/K/Pr—La | La/Dy/K/Ce—La |
| Dy/K | Dy/K/La$_{3.8}$Nd$_{0.2}$O$_6$ | Dy/K/Y—La | Dy/K/Zr—La | Dy/K/Pr—La | Dy/K/Ce—La |
| La/Mg | La/Mg/La$_{3.8}$Nd$_{0.2}$O$_6$ | La/Mg/Y—La | La/Mg/Zr—La | La/Mg/Pr—La | La/Mg/Ce—La |
| Na/Nd/In/K | Na/Nd/In/K/La$_{3.8}$Nd$_{0.2}$O$_6$ | Na/Nd/In/K/Y—La | Na/Nd/In/K/Zr—La | Na/Nd/In/K/Pr—La | Na/Nd/In/K/Ce—La |
| In/Sr | In/Sr/La$_{3.8}$Nd$_{0.2}$O$_6$ | In/Sr/Y—La | In/Sr/Zr—La | In/Sr/Pr—La | In/Sr/Ce—La |
| Sr/Cs | Sr/Cs/La$_{3.8}$Nd$_{0.2}$O$_6$ | Sr/Cs/Y—La | Sr/Cs/Zr—La | Sr/Cs/Pr—La | Sr/Cs/Ce—La |
| Rb/Ga/Tm/Cs | Rb/Ga/Tm/Cs/La$_{3.8}$Nd$_{0.2}$O$_6$ | Rb/Ga/Tm/Cs/Y—La | Rb/Ga/Tm/Cs/Zr—La | Rb/Ga/Tm/Cs/Pr—La | Rb/Ga/Tm/Cs/Ce—La |
| Ga/Cs | Ga/Cs/La$_{3.8}$Nd$_{0.2}$O$_6$ | Ga/Cs/Y—La | Ga/Cs/Zr—La | Ga/Cs/Pr—La | Ga/Cs/Ce—La |
| K/La/Zr/Ag | K/La/Zr/Ag/La$_{3.8}$Nd$_{0.2}$O$_6$ | K/La/Zr/Ag/Y—La | K/La/Zr/Ag/Zr—La | K/La/Zr/Ag/Pr—La | K/La/Zr/Ag/Ce—La |
| Sr/Zr | Sr/Zr/La$_{3.8}$Nd$_{0.2}$O$_6$ | Sr/Zr/Y—La | Sr/Zr/Zr—La | Sr/Zr/Pr—La | Sr/Zr/Ce—La |
| Lu/Fe | Lu/Fe/La$_{3.8}$Nd$_{0.2}$O$_6$ | Lu/Fe/Y—La | Lu/Fe/Zr—La | Lu/Fe/Pr—La | Lu/Fe/Ce—La |
| Sr/Tm | Sr/Tm/La$_{3.8}$Nd$_{0.2}$O$_6$ | Sr/Tm/Y—La | Sr/Tm/Zr—La | Sr/Tm/Pr—La | Sr/Tm/Ce—La |
| La/Dy | La/Dy/La$_{3.8}$Nd$_{0.2}$O$_6$ | La/Dy/Y—La | La/Dy/Zr—La | La/Dy/Pr—La | La/Dy/Ce—La |
| Sm/Li/Sr | Sm/Li/Sr/La$_{3.8}$Nd$_{0.2}$O$_6$ | Sm/Li/Sr/Y—La | Sm/Li/Sr/Zr—La | Sm/Li/Sr/Pr—La | Sm/Li/Sr/Ce—La |
| Mg/K | Mg/K/La$_{3.8}$Nd$_{0.2}$O$_6$ | Mg/K/Y—La | Mg/K/Zr—La | Mg/K/Pr—La | Mg/K/Ce—La |
| Li/Rb/Ga | Li/Rb/Ga/La$_{3.8}$Nd$_{0.2}$O$_6$ | Li/Rb/Ga/Y—La | Li/Rb/Ga/Zr—La | Li/Rb/Ga/Pr—La | Li/Rb/Ga/Ce—La |
| Li/Cs/Tm | Li/Cs/Tm/La$_{3.8}$Nd$_{0.2}$O$_6$ | Li/Cs/Tm/Y—La | Li/Cs/Tm/Zr—La | Li/Cs/Tm/Pr—La | Li/Cs/Tm/Ce—La |
| Zr/K | Zr/K/La$_{3.8}$Nd$_{0.2}$O$_6$ | Zr/K/Y—La | Zr/K/Zr—La | Zr/K/Pr—La | Zr/K/Ce—La |

TABLE 11-continued

NANOWIRES (NW) DOPED WITH SPECIFIC DOPANTS (DOP)

| Dop\NW | La$_{3.8}$Nd$_{0.2}$O$_6$ | Y—La | Zr—La | Pr—La | Ce—La |
|---|---|---|---|---|---|
| Li/Cs | Li/Cs/La$_{3.8}$Nd$_{0.2}$O$_6$ | Li/Cs/Y—La | Li/Cs/Zr—La | Li/Cs/Pr—La | Li/Cs/Ce—La |
| Sr/Ce | Sr/Ce/La$_{3.8}$Nd$_{0.2}$O$_6$ | Sr/Ce/Y—La | Sr/Ce/Zr—La | Sr/Ce/Pr—La | Sr/Ce/Ce—La |
| Li/K/La | Li/K/La/La$_{3.8}$Nd$_{0.2}$O$_6$ | Li/K/La/Y—La | Li/K/La/Zr—La | Li/K/La/Pr—La | Li/K/La/Ce—La |
| Ce/Zr/La | Ce/Zr/La/La$_{3.8}$Nd$_{0.2}$O$_6$ | Ce/Zr/La/Y—La | Ce/Zr/La/Zr—La | Ce/Zr/La/Pr—La | Ce/Zr/La/Ce—La |
| Ca/Al/La | Ca/Al/La/La$_{3.8}$Nd$_{0.2}$O$_6$ | Ca/Al/La/Y—La | Ca/Al/La/Zr—La | Ca/Al/La/Pr—La | Ca/Al/La/Ce—La |
| Sr/Zn/La | Sr/Zn/La/La$_{3.8}$Nd$_{0.2}$O$_6$ | Sr/Zn/La/Y—La | Sr/Zn/La/Zr—La | Sr/Zn/La/Pr—La | Sr/Zn/La/Ce—La |
| Sr/Cs/Zn | Sr/Cs/Zn/La$_{3.8}$Nd$_{0.2}$O$_6$ | Sr/Cs/Zn/Y—La | Sr/Cs/Zn/Zr—La | Sr/Cs/Zn/Pr—La | Sr/Cs/Zn/Ce—La |
| Sm/Cs | Sm/Cs/La$_{3.8}$Nd$_{0.2}$O$_6$ | Sm/Cs/Y—La | Sm/Cs/Zr—La | Sm/Cs/Pr—La | Sm/Cs/Ce—La |
| In/K | In/K/La$_{3.8}$Nd$_{0.2}$O$_6$ | In/K/Y—La | In/K/Zr—La | In/K/Pr—La | In/K/Ce—La |
| Ho/Cs/Li/La | Ho/Cs/Li/La/La$_{3.8}$Nd$_{0.2}$O$_6$ | Ho/Cs/Li/La/Y—La | Ho/Cs/Li/La/Zr—La | Ho/Cs/Li/La/Pr—La | Ho/Cs/Li/La/Ce—La |
| Cs/La/Na | Cs/La/Na/La$_{3.8}$Nd$_{0.2}$O$_6$ | Cs/La/Na/Y—La | Cs/La/Na/Zr—La | Cs/La/Na/Pr—La | Cs/La/Na/Ce—La |
| La/S/Sr | La/S/Sr/La$_{3.8}$Nd$_{0.2}$O$_6$ | La/S/Sr/Y—La | La/S/Sr/Zr—La | La/S/Sr/Pr—La | La/S/Sr/Ce—La |
| K/La/Zr/Ag | K/La/Zr/Ag/La$_{3.8}$Nd$_{0.2}$O$_6$ | K/La/Zr/Ag/Y—La | K/La/Zr/Ag/Zr—La | K/La/Zr/Ag/Pr—La | K/La/Zr/Ag/Ce—La |
| Lu/Tl | Lu/Tl/La$_{3.8}$Nd$_{0.2}$O$_6$ | Lu/Tl/Y—La | Lu/Tl/Zr—La | Lu/Tl/Pr—La | Lu/Tl/Ce—La |
| Pr/Zn | Pr/Zn/La$_{3.8}$Nd$_{0.2}$O$_6$ | Pr/Zn/Y—La | Pr/Zn/Zr—La | Pr/Zn/Pr—La | Pr/Zn/Ce—La |
| Rb/Sr/La | Rb/Sr/La/La$_{3.8}$Nd$_{0.2}$O$_6$ | Rb/Sr/La/Y—La | Rb/Sr/La/Zr—La | Rb/Sr/La/Pr—La | Rb/Sr/La/Ce—La |
| Na/Sr/Eu/Ca | Na/Sr/Eu/Ca/La$_{3.8}$Nd$_{0.2}$O$_6$ | Na/Sr/Eu/Ca/Y—La | Na/Sr/Eu/Ca/Zr—La | Na/Sr/Eu/Ca/Pr—La | Na/Sr/Eu/Ca/Ce—La |
| K/Cs/Sr/La | K/Cs/Sr/La/La$_{3.8}$Nd$_{0.2}$O$_6$ | K/Cs/Sr/La/Y—La | K/Cs/Sr/La/Zr—La | K/Cs/Sr/La/Pr—La | K/Cs/Sr/La/Ce—La |
| Na/Sr/Lu | Na/Sr/Lu/La$_{3.8}$Nd$_{0.2}$O$_6$ | Na/Sr/Lu/Y—La | Na/Sr/Lu/Zr—La | Na/Sr/Lu/Pr—La | Na/Sr/Lu/Ce—La |
| Sr/Eu/Dy | Sr/Eu/Dy/La$_{3.8}$Nd$_{0.2}$O$_6$ | Sr/Eu/Dy/Y—La | Sr/Eu/Dy/Zr—La | Sr/Eu/Dy/Pr—La | Sr/Eu/Dy/Ce—La |
| Lu/Nb | Lu/Nb/La$_{3.8}$Nd$_{0.2}$O$_6$ | Lu/Nb/Y—La | Lu/Nb/Zr—La | Lu/Nb/Pr—La | Lu/Nb/Ce—La |
| Sr/Tb | Sr/Tb/La$_{3.8}$Nd$_{0.2}$O$_6$ | Sr/Tb/Y—La | Sr/Tb/Zr—La | Sr/Tb/Pr—La | Sr/Tb/Ce—La |
| La/Dy/Gd | La/Dy/Gd/La$_{3.8}$Nd$_{0.2}$O$_6$ | La/Dy/Gd/Y—La | La/Dy/Gd/Zr—La | La/Dy/Gd/Pr—La | La/Dy/Gd/Ce—La |
| Na/Mg/Tl/P | Na/Mg/Tl/P/La$_{3.8}$Nd$_{0.2}$O$_6$ | Na/Mg/Tl/P/Y—La | Na/Mg/Tl/P/Zr—La | Na/Mg/Tl/P/Pr—La | Na/Mg/Tl/P/Ce—La |
| Na/Pt | Na/Pt/La$_{3.8}$Nd$_{0.2}$O$_6$ | Na/Pt/Y—La | Na/Pt/Zr—La | Na/Pt/Pr—La | Na/Pt/Ce—La |
| Gd/Li/K | Gd/Li/K/La$_{3.8}$Nd$_{0.2}$O$_6$ | Gd/Li/K/Y—La | Gd/Li/K/Zr—La | Gd/Li/K/Pr—La | Gd/Li/K/Ce—La |
| Rb/K/Lu | Rb/K/Lu/La$_{3.8}$Nd$_{0.2}$O$_6$ | Rb/K/Lu/Y—La | Rb/K/Lu/Zr—La | Rb/K/Lu/Pr—La | Rb/K/Lu/Ce—La |
| Sr/La/Dy/S | Sr/La/Dy/S/La$_{3.8}$Nd$_{0.2}$O$_6$ | Sr/La/Dy/S/Y—La | Sr/La/Dy/S/Zr—La | Sr/La/Dy/S/Pr—La | Sr/La/Dy/S/Ce—La |
| Na/Ce/Co | Na/Ce/Co/La$_{3.8}$Nd$_{0.2}$O$_6$ | Na/Ce/Co/Y—La | Na/Ce/Co/Zr—La | Na/Ce/Co/Pr—La | Na/Ce/Co/Ce—La |
| Na/Ce | Na/Ce/La$_{3.8}$Nd$_{0.2}$O$_6$ | Na/Ce/Y—La | Na/Ce/Zr—La | Na/Ce/Pr—La | Na/Ce/Ce—La |
| Na/Ga/Gd/Al | Na/Ga/Gd/Al/La$_{3.8}$Nd$_{0.2}$O$_6$ | Na/Ga/Gd/Al/Y—La | Na/Ga/Gd/Al/Zr—La | Na/Ga/Gd/Al/Pr—La | Na/Ga/Gd/Al/Ce—La |
| Ba/Rh/Ta | Ba/Rh/Ta/La$_{3.8}$Nd$_{0.2}$O$_6$ | Ba/Rh/Ta/Y—La | Ba/Rh/Ta/Zr—La | Ba/Rh/Ta/Pr—La | Ba/Rh/Ta/Ce—La |
| Ba/Ta | Ba/Ta/La$_{3.8}$Nd$_{0.2}$O$_6$ | Ba/Ta/Y—La | Ba/Ta/Zr—La | Ba/Ta/Pr—La | Ba/Ta/Ce—La |
| Na/Al/Bi | Na/Al/Bi/La$_{3.8}$Nd$_{0.2}$O$_6$ | Na/Al/Bi/Y—La | Na/Al/Bi/Zr—La | Na/Al/Bi/Pr—La | Na/Al/Bi/Ce—La |
| Cs/Eu/S | Cs/Eu/S/La$_{3.8}$Nd$_{0.2}$O$_6$ | Cs/Eu/S/Y—La | Cs/Eu/S/Zr—La | Cs/Eu/S/Pr—La | Cs/Eu/S/Ce—La |
| Sm/Tm/Yb/Fe | Sm/Tm/Yb/Fe/La$_{3.8}$Nd$_{0.2}$O$_6$ | Sm/Tm/Yb/Fe/Y—La | Sm/Tm/Yb/Fe/Zr—La | Sm/Tm/Yb/Fe/Pr—La | Sm/Tm/Yb/Fe/Ce—La |
| Sm/Tm/Yb | Sm/Tm/Yb/La$_{3.8}$Nd$_{0.2}$O$_6$ | Sm/Tm/Yb/Y—La | Sm/Tm/Yb/Zr—La | Sm/Tm/Yb/Pr—La | Sm/Tm/Yb/Ce—La |
| Hf/Zr/Ta | Hf/Zr/Ta/La$_{3.8}$Nd$_{0.2}$O$_6$ | Hf/Zr/Ta/Y—La | Hf/Zr/Ta/Zr—La | Hf/Zr/Ta/Pr—La | Hf/Zr/Ta/Ce—La |

TABLE 11-continued

NANOWIRES (NW) DOPED WITH SPECIFIC DOPANTS (DOP)

| Dop\NW | $La_{3.8}Nd_{0.2}O_6$ | Y—La | Zr—La | Pr—La | Ce—La |
|---|---|---|---|---|---|
| Rb/Gd/Li/K | Rb/Gd/Li/K/ $La_{3.8}Nd_{0.2}O_6$ | Rb/Gd/Li/K/ Y—La | Rb/Gd/Li/K/ Zr—La | Rb/Gd/Li/K/ Pr—Lai/K | Rb/Gd/Li/K/ Ce—La |
| Gd/Ho/Al/P | Gd/Ho/Al/P/ $La_{3.8}Nd_{0.2}O_6$ | Gd/Ho/Al/P/ Y—La | Gd/Ho/Al/P/ Zr—La | Gd/Ho/Al/P/ Pr—La | Gd/Ho/Al/P/ Ce—La |
| Na/Ca/Lu | Na/Ca/Lu/ $La_{3.8}Nd_{0.2}O_6$ | Na/Ca/Lu/ Y—La | Na/Ca/Lu/ Zr—La | Na/Ca/Lu/ Pr—La | Na/Ca/Lu/ Ce—La |
| Cu/Sn | Cu/Sn/ $La_{3.8}Nd_{0.2}O_6$ | Cu/Sn/ Y—La | Cu/Sn/ Zr—La | Cu/Sn/ Pr—La | Cu/Sn/ Ce—La |
| Ag/Au | Ag/Au/ $La_{3.8}Nd_{0.2}O_6$ | Ag/Au/ Y—La | Ag/Au/ Zr—La | Ag/Au/ Pr—La | Ag/Au/ Ce—La |
| Al/Bi | Al/Bi/ $La_{3.8}Nd_{0.2}O_6$ | Al/Bi/ Y—La | Al/Bi/ Zr—La | Al/Bi/ Pr—La | Al/Bi/ Ce—La |
| Al/Mo | Al/Mo/ $La_{3.8}Nd_{0.2}O_6$ | Al/Mo/ Y—La | Al/Mo/ Zr—La | Al/Mo/ Pr—La | Al/Mo/ Ce—La |
| Al/Nb | Al/Nb/ $La_{3.8}Nd_{0.2}O_6$ | Al/Nb/ Y—La | Al/Nb/ Zr—La | Al/Nb/ Pr—La | Al/Nb/ Ce—La |
| Sr/Ce/K | Sr/Ce/K/ $La_{3.8}Nd_{0.2}O_6$ | Sr/Ce/K/ Y—La | Sr/Ce/K/ Zr—La | Sr/Ce/K/ Pr—La | Sr/Ce/K/ Ce—La |
| Au/Pt | Au/Pt/ $La_{3.8}Nd_{0.2}O_6$ | Au/Pt/ Y—La | Au/Pt/ Zr—La | Au/Pt/ Pr—La | Au/Pt/ Ce—La |
| Ga/Bi | Ga/Bi/ $La_{3.8}Nd_{0.2}O_6$ | Ga/Bi/ Y—La | Ga/Bi/ Zr—La | Ga/Bi/ Pr—La | Ga/Bi/ Ce—La |
| Mg/W | Mg/W/ $La_{3.8}Nd_{0.2}O_6$ | Mg/W/ Y—La | Mg/W/ Zr—La | Mg/W/ Pr—La | Mg/W/ Ce—La |
| Pb/Au | Pb/Au/ $La_{3.8}Nd_{0.2}O_6$ | Pb/Au/ Y—La | Pb/Au/ Zr—La | Pb/Au/ Pr—La | Pb/Au/ Ce—La |
| Sn/Mg | Sn/Mg/ $La_{3.8}Nd_{0.2}O_6$ | Sn/Mg/ Y—La | Sn/Mg/ Zr—La | Sn/Mg/ Pr—La | Sn/Mg/ Ce—La |
| Zn/Bi | Zn/Bi/ $La_{3.8}Nd_{0.2}O_6$ | Zn/Bi/ Y—La | Zn/Bi/ Zr—La | Zn/Bi/ Pr—La | Zn/Bi/ Ce—La |
| Sr/Ta | Sr/Ta/ $La_{3.8}Nd_{0.2}O_6$ | Sr/Ta/ Y—La | Sr/Ta/ Zr—La | Sr/Ta/ Pr—La | Sr/Ta/ Ce—La |
| Na | Na/ $La_{3.8}Nd_{0.2}O_6$ | Na/ Y—La | Na/ Zr—La | Na/ Pr—La | Na/ Ce—La |
| Sr | Sr/ $La_{3.8}Nd_{0.2}O_6$ | Sr/ Y—La | Sr/ Zr—La | Sr/ Pr—La | Sr/ Ce—La |
| Ca | Ca/ $La_{3.8}Nd_{0.2}O_6$ | Ca/ Y—La | Ca/ Zr—La | Ca/ Pr—La | Ca/ Ce—La |
| Yb | Yb/ $La_{3.8}Nd_{0.2}O_6$ | Yb/ Y—La | Yb/ Zr—La | Yb/ Pr—La | Yb/ Ce—La |
| Cs | Cs/ $La_{3.8}Nd_{0.2}O_6$ | Cs/ Y—La | Cs/ Zr—La | Cs/ Pr—La | Cs/ Ce—La |
| Sb | Sb/ $La_{3.8}Nd_{0.2}O_6$/ Zn/Bi | Sb/ Y—La/ Zn/Bi | Sb/ Zr—La/ Zn/Bi | Sb/ Pr—La/ Zn/Bi | Sb/ Ce—La/ Zn/Bi |
| Gd/Ho | Gd/Ho/ $La_{3.8}Nd_{0.2}O_6$ | Gd/Ho/ Y—La | Gd/Ho/ Zr—La | Gd/Ho/ Pr—La | Gd/Ho/ Ce—La |
| Zr/Bi | Zr/Bi/ $La_{3.8}Nd_{0.2}O_6$ | Zr/Bi/ Y—La | Zr/Bi/ Zr—La | Zr/Bi/ Pr—La | Zr/Bi/ Ce—La |
| Ho/Sr | Ho/Sr/ $La_{3.8}Nd_{0.2}O_6$ | Ho/Sr/ Y—La | Ho/Sr/ Zr—La | Ho/Sr/ Pr—La | Ho/Sr/ Ce—La |
| Gd/Ho/Sr | Gd/Ho/Sr/ $La_{3.8}Nd_{0.2}O_6$ | Gd/Ho/Sr/ Y—La | Gd/Ho/Sr/ Zr—La | Gd/Ho/Sr/ Pr—La | Gd/Ho/Sr/ Ce—La |
| Ca/Sr | Ca/Sr/ $La_{3.8}Nd_{0.2}O_6$ | Ca/Sr/ Y—La | Ca/Sr/ Zr—La | Ca/Sr/ Pr—La | Ca/Sr/ Ce—La |
| Ca/Sr/W | Ca/Sr/W/ $La_{3.8}Nd_{0.2}O_6$ | Ca/Sr/W/ Y—La | Ca/Sr/W/ Zr—La | Ca/Sr/W/ Pr—La | Ca/Sr/W/ Ce—La |
| Na/Zr/Eu/Tm | Na/Zr/Eu/Tm/ $La_{3.8}Nd_{0.2}O_6$ | Na/Zr/Eu/Tm/ Y—La | Na/Zr/Eu/Tm/ Zr—La | Na/Zr/Eu/Tm/ Pr—La | Na/Zr/Eu/Tm/ Ce—La |
| Sr/Ho/Tm/Na | Sr/Ho/Tm/Na/ $La_{3.8}Nd_{0.2}O_6$ | Sr/Ho/Tm/Na/ Y—La | Sr/Ho/Tm/Na/ Zr—La | Sr/Ho/Tm/Na/ Pr—La | Sr/Ho/Tm/Na/ Ce—La |
| Sr/Pb | Sr/Pb/ $La_{3.8}Nd_{0.2}O_6$ | Sr/Pb/ Y—La | Sr/Pb/ Zr—La | Sr/Pb/ Pr—La | Sr/Pb/ Ce—La |
| Sr/W/Li | Sr/W/Li/ $La_{3.8}Nd_{0.2}O_6$ | Sr/W/Li/ Y—La | Sr/W/Li/ Zr—La | Sr/W/Li/ Pr—La | Sr/W/Li/ Ce—La |
| Ca/Sr/W | Ca/Sr/W/ $La_{3.8}Nd_{0.2}O_6$ | Ca/Sr/W/ Y—La | Ca/Sr/W/ Zr—La | Ca/Sr/W/ Pr—La | Ca/Sr/W/ Ce—La |
| Sr/Hf | Sr/Hf/ $La_{3.8}Nd_{0.2}O_6$ | Sr/Hf/ Y—La | Sr/Hf/ Zr—La | Sr/Hf/ Pr—La | Sr/Hf/ Ce—La |
| Au/Re | Au/Re/ $La_{3.8}Nd_{0.2}O_6$ | Au/Re/ Y—La | Au/Re/ Zr—La | Au/Re/ Pr—La | Au/Re/ Ce—La |
| Sr/W | Sr/W/ $La_{3.8}Nd_{0.2}O_6$ | Sr/W/ Y—La | Sr/W/ Zr—La | Sr/W/ Pr—La | Sr/W/ Ce—La |
| La/Nd | La/Nd/ $La_{3.8}Nd_{0.2}O_6$ | La/Nd/ Y—La | La/Nd/ Zr—La | La/Nd/ Pr—La | La/Nd/ Ce—La |

TABLE 11-continued

NANOWIRES (NW) DOPED WITH SPECIFIC DOPANTS (DOP)

| Dop\NW | La$_{3.8}$Nd$_{0.2}$O$_6$ | Y—La | Zr—La | Pr—La | Ce—La |
|---|---|---|---|---|---|
| La/Sm | La/Sm/ La$_{3.8}$Nd$_{0.2}$O$_6$ | La/Sm/ Y—La | La/Sm/ Zr—La | La/Sm/ Pr—La | La/Sm/ Ce—La |
| La/Ce | La/Ce/ La$_{3.8}$Nd$_{0.2}$O$_6$ | La/Ce/ Y—La | La/Ce/ Zr—La | La/Ce/ Pr—La | La/Ce/ Ce—La |
| La/Sr | La/Sr/ La$_{3.8}$Nd$_{0.2}$O$_6$ | La/Sr/ Y—La | La/Sr/ Zr—La | La/Sr/ Pr—La | La/Sr/ Ce—La |
| La/Nd/Sr | La/Nd/Sr/ La$_{3.8}$Nd$_{0.2}$O$_6$ | La/Nd/Sr/ Y—La | La/Nd/Sr/ Zr—La | La/Nd/Sr/ Pr—La | La/Nd/Sr/ Ce—La |
| La/Bi/Sr | La/Bi/Sr/ La$_{3.8}$Nd$_{0.2}$O$_6$ | La/Bi/Sr/ Y—La | La/Bi/Sr/ Zr—La | La/Bi/Sr/ Pr—La | La/Bi/Sr/ Ce—La |
| La/Ce/Nd/Sr | La/Ce/Nd/Sr/ La$_{3.8}$Nd$_{0.2}$O$_6$ | La/Ce/Nd/Sr/ Y—La | La/Ce/Nd/Sr/ Zr—La | La/Ce/Nd/Sr/ Pr—La | La/Ce/Nd/Sr/ Ce—La |
| La/Bi/Ce/Nd/Sr | La/Bi/Ce/Nd/Sr/ La$_{3.8}$Nd$_{0.2}$O$_6$ | La/Bi/Ce/Nd/Sr/ Y—La | La/Bi/Ce/Nd/Sr/ Zr—La | La/Bi/Ce/Nd/Sr/ Pr—La | La/Bi/Ce/Nd/Sr/ Ce—La |
| Eu/Gd | Eu/Gd/ La$_{3.8}$Nd$_{0.2}$O$_6$ | Eu/Gd/ Y—La | Eu/Gd/ Zr—La | Eu/Gd/ Pr—La | Eu/Gd/ Ce—La |
| Ca/Na | Ca/Na/ La$_{3.8}$Nd$_{0.2}$O$_6$ | Ca/Na/ Y—La | Ca/Na/ Zr—La | Ca/Na/ Pr—La | Ca/Na/ Ce—La |
| Eu/Sm | Eu/Sm/ La$_{3.8}$Nd$_{0.2}$O$_6$ | Eu/Sm/ Y—La | Eu/Sm/ Zr—La | Eu/Sm/ Pr—La | Eu/Sm/ Ce—La |
| Eu/Sr | Eu/Sr/ La$_{3.8}$Nd$_{0.2}$O$_6$ | Eu/Sr/ Y—La | Eu/Sr/ Zr—La | Eu/Sr/ Pr—La | Eu/Sr/ Ce—La |
| Mg/Sr | Mg/Sr/ La$_{3.8}$Nd$_{0.2}$O$_6$ | Mg/Sr/ Y—La | Mg/Sr/ Zr—La | Mg/Sr/ Pr—La | Mg/Sr/ Ce—La |
| Ce/Mg | Ce/Mg/ La$_{3.8}$Nd$_{0.2}$O$_6$ | Ce/Mg/ Y—La | Ce/Mg/ Zr—La | Ce/Mg/ Pr—La | Ce/Mg/ Ce—La |
| Gd/Sm | Gd/Sm/ La$_{3.8}$Nd$_{0.2}$O$_6$ | Gd/Sm/ Y—La | Gd/Sm/ Zr—La | Gd/Sm/ Pr—La | Gd/Sm/ Ce—La |
| Au/Pb | Au/Pb/ La$_{3.8}$Nd$_{0.2}$O$_6$ | Au/Pb/ Y—La | Au/Pb/ Zr—La | Au/Pb/ Pr—La | Au/Pb/ Ce—La |
| Bi/Hf | Bi/Hf/ La$_{3.8}$Nd$_{0.2}$O$_6$ | Bi/Hf/ Y—La | Bi/Hf/ Zr—La | Bi/Hf/ Pr—La | Bi/Hf/ Ce—La |
| Rb/S | Rb/S/ La$_{3.8}$Nd$_{0.2}$O$_6$ | Rb/S/ Y—La | Rb/S/ Zr—La | Rb/S/ Pr—La | Rb/S/ Ce—La |
| Sr/Nd | Sr/Nd/ La$_{3.8}$Nd$_{0.2}$O$_6$ | Sr/Nd/ Y—La | Sr/Nd/ Zr—La | Sr/Nd/ Pr—La | Sr/Nd/ Ce—La |
| Eu/Y | Eu/Y/ La$_{3.8}$Nd$_{0.2}$O$_6$ | Eu/Y/ Y—La | Eu/Y/ Zr—La | Eu/Y/ Pr—La | Eu/Y/ Ce—La |
| Mg/Nd | Mg/Nd/ La$_{3.8}$Nd$_{0.2}$O$_6$ | Mg/Nd/ Y—La | Mg/Nd/ Zr—La | Mg/Nd/ Pr—La | Mg/Nd/ Ce—La |
| La/Mg | La/Mg/ La$_{3.8}$Nd$_{0.2}$O$_6$ | La/Mg/ N Y—La | La/Mg/ Zr—La | La/Mg/ Pr—La | La/Mg/ Ce—La |
| Mg/Nd/Fe | Mg/Nd/Fe/ La$_{3.8}$Nd$_{0.2}$O$_6$ | Mg/Nd/Fe/ Y—La | Mg/Nd/Fe/ Zr—La | Mg/Nd/Fe/ Pr—La | Mg/Nd/Fe/ Ce—La |
| Rb/Sr | Rb/Sr/ La$_{3.8}$Nd$_{0.2}$O$_6$ | Rb/Sr/ Y—La | Rb/Sr/ Zr—La | Rb/Sr/ Pr—La | Rb/Sr/ Ce—La |

TABLE 12

NANOWIRES (NW) DOPED WITH SPECIFIC DOPANTS (DOP)

| Dop\NW | Ln1$_{4-x}$Ln2$_x$O$_6$* | La$_{4-x}$Ln1$_x$O$_6$ | Y$_2$O$_3$ | MgO |
|---|---|---|---|---|
| Eu/Na | Eu/Na/ Ln1$_{4-x}$Ln2$_x$O$_6$ | Eu/Na/ La$_{4-x}$Ln1$_x$O$_6$ | Eu/Na/ Y$_2$O$_3$ | Eu/Na/ MgO |
| Sr/Na | Sr/Na/ Ln1$_{4-x}$Ln2$_x$O$_6$ | Sr/Na/ La$_{4-x}$Ln1$_x$O$_6$ | Sr/Na/ Y$_2$O$_3$ | Sr/Na/ MgO |
| Na/Zr/Eu/Ca | Na/Zr/Eu/Ca/ Ln1$_{4-x}$Ln2$_x$O$_6$ | Na/Zr/Eu/Ca/ La$_{4-x}$Ln1$_x$O$_6$ | Na/Zr/Eu/Ca/ Y$_2$O$_3$ | Na/Zr/Eu/Ca/ MgO |
| Mg/Na | Mg/Na/ Ln1$_{4-x}$Ln2$_x$O$_6$ | Mg/Na/ La$_{4-x}$Ln1$_x$O$_6$ | Mg/Na/ Y$_2$O$_3$ | Mg/Na/ MgO |
| Sr/Sm/Ho/Tm | Sr/Sm/Ho/Tm/ Ln1$_{4-x}$Ln2$_x$O$_6$ | Sr/Sm/Ho/Tm/ La$_{4-x}$Ln1$_x$O$_6$ | Sr/Sm/Ho/Tm/ Y$_2$O$_3$ | Sr/Sm/Ho/Tm/ MgO |
| Sr/W | Sr/W/ Ln1$_{4-x}$Ln2$_x$O$_6$ | Sr/W/ La$_{4-x}$Ln1$_x$O$_6$ | Sr/W/ Y$_2$O$_3$ | Sr/W/ MgO |
| Mg/La/K | Mg/La/K/ Ln1$_{4-x}$Ln2$_x$O$_6$ | Mg/La/K/ La$_{4-x}$Ln1$_x$O$_6$ | Mg/La/K/ Y$_2$O$_3$ | Mg/La/K/ MgO |
| Na/K/Mg/Tm | Na/K/Mg/Tm/ Ln1$_{4-x}$Ln2$_x$O$_6$ | Na/K/Mg/Tm/ La$_{4-x}$Ln1$_x$O$_6$ | Na/K/Mg/Tm/ Y$_2$O$_3$ | Na/K/Mg/Tm/ MgO |
| Na/Dy/K | Na/Dy/K/ Ln1$_{4-x}$Ln2$_x$O$_6$ | Na/Dy/K/ La$_{4-x}$Ln1$_x$O$_6$ | Na/Dy/K/ Y$_2$O$_3$ | Na/Dy/K/ MgO |
| Na/La/Dy | Na/La/Dy/ Ln1$_{4-x}$Ln2$_x$O$_6$ | Na/La/Dy/ La$_{4-x}$Ln1$_x$O$_6$ | Na/La/Dy/ Y$_2$O$_3$ | Na/La/Dy/ MgO |

TABLE 12-continued

NANOWIRES (NW) DOPED WITH SPECIFIC DOPANTS (DOP)

| Dop\NW | $Ln1_{4-x}Ln2_xO_6$* | $La_{4-x}Ln1_xO_6$ | $Y_2O_3$ | MgO |
|---|---|---|---|---|
| Na/La/Eu | Na/La/Eu/ $Ln1_{4-x}Ln2_xO_6$ | Na/La/Eu/ $La_{4-x}Ln1_xO_6$ | Na/La/Eu/ $Y_2O_3$ | Na/La/Eu/ MgO |
| Na/La/Eu/In | Na/La/Eu/In/ $Ln1_{4-x}Ln2_xO_6$ | Na/La/Eu/In/ $La_{4-x}Ln1_xO_6$ | Na/La/Eu/In/ $Y_2O_3$ | Na/La/Eu/In/ MgO |
| Na/La/K | Na/La/K/ $Ln1_{4-x}Ln2_xO_6$ | Na/La/K/ $La_{4-x}Ln1_xO_6$ | Na/La/K/ $Y_2O_3$ | Na/La/K/ MgO |
| Na/La/Li/Cs | Na/La/Li/Cs/ $Ln1_{4-x}Ln2_xO_6$ | Na/La/Li/Cs/ $La_{4-x}Ln1_xO_6$ | Na/La/Li/Cs/ $Y_2O_3$ | Na/La/Li/Cs/ MgO |
| K/La | K/La/ $Ln1_{4-x}Ln2_xO_6$ | K/La/ $La_{4-x}Ln1_xO_6$ | K/La/ $Y_2O_3$ | K/La/ MgO |
| K/La/S | K/La/S/ $Ln1_{4-x}Ln2_xO_6$ | K/La/S/ $La_{4-x}Ln1_xO_6$ | K/La/S/ $Y_2O_3$ | K/La/S/ MgO |
| K/Na | K/Na/ $Ln1_{4-x}Ln2_xO_6$ | K/Na/ $La_{4-x}Ln1_xO_6$ | K/Na/ $Y_2O_3$ | K/Na/ MgO |
| Li/Cs | Li/Cs/ $Ln1_{4-x}Ln2_xO_6$ | Li/Cs/ $La_{4-x}Ln1_xO_6$ | Li/Cs/ $Y_2O_3$ | Li/Cs/ MgO |
| Li/Cs/La | Li/Cs/La/ $Ln1_{4-x}Ln2_xO_6$ | Li/Cs/La/ $La_{4-x}Ln1_xO_6$ | Li/Cs/La/ $Y_2O_3$ | Li/Cs/La/ MgO |
| Li/Cs/La/Tm | Li/Cs/La/Tm/ $Ln1_{4-x}Ln2_xO_6$ | Li/Cs/La/Tm/ $La_{4-x}Ln1_xO_6$ | Li/Cs/La/Tm/ $Y_2O_3$ | Li/Cs/La/Tm/ MgO |
| Li/Cs/Sr/Tm | Li/Cs/Sr/Tm/ $Ln1_{4-x}Ln2_xO_6$ | Li/Cs/Sr/Tm/ $La_{4-x}Ln1_xO_6$ | Li/Cs/Sr/Tm/ $Y_2O_3$ | Li/Cs/Sr/Tm/ MgO |
| Li/Sr/Cs | Li/Sr/Cs/ $Ln1_{4-x}Ln2_xO_6$ | Li/Sr/Cs/ $La_{4-x}Ln1_xO_6$ | Li/Sr/Cs/ $Y_2O_3$ | Li/Sr/Cs/ MgO |
| Li/Sr/Zn/K | Li/Sr/Zn/K/ $Ln1_{4-x}Ln2_xO_6$ | Li/Sr/Zn/K/ $La_{4-x}Ln1_xO_6$ | Li/Sr/Zn/K/ $Y_2O_3$ | Li/Sr/Zn/K/ MgO |
| Li/Ga/Cs | Li/Ga/Cs/ $Ln1_{4-x}Ln2_xO_6$ | Li/Ga/Cs/ $La_{4-x}Ln1_xO_6$ | Li/Ga/Cs/ $Y_2O_3$ | Li/Ga/Cs/ MgO |
| Li/K/Sr/La | Li/K/Sr/La/ $Ln1_{4-x}Ln2_xO_6$ | Li/K/Sr/La/ $La_{4-x}Ln1_xO_6$ | Li/K/Sr/La/ $Y_2O_3$ | Li/K/Sr/La/ MgO |
| Li/Na | Li/Na/ $Ln1_{4-x}Ln2_xO_6$ | Li/Na/ $La_{4-x}Ln1_xO_6$ | Li/Na/ $Y_2O_3$ | Li/Na/ MgO |
| Li/Na/Rb/Ga | Li/Na/Rb/Ga/ $Ln1_{4-x}Ln2_xO_6$ | Li/Na/Rb/Ga/ $La_{4-x}Ln1_xO_6$ | Li/Na/Rb/Ga/ $Y_2O_3$ | Li/Na/Rb/Ga/ MgO |
| Sr/Zr | Sr/Zr/ $Ln1_{4-x}Ln2_xO_6$ | Sr/Zr/ $La_{4-x}Ln1_xO_6$ | Sr/Zr/ $Y_2O_3$ | Sr/Zr/ MgO |
| Li/Na/Sr | Li/Na/Sr/ $Ln1_{4-x}Ln2_xO_6$ | Li/Na/Sr/ $La_{4-x}Ln1_xO_6$ | Li/Na/Sr/ $Y_2O_3$ | Li/Na/Sr/ MgO |
| Li/Na/Sr/La | Li/Na/Sr/La/ $Ln1_{4-x}Ln2_xO_6$ | Li/Na/Sr/La/ $La_{4-x}Ln1_xO_6$ | Li/Na/Sr/La/ $Y_2O_3$ | Li/Na/Sr/La/ MgO |
| Li/Sm/Cs | Li/Sm/Cs/ $Ln1_{4-x}Ln2_xO_6$ | Li/Sm/Cs/ $La_{4-x}Ln1_xO_6$ | Li/Sm/Cs/ $Y_2O_3$ | Li/Sm/Cs/ MgO |
| Ba/Sm/Yb/S | Ba/Sm/Yb/S/ $Ln1_{4-x}Ln2_xO_6$ | Ba/Sm/Yb/S/ $La_{4-x}Ln1_xO_6$ | Ba/Sm/Yb/S/ $Y_2O_3$ | Ba/Sm/Yb/S/ MgO |
| Ba/Tm/K/La | Ba/Tm/K/La/ $Ln1_{4-x}Ln2_xO_6$ | Ba/Tm/K/La/ $La_{4-x}Ln1_xO_6$ | Ba/Tm/K/La/ $Y_2O_3$ | Ba/Tm/K/La/ MgO |
| Ba/Tm/Zn/K | Ba/Tm/Zn/K/ $Ln1_{4-x}Ln2_xO_6$ | Ba/Tm/Zn/K/ $La_{4-x}Ln1_xO_6$ | Ba/Tm/Zn/K/ $Y_2O_3$ | Ba/Tm/Zn/K/ MgO |
| Cs/K/La | Cs/K/La/ $Ln1_{4-x}Ln2_xO_6$ | Cs/K/La/ $La_{4-x}Ln1_xO_6$ | Cs/K/La/ $Y_2O_3$ | Cs/K/La/ MgO |
| Cs/La/Tm/Na | Cs/La/Tm/Na/ $Ln1_{4-x}Ln2_xO_6$ | Cs/La/Tm/Na/ $La_{4-x}Ln1_xO_6$ | Cs/La/Tm/Na/ $Y_2O_3$ | Cs/La/Tm/Na/ MgO |
| Cs/Li/K/La | Cs/Li/K/La/ $Ln1_{4-x}Ln2_xO_6$ | Cs/Li/K/La/ $La_{4-x}Ln1_xO_6$ | Cs/Li/K/La/ $Y_2O_3$ | Cs/Li/K/La/ MgO |
| Sm/Li/Sr/Cs | Sm/Li/Sr/Cs/ $Ln1_{4-x}Ln2_xO_6$ | Sm/Li/Sr/Cs/ $La_{4-x}Ln1_xO_6$ | Sm/Li/Sr/Cs/ $Y_2O_3$ | Sm/Li/Sr/Cs/ MgO |
| Sr/Cs/La | Sr/Cs/La/ $Ln1_{4-x}Ln2_xO_6$ | Sr/Cs/La/ $La_{4-x}Ln1_xO_6$ | Sr/Cs/La/ $Y_2O_3$ | Sr/Cs/La/ MgO |
| Sr/Tm/Li/Cs | Sr/Tm/Li/Cs/ $Ln1_{4-x}Ln2_xO_6$ | Sr/Tm/Li/Cs/ $La_{4-x}Ln1_xO_6$ | Sr/Tm/Li/Cs/ $Y_2O_3$ | Sr/Tm/Li/Cs/ MgO |
| Zn/K | Zn/K/ $Ln1_{4-x}Ln2_xO_6$ | Zn/K/ $La_{4-x}Ln1_xO_6$ | Zn/K/ $Y_2O_3$ | Zn/K/ MgO |
| Zr/Cs/K/La | Zr/Cs/K/La/ $Ln1_{4-x}Ln2_xO_6$ | Zr/Cs/K/La/ $La_{4-x}Ln1_xO_6$ | Zr/Cs/K/La/ $Y_2O_3$ | Zr/Cs/K/La/ MgO |
| Rb/Ca/In/Ni | Rb/Ca/In/Ni/ $Ln1_{4-x}Ln2_xO_6$ | Rb/Ca/In/Ni/ $La_{4-x}Ln1_xO_6$ | Rb/Ca/In/Ni/ $Y_2O_3$ | Rb/Ca/In/Ni/ MgO |
| Sr/Ho/Tm | Sr/Ho/Tm/ $Ln1_{4-x}Ln2_xO_6$ | Sr/Ho/Tm/ $La_{4-x}Ln1_xO_6$ | Sr/Ho/Tm/ $Y_2O_3$ | Sr/Ho/Tm/ MgO |
| La/Nd/S | La/Nd/S/ $Ln1_{4-x}Ln2_xO_6$ | La/Nd/S/ $La_{4-x}Ln1_xO_6$ | La/Nd/S/ $Y_2O_3$ | La/Nd/S/ MgO |
| Sr/Tb | Sr/Tb/ $Ln1_{4-x}Ln2_xO_6$ | Sr/Tb/ $La_{4-x}Ln1_xO_6$ | Sr/Tb/ $Y_2O_3$ | Sr/Tb/ MgO |
| Li/Rb/Ca | Li/Rb/Ca/ $Ln1_{4-x}Ln2_xO_6$ | Li/Rb/Ca/ $La_{4-x}Ln1_xO_6$ | Li/Rb/Ca/ $Y_2O_3$ | Li/Rb/Ca/ MgO |
| Li/K | Li/K/ $Ln1_{4-x}Ln2_xO_6$ | Li/K/ $La_{4-x}Ln1_xO_6$ | Li/K/ $Y_2O_3$ | Li/K/ MgO |

TABLE 12-continued

NANOWIRES (NW) DOPED WITH SPECIFIC DOPANTS (DOP)

| Dop\NW | Ln1$_{4-x}$Ln2$_x$O$_6$* | La$_{4-x}$Ln1$_x$O$_6$ | Y$_2$O$_3$ | MgO |
|---|---|---|---|---|
| Tm/Lu/Ta/P | Tm/Lu/Ta/P/ Ln1$_{4-x}$Ln2$_x$O$_6$ | Tm/Lu/Ta/P/ La$_{4-x}$Ln1$_x$O$_6$ | Tm/Lu/Ta/P/ Y$_2$O$_3$ | Tm/Lu/Ta/P/ MgO |
| Rb/Ca/Dy/P | Rb/Ca/Dy/P/ Ln1$_{4-x}$Ln2$_x$O$_6$ | Rb/Ca/Dy/P/ La$_{4-x}$Ln1$_x$O$_6$ | Rb/Ca/Dy/P/ Y$_2$O$_3$ | Rb/Ca/Dy/P/ MgO |
| Mg/La/Yb/Zn | Mg/La/Yb/Zn/ Ln1$_{4-x}$Ln2$_x$O$_6$ | Mg/La/Yb/Zn/ La$_{4-x}$Ln1$_x$O$_6$ | Mg/La/Yb/Zn/ Y$_2$O$_3$ | Mg/La/Yb/Zn/ MgO |
| Rb/Sr/Lu | Rb/Sr/Lu/ Ln1$_{4-x}$Ln2$_x$O$_6$ | Rb/Sr/Lu/ La$_{4-x}$Ln1$_x$O$_6$ | Rb/Sr/Lu/ Y$_2$O$_3$ | Rb/Sr/Lu/ MgO |
| Na/Sr/Lu/Nb | Na/Sr/Lu/Nb/ Ln1$_{4-x}$Ln2$_x$O$_6$ | Na/Sr/Lu/Nb/ La$_{4-x}$Ln1$_x$O$_6$ | Na/Sr/Lu/Nb/ Y$_2$O$_3$ | Na/Sr/Lu/Nb/ MgO |
| Na/Eu/Hf | Na/Eu/Hf/ Ln1$_{4-x}$Ln2$_x$O$_6$ | Na/Eu/Hf/ La$_{4-x}$Ln1$_x$O$_6$ | Na/Eu/Hf/ Y$_2$O$_3$ | Na/Eu/Hf/ MgO |
| Dy/Rb/Gd | Dy/Rb/Gd/ Ln1$_{4-x}$Ln2$_x$O$_6$ | Dy/Rb/Gd/ La$_{4-x}$Ln1$_x$O$_6$ | Dy/Rb/Gd/ Y$_2$O$_3$ | Dy/Rb/Gd/ MgO |
| Na/Pt/Bi | Na/Pt/Bi/ Ln1$_{4-x}$Ln2$_x$O$_6$ | Na/Pt/Bi/ La$_{4-x}$Ln1$_x$O$_6$ | Na/Pt/Bi/ Y$_2$O$_3$ | Na/Pt/Bi/ MgO |
| Rb/Hf | Rb/Hf/ Ln1$_{4-x}$Ln2$_x$O$_6$ | Rb/Hf/ La$_{4-x}$Ln1$_x$O$_6$ | Rb/Hf/ Y$_2$O$_3$ | Rb/Hf/ MgO |
| Ca/Cs | Ca/Cs/ Ln1$_{4-x}$Ln2$_x$O$_6$ | Ca/Cs/ La$_{4-x}$Ln1$_x$O$_6$ | Ca/Cs/ Y$_2$O$_3$ | Ca/Cs/ MgO |
| Ca/Mg/Na | Ca/Mg/Na/ Ln1$_{4-x}$Ln2$_x$O$_6$ | Ca/Mg/Na/ La$_{4-x}$Ln1$_x$O$_6$ | Ca/Mg/Na/ Y$_2$O$_3$ | Ca/Mg/Na/ MgO |
| Hf/Bi | Hf/Bi/ Ln1$_{4-x}$Ln2$_x$O$_6$ | Hf/Bi/ La$_{4-x}$Ln1$_x$O$_6$ | Hf/Bi/ Y$_2$O$_3$ | Hf/Bi/ MgO |
| Sr/Sn | Sr/Sn/ Ln1$_{4-x}$Ln2$_x$O$_6$ | Sr/Sn/ La$_{4-x}$Ln1$_x$O$_6$ | Sr/Sn/ Y$_2$O$_3$ | Sr/Sn/ MgO |
| Sr/W | Sr/W/ Ln1$_{4-x}$Ln2$_x$O$_6$ | Sr/W/ La$_{4-x}$Ln1$_x$O$_6$ | Sr/W/ Y$_2$O$_3$ | Sr/W/ MgO |
| Sr/Nb | Sr/Nb/ Ln1$_{4-x}$Ln2$_x$O$_6$ | Sr/Nb/ La$_{4-x}$Ln1$_x$O$_6$ | Sr/Nb/ Y$_2$O$_3$ | Sr/Nb/ MgO |
| Zr/W | Zr/W/ Ln1$_{4-x}$Ln2$_x$O$_6$ | Zr/W/ La$_{4-x}$Ln1$_x$O$_6$ | Zr/W/ Y$_2$O$_3$ | Zr/W/ MgO |
| Y/W | Y/W/ Ln1$_{4-x}$Ln2$_x$O$_6$ | Y/W/ La$_{4-x}$Ln1$_x$O$_6$ | Y/W/ Y$_2$O$_3$ | Y/W/ MgO |
| Na/W | Na/W/ Ln1$_{4-x}$Ln2$_x$O$_6$ | Na/W/ La$_{4-x}$Ln1$_x$O$_6$ | Na/W/ Y$_2$O$_3$ | Na/W/ MgO |
| Sr/Ce | Sr/Ce/ Ln1$_{4-x}$Ln2$_x$O$_6$ | Sr/Ce/ La$_{4-x}$Ln1$_x$O$_6$ | Sr/Ce/ Y$_2$O$_3$ | Sr/Ce/ MgO |
| Bi/W | Bi/W/ Ln1$_{4-x}$Ln2$_x$O$_6$ | Bi/W/ La$_{4-x}$Ln1$_x$O$_6$ | Bi/W/ Y$_2$O$_3$ | Bi/W/ MgO |
| Bi/Cs | Bi/Cs/ Ln1$_{4-x}$Ln2$_x$O$_6$ | Bi/Cs/ La$_{4-x}$Ln1$_x$O$_6$ | Bi/Cs/ Y$_2$O$_3$ | Bi/Cs/ MgO |
| Bi/Ca | Bi/Ca/ Ln1$_{4-x}$Ln2$_x$O$_6$ | Bi/Ca/ La$_{4-x}$Ln1$_x$O$_6$ | Bi/Ca/ Y$_2$O$_3$ | Bi/Ca/ MgO |
| Bi/Sn | Bi/Sn/ Ln1$_{4-x}$Ln2$_x$O$_6$ | Bi/Sn/ La$_{4-x}$Ln1$_x$O$_6$ | Bi/Sn/ Y$_2$O$_3$ | Bi/Sn/ MgO |
| Bi/Sb | Bi/Sb/ Ln1$_{4-x}$Ln2$_x$O$_6$ | Bi/Sb/ La$_{4-x}$Ln1$_x$O$_6$ | Bi/Sb/ Y$_2$O$_3$ | Bi/Sb/ MgO |
| Ge/Hf | Ge/Hf/ Ln1$_{4-x}$Ln2$_x$O$_6$ | Ge/Hf/ La$_{4-x}$Ln1$_x$O$_6$ | Ge/Hf/ Y$_2$O$_3$ | Ge/Hf/ MgO |
| Hf/Sm | Hf/Sm/ Ln1$_{4-x}$Ln2$_x$O$_6$ | Hf/Sm/ La$_{4-x}$Ln1$_x$O$_6$ | Hf/Sm/ Y$_2$O$_3$ | Hf/Sm/ MgO |
| Sb/Ag | Sb/Ag/ Ln1$_{4-x}$Ln2$_x$O$_6$ | Sb/Ag/ La$_{4-x}$Ln1$_x$O$_6$ | Sb/Ag/ Y$_2$O$_3$ | Sb/Ag/ MgO |
| Sb/Bi | Sb/Bi/ Ln1$_{4-x}$Ln2$_x$O$_6$ | Sb/Bi/ La$_{4-x}$Ln1$_x$O$_6$ | Sb/Bi/ Y$_2$O$_3$ | Sb/Bi/ MgO |
| Sb/Au | Sb/Au/ Ln1$_{4-x}$Ln2$_x$O$_6$ | Sb/Au/ La$_{4-x}$Ln1$_x$O$_6$ | Sb/Au/ Y$_2$O$_3$ | Sb/Au/ MgO |
| Sb/Sm | Sb/Sm/ Ln1$_{4-x}$Ln2$_x$O$_6$ | Sb/Sm/ La$_{4-x}$Ln1$_x$O$_6$ | Sb/Sm/ Y$_2$O$_3$ | Sb/Sm/ MgO |
| Sb/Sr | Sb/Sr/ Ln1$_{4-x}$Ln2$_x$O$_6$ | Sb/Sr/ La$_{4-x}$Ln1$_x$O$_6$ | Sb/Sr/ Y$_2$O$_3$ | Sb/Sr/ MgO |
| Sb/W | Sb/W/ Ln1$_{4-x}$Ln2$_x$O$_6$ | Sb/W/ La$_{4-x}$Ln1$_x$O$_6$ | Sb/W/ Y$_2$O$_3$ | Sb/W/ MgO |
| Sb/Hf | Sb/Hf/ Ln1$_{4-x}$Ln2$_x$O$_6$ | Sb/Hf/ La$_{4-x}$Ln1$_x$O$_6$ | Sb/Hf/ Y$_2$O$_3$ | Sb/Hf/ MgO |
| Sb/Yb | Sb/Yb/ Ln1$_{4-x}$Ln2$_x$O$_6$ | Sb/Yb/ La$_{4-x}$Ln1$_x$O$_6$ | Sb/Yb/ Y$_2$O$_3$ | Sb/Yb/ MgO |
| Sr/Pr/K | Sr/Pr/K/ Ln1$_{4-x}$Ln2$_x$O$_6$ | Sr/Pr/K/ La$_{4-x}$Ln1$_x$O$_6$ | Sr/Pr/K/ Y$_2$O$_3$ | Sr/Pr/K/ MgO |
| Sb/Sn | Sb/Sn/ Ln1$_{4-x}$Ln2$_x$O$_6$ | Sb/Sn/ La$_{4-x}$Ln1$_x$O$_6$ | Sb/Sn/ Y$_2$O$_3$ | Sb/Sn/ MgO |
| Yb/Au | Yb/Au/ Ln1$_{4-x}$Ln2$_x$O$_6$ | Yb/Au/ La$_{4-x}$Ln1$_x$O$_6$ | Yb/Au/ Y$_2$O$_3$ | Yb/Au/ MgO |
| Yb/Ta | Yb/Ta/ Ln1$_{4-x}$Ln2$_x$O$_6$ | Yb/Ta/ La$_{4-x}$Ln1$_x$O$_6$ | Yb/Ta/ Y$_2$O$_3$ | Yb/Ta/ MgO |

TABLE 12-continued

NANOWIRES (NW) DOPED WITH SPECIFIC DOPANTS (DOP)

| Dop\NW | Ln1$_{4-x}$Ln2$_x$O$_6$* | La$_{4-x}$Ln1$_x$O$_6$ | Y$_2$O$_3$ | MgO |
|---|---|---|---|---|
| Yb/W | Yb/W/ Ln1$_{4-x}$Ln2$_x$O$_6$ | Yb/W/ La$_{4-x}$Ln1$_x$O$_6$ | Yb/W/ Y$_2$O$_3$ | Yb/W/ MgO |
| Yb/Sr | Yb/Sr/ Ln1$_{4-x}$Ln2$_x$O$_6$ | Yb/Sr/ La$_{4-x}$Ln1$_x$O$_6$ | Yb/Sr/ Y$_2$O$_3$ | Yb/Sr/ MgO |
| Yb/Pb | Yb/Pb/ Ln1$_{4-x}$Ln2$_x$O$_6$ | Yb/Pb/ La$_{4-x}$Ln1$_x$O$_6$ | Yb/Pb/ Y$_2$O$_3$ | Yb/Pb/ MgO |
| Yb/W | Yb/W/ Ln1$_{4-x}$Ln2$_x$O$_6$ | Yb/W/ La$_{4-x}$Ln1$_x$O$_6$ | Yb/W/ Y$_2$O$_3$ | Yb/W/ MgO |
| Yb/Ag | Yb/Ag/ Ln1$_{4-x}$Ln2$_x$O$_6$ | Yb/Ag/ La$_{4-x}$Ln1$_x$O$_6$ | Yb/Ag/ Y$_2$O$_3$ | Yb/Ag/ MgO |
| Au/Sr | Au/Sr/ Ln1$_{4-x}$Ln2$_x$O$_6$ | Au/Sr/ La$_{4-x}$Ln1$_x$O$_6$ | Au/Sr/ Y$_2$O$_3$ | Au/Sr/ MgO |
| W/Ge | W/Ge/ Ln1$_{4-x}$Ln2$_x$O$_6$ | W/Ge/ La$_{4-x}$Ln1$_x$O$_6$ | W/Ge/ Y$_2$O$_3$ | W/Ge/ MgO |
| Ta/Sr | Ta/Sr/ Ln1$_{4-x}$Ln2$_x$O$_6$ | Ta/Sr/ La$_{4-x}$Ln1$_x$O$_6$ | Ta/Sr/ Y$_2$O$_3$ | Ta/Sr/ MgO |
| Ta/Hf | Ta/Hf/ Ln1$_{4-x}$Ln2$_x$O$_6$ | Ta/Hf/ La$_{4-x}$Ln1$_x$O$_6$ | Ta/Hf/ Y$_2$O$_3$ | Ta/Hf/ MgO |
| W/Au | W/Au/ Ln1$_{4-x}$Ln2$_x$O$_6$ | W/Au/ La$_{4-x}$Ln1$_x$O$_6$ | W/Au/ Y$_2$O$_3$ | W/Au/ MgO |
| Ca/W | Ca/W/ Ln1$_{4-x}$Ln2$_x$O$_6$ | Ca/W/ La$_{4-x}$Ln1$_x$O$_6$ | Ca/W/ Y$_2$O$_3$ | Ca/W/ MgO |
| Au/Re | Au/Re/ Ln1$_{4-x}$Ln2$_x$O$_6$ | Au/Re/ La$_{4-x}$Ln1$_x$O$_6$ | Au/Re/ Y$_2$O$_3$ | Au/Re/ MgO |
| Sm/Li | Sm/Li/ Ln1$_{4-x}$Ln2$_x$O$_6$ | Sm/Li/ La$_{4-x}$Ln1$_x$O$_6$ | Sm/Li/ Y$_2$O$_3$ | Sm/Li/ MgO |
| La/K | La/K/ Ln1$_{4-x}$Ln2$_x$O$_6$ | La/K/ La$_{4-x}$Ln1$_x$O$_6$ | La/K/ Y$_2$O$_3$ | La/K/ MgO |
| Zn/Cs | Zn/Cs/ Ln1$_{4-x}$Ln2$_x$O$_6$ | Zn/Cs/ La$_{4-x}$Ln1$_x$O$_6$ | Zn/Cs/ Y$_2$O$_3$ | Zn/Cs/ MgO |
| Sr/Zr/K | Sr/Zr/K/ Ln1$_{4-x}$Ln2$_x$O$_6$ | Sr/Zr/K/ La$_{4-x}$Ln1$_x$O$_6$ | Sr/Zr/K/ Y$_2$O$_3$ | Sr/Zr/K/ MgO |
| Na/K/Mg | Na/K/Mg/ Ln1$_{4-x}$Ln2$_x$O$_6$ | Na/K/Mg/ La$_{4-x}$Ln1$_x$O$_6$ | Na/K/Mg/ Y$_2$O$_3$ | Na/K/Mg/ MgO |
| Zr/Cs | Zr/Cs/ Ln1$_{4-x}$Ln2$_x$O$_6$ | Zr/Cs/ La$_{4-x}$Ln1$_x$O$_6$ | Zr/Cs/ Y$_2$O$_3$ | Zr/Cs/ MgO |
| Ca/Ce | Ca/Ce/ Ln1$_{4-x}$Ln2$_x$O$_6$ | Ca/Ce/ La$_{4-x}$Ln1$_x$O$_6$ | Ca/Ce/ Y$_2$O$_3$ | Ca/Ce/ MgO |
| Na/Li/Cs | Na/Li/Cs/ Ln1$_{4-x}$Ln2$_x$O$_6$ | Na/Li/Cs/ La$_{4-x}$Ln1$_x$O$_6$ | Na/Li/Cs/ Y$_2$O$_3$ | Na/Li/Cs/ MgO |
| Li/Sr | Li/Sr/ Ln1$_{4-x}$Ln2$_x$O$_6$ | Li/Sr/ La$_{4-x}$Ln1$_x$O$_6$ | Li/Sr/ Y$_2$O$_3$ | Li/Sr/ MgO |
| La/Dy/K | La/Dy/K/ Ln1$_{4-x}$Ln2$_x$O$_6$ | La/Dy/K/ La$_{4-x}$Ln1$_x$O$_6$ | La/Dy/K/ Y$_2$O$_3$ | La/Dy/K/ MgO |
| Dy/K | Dy/K/ Ln1$_{4-x}$Ln2$_x$O$_6$ | Dy/K/ La$_{4-x}$Ln1$_x$O$_6$ | Dy/K/ Y$_2$O$_3$ | Dy/K/ MgO |
| La/Mg | La/Mg/ Ln1$_{4-x}$Ln2$_x$O$_6$ | La/Mg/ La$_{4-x}$Ln1$_x$O$_6$ | La/Mg/ Y$_2$O$_3$ | La/Mg/ MgO |
| Na/Nd/In/K | Na/Nd/In/K/ Ln1$_{4-x}$Ln2$_x$O$_6$ | Na/Nd/In/K/ La$_{4-x}$Ln1$_x$O$_6$ | Na/Nd/In/K/ Y$_2$O$_3$ | Na/Nd/In/K/ MgO |
| In/Sr | In/Sr/ Ln1$_{4-x}$Ln2$_x$O$_6$ | In/Sr/ La$_{4-x}$Ln1$_x$O$_6$ | In/Sr/ Y$_2$O$_3$ | In/Sr/ MgO |
| Sr/Cs | Sr/Cs/ Ln1$_{4-x}$Ln2$_x$O$_6$ | Sr/Cs/ La$_{4-x}$Ln1$_x$O$_6$ | Sr/Cs/ Y$_2$O$_3$ | Sr/Cs/ MgO |
| Rb/Ga/Tm/Cs | Rb/Ga/Tm/Cs/ Ln1$_{4-x}$Ln2$_x$O$_6$ | Rb/Ga/Tm/Cs/ La$_{4-x}$Ln1$_x$O$_6$ | Rb/Ga/Tm/Cs/ Y$_2$O$_3$ | Rb/Ga/Tm/Cs/ MgO |
| Ga/Cs | Ga/Cs/ Ln1$_{4-x}$Ln2$_x$O$_6$ | Ga/Cs/ La$_{4-x}$Ln1$_x$O$_6$ | Ga/Cs/ Y$_2$O$_3$ | Ga/Cs/ MgO |
| K/La/Zr/Ag | K/La/Zr/Ag/ Ln1$_{4-x}$Ln2$_x$O$_6$ | K/La/Zr/Ag/ La$_{4-x}$Ln1$_x$O$_6$ | K/La/Zr/Ag/ Y$_2$O$_3$ | K/La/Zr/Ag/ MgO |
| Lu/Fe | Lu/Fe/ Ln1$_{4-x}$Ln2$_x$O$_6$ | Lu/Fe/ La$_{4-x}$Ln1$_x$O$_6$ | Lu/Fe/ Y$_2$O$_3$ | Lu/Fe/ MgO |
| Sr/Tm | Sr/Tm/ Ln1$_{4-x}$Ln2$_x$O$_6$ | Sr/Tm/ La$_{4-x}$Ln1$_x$O$_6$ | Sr/Tm/ Y$_2$O$_3$ | Sr/Tm/ MgO |
| La/Dy | La/Dy/ Ln1$_{4-x}$Ln2$_x$O$_6$ | La/Dy/ La$_{4-x}$Ln1$_x$O$_6$ | La/Dy/ Y$_2$O$_3$ | La/Dy/ MgO |
| Sm/Li/Sr | Sm/Li/Sr/ Ln1$_{4-x}$Ln2$_x$O$_6$ | Sm/Li/Sr/ La$_{4-x}$Ln1$_x$O$_6$ | Sm/Li/Sr/ Y$_2$O$_3$ | Sm/Li/Sr/ MgO |
| Mg/K | Mg/K/ Ln1$_{4-x}$Ln2$_x$O$_6$ | Mg/K/ La$_{4-x}$Ln1$_x$O$_6$ | Mg/K/ Y$_2$O$_3$ | Mg/K/ MgO |
| Li/Rb/Ga | Li/Rb/Ga/ Ln1$_{4-x}$Ln2$_x$O$_6$ | Li/Rb/Ga/ La$_{4-x}$Ln1$_x$O$_6$ | Li/Rb/Ga/ Y$_2$O$_3$ | Li/Rb/Ga/ MgO |
| Sr/Ce/K | Sr/Ce/K/ Ln1$_{4-x}$Ln2$_x$O$_6$ | Sr/Ce/K/ La$_{4-x}$Ln1$_x$O$_6$ | Sr/Ce/K/ Y$_2$O$_3$ | Sr/Ce/K/ MgO |
| Li/Cs/Tm | Li/Cs/Tm/ Ln1$_{4-x}$Ln2$_x$O$_6$ | Li/Cs/Tm/ La$_{4-x}$Ln1$_x$O$_6$ | Li/Cs/Tm/ Y$_2$O$_3$ | Li/Cs/Tm/ MgO |

TABLE 12-continued

NANOWIRES (NW) DOPED WITH SPECIFIC DOPANTS (DOP)

| Dop\NW | $Ln1_{4-x}Ln2_xO_6$* | $La_{4-x}Ln1_xO_6$ | $Y_2O_3$ | MgO |
|---|---|---|---|---|
| Zr/K | Zr/K/ $Ln1_{4-x}Ln2_xO_6$ | Zr/K/ $La_{4-x}Ln1_xO_6$ | Zr/K/ $Y_2O_3$ | Zr/K/ MgO |
| Li/Cs | Li/Cs/ $Ln1_{4-x}Ln2_xO_6$ | Li/Cs/ $La_{4-x}Ln1_xO_6$ | Li/Cs/ $Y_2O_3$ | Li/Cs/ MgO |
| Li/K/La | Li/K/La/ $Ln1_{4-x}Ln2_xO_6$ | Li/K/La/ $La_{4-x}Ln1_xO_6$ | Li/K/La/ $Y_2O_3$ | Li/K/La/ MgO |
| Ce/Zr/La | Ce/Zr/La/ $Ln1_{4-x}Ln2_xO_6$ | Ce/Zr/La/ $La_{4-x}Ln1_xO_6$ | Ce/Zr/La/ $Y_2O_3$ | Ce/Zr/La/ MgO |
| Ca/Al/La | Ca/Al/La/ $Ln1_{4-x}Ln2_xO_6$ | Ca/Al/La/ $La_{4-x}Ln1_xO_6$ | Ca/Al/La/ $Y_2O_3$ | Ca/Al/La/ MgO |
| Sr/Zn/La | Sr/Zn/La/ $Ln1_{4-x}Ln2_xO_6$ | Sr/Zn/La/ $La_{4-x}Ln1_xO_6$ | Sr/Zn/La/ $Y_2O_3$ | Sr/Zn/La/ MgO |
| Sr/Cs/Zn | Sr/Cs/Zn/ $Ln1_{4-x}Ln2_xO_6$ | Sr/Cs/Zn/ $La_{4-x}Ln1_xO_6$ | Sr/Cs/Zn/ $Y_2O_3$ | Sr/Cs/Zn/ MgO |
| Sm/Cs | Sm/Cs/ $Ln1_{4-x}Ln2_xO_6$ | Sm/Cs/ $La_{4-x}Ln1_xO_6$ | Sm/Cs/ $Y_2O_3$ | Sm/Cs/ MgO |
| In/K | In/K/ $Ln1_{4-x}Ln2_xO_6$ | In/K/ $La_{4-x}Ln1_xO_6$ | In/K/ $Y_2O_3$ | In/K/ MgO |
| Sr/Pr | Sr/Pr/ $Ln1_{4-x}Ln2_xO_6$ | Sr/Pr/ $La_{4-x}Ln1_xO_6$ | Sr/Pr/ $Y_2O_3$ | Sr/Pr/ MgO |
| Ho/Cs/Li/La | Ho/Cs/Li/La/ $Ln1_{4-x}Ln2_xO_6$ | Ho/Cs/Li/La/ $La_{4-x}Ln1_xO_6$ | Ho/Cs/Li/La/ $Y_2O_3$ | Ho/Cs/Li/La/ MgO |
| Cs/La/Na | Cs/La/Na/ $Ln1_{4-x}Ln2_xO_6$ | Cs/La/Na/ $La_{4-x}Ln1_xO_6$ | Cs/La/Na/ $Y_2O_3$ | Cs/La/Na/ MgO |
| La/S/Sr | La/S/Sr/ $Ln1_{4-x}Ln2_xO_6$ | La/S/Sr/ $La_{4-x}Ln1_xO_6$ | La/S/Sr/ $Y_2O_3$ | La/S/Sr/ MgO |
| K/La/Zr/Ag | K/La/Zr/Ag/ $Ln1_{4-x}Ln2_xO_6$ | K/La/Zr/Ag/ $La_{4-x}Ln1_xO_6$ | K/La/Zr/Ag/ $Y_2O_3$ | K/La/Zr/Ag/ MgO |
| Lu/Tl | Lu/Tl/ $Ln1_{4-x}Ln2_xO_6$ | Lu/Tl/ $La_{4-x}Ln1_xO_6$ | Lu/Tl/ $Y_2O_3$ | Lu/Tl/ MgO |
| Pr/Zn | Pr/Zn/ $Ln1_{4-x}Ln2_xO_6$ | Pr/Zn/ $La_{4-x}Ln1_xO_6$ | Pr/Zn/ $Y_2O_3$ | Pr/Zn/ MgO |
| Rb/Sr/La | Rb/Sr/La/ $Ln1_{4-x}Ln2_xO_6$ | Rb/Sr/La/ $La_{4-x}Ln1_xO_6$ | Rb/Sr/La/ $Y_2O_3$ | Rb/Sr/La/ MgO |
| Na/Sr/Eu/Ca | Na/Sr/Eu/Ca/ $Ln1_{4-x}Ln2_xO_6$ | Na/Sr/Eu/Ca/ $La_{4-x}Ln1_xO_6$ | Na/Sr/Eu/Ca/ $Y_2O_3$ | Na/Sr/Eu/Ca/ MgO |
| K/Cs/Sr/La | K/Cs/Sr/La/ $Ln1_{4-x}Ln2_xO_6$ | K/Cs/Sr/La/ $La_{4-x}Ln1_xO_6$ | K/Cs/Sr/La/ $Y_2O_3$ | K/Cs/Sr/La/ MgO |
| Na/Sr/Lu | Na/Sr/Lu/ $Ln1_{4-x}Ln2_xO_6$ | Na/Sr/Lu/ $La_{4-x}Ln1_xO_6$ | Na/Sr/Lu/ $Y_2O_3$ | Na/Sr/Lu/ MgO |
| Sr/Eu/Dy | Sr/Eu/Dy/ $Ln1_{4-x}Ln2_xO_6$ | Sr/Eu/Dy/ $La_{4-x}Ln1_xO_6$ | Sr/Eu/Dy/ $Y_2O_3$ | Sr/Eu/Dy/ MgO |
| Lu/Nb | Lu/Nb/ $Ln1_{4-x}Ln2_xO_6$ | Lu/Nb/ $La_{4-x}Ln1_xO_6$ | Lu/Nb/ $Y_2O_3$ | Lu/Nb/ MgO |
| La/Dy/Gd | La/Dy/Gd/ $Ln1_{4-x}Ln2_xO_6$ | La/Dy/Gd/ $La_{4-x}Ln1_xO_6$ | La/Dy/Gd/ $Y_2O_3$ | La/Dy/Gd/ MgO |
| Na/Mg/Tl/P | Na/Mg/Tl/P/ $Ln1_{4-x}Ln2_xO_6$ | Na/Mg/Tl/P/ $La_{4-x}Ln1_xO_6$ | Na/Mg/Tl/P/ $Y_2O_3$ | Na/Mg/Tl/P/ MgO |
| Na/Pt | Na/Pt/ $Ln1_{4-x}Ln2_xO_6$ | Na/Pt/ $La_{4-x}Ln1_xO_6$ | Na/Pt/ $Y_2O_3$ | Na/Pt/ MgO |
| Gd/Li/K | Gd/Li/K/ $Ln1_{4-x}Ln2_xO_6$ | Gd/Li/K/ $La_{4-x}Ln1_xO_6$ | Gd/Li/K/ $Y_2O_3$ | Gd/Li/K/ MgO |
| Rb/K/Lu | Rb/K/Lu/ $Ln1_{4-x}Ln2_xO_6$ | Rb/K/Lu/ $La_{4-x}Ln1_xO_6$ | Rb/K/Lu/ $Y_2O_3$ | Rb/K/Lu/ MgO |
| Sr/La/Dy/S | Sr/La/Dy/S/ $Ln1_{4-x}Ln2_xO_6$ | Sr/La/Dy/S/ $La_{4-x}Ln1_xO_6$ | Sr/La/Dy/S/ $Y_2O_3$ | Sr/La/Dy/S/ MgO |
| Na/Ce/Co | Na/Ce/Co/ $Ln1_{4-x}Ln2_xO_6$ | Na/Ce/Co/ $La_{4-x}Ln1_xO_6$ | Na/Ce/Co/ $Y_2O_3$ | Na/Ce/Co/ MgO |
| Na/Ce | Na/Ce/ $Ln1_{4-x}Ln2_xO_6$ | Na/Ce/ $La_{4-x}Ln1_xO_6$ | Na/Ce/ $Y_2O_3$ | Na/Ce/ MgO |
| Sr/Tb/K | Sr/Tb/K/ $Ln1_{4-x}Ln2_xO_6$ | Sr/Tb/K/ $La_{4-x}Ln1_xO_6$ | Sr/Tb/K/ $Y_2O_3$ | Sr/Tb/K/ MgO |
| Na/Ga/Gd/Al | Na/Ga/Gd/Al/ $Ln1_{4-x}Ln2_xO_6$ | Na/Ga/Gd/Al/ $La_{4-x}Ln1_xO_6$ | Na/Ga/Gd/Al/ $Y_2O_3$ | Na/Ga/Gd/Al/ MgO |
| Ba/Rh/Ta | Ba/Rh/Ta/ $Ln1_{4-x}Ln2_xO_6$ | Ba/Rh/Ta/ $La_{4-x}Ln1_xO_6$ | Ba/Rh/Ta/ $Y_2O_3$ | Ba/Rh/Ta/ MgO |
| Ba/Ta | Ba/Ta/ $Ln1_{4-x}Ln2_xO_6$ | Ba/Ta/ $La_{4-x}Ln1_xO_6$ | Ba/Ta/ $Y_2O_3$ | Ba/Ta/ MgO |
| Na/Al/Bi | Na/Al/Bi/ $Ln1_{4-x}Ln2_xO_6$ | Na/Al/Bi/ $La_{4-x}Ln1_xO_6$ | Na/Al/Bi/ $Y_2O_3$ | Na/Al/Bi/ MgO |
| Cs/Eu/S | Cs/Eu/S/ $Ln1_{4-x}Ln2_xO_6$ | Cs/Eu/S/ $La_{4-x}Ln1_xO_6$ | Cs/Eu/S/ $Y_2O_3$ | Cs/Eu/S/ MgO |
| Sm/Tm/Yb/Fe | Sm/Tm/Yb/Fe/ $Ln1_{4-x}Ln2_xO_6$ | Sm/Tm/Yb/Fe/ $La_{4-x}Ln1_xO_6$ | Sm/Tm/Yb/Fe/ $Y_2O_3$ | Sm/Tm/Yb/Fe/ MgO |
| Sm/Tm/Yb | Sm/Tm/Yb/ $Ln1_{4-x}Ln2_xO_6$ | Sm/Tm/Yb/ $La_{4-x}Ln1_xO_6$ | Sm/Tm/Yb/ $Y_2O_3$ | Sm/Tm/Yb/ MgO |

TABLE 12-continued

NANOWIRES (NW) DOPED WITH SPECIFIC DOPANTS (DOP)

| Dop\NW | $Ln1_{4-x}Ln2_xO_6$* | $La_{4-x}Ln1_xO_6$ | $Y_2O_3$ | MgO |
|---|---|---|---|---|
| Hf/Zr/Ta | Hf/Zr/Ta/$Ln1_{4-x}Ln2_xO_6$ | Hf/Zr/Ta/$La_{4-x}Ln1_xO_6$ | Hf/Zr/Ta/$Y_2O_3$ | Hf/Zr/Ta/MgO |
| Rb/Gd/Li/K | Rb/Gd/Li/K/$Ln1_{4-x}Ln2_xO_6$ | Rb/Gd/Li/K/$La_{4-x}Ln1_xO_6$ | Rb/Gd/Li/K/$Y_2O_3$ | Rb/Gd/Li/K/MgO |
| Gd/Ho/Al/P | Gd/Ho/Al/P/$Ln1_{4-x}Ln2_xO_6$ | Gd/Ho/Al/P/$La_{4-x}Ln1_xO_6$ | Gd/Ho/Al/P/$Y_2O_3$ | Gd/Ho/Al/P/MgO |
| Na/Ca/Lu | Na/Ca/Lu/$Ln1_{4-x}Ln2_xO_6$ | Na/Ca/Lu/$La_{4-x}Ln1_xO_6$ | Na/Ca/Lu/$Y_2O_3$ | Na/Ca/Lu/MgO |
| Cu/Sn | Cu/Sn/$Ln1_{4-x}Ln2_xO_6$ | Cu/Sn/$La_{4-x}Ln1_xO_6$ | Cu/Sn/$Y_2O_3$ | Cu/Sn/MgO |
| Ag/Au | Ag/Au/$Ln1_{4-x}Ln2_xO_6$ | Ag/Au/$La_{4-x}Ln1_xO_6$ | Ag/Au/$Y_2O_3$ | Ag/Au/MgO |
| Al/Bi | Al/Bi/$Ln1_{4-x}Ln2_xO_6$ | Al/Bi/$La_{4-x}Ln1_xO_6$ | Al/Bi/$Y_2O_3$ | Al/Bi/MgO |
| Al/Mo | Al/Mo/$Ln1_{4-x}Ln2_xO_6$ | Al/Mo/$La_{4-x}Ln1_xO_6$ | Al/Mo/$Y_2O_3$ | Al/Mo/MgO |
| Sr/Hf/Rb | Sr/Hf/Rb/$Ln1_{4-x}Ln2_xO_6$ | Sr/Hf/Rb/$La_{4-x}Ln1_xO_6$ | Sr/Hf/Rb/$Y_2O_3$ | Sr/Hf/Rb/MgO |
| Al/Nb | Al/Nb/$Ln1_{4-x}Ln2_xO_6$ | Al/Nb/$La_{4-x}Ln1_xO_6$ | Al/Nb/$Y_2O_3$ | Al/Nb/MgO |
| Au/Pt | Au/Pt/$Ln1_{4-x}Ln2_xO_6$ | Au/Pt/$La_{4-x}Ln1_xO_6$ | Au/Pt/$Y_2O_3$ | Au/Pt/MgO |
| Ga/Bi | Ga/Bi/$Ln1_{4-x}Ln2_xO_6$ | Ga/Bi/$La_{4-x}Ln1_xO_6$ | Ga/Bi/$Y_2O_3$ | Ga/Bi/MgO |
| Mg/W | Mg/W/$Ln1_{4-x}Ln2_xO_6$ | Mg/W/$La_{4-x}Ln1_xO_6$ | Mg/W/$Y_2O_3$ | Mg/W/MgO |
| Pb/Au | Pb/Au/$Ln1_{4-x}Ln2_xO_6$ | Pb/Au/$La_{4-x}Ln1_xO_6$ | Pb/Au/$Y_2O_3$ | Pb/Au/MgO |
| Sn/Mg | Sn/Mg/$Ln1_{4-x}Ln2_xO_6$ | Sn/Mg/$La_{4-x}Ln1_xO_6$ | Sn/Mg/$Y_2O_3$ | Sn/Mg/MgO |
| Zn/Bi | Zn/Bi/$Ln1_{4-x}Ln2_xO_6$ | Zn/Bi/$La_{4-x}Ln1_xO_6$ | Zn/Bi/$Y_2O_3$ | Zn/Bi/MgO |
| Sr/Ta | Sr/Ta/$Ln1_{4-x}Ln2_xO_6$ | Sr/Ta/$La_{4-x}Ln1_xO_6$ | Sr/Ta/$Y_2O_3$ | Sr/Ta/MgO |
| Na | Na/$Ln1_{4-x}Ln2_xO_6$ | Na/$La_{4-x}Ln1_xO_6$ | Na/$Y_2O_3$ | Na/MgO |
| Sr | Sr/$Ln1_{4-x}Ln2_xO_6$ | Sr/$La_{4-x}Ln1_xO_6$ | Sr/$Y_2O_3$ | Sr/MgO |
| Ca | Ca/$Ln1_{4-x}Ln2_xO_6$ | Ca/$La_{4-x}Ln1_xO_6$ | Ca/$Y_2O_3$ | Ca/MgO |
| Yb | Yb/$Ln1_{4-x}Ln2_xO_6$ | Yb/$La_{4-x}Ln1_xO_6$ | Yb/$Y_2O_3$ | Yb/MgO |
| Cs | Cs/$Ln1_{4-x}Ln2_xO_6$ | Cs/$La_{4-x}Ln1_xO_6$ | Cs/$Y_2O_3$ | Cs/MgO |
| Sb | Sb/$Ln1_{4-x}Ln2_xO_6$ | Sb/$La_{4-x}Ln1_xO_6$ | Sb/$Y_2O_3$ | Sb/MgO |
| Gd/Ho | Gd/Ho/$Ln1_{4-x}Ln2_xO_6$ | Gd/Ho/$La_{4-x}Ln1_xO_6$ | Gd/Ho/$Y_2O_3$ | Gd/Ho/MgO |
| Zr/Bi | Zr/Bi/$Ln1_{4-x}Ln2_xO_6$ | Zr/Bi/$La_{4-x}Ln1_xO_6$ | Zr/Bi/$Y_2O_3$ | Zr/Bi/MgO |
| Ho/Sr | Ho/Sr/$Ln1_{4-x}Ln2_xO_6$ | Ho/Sr/$La_{4-x}Ln1_xO_6$ | Ho/Sr/$Y_2O_3$ | Ho/Sr/MgO |
| Sr/B | Sr/B/$Ln1_{4-x}Ln2_xO_6$ | Sr/B/$La_{4-x}Ln1_xO_6$ | Sr/B/$Y_2O_3$ | Sr/B/MgO |
| Gd/Ho/Sr | Gd/Ho/Sr/$Ln1_{4-x}Ln2_xO_6$ | Gd/Ho/Sr/$La_{4-x}Ln1_xO_6$ | Gd/Ho/Sr/$Y_2O_3$ | Gd/Ho/Sr/MgO |
| Ca/Sr | Ca/Sr/$Ln1_{4-x}Ln2_xO_6$ | Ca/Sr/$La_{4-x}Ln1_xO_6$ | Ca/Sr/$Y_2O_3$ | Ca/Sr/MgO |
| Ca/Sr/W | Ca/Sr/W/$Ln1_{4-x}Ln2_xO_6$ | Ca/Sr/W/$La_{4-x}Ln1_xO_6$ | Ca/Sr/W/$Y_2O_3$ | Ca/Sr/W/MgO |
| Na/Zr/Eu/Tm | Na/Zr/Eu/Tm/$Ln1_{4-x}Ln2_xO_6$ | Na/Zr/Eu/Tm/$La_{4-x}Ln1_xO_6$ | Na/Zr/Eu/Tm/$Y_2O_3$ | Na/Zr/Eu/Tm/MgO |
| Sr/Ho/Tm/Na | Sr/Ho/Tm/Na/$Ln1_{4-x}Ln2_xO_6$ | Sr/Ho/Tm/Na/$La_{4-x}Ln1_xO_6$ | Sr/Ho/Tm/Na/$Y_2O_3$ | Sr/Ho/Tm/Na/MgO |
| Sr/Pb | Sr/Pb/$Ln1_{4-x}Ln2_xO_6$ | Sr/Pb/$La_{4-x}Ln1_xO_6$ | Sr/Pb/$Y_2O_3$ | Sr/Pb/MgO |
| Sr/W/Li | Sr/W/Li/$Ln1_{4-x}Ln2_xO_6$ | Sr/W/Li/$La_{4-x}Ln1_xO_6$ | Sr/W/Li/$Y_2O_3$ | Sr/W/Li/MgO |
| Ca/Sr/W | Ca/Sr/W/$Ln1_{4-x}Ln2_xO_6$ | Ca/Sr/W/$La_{4-x}Ln1_xO_6$ | Ca/Sr/W/$Y_2O_3$ | Ca/Sr/W/MgO |
| Sr/Hf | Sr/Hf/$Ln1_{4-x}Ln2_xO_6$ | Sr/Hf/$La_{4-x}Ln1_xO_6$ | Sr/Hf/$Y_2O_3$ | Sr/Hf/MgO |
| Au/Re | Au/Re/$Ln1_{4-x}Ln2_xO_6$ | Au/Re/$La_{4-x}Ln1_xO_6$ | Au/Re/$Y_2O_3$ | Au/Re/MgO |
| Sr/W | Sr/W/$Ln1_{4-x}Ln2_xO_6$ | Sr/W/$La_{4-x}Ln1_xO_6$ | Sr/W/$Y_2O_3$ | Sr/W/MgO |

TABLE 12-continued

NANOWIRES (NW) DOPED WITH SPECIFIC DOPANTS (DOP)

| Dop\NW | $Ln1_{4-x}Ln2_xO_6$* | $La_{4-x}Ln1_xO_6$ | $Y_2O_3$ | MgO |
|---|---|---|---|---|
| La/Nd | La/Nd/$Ln1_{4-x}Ln2_xO_6$ | La/Nd/$La_{4-x}Ln1_xO_6$ | La/Nd/$Y_2O_3$ | La/Nd/MgO |
| La/Sm | La/Sm/$Ln1_{4-x}Ln2_xO_6$ | La/Sm/$La_{4-x}Ln1_xO_6$ | La/Sm/$Y_2O_3$ | La/Sm/MgO |
| La/Ce | La/Ce/$Ln1_{4-x}Ln2_xO_6$ | La/Ce/$La_{4-x}Ln1_xO_6$ | La/Ce/$Y_2O_3$ | La/Ce/MgO |
| La/Sr | La/Sr/$Ln1_{4-x}Ln2_xO_6$ | La/Sr/$La_{4-x}Ln1_xO_6$ | La/Sr/$Y_2O_3$ | La/Sr/MgO |
| La/Nd/Sr | La/Nd/Sr/$Ln1_{4-x}Ln2_xO_6$ | La/Nd/Sr/$La_{4-x}Ln1_xO_6$ | La/Nd/Sr/$Y_2O_3$ | La/Nd/Sr/MgO |
| La/Bi/Sr | La/Bi/Sr/L $Ln1_{4-x}Ln2_xO_6$ | La/Bi/Sr/$La_{4-x}Ln1_xO_6$ | La/Bi/Sr/$Y_2O_3$ | La/Bi/Sr/MgO |
| La/Ce/Nd/Sr | La/Ce/Nd/Sr/$Ln1_{4-x}Ln2_xO_6$ | La/Ce/Nd/Sr/$La_{4-x}Ln1_xO_6$ | La/Ce/Nd/Sr/$Y_2O_3$ | La/Ce/Nd/Sr/MgO |
| La/Bi/Ce/Nd/Sr | La/Bi/Ce/Nd/Sr/$Ln1_{4-x}Ln2_xO_6$ | La/Bi/Ce/Nd/Sr/$La_{4-x}Ln1_xO_6$ | La/Bi/Ce/Nd/Sr/$Y_2O_3$ | La/Bi/Ce/Nd/Sr/MgO |
| Eu/Gd | Eu/Gd/$Ln1_{4-x}Ln2_xO_6$ | Eu/Gd/$La_{4-x}Ln1_xO_6$ | Eu/Gd/$Y_2O_3$ | Eu/Gd/MgO |
| Ca/Na | Ca/Na/$Ln1_{4-x}Ln2_xO_6$ | Ca/Na/$La_{4-x}Ln1_xO_6$ | Ca/Na/$Y_2O_3$ | Ca/Na/MgO |
| Eu/Sm | Eu/Sm/$Ln1_{4-x}Ln2_xO_6$ | Eu/Sm/$La_{4-x}Ln1_xO_6$ | Eu/Sm/$Y_2O_3$ | Eu/Sm/MgO |
| Eu/Sr | Eu/Sr/$Ln1_{4-x}Ln2_xO_6$ | Eu/Sr/$La_{4-x}Ln1_xO_6$ | Eu/Sr/$Y_2O_3$ | Eu/Sr/MgO |
| Mg/Sr | Mg/Sr/$Ln1_{4-x}Ln2_xO_6$ | Mg/Sr/$La_{4-x}Ln1_xO_6$ | Mg/Sr/$Y_2O_3$ | Mg/Sr/MgO |
| Ce/Mg | Ce/Mg/$Ln1_{4-x}Ln2_xO_6$ | Ce/Mg/$La_{4-x}Ln1_xO_6$ | Ce/Mg/$Y_2O_3$ | Ce/Mg/MgO |
| Gd/Sm | Gd/Sm/$Ln1_{4-x}Ln2_xO_6$ | Gd/Sm/$La_{4-x}Ln1_xO_6$ | Gd/Sm/$Y_2O_3$ | Gd/Sm/MgO |
| Au/Pb | Au/Pb/$Ln1_{4-x}Ln2_xO_6$ | Au/Pb/$La_{4-x}Ln1_xO_6$ | Au/Pb/$Y_2O_3$ | Au/Pb/MgO |
| Bi/Hf | Bi/Hf/$Ln1_{4-x}Ln2_xO_6$ | Bi/Hf/$La_{4-x}Ln1_xO_6$ | Bi/Hf/$Y_2O_3$ | Bi/Hf/MgO |
| Rb/S | Rb/S/$Ln1_{4-x}Ln2_xO_6$ | Rb/S/$La_{4-x}Ln1_xO_6$ | Rb/S/$Y_2O_3$ | Rb/S/MgO |
| Sr/Nd | Sr/Nd/$Ln1_{4-x}Ln2_xO_6$ | Sr/Nd/$La_{4-x}Ln1_xO_6$ | Sr/Nd/$Y_2O_3$ | Sr/Nd/MgO |
| Eu/Y | Eu/Y/$Ln1_{4-x}Ln2_xO_6$ | Eu/Y/$La_{4-x}Ln1_xO_6$ | Eu/Y/$Y_2O_3$ | Eu/Y/MgO |
| Sr/Hf/K | Sr/Hf/K/$Ln1_{4-x}Ln2_xO_6$ | Sr/Hf/K/$La_{4-x}Ln1_xO_6$ | Sr/Hf/K/$Y_2O_3$ | Sr/Hf/K/MgO |
| Mg/Nd | Mg/Nd/$Ln1_{4-x}Ln2_xO_6$ | Mg/Nd/$La_{4-x}Ln1_xO_6$ | Mg/Nd/$Y_2O_3$ | Mg/Nd/MgO |
| La/Mg | La/Mg/$Ln1_{4-x}Ln2_xO_6$ | La/Mg/$La_{4-x}Ln1_xO_6$ | La/Mg/$Y_2O_3$ | La/Mg/MgO |
| Mg/Nd/Fe | Mg/Nd/Fe/$Ln1_{4-x}Ln2_xO_6$ | Mg/Nd/Fe/$La_{4-x}Ln1_xO_6$ | Mg/Nd/Fe/$Y_2O_3$ | Mg/Nd/Fe/MgO |
| Rb/Sr | Rb/Sr/$Ln1_{4-x}Ln2_xO_6$ | Rb/Sr/$La_{4-x}Ln1_xO_6$ | Rb/Sr/$Y_2O_3$ | Rb/Sr/MgO |

*Ln1 and Ln2 are each independently a lanthanide element, wherein Ln1 and Ln2 are not the same and x is a number ranging from greater than 0 to less than 4.

As used in Tables 1-12 and throughout the specification, a nanowire composition represented by $E^1/E^2/E^3$ etc., wherein $E^1$, $E^2$ and $E^3$ are each independently an element or a compound comprising one or more elements, refers to a nanowire composition comprised of a mixture of $E^1$, $E^2$ and $E^3$. $E^1/E^2/E^3$, etc. are not necessarily present in equal amounts and need not form a bond with one another. For example, a nanowire comprising Li/MgO refers to a nanowire comprising Li and MgO, for example, Li/MgO may refer to a MgO nanowire doped with Li. By way of another example, a nanowire comprising $NaMnO_4$/MgO refers to a nanowire comprised of a mixture of $NaMnO_4$ and MgO. Dopants may be added in suitable form. For example in a lithium doped magnesium oxide nanowire (Li/MgO), the Li dopant can be incorporated in the form of $Li_2O$, $Li_2CO_3$, LiOH, or other suitable forms. Li may be fully incorporated in the MgO crystal lattice (e.g., (Li,Mg)O) as well. Dopants for other nanowires may be incorporated analogously.

In some more specific embodiments, the dopant is selected from Li, Ba and Sr. In other specific embodiments, the nanowires comprise Li/MgO, Ba/MgO, Sr/$La_2O_3$, Ba/$La_2O_3$, Mn/$Na_2WO_4$, $Mn_2O_3$/$Na_2WO_4$, $Mn_3O_4$/$Na_2WO_4$, $Mg_6MnO_8$, Li/B/$Mg_6MnO_8$, Na/B/$Mg_6MnO_8$, $Zr_2Mo_2O_8$ or $NaMnO_4$/MgO.

In some other specific embodiments, the nanowire comprises a mixed oxide of Mn and Mg with or without B and with or without Li. Additional dopants for such nanowires may comprise doping elements selected from Group 1 and 2 and groups 7-13. The dopants may be present as single dopants or in combination with other dopants. In certain specific embodiments of nanowires comprising a mixed oxide of Mn and Mg with or without B and with or without Li., the dopant comprises a combination of elements from group 1 and group 8-11.

Nanowires comprising mixed oxides of Mn and Mg are well suited for incorporation of dopants because magnesium atoms can be easily substituted by other atoms as long as their size is comparable with magnesium. A family of "doped" $Mg_6MnO_8$ compounds with the composition $M_{(x)}Mg_{(6-x)}MnO_8$, wherein each M is independently a dopant as defined herein and x is 0 to 6, can thus be created. The oxidation state of Mn can be tuned by selecting different amounts (i.e., different values of x) of M with different oxidation states, for example $Li_{(x)}Mg_{(6-x)}MnO_8$ would contain a mixture of Mn(IV) and Mn(V) with x<1 and a mixture that may include Mn(V), Mn(VI), Mn(VII) with x>1. The maximum value of x depends on the ability of a particular atom M to be incorporated in the $Mg_6MnO_8$ crystal structure and therefore varies depending on M. It is believed that the ability to tune the manganese oxidation state as described above could have advantageous effect on the catalytic activity of the disclosed nanowires.

Examples of nanowires comprising Li/Mn/Mg/B and an additional dopant include; Li/Mn/Mg/B doped with Co; Li/Mn/Mg/B doped with Na, Li/Mn/Mg/B doped with Be; Li/Mn/Mg/B doped with Al; Li/Mn/Mg/B doped with Hf; Li/Mn/Mg/B doped with Zr; Li/Mn/Mg/B doped with Zn; Li/Mn/Mg/B doped with Rh and Li/Mn/Mg/B doped with Ga. Nanowires comprising Li/Mn/Mg/B doped with different combinations of these dopants are also provided. For example, in some embodiments the Li/Mn/Mg/B nanowires are doped with Na and Co. In other embodiments, the Li/Mn/Mg/B nanowires are doped with Ga and Na.

In other embodiments, nanowires comprising Mn/W with or without dopants are provided. For example, the present inventors have found through high throughput testing that nanowires comprising Mn/W and various dopants are good catalysts in the OCM reaction. Accordingly, in some embodiments, the Mn/W nanowires are doped with Ba. In other embodiments, the Mn/W nanowires are doped with Be. In yet other embodiments, the Mn/W nanowires are doped with Te.

In any of the above embodiments, the Mn/W nanowires may comprise a $SiO_2$ support. Alternatively, the use of different supports such as $ZrO_2$, $HfO_2$ and $In_2O_3$ in any of the above embodiments has been shown to promote OCM activity at reduced temperature compared to the same catalyst supported on silica with limited reduction in selectivity.

Nanowires comprising rare earth oxides doped with various elements are also effective catalysts in the OCM reaction. In certain specific embodiments, the rare earth oxide or oxy-hydroxide can be any rare earth, preferably La, Nd, Eu, Sm, Yb, Gd. In certain embodiments of the nanowires comprising rare earth elements or yttria, the dopant comprises alkali earth (group 2) elements. The degree of effectiveness of a particular dopant is a function of the rare earth used and the concentration of the alkali earth dopant. In addition to Alkali earth elements, further embodiments of the rare earth or yttria nanowires include embodiments wherein the nanowires comprise alkali elements as dopants, which further promote the selectivity of the OCM catalytic activity of the doped material. In yet other embodiments of the foregoing, the nanowires comprise both an alkali element and alkali earth element as dopant. In still further embodiments, an additional dopant can be selected from an additional rare earth and groups 3, 4, 8, 9, 10, 13, 14.

The foregoing rare earth catalyst may be doped prior to, or after formation of the rare earth oxide. In one embodiment, the corresponding rare earth salt is mixed with the corresponding dopant salt to form a solution or a slurry which is dried and then calcined in a range of 400° C. to 900° C., or between 500° C. and 700° C. In another embodiment, the rare earth oxide is formed first through calcination of a rare earth salt and then contacted with a solution comprising the doping element prior to drying and calcination between 300° C. and 800° C., or between 400° C. and 700° C.

In other embodiments, the nanowires comprise $La_2O_3$ or $LaO_y(OH)_x$, wherein y ranges from 0 to 1.5, x ranges from 0 to 3 and 2y+x=3, doped with Na, Mg, Ca, Sr, Ga, Sc, Y, Zr, In, Nd, Eu, Sm, Ce, Gd or combinations thereof. In yet further embodiments, the $La_2O_3$ or $LaO_y(OH)_x$ nanowires are doped with binary dopant combinations, for example Eu/Na; Eu/Gd; Ca/Na; Eu/Sm; Eu/Sr; Mg/Sr; Ce/Mg; Gd/Sm, Mg/Na, Mg/Y, Ga/Sr, Nd/Mg, Gd/Na or Sm/Na. In some other embodiments, the $La_2O_3$ or $LaO_y(OH)_x$ nanowires are doped with a ternary dopant combination, for example Ca—Mg—Na.

In other embodiments, the nanowires comprise $Nd_2O_3$ or $NdO_y(OH)_x$, wherein y ranges from 0 to 1.5, x ranges from 0 to 3 and 2y+x=3, doped with Sr, Ca, Rb, Li, Na or combinations thereof. In certain other embodiments, the $Nd_2O_3$ or $NdO_y(OH)_x$ nanowires are doped with binary dopant combinations, for example Ca/Sr, Rb/Sr, Ta/Sr or Al/Sr.

In still other examples of doped nanowires, the nanowires comprise $Yb_2O_3$ or $YbO_y(OH)_x$, wherein y ranges from 0 to 1.5, x ranges from 0 to 3 and 2y+x=3, doped with Sr, Ca, Ba, Nd or combinations thereof. In certain other embodiments, the $Yb_2O_3$ or $YbO_y(OH)_x$ OCM nanowires are doped with a binary combination, for example of Sr/Nd.

Still other examples of doped nanowires $Eu_2O_3$ or $EuO_y(OH)_x$ nanowires, wherein y ranges from 0 to 1.5, x ranges from 0 to 3 and 2y+x=3, doped with Sr, Ba, Sm, Gd, Na or combinations thereof or a binary dopant combination, for example Sr/Na or Sm/Na.

Example of dopants for $Sm_2O_3$ or $SmO_y(OH)_x$ nanowires, wherein x and y are each independently an integer from 1 to 10, include Sr, and examples of dopants for $Y_2O_3$ or $YO_y(OH)_x$ nanowires, wherein y ranges from 0 to 1.5, x ranges from 0 to 3 and 2y+x=3, comprise Ga, La, Nd or combinations thereof. In certain other embodiments, the $Y_2O_3$ or $YO_y(OH)_x$ nanowires comprise a binary dopant combination, for example Sr/Nd, Eu/Y or Mg/Nd or a tertiary dopant combination, for example Mg/Nd/Fe.

In yet other embodiments, the nanowires comprise $Ln_2O_3$ or $Ln_zO_y(OH)_x$, wherein Ln is at each occurrence, independently a lanthanide, x ranges from 0 to 3 and 2y+x=3, y ranges from 0 to 1.5, and z is 1, 2 or 3, and the nanowires are doped with Li, Na, K, Rb, Cs, Mg, Ca, Sr, Ba, Sc, Y, La, Ce, Pr, Nd, Sm, Eu, Gd, Tb, Dy, Ho, Er, Tm, Yb, Lu, Ti, Zr, Hf, V, Nb, Ta, Mo, W, Mn, Ni, Pd, Pt, Cu, Ag, Au, Zn, Al, Ga, In, Tl, Ge, Sn, Pb, P, As, Sb, Bi, S, Se, Te or combinations thereof. In certain other embodiments, the $Ln_2O_3$ or $Ln_zO_y(OH)_x$ nanowires comprise only one dopant, for example Sr, a binary dopant combination, for example Na/Mg, Na/Sr, Mg/Sr, Li/Cs, Sr/W, Hf/Bi, Na/Eu, Zn/K, Sb/Ag, Sr/Ta, a tertiary dopant combination, for example Li/Na/Sr, Na/La/Eu, Li/Sr/Cs, Dy/Rb/Gd, Mg/La/K, or a quaternary dopant combination, for example Na/Zr/Eu/Ca, Na/La/Eu/In, Na/K/Mg/Tm, Li/Cs/Sr/Tm, Ba/Tm/Zn/K, Mg/La/Yb/Zn.

Rare earth nanowires, which without doping often have low OCM selectivity, can be greatly improved by doping to reduce their combustion activity. In particular, nanowires comprising $CeO_2$ and $Pr_2O_3$ tend to have strong total oxidation activity for methane, however doping with additional rare earth elements can significantly moderate the combustion activity and improve the overall utility of the catalyst. Example of dopants for improving the selectivity for $Pr_2O_3$ or $PrO_y(OH)_x$ nanowires, wherein y ranges from 0 to 1.5, x ranges from 0 to 3 and 2y+x=3, comprise binary dopants, for example Nd/Mg, La/Mg or Yb/Sr.

In some embodiments, dopants are present in the nanowires in, for example, less than 50 at %, less than 25 at %, less than 10 at %, less than 5 at % or less than 1 at %.

In other embodiments of the nanowires, the atomic ratio (w/w) of the one or more metal elements selected from Groups 1-7 and lanthanides and actinides in the form of an oxide and the dopant ranges from 1:1 to 10,000:1, 1:1 to 1,000:1 or 1:1 to 500:1.

In further embodiments, the nanowires comprise one or more metal elements from Group 2 in the form of an oxide and a dopant from Group 1. In further embodiments, the nanowires comprise magnesium and lithium. In other embodiments, the nanowires comprise one or more metal elements from Group 2 and a dopant from Group 2, for example, in some embodiments, the nanowires comprise magnesium oxide and barium. In other embodiments, the nanowires comprise one or more metal elements from Group 2, a dopant from Group 2 and an additional dopant, for example, in some embodiments, the nanowires comprise magnesium oxide and are doped with strontium and tungsten dopants (i.e., Sr/W/MgO). In another embodiment, the nanowires comprise an element from the lanthanides in the form of an oxide and a dopant from Group 1 or Group 2. In further embodiments, the nanowires comprise lanthanum and strontium.

Various methods for preparing doped nanowires are provided. In one embodiment, the doped nanowires can be prepared by co-precipitating a nanowire metal oxide precursor and a dopant precursor. In these embodiments, the doping element may be directly incorporated into the nanowire.

Template Directed Synthesis of Nanowires

In some embodiments, the nanowires can be prepared in a solution phase using an appropriate template. In this context, an appropriate template can be any synthetic or natural material, or combination thereof, that provides nucleation sites for binding ions (e.g. metal element ions and/or hydroxide or other anions) and causing the growth of a nanowire. The templates can be selected such that certain control of the nucleation sites, in terms of their composition, quantity and location can be achieved in a statistically significant manner. The templates are typically linear or anisotropic in shape, thus directing the growth of a nanowire.

In contrast to other template directed preparation of nanostructures, the nanowires of the invention are generally not prepared from nanoparticles deposited on a template in a reduced state which are then heat treated and fused into an elongated nanoporous nanostructure. In particular, such methods are not generally applicable to continuous nanowires comprising one or more elements from any of Groups 1 through 7, lanthanides, actinides or combinations thereof. Instead of forming a plurality of catalyst nanoparticles, nanocrystals, or nanocrystallites on the surface of the template (e.g., phage), the nanowires of the invention are preferably prepared by nucleation of an oxidized metal element (e.g., in the form of a metal ion) and subsequent growth of a nanowire. After nucleation of the oxidized metal element, the nanowires are generally calcined to produce the desired oxide, but annealing of nanoparticles is not necessary to form the nanowires.

Accordingly, the nanowires used in the context of the invention have a number of properties that differentiate them from other nanostructures, such as those created as fused aggregates of nanoparticles. In particular, the nanowires are characterized as having one or more of; a substantially non-nanoporous structure, an average crystal domain size, either before and/or after calcination, of greater than 5 nm, and an anisotropic crystal habit.

In the context of non-nanoporous nanowires, preferred compositions are distinguished from elongated nanostructures formed as nanoporous aggregates of nanoparticles by virtue of their substantially non-nanoporous structures. Such substantially non-nanoporous nanowire structures will preferably have a surface area of less than 150 $m^2/g$, more preferably less than 100 $m^2/g$, less than 50 $m^2/g$, less than 40 $m^2/g$, less than 30 $m^2/g$ less than 25 $m^2/g$, less than 20 $m^2/g$, less than 15 $m^2/g$, less than 10 $m^2/g$, or between 1 $m^2/g$ and any of the foregoing. As will be appreciated, nanowires created through templating processes, where additional aggregates may fuse to a non-nanoporous or substantially non-nanoporous nanowire core, will typically have higher surface areas, e.g., surface areas toward the higher end of the range, while nanowires created from other processes, e.g., by hydrothermal processes, will typically have lower surface areas.

In certain aspects, the nanowires of the invention are characterized by relatively large crystal domain sizes in the context of relatively high surface area nanowire structures. In particular, and as noted previously, for those nanowires of the invention having an average crystal domain size in at least one crystal dimension that is greater than 5 nm, preferred nanowires of the invention will typically have an average crystal domain size in at least one crystal dimension that is greater than 10 nm, and in more preferred aspects, greater than 20 nm.

In certain embodiments, the nanowires of the invention may also be characterized by additional structural properties. For example, in certain aspects, the nanowires of the invention may be characterized by a continuous crystal structure within the nanowire, excluding stacking faults. In certain aspects, the nanowires of the invention may be characterized by an aligned crystal structure within the nanowire consisting of parallel, aligned crystal domains.

In some embodiments, methods for forming nanowires having the empirical formula $M4_wM5_xM6_yO_z$ are provided, wherein M4 comprises one or more elements selected from Groups 1 through 4, M5 comprises one or more elements selected from Group 7 and M6 comprises one or more elements selected from Groups 5 through 8 and Groups 14 through 15 and w, x, y and z are integers such that the overall charge is balanced. The methods comprise combining one or more sources of M4, one or more sources of M5, and one or more sources of M6 in the presence of a templating agent and a solvent to form a mixture.

In certain embodiments, M4 includes one or more elements selected from Group 1, such as Na, while M6 includes one or more elements selected from Group 6, such as W and M3 is Mn. In one embodiment, M4 is Na and the source of M4 is NaCl, M5 is Mn and the source of M5 is $Mn(NO_3)_2$, M6 is W and the source of M6 is $WO_3$, the solvent is water, and the templating agent is a bacteriophage.

In various embodiments, the source of M4 can be one or more of a chloride, bromide, iodide, oxychloride, oxybromide, oxyiodide, nitrate, oxynitrate, sulfate or phosphate salt of any of Group 1, Group 2, Group 3, or a Group 4 element. In an embodiment, sources of M4 include LiCl, KCl, $MgCl_2$, $CaCl_2$, $ScCl_3$, $TiCl_4$, KBr, $CaBr_2$, $Sc(NO_3)_3$, $Y(NO_3)_3$, $TiBr_4$, $ZrBr_4$, $Zr(NO_3)_4$, $ZrOCl_2$, $ZrO(NO_3)_2$, $Na_2SO_4$, and $Zr(SO_4)_2$. For any given source of M4, a source of M6 can be one or more of an oxide, oxide salt, or an oxyacid of any of Group 5, Group 6, Group 7, Group 8, Group 14 and Group 15 elements. In an embodiment, sources of M6 include $MoO_3$, $(NH_4)_6Mo_7O_{24}$, $WO_3$, $Na_2WO_4$, $H_2WO_4$, $CO_2O_3$, $P_2O_5$, $H_3PO_4$ and $H_2SiO_4$. For any given combination of a source of M4 and a source of M6, a source of Mn can be, but is not limited to, any chloride, bromide, nitrate, or sulfate of manganese, including $MnCl_2$, $MnCl_3$, $MnCl_4$, $Mn(NO_3)_3$, $MnSO_4$ and $Mn_2(SO_4)_3$.

In still other embodiments, the templating agent can include a surfactant, such as tetraoctylammonium chloride, ammonium lauryl sulfate, or lauryl glucoside. For any templating agent or any source of M4, M6, or Mn, the solvent can include an organic solvent, such as ethanol, diethyl ether, or acetonitrile. Additionally, any embodiment of the method for forming a nanowire described above can include any additional component in the reaction mixture, such as a base.

Nanowire-forming methods of various embodiments of the invention comprise combining a source of M4, a source of M5, a source of M6, a templating agent, and a solvent in a reaction mixture. In other embodiments, however, nanowire-forming methods of the present invention comprise combining two of a source of M4, a source of M5 and a source of M6 in the presence of a templating agent and a solvent to form an intermediate nanowire and then combining a remainder of the source of M4, the source of M5 and the source of M6 with the intermediate nanowire, wherein M4 includes one or more elements selected from Group 1, Group 2, Group 3 and Group 4 elements, wherein M5 includes one or more elements selected from Group 7, and wherein M6 includes one or more elements selected from Group 5, Group 6, Group 7, Group 8, Group 14 and Group 15 elements. In an embodiment, an intermediate nanowire is formed by combining the source of M5 and the source of M6 in the presence of the templating agent and the solvent, followed by combining the intermediate nanowire with the source of M4.

1. Biological Template

Because peptide sequences have been shown to have specific and selective binding affinity for many different types of metal element ions, biological templates incorporating peptide sequences as nucleation sites are preferred. Moreover, biological templates can be engineered to comprise pre-determined nucleation sites in pre-determined spatial relationships (e.g., separated by a few to tens of nanometers).

Both wild type (i.e., naturally occurring) and genetically engineered biological templates can be used. As discussed herein, biological templates such as proteins and bacteriophage can be engineered based on genetics to ensure control over the type of nucleation sites (e.g., by controlling the peptide sequences), their locations on the templates and their respective density and/or ratio to other nucleation sites. See, e.g., Mao, C. B. et al., (2004) Science, 303, 213-217; Belcher, A. et al., (2002) Science 296, 892-895; Belcher, A. et al., (2000) Nature 405 (6787) 665-668; Reiss et al., (2004) Nanoletters, 4 (6), 1127-1132, Flynn, C. et al., (2003) J. Mater. Sci., 13, 2414-2421; Mao, C. B. et al., (2003) PNAS, 100 (12), 6946-6951, which references are hereby incorporated by reference in their entireties. This allows for the ability to control the composition and distribution of the nucleation sites on the biological template.

Thus, biological templates may be particularly advantageous for a controlled growth of nanowires. Biological templates can be biomolecules (e.g., proteins) as well as multi-molecular structures of a biological origin, including, for example, bacteriophage, virus, amyloid fiber, and capsid.

(a) Biomolecules

In certain embodiments, the biological templates are biomolecules. In more specific embodiments, the biological templates are anisotropic biomolecules. Typically, a biomolecule comprises a plurality of subunits (building blocks) joined together in a sequence via chemical bonds. Each subunit comprises at least two reactive groups such as hydroxyl, carboxylic acid and amino groups, which enable the bond formations that interconnect the subunits. Examples of the subunits include, but are not limited to: amino acids (both natural and synthetic) and nucleotides. Accordingly, in some embodiments, the biomolecule template is a peptide, protein, nucleic acid, polynucleotide, amino acid, antibody, enzyme, or single-stranded or double-stranded nucleic acid or any modified and/or degraded forms thereof.

Because protein synthesis can be genetically directed, proteins can be readily manipulated and functionalized to contain desired peptide sequences (i.e., nucleation sites) at desired locations within the primary structure of the protein. The protein can then be assembled to provide a template.

Thus, in various embodiments, the templates are biomolecules are native proteins or proteins that can be engineered to have nucleation sites for specific ions.

(b) Baceteriophage

In one particular embodiment, the biological template comprises a M13 bacteriophage which has or can be engineered to have one or more particular peptide sequences to be expressed on the coat proteins. M13 bacteriophage is a filamentous bacterial virus that is produced by amplification through *E. coli* bacteria. It is 880 nm long and 6.7 nm in diameter. The surface of the filamentous phage is mostly composed of its major coat protein, pVIII. 2700 copies of this protein pack around the phage DNA to make a tight and cylindrical shell. The N-termini of pVIII form a dense periodic display spaced at 2.7 nm. The final five residues of pVIII are structurally unconstrained and exposed to the solvent, therefore presenting an optimal target for engineering, manipulation, and substrate interaction.

Figure 6:
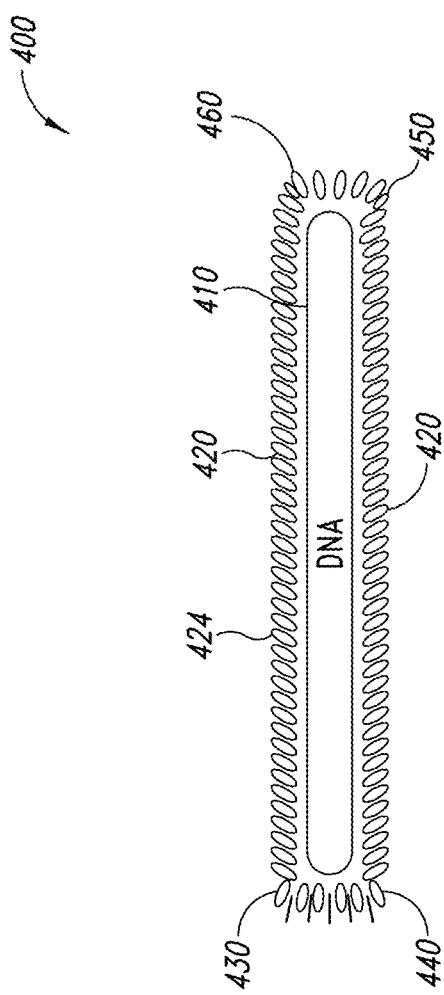
FIG. 6 illustrates a filamentous bacteriophage.

FIG. 6 schematically shows a filamentous bacteriophage 400, in which a single-stranded DNA core 410 is surrounded by a proteinaceous coat 420. The coat is composed mainly of pVIII proteins 424 that cover the length of the bacteriophage. The ends of the bacteriophage are capped by minor coat proteins 430 (pIII), 440 (pVI), 450 (pVII) and 460 (pIX). Using genetic engineering, a library of diverse, novel peptide sequences (up to $10^{12}$ unique peptides) can be expressed on the surface of the phage, so that each individual phage displays at least one unique peptide sequence. These externally facing peptide sequences can be tested, through the iterative steps of screening, amplification and optimization, for the ability to control nucleation and growth of specific catalytic nanowires. Small peptides engineered and presented on the phage surface provide a dense periodic display of functional groups that are available to bind and coordinate with materials for nucleation and synthesis. The large number of groups presented additionally provides a potential chelating effect, therefore increasing the affinity of binding. As the nucleation sites are available in solution co-precipitation of various materials can take place. Furthermore the filamentous geometry of bacteriophage result in filamentous nanowire structures of templated materials that present a large surface area for potential catalytic activity. Controlled display of a large variety of chemical functional groups, as well as filamentous nature of formed materials are potential advantages of the M13 bacteriophage system for catalytic material synthesis.

For example, in a further embodiment peptide sequences having one or more particular nucleation sites specific for various ions are expressed on the coat proteins. For example, in one embodiment, the coat protein is pVIII with peptide sequences having one or more particular nucleation sites specific for various ions bound thereto. In other further embodiments, the peptide sequences bound to the coat protein comprise 2 or more amino acids, 5 or more amino acids, 10 or more amino acids, 20 or more amino acids, or 40 or more amino acids. In other embodiments, the peptide sequences expressed on the coat protein comprise between 2 and 40 amino acids, between 5 and 20 amino acids, or between 7 and 12 amino acids.

One of the approaches to obtain different types of M13 bacteriophage is to modify the viral genetic code in order to change the amino acid sequence of the major coat protein pVIII. The changes in sequence only affect the N-terminus amino acids of the pVIII protein, which are the ones that make the surface of the M13 phage, while the first 45 amino acids are left unchanged so that the packing of the pVIII proteins around the phage is not compromised. By changing the N-terminus amino acids on the pVIII protein, the surface characteristics of the phage can be tailored to higher affinities to specific metal ions and thus promoting selective growth of specific inorganic materials on the phage surface.

Many short amino acid sequences can be engineered at the pVIII N-terminus for precipitation of various materials or combinations thereof. Typical functional groups in amino acids that can be used to tailor the phage surface affinity to metal ions include: carboxylic acid (—COOH), amino (—$NH_3^+$ or —$NH_2$), hydroxyl (—OH), and/or thiol (—SH) functional groups. Table 13 summarizes a number of exemplary phages used in the present invention for preparing nanowires of inorganic metal oxides. In certain embodiment, the present disclosure is directed to any of the peptide sequences in Table 13. Sequences within Table 13 refer to the amino acid sequence of the pVIII protein (single-letter amino acid code). Underlined portions indicate the terminal sequence that was varied to tailor the phage surface affinity to metal ions. SEQ ID NO 30 represents wild type pVIII protein while SEQ ID NO 31 represents wild type pVIII protein including the signaling peptide portion (bold).

TABLE 13

Phage Surface Protein Sequences

| SEQ ID NO | Sequence |
|---|---|
| 1 | AEEGSEDPAKAAFNSLQASATEYIGYAWAMVVVIVGATIGIKLFKKFTSKAS |
| 2 | EEGSDDPAKAAFNSLQASATEYIGYAWAMVVVIVGATIGIKLFKKFTSKAS |
| 3 | AEEEDPAKAAFNSLQASATEYIGYAWAMVVVIVGATIGIKLFKKFTSKAS |
| 4 | EEEDPAKAAFNSLQASATEYIGYAWAMVVVIVGATIGIKLFKKFTSKAS |
| 5 | AEEEEDPAKAAFNSLQASATEYIGYAWAMVVVIVGATIGIKLFKKFTSKAS |
| 6 | AEEAEDPAKAAFNSLQASATEYIGYAWAMVVVIVGATIGIKLFKKFTSKAS |
| 7 | EEXEDPAKAAFNSLQASATEYIGYAWAMVVVIVGATIGIKLFKKFTSKAS  X = E or G |
| 8 | AEDDDPAKAAFNSLQASATEYIGYAWAMVVVIVGATIGIKLFKKFTSKAS |
| 9 | AVSGSSPGDDPAKAAFNSLQASATEYIGYAWAMVVVIVGATIGIKLFKKFTSKAS |
| 10 | AVSGSSPDSDPAKAAFNSLQASATEYIGYAWAMVVVIVGATIGIKLFKKFTSKAS |
| 11 | AGETQQAMEDPAKAAFNSLQASATEYIGYAWAMVVVIVGATIGIKLFKKFTSKAS |
| 12 | AAGETQQAMDPAKAAFNSLQASATEYIGYAWAMVVVIVGATIGIKLFKKFTSKAS |
| 13 | AEPGHDAVPEDPAKAAFNSLQASATEYIGYAWAMVVVIVGATIGIKLFKKFTSKAS |
| 14 | AEDPAEDPAKAAFNSLQASATEYIGYAWAMVVVIVGATIGIKLFKKFTSKAS |
| 15 | AEDPAKDPAKAAFNSLQASATEYIGYAWAMVVVIVGATIGIKLFKKFTSKAS |
| 16 | AEFEVEADPAKAAFNSLQASATEYIGYAWAMVVVIVGATIGIKLFKKFTSKAS |
| 17 | AEHEAEEDPAKAAFNSLQASATEYIGYAWAMVVVIVGATIGIKLFKKFTSKAS |
| 18 | AESEFELDPAKAAFNSLQASATEYIGYAWAMVVVIVGATIGIKLFKKFTSKAS |
| 19 | ADNDVDLDPAKAAFNSLQASATEYIGYAWAMVVVIVGATIGIKLFKKFTSKAS |
| 20 | ADSDYDGDPAKAAFNSLQASATEYIGYAWAMVVVIVGATIGIKLFKKFTSKAS |
| 21 | ADADRDGDPAKAAFNSLQASATEYIGYAWAMVVVIVGATIGIKLFKKFTSKAS |
| 22 | ADSDPDGDPAKAAFNSLQASATEYIGYAWAMVVVIVGATIGIKLFKKFTSKAS |
| 23 | ADSDTDSDPAKAAFNSLQASATEYIGYAWAMVVVIVGATIGIKLFKKFTSKAS |
| 24 | ADKDYDLDPAKAAFNSLQASATEYIGYAWAMVVVIVGATIGIKLFKKFTSKAS |
| 25 | AEFEVGADPAKAAFNSLQASATEYIGYAWAMVVVIVGATIGIKLFKKFTSKAS |
| 26 | AGFEGEADPAKAAFNSLQASATEYIGYAWAMVVVIVGATIGIKLFKKFTSKAS |
| 27 | ADGDLDQDPAKAAFNSLQASATEYIGYAWAMVVVIVGATIGIKLFKKFTSKAS |
| 28 | AEFEAEADPAKAAFNSLQASATEYIGYAWAMVVVIVGATIGIKLFKKFTSKAS |
| 29 | AGFEVEADPAKAAFNSLQASATEYIGYAWAMVVVIVGATIGIKLFKKFTSKAS |
| 30 | AEGDDDPAKAAFNSLQASATEYIGYAWAMVVVIVGATIGIKLFKKFTSKAS |
| 31 | MKKSLVLKASVAVATLVPMLSFAAEGDDDPAKAAFNSLQASATEYIGYAWAMVVVIVGATIGIKLFKKFTSKAS |

Amino acid side chains have assorted chemical properties that can be used for material synthesis. Glutamic acid (E) and aspartic acid (D) have carboxylic acid side chains and are therefore negative at neutral pH. Negative residues are attractive to positively charged metal cations and therefore can nucleate biomineralization. Proline (P) is a cyclically constrained amino acid, and as a part of a protein gives it structural rigidity, potentially contributing to stronger binging interactions. Furthermore, through such rigidity proline can aid in bringing other functional side chains closer together for better coordination. Other amino acids of interest for use in phage-templated preparation of nanowires include histidine (H) that has a side chain with a pKa=6.0 and is very sensitive to the environment and can be made positive in only a slightly acidic environment. Tryptophan (W) has a large aromatic and polar side chain that can contribute to synthesis by metal pi-interactions.

Accordingly, in certain embodiments the present disclosure provides phage sequences useful for templating of catalytic nanowires. In some embodiments, the engineered pVIII sequence comprises at least one constraining amino acid (e.g., P) and a repeat of 2 negative amino acids (e.g., E & D). Alanine is the one of the smallest side chain amino acids, and in some embodiments may be included as a spacer. The negative charges may be spread on both E & D amino acids as to avoid too many repeats of the same amino acid which may contribute to lower yield of phage. In a variation of the above sequence, Lysine (K) maybe included in the terminal phage sequence. Lysine has an active amine group, and therefore can potentially be attractive to higher group transition metals (e.g., Pt, Pd, Au) that exist as negatively charged ions in solution.

In other embodiments, the sequences are based on an alternating peptide library approach. The engineered sequence is constrained to have an alternating negatively charged residue, for example either AEXEXEX or ADXDXDX, wherein X is any amino acid.

In other embodiments, a degenerate library approach is used to detect other viable sequences, i.e. amino acids of interest can be constrained and others can be left to be chosen by what is biologically favorable for phage production by bacteria. For example alternate libraries based on the negative residues AEXEXEX or ADXDXDX can be prepared using a degenerate library approach. In some embodiments, Histidine constrained or Tryptophan constrained libraries (e.g., AHXHXHX, AWXWXWX, AXXWHWX), are useful for identifying aromatic and hydrophobic interactions. Other embodiments include altering the placement and order of the amino acids (e.g., ADDXEE), and still other embodiments include constraining the sequences with proline amino acids (e.g., AEPEPEP, ADPDPDP), to explore the effect of peptide structure on synthesis. Any combination of the above can be engineered and explored for biological viability and the templation behaviors. Non-limiting examples of phage surface protein sequences useful in the present invention are provided in Table 9 below.

In one embodiment, the present disclosure provides methods for preparation and purification of filamentous bacteriophage. The purification methods may be based on standard methods or on the novel filtration methods described below. Such filtration methods can be advantageous in practice of certain embodiments of the invention since the methods are amenable to large scale preparations. Standard methods for purification of viruses, bacteriophage, DNA and recombinant proteins from feedstock solution generally include several steps. For example, the heavier components of feedstock, such as bacterial cells and cell debris, are first separated by centrifugation. Further, the particles of interest are then precipitated from the remaining supernatant by using a solution of polyethylene glycol and salt.

While not wishing to be bound by theory, it is believed that polyethylene glycol (PEG) as a big inert molecule adds osmotic stress to the solution by steric hindrance and increasing crowding, while the high concentration of salt screens the charge repulsion between the particles. The concentration of PEG, type and quantity of salts, as well as the subsequent processing steps depend upon the particular application. In the instance of filamentous bacteriophage, its long rod anisotropic geometry allows for minimal quantity of PEG to selectively precipitate these particles from the supernatant remaining after centrifugation, that might contain components of nutritious media used for amplification, as well as proteins and DNA excreted by bacteria during amplification and potential cell lysis. Following the precipitation, the solution is generally centrifuged once again to pellet the particle of interest such as bacteriophage, and then resuspended in the desired volume of buffer solution.

The standard process described above works well on a small scale, however it may be limited by the centrifuge capacity as it is scaled up. Often the final solution has to be further clarified of remaining bacteria, by further centrifugation or filtration. Additionally the purified product may contain both trace amounts of polyethylene glycol as well as the salt used for precipitation in quantities difficult to quantitate, yet potentially influencing further chemical processing. In the case of bacteriophage, the solution can be purified further by a CsCl gradient and ultracentrifugation, however these steps are sometimes difficult to scale up due to the volumes that can be processed as well as the time and cost involved. Accordingly, there remains a need for improved phage preparation methods which are amenable to large scale production of purified phage.

The novel methods described herein are useful for large scale preparation of phage. In one embodiment, the method comprises a two-step filtration to purify bacteriophage from a feedstock solution. In the following description these two filtration steps are sometimes referred to as the first filtration step and the second filtration step, respectively. In some embodiments, the types of filtration employed comprise tangential flow filtration (TFF) and/or depth filtration. It is believed that such methods have not previously been employed with filamentous bacteriophage.

Tangential flow filtration is a technique that separates the solution based on a size exclusion principle dictated by the pore size of the membrane used. The solution to be filtered is flowed over the membrane, with pressure applied across the membrane. One aspect of TFF is that the solvent is split in two parts, the retentate and the permeate; therefore, particles in both the retentate and the permeate remain in solution. Particles smaller than the pore size filter through to the permeate side, and the larger particles are retained in the solution on the retentate side of the membrane. Fouling of the membrane is minimized by the continuous flow and recirculation of the solution on the retentate side of the membrane. Depending on the particular application, the particles of interest can be harvested either in the retentate or in the permeate, since both are still in solution.

Depth filtration also separates the solution based on a size exclusion principle dictated by the pore size of the membrane used, but the solution to be filtered is flowed through the membrane instead of tangentially flowing along it as in TFF. Contrary to TFF, the entire amount of the solution is flowed through the membrane. Particles smaller than the pore size filter through to the permeate side, and the larger particles are retained in the solution on the retentate side of the membrane. Accordingly, the main difference between TFF and depth filtration is the nature of the retentate, which is a solution in TFF and a solid ("cake") in depth filtration. Typically, in depth filtration the particles of interest will be harvested in the permeate and not in the retentate, which is trapped in the membrane.

In one embodiment, a two-step TFF process for purifying bacteriophage is provided. In the first step a micro filtration is performed and in the second step an ultrafiltration is performed. In this respect a microfiltration comprises filtering a phage-containing solution through membranes of higher pore size (e.g., 0.1 to 3 µm). During this step the bigger particles of the feedstock such as cells and cell debris are clarified from solution and retained in the retentate, while the particles of interest (e.g., phage) are filtered through with the permeate. Ultrafiltration refers to filtration using smaller pore size membranes (e.g., 1 to 1000 kDa), the size being dependent on the specific application. During this filtration the particles of interest are retained while smaller particles, such as media components and small proteins are filtered out. In certain embodiments the ultrafiltration step can also be used to concentrate the solution by filtering out water. In an optional third step, diafiltration may be used to exchange the remaining concentrated media for buffer solution. Diafiltration may be performed over the same membrane as ultrafiltration.

Various parameters of the foregoing filtration process may be varied for optimal purification results. In some embodiments, for both microfiltration and ultrafiltration, parameters that control the flow of material over and through the membrane are important and can be varied. For example, the transmembrane pressure that is seen by the membrane as well as the flow rate of the recirculating solution can be varied from 0 to 40 psig and 100 to 3500 µL/h/m².

One embodiment of the present disclosure provides a tangential flow filtration process that is easily scalable. In this embodiment, the volume of the feedstock that can be processed in a given time, scales directly with the surface area of the membrane used. As the surface area is increased and the flow rate adjusted accordingly, the other parameters of the process may remain the same. This allows for a manufacturing process to be initially designed and optimized using lab scale equipment and then later directly scaled to larger scales.

In one embodiment of the foregoing filtration purification process for M13 phage, both the microfiltration and the ultrafiltration are performed using TFF. For microfiltration, a nylon flat sheet membrane cartridge having pore sizes ranging from 0.1 to 3 µm, 0.1 to 1 µm or 0.2 to 0.45 µm may be used. In some embodiments, the flow rate in microfiltration ranges from 100 to 3500 L/h/m², 300 to 3000 l/h/m² or 500 to 2500 l/h/m². In some embodiments, the flow rate in microfiltration is about 550 L/h/m². In other embodiments, the transmembrane pressure in microfiltration ranges from 1 to 30 psig or from 2 to 20 psig, and in some embodiments the transmembrane pressure is about 15 psig.

For the ultrafiltration and diafiltration steps a polyethersulfone flat sheet membrane cartridge having pore sizes ranging from 100 to 1000 kDa may be used. In some embodiments, the cartridge comprises pores having sizes of about 500 kDa. Flow parameters of approximately 100 to 3500 L/h/m², 300 to 3000 l/h/m² or 500 to 2500 l/h/m², for example about 2200 Llhr/m² may be used. The transmembrane pressures range from 1 to 30 psig or from 2 to 20 psig, and in some embodiments the transmembrane pressure is about 6 psig. In some embodiments, the solution may be diafiltered with from 1 to 20 volumes of water, for example 10 volumes of water. The optimum number of volumes depends on the desired purity of the final product. Any of the above parameters including the membrane material and configuration as well as flow parameters can be altered depending on the application, the particle of interest and purity and yield desired in the final product.

In another embodiment, the microfiltration step is performed with depth filtration instead of TFF to eliminate bacterial cells and cell debris. The depth filtration may be performed using two filters connected in series. In some embodiments, the first filter comprises a glass fiber capsule with nominal porosity of from 0.5 to 3 µm, for example about 1.2 µm and followed by a double membrane filter capsule having, each membrane filter capsule having a pore size of from 0.1 to 1 µm, for example about 0.8 µm and about 0.45 µm, respectively. This filtration system allows for clarification of the feedstock solution prior to the ultrafiltration step, which may be carried out using the same parameters described in any of the embodiments described herein.

Any of the above parameters may be modified to arrive at other embodiments. For example, in the initial step of clarifying the solution of cells and cell debris either TFF or depth filtration can be used. For the 2nd step of purifying the filamentous bacteriophage from the remaining solution TFF or depth filtration may also be used; however, in certain embodiments TFF is used.

The disclosed filtration purification methods can be applied to any other biological particles that are currently purified using a combination of centrifugation and precipitation methods. Such biological particles include, but are not limited to, other bacteriophage (i.e., not just M13), viruses, proteins, etc. The filter membrane geometry can be either a flat sheet or hollow fiber.

In some embodiments, the membranes used for TFF are chemically activated, via charge or affinity molecules, and such membranes may exhibit preferential binding to particles of interest to either be filtered out or retained. In other embodiments, the filter materials used for depth filtration may be activated, via charge or affinity molecules and may exhibit preferential binding for particles to be filtered out. Furthermore, some embodiments employ membranes for TFF which are mechanically activated via vibration to reduce fouling and enhance filtration.

(c) Amyloid Fibers

In another embodiment, amyloid fibers can be used as the biological template on which metal ions can nucleate and assemble into a catalytic nanowire. Under certain conditions, one or more normally soluble proteins (i.e., a precursor protein) may fold and assemble into a filamentous structure and become insoluble. Amyloid fibers are typically composed of aggregated β-strands, regardless of the structure origin of the precursor protein. As used herein, the precursor protein may contain natural or unnatural amino acids. The precursor protein may be further modified with a fatty acid tail.

(d) Virus and Capsid

In further embodiments, a virus or a capsid can be used as a biological template. Similar to a bacteriophage, a virus also comprises a protein coat and a nucleic acid core. In particular, viruses of anisotropic shapes, such as viral fibers, are suitable for nucleating and growing the catalytic nanowires described herein. Further, a virus can be genetically manipulated to express specific peptides on its coat for desirable binding to the ions. Viruses that have elongated or filamentous structures include those that are described in, for example, Christopher Ring, *Genetically Engineered Viruses*, (Ed) Bios Scientific (2001).

In certain embodiments, the virus may have its genetic materials removed and only the exterior protein coat (capsid) remains as the biological template.

2. Nucleation

Nucleation is the process of forming an inorganic nanowire in situ by converting soluble precursors (e.g., metal salts and anions) into nanocrystals in the presence of a template (e.g., a biological template). Typically, the nucleation and growth takes place from multiple binding sites along the length of the biological template in parallel. The growth continues until a structure encasing the biological template is formed. In some embodiments this structure is single-crystalline. In other embodiments the structure is amorphous, and in other embodiments the structure is polycrystalline. If desired, upon completion of the synthesis the organic biological template (e.g., bacteriophage) can be removed by thermal treatment (~300° C.) in air or oxygen, without significantly affecting either the structure or shape of the inorganic material. In addition, dopants can be either simultaneously incorporated during the growth process or, in another embodiment, dopants can be incorporated via impregnation techniques.

(a) Nanowire Growth Methods

Figure 7:
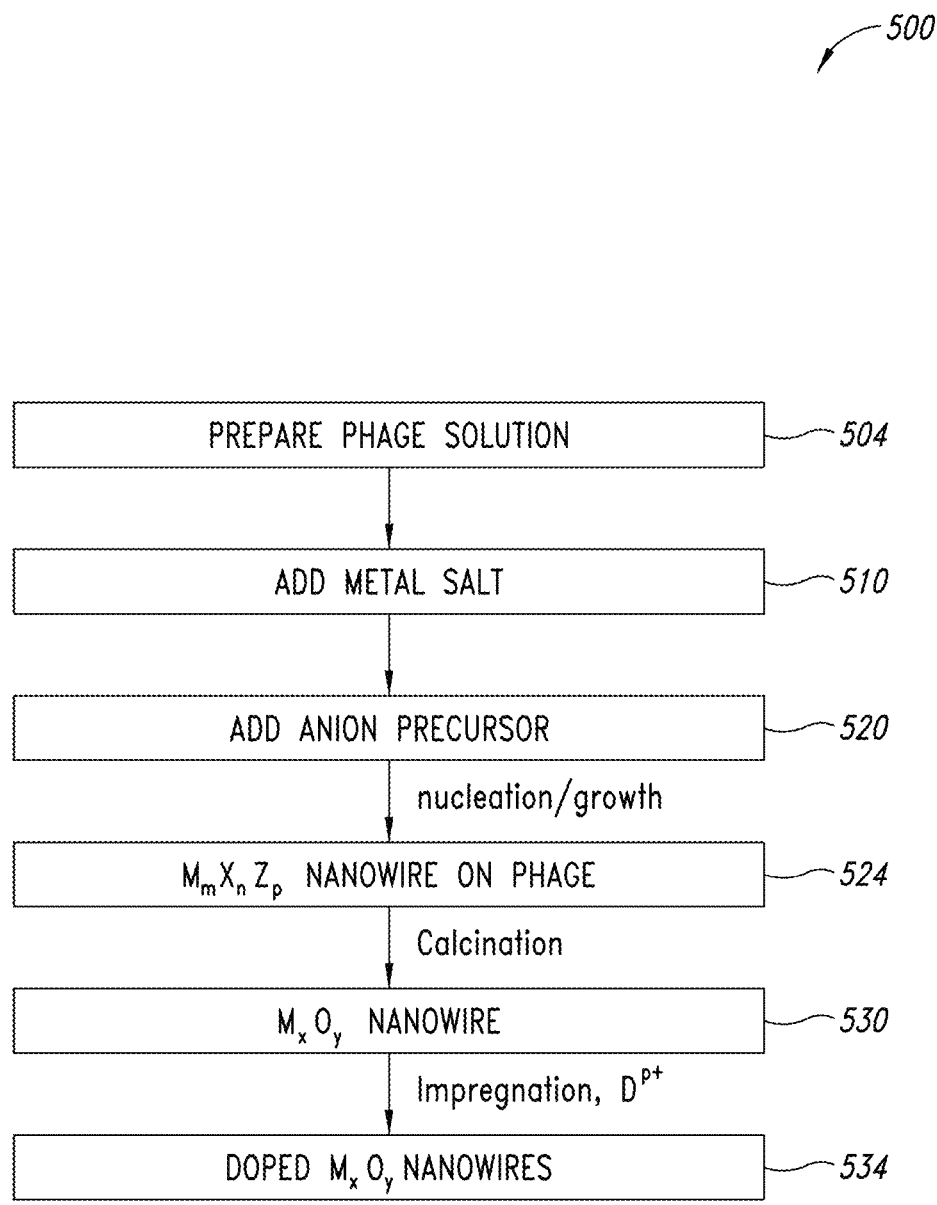
FIG. 7 is a flow chart of an exemplary nucleation process for forming a metal oxide nanowire.

FIG. 7 shows a flow chart of a nucleation process for forming a nanowire comprising a metal oxide. A phage solution is first prepared (block 504), to which metal salt precursor comprising metal ions is added (block 510). Thereafter, an anion precursor is added (block 520). It is noted that, in various embodiments, the additions of the metal ions and anion precursor can be simultaneous or sequentially in any order. Under appropriate conditions (e.g., pH, molar ratio of the phage and metal salt, molar ratio of the metal ions and anions, addition rate, etc.), the metal ions and anions become bound to the phage, nucleate and grow into a nanowire of $M_mX_nZ_p$ composition (block 524). Following calcinations, nanowires comprising $M_mX_n$ are transformed to nanowires comprising metal oxide ($M_xO_y$) (block 530). An optional step of doping (block 534) incorporates a dopant ($D^{p+}$) in the nanowires comprising metal oxide ($M_xO_y$, wherein x and y are each independently a number from 1 to 100. For ease of illustration, FIG. 7 depicts calcinations prior to doping; however, in certain embodiments doping may be performed prior to calcinations.

In one embodiment, a method for preparing inorganic catalytic polycrystalline nanowires is provided, the nanowires each having a ratio of effective length to actual length of less than one and an aspect ratio of greater than ten as measured by TEM in bright field mode at 5 keV, wherein the nanowires each comprise one or more elements selected from Groups 1 through 7, lanthanides, actinides or combinations thereof. The method comprises:

admixing (A) with a mixture comprising (B) and (C);
admixing (B) with a mixture comprising (A) and (C); or
admixing (C) with a mixture comprising (A) and (B) to obtain a mixture comprising (A), (B) and (C), wherein (A), (B), and (C) comprise, respectively:

(A) a biological template;

(B) one or more salts comprising one or more metal elements from any of Groups 1 through 7, lanthanides, actinides or combinations thereof; and (C) one or more anion precursors.

Another embodiment provides a method for preparing a nanowire comprising a metal oxide, a metal oxy-hydroxide, a metal oxycarbonate or a metal carbonate, the method comprising:

a) providing a solution comprising a plurality of biological templates;

(b) introducing at least one metal ion and at least one anion to the solution under conditions and for a time sufficient to allow for nucleation and growth of a nanowire comprising a plurality of metal salts ($M_mX_nZ_p$) on the template; and (c) converting the nanowire ($M_mX_nZ_p$) to a nanowire comprising a plurality of metal oxides ($M_xO_y$), metal oxy-hydroxides ($M_xO_yOH_z$), metal oxycarbonates ($M_xO_y(CO_3)_z$), metal carbonate ($M_x(CO_3)_y$) or combinations thereof wherein:

M is, at each occurrence, independently a metal element from any of Groups 1 through 7, lanthanides or actinides;

X is, at each occurrence, independently hydroxide, carbonate, bicarbonate, phosphate, hydrogenphosphate, dihydrogenphosphate, sulfate, nitrate or oxalate;

Z is O;

n, m, x and y are each independently a number from 1 to 100; and p is a number from 0 to 100.

In certain variations of the foregoing, two or more different metal ions may be used. This produces nanowires comprising a mixture of two or more metal oxides. Such nanowires may be advantageous in certain catalytic reactions. For example, in some embodiments the nanowire catalysts may comprise at least a first and second metal oxide wherein the first metal oxide has better OCM activity than the second metal oxide and the second metal oxide has better ODH activity than the first metal oxide. In certain embodiments of the above, Applicants have found that it may be advantageous to perform multiple sequential additions of the metal ion, This addition technique may be particularily applicable to embodiments wherein two or more different metal ions are employed to form a mixed nanowire (M1M2X$_x$Y$_y$, wherein M1 and M2 are different metal elements), which can be converted to M1M2O$_z$, for example by calcination. The slow addition may be performed over any period of time, for example from 1 day to 1 week. In this regard, use of a syringe pump or an automatic (e.g., robotic) liquid dispenser may be advantageous. Slow addition of the components help ensure that they will nucleate on the biological template instead of non-selectively precipitate.

In various embodiments, the biological templates are phages, as defined herein. In further embodiments, the metal ion is provided by adding one or more metal salt (as described herein) to the solution. In other embodiments, the anion is provided by adding one or more anion precursor to the solution. In various embodiments, the metal ion and the anion can be introduced to the solution simultaneously or sequentially in any order. In some embodiments, the nanowire ($M_mX_nZ_p$) is converted to a metal oxide nanowire by calcination, which is a thermal treatment that transforms or decomposes the $M_mX_nZ_p$ nanowire to a metal oxide. In yet another embodiment, the method further comprises doping the metal oxide nanowire with a dopant. Doping may be performed either before or after calcination. Converting the nanowire to a metal oxide (or oxy-hydroxide, oxy-carbonate, or carbonate, etc.) generally comprises calcining.

In a variation of the above method, mixed metal oxides can be prepared (as opposed to a mixture of metal oxides). Mixed metal oxides can be represented by the following formula $M1_wM2_xM3_yO_z$, wherein M1, M2 and M3 are each independently absent or a metal element, and w, x, y and z are integers such that the overall charge is balanced. Mixed metal oxides comprising more than three metals are also contemplated and can be prepared via an analogous method. Such mixed metal oxides find utility in a variety of the catalytic reactions disclosed herein. One exemplary mixed metal oxide is $Na_{10}MnW_5O_{17}$ (Example 18).

Thus, one embodiment provides a method for preparing a mixed metal oxide nanowire comprising a plurality of mixed metal oxides ($M1_wM2_xM3_yO_z$), the method comprising:

a) providing a solution comprising a plurality of biological templates;

(b) introducing metal salts comprising M1, M2 and M3 to the solution under conditions and for a time sufficient to allow for nucleation and growth of a nanowire comprising a plurality of the metal salts on the template; and (c) converting the nanowire to a mixed metal oxide nanowire comprising a plurality of mixed metal oxides ($M1_wM2_xM3_yO_z$), wherein:

M1, M2 and M3 are, at each occurrence, independently a metal element from any of Groups 1 through 7, lanthanides or actinides;

n, m, x and y are each independently a number from 1 to 100; and p is a number from 0 to 100.

In other embodiments, the present disclosure provides a method for preparing metal oxide nanowires which may not require a calcination step. Thus, in some embodiments the method for preparing metal oxide nanowires comprises:

(a) providing a solution that includes a plurality of biological templates; and (b) introducing a compound comprising a metal to the solution under conditions and for a time sufficient to allow for nucleation and growth of a nanowire ($M_mY_n$) on the template;

wherein:

M is a metal element from any of Groups 1 through 7, lanthanides or actinides;

Y is O;

n and m are each independently a number from 1 to 100.

In some specific embodiments of the foregoing method, M is an early transition metal, for example V, Nb, Ta, Ti, Zr, Hf, W, Mo or Cr. In other embodiments, the metal oxide is $WO_3$. In yet another embodiment, the method further comprises doping the metal oxide nanowire with a dopant. In some further embodiments, a reagent is added which converts the compound comprising a metal into a metal oxide.

In another embodiment, nanowires are prepared by using metal salts sensitive to water hydrolysis, for example $NbCl_5$, $WCl_6$, $TiCl_4$, $ZrCl_4$. A template can be placed in ethanol along with the metal salt. Water is then slowly added to the reaction in order to convert the metals salts to metal oxide coated template.

By varying the nucleation conditions, including (without limitation): incubation time of phage and metal salt; incubation time of phage and anion; concentration of phage; metal ion concentration, anion concentration, sequence of adding anion and metal ions; pH; phage sequences; solution temperature in the incubation step and/or growth step; types of metal precursor salt; types of anion precursor; addition rate; number of additions; amount of metal salt and/or anion precursor per addition, the time that lapses between the additions of the metal salt and anion precursor, including, e.g., simultaneous (zero lapse) or sequential additions followed by respective incubation times for the metal salt and the anion precursor, stable nanowires of diverse compositions and surface properties can be prepared. For example, in certain embodiments the pH of the nucleation conditions is at least 7.0, at least 8.0, at least 9.0, at least 10.0, at least 11.0, at least 12.0 or at least 13.0.

As noted above, the rate of addition of reactants (e.g., metal salt, metal oxide, anion precursor, etc.) is one parameter that can be controlled and varied to produce nanowires having different properties. During the addition of reactants to a solution containing an existing nanowire and/or a templating material (e.g., phage), a critical concentration is reached for which the speed of deposition of solids on the existing nanowire and/or templating material matches the rate of addition of reactants to the reaction mixture. At this point, the concentration of soluble cation stabilizes and stops rising. Thus, nanowire growth can be controlled and maximized by maintaining the speed of addition of reactants such that near super-saturation concentration of the cation is maintained. This helps ensure that no undesirable nucleation occurs. If super-saturation of the anion (e.g., hydroxide) is exceeded, a new solid phase can start nucleating which allows for non-selective solid precipitation, rather than nanowire growth. Thus, in order to selectively deposit an inorganic layer on an existing nanowire and/or a templating material, the addition rate of reactants should be controlled to avoid reaching super-saturation of the solution containing the suspended solids.

Accordingly, in one embodiment, reactant is repeatedly added in small doses to slowly build up the concentration of the reactant in the solution containing the template. In some embodiments, the speed of addition of reactant is such that the reactant concentration in the solution containing the template is near (but less than) the saturation point of the reactant. In some other embodiments, the reactant is added portion wise (i.e., step addition) rather than continuously. In these embodiments, the amount of reactant in each portion, and the time between addition of each portion, is controlled such that the reactant concentration in the solution containing the template is near (but less than) the saturation point of the reactant. In certain embodiments of the foregoing, the reactant is a metal cation while in other embodiments the reactant is an anion.

Initial formation of nuclei on a template can be obtained by the same method described above, wherein the concentration of reactant is increased until near, but not above, the supersaturation point of the reactant. Such an addition method facilitates nucleation of the solid phase on the template, rather than homogeneous non-seeding nucleation. In some embodiments, it is desirable to use a slower reactant addition speed during the initial nucleation phase as the super-saturation depression due to the template might be quite small at this point. Once the first layer of solid (i.e., nanowire) is formed on the template, the addition speed can be increased.

In some embodiments, the addition rate of reactant is controlled such that the precipitation rate matches the addition rate of the reactant. In these embodiments, nanowires comprising two or more different metals can be prepared by controlling the addition rates of two or more different metal cation solutions such that the concentration of each cation in the templating solution is maintained at or near (but does not exceed) the saturation point for each cation.

In some embodiments, the optimal speed of addition (and step size if using step additions) is controlled as a function of temperature. For example, in some embodiments the nanowire growth rate is accelerated at higher temperatures.

Thus, the addition rate of reactants is adjusted according to the temperature of the templating solution.

In other embodiments, modeling (iterative numeric rather than algebraic) of the nanowire growth process is used to determine optimal solution concentrations and supernatant re-cycling strategies.

As noted above, the addition rate of reactants can be controlled and modified to change the properties of the nanowires. In some embodiments, the addition rate of a hydroxide source must be controlled such that the pH of the templating solution is maintained at the desired level. This method may require specialized equipment, and depending on the addition rate, the potential for localized spikes in pH upon addition of the hydroxide source is possible. Thus, in an alternative embodiment the present disclosure provides a method wherein the template solution comprises a weak base that slowly generates hydroxide in-situ, obviating the need for an automated addition sequence.

In the above embodiment, organic epoxides, such as but not limited to propylene oxide and epichlorohydrin, are used to slowly increase the template solution pH without the need for automated pH control. The epoxides are proton scavengers and undergo an irreversible ring-opening reaction with a nucleophilic anion of the metal oxide precursor (such as but not limited to $Cl^-$ or $NO_3^-$). The net effect is a slow homogenous raise in pH to form metal hydroxy species in solution that deposit onto the template surface. In some embodiments, the organic epoxide is propylene oxide.

An attractive feature of this method is that the organic epoxide can be added all at once, there is no requirement for subsequent additions of organic epoxide to grow metal oxide coatings over the course of the reaction. Due to the flexibility of the "epoxide-assisted" coatings, it is anticipated that many various embodiments can be employed to make new templated materials (e.g., nanowires). For example, mixed metal oxide nanowires can be prepared by starting with appropriate ratios of metal oxide precursors and propylene oxide in the presence of bacteriophage. In other embodiments, metal oxide deposition on bacteriophage can be done sequentially to prepare core/shell materials (described in more detail below).

(b) Metal Salt

As noted above, the nanowires are prepared by nucleation of metal ions in the presence of an appropriate template, for example, a bacteriophage. In this respect, any soluble metal salt may be used as the precursor of metal ions that nucleate on the template. Soluble metal salts of the metals from Groups 1 through 7, lanthanides and actinides are particularly useful and all such salts are contemplated.

In one embodiment, the soluble metal salt comprises chlorides, bromides, iodides, nitrates, sulfates, acetates, oxides, oxyhalides, oxynitrates, phosphates (including hydrogenphosphate and dihydrogenphosphate) formates, alkoxides or oxalates of metal elements from Groups 1 through 7, lanthanides, actinides or combinations thereof. In more specific embodiments, the soluble metal salt comprises chlorides, nitrates or sulfates of metal elements from Groups 1 through 7, lanthanides, actinides or combinations thereof. The present disclosure contemplates all possible chloride, bromide, iodide, nitrate, sulfate, acetate, oxide, oxyhalides, oxynitrates, phosphates (including hydrogenphosphate and dihydrogenphosphate) formates, alkoxides and oxalate salts of metal elements from Groups 1 through 7, lanthanides, actinides or combinations thereof.

In another embodiment, the metal salt comprises LiCl, LiBr, LiI, $LiNO_3$, $Li_2SO_4$, $LiCO_2CH_3$, $Li_2C_2O_4$, $Li_3PO_4$, $Li_2HPO_4$, $LiH_2PO_4$, $LiCO_2H$, LiOR, NaCl, NaBr, NaI, $NaNO_3$, $Na_2SO_4$, $NaCO_2CH_3$, $Na_2C_2O_4$, $Na_3PO_4$, $Na_2HPO_4$, $NaH_2PO_4$, $NaCO_2H$, NaOR, KCl, KBr, KI, $KNO_3$, $K_2SO_4$, $KCO_2CH_3$, $K_2C_2O_4$, $K_3PO4$, $K_2HPO_4$, $KH_2PO_4$, $KCO_2H$, KOR, RbCl, RbBr, RbI, $RbNO_3$, $Rb_2SO_4$, $RbCO_2CH_3$, $Rb_2C_2O_4$, $Rb_3PO_4$, $Rb_2HPO_4$, $RbH_2PO_4$, $RbCO_2H$, RbOR, CsCl, CsBr, CsI, $CsNO_3$, $Cs_2SO_4$, $CsCO_2CH_3$, $Cs_2C_2O_4$, $Cs_3PO_4$, $Cs_2HPO_4$, $CsH_2PO_4$, $CsCO_2H$, CsOR, $BeCl_2$, $BeBr_2$, $BeI_2$, $Be(NO_3)_2$, $BeSO_4$, $Be(CO_2CH_3)_2$, $BeC_2O_4$, $Be_3(PO4)_2$, $BeHPO_4$, $Be(H_2PO_4)_2$, $Be(CO_2H)_2$, $Be(OR)_2$, $MgCl_2$, $MgBr_2$, $MgI_2$, $Mg(NO_3)_2$, $MgSO_4$, $Mg(CO_2CH_3)_2$, $MgC_2O_4$, $Mg_3(PO_4)_2$, $MgHPO_4$, $Mg(H_2PO_4)_2$, $Mg(CO_2H)_2$, $Mg(OR)_2$, $CaCl_2$, $CaBr_2$, $CaI_2$, $Ca(NO_3)_2$, $CaSO_4$, $Ca(CO_2CH_3)_2$, $CaC_2O_4$, $Mg_3(PO_4)_2$, $MgHPO_4$, $Mg(H_2PO_4)_2$, $Mg(CO_2H)_2$, $Mg(OR)_2$, $SrCl_2$, $SrBr_2$, $SrI_2$, $Sr(NO_3)_2$, $SrSO_4$, $Sr(CO_2CH_3)_2$, $SrC_2O_4$, $Sr_3(PO_4)_2$, $SrHPO_4$, $Sr(H_2PO_4)_2$, $Sr(CO_2H)_2$, $Sr(OR)_2$, $BaCl_2$, $BaBr_2$, $BaI_2$, $Ba(NO_3)_2$, $BaSO_4$, $Ba(CO_2CH_3)_2$, $BaC_2O_4$, $Ba_3(PO_4)_2$, $BaHPO_4$, $Ba(H_2PO_4)_2$, $Ba(CO_2H)_2$, $Ba(OR)_2$, $ScCl_3$, $ScBr_3$, $ScI_3$, $Sc(NO_3)_3$, $Sc_2(SO_4)_3$, $Sc(CO_2CH_3)_3$, $Sc_2(C_2O_4)_3$, $ScPO_4$, $Sc_2(HPO_4)_3$, $Sc(H_2PO_4)_3$, $SC(CO_2H)_3$, $SC(OR)_3$, $YCl_3$, $YBr_3$, $YI_3$, $Y(NO_3)_3$, $Y_2(SO_4)_3$, $Y(CO_2CH_3)_3$, $Y_2(C_2O_4)_3$, $YPO_4$, $Y_2(HPO_4)_3$, $Y(H_2PO_4)_3$, $Y(CO_2H)_3$, $Y(OR)_3$, $TiCl_4$, $TiBr_4$, $TiI_4$, $Ti(NO_3)_4$, $Ti(SO_4)_2$, $Ti(CO_2CH_3)_4$, $Ti(C_2O_4)_2$, $Ti_3(PO_4)_4$, $Ti(HPO_4)_2$, $Ti(H_2PO_4)_4$, $Ti(CO_2H)_4$, $Ti(OR)_4$, $ZrCl_4$, $ZrOCl_2$, $ZrBr_4$, $ZrI_4$, $Zr(NO_3)_4$, $ZrO(NO_3)_2$, $Zr(SO_4)_2$, $Zr(CO_2CH_3)_4$, $Zr(C_2O_4)_2$, $Zr_3(PO_4)_4$, $Zr(HPO_4)_2$, $Zr(H_2PO_4)_4$, $Zr(CO_2H)_4$, $Zr(OR)_4$, $HfCl_4$, $HfBr_4$, $HfI_4$, $Hf(NO_3)_4$, $Hf(SO_4)_2$, $Hf(CO_2CH_3)_4$, $Hf(C_2O_4)_2$, $Hf_3(PO_4)_4$, $Hf(HPO_4)_2$, $Hf(H_2PO_4)_4$, $Hf(CO_2H)_4$, $Hf(OR)_4$, $LaCl_3$, $LaBr_3$, $LaI_3$, $La(NO_3)_3$, $La_2(SO_4)_3$, $La(CO_2CH_3)_3$, $La_2(C_2O_4)_3$, $LaPO_4$, $La_2(HPO_4)_3$, $La(H_2PO_4)_3$, $La(CO_2H)_3$, $La(OR)_3$, $WCl_2$, $WCl_3$, $WCl_4$, $WCl_5$, $WCl_6$, $WBr_2$, $WBr_3$, $WBr_4$, $WBr_5$, $WBr_6$, $WI_2$, $WI_3$, $WI_4$, $WI_5$, $WI_6$, $W(NO_3)_2$, $W(NO_3)_3$, $W(NO_3)_4$, $W(NO_3)_5$, $W(NO_3)_6$, $W(CO_2CH_3)_2$, $W(CO_2CH_3)_3$, $W(CO_2CH_3)_4$, $W(CO_2CH_3)_5$, $W(CO_2CH_3)_6$, $WC_2O_4$, $W_2(C_2O_4)_3$, $W(C_2O_4)_2$, $W_2(C_2O_4)_5$, $W(C_2O_4)_6$, $WPO_4$, $W_2(HPO_4)_3$, $W(H_2PO_4)_3$, $W(CO_2H)_3$, $W(OR)_3$, $W_3(PO_4)_4$, $W(HPO_4)_2$, $W(H_2PO_4)_4$, $W(CO_2H)_4$, $W(OR)_4$, $W_3(PO_4)_5$, $W_2(HPO_4)_5$, $W(H_2PO_4)_5$, $W(CO_2H)_5$, $W(OR)_5$, $W(PO_4)_2$, $W(H_3PO_4)_3$, $W(H_2PO_4)_6$, $W(CO_2H)_6$, $W(OR)_6$, $MnCl_2$, $MnCl_3$, $MnBr_2$, $MnBr_3$, $MnI_2$, $MnI_3$, $Mn(NO_3)_2$, $Mn(NO_3)_3$, $MnSO_4$, $Mn_2(SO_4)_3$, $Mn(CO_2CH_3)_2$, $Mn(CO_2CH_3)_3$, $MnC_2O_4$, $Mn_2(C_2O_4)_3$, $Mn_3(PO_4)_2$, $MnHPO_4$, $Mn(H_2PO_4)_2$, $Mn(CO_2H)_2$, $Mn(OR)_2$, $MnPO_4$, $Mn_2(HPO_4)_3$, $Mn(H_2PO_4)_3$, $Mn(CO_2H)_3$, $Mn(OR)_3$, $MoCl_2$, $MoCl_3$, $MoCl_4$, $MoCl_5$, $MoBr_2$, $MoBr_3$, $MoBr_4$, $MoBr_5$, $MoI_2$, $MoI_3$, $MoI_4$, $MoI_5$, $Mo(NO_3)_2$, $Mo(NO_3)_3$, $Mo(NO_3)_4$, $Mo(NO_3)_5$, $MoSO_4$, $Mo_2(SO_4)_3$, $Mo(SO_4)_2$, $Mo_2(SO_4)_5$, $Mo(CO_2CH_3)_2$, $Mo(CO_2CH_3)_3$, $Mo(CO_2CH_3)_4$, $Mo(CO_2CH_3)_5$, $MoC_2O_4$, $Mo_2(C_2O_4)_3$, $Mo(C_2O_4)_2$, $MO_2(C_2O_4)_5$, $Mo_3(PO_4)_2$, $MoHPO_4$, $Mo(H_2PO_4)_2$, $Mo(CO_2H)_2$, $Mo(OR)_2$, $MoPO_4$, $Mo_2(HPO_4)_3$, $Mo(H_2PO_4)_3$, $Mo(CO_2H)_3$, $Mo(OR)_3$, $Mo_3(PO_4)_4$, $Mo(HPO_4)_2$, $Mo(H_2PO_4)_4$, $Mo(CO_2H)_4$, $Mo(OR)_4$, $Mo_3(PO_4)_5$, $Mo_2(HPO_4)_5$, $Mo(H_2PO_4)_5$, $Mo(CO_2H)_5$, $Mo(OR)_5$, VCl, $VCl_2$, $VCl_3$, $VCl_4$, $VCl_5$ VBr, $VBr_2$, $VBr_3$, $VBr_4$, $VBr_5$, $VI_3$ $VI_2$, $VI_3$, $VI_4$, $VI_5$, $VNO_3$, $V(NO_3)_2$, $V(NO_3)_3$, $V(NO_3)_4$, $V(NO_3)_5$, $V_2SO_4$, $VSO_4$, $V_2(SO_4)_3$, $V(SO_4)_4$, $VCO_2CH_3$, $V(CO_2CH_3)_2$, $V(CO_2CH_3)_3$, $V(CO_2CH_3)_4$, $V_2C_2O_4$, $VC_2O_4$, $V_2(C_2O_4)_3$, $V(C_2O_4)_4$, $V_3PO_4$, $V_2HPO_{43}$ $VH_2PO_4$, $VCO_2H$, VOR, $V_3(PO_4)_2$, $VHPO_4$, $V(H_2PO_4)_2$, $V(CO_2H)_2$, $V(OR)_2$, $VPO_4$, $V_2(HPO_4)_3$, $V(H_2PO_4)_3$, $V(CO_2H)_3$, $V(OR)_3$, $V_3(PO_4)_4$, $V(HPO_4)_2$, $V(H_2PO_4)_4$, $V(CO_2H)_4$, $V(OR)_4$, $V_3(PO_4)_5$, $V_2(HPO_4)_5$, $V(H_2PO_4)_5$, $V(CO_2H)_5$, $V(OR)_5$, TaCl, $TaCl_2$, $TaCl_3$, $TaCl_4$, $TaCl_5$, TaBr, $TaBr_2$, $TaBr_3$, $TaBr_4$, $TaBr_5$, TaI, $TaI_2$, $TaI_3$, $TaI_4$, $TaI_5$, $TaNO_3$, $Ta(NO_3)_2$, $Ta(NO_3)_3$, $Ta(NO_3)_4$, $Ta(NO_3)_5$, $Ta_2SO_4$, $TaSO_4$, $Ta_2(SO_4)_3$, $Ta(SO_4)_4$, $TaCO_2CH_3$, $Ta(CO_2CH_3)_2$, $Ta(CO_2CH_3)_3$, $Ta(CO_2CH_3)_4$, $Ta_2C_2O_4$, $TaC_2O_4$, $Ta_2(C_2O_4)_3$, $Ta(C_2O_4)_4$, $Ta_3PO_4$, $Ta_2HPO_4$, $TaH_2PO_4$, $TaCO_2H$, $TaOR$, $Ta_3(PO_4)_2$, $TaHPO_4$, $Ta(H_2PO_4)_2$, $Ta(CO_2H)_2$, $Ta(OR)_2$, $TaPO_4$, $Ta_2(HPO_4)_3$, $Ta(H_2PO_4)_3$, $Ta(CO_2H)_3$, $Ta(OR)_3$, $Ta_3(PO_4)_4$, $Ta(HPO_4)_2$, $Ta(H_2PO_4)_4$, $Ta(CO_2H)_4$, $Ta(OR)_4$, $Ta_3(PO_4)_5$, $Ta_2(HPO_4)_5$, $Ta(H_2PO_4)_5$, $Ta(CO_2H)_5$, $Ta(OR)_5$, $NbCl$, $NbCl_2$, $NbCl_3$, $NbCl_4$, $NbCl_5$, $NbBr$, $NbBr_2$, $NbBr_3$, $NbBr_4$, $NbBr_5$, $NbI$, $NbI_2$, $NbI_3$, $NbI_4$, $NbI_5$, $NbNO_3$, $Nb(NO_3)_2$, $Nb(NO_3)_3$, $Nb(NO_3)_4$, $Nb(NO_3)_5$, $Nb_2SO_4$, $NbSO_4$, $Nb_2(SO_4)_3$, $Nb(SO_4)_4$, $NbCO_2CH_3$, $Nb(CO_2CH_3)_2$, $Nb(CO_2CH_3)_3$, $Nb(CO_2CH_3)_4$, $Nb_2C_2O_4$, $NbC_2O_4$, $Nb_2(C_2O_4)_3$, $Nb(C_2O_4)_4$, $Nb_3PO_4$, $Nb_2HPO_4$, $NbH_2PO_4$, $NbCO_2H$, $NbOR$, $Nb_3(PO_4)_2$, $NbHPO_4$, $Nb(H_2PO_4)_2$, $Nb(CO_2H)_2$, $Nb(OR)_2$, $NbPO_4$, $Nb_2(HPO_4)_3$, $Nb(H_2PO_4)_3$, $Nb(CO_2H)_3$, $Nb(OR)_3$, $Nb_3(PO_4)_4$, $Nb(HPO_4)_2$, $Nb(H_2PO_4)_4$, $Nb(CO_2H)_4$, $Nb(OR)_4$, $Nb_3(PO_4)_5$, $Nb_2(HPO_4)_5$, $Nb(H_2PO_4)_5$, $Nb(CO_2H)_5$, $Nb(OR)_5$, $NdCl_3$, $NdBr_3$, $NdI_3$, $Nd(NO_3)_3$, $Nd_2(SO_4)_3$, $Nd(CO_2CH_3)_3$, $Nd_2(C_2O_4)_3$, $NdPO_4$, $Nd_2(HPO_4)_3$, $Nd(H_2PO_4)_3$, $Nd(CO_2H)_3$, $Nd(OR)_3$, $EuCl_3$, $EuBr_3$, $EuI_3$, $Eu(NO_3)_3$, $Eu_2(SO_4)_3$, $Eu(CO_2CH_3)_3$, $Eu_2(C_2O_4)_3$, $NdPO_4$, $Nd_2(HPO_4)_3$, $Nd(H_2PO_4)_3$, $Nd(CO_2H)_3$, $Nd(OR)_3$, $PrCl_3$, $PrBr_3$, $PrI_3$, $Pr(NO_3)_3$, $Pr_2(SO_4)_3$, $Pr(CO_2CH_3)_3$, $Pr_2(C_2O_4)_3$, $PrPO_4$, $Pr_2(HPO_4)_3$, $Pr(H_2PO_4)_3$, $Pr(CO_2H)_3$, $Pr(OR)_3$, $SmCl_3$, $SmBr_3$, $SmI_3$, $Sm(NO_3)_3$, $Sm_2(SO_4)_3$, $Sm(CO_2CH_3)_3$, $Sm_2(C_2O_4)_3$, $SmPO_4$, $Sm_2(HPO_4)_3$, $Sm(H_2PO_4)_3$, $Sm(CO_2H)_3$, $Sm(OR)_3$, $CeCl_3$, $CeBr_3$, $CeI_3$, $Ce(NO_3)_3$, $Ce_2(SO_4)_3$, $Ce(CO_2CH_3)_3$, $Ce_2(C_2O_4)_3$, $CePO_4$, $Ce_2(HPO_4)_3$, $Ce(H_2PO_4)_3$, $Ce(CO_2H)_3$, $Ce(OR)_3$, or combinations thereof, wherein R is alkyl, alkenyl, alkynyl or aryl.

In more specific embodiments, the metal salt comprises $MgCl_2$, $LaCl_3$, $ZrCl_4$, $WCl_4$, $MoCl_4$, $MnCl_2$ $MnCl_3$, $Mg(NO_3)_2$, $La(NO_3)_3$, $ZrOCl_2$, $Mn(NO_3)_2$, $Mn(NO_3)_3$, $ZrO(NO_3)_2$, $Zr(NO_3)_4$, or combinations thereof.

In other embodiments, the metal salt comprises $NdCl_3$, $NdBr_3$, $NdI_3$, $Nd(NO_3)_3$, $Nd_2(SO_4)_3$, $Nd(CO_2CH_3)_3$, $Nd_2(C_2O_4)_3$, $EuCl_3$, $EuBr_3$, $EuI_3$, $Eu(NO_3)_3$, $Eu_2(SO_4)_3$, $Eu(CO_2CH_3)_3$, $Eu_2(C_2O_4)_3$, $PrCl_3$, $PrBr_3$, $PrI_3$, $Pr(NO_3)_3$, $Pr_2(SO_4)_3$, $Pr(CO_2CH_3)_3$, $Pr_2(C_2O_4)_3$ or combinations thereof.

In still other embodiments, the metal salt comprises Mg, Ca, Mg, W, La, Nd, Sm, Eu, W, Mn, Zr or mixtures thereof. The salt may be in the form of (oxy)chlorides, (oxy)nitrates or tungstates.

(c) Anion Precursor

The anions, or counter ions of the metal ions that nucleate on the template, are provided in the form of an anion precursor. The anion precursor dissociates in the solution phase and releases an anion. Thus, the anion precursor can be any stable soluble salts having the desired anion. For instance, bases such as alkali metal hydroxides (e.g., sodium hydroxide, lithium hydroxide, potassium hydroxides) and ammonium hydroxide are anion precursors that provide hydroxide ions for nucleation. Alkali metal carbonates (e.g., sodium carbonate, potassium carbonates) and ammonium carbonate are anion precursors that provide carbonates ions for nucleation.

In certain embodiments, the anion precursor comprises one or more metal hydroxide, metal carbonate, metal bicarbonate, metal sulfate, metal phosphate or metal oxalate. Preferably, the metal is an alkali or an alkaline earth metal. Thus, the anion precursor may comprise any one of alkali metal hydroxides, carbonates, bicarbonates, sulfates, phosphates or oxalate; or any one of alkaline earth metal hydroxides, carbonates, bicarbonates, sulfates, phosphates or oxalates.

In some specific embodiments, the one or more anion precursors comprise LiOH, NaOH, KOH, $Sr(OH)_2$, $Ba(OH)_2$, $Na_2CO_3$, $K_2CO_3$, $NaHCO_3$, $KHCO_3$ $(NR_4)_2CO_3$, and $NR_4OH$, wherein each R is independently selected from H, $C_1$-$C_{18}$ alkyl, $C_1$-$C_{18}$ alkenyl, $C_1$-$C_{18}$ alkynyl and $C_1$-$C_{18}$ aryl. Ammonium salts may provide certain advantages in that there is less possibility of introducing unwanted metal impurities. Accordingly, in a further embodiment, the anion precursor comprises ammonium hydroxide or ammonium carbonate.

The dimensions of the nanowires are comparable to those of the biological templates (e.g., phage), although they can have different aspect ratios as longer growth can be used to increase the diameter while the length will increase in size at a much slower rate. The spacing of peptides on the phage surface controls the nucleation location and the catalytic nanowire size based on steric hindrance. The specific peptide sequence information can (or may) dictate the identity, size, shape and crystalline face of the catalytic nanowire being nucleated. To achieve the desired stochiometry between metal elements, support and dopants, multiple peptides specific for these discrete materials can be co-expressed within the same phage. Alternatively, precursor salts for the materials can be combined in the reaction at the desired stochiometry. The techniques for phage propagation and purification are also well established, robust and scalable. Multi-kilogram amounts of phage can be easily produced, thus assuring straightforward scale up to large, industrial quantities.

3. Core/Shell Structures

Figure 8:
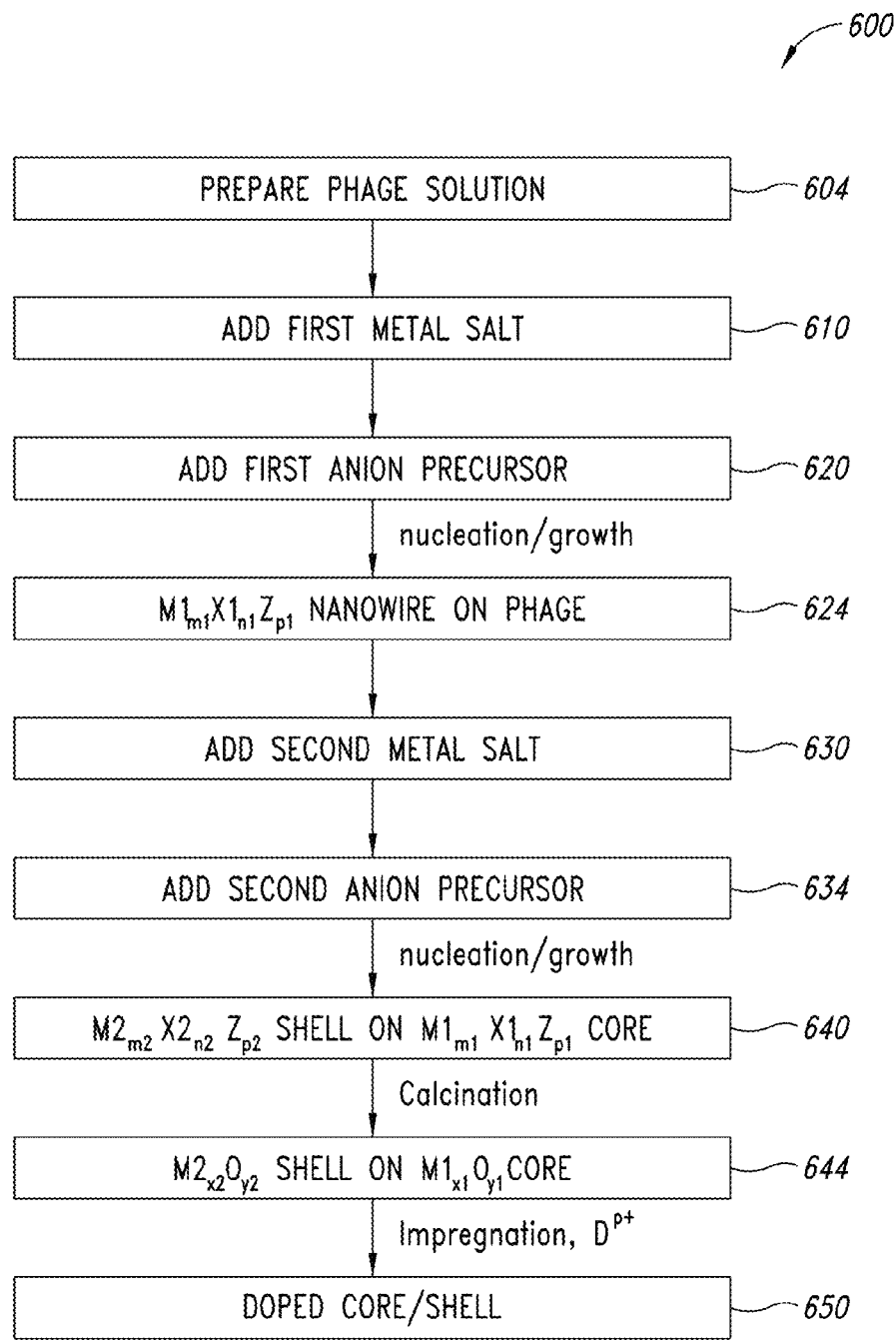
FIG. 8 is a flow chart of an exemplary sequential nucleation process for forming a nanowire in a core/shell configuration.

In certain embodiments, nanowires can be grown on a support nanowire that has no or a different catalytic property. FIG. 8 shows an exemplary process 600 for growing a core/shell structure. Similar to FIG. 7, a phage solution is prepared (block 604), to which a first metal salt and a first anion precursor are sequentially added (blocks 610 and 620) in appropriate conditions to allow for the nucleation and growth of a nanowire ($M1_{m1}X1_{n1}Z_{p1}$) on the phage (block 624). Thereafter, a second metal salt and a second anion precursor are sequentially added (blocks 630 and 634), under conditions to cause the nucleation and growth of a coating of $M2_{m2}X2_{n2}Z_{p2}$ on the nanowire $M1_{m1}X1_{n1}Z_{p1}$ (block 640). Following calcinations, nanowires of a core/shell structure $M1_{x1}O_{y1}/M2_{x2}O_{y2}$ are formed, wherein x1, y1, x2 and y2 are each independently a number from 1 to 100, and p1 and p2 are each independently a number from 0 to 100 (block 644). A further step of impregnation (block 650) produces a nanowire comprising a dopant and comprising a core of $M1_{x1}O_{y1}$ coated with a shell of $M2_{x2}O_{y2}$. For ease of illustration, FIG. 8 depicts calcinations prior to doping; however, in certain embodiments doping may be performed prior to calcinations. In some embodiments, M1 is Mg, Al, Ga, Ca or Zr. In certain embodiments of the foregoing, M1 is Mn and M2 is Mg. In other embodiments, M1 is Mg and M2 is Mn. In other embodiments, M1 is La and M2 is Mg, Ca, Sr, Ba, Zr, Nd, Y, Yb, Eu, Sm or Ce. In other embodiments, M1 is Mg and M2 is La or Nd.

In other embodiments, $M1_{x1}O_{y1}$ comprises $La_2O_3$ while in other embodiments $M2_{x2}O_{y2}$ comprises $La_2O_3$. In other embodiments of the foregoing, $M1_{x1}O_{y1}$ or $M2_{x2}O_{y2}$ further comprises a dopant, wherein the dopant comprises Nd, Mn, Fe, Zr, Sr, Ba, Y or combinations thereof. Other specific combinations of core/shell nanowires are also envisioned within the scope of the present disclosure.

Thus, one embodiment provides a method for preparing metal oxide, metal oxy-hydroxide, metal oxycarbonate or metal carbonate nanowires in a core/shell structure, the method comprising:

(a) providing a solution that includes a plurality of biological templates;

(b) introducing a first metal ion and a first anion to the solution under conditions and for a time sufficient to allow for nucleation and growth of a first nanowire $(M1_{m1}X1_{n1}Z_{p1})$ on the template;

(c) introducing a second metal ion and optionally a second anion to the solution under conditions and for a time sufficient to allow for nucleation and growth of a second nanowire $(M2_{m2}X2_{n2}Z_{p2})$ on the first nanowire $(M1_{m1}X1_{n1}Z_{p1})$; and (d) converting the first nanowire $(M1_{m1}X1_{n1}Z_{p1})$ and the second nanowire $(M2_{m2}X2_{n2}Z_{p2})$ to the respective metal oxide nanowires $(M1_{x1}O_{y1})$ and $(M2_{x2}O_{y2})$, the respective metal oxy-hydroxide nanowires $(M1_{x1}O_{y1}H_{z1})$ and $(M2_{x2}O_{y2}OH_{z2})$ the respective metal oxycarbonate nanowires $(M1_{x1}O_{y1}(CO_3)_{z1})$ and $(M2_{x2}O_{y2}(CO_3)_{z2})$ or the respective metal carbonate nanowires $(M1_{x1}(CO_3)_{y1})$ and $(M2_{x2}(CO_3)_{y2})$, wherein:

M1 and M2 are the same or different and independently selected from a metal element;

X1 and X2 are the same or different and independently hydroxide, carbonate, bicarbonate, phosphate, hydrogenphosphate, dihydrogenphosphate, sulfate, nitrate or oxalate;

Z is O;

n1, m1, n2, m2, x1, y1, z1, x2, y2 and z2 are each independently a number from 1 to 100; and p1 and p2 are independently a number from 0 to 100.

In some embodiments, M1 and M2 are the same or different and independently selected from a metal element from any of Groups 2 through 7, lanthanides or actinides In various embodiments, the biological templates are phages, as defined herein. In further embodiments, the respective metal ion is provided by adding one or more respective metal salts (as described herein) to the solution. In other embodiments, the respective anions are provided by adding one or more respective anion precursors to the solution. In various embodiments, the first metal ion and the first anion can be introduced to the solution simultaneously or sequentially in any order. Similarly, the second metal ion and optionally the second anion can be introduced to the solution simultaneously or sequentially in any order. The first and second nanowire are typically converted to a metal oxide, metal oxy-hydroxide, metal oxycarbonate or metal carbonate nanowire in a core/shell structure by calcination.

In yet another embodiment, the method further comprises doping the metal oxide nanowire in a core/shell structure with a dopant.

By varying the nucleation conditions, including the pH of the solution, relative ratio of metal salt precursors and the anion precursors, relative ratios of the precursors and the phage of the synthetic mixture, stable nanowires of diverse compositions and surface properties can be prepared.

In certain embodiments, the core nanowire (the first nanowire) is not catalytically active or less so than the shell nanowire (the second nanowire), and the core nanowire serve as an intrinsic catalytic support for the more active shell nanowire. For example, $ZrO_2$ may not have high catalytic activity in an OCM reaction, whereas $Sr^{2+}$ doped $La_2O_3$ does. A $ZrO_2$ core thus may serve as a support for the catalytic $Sr^{2+}$ doped $La_2O_3$ shell.

In some embodiments, the present disclosure provides a nanowire comprising a core/shell structure and comprising a ratio of effective length to actual length of less than one. In other embodiments, the nanowires having a core/shell structure comprise a ratio of effective length to actual length equal to one.

Nanowires in a core/shell arrangement may be prepared in the absence of a biological template. For example, a nanowire comprising a first metal may be prepared according to any of the non-template directed methods described herein. A second metal may then be nucleated or plated onto the nanowire to form a core/shell nanowire. The first and second metals may be the same or different. Other methods for preparing core/shell nanowires in the absence of a biological template are also envisaged.

4. Diversity

As noted above, in some embodiments, the disclosed template-directed synthesis provides nanowires having diverse compositions and/or morphologies. This method combines two extremely powerful approaches, evolutionary selection and inorganic synthesis, to produce a library of nanowire catalysts with a new level of control over materials composition, materials surface and crystal structure. These nanowires prepared by biologically-templated methods take advantage of genetic engineering techniques to enable combinatorial synthesis of robust, active and selective inorganic catalytic polycrystalline nanowires. With selection, evolution and a combinatorial library with over a hundred billion sequence possibilities, nanowires having high specificity and product conversion yields in catalytic reactions are generated. This permits simultaneous optimization the nanowires' catalytic properties in a high-dimensional space.

In various embodiments, the synthetic parameters for nucleating and growing nanowires can be manipulated to create nanowires of diverse compositions and morphologies. Typical synthetic parameters include, without limitation, concentration ratios of metal ions and active functional groups on the phage; concentration ratios of metal and anions (e.g., hydroxide); incubation time of phage and metal salt; incubation time of phage and anion; concentration of phage; sequence of adding anion and metal ions; pH; phage sequences; solution temperature in the incubation step and/or growth step; types of metal precursor salt; types of anion precursor; addition rate, number of additions; the time that lapses between the additions of the metal salt and anion precursor, including, e.g., simultaneous (zero lapse) or sequential additions followed by respective incubation times for the metal salt and the anion precursor.

Additional variable synthetic parameters include, growth time once both metal and anion are present in the solution; choice of solvents (although water is typically used, certain amounts of alcohol, such as methanol, ethanol and propanol, can be mixed with water); choice of, or the number of, metal salts used (e.g., both $LaCl_3$ and $La(NO_3)_3$ can be used to provide $La^{3+}$ ions); choice of, or the number of, anion precursors used (e.g., both NaOH then LiOH can be used to provide the hydroxide); choice of, or the number of, different phage sequences used; the presence or absence of a buffer solution; the different stages of the growing step (e.g., nanowires may be precipitated and cleaned and resuspended in a second solution and perform a second growth of the same material (thicker core) or different material to form a core/shell structure.

Thus, libraries of nanowires can be generated with diverse physical properties and characteristics such as: composition, e.g., basic metal oxides ($M_xO_y$), size, shape, surface morphology, exposed crystal faces/edge density, crystallinity, dispersion, and stoichiometry and nanowire template physical characteristics including length, width, porosity and pore density. High throughput, combinatorial screening methods are then applied to evaluate the catalytic performance characteristics of the nanowires (see, e.g., FIG. 2). Based on these results, lead target candidates are identified. From these lead targets, further rational modifications to the synthetic designs can be made to create nanowires that satisfy certain catalytic performance criteria. This results in further refinement of the nanowire design and material structure.

Direct Synthesis of Nanowires

In some embodiments, the nanowires can be synthesized in a solution phase in the absence of a template. Typically, a hydrothermal or sol gel approach can be used to create straight (i.e., ratio of effective length to actual length equal to one) and substantially single crystalline nanowires. As an example, nanowires comprising a metal oxide can be prepared by (1) forming nanowires of a metal oxide precursor (e.g., metal hydroxide) in a solution of a metal salt and an anion precursor; (2) isolating the nanowires of the metal oxide precursor; and (3) calcining the nanowires of the metal oxide precursor to provide nanowires of a corresponding metal oxide. In other embodiments (for example MgO nanowires), the synthesis goes through an intermediate which can be prepared as a nanowire and then converted into the desired product while maintaining its morphology. Optionally, the nanowires comprising a metal oxide can be doped according to methods described herein. Dopant may be incorporated either before or after an optional calcination step.

In other certain embodiment, nanowires comprising a core/shell structure are prepared in the absence of a biological template. Such methods may include, for example, preparing a nanowire comprising a first metal and growing a shell on the outer surface of this nanowire, wherein the shell comprises a second metal. The first and second metals may be the same or different.

In other aspects, a core/shell nanowire is prepared in the absence of a biological template. Such methods comprise preparing a nanowire comprising an inner core and an outer shell, wherein the inner core comprises a first metal, and the outer shell comprises a second metal, the method comprising:
  a) preparing a first nanowire comprising the first metal; and
  b) treating the first nanowire with a salt comprising the second metal.

In some embodiments of the foregoing method, the method further comprises addition of an anion precursor to a mixture obtained in step b). In yet other examples, the first metal and the second metal are different. In yet further embodiments, the salt comprising the second metal is a halide or a nitrate. In certain aspects it may be advantageous to perform one or more sequential additions of the salt comprising the second metal and an anion precursor. Such sequential additions help prevent non-selective precipitation of the second metal and favor conditions wherein the second metal nucleates on the surface of the first nanowire to form a shell of the second metal. Furthermore, the first nanowire may be prepared by any method, for example via a template directed method (e.g., phage).

As in the template-directed synthesis, the synthetic conditions and parameters of the direct synthesis of nanowires can also be adjusted to create diverse compositions and surface morphologies (e.g., crystal faces) and dopant levels. For example, variable synthetic parameters include: concentration ratios of metal and anions (e.g., hydroxide); reaction temperature; reaction time; sequence of adding anion and metal ions; pH; types of metal precursor salt; types of anion precursor; number of additions; the time that lapses between the additions of the metal salt and anion precursor, including, e.g., simultaneous (zero lapse) or sequential additions followed by respective incubation times for the metal salt and the anion precursor.

In addition, the choice of solvents or surfactants may influence the crystal growth of the nanowires, thereby generating different nanowire dimensions (including aspect ratios). For example, solvents such as ethylene glycol, poly(ethylene glycol), polypropylene glycol and poly(vinyl pyrrolidone) can serve to passivate the surface of the growing nanowires and facilitate a linear growth of the nanowire.

In some embodiments, nanowires can be prepared directly from the corresponding oxide. For example, metal oxides may be treated with ammonium salts to produce nanowires. The ammonium salt comprises salts with the formula $NR_4X$, wherein each R is independently selected from H, alkyl, alkenyl, alkynyls and aryl (e.g., methyl, ethyl, propyl, isopropyl, butyl, tert-butyl, pentenyl, cyclohexyl, phenyl, tolyl, benzyl, hexynyl, octyl, octenyl, octynyl, dodecyl, cetyl, oleyl, stearyl, and the like) and X is an anion, for example halide, phosphate, hydrogenphosphate, dihydrogenphosphate, metatungstate, tungstate, molybdate, bicarbonate sulfate, nitrate or acetate. In other embodiments, X is phosphate, hydrogenphosphate, dihydrogenphosphate, metatungstate, tungstate, molybdate, bicarbonate sulfate, nitrate or acetate. Examples of the ammonium salt comprise ammonium chloride, dimethylammonium chloride, methylammonium chloride, ammonium acetate, ammonium nitrate, dimethylammonium nitrate, methylammonium nitrate, cetyl trimethylammonium bromide (CTAB) and the like. The methods may include treating the metal oxide and ammonium salts at temperatures ranging from room temperature (or lower) to reflux temperature in an appropriate solvent (e.g., water) for a time sufficient to produce the nanowires. Certain embodiments comprise heating the metal oxide and ammonium salt under hydrothermal conditions at temperatures ranging from reflux temperature (at atmospheric pressure) to 300° C. Such embodiments find particular utility in the context of lanthanide oxides, for example $La_2O_3$, are particularly useful since the procedure is quite simple and economically efficient. Nanowires comprising two or more metals and/or dopants may also be prepared according to these methods. Accordingly, in some embodiments at least one of the metal compounds is an oxide of a lanthanide element. Such methods are described in more detail in the examples.

Accordingly, in one embodiment the present disclosure provides a method for preparing a nanowire in the absence of a biological template, the method comprising treating at least one metal compound with an ammonium salt. In certain embodiments, nanowires comprising more than one type of metal and/or one or more dopants can be prepared by such methods. For example, in one embodiment the method comprises treating two or more different metal compounds with an ammonium salt and the nanowire comprises two or more different metals. The nanowire may comprise a mixed metal oxide, metal oxyhalide, metal oxynitrate or metal sulfate.

In some other embodiments of the foregoing, the ammonium salt is in the form of $NR_4X$, wherein each R is independently selected from H, alkyl, alkenyl, and aryl and X is a halide, sulfate, nitrate or acetate. Examples of the ammonium salt comprise ammonium chloride, dimethylammonium chloride, methylammonium chloride, ammonium acetate, ammonium nitrate, dimethylammonium nitrate, methylammonium nitrate. In some other embodiments, each R is independently methyl, ethyl, propyl, isopropyl, butyl, tert-butyl, pentenyl, cyclohexyl, phenyl, tolyl, benzyl, hexynyl, octyl, octenyl, octynyl, dodecyl, cetyl, oleyl or stearyl. In yet other embodiments, the ammonium salt is contacted with the metal compound in solution or in the solid state.

In certain embodiments, the method is useful for incorporation of one or more doping elements into a nanowire. For example, the method may comprise treating at least one metal compound with a halide in the presence of at least one doping element, and the nanowire comprises at least one doping element. In some aspects, the at least one doping element is present in the nanowire in an atomic percent ranging from 0.1 to 50 at %.

Other methods for preparation of nanowires in the absence of a biological template include preparing a metal hydroxide gel by reaction of at least one metal salt and a base. In some embodiments the metal salt comprises a lanthanide halide and the resulting nanowire comprises a lanthanide oxide (e.g., $La_2O_3$). For example, the method may further comprise aging the gel, heating the gel or combinations thereof. Aging or heating the gel includes aging at temperatures ranging from room temperature (e.g., 20° C.) or below to reflux for a time sufficient to produce the desired nanowires. In certain other embodiments, the method comprises reaction of two or more different metal salts, and the nanowire comprises two or more different metals. In yet other embodiments, the method comprises reaction of two or more different metal salts, and the product comprises nanowires of two or more different metals.

Doping elements may also be incorporated by using the hydroxide gel method described above, further comprising addition of at least one doping element to the hydroxide gel, and wherein the nanowire comprises the at least one doping element. For example, the at least one doping element may be present in the nanowire in an atomic percent ranging from 0.1 to 50 at %.

In some embodiments, metal oxide nanowires can be prepared by mixing a metal salt solution and an anion precursor so that a gel of a metal oxide precursor is formed. This method can work for cases where the typical morphology of the metal oxide precursor is a nanowire. The gel is thermally treated so that crystalline nanowires of the metal oxide precursor are formed. The metal oxide precursor nanowires are converted to metal oxide nanowires by calcination, further chemical reaction or combinations thereof. In some embodiments, this method is useful for lanthanides and group 3 elements. In some embodiments, the thermal treatment of the gel is hydrothermal (or solvothermal) at temperatures above the boiling point (at standard pressure) of the reaction mixture and at pressures above ambient pressure, in other embodiments it's done at ambient pressure and at temperatures equal to or below the boiling point of the reaction mixture. In some embodiments the thermal treatment is done under reflux conditions at temperatures equal to the boiling point of the mixture. In some specific embodiments the anion precursor is a hydroxide, e.g. Ammonium hydroxide, sodium hydroxide, lithium hydroxide, tetramethyl ammonium hydroxide, and the like. In some other specific embodiments the metal salt is $LnCl_3$ (Ln=Lanthanide), in other embodiment the metal salt is $Ln(NO_3)_3$. In yet other embodiments, the metal salt is $YCl_3$, $ScCl_3$, $Y(NO_3)_3$, $Sc(NO_3)_3$. In some other embodiments, the metal precursor solution is an aqueous solution. In other embodiments, the thermal treatment is done at T=100° C. under reflux conditions.

This method can be used to make mixed metal oxide nanowires, by mixing at least two metal salt solutions and an anion precursor so that a mixed oxide precursor gel is formed. In such cases, the first metal may be a lathanide or a group 3 element, and the other metals can be from other groups, including groups 1-14 and lanthanides.

In some different embodiments, metal oxide nanowires can be prepared in a similar way as described above by mixing a metal salt solution and an anion precursor so that a gel of a metal hydroxide precursor is formed. This method works for cases where the typical morphology of the metal hydroxide precursor is a nanowire. The gel is treated so that crystalline nanowires of the metal hydroxide precursor are formed. The metal hydroxide precursor nanowires are converted to metal hydroxide nanowires by base treatment and finally converted to metal oxide nanowires by calcination. In some embodiments, this method may be especially applicable for group 2 elements, for example Mg. In some specific embodiments, the gel treatment is a thermal treatment at temperatures in the range 50-100° C. followed by hydrothermal treatment. In other embodiments, the gel treatment is an aging step. In some embodiments, the aging step takes at least one day. In some specific embodiments, the metal salt solution is a concentrated metal chloride aqueous solution and the anion precursor is the metal oxide. In some more specific embodiments, the metal is Mg. In certain embodiments of the above, these methods can be used to make mixed metal oxide nanowires. In these embodiments, the first metal is Mg and the other metal can be any other metal of groups 1-14+Ln.

Catalytic Reactions

The present disclosure provides for the use of catalytic nanowires as catalysts in catalytic reactions and related methods. In some embodiments, the catalytic reaction is any of the reactions described herein. The morphology and composition of the catalytic nanowires is not limited, and the nanowires may be prepared by any method. For example the nanowires may have a bent morphology or a straight morphology and may have any molecular composition. In some embodiments, the nanowires have better catalytic properties than a corresponding bulk catalyst (i.e., a catalyst having the same chemical composition as the nanowire, but prepared from bulk material). In some embodiments, the nanowire having better catalytic properties than a corresponding bulk catalyst has a ratio of effective length to actual length equal to one. In other embodiments, the nanowire having better catalytic properties than a corresponding bulk catalyst has a ratio of effective length to actual length of less than one. In other embodiments, the nanowire having better catalytic properties than a corresponding bulk catalyst comprises one or more elements from Groups 1 through 7, lanthanides or actinides.

Nanowires may be useful in any number of reactions catalyzed by a heterogeneous catalyst. Examples of reactions wherein nanowires having catalytic activity may be employed are disclosed in Farrauto and Bartholomew, "Fundamentals of Industrial Catalytic Processes" Blackie Academic and Professional, first edition, 1997, which is hereby incorporated in its entirety. Other non-limiting examples of reactions wherein nanowires having catalytic activity may be employed include: the oxidative coupling of methane (OCM) to ethane and ethylene; oxidative dehydrogenation (ODH) of alkanes to the corresponding alkenes, for example oxidative dehydrogenation of ethane or propane to ethylene or propylene, respectively; selective oxidation of alkanes, alkenes, and alkynes; oxidation of CO, dry reforming of methane, selective oxidation of aromatics; Fischer-Tropsch, hydrocarbon cracking; combustion of hydrocarbons and the like. Reactions catalyzed by the disclosed nanowires are discussed in more detail below.

The nanowires are generally useful as catalysts in methods for converting a first carbon-containing compound (e.g., a hydrocarbon, CO or $CO_2$) to a second carbon-containing compound. In some embodiments the methods comprise contacting a nanowire, or material comprising the same, with a gas comprising a first carbon-containing compound and an oxidant to produce a carbon-containing compound. In some embodiments, the first carbon-containing compound is a hydrocarbon, CO, $CO_2$, methane, ethane, propane, hexane, cyclohexane, octane or combinations thereof. In other embodiments, the second carbon-containing compound is a hydrocarbon, CO, $CO_2$, ethane, ethylene, propane, propylene, hexane, hexene, cyclohexane, cyclohexene, bicyclohexane, octane, octene or hexadecane. In some embodiments, the oxidant is oxygen, ozone, nitrous oxide, nitric oxide, carbon dioxide, water or combinations thereof.

In other embodiments of the foregoing, the method for conversion of a first carbon-containing compound to a second carbon-containing compound is performed at a temperature below 100° C., below 200° C., below 300° C., below 400° C., below 500° C., below 600° C., below 700° C., below 800° C., below 900° C. or below 1000° C. In other embodiments, the method for conversion of a first carbon-containing compound to a second carbon-containing compound is performed at a pressure above 0.5 ATM, above 1 ATM, above 2 ATM, above 5 ATM, above 10 ATM, above 25 ATM or above 50 ATM.

The catalytic reactions described herein can be performed using standard laboratory equipment known to those of skill in the art, for example as described in U.S. Pat. No. 6,350,716, which is incorporated herein in its entirety.

As noted above, the nanowires disclosed herein have better catalytic activity than a corresponding bulk catalyst. In some embodiments, the selectivity, yield, conversion, or combinations thereof, of a reaction catalyzed by the nanowires is better than the selectivity, yield, conversion, or combinations thereof, of the same reaction catalyzed by a corresponding bulk catalyst under the same conditions. For example, in some embodiments, the nanowire possesses a catalytic activity such that conversion of reactant to product in a reaction catalyzed by the nanowire is greater than at least 1.1 times, greater than at least 1.25 times, greater than at least 1.5 times, greater than at least 2.0 times, greater than at least 3.0 times or greater than at least 4.0 times the conversion of reactant to product in the same reaction catalyzed by a catalyst prepared from bulk material having the same chemical composition as the nanowire.

In other embodiments, the nanowire possesses a catalytic activity such that selectivity for product in a reaction catalyzed by the nanowire is greater than at least 1.1 times, greater than at least 1.25 times, greater than at least 1.5 times, greater than at least 2.0 times, greater than at least 3.0 times, or greater than at least 4.0 times the selectivity for product in the same reaction under the same conditions but catalyzed by a catalyst prepared from bulk material having the same chemical composition as the nanowire.

In yet other embodiments, the nanowire possesses a catalytic activity such that yield of product in a reaction catalyzed by the nanowire is greater than at least 1.1 times, greater than at least 1.25 times, greater than at least 1.5 times, greater than at least 2.0 times, greater than at least 3.0 times, or greater than at least 4.0 times the yield of product in the same reaction under the same conditions but catalyzed by a catalyst prepared from bulk material having the same chemical composition as the nanowire.

In yet other embodiments, the nanowire possesses a catalytic activity such that activation temperature of a reaction catalyzed by the nanowire is at least 25° C. lower, at least 50° C. lower, at least 75° C. lower, or at least 100° C. lower than the temperature of the same reaction under the same conditions but catalyzed by a catalyst prepared from bulk material having the same chemical composition as the nanowire.

In certain reactions (e.g., OCM), production of unwanted oxides of carbon (e.g., CO and $CO_2$) is a problem that reduces overall yield of desired product and results in an environmental liability. Accordingly, in one embodiment the present disclosure addresses this problem and provides nanowires with a catalytic activity such that the selectivity for CO and/or $CO_2$ in a reaction catalyzed by the nanowires is less than the selectivity for CO and/or $CO_2$ in the same reaction under the same conditions but catalyzed by a corresponding bulk catalyst. Accordingly, in one embodiment, the present disclosure provides a nanowire which possesses a catalytic activity such that selectivity for $CO_x$, wherein x is 1 or 2, in a reaction catalyzed by the nanowire is less than at least 0.9 times, less than at least 0.8 times, less than at least 0.5 times, less than at least 0.2 times or less than at least 0.1 times the selectivity for $CO_x$ in the same reaction under the same conditions but catalyzed by a catalyst prepared from bulk material having the same chemical composition as the nanowire.

In some embodiments, the absolute selectivity, yield, conversion, or combinations thereof, of a reaction catalyzed by the nanowires disclosed herein is better than the absolute selectivity, yield, conversion, or combinations thereof, of the same reaction under the same conditions but catalyzed by a corresponding bulk catalyst. For example, in some embodiments the yield of product in a reaction catalyzed by the nanowires is greater than 20%, greater than 30%, greater than 50%, greater than 75%, or greater than 90%. In other embodiments, the selectivity for product in a reaction catalyzed by the nanowires is greater than 20%, greater than 30%, greater than 50%, greater than 75%, or greater than 90%. In other embodiments, the conversion of reactant to product in a reaction catalyzed by the nanowires is greater than 20%, greater than 30%, greater than 50%, greater than 75%, or greater than 90%.

In addition to the improved catalytic performance of the disclosed nanowires, the morphology of the nanowires is expected to provide for improved mixing properties for the nanowires compared to standard colloidal (e.g., bulk) catalyst materials. The improved mixing properties are expected to improve the performance of any number of catalytic reactions, for example, in the area of transformation of heavy hydrocarbons where transport and mixing phenomena are known to influence the catalytic activity. In other reactions, the shape of the nanowires is expected to provide for good blending, reduce settling, and provide for facile separation of any solid material.

In some other chemical reactions, the nanowires are useful for absorption and/or incorporation of a reactant used in chemical looping. For example, the nanowires find utility as $NO_x$ traps, in unmixed combustion schemes, as oxygen storage materials, as $CO_2$ sorption materials (e.g., cyclic reforming with high $H_2$ output) and in schemes for conversion of water to $H_2$.

1. Oxidative Coupling of Methane (OCM)

As noted above, the present disclosure provides nanowires having catalytic activity and related approaches to nanowire design and preparation for improving the yield, selectivity and/or conversion of any number of catalyzed reactions, including the OCM reaction. As mentioned above, there exists a tremendous need for catalyst technology capable of addressing the conversion of methane into high value chemicals (e.g., ethylene and products prepared therefrom) using a direct route that does not go through syngas. Accomplishing this task will dramatically impact and redefine a non-petroleum based pathway for feedstock manufacturing and liquid fuel production yielding reductions in GHG emissions, as well as providing new fuel sources.

Ethylene has the largest carbon footprint compared to all industrial chemical products in part due to the large total volume consumed into a wide range of downstream important industrial products including plastics, surfactants and pharmaceuticals. In 2008, worldwide ethylene production exceeded 120 M metric tons while growing at a robust rate of 4% per year. The United States represents the largest single producer at 28% of the world capacity. Ethylene is primarily manufactured from high temperature cracking of naphtha (e.g., oil) or ethane that is separated from natural gas. The true measurement of the carbon footprint can be difficult as it depends on factors such as the feedstock and the allocation as several products are made and separated during the same process. However, some general estimates can be made based on published data.

Cracking consumes a significant portion (about 65%) of the total energy used in ethylene production and the remainder is for separations using low temperature distillation and compression. The total tons of $CO_2$ emission per ton of ethylene are estimated at between 0.9 to 1.2 from ethane cracking and 1 to 2 from naphtha cracking. Roughly, 60% of ethylene produced is from naphtha, 35% from ethane and 5% from others sources (Ren, T.; Patel, M. *Res. Conserv. Recycl.* 53:513, 2009). Therefore, based on median averages, an estimated amount of $CO_2$ emissions from the cracking process is 114M tons per year (based on 120M tons produced). Separations would then account for an additional 61M tons $CO_2$ per year.

Nanowires provide an alternative to the need for the energy intensive cracking step. Additionally, because of the high selectivity of the nanowires, downstream separations are dramatically simplified, as compared to cracking which yields a wide range of hydrocarbon products. The reaction is also exothermic so it can proceed via an autothermal process mechanism. Overall, it is estimated that up to a potential 75% reduction in $CO_2$ emission compared to conventional methods could be achieved. This would equate to a reduction of one billion tons of $CO_2$ over a ten-year period and would save over 1M barrels of oil per day.

The nanowires also permit converting ethylene into liquid fuels such as gasoline or diesel, given ethylene's high reactivity and numerous publications demonstrating high yield reactions, in the lab setting, from ethylene to gasoline and diesel. On a life cycle basis from well to wheel, recent analysis of methane to liquid (MTL) using F-T process derived gasoline and diesel fuels has shown an emission profile approximately 20% greater to that of petroleum based production (based on a worst case scenario) (Jaramillo, P., Griffin, M., Matthews, S., *Env. Sci. Tech* 42:7559, 2008). In the model, the $CO_2$ contribution from plant energy was a dominating factor at 60%. Thus, replacement of the cracking and F-T process would be expected to provide a notable reduction in net emissions, and could be produced at lower $CO_2$ emissions than petroleum based production.

Furthermore, a considerable portion of natural gas is found in regions that are remote from markets or pipelines. Most of this gas is flared, re-circulated back into oil reservoirs, or vented given its low economic value. The World Bank estimates flaring adds 400M metric tons of $CO_2$ to the atmosphere each year as well as contributing to methane emissions. The nanowires of this disclosure also provide economic and environmental incentive to stop flaring. Also, the conversion of methane to fuel has several environmental advantages over petroleum-derived fuel. Natural gas is the cleanest of all fossil fuels, and it does not contain a number of impurities such as mercury and other heavy metals found in oil. Additionally, contaminants including sulfur are also easily separated from the initial natural gas stream. The resulting fuels burn much cleaner with no measurable toxic pollutants and provide lower emissions than conventional diesel and gasoline in use today.

In view of its wide range of applications, the nanowires of this disclosure can be used to not only selectively activate alkanes, but also to activate other classes of inert unreactive bonds, such as C—F, C—Cl or C—O bonds. This has importance, for example, in the destruction of man-made environmental toxins such as CFCs, PCBs, dioxins and other pollutants. Accordingly, while the invention is described in greater detail below in the context of the OCM reaction and other the other reactions described herein, the nanowire catalysts are not in any way limited to this particular reaction.

The selective, catalytic oxidative coupling of methane to ethylene (i.e. the OCM reaction) is shown by the following reaction (1):

$$2CH_4 + O_2 \rightarrow CH_2CH_2 + 2\ H_2O \tag{1}$$

This reaction is exothermic (Heat of Reaction −67 kcals/mole) and usually occurs at very high temperatures (>700° C.). During this reaction, it is believed that the methane ($CH_4$) is first oxidatively coupled into ethane ($C_2H_6$), and subsequently the ethane ($C_2H_6$) is oxidatively dehydrogenated into ethylene ($C_2H_4$). Because of the high temperatures used in the reaction, it has been suggested that the ethane is produced mainly by the coupling in the gas phase of the surface-generated methyl ($CH_3$) radicals. Reactive metal oxides (oxygen type ions) are apparently required for the activation of $CH_4$ to produce the $CH_3$ radicals. The yield of $C_2H_4$ and $C_2H_6$ is limited by further reactions in the gas phase and to some extent on the catalyst surface. A few of the possible reactions that occur during the oxidation of methane are shown below as reactions (2) through (8):

$$CH_4 \rightarrow CH_3\ \text{radical} \tag{2}$$

$$CH_3\ \text{radical} \rightarrow C_2H_6 \tag{3}$$

$$CH_3\ \text{radical} + 2.5\ O_2 \rightarrow CO_2 + 1.5\ H_2O \tag{4}$$

$$C_2H_6 \rightarrow C_2H_4 + H_2 \tag{5}$$

$$C_2H_6 + 0.5\ O_2 \rightarrow C_2H_4 + H_2O \tag{6}$$

$$C_2H_4 + 3\ O_2 \rightarrow 2CO_2 + 2H_2O \tag{7}$$

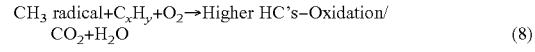
$$CH_3\ \text{radical} + C_xH_y + O_2 \rightarrow \text{Higher HC's–Oxidation/} CO_2 + H_2O \tag{8}$$

With conventional heterogeneous catalysts and reactor systems, the reported performance is generally limited to <25% $CH_4$ conversion at <80% combined $C_2$ selectivity, with the performance characteristics of high selectivity at low conversion, or the low selectivity at high conversion. In contrast, the nanowires of this disclosure are highly active and can optionally operate at a much lower temperature. In one embodiment, the nanowires disclosed herein enable efficient conversion of methane to ethylene in the OCM reaction at temperatures less than when the corresponding bulk material is used as a catalyst. For example, in one embodiment, the nanowires disclosed herein enable efficient conversion (i.e., high yield, conversion, and/or selectivity) of methane to ethylene at temperatures of less than 900° C., less than 800° C., less than 700° C., less than 600° C., or less than 500° C. In other embodiments, the use of staged oxygen addition, designed heat management, rapid quench and/or advanced separations may also be employed.

Accordingly, one embodiment of the present disclosure is a method for the preparation of ethane and/or ethylene, the method comprising converting methane to ethane and/or ethylene in the presence of a catalytic material, wherein the catalytic material comprises at least one catalytic nanowire as disclosed herein.

Accordingly, in one embodiment a stable, very active, high surface area, multifunctional nanowire catalyst is disclosed having active sites that are isolated and precisely engineered with the catalytically active metal centers/sites in the desired proximity (see, e.g., FIG. 1).

The exothermic heats of reaction (free energy) follow the order of reactions depicted above and, because of the proximity of the active sites, will mechanistically favor ethylene formation while minimizing complete oxidation reactions that form CO and $CO_2$. Representative nanowire compositions useful for the OCM reaction include, but are not limited to: highly basic oxides selected from the early members of the Lanthanide oxide series; Group 1 or 2 ions supported on basic oxides, such as Li/MgO, Ba/MgO and Sr/$La_2O_3$; and single or mixed transition metal oxides, such as $VO_x$ and Re/Ru that may also contain Group 1 ions. Other nanowire compositions useful for the OCM reaction comprise any of the compositions disclosed herein, for example MgO, $La_2O_3$, $Na_2WO_4$, $Mn_2O_3$, $Mn_3O_4$, $Mg_6MnO_8$, $Zr_2Mo_2O_8$, $NaMnO_4$, $Mn_2O_3$/$Na_2WO_4$, $Mn_3O_4$/$Na_2WO_4$ or Na/$MnO_4$/MgO, Mn/WO4, $Nd_2O_3$, $Sm_2O_3$, $Eu_2O_3$ or combinations thereof. Activating promoters (i.e., dopants), such as chlorides, nitrates and sulfates, or any of the dopants described above may also be employed.

As noted above, the presently disclosed nanowires comprise a catalytic performance better than corresponding bulk catalysts, for example in one embodiment the catalytic performance of the nanowires in the OCM reaction is better than the catalytic performance of a corresponding bulk catalyst. In this regard, various performance criteria may define the "catalytic performance" of the catalysts in the OCM (and other reactions). In one embodiment, catalytic performance is defined by C2 selectivity in the OCM reaction, and the C2 selectivity of the nanowires in the OCM reaction is >5%, >10%, >15%, >20%, >25%, >30%, >35%, >40%, >45%, >50%, >55%, >60%, >65%, >70%, >75% or >80%.

Other important performance parameters used to measure the nanowires' catalytic performance in the OCM reaction are selected from single pass methane conversion percentage (i.e., the percent of methane converted on a single pass over the catalyst or catalytic bed, etc.), reaction inlet gas temperature, reaction operating temperature, total reaction pressure, methane partial pressure, gas-hour space velocity (GHSV), $O_2$ source, catalyst stability and ethylene to ethane ratio. In certain embodiments, improved catalytic performance is defined in terms of the nanowires' improved performance (relative to a corresponding bulk catalyst) with respect to at least one of the foregoing performance parameters.

The reaction inlet gas temperature in an OCM reaction catalyzed by the disclosed nanowires can generally be maintained at a lower temperature, while maintaining better performance characteristics (e.g., conversion, C2 yield, C2 selectivity and the like) compared to the same reaction catalyzed by a corresponding bulk catalyst under the same reaction conditions. In certain embodiments, the inlet gas temperature in an OCM reaction catalyzed by the disclosed nanowires is <700° C., <675° C., <650° C., <625° C., <600° C., <593° C., <580° C., <570° C., <560° C., <550° C., <540° C., <530° C., <520° C., <510° C., <500° C., <490° C., <480° C. or even <470° C.

The reaction operating temperature in an OCM reaction catalyzed by the disclosed nanowires can generally be maintained at a lower temperature, while maintaining better performance characteristics compared to the same reaction catalyzed by a corresponding bulk catalyst under the same reaction conditions. In certain embodiments, the reaction operating temperature in an OCM reaction catalyzed by the disclosed nanowires is <700° C., <675° C., <650° C., <625° C., <600° C., <593° C., <580° C., <570° C., <560° C., <550° C., <540° C., <530° C., <520° C., <510° C., <500° C., <490° C., <480° C., <470° C.

The single pass methane conversion in an OCM reaction catalyzed by the nanowires is also generally better compared to the single pass methane conversion in the same reaction catalyzed by a corresponding bulk catalyst under the same reaction conditions. For single pass methane conversion it is preferably >5%, >10%, >15%, >20%, >25%, >30%, >35%, >40%, >45%, >50%, >55%, >60%, >65%, >70%, >75%, >80%.

In certain embodiments, the total reaction pressure in an OCM reaction catalyzed by the nanowires is >1 atm, >1.1 atm, >1.2 atm, >1.3 atm, >1.4 atm, >1.5 atm, >1.6 atm, >1.7 atm, >1.8 atm, >1.9 atm, >2 atm, >2.1 atm, >2.1 atm, >2.2 atm, >2.3 atm, >2.4 atm, >2.5 atm, >2.6 atm, >2.7 atm, >2.8 atm, >2.9 atm, >3.0 atm, >3.5 atm, >4.0 atm, >4.5 atm, >5.0 atm, >5.5 atm, >6.0 atm, >6.5 atm, >7.0 atm, >7.5 atm, >8.0 atm, >8.5 atm, >9.0 atm, >10.0 atm, >11.0 atm, >12.0 atm, >13.0 atm, >14.0 atm, >15.0 atm, >16.0 atm, >17.0 atm, >18.0 atm, >19.0 atm or >20.0 atm.

In certain other embodiments, the total reaction pressure in an OCM reaction catalyzed by the nanowires ranges from about 1 atm to about 10 atm, from about 1 atm to about 7 atm, from about 1 atm to about 5 atm, from about 1 atm to about 3 atm or from about 1 atm to about 2 atm.

In some embodiments, the methane partial pressure in an OCM reaction catalyzed by the nanowires is >0.3 atm, >0.4 atm, >0.5 atm, >0.6 atm, >0.7 atm, >0.8 atm, >0.9 atm, >1 atm, >1.1 atm, >1.2 atm, >1.3 atm, >1.4 atm, >1.5 atm, >1.6 atm, >1.7 atm, >1.8 atm, >1.9 atm, >2.0 atm, >2.1 atm, >2.2 atm, >2.3 atm, >2.4 atm, >2.5 atm, >2.6 atm, >2.7 atm, >2.8 atm, >2.9 atm, >3.0 atm, >3.5 atm, >4.0 atm, >4.5 atm, >5.0 atm, >5.5 atm, >6.0 atm, >6.5 atm, >7.0 atm, >7.5 atm, >8.0 atm, >8.5 atm, >9.0 atm, >10.0 atm, >11.0 atm, >12.0 atm, >13.0 atm, >14.0 atm, >15.0 atm, >16.0 atm, >17.0 atm, >18.0 atm, >19.0 atm or >20.0 atm.

In some embodiments, the GSHV in an OCM reaction catalyzed by the nanowires is >20,000/hr, >50,000/hr, >75,000/hr, >100,000/hr, >120,000/hr, >130,000/hr, >150,000/hr, >200,000/hr, >250,000/hr, >300,000/hr, >350,000/hr, >400,000/hr, >450,000/hr, >500,000/hr, >750,000/hr, >1,000,000/hr, >2,000,000/hr, >3,000,000/hr, >4,000,000/hr.

In contrast to other OCM reactions, the present inventors have discovered that OCM reactions catalyzed by the disclosed nanowires can be performed (and still maintain high C2 yield, C2 selectivity, conversion, etc.) using $O_2$ sources other than pure $O_2$. For example, in some embodiments the $O_2$ source in an OCM reaction catalyzed by the disclosed nanowires is air, oxygen enriched air, pure oxygen, oxygen diluted with nitrogen (or another inert gas) or oxygen diluted with $CO_2$. In certain embodiments, the $O_2$ source is $O_2$ diluted by >99%, >98%, >97%, >96%, >95%, >94%, >93%, >92%, >91%, >90%, >85%, >80%, >75%, >70%, >65%, >60%, >55%, >50%, >45%, >35%, >30%, >25%, >40%, >20%, >15%, >10%, >9%, >8%, >7%, >6%, >5%, >4%, >3%, >2% or >1% with $CO_2$ or an inert gas, for example nitrogen.

The disclosed nanowires are also very stable under conditions required to perform any number of catalytic reactions, for example the OCM reaction. The stability of the nanowires is defined as the length of time a catalyst will maintain its catalytic performance without a significant decrease in performance (e.g., a decrease >20%, >15%, >10%, >5%, or greater than 1% in C2 yield, C2 selectivity or conversion, etc.). In some embodiments, the nanowires have stability under conditions required for the OCM reaction of >1 hr, >5 hrs, >10 hrs, >20 hrs, >50 hrs, >80 hrs, >90 hrs, >100 hrs, >150 hrs, >200 hrs, >250 hrs, >300 hrs, >350 hrs, >400 hrs, >450 hrs, >500 hrs, >550 hrs, >600 hrs, >650 hrs, >700 hrs, >750 hrs, >800 hrs, >850 hrs, >900 hrs, >950 hrs, >1,000 hrs, >2,000 hrs, >3,000 hrs, >4,000 hrs, >5,000 hrs, >6,000 hrs, >7,000 hrs, >8,000 hrs, >9,000 hrs, >10,000 hrs, >11,000 hrs, >12,000 hrs, >13,000 hrs, >14,000 hrs, >15,000 hrs, >16,000 hrs, >17,000 hrs, >18,000 hrs, >19,000 hrs, >20,000 hrs, >1 yrs, >2 yrs, >3 yrs, >4 yrs or >5 yrs.

In some embodiments, the ratio of ethylene to ethane in an OCM reaction catalyzed by the nanowires is better than the ratio of ethylene to ethane in an OCM reaction catalyzed by a corresponding bulk catalyst under the same conditions. In some embodiments, the ratio of ethylene to ethane in an OCM reaction catalyzed by the nanowires is >0.3, >0.4, >0.5, >0.6, >0.7, >0.8, >0.9, >1, >1.1, >1.2, >1.3, >1.4, >1.5, >1.6, >1.7, >1.8, >1.9, >2.0, >2.1, >2.2, >2.3, >2.4, >2.5, >2.6, >2.7, >2.8, >2.9, >3.0, >3.5, >4.0, >4.5, >5.0, >5.5, >6.0, >6.5, >7.0, >7.5, >8.0, >8.5, >9.0, >9.5, >10.0.

As noted above, the OCM reaction employing known bulk catalysts suffers from poor yield, selectivity, or conversion. In contrast to a corresponding bulk catalyst, Applicants have found that certain nanowires, for example the exemplary nanowires disclosed herein, posses a catalytic activity in the OCM reaction such that the yield, selectivity, and/or conversion is better than when the OCM reaction is catalyzed by a corresponding bulk catalyst. In one embodiment, the disclosure provides a nanowire having a catalytic activity such that the conversion of methane to ethylene in the oxidative coupling of methane reaction is greater than at least 1.1 times, 1.25 times, 1.50 times, 2.0 times, 3.0 times, or 4.0 times the conversion of methane to ethylene compared to the same reaction under the same conditions but performed with a catalyst prepared from bulk material having the same chemical composition as the nanowire. In other embodiments, the conversion of methane to ethylene in an OCM reaction catalyzed by the nanowire is greater than 10%, greater than 20%, greater than 30%, greater than 50%, greater than 75%, or greater than 90%.

In another embodiment, the disclosure provides a nanowire having a catalytic activity such that the yield of ethylene in the oxidative coupling of methane reaction is greater than at least 1.1 times, 1.25 times, 1.50 times, 2.0 times, 3.0 times, or 4.0 times the yield of ethylene compared to the same reaction under the same conditions but performed with a catalyst prepared from bulk material having the same chemical composition as the nanowire. In some embodiments the yield of ethylene in an OCM reaction catalyzed by the nanowire is greater than 10%, greater than 20%, greater than 30%, greater than 50%, greater than 75%, or greater than 90%.

As noted above, the OCM reaction employing known bulk catalysts suffers from poor yield, selectivity, or conversion. In contrast to a corresponding bulk catalyst, Applicants have found that certain nanowires, for example the exemplary nanowires disclosed herein, posses a catalytic activity in the OCM reaction such that the yield, selectivity, and/or conversion is better than when the OCM reaction is catalyzed by a corresponding bulk catalyst. In one embodiment, the disclosure provides a nanowire having a catalytic activity such that the conversion of methane in the oxidative coupling of methane reaction is greater than at least 1.1 times, 1.25 times, 1.50 times, 2.0 times, 3.0 times, or 4.0 times the conversion of methane compared to the same reaction under the same conditions but performed with a catalyst prepared from bulk material having the same chemical composition as the nanowire. In other embodiments, the conversion of methane in an OCM reaction catalyzed by the nanowire is greater than 10%, greater than 20%, greater than 30%, greater than 50%, greater than 75%, or greater than 90%. In some embodiments the conversion of methane is determined when the catalyst is employed as a heterogenous catalyst in the oxidative coupling of methane at a temperature of 750° C. or less, 700° C. or less, 650° C. or less or even 600° C. or less. The conversion of methane may also be determined based on a single pass of a gas comprising methane over the catalyst or may be determined based on multiple passes over the catalyst.

In another embodiment, the disclosure provides a nanowire having a catalytic activity such that the C2 yield in the oxidative coupling of methane reaction is greater than at least 1.1 times, 1.25 times, 1.50 times, 2.0 times, 3.0 times, or 4.0 times the C2 yield compared to the same reaction under the same conditions but performed with a catalyst prepared from bulk material having the same chemical composition as the nanowire. In some embodiments the C2 yield in an OCM reaction catalyzed by the nanowire is greater than 10%, greater than 20%, greater than 30%, greater than 50%, greater than 75%, or greater than 90%. In some embodiments the C2 yield is determined when the catalyst is employed as a heterogenous catalyst in the oxidative coupling of methane at a temperature of 750° C. or less, 700° C. or less, 650° C. or less or even 600° C. or less. The C2 yield may also be determined based on a single pass of a gas comprising methane over the catalyst or may be determined based on multiple passes over the catalyst.

In another embodiment, the disclosure provides a nanowire having a catalytic activity in the OCM reaction such that the nanowire has the same catalytic activity (i.e., same selectivity, conversion or yield), but at a lower temperature, compared a catalyst prepared from bulk material having the same chemical composition as the nanowire. In some embodiments the catalytic activity of the nanowires in the OCM reaction is the same as the catalytic activity of a catalyst prepared from bulk material having the same chemical composition as the nanowire, but at a temperature of at least 20° C. less. In some embodiments the catalytic activity of the nanowires in the OCM reaction is the same as the catalytic activity of a catalyst prepared from bulk material having the same chemical composition as the nanowire, but at a temperature of at least 50° C. less. In some embodiments the catalytic activity of the nanowires in the OCM reaction is the same as the catalytic activity of a catalyst prepared from bulk material having the same chemical composition as the nanowire, but at a temperature of at least 100° C. less. In some embodiments the catalytic activity of the nanowires in the OCM reaction is the same as the catalytic activity of a catalyst prepared from bulk material having the same chemical composition as the nanowire, but at a temperature of at least 200° C. less.

In another embodiment, the disclosure provides a nanowire having a catalytic activity such that the selectivity for CO or $CO_2$ in the oxidative coupling of methane reaction is less than at least 0.9 times, 0.8 times, 0.5 times, 0.2 times, or 0.1 times the selectivity for CO or $CO_2$ compared to the same reaction under the same conditions but performed with a catalyst prepared from bulk material having the same chemical composition as the nanowire.

In some other embodiments, a method for converting methane into ethylene comprising use of catalyst mixture comprising two or more catalysts is provided. For example, the catalyst mixture may be a mixture of a catalyst having good OCM activity and a catalyst having good ODH activity. Such catalyst mixture are described in more detail above.

Typically, the OCM reaction is run in a mixture of oxygen and nitrogen or other inert gas. Such gasses are expensive and increase the overall production costs associated with preparation of ethylene or ethane from methane. However, the present inventors have now discovered that such expensive gases are not required and high yield, conversion, selectivity, etc. can be obtained when air is used as the gas mixture instead of pre-packaged and purified sources of oxygen and other gases. Accordingly, in one embodiment the disclosure provides a method for performing the OCM reaction in air.

In addition to air or $O_2$ gas, the presently disclosed nanowires and associated methods provide for use of other sources of oxygen in the OCM reaction. In this respect, an alternate source of oxygen such a $CO_2$, $H_2O$, $SO_2$ or $SO_3$ may be used either in place of, or in addition to, air or oxygen as the oxygen source. Such methods have the potential to increase the efficiency of the OCM reaction, for example by consuming a reaction byproduct (e.g., $CO_2$ or $H_2O$) and controlling the OCM exotherm as described below.

As noted above, in the OCM reaction, methane is oxidatively converted to methyl radicals, which are then coupled to form ethane, which is subsequently oxidized to ethylene. In traditional OCM reactions, the oxidation agent for both the methyl radical formation and the ethane oxidation to ethylene is oxygen. In order to minimize full oxidation of methane or ethane to carbon dioxide, i.e. maximize C2 selectivity, the methane to oxygen ratio is generally kept at 4 (i.e. full conversion of methane into methyl radicals) or above. As a result, the OCM reaction is typically oxygen limited and thus the oxygen concentration in the effluent is zero.

Accordingly, in one embodiment the present disclosure provides a method for increasing the methane conversion and increasing, or in some embodiments, not reducing, the C2 selectivity in an OCM reaction. The disclosed methods include adding to a traditional OCM catalyst another OCM catalyst that uses an oxygen source other than molecular oxygen. In some embodiments, the alternate oxygen source is $CO_2$, $H_2O$, $SO_2$, $SO_3$ or combinations thereof. For example in some embodiments, the alternate oxygen source is $CO_2$. In other embodiments the alternate oxygen source is $H_2O$.

Because C2 selectivity is typically between 50% and 80% in the OCM reaction, OCM typically produces significant amounts of $CO_2$ as a byproduct ($CO_2$ selectivity can typically range from 20-50%). Additionally, $H_2O$ is produced in copious amounts, regardless of the C2 selectivity. Therefore both $CO_2$ and $H_2O$ would are attractive oxygen sources for OCM in an $O_2$ depleted environment.

Accordingly, one embodiment of the present disclosure provides a catalyst (and related methods for use thereof) which is catalytic in the OCM reaction and which uses $CO_2$, $H_2O$, $SO_2$, $SO_3$ or another alternative oxygen source or combinations thereof as a source of oxygen. Other embodiments, provide a catalytic material comprising two or more catalysts, wherein the catalytic material comprises at least one catalyst which is catalytic in the OCM reaction and uses $O_2$ for at least one oxygen source and at least one catalysts which is catalytic in the OCM reaction and uses at least of $CO_2$, $H_2O$, $SO_2$, $SO_3$, NO, $NO_2$, $NO_3$ or another alternative oxygen source. Methods for performing the OCM reaction with such catalytic materials are also provided. Such catalysts comprise any of the compositions disclosed herein and are effective as catalysts in an OCM reaction using an alternative oxygen source at temperatures of 900° C. or lower, 850° C. or lower, 800° C. or lower, 750° C. or lower, 700° C. or lower or even 650° C. or lower. In some embodiments of the above, the catalyst is a nanowire catalyst.

Examples of OCM catalysts that use $CO_2$ or other oxygen sources rather than $O_2$ include, but are not limited to, catalysts comprising $La_2O_3$/ZnO, $CeO_2$/ZnO, CaO/ZnO, CaO/$CeO_2$, CaO/$Cr_2O_3$, CaO/$MnO_2$, SrO/ZnO, SrO/$CeO_2$, SrO/$Cr_2O_3$, SrO/$MnO_2$, $SrCO_3$/$MnO_2$, BaO/ZnO, BaO/$CeO_2$, BaO/$Cr_2O_3$, BaO/$MnO_2$, CaO/$MnO_2$/$CeO_2$, $Na_2WO_4$/Mn/$SiO_2$, $Pr_2O_3$, $Tb_2O_3$.

Some embodiments provide a method for performing OCM, wherein a mixture of an OCM catalyst which use $O_2$ as an oxygen source (referred to herein as an $O_2$-OCM catalyst) and an OCM catalyst which use $CO_2$ as an oxygen source (referred to herein as a $CO_2$-OCM catalyst) is employed as the catalytic material, for example in a catalyst bed. Such methods have certain advantages. For example, the $CO_2$-OCM reaction is endothermic and the $O_2$-OCM reaction is exothermic, and thus if the right mixture and/or arrangement of $CO_2$-OCM and $O_2$-OCM catalysts is used, the methods are particularly useful for controlling the exotherm of the OCM reaction. In some embodiments, the catalyst bed comprises a mixture of $O_2$-OCM catalyst and $CO_2$-OCM catalysts. The mixture may be in a ratio of 1:99 to 99:1. The two catalysts work synergistically as the $O_2$-OCM catalyst supplies the $CO_2$-OCM catalyst with the necessary carbon dioxide and the endothermic nature of the $C_2$-OCM reaction serves to control the exotherm of the overall reaction. Alternatively, the $CO_2$ source may be external to the reaction (e.g., fed in from a $CO_2$ tank, or other source) and/or the heat required for the $CO_2$-OCM reaction is supplied from an external source (e.g., heating the reactor).

Since the gas composition will tend to become enriched in $CO_2$ as it flows through the catalyst bed (i.e., as the OCM reaction proceeds, more $CO_2$ is produced), some embodiments of the present invention provide an OCM method wherein the catalyst bed comprises a gradient of catalysts which changes from a high concentration of $O_2$-OCM catalysts at the front of the bed to a high concentration of $CO_2$-OCM catalysts at the end of the catalyst bed.

The $O_2$-OCM catalyst and $CO_2$ OCM catalyst may have the same or different compositions. For example, in some embodiments the $O_2$-OCM catalyst and $CO_2$-OCM catalyst have the same composition but different morphologies (e.g., nanowire, bent nanowire, bulk, etc.). In other embodiments the $O_2$-OCM and the $CO_2$-OCM catalyst have different compositions.

Furthermore, $CO_2$-OCM catalysts will typically have higher selectivity, but lower yields than an $O_2$-OCM catalyst. Accordingly, in one embodiment the methods comprise use of a mixture of an $O_2$-OCM catalyst and a $CO_2$-OCM catalyst and performing the reaction in $O_2$ deprived environment so that the $CO_2$-OCM reaction is favored and the selectivity is increased. Under appropriate conditions the yield and selectivity of the OCM reaction can thus be optimized.

In some other embodiments, the catalyst bed comprises a mixture of one or more low temperature $O_2$-OCM catalyst (i.e., a catalyst active at low temperatures, for example less than 700° C.) and one or more high temperature $CO_2$-OCM catalyst (i.e., a catalyst active at high temperatures, for example 800° C. or higher). Here, the required high temperature for the $CO_2$-OCM may be provided by the hotspots produced by the $O_2$-OCM catalyst. In such a scenario, the mixture may be sufficiently coarse such that the hotspots are not being excessively cooled down by excessive dilution effect.

In other embodiments, the catalyst bed comprises alternating layers of $O_2$-OCM and $CO_2$-OCM catalysts. The catalyst layer stack may begin with a layer of $O_2$-OCM catalyst, so that it can supply the next layer (e.g., a $CO_2$-OCM layer) with the necessary $CO_2$. The $O_2$-OCM layer thickness may be optimized to be the smallest at which $O_2$ conversion is 100% and thus the $CH_4$ conversion of the layer is maximized. The catalyst bed may comprise any number of catalyst layers, for example the overall number of layers may be optimized to maximize the overall $CH_4$ conversion and C2 selectivity.

In some embodiments, the catalyst bed comprises alternating layers of low temperature $O_2$-OCM catalysts and high temperature $CO_2$-OCM catalysts. Since the $CO_2$-OCM reaction is endothermic, the layers of $CO_2$-OCM catalyst may be sufficiently thin such that in can be "warmed up" by the hotspots of the $O_2$-OCM layers. The endothermic nature of the $CO_2$-OCM reaction can be advantageous for the overall thermal management of an OCM reactor. In some embodiments, the $CO_2$-OCM catalyst layers act as "internal" cooling for the $O_2$-OCM layers, thus simplifying the requirements for the cooling, for example in a tubular reactor. Therefore, an interesting cycle takes place with the endothermic reaction providing the necessary heat for the endothermic reaction and the endothermic reaction providing the necessary cooling for the exothermic reaction.

Accordingly, one embodiment of the present invention is a method for the oxidative coupling of methane, wherein the method comprises conversion of methane to ethane and/or ethylene in the presence of a catalytic material, and wherein the catalytic material comprises a bed of alternating layers of $O_2$-OCM catalysts and $CO_2$-OCM catalysts. In other embodiments the bed comprises a mixture (i.e., not alternating layers) of $O_2$-OCM catalysts and $CO_2$-OCM catalysts.

In other embodiments, the OCM methods include use of a jacketed reactor with the exothermic $O_2$-OCM reaction in the core and the endothermic $CO_2$-OCM reaction in the mantel. In other embodiments, the unused $CO_2$ can be recycled and reinjected into the reactor, optionally with the recycled $CH_4$. Additional $CO_2$ can also be injected to increase the overall methane conversion and help reduce greenhouse gases.

In other embodiments, the reactor comprises alternating stages of $O_2$-OCM catalyst beds and $CO_2$-OCM catalyst beds. The $CO_2$ necessary for the $CO_2$-OCM stages is provided by the $O_2$-OCM stage upstream. Additional $CO_2$ may also be injected. The $O_2$ necessary for the subsequent $O_2$-OCM stages is injected downstream from the $CO_2$-OCM stages. The $CO_2$-OCM stages may provide the necessary cooling for the $O_2$-OCM stages. Alternatively, separate cooling may be provided. Likewise, if necessary the inlet gas of the $CO_2$-OCM stages can be additionally heated, the $CO_2$-OCM bed can be heated or both.

In related embodiments, the $CO_2$ naturally occurring in natural gas is not removed prior to performing the OCM, alternatively CO2 is added to the feed with the recycled methane. Instead the $CO_2$ containing natural gas is used as a feedstock for $CO_2$-OCM, thus potentially saving a separation step. The amount of naturally occurring $CO_2$ in natural gas depends on the well and the methods can be adjusted accordingly depending on the source of the natural gas.

The foregoing methods can be generalized as a method to control the temperature of very exothermic reactions by coupling them with an endothermic reaction that uses the same feedstock (or byproducts of the exothermic reaction) to make the same product (or a related product). This concept can be reversed, i.e. providing heat to an endothermic reaction by coupling it with an exothermic reaction. This will also allow a higher per pass yield in the OCM reactor.

For purpose of simplicity, the above description relating to the use of $O_2$-OCM and $CO_2$-OCM catalysts was described in reference to the oxidative coupling of methane (OCM); however, the same concept is applicable to other catalytic reactions including but not limited to: oxidative dehydrogenation (ODH) of alkanes to their corresponding alkenes, selective oxidation of alkanes and alkenes and alkynes, etc. For example, in a related embodiment, a catalyst capable of using an alternative oxygen source (e.g., $CO_2$, $H_2O$, $SO_2$, $SO_3$ or combinations thereof) to catalyze the oxidative dehydrogenation of ethane is provided. Such catalysts, and uses thereof are described in more detail below.

Furthermore, the above methods are applicable for creating novel catalysts by blending catalysts that use different reactants for the same catalytic reactions, for example different oxidants for an oxidation reaction and at least one oxidant is a byproduct of one of the catalytic reactions. In addition, the methods can also be generalized for internal temperature control of reactors by blending catalysts that catalyze reactions that share the same or similar products but are exothermic and endothermic, respectively. These two concepts can also be coupled together.

2. Oxidative Dehydrogenation

Worldwide demand for alkenes, especially ethylene and propylene, is high. The main sources for alkenes include steam cracking, fluid-catalytic-cracking and catalytic dehydrogenation. The current industrial processes for producing alkenes, including ethylene and propylene, suffer from some of the same disadvantages described above for the OCM reaction. Accordingly, a process for the preparation of alkenes, which is more energy efficient and has higher yield, selectivity, and conversion than current processes is needed.

Applicants have now found that nanowires, for example the exemplary nanowires disclosed herein, fulfill this need and provide related advantages.

In one embodiment, the disclosed nanowires are useful as catalysts for the oxidative dehydrogenation (ODH) of hydrocarbons (e.g. alkanes, alkenes, and alkynes). For example, in one embodiment the nanowires are useful as catalysts in an ODH reaction for the conversion of ethane or propane to ethylene or propylene, respectively. Reaction scheme (9) depicts the oxidative dehydrogenation of hydrocarbons:

$$C_xH_y + \tfrac{1}{2}O_2 \rightarrow C_xH_{y-2} + H_2O \quad (9)$$

Representative catalysts useful for the ODH reaction include, but are not limited to nanowires comprising Zr, V, Mo, Ba, Nd, Ce, Ti, Mg, Nb, La, Sr, Sm, Cr, W, Y or Ca or oxides or combinations thereof. Activating promoters (i.e. dopants) comprising P, K, Ca, Ni, Cr, Nb, Mg, Au, Zn, or Mo, or combinations thereof, may also be employed.

As noted above, improvements to the yield, selectivity, and/or conversion in the ODH reaction employing bulk catalysts are needed. Accordingly, in one embodiment, the present disclosure provides a nanowire which posses a catalytic activity in the ODH reaction such that the yield, selectivity, and/or conversion is better than when the ODH reaction is catalyzed by a corresponding bulk catalyst. In one embodiment, the disclosure provides a nanowire having a catalytic activity such that the conversion of hydrocarbon to alkene in the ODH reaction is greater than at least 1.1 times, 1.25 times, 1.50 times, 2.0 times, 3.0 times, or 4.0 times the conversion of alkane to alkene compared to the same reaction under the same conditions but performed with a catalyst prepared from bulk material having the same chemical composition as the nanowire. In other embodiments, the conversion of hydrocarbon to alkene in an ODH reaction catalyzed by the nanowire is greater than 10%, greater than 20%, greater than 30%, greater than 50%, greater than 75%, or greater than 90%.

In another embodiment, the disclosure provides a nanowire having a catalytic activity such that the yield of alkene in an ODH reaction is greater than at least 1.1 times, 1.25 times, 1.50 times, 2.0 times, 3.0 times, or 4.0 times the yield of alkenes compared to the same reaction under the same conditions but performed with a catalyst prepared from bulk material having the same chemical composition as the nanowire. In some embodiments the yield of alkene in an ODH reaction catalyzed by the nanowire is greater than 10%, greater than 20%, greater than 30%, greater than 50%, greater than 75%, or greater than 90%.

In another embodiment, the disclosure provides a nanowire having a catalytic activity in the ODH reaction such that the nanowire has the same catalytic activity, but at a lower temperature, compared a catalyst prepared from bulk material having the same chemical composition as the nanowire. In some embodiments the catalytic activity of the nanowires in the ODH reaction is the same or better than the catalytic activity of a catalyst prepared from bulk material having the same chemical composition as the nanowire, but at a temperature of at least 20° C. less. In some embodiments the catalytic activity of the nanowires in the ODH reaction is the same or better than the catalytic activity of a catalyst prepared from bulk material having the same chemical composition as the nanowire, but at a temperature of at least 50° C. less. In some embodiments the catalytic activity of the nanowires in the ODH reaction is the same or better than the catalytic activity of a catalyst prepared from bulk material having the same chemical composition as the nanowire, but at a temperature of at least 100° C. less. In some embodiments the catalytic activity of the nanowires in the ODH reaction is the same or better than the catalytic activity of a catalyst prepared from bulk material having the same chemical composition as the nanowire, but at a temperature of at least 200° C. less.

In another embodiment, the disclosure provides a nanowire having a catalytic activity such that the selectivity for alkenes in an ODH reaction is greater than at least 1.1 times, 1.25 times, 1.50 times, 2.0 times, 3.0 times, or 4.0 times the selectivity for alkenes compared to the same reaction under the same conditions but performed with a catalyst prepared from bulk material having the same chemical composition as the nanowire. In other embodiments, the selectivity for alkenes in an ODH reaction catalyzed by the nanowire is greater than 50%, greater than 60%, greater than 70%, greater than 80%, greater than 90%, or greater than 95%.

In another embodiment, the disclosure provides a nanowire having a catalytic activity such that the selectivity for CO or $CO_2$ in an ODH reaction is less than at least 0.9 times, 0.8 times, 0.5 times, 0.2 times, or 0.1 times the selectivity for CO or $CO_2$ compared to the same reaction under the same conditions but performed with a catalyst prepared from bulk material having the same chemical composition as the nanowire.

In one embodiment, the nanowires disclosed herein enable efficient conversion of hydrocarbon to alkene in the ODH reaction at temperatures less than when the corresponding bulk material is used as a catalyst. For example, in one embodiment, the nanowires disclosed herein enable efficient conversion (i.e. high yield, conversion, and/or selectivity) of hydrocarbon to alkene at temperatures of less than 800° C., less than 700° C., less than 600° C., less than 500° C., less than 400° C., or less than 300° C.

The stability of the nanowires is defined as the length of time a catalyst will maintain its catalytic performance without a significant decrease in performance (e.g., a decrease >20%, >15%, >10%, >5%, or greater than 1% in ODH activity or alkene selectivity, etc.). In some embodiments, the nanowires have stability under conditions required for the ODH reaction of >1 hr, >5 hrs, >10 hrs, >20 hrs, >50 hrs, >80 hrs, >90 hrs, >100 hrs, >150 hrs, >200 hrs, >250 hrs, >300 hrs, >350 hrs, >400 hrs, >450 hrs, >500 hrs, >550 hrs, >600 hrs, >650 hrs, >700 hrs, >750 hrs, >800 hrs, >850 hrs, >900 hrs, >950 hrs, >1,000 hrs, >2,000 hrs, >3,000 hrs, >4,000 hrs, >5,000 hrs, >6,000 hrs, >7,000 hrs, >8,000 hrs, >9,000 hrs, >10,000 hrs, >11,000 hrs, >12,000 hrs, >13,000 hrs, >14,000 hrs, >15,000 hrs, >16,000 hrs, >17,000 hrs, >18,000 hrs, >19,000 hrs, >20,000 hrs, >1 yrs, >2 yrs, >3 yrs, >4 yrs or >5 yrs.

As noted above, one embodiment of the present disclosure is directed to a catalyst capable of using an alternative oxygen source (e.g., $CO_2$, $H_2O$, $SO_2$, $SO_3$ or combinations thereof) to catalyze the oxidative dehydrogenation of ethane is provided. For example, the ODH reaction may proceed according to the following reaction (10):

$$CO_2 + C_xH_y \rightarrow C_xH_{y-2} + CO + H_2O \quad (10)$$

wherein x is an integer and Y is 2x+2. Compositions useful in this regard include $Fe_2O_3$, $Cr_2O_3$, $MnO_2$, $Ga_2O_3$, $Cr/SiO_2$, $Cr/SO_4$—$SiO_2$, Cr—$K/SO_4$—$SiO_2$, $Na_2WO_4$—$Mn/SiO_2$, Cr—HZSM-5, Cr/Si-MCM-41 (Cr—HZSM-5 and Cr/Si-MCM-41 refer to known zeolites) and $MoC/SiO_2$. In some embodiments, any of the foregoing catalyst compositions may be supported on $SiO_2$, $ZrO_2$, $Al_2O_3$, $TiO_2$ or combinations thereof. In certain embodiments, the catalyst may be a nanowire catalyst and in other embodiments the catalyst is a bulk catalyst.

The catalysts having ODH activity with alternative oxygen sources (e.g., $CO_2$, referred to herein as a $CO_2$-ODH catalyst) have a number of advantages. For example, in some embodiments a method for converting methane to ethylene comprises use of an $O_2$-OCM catalyst in the presence of a $CO_2$-ODH catalyst is provided. Catalytic materials comprising at least one $O_2$-OCM catalyst and at least one $CO_2$-ODH catalyst are also provided in some embodiments. This combination of catalysts results in a higher yield of ethylene (and/or ratio of ethylene to ethane) since the $CO_2$ produced by the OCM reaction is consumed and used to convert ethane to ethylene.

In one embodiment, a method for preparation of ethylene comprises converting methane to ethylene in the presence of two or more catalysts, wherein at least one catalyst is an $O_2$-OCM catalyst and at least one catalyst is a $CO_2$-ODH catalyst. Such methods have certain advantages. For example, the CO2-ODH reaction is endothermic and the $O_2$-OCM reaction is exothermic, and thus if the right mixture and/or arrangement of $CO_2$-ODH and $O_2$-OCM catalysts is used, the methods are particularily useful for controlling the exotherm of the OCM reaction. In some embodiments, the catalyst bed comprises a mixture of $O_2$-OCM catalyst and CO2-ODH catalysts. The mixture may be in a ratio of 1:99 to 99:1. The two catalysts work synergistically as the $O_2$-OCM catalyst supplies the $CO_2$-ODH catalyst with the necessary carbon dioxide and the endothermic nature of the $C_2$-OCM reaction serves to control the exotherm of the overall reaction.

Since the gas composition will tend to become enriched in $CO_2$ as it flows through the catalyst bed (i.e., as the OCM reaction proceeds, more $CO_2$ is produced), some embodiments of the present invention provide an OCM method wherein the catalyst bed comprises a gradient of catalysts which changes from a high concentration of $O_2$-OCM catalysts at the front of the bed to a high concentration of $CO_2$-ODH catalysts at the end of the catalyst bed.

The $O_2$-ODH catalyst and $CO_2$-ODH catalyst may have the same or different compositions. For example, in some embodiments the $O_2$-ODH catalyst and $CO_2$-ODH catalyst have the same composition but different morphologies (e.g., nanowire, bent nanowire, bulk, etc.). In other embodiments the $O_2$-ODH and the $CO_2$-ODH catalyst have different compositions.

In other embodiments, the catalyst bed comprises alternating layers of $O_2$-OCM and $CO_2$-ODH catalysts. The catalyst layer stack may begin with a layer of $O_2$-OCM catalyst, so that it can supply the next layer (e.g., a CO2-ODH layer) with the necessary $CO_2$. The $O_2$-OCM layer thickness may be optimized to be the smallest at which $O_2$ conversion is 100% and thus the $CH_4$ conversion of the layer is maximized. The catalyst bed may comprise any number of catalyst layers, for example the overall number of layers may be optimized to maximize the overall $CH_4$ conversion and C2 selectivity.

In some embodiments, the catalyst bed comprises alternating layers of low temperature $O_2$-OCM catalysts and high temperature $CO_2$-ODH catalysts. Since the $CO_2$-ODH reaction is endothermic, the layers of $CO_2$-ODH catalyst may be sufficiently thin such that in can be "warmed up" by the hotspots of the $O_2$-OCM layers. The endothermic nature of the $CO_2$-ODH reaction can be advantageous for the overall thermal management of an OCM reactor. In some embodiments, the $CO_2$-ODH catalyst layers act as "internal" cooling for the $O_2$-OCM layers, thus simplifying the requirements for the cooling, for example in a tubular reactor. Therefore, an interesting cycle takes place with the endothermic reaction providing the necessary heat for the endothermic reaction and the endothermic reaction providing the necessary cooling for the exothermic reaction.

Accordingly, one embodiment of the present invention is a method for the oxidative coupling of methane, wherein the method comprises conversion of methane to ethane and/or ethylene in the presence of a catalytic material, and wherein the catalytic material comprises a bed of alternating layers of $O_2$-OCM catalysts and $CO_2$-ODH catalysts. In other embodiments the bed comprises a mixture (i.e., not alternating layers) of $O_2$-OCM catalysts and $CO_2$-ODH catalysts. Such methods increase the ethylene yield and/or ratio of ethylene to ethane compared to other known methods.

In other embodiments, the OCM methods include use of a jacketed reactor with the exothermic $O_2$-OCM reaction in the core and the endothermic $CO_2$-ODH reaction in the mantel. In other embodiments, the unused $CO_2$ can be recycled and reinjected into the reactor, optionally with the recycled $CH_4$. Additional $CO_2$ can also be injected to increase the overall methane conversion and help reduce greenhouse gases.

In other embodiments, the reactor comprises alternating stages of $O_2$-OCM catalyst beds and $CO_2$-ODH catalyst beds. The $CO_2$ necessary for the $CO_2$-ODH stages is provided by the $O_2$-OCM stage upstream. Additional $CO_2$ may also be injected. The $O_2$ necessary for the subsequent $O_2$-OCM stages is injected downstream from the $CO_2$-ODH stages. The $CO_2$-ODH stages may provide the necessary cooling for the $O_2$-OCM stages. Alternatively, separate cooling may be provided. Likewise, if necessary the inlet gas of the $CO_2$-ODH stages can be additionally heated, the $CO_2$-ODH bed can be heated or both.

In related embodiments, the $CO_2$ naturally occurring in natural gas is not removed prior to performing the OCM, alternatively $CO_2$ is added to the feed with the recycled methane. Instead the $CO_2$ containing natural gas is used as a feedstock for $CO_2$-ODH, thus potentially saving a separation step. The amount of naturally occurring $CO_2$ in natural gas depends on the well and the methods can be adjusted accordingly depending on the source of the natural gas.

3. Carbon Dioxide Reforming of Methane

Carbon dioxide reforming (CDR) of methane is an attractive process for converting $CO_2$ in process streams or naturally occurring sources into the valuable chemical product, syngas (a mixture of hydrogen and carbon monoxide). Syngas can then be manufactured into a wide range of hydrocarbon products through processes such as the Fischer-Tropsch synthesis (discussed below) to form liquid fuels including methanol, ethanol, diesel, and gasoline. The result is a powerful technique to not only remove $CO_2$ emissions but also create a new alternative source for fuels that are not derived from petroleum crude oil. The CDR reaction with methane is exemplified in reaction scheme (11).

$$CO_2 + CH_4 \rightarrow 2CO + 2H_2 \quad (11)$$

Unfortunately, no established industrial technology for CDR exists today in spite of its tremendous potential value. While not wishing to be bound by theory, it is thought that the primary problem with CDR is due to side-reactions from catalyst deactivation induced by carbon deposition via the Boudouard reaction (reaction scheme (12)) and/or methane cracking (reaction scheme (13)) resulting from the high temperature reaction conditions. The occurrence of the coking effect is intimately related to the complex reaction mechanism, and the associated reaction kinetics of the catalysts employed in the reaction.

$$2CO \rightarrow C + CO_2 \qquad (12)$$

$$CH_4 \rightarrow C + 2H_2 \qquad (13)$$

Figure 9:
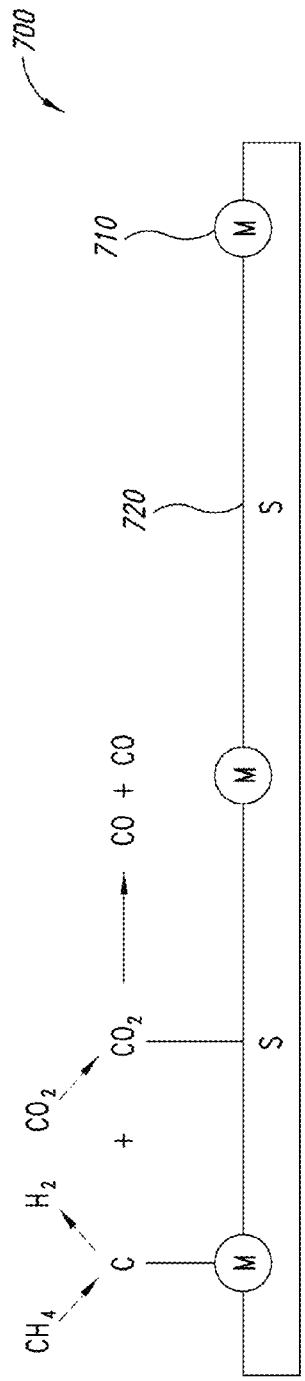
FIG. 9 schematically depicts a carbon dioxide reforming reaction on a catalytic surface.

While not wishing to be bound by theory, the CDR reaction is thought to proceed through a multistep surface reaction mechanism. FIG. 9 schematically depicts a CDR reaction 700, in which activation and dissociation of $CH_4$ occurs on the metal catalyst surface 710 to form intermediate "M-C". At the same time, absorption and activation of $CO_2$ takes place at the oxide support surface 720 to provide intermediate "S—$CO_2$", since the carbon in a $CO_2$ molecule as a Lewis acid tends to react with the Lewis base center of an oxide. The final step is the reaction between the M-C species and the activated S—$CO_2$ to form CO.

In one embodiment, the present disclosure provides nanowires, for example the exemplary nanowires disclosed herein, which are useful as catalysts for the carbon dioxide reforming of methane. For example, in one embodiment the nanowires are useful as catalysts in a CDR reaction for the production of syn gas.

Improvements to the yield, selectivity, and/or conversion in the CDR reaction employing bulk catalysts are needed. Accordingly, in one embodiment, the nanowires posses a catalytic activity in the CDR reaction such that the yield, selectivity, and/or conversion is better than when the CDR reaction is catalyzed by a corresponding bulk catalyst. In one embodiment, the disclosure provides a nanowire having a catalytic activity such that the conversion of $CO_2$ to CO in the CDR reaction is greater than at least 1.1 times, 1.25 times, 1.50 times, 2.0 times, 3.0 times, or 4.0 times the conversion of $CO_2$ to CO compared to the same reaction under the same conditions but performed with a catalyst prepared from bulk material having the same chemical composition as the nanowire. In other embodiments, the conversion of $CO_2$ to CO in a CDR reaction catalyzed by the nanowire is greater than 10%, greater than 20%, greater than 30%, greater than 50%, greater than 75%, or greater than 90%.

In another embodiment, the disclosure provides a nanowire having a catalytic activity such that the yield of CO in a CDR reaction is greater than at least 1.1 times, 1.25 times, 1.50 times, 2.0 times, 3.0 times, or 4.0 times the yield of CO compared to the same reaction under the same conditions but performed with a catalyst prepared from bulk material having the same chemical composition as the nanowire. In some embodiments the yield of CO in a CDR reaction catalyzed by the nanowire is greater than 10%, greater than 20%, greater than 30%, greater than 50%, greater than 75%, or greater than 90%.

In another embodiment, the disclosure provides a nanowire having a catalytic activity in a CDR reaction such that the nanowire has the same or better catalytic activity, but at a lower temperature, compared a catalyst prepared from bulk material having the same chemical composition as the nanowire. In some embodiments the catalytic activity of the nanowires in a CDR reaction is the same or better than the catalytic activity of a catalyst prepared from bulk material having the same chemical composition as the nanowire, but at a temperature of at least 20° C. less. In some embodiments the catalytic activity of the nanowires in a CDR reaction is the same or better than the catalytic activity of a catalyst prepared from bulk material having the same chemical composition as the nanowire, but at a temperature of at least 50° C. less. In some embodiments the catalytic activity of the nanowires in a CDR reaction is the same or better than the catalytic activity of a catalyst prepared from bulk material having the same chemical composition as the nanowire, but at a temperature of at least 100° C. less. In some embodiments the catalytic activity of the nanowires in a CDR reaction is the same or better than the catalytic activity of a catalyst prepared from bulk material having the same chemical composition as the nanowire, but at a temperature of at least 200° C. less.

In another embodiment, the disclosure provides a nanowire having a catalytic activity such that the selectivity for CO in a CDR reaction is greater than at least 1.1 times, 1.25 times, 1.50 times, 2.0 times, 3.0 times, or 4.0 times the selectivity for CO compared to the same reaction under the same conditions but performed with a catalyst prepared from bulk material having the same chemical composition as the nanowire. In other embodiments, the selectivity for CO in a CDR reaction catalyzed by the nanowire is greater than 10%, greater than 20%, greater than 30%, greater than 50%, greater than 75%, or greater than 90%.

In one embodiment, the nanowires disclosed herein enable efficient conversion of $CO_2$ to CO in the CDR reaction at temperatures less than when the corresponding bulk material is used as a catalyst. For example, in one embodiment, the nanowires enable efficient conversion (i.e., high yield, conversion, and/or selectivity) of $CO_2$ to CO at temperatures of less than 900° C., less than 800° C., less than 700° C., less than 600° C., or less than 500° C.

4. Fischer-Tropsch Synthesis

Fischer-Tropsch synthesis (FTS) is a valuable process for converting synthesis gas (i.e., CO and $H_2$) into valuable hydrocarbon fuels, for example, light alkenes, gasoline, diesel fuel, etc. FTS has the potential to reduce the current reliance on the petroleum reserve and take advantage of the abundance of coal and natural gas reserves. Current FTS processes suffer from poor yield, selectivity, conversion, catalyst deactivation, poor thermal efficiency and other related disadvantages. Production of alkanes via FTS is shown in reaction scheme (14), wherein n is an integer.

$$CO + 2H_2 \rightarrow (1/n)(C_nH_{2n}) + H_2O \qquad (14)$$

In one embodiment, nanowires are provided which are useful as catalysts in FTS processes. For example, in one embodiment the nanowires are useful as catalysts in a FTS process for the production of alkanes.

Improvements to the yield, selectivity, and/or conversion in FTS processes employing bulk catalysts are needed. Accordingly, in one embodiment, the nanowires posses a catalytic activity in an FTS process such that the yield, selectivity, and/or conversion is better than when the FTS process is catalyzed by a corresponding bulk catalyst. In one embodiment, the disclosure provides a nanowire having a catalytic activity such that the conversion of CO to alkane in an FTS process is greater than at least 1.1 times, 1.25 times, 1.50 times, 2.0 times, 3.0 times, or 4.0 times the conversion of CO to alkane compared to the same reaction under the same conditions but performed with a catalyst prepared from bulk material having the same chemical composition as the nanowire. In other embodiments, the conversion of CO to alkane in an FTS process catalyzed by the nanowire is greater than 10%, greater than 20%, greater than 30%, greater than 50%, greater than 75%, or greater than 90%.

In another embodiment, the disclosure provides a nanowire having a catalytic activity in an FTS process such that the nanowire has the same or better catalytic activity, but at a lower temperature, compared a catalyst prepared from bulk material having the same chemical composition as the nanowire. In some embodiments the catalytic activity of the nanowires in an FTS process is the same or better than the catalytic activity of a catalyst prepared from bulk material having the same chemical composition as the nanowire, but at a temperature of at least 20° C. less. In some embodiments the catalytic activity of the nanowires in an FTS process is the same or better than the catalytic activity of a catalyst prepared from bulk material having the same chemical composition as the nanowire, but at a temperature of at least 50° C. less. In some embodiments the catalytic activity of the nanowires in an FTS process is the same or better than the catalytic activity of a catalyst prepared from bulk material having the same chemical composition as the nanowire, but at a temperature of at least 100° C. less. In some embodiments the catalytic activity of the nanowires in an FTS process is the same or better than the catalytic activity of a catalyst prepared from bulk material having the same chemical composition as the nanowire, but at a temperature of at least 200° C. less.

In another embodiment, the disclosure provides a nanowire having a catalytic activity such that the yield of alkane in a FTS process is greater than at least 1.1 times, 1.25 times, 1.50 times, 2.0 times, 3.0 times, or 4.0 times the yield of alkane compared to the same reaction under the same conditions but performed with a catalyst prepared from bulk material having the same chemical composition as the nanowire. In some embodiments the yield of alkane in an FTS process catalyzed by the nanowire is greater than 10%, greater than 20%, greater than 30%, greater than 50%, greater than 75%, or greater than 90%.

In another embodiment, the disclosure provides a nanowire having a catalytic activity such that the selectivity for alkanes in an FTS process is greater than at least 1.1 times, 1.25 times, 1.50 times, 2.0 times, 3.0 times, or 4.0 times the selectivity for alkanes compared to the same reaction under the same conditions but performed with a catalyst prepared from bulk material having the same chemical composition as the nanowire. In other embodiments, the selectivity for alkanes in an FTS process catalyzed by the nanowire is greater than 10%, greater than 20%, greater than 30%, greater than 50%, greater than 75%, or greater than 90%.

In one embodiment, the nanowires disclosed herein enable efficient conversion of CO to alkanes in a CDR process at temperatures less than when the corresponding bulk material is used as a catalyst. For example, in one embodiment, the nanowires enable efficient conversion (i.e., high yield, conversion, and/or selectivity) of CO to alkanes at temperatures of less than 400° C., less than 300° C., less than 250° C., less than 200° C., less the 150° C., less than 100° C. or less than 50° C.

5. Oxidation of CO

Carbon monoxide (CO) is a toxic gas and can convert hemoglobin to carboxyhemoglobin resulting in asphyxiation. Dangerous levels of CO can be reduced by oxidation of CO to $CO_2$ as shown in reaction scheme 15:

$$CO + \tfrac{1}{2}O_2 \rightarrow CO_2 \qquad (15)$$

Catalysts for the conversion of CO into $CO_2$ have been developed but improvements to the known catalysts are needed. Accordingly in one embodiment, the present disclosure provides nanowires useful as catalysts for the oxidation of CO to $CO_2$.

In one embodiment, the nanowires posses a catalytic activity in a process for the conversion of CO into $CO_2$ such that the yield, selectivity, and/or conversion is better than when the oxidation of CO into $CO_2$ is catalyzed by a corresponding bulk catalyst. In one embodiment, the disclosure provides a nanowire having a catalytic activity such that the conversion of CO to $CO_2$ is greater than at least 1.1 times, 1.25 times, 1.50 times, 2.0 times, 3.0 times, or 4.0 times the conversion of CO to $CO_2$ compared to the same reaction under the same conditions but performed with a catalyst prepared from bulk material and having the same chemical composition as the nanowire. In other embodiments, the conversion of CO to $CO_2$ catalyzed by the nanowire is greater than 10%, greater than 20%, greater than 30%, greater than 50%, greater than 75%, or greater than 90%.

In another embodiment, the disclosure provides a nanowire having a catalytic activity such that the yield of $CO_2$ from the oxidation of CO is greater than at least 1.1 times, 1.25 times, 1.50 times, 2.0 times, 3.0 times, or 4.0 times the yield of $CO_2$ compared to the same reaction under the same conditions but performed with a catalyst prepared from bulk material having the same chemical composition as the nanowire. In some embodiments the yield of $CO_2$ from the oxidation of CO catalyzed by the nanowire is greater than 10%, greater than 20%, greater than 30%, greater than 50%, greater than 75%, or greater than 90%.

In another embodiment, the disclosure provides a nanowire having a catalytic activity in an oxidation of CO reaction such that the nanowire has the same or better catalytic activity, but at a lower temperature, compared a catalyst prepared from bulk material having the same chemical composition as the nanowire. In some embodiments the catalytic activity of the nanowires in an oxidation of CO reaction is the same or better than the catalytic activity of a catalyst prepared from bulk material having the same chemical composition as the nanowire, but at a temperature of at least 20° C. less. In some embodiments the catalytic activity of the nanowires in an oxidation of CO reaction is the same or better than the catalytic activity of a catalyst prepared from bulk material having the same chemical composition as the nanowire, but at a temperature of at least 50° C. less. In some embodiments the catalytic activity of the nanowires in an oxidation of CO reaction is the same or better than the catalytic activity of a catalyst prepared from bulk material having the same chemical composition as the nanowire, but at a temperature of at least 100° C. less. In some embodiments the catalytic activity of the nanowires in an oxidation of CO reaction is the same or better than the catalytic activity of a catalyst prepared from bulk material having the same chemical composition as the nanowire, but at a temperature of at least 200° C. less.

In another embodiment, the disclosure provides a nanowire having a catalytic activity such that the selectivity for $CO_2$ in the oxidation of CO is greater than at least 1.1 times, 1.25 times, 1.50 times, 2.0 times, 3.0 times, or 4.0 times the selectivity for $CO_2$ compared to the same reaction under the same conditions but performed with a catalyst prepared from bulk material having the same chemical composition as the nanowire. In other embodiments, the selectivity for $CO_2$ in the oxidation of CO catalyzed by the nanowire is greater than 10%, greater than 20%, greater than 30%, greater than 50%, greater than 75%, or greater than 90%.

In one embodiment, the nanowires disclosed herein enable efficient conversion of CO to $CO_2$ at temperatures less than when the corresponding bulk material is used as a catalyst. For example, in one embodiment, the nanowires enable efficient conversion (i.e., high yield, conversion, and/or selectivity) of CO to $CO_2$ at temperatures of less than 500° C., less than 400° C., less than 300° C., less than 200° C., less than 100° C., less than 50° C. or less than 20° C.

Although various reactions have been described in detail, the disclosed nanowires are useful as catalysts in a variety of other reactions. In general, the disclosed nanowires find utility in any reaction utilizing a heterogeneous catalyst and have a catalytic activity such that the yield, conversion, and/or selectivity in reaction catalyzed by the nanowires is better than the yield, conversion and/or selectivity in the same reaction catalyzed by a corresponding bulk catalyst.

6. Combustion of Hydrocarbons

In another embodiment, the present disclosure provides a nanowire having catalytic activity in a reaction for the catalyzed combustion of hydrocarbons. Such catalytic reactions find utility in catalytic converters for automobiles, for example by removal of unburned hydrocarbons in the exhaust by catalytic combustion or oxidation of soot captured on catalyzed particle filters resulting in reduction on diesel emissions from the engine. When running "cold", the exhausts temperature of a diesel engine is quite low, thus a low temperature catalyst, such as the disclosed nanowires, is needed to efficiently eliminate all unburned hydrocarbons. In addition, in case of soot removal on catalyzed particulate filters, intimate contact between the soot and the catalyst is require; the open mesh morphology of nanowire catalyst coating is advantageous to promote such intimate contact between soot and oxidation catalyst.

In contrast to a corresponding bulk catalyst, Applicants have found that certain nanowires, for example the exemplary nanowires disclosed herein, posses a catalytic activity (for example because of their morphology) in the combustion of hydrocarbons or soot such that the yield, selectivity, and/or conversion is better than when the combustion of hydrocarbons is catalyzed by a corresponding bulk catalyst. In one embodiment, the disclosure provides a nanowire having a catalytic activity such that the combustion of hydrocarbons is greater than at least 1.1 times, 1.25 times, 1.50 times, 2.0 times, 3.0 times, or 4.0 times the combustion of hydrocarbons compared to the same reaction under the same conditions but performed with a catalyst prepared from bulk material having the same chemical composition as the nanowire. In other embodiments, the total combustion of hydrocarbons catalyzed by the nanowire is greater than 10%, greater than 20%, greater than 30%, greater than 50%, greater than 75%, or greater than 90%.

In another embodiment, the disclosure provides a nanowire having a catalytic activity such that the yield of combusted hydrocarbon products is greater than at least 1.1 times, 1.25 times, 1.50 times, 2.0 times, 3.0 times, or 4.0 times the yield of combusted hydrocarbon products compared to the same reaction under the same conditions but performed with a catalyst prepared from bulk material having the same chemical composition as the nanowire. In some embodiments the yield of combusted hydrocarbon products in a reaction catalyzed by the nanowire is greater than 10%, greater than 20%, greater than 30%, greater than 50%, greater than 75%, or greater than 90%.

The stability of the nanowires is defined as the length of time a catalyst will maintain its catalytic performance without a significant decrease in performance (e.g., a decrease >20%, >15%, >10%, >5%, or greater than 1% in hydrocarbon or soot combustion activity). In some embodiments, the nanowires have stability under conditions required for the hydrocarbon combustion reaction of >1 hr, >5 hrs, >10 hrs, >20 hrs, >50 hrs, >80 hrs, >90 hrs, >100 hrs, >150 hrs, >200 hrs, >250 hrs, >300 hrs, >350 hrs, >400 hrs, >450 hrs, >500 hrs, >550 hrs, >600 hrs, >650 hrs, >700 hrs, >750 hrs, >800 hrs, >850 hrs, >900 hrs, >950 hrs, >1,000 hrs, >2,000 hrs, >3,000 hrs, >4,000 hrs, >5,000 hrs, >6,000 hrs, >7,000 hrs, >8,000 hrs, >9,000 hrs, >10,000 hrs, >11,000 hrs, >12,000 hrs, >13,000 hrs, >14,000 hrs, >15,000 hrs, >16,000 hrs, >17,000 hrs, >18,000 hrs, >19,000 hrs, >20,000 hrs, >1 yrs, >2 yrs, >3 yrs, >4 yrs or >5 yrs.

In another embodiment, the disclosure provides a nanowire having a catalytic activity in the combustion of hydrocarbons such that the nanowire has the same or better catalytic activity, but at a lower temperature, compared a catalyst prepared from bulk material having the same chemical composition as the nanowire. In some embodiments the catalytic activity of the nanowires in the combustion of hydrocarbons is the same or better than the catalytic activity of a catalyst prepared from bulk material having the same chemical composition as the nanowire, but at a temperature of at least 20° C. less. In some embodiments the catalytic activity of the nanowires in the combustion of hydrocarbons is the same or better than the catalytic activity of a catalyst prepared from bulk material having the same chemical composition as the nanowire, but at a temperature of at least 50° C. less. In some embodiments the catalytic activity of the nanowires in the combustion of hydrocarbons is the same or better than the catalytic activity of a catalyst prepared from bulk material having the same chemical composition as the nanowire, but at a temperature of at least 100° C. less. In some embodiments the catalytic activity of the nanowires in the combustion of hydrocarbons is the same or better than the catalytic activity of a catalyst prepared from bulk material having the same chemical composition as the nanowire, but at a temperature of at least 200° C. less.

7. Evaluation of Catalytic Properties

To evaluate the catalytic properties of the nanowires in a given reaction, for example those reactions discussed above, various methods can be employed to collect and process data including measurements of the kinetics and amounts of reactants consumed and the products formed. In addition to allowing for the evaluation of the catalytic performances, the data can also aid in designing large scale reactors, experimentally validating models and optimizing the catalytic process.

One exemplary methodology for collecting and processing data is depicted in FIG. 10. Three main steps are involved. The first step (block 750) comprises the selection of a reaction and catalyst. This influences the choice of reactor and how it is operated, including batch, flow, etc. (block 754). Thereafter, the data of the reaction are compiled and analyzed (block 760) to provide insights to the mechanism, rates and process optimization of the catalytic reaction. In addition, the data provide useful feedbacks for further design modifications of the reaction conditions. Additional methods for evaluating catalytic performance in the laboratory and industrial settings are described in, for example, Bartholomew, C. H. et al. *Fundamentals of Industrial Catalytic Processes*, Wiley-AIChE; 2Ed (1998).

As an example, in a laboratory setting, an Altamira Benchcat 200 can be employed using a 4 mm ID diameter quartz tube with a 0.5 mm ID capillary downstream. Quartz tubes with 2 mm or 6 mm ID can also be used. Nanowires are tested in a number of different dilutions and amounts. In some embodiments, the range of testing is between 10 and 300 mg. In some embodiments, the nanowires are diluted with a non-reactive diluent. This diluent can be quartz ($SiO_2$) or other inorganic materials, which are known to be inert in the reaction condition. The purpose of the diluent is to minimize hot spots and provide an appropriate loading into the reactor. In addition, the catalyst can be blended with less catalytically active components as described in more detail above.

In a typical procedure, 50 mg is the total charge of nanowire, optionally including diluent. On either side of the nanowires a small plug of glass wool is loaded to keep the nanowires in place. A thermocouple is placed on the inlet side of the nanowire bed into the glass wool to get the temperature in the reaction zone. Another thermocouple can be placed on the downstream end of the nanowire bed into the catalyst bed itself to measure the exotherms, if any.

When blending the pure nanowire with diluent, the following exemplary procedure may be used: x (usually 10-50) mg of the catalyst (either bulk or test nanowire catalyst) is blended with (100-x) mg of diluent. Thereafter, about 2 ml of ethanol or water is added to form a slurry mixture, which is then sonicated for about 10 minutes. The slurry is then dried in an oven at about 100-140° C. for 2 hours to remove solvent. The resulting solid mixture is then scraped out and loaded into the reactor between the plugs of quartz wool.

Once loaded into the reactor, the reactor is inserted into the Altamira instrument and furnace and then a temperature and flow program is started. In some embodiment, the total flow is 50 to 100 sccm of gases but this can be varied and programmed with time. In one embodiment, the temperatures range from 450° C. to 900° C. The reactant gases comprise air or oxygen (diluted with nitrogen or argon) and methane in the case of the OCM reaction and gas mixtures comprising ethane and/or propane with oxygen for oxidative dehydrogenation (ODH) reactions. Other gas mixtures can be used for other reactions.

The primary analysis of these oxidation catalysis runs is the Gas Chromatography (GC) analysis of the feed and effluent gases. From these analyses, the conversion of the oxygen and alkane feed gases can easily be attained and estimates of yields and selectivities of the products and by-products can be determined.

The GC method developed for these experiments employs 4 columns and 2 detectors and a complex valve switching system to optimize the analysis. Specifically, a flame ionization detector (FID) is used for the analysis of the hydrocarbons only. It is a highly sensitive detector that produces accurate and repeatable analysis of methane, ethane, ethylene, propane, propylene and all other simple alkanes and alkenes up to five carbons in length and down to ppm levels.

There are two columns in series to perform this analysis, the first is a stripper column (alumina) which traps polar materials (including the water by-product and any oxygenates generated) until back-flushed later in the cycle. The second column associated with the FID is a capillary alumina column known as a PLOT column, which performs the actual separation of the light hydrocarbons. The water and oxygenates are not analyzed in this method.

For the analysis of the light non-hydrocarbon gases, a Thermal Conductivity Detector (TCD) may be employed which also employees two columns to accomplish its analysis. The target molecules for this analysis are $CO_2$, ethylene, ethane, hydrogen, oxygen, nitrogen, methane and CO. The two columns used here are a porous polymer column known as the Hayes Sep N, which performs some of the separation for the $CO_2$, ethylene and ethane. The second column is a molecular sieve column, which uses size differentiation to perform the separation. It is responsible for the separation of $H_2$, $O_2$, $N_2$, methane and CO.

There is a sophisticated and timing sensitive switching between these two columns in the method. In the first 2 minutes or so, the two columns are operating in series but at about 2 minutes, the molecular sieve column is by-passed and the separation of the first 3 components is completed. At about 5-7 minutes, the columns are then placed back in series and the light gases come off of the sieve according to their molecular size.

The end result is an accurate analysis of all of the aforementioned components from these fixed-bed, gas phase reactions. Analysis of other reactions and gases not specifically described above can be performed in a similar manner.

8. Downstream Products

Figure 11:
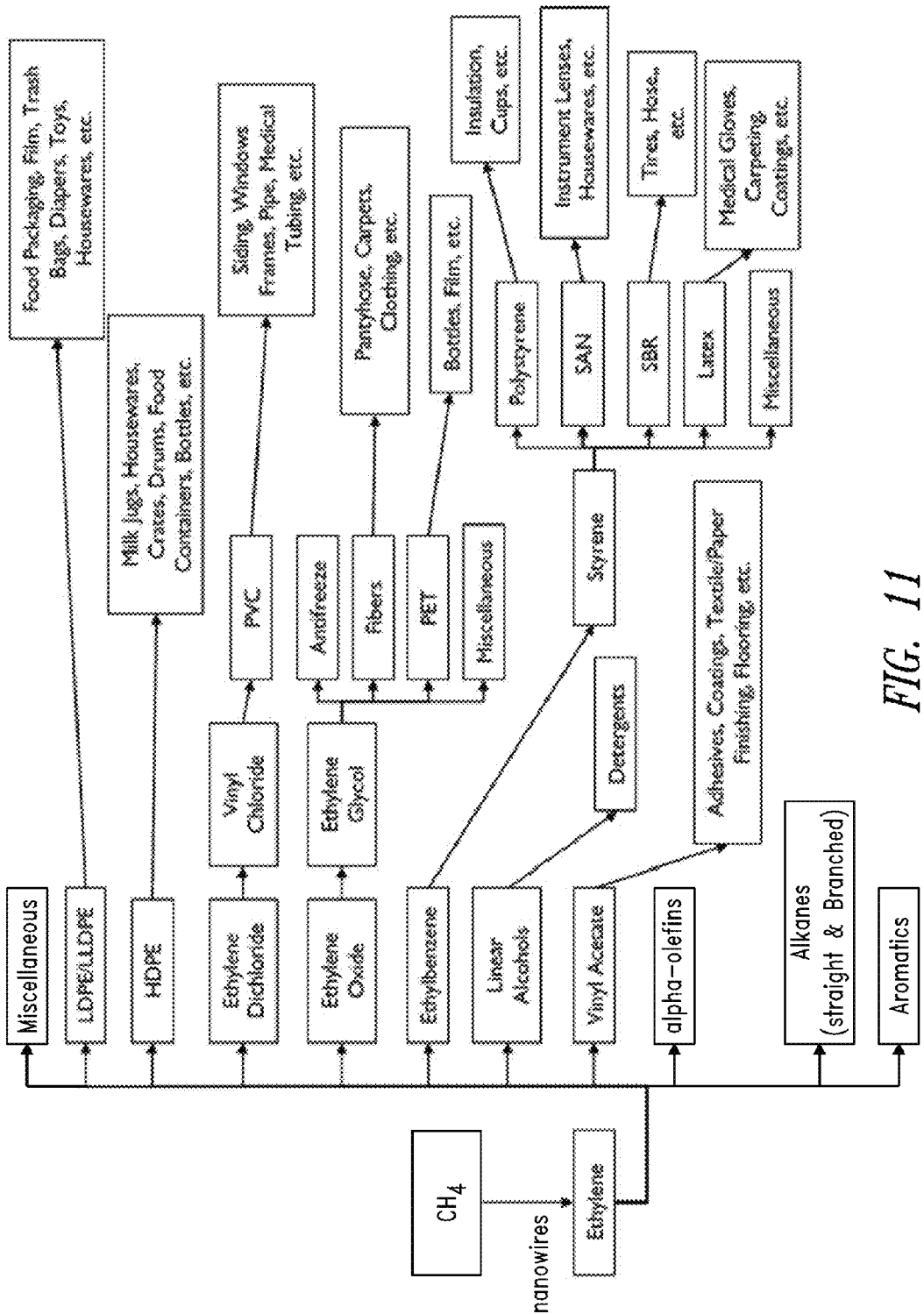
FIG. 11 illustrates a number of downstream products of ethylene.

As noted above, in one embodiment the present disclosure is directed to nanowires useful as catalysts in reactions for the preparation of a number of valuable hydrocarbon compounds. For example, in one embodiment the nanowires are useful as catalysts for the preparation of ethylene from methane via the OCM reaction. In another embodiment, the nanowires are useful as catalysts for the preparation of ethylene or propylene via oxidative dehydrogenation of ethane or propane, respectively. Ethylene and propylene are valuable compounds, which can be converted into a variety of consumer products. For example, as shown in FIG. 11, ethylene can be converted into many various compounds including low density polyethylene, high density polyethylene, ethylene dichloride, ethylene oxide, ethylbenzene, linear alcohols, vinyl acetate, alkanes, alpha olefins, various hydrocarbon-based fuels, ethanol and the like. These compounds can then be further processed using methods well known to one of ordinary skill in the art to obtain other valuable chemicals and consumer products (e.g. the downstream products shown in FIG. 11). Propylene can be analogously converted into various compounds and consumer goods including polypropylenes, propylene oxides, propanol, and the like.

Accordingly, in one embodiment the invention is directed to a method for the preparation of C2 hydrocarbons via the OCM reaction, the method comprises contacting a catalyst as described herein with a gas comprising methane. In some embodiments the C2 hydrocarbons are selected from ethane and ethylene. In other embodiments the disclosure provides a method of preparing any of the downstream products of ethylene noted in FIG. 11. The method comprises converting ethylene into a downstream product of ethylene, wherein the ethylene has been prepared via a catalytic reaction employing a nanowire, for example any of the nanowires disclosed herein. In some embodiments, the downstream product of ethylene is low density polyethylene, high density polyethylene, ethylene dichloride, ethylene oxide, ethylbenzene, ethanol or vinyl acetate from ethylene, wherein the ethylene has been prepared as described above. In other embodiments, the downstream product of ethylene is natural gasoline. In still other embodiments, the downstream product of ethylene comprises 1-hexene, 1-octene, hexane, octane, benzene, toluene, xylene or combinations thereof.

In another embodiment, a process for the preparation of ethylene from methane comprising contacting a mixture comprising oxygen and methane at a temperature below 900° C., below 850° C., below 800° C., below 750° C., below 700° C. or below 650° C. with a nanowire catalyst as disclosed herein is provided.

In another embodiment, the disclosure provides a method of preparing a product comprising low density polyethylene, high density polyethylene, ethylene dichloride, ethylene oxide, ethylbenzene, ethanol or vinyl acetate, alkenes, alkanes, aromatics, alcohols, or mixtures thereof. The method comprises converting ethylene into low density polyethylene, high density polyethylene, ethylene dichloride, ethylene oxide, ethylbenzene, ethanol or vinyl acetate, wherein the ethylene has been prepared via a catalytic reaction employing a nanowires, for example any of the exemplary nanowires disclosed herein.

In more specific embodiments of any of the above methods, the ethylene is produced via an OCM or ODH reaction or combinations thereof.

In one particular embodiment, the disclosure provides a method of preparing a downstream product of ethylene and/or ethane, wherein the downstream product is a hydrocarbon fuel. For example, the downstream product of ethylene may be a hydrocarbon fuel such as natural gasoline or a $C_4$-$C_{14}$ hydrocarbon, including alkanes, alkenes and aromatics. Some specific examples include 1-butene, 1-hexene, 1-octene, hexane, octane, benzene, toluene, xylenes and the like. The method comprises converting methane into ethylene, ethane or combinations thereof by use of a catalytic nanowire, for example any of the catalytic nanowires disclosed herein, and further oligomerizing the ethylene and/or ethane to prepare a downstream product of ethylene and/or ethane. For example, the methane may be converted to ethylene, ethane or combinations thereof via the OCM reaction as discussed above. The catalytic nanowire may be any nanowire and is not limited with respect to morphology or composition. The catalytic nanowire may be an inorganic catalytic polycrystalline nanowire, the nanowire having a ratio of effective length to actual length of less than one and an aspect ratio of greater than ten as measured by TEM in bright field mode at 5 keV, wherein the nanowire comprises one or more elements from any of Groups 1 through 7, lanthanides, actinides or combinations thereof. Alternatively, the catalytic nanowire may be an inorganic nanowire comprising one or more metal elements from any of Groups 1 through 7, lanthanides, actinides or combinations thereof and a dopant comprising a metal element, a semi-metal element, a non-metal element or combinations thereof. The nanowires may additionally comprise any number of doping elements as discussed above.

Figure 21:
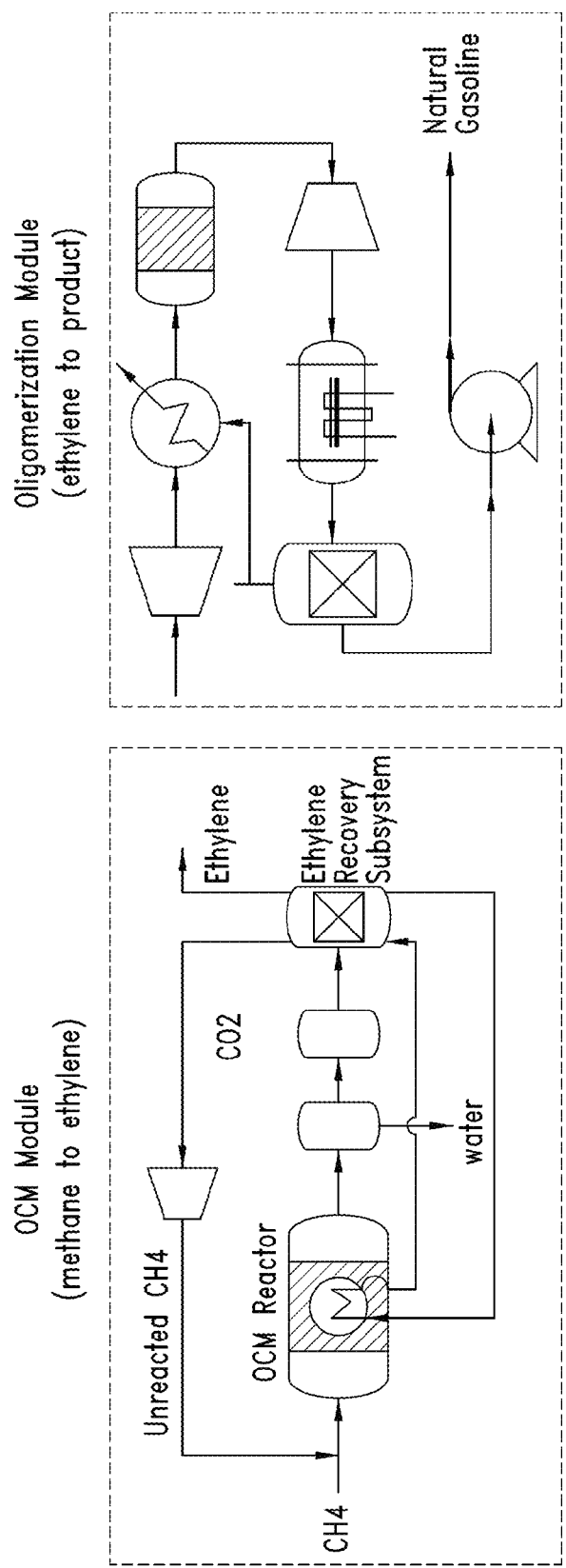
FIG. 21 depicts OCM and ethylene oligomerization modules.

As depicted in FIG. 21, the method begins with charging methane (e.g., as a component in natural gas) into an OCM reactor. The OCM reaction may then be performed utilizing a nanowire under any variety of conditions. Water and $CO_2$ are optionally removed from the effluent and unreacted methane is recirculated to the OCM reactor.

Ethylene is recovered and charged to an oligomerization reactor. Optionally the ethylene stream may contain $CO_2$, $H_2O$, $N_2$, ethane, C3's and/or higher hydrocarbons. Oligomerization to higher hydrocarbons (e.g., $C_4$-$C_{14}$) then proceeds under any number of conditions known to those of skill in the art. For example oligomerization may be effected by use of any number of catalysts known to those skilled in the art. Examples of such catalysts include catalytic zeolites, crystalline borosilicate molecular sieves, homogeneous metal halide catalysts, Cr catalysts with pyrrole ligands or other catalysts. Exemplary methods for the conversion of ethylene into higher hydrocarbon products are disclosed in the following references: Catalysis Science & Technology (2011), 1(1), 69-75; Coordination Chemistry Reviews (2011), 255(7-8), 861-880; Eur. Pat. Appl. (2011), EP 2287142 A1 20110223; Organometallics (2011), 30(5), 935-941; Designed Monomers and Polymers (2011), 14(1), 1-23; Journal of Organometallic Chemistry 689 (2004) 3641-3668; Chemistry—A European Journal (2010), 16(26), 7670-7676; Acc. Chem. Res. 2005, 38, 784-793; Journal of Organometallic Chemistry, 695 (10-11): 1541-1549 May 15, 2010; Catalysis Today Volume 6, Issue 3, January 1990, Pages 329-349; U.S. Pat. Nos. 5,968,866; 6,800,702; 6,521,806; 7,829,749; 7,867,938; 7,910,670; 7,414,006 and Chem. Commun., 2002, 858-859, each of which are hereby incorporated in their entirety by reference.

In certain embodiments, the exemplary OCM and oligomerization modules depicted in FIG. 21 may be adapted to be at the site of natural gas production, for example a natural gas field. Thus the natural gas can be efficiently converted to more valuable and readily transportable hydrocarbon commodities without the need for transport of the natural gas to a processing facility.

Referring to FIG. 21, "natural gasoline" refers to a mixture of oligomerized ethylene products. In this regard, natural gasoline comprises hydrocarbons containing 5 or more carbon atoms. Exemplary components of natural gasoline include linear, branched or cyclic alkanes, alkenes and alkynes, as well as aromatic hydrocarbons. For example, in some embodiments the natural gasoline comprises 1-pentene, 1-hexene, cyclohexene, 1-octene, benzene, toluene, dimethyl benzene, xylenes, napthalene, or other oligomerized ethylene products or combinations thereof. In some embodiments, natural gasoline may also include C3 and C4 hydrocarbons dissolved within the liquid natural gasoline. This mixture finds particular utility in any number of industrial applications, for example natural gasoline is used as feedstock in oil refineries, as fuel blend stock by operators of fuel terminals, as diluents for heavy oils in oil pipelines and other applications. Other uses for natural gasoline are well-known to those of skill in the art.

EXAMPLES

Example 1

Genetic Engineering/Preparation of Phage

Phage were amplified in DH5 derivative *E. coli* (New England Biolabs, NEB5-alpha F' lq; genotype: F" proA+B+ lacIq Δ(lacZ)M15 zzf::Tn10 (TetR)/fhuA2Δ(argF-lacZ) U169 phoA glnV44 φ80Δ(lacZ)M15 gyrA96 recA1 endA1 thi-1 hsdR17) and purified using standard polyethylene glycol and sodium chloride precipitation protocols as described in the following references: Kay, B. K.; Winter, J.; McCafferty, J. *Phage Display of Peptides and Proteins: A Laboratory Manual; Academic Press*: San Diego (1996); C. F. Barbas, et al., ed., *Phage Display: A Laboratory Manual; Cold Spring Harbor Laboratory Press*, Cold Spring Harbor, N.Y., USA (2001); and Joseph Sambrook and David W. Russell, *Molecular Cloning*, 3rd edition, Cold Spring Harbor Laboratory Press, Cold Spring Harbor, N.Y., USA, 2001.

Example 2

Preparation of Phage Solutions

The phage solutions were additionally purified by centrifuging at an acceleration of 10000 g at least once (until no precipitated material was observed), decanting the supernatant and splitting it in 50 ml containers, which were then stored frozen at −20° C. The frozen phage solutions were thawed only shortly before being used.

The concentration of the phage solutions was measured using a UV-VIS spectrometer. The concentration of each of the frozen phage aliquots was measured prior to use. This spectroscopic method relies on the absorption of the nucleotides in the DNA of the phage and is described in more detail in "Phage Display: A Laboratory Manual" by Barbas, Burton, Scott and Silverman (Cold Spring Harbor Laboratory Press, 2001). The concentration of phage solutions is expressed in pfu/ml (plague forming units per milliliter).

Example 3

Preparation $Mg(OH)_2$ Nanowires

Figure 12:
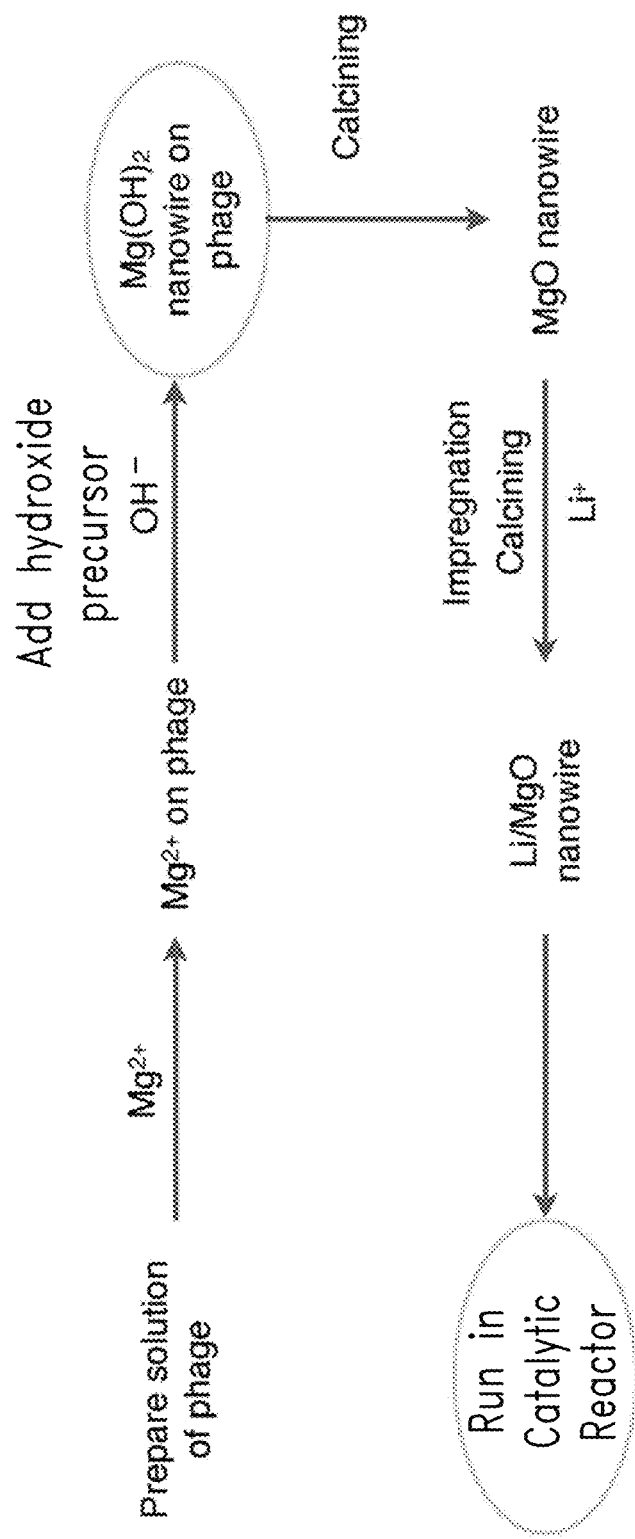
FIG. 12 depicts a representative process for preparing a lithium doped MgO nanowire.

FIG. 12 shows a generic reaction scheme for preparing MgO nanowires (with dopant). First, the phage solution is thawed and its concentration determined according to the method described above. The phage solution is diluted with water to adjust its concentration in the reaction mixture (i.e. with all the ingredients added) to the desired value, typically 5e12 pfu/ml or higher. The reaction container can be anything from a small vial (for milliliter scale reactions) up to large bottles (for liter reaction scale reactions).

A magnesium solution and a base solution are added to the phage solution in order to precipitate $Mg(OH)_2$. The magnesium solution can be of any soluble magnesium salt, e.g. $MgX_2 \cdot 6H_2O$ (X=Cl, Br, I), $Mg(NO_3)_2$, $MgSO_4$, magnesium acetate, etc. The range of the magnesium concentration in the reaction mixture is quite narrow, typically at 0.01M. The combination of the phage concentration and the magnesium concentration (i.e. the ratio between the pVIII proteins and magnesium ions) is very important in determining both the nanowires formation process window and their morphology.

The base can be any alkali metal hydroxide (e.g. LiOH, NaOH, KOH), soluble alkaline earth metal hydroxide (e.g. $Sr(OH)_2$, $Ba(OH)_2$) or any ammonium hydroxide (e.g., $NR_4OH$, R=H, $CH_3$, $C_2H_5$, etc.). Certain selection criteria for the base include: adequate solubility (at least several orders of magnitude higher than $Mg(OH)_2$ for $Mg(OH)_2$ nanowires), high enough strength (pH of the reaction mixture should be at least 11) and an inability to coordinate magnesium (for $Mg(OH)_2$ nanowires) to form soluble products. LiOH is a preferred choice for $Mg(OH)_2$ nanowires formation because lithium may additionally be incorporated in the $Mg(OH)_2$ as a dopant, providing a Li/MgO doped catalyst for OCM.

Another factor concerning the base is the amount of base used or the concentration ratio of $OH^-/Mg^{2+}$, i.e. the ratio between the number of OH equivalents added and the number of moles of Mg added. In order to fully convert the Mg ions in solution to $Mg(OH)_2$, the OH/Mg ratio needed is 2. The $OH^-/Mg^{2+}$ used in the formation of $Mg(OH)_2$ nanowires ranges from 0.5 to 2 and, depending on this ratio, the morphology of the reaction product changes from thin nanowires to agglomerations of nanoparticles. The $OH^-/Mg^{2+}$ ratio is determined by the pH of the reaction mixture, which needs to be at least 11. If the pH is below 11, no precipitation is observed, i.e. no $Mg(OH)_2$ is formed. If the pH is above 12, the morphology of the nanowires begins to change and more nanoparticles are obtained, i.e. non-selective precipitation.

Considering the narrow window of magnesium concentration in which $Mg(OH)_2$ nanowires can be obtained, the other key synthetic parameters that determine the nanowires formation and morphology include but are not limited to: phage sequence and concentration thereof, the concentration ratio of $Mg^{2+}$/pVIII protein, the concentration ratio of $OH^-/Mg^{2+}$, the incubation time of phage and $Mg^{2+}$; incubation time of phage and the $OH^-$; the sequence of adding anion and metal ions; pH; the solution temperature in the incubation step and/or growth step; the types of metal precursor salt (e.g., $MgCl_2$ or $Mg(NO_3)_2$); the types of anion precursor (e.g., NaOH or LiOH); the number of additions; the time that lapses between the additions of the metal salt and anion precursor, including, e.g., simultaneous (zero lapse) or sequential additions.

The Mg salt solution and the base were added sequentially, separated by an incubation time (i.e., the first incubation time). The sequence of addition has an effect on the morphology of the nanowires. The first incubation time can be at least 1 h and it should be longer in the case the magnesium salt solution is added first. The Mg salt solution and the base can be added in a single "shot" or in a continuous slow flow using a syringe pump or in multiple small shots using a liquid dispenser robot. The reaction is then carried either unstirred or with only mild to moderate stirring for a specific time (i.e., the second incubation time). The second incubation time is not as strong a factor in the synthesis of $Mg(OH)_2$ nanowires, but it should be long enough for the nanowires to precipitate out of the reaction solution (e.g., several minutes). For practical reasons, the second incubation time can be as long as several hours. The reaction temperature can be anything from just above freezing temperature (e.g., 4° C.) up to 80° C. The temperature affects the nanowires morphology.

The precipitated $Mg(OH)_2$ nanowires are isolated by centrifuging the reaction mixture and decanting the supernatant. The precipitated material is then washed at least once with a water solution with pH>10 to avoid redissolution of the $Mg(OH)_2$ nanowires. Typically, the washing solution used can be ammonium hydroxide water solution or an alkali metal hydroxide solution (e.g., LiOH, NaOH, KOH). This mixture is centrifuged and the supernatant decanted. Finally, the product can be either dried (see, Example 5) or resuspended in ethanol for TEM analysis.

The decanted supernatant of the reaction mixture can be analyzed by UV-VIS to determine the phage concentration (see, Example 2) and thus give an estimate of the amount of phage incorporated in the precipitated $Mg(OH)_2$, i.e. the amount of "mineralized" phage.

FIG. 12 depicts one embodiment for preparing $Mg(OH)_2$ nanowires. In a different embodiment, the order of addition may be reversed, for example in an exemplary 4 ml scale synthesis of $Mg(OH)_2$ nanowires, 3.94 ml of concentrated solution of phages (e.g., SEQ ID NO: 3 at a concentration of ~5E12 pfu/ml) were mixed in a 8 ml vial with 0.02 ml of 1 M LiOH aqueous solution and left incubating overnight (~15 h). 0.04 ml of 1 M $MgCl_2$ aqueous solution were then added using a pipette and the mixture was mixed by gentle shaking. The reaction mixture was left incubating unstirred for 24 h. After the incubation time, the mixture was centrifuged, and the supernatant was decanted and saved for phage concentration measurement by UV-VIS. The precipitated material was resuspended in 2 ml of 0.001 M LiOH aqueous solution (pH=11), the mixture was centrifuged and the supernatant decanted. The obtained $Mg(OH)_2$ nanowires were characterized by TEM as described in Example 4.

Example 4

Characterization of $Mg(OH)_2$ Nanowires $Mg(OH)_2$ nanowires prepared according to Example 3 were characterized by TEM in order to determine their morphology. First, a few microliters (~500) of ethanol was used to suspend the isolated $Mg(OH)_2$. The nanowires were then deposited on a TEM grid (copper grid with a very thin carbon layer) placed on filter paper to help wick out any extra liquid. After allowing the ethanol to dry, the TEM grid was loaded in a TEM and characterized. TEM was carried out at 5 KeV in bright field mode in a DeLong LVEM5.

The nanowires were additionally characterized by XRD (for phase identification) and TGA (for calcination optimization).

Example 5

Calcination of Mg(OH)$_2$ Nanowires

The isolated nanowires as prepared in Example 3 were dried in an oven at relatively low temperature (60-120° C.) prior to calcination.

The dried material was placed in a ceramic boat and calcined in air at 450 C.° in order to convert the Mg(OH)$_2$ nanowires into MgO nanowires. The calcination recipe can be varied considerably. For example, the calcination can be done relatively quickly like in these two examples:
- load in a muffle oven preheated at 450° C., calcination time=120 min
- load in a muffle oven (or tube furnace) at room temperature and ramp to 450° C. with 5° C./min rate, calcination time=60 min Alternatively, the calcination can be done in steps that are chosen according to the TGA signals like in the following example:
- load in a muffle oven (or tube furnace) at room temperature, ramp to 100° C. with 2° C./min rate, dwell for 60 min, ramp to 280° C. with 2° C./min rate, dwell for 60 min, ramp to 350° C. with 2° C./min rate, dwell for 60 min and finally ramp to 450° C. with 2° C./min rate, dwell for 60 min.

Generally, a step recipe is preferable since it should allow for a better, smoother and more complete conversion of Mg(OH)$_2$ into MgO. Optionally, the calcined product is ground into a fine powder.

Figure 13:
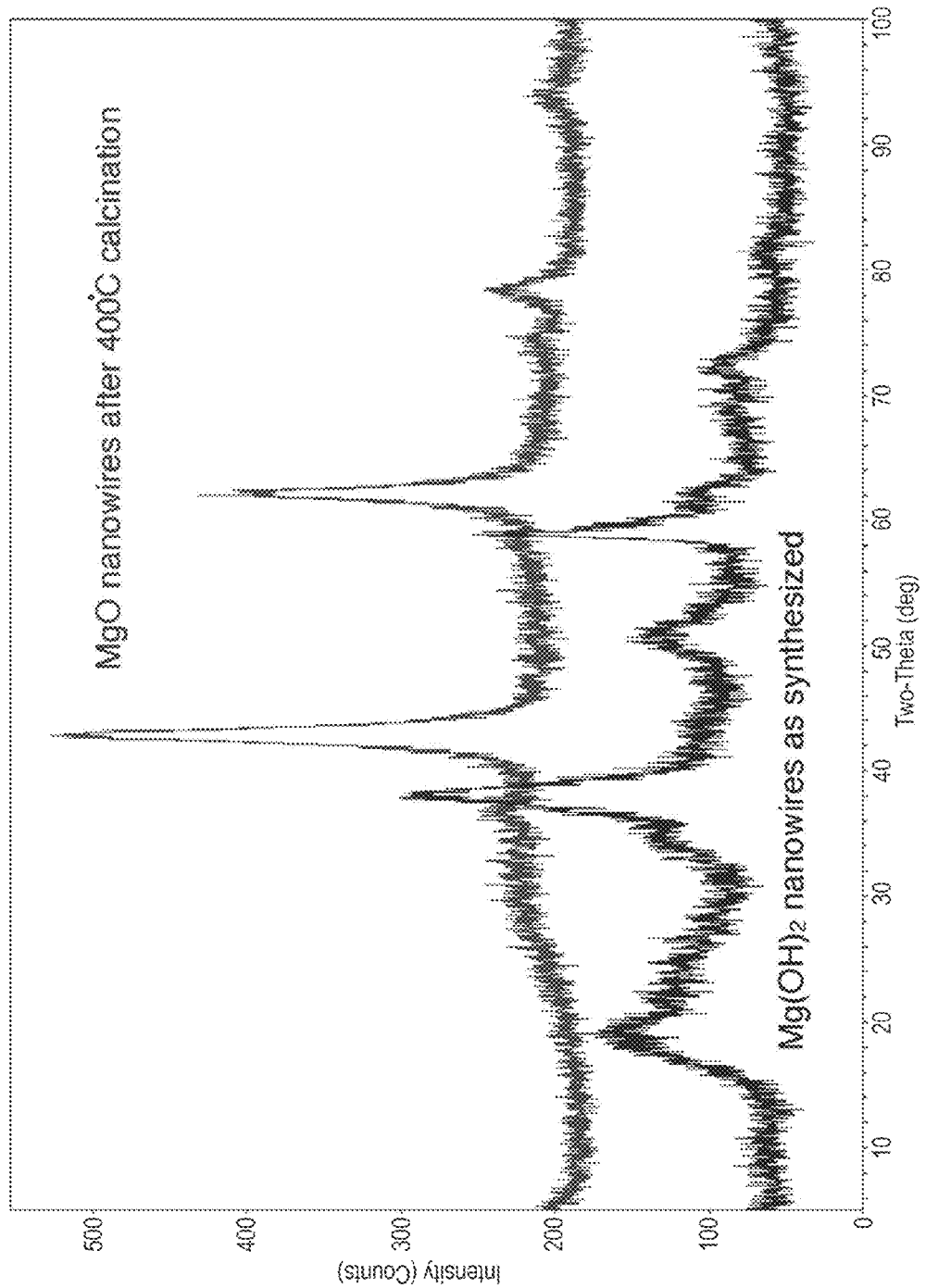
FIG. 13 presents the X-ray diffraction patterns of Mg(OH)2 nanowires and MgO nanowires.

FIG. 13 shows the X-ray diffraction patterns of the Mg(OH$_2$) nanowires and the MgO nanowires following calcinations. Crystalline structures of both types of nanowires were confirmed.

Example 6

Preparation of Li Doped MgO Nanowires

Doping of nanowires is achieved by using the incipient wetness impregnation method. Before impregnating the MgO nanowires with the doping solution, the maximum wettability (i.e. the ability of the nanowires to absorb the doping solution before becoming a suspension or before "free" liquid is observed) of the nanowires was determined. This is a very important step for an accurate absorption of the doping metal on the MgO surface. If too much dopant solution is added and a suspension is formed, a significant amount of dopant will crystallize unabsorbed upon drying and if not enough dopant solution is added, significant portions of the MgO surface will not be doped.

In order to determine the maximum wettability of the MgO nanowires, small portions of water were dropped on the calcined MgO powder until a suspension was formed, i.e. until "free" liquid is observed. The maximum wettability was determined to be the total amount of water added before the suspension formed. The concentration of the doping solution was then calculated so that the desired amount of dopant was contained in the volume of doping solution corresponding to the maximum wettability of the MgO nanowires. In another way to describe the incipient wetness impregnation method, the volume of the doping solution is set to be equal to the pore volume of the nanowires, which can be determined by BET (Brunauer, Emmett, Teller) measurements. The doping solution is then drawn into the pores by capillary action.

In one embodiment, the doping metal for MgO based catalysts for OCM is lithium (see, also, FIG. 12). Thus, in one embodiment the dopant source can be any soluble lithium salt as long as it does not introduce undesired contaminants. Typically, the lithium salts used were LiNO$_3$, LiOH or Li$_2$CO$_3$. LiNO$_3$ and LiOH are preferred because of their higher solubility. In one embodiment, the lithium content in MgO catalysts for OCM ranges from 0 to 10 wt % (i.e. about 0 to 56 at %).

The calculated amount of dopant solution of the desired concentration was dropped onto the calcined MgO nanowires. The obtained wet powder was dried in an oven at relatively low temperature (60-120° C.) and calcined using one of the recipes described above. It is noted that, during this step, no phase transition occurs (MgO has already been formed in the previous calcination step) and thus a step recipe (see previous paragraph) may not be necessary.

The dopant impregnation step can also be done prior to the calcination, after drying the Mg(OH)$_2$ nanowires isolated from the reaction mixture. In this case, the catalyst can be calcined immediately after the dopant impregnation, i.e. no drying and second calcination steps would be required since its goals are accomplished during the calcination step.

Three identical syntheses were made in parallel. In each synthesis, 80 ml of concentrated solution of phages (SEQ ID NO: 3 at a concentration of ≥5E12 pfu/ml) were mixed in a 100 ml glass bottle with 0.4 ml of 1 M LiOH aqueous solution and left incubating for 1 h. 0.8 ml of 1 M MgCl$_2$ aqueous solution were added using a pipette and the mixture was mixed by gently shaking it. The reaction mixture was left incubating unstirred for 72 h at 60° C. in an oven. After the incubation time, the mixture was centrifuged. The precipitated material was resuspended in 20 ml of 0.06 M NH$_4$OH aqueous solution (pH=11), the mixture was centrifuged and the supernatant decanted. The obtained Mg(OH)$_2$ nanowires were resuspended in ethanol. The ethanol suspensions of the three identical syntheses were combined and a few microliters of the ethanol suspension were used for TEM analysis. The ethanol suspension was centrifuged and the supernatant decanted. The gel-like product was transferred in a ceramic boat and dried for 1 h at 120° C. in a vacuum oven.

The dried product was calcined in a tube furnace using a step recipe (load in the furnace at room temperature, ramp to 100° C. with 2° C./min rate, dwell for 60 min, ramp to 280° C. with 2° C./min rate, dwell for 60 min, ramp to 350° C. with 2° C./min rate, dwell for 60 min, ramp to 450° C. with 2° C./min rate, dwell for 60 min and finally cool to room temperature). The yield was 24 mg. The calcined product was ground to a fine powder.

10 mg of the calcined product were impregnated with a LiOH aqueous solution. First, the maximum wettability was determined by adding water to the calcined product in a ceramic boat until the powder was saturated but no "free" liquid was observed. The maximum wettability was 12 μl. Since the target doping level was 1 wt % lithium, the necessary concentration of the LiOH aqueous solution was calculated to be 1.2 M. The calcined product was dried again for 1 h at 120° C. to remove the water used to determine the wettability of the powder. 12 μl of the 1.2 M LiOH solution were dropped on the MgO nanowires powder. The wet

Example 7

Creating Diversity by Varying the Reaction Parameters

Figure 14:
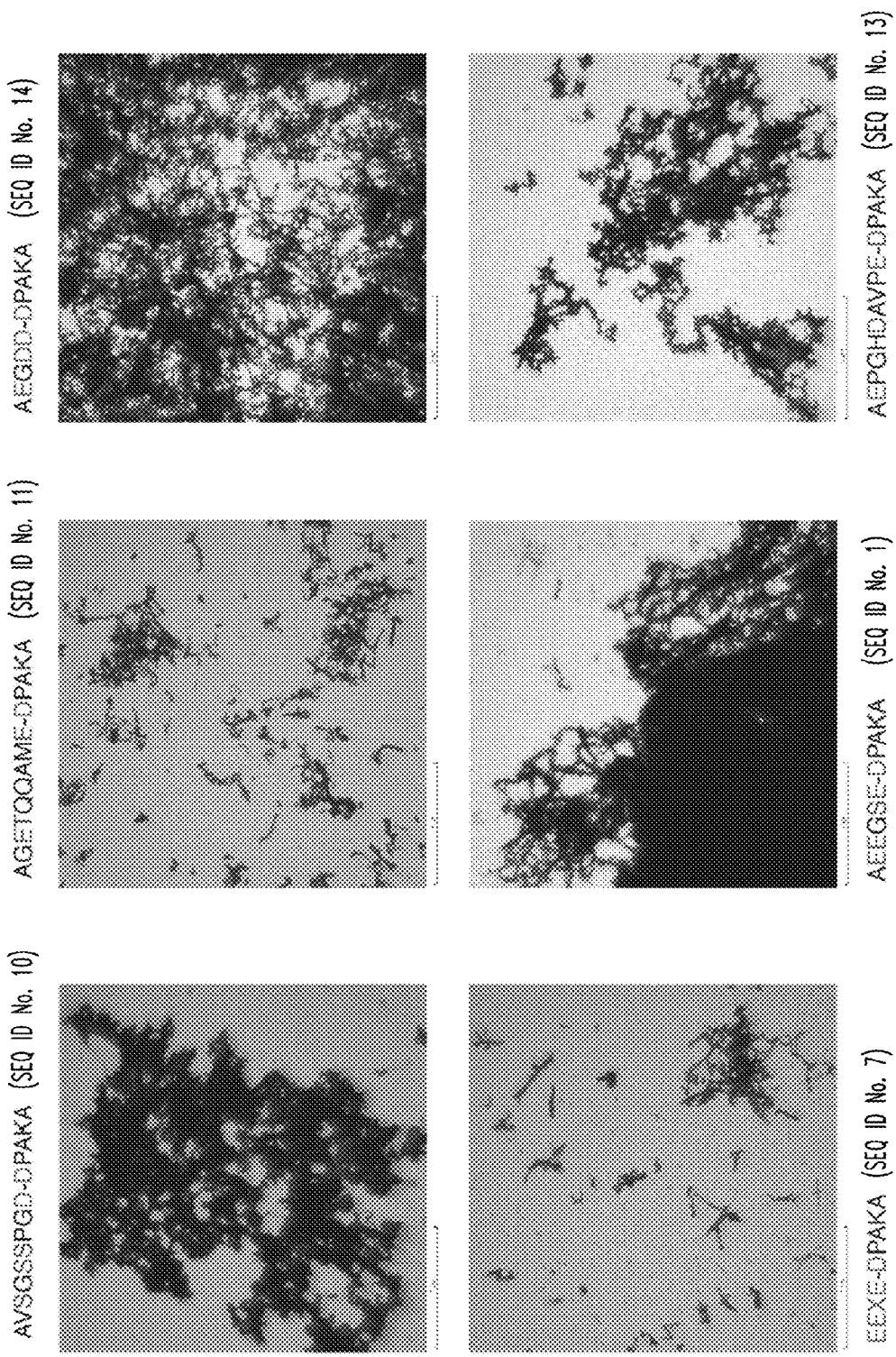
FIG. 14 shows a number of MgO nanowires each synthesized in the presence of a different phage sequence.

Certain synthetic parameters strongly influence the nanowire formation on phage, including selective binding of metal and/or anions, as well as surface morphologies. FIG. 14 shows a number of MgO nanowires synthesized in the presence of different phage sequence (e.g., different pVIII) while keeping the other reaction conditions constant. Phages of SEQ ID NOs. 1, 7, 10, 11, 13 and 14 were the respective phage of choice in six reactions carried out in otherwise identical conditions. The constant reaction conditions may include: concentration ratios of $Mg^{2+}$ and active functional groups on the phage; concentration ratios of $OH^-/Mg^{2+}$; incubation time of phage and $Mg^{2+}$; incubation time of phage and $OH^-$; concentration of phage; sequence of adding anion and metal ions; solution temperature in the incubation step and/or growth step; etc. As shown, the morphologies of MgO nanowires are significantly influenced by the phage sequences.

Thus, varying these and other reaction conditions may produce a diverse class of nanowire catalysts. In addition, certain correlation between the reaction conditions and the surface morphologies of the nanowires can be empirically established, thus enabling rational designs of catalytic nanowires.

Example 8

Preparation of Sr-Doped $La_2O_3$ Nanowires 23 ml of 2.5 e12 pfu solution of phages (SEQ ID NO: 3) was mixed in a 40 ml glass bottle with 0.046 ml of 0.1 M $LaCl_3$ aqueous solution and left incubating for 16 h. After this incubation period, a slow multistep addition is conducted with 1.15 ml of 0.05 M $LaCl_3$ solution and 1.84 ml of 0.3 M $NH_4OH$. This addition is conducted in six hours and twenty steps. The reaction mixture was left stirred another 2 h at room temperature. After that time the suspension was centrifuged in order to separate the solid phase from the liquid phase. The precipitated material was then resuspended in 5 ml of water and centrifuged in order to further remove un-reacted species. A final wash was conducted with 2 ml ethanol. The gel-like product remaining is then dried for 30 minutes at 110° C. in a vacuum oven.

The dried product was then calcined in a muffle furnace using a step recipe (load in the furnace at room temperature, ramp to 200° C. with 3° C./min rate, dwell for 120 min, ramp to 400° C. with 3° C./min rate, dwell for 120 min, cool to room temperature). The calcined product was then ground to a fine powder.

5 mg of the calcined product were impregnated with 0.015 ml $Sr(NO_3)_2$ 0.1M aqueous solution. Powder and solution is mixed on hot plate at 90 C until forming a paste. The paste was then dried for 1 h at 120° C. in a vacuum oven and finally calcined in a muffle oven in air (load in the furnace at room temperature, ramp to 200° C. with 3° C./min rate, dwell for 120 min, ramp to 400° C. with 3° C./min rate, dwell for 120 min, ramp to 500° C. with 3° C./min rate, dwell for 120 min, cool to room temperature).

Example 9

Preparation of $ZrO_2/La_2O_3$ Core/Shell Nanowires

Figure 15:
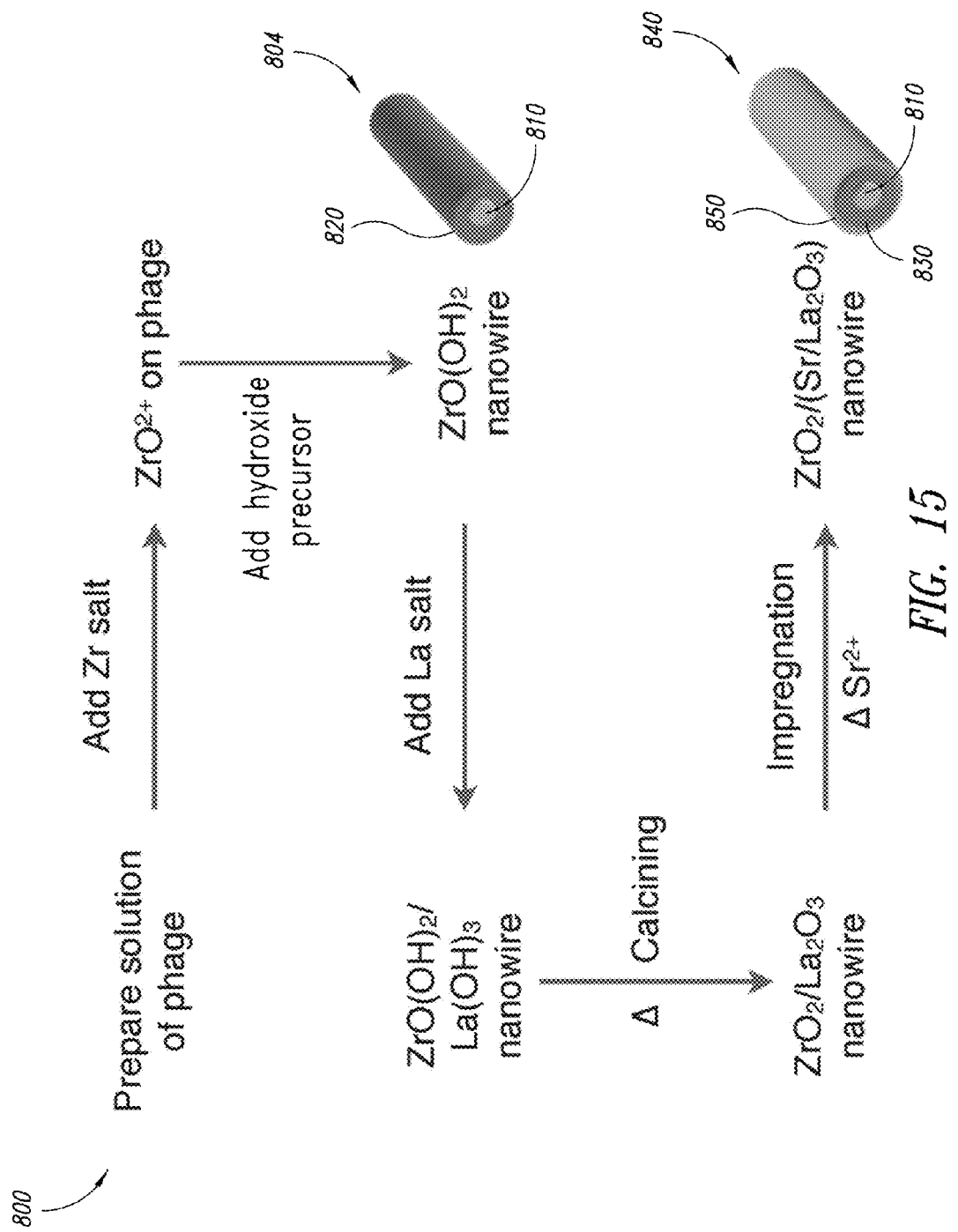
FIG. 15 depicts a representative process for growing a core/shell structure of $ZrO_2/La_2O_3$ nanowires with Strontium dopant.

As an example, FIG. 15 shows schematically an integrated process 800 for growing a core/shell structure of $ZrO_2/La_2O_3$ nanowire. A phase solution is prepared, to which a zirconium salt precursor (e.g., $ZrCl_2$) is added to allow for the nucleation of $ZrO^{2+}$ on the phage. Subsequently, a hydroxide precursor (e.g., LiOH) is added to cause the nucleation of hydroxide ions on the phage. Nanowires 804 is thus formed in which the phage 810 is coated with a continuous and crystalline layer 820 of $ZrO(OH)_2$. To this reaction mixture, a lanthanum salt precursor (e.g., $LaCl_3$) is added under a condition to cause the nucleation of $La(OH)_3$ over the $ZrO(OH)_2$ nanowire 804. Following calcinations, nanowires of a core/shell structure of $ZrO_2/La_2O_3$ are formed. A further step of impregnation produces nanowires of $ZrO_2/La_2O_3$ doped with strontium ions ($Sr^{2+}$) 840, in which the phage 810 is coated with a layer of $ZrO_2$ 830, which is in turn coated with a shell of $La_2O_3$ 850.

$ZrO_2/La_2O_3$ nanowires were thus prepared by mixing 20 ml of 2.5e12 pfu E3 Phage solution to 0.1 ml of 0.5M $ZrO(NO_3)_2$ aqueous solution. The solution was incubated under stirring for 16 hours. Any solids formed following incubation were removed by centrifugation at 4000 rpm for 5 minutes and redispersed in 0.5 ml ethanol. A small aliquot was retrieved for TEM characterization.

Thereafter, the ethanol solution was mixed with 10 ml water and 2 ml of 0.05M $ZrO(NO_3)_2$ with 2 ml of 0.1M $NH_4OH$ were added during a period of 200 minutes using syringe pumps. Wash solids with water and resuspend in ethanol for TEM observation.

To about 18 mg of $ZrO(OH)_2$ nanowires in suspension, 10 ml of water was added, followed by the addition of 0.5 ml of $LaCl_3$ 0.083 M with 0.5 ml of $NH_4OH$ 0.3 M solution during a period of 50 minutes using syringe pumps. The solids thus formed were separated by centrifugation to obtain a powder, which was dried in a vacuum oven at 110° C. for one hour. A small aliquot of the dried powder is then suspended in ethanol for TEM observation.

Example 10

Preparation of $La(OH)_3/ZrO_2$ Core/Shell Nanowires

Similar to Example 9, $La(OH)_3$ nanowires were coated with $ZrO_2$ shell according to the following process. To 6.8 mg of $La(OH)_3$ nanowires (prepared by $LaCl_3$ and $NH_4OH$ in a process similar to that of Example 9), which had been dried at 110° C., was added 4 ml of water to suspend the solids. 0.5 ml of 0.05M $ZrO(NO_3)_2$ and 0.5 ml of 0.1 M $NH_4OH$ were slowly added in 50 minutes. The solids were retrieved by centrifugation and calcined at 500° C. for one hour. TEM observation showed nanowires as the major morphology.

Example 11

Preparation of Hollow-Cored $ZrO_2$ Nanowires

To the $La(OH)_3/ZrO_2$ core/shell nanowires prepared Example 10, additional processing can be used to create hollow $ZrO_2$ shell nanowires. The $La(OH)_3$ core can be etched using 1M citric acid solution. Controlled experiments on calcined and un-calcined $La(OH)_3$ nanowires shows that the entire nanowires are fully etched in about one hour at room temperature. Etching of La(OH)$_3$/ZrO$_2$ core/shell nanowires was conducted overnight (about 16 hours).

The remaining solid was then separated by centrifugation and TEM observation is conducted on the washed solids (water wash). Low contrast zirconia nanowires were observed after etching, which indicates that hollow zirconia "straws" can be formed using La(OH)$_3$ nanowire as template.

Example 12

OCM Catalyzed by La$_2$O$_3$ Nanowires

A 20 mg sample of a phage-based Sr (5%) doped La$_2$O$_3$ catalyst was diluted with 80 mg of quartz sand and placed into a reactor (run WPS21). The gas flows were held constant at 9 sccm methane, 3 sccm oxygen and 6 sccm of argon. The upstream temperature (just above the bed) was varied from 500° C. to 800° C. in 100° C. increments and then decreased back down to 600° C. in 50° C. increments. The vent gas analysis was gathered at each temperature level.

As a point of comparison, 20 mg of bulk 5% Sr on La$_2$O$_3$ catalyst was diluted in the same manner and run through the exact flow and temperature protocol.

Figure 16:
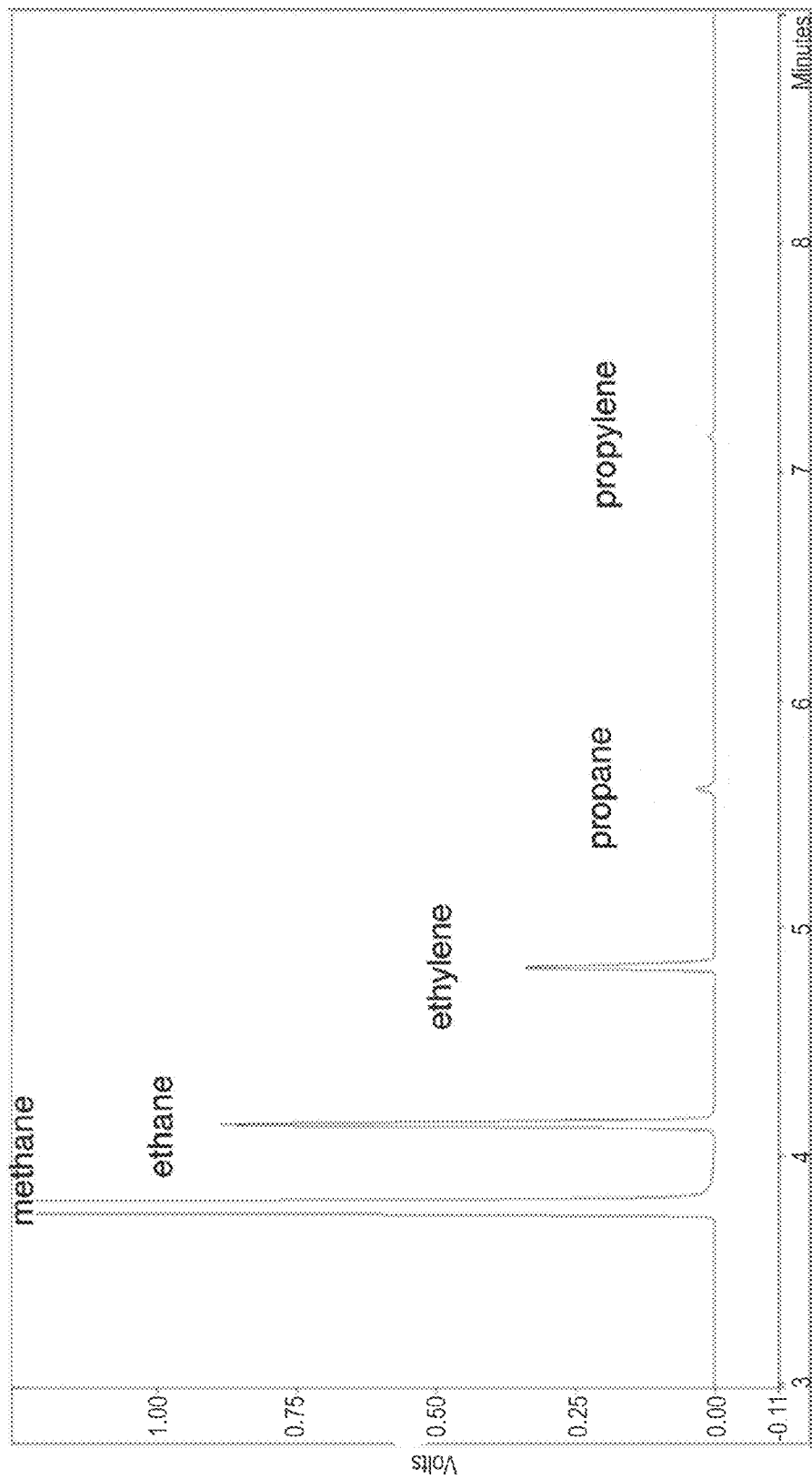
FIG. 16 is a gas chromatograph showing the formation of OCM products at 700° C. when passed over a Sr doped $La_2O_3$ nanowire.

FIG. 16 shows the formation of OCM products at 700° C., including C2 (ethane and ethylene) as well as further coupling products (propane and propylene).

Figure 17A:
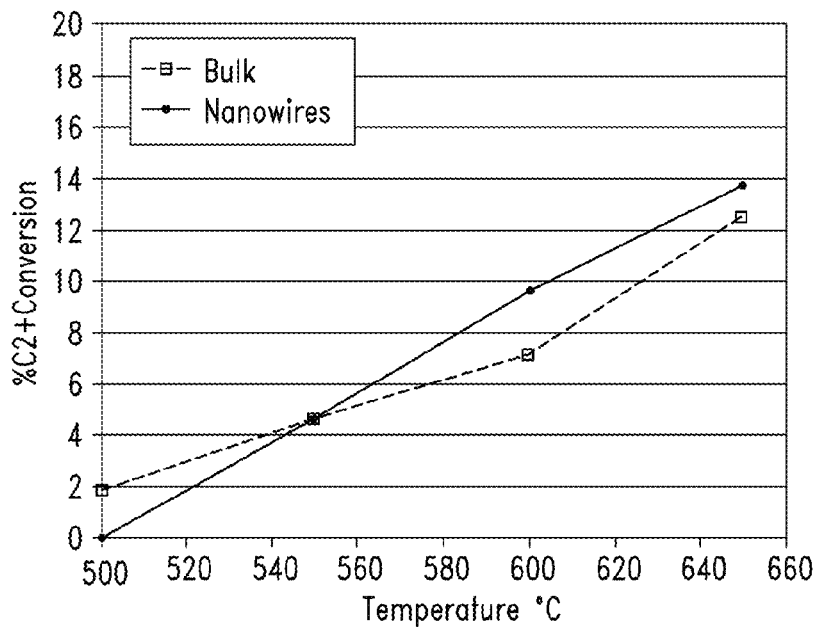
FIGS. 17A-17C are graphs showing methane conversion, C2 selectivity, and C2 yield, in an OCM reaction catalyzed by Sr doped $La_2O_3$ nanowires vs. the corresponding bulk material in the same reaction temperature range.
Figure 17B:
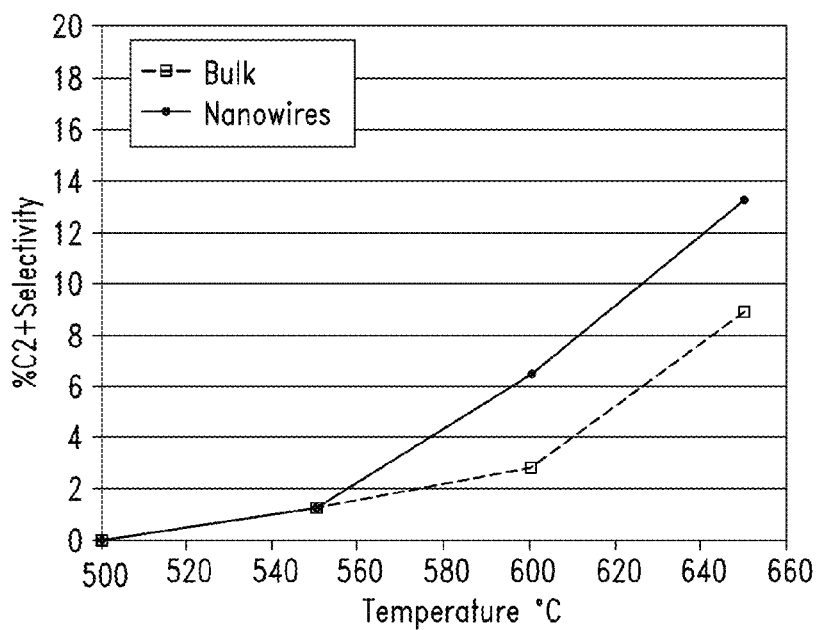
Figure 17C:
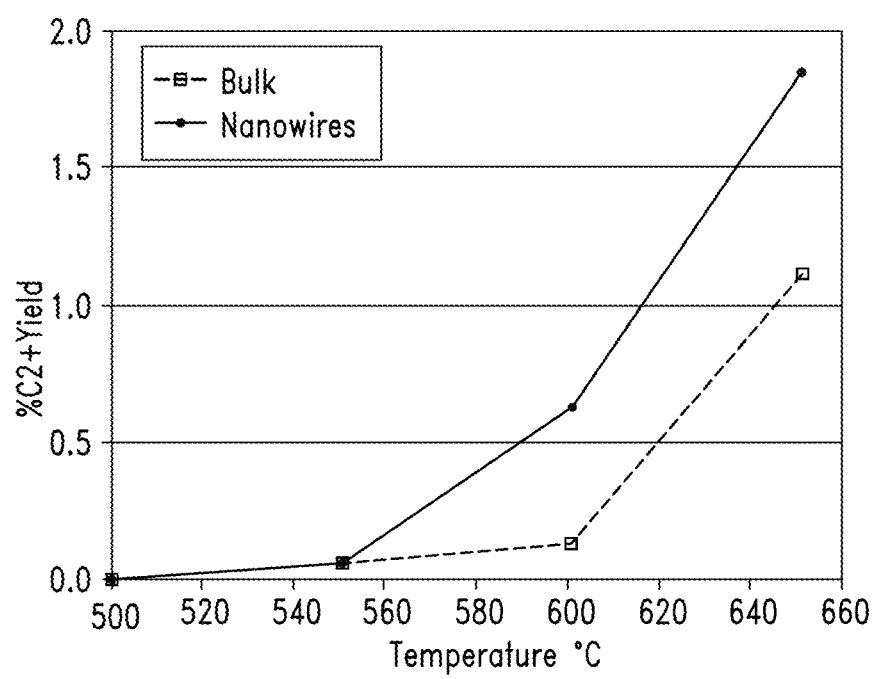

FIGS. 17A, 17B and 17C show the comparative results in catalytic performance parameters for a nanowire catalyst (Sr$^{2+}$/La$_2$O$_3$) vs. its corresponding bulk material (Sr$^{2+}$/La$_2$O$_3$ bulk). Methane conversion rates, C2 selectivities and C2 yields are among the important parameters by which the catalytic properties were measured. More specifically, FIG. 17A shows the methane conversion rates are higher for the nanowire catalyst compared to the bulk material across a wide temperature range (e.g., 550 to 650° C.). Likewise, FIG. 17B and FIG. 17C show that the C2 selectivities and C2 yields are also higher for the nanowire catalyst as compared to the bulk catalyst across a wide temperature range (e.g., 550 to 650° C.). Thus, it is demonstrated that by improving both conversion and selectivity simultaneously that the C2 yield can be improved over traditional bulk catalysts.

Figure 18A:
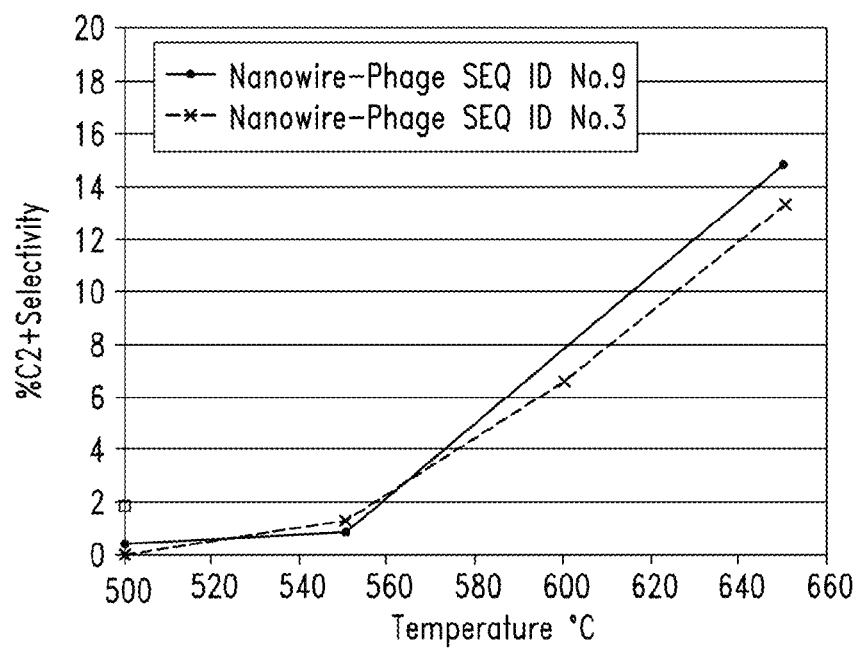
FIGS. 18A-18B are graphs showing the comparative results of C2 selectivities in an OCM reaction catalyzed by Sr doped $La_2O_3$ nanowire catalysts prepared by different synthetic conditions.
Figure 18B:
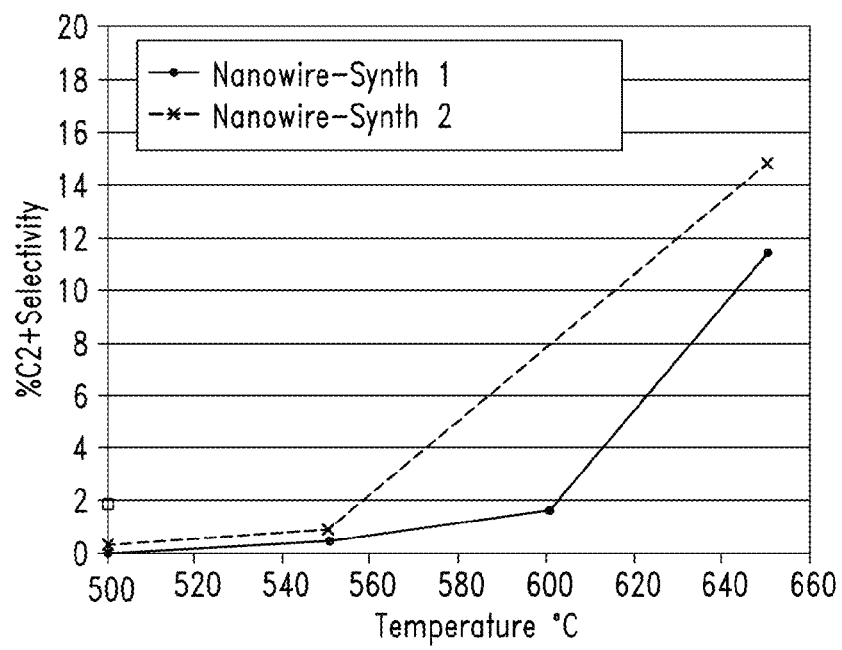

FIGS. 18A-18B demonstrate that nanowires prepared under different synthetic conditions afforded different catalytic performances, suggesting that the various synthetic parameters resulted in divergent nanowire morphologies. FIG. 18A shows that nanowires prepared using different phage templates (SEQ ID NO: 9 and SEQ ID NO:3) in otherwise identical synthetic conditions created nanowire catalysts that perform differently in terms of the C2 selectivity in an OCM reaction. FIG. 18B shows the comparative C2 selectivities of nanowires prepared by an alternative adjustment of the synthetic parameters. In this case, the phage template was the same for both nanowires (SEQ ID NO:3), but the synthetic conditions were different. Specifically, the nanowires of FIG. 18A were prepared with shorter incubation and growth times than the nanowires of FIG. 18B. Additionally, the nanowires of FIG. 18A were calcined in a single step at 400° C. instead of the ramped temperature calcinations performed on the nanowires of FIG. 18B.

These results confirm that the nanowire catalysts behave differently from their bulk material counterparts. In particular, the nanowire catalysts allow for adjustments of the surface morphologies through synthetic design and screening to ultimately produce high-performance catalysts.

Example 13

Oxidative Dehydrogenation Catalyzed by MgO Nanowires

A 10 mg sample of phage-based Li doped MgO catalyst was diluted with 90 mg of quartz sand and placed in a reactor. The gas flows were held constant at 8 sccm alkane mix, 2 sccm oxygen and 10 sccm of argon. The upstream temperature (just above the bed) was varied from 500° C. to 750° C. in 50-100° C. increments. The vent gas analysis was gathered at each temperature level.

Figure 19:
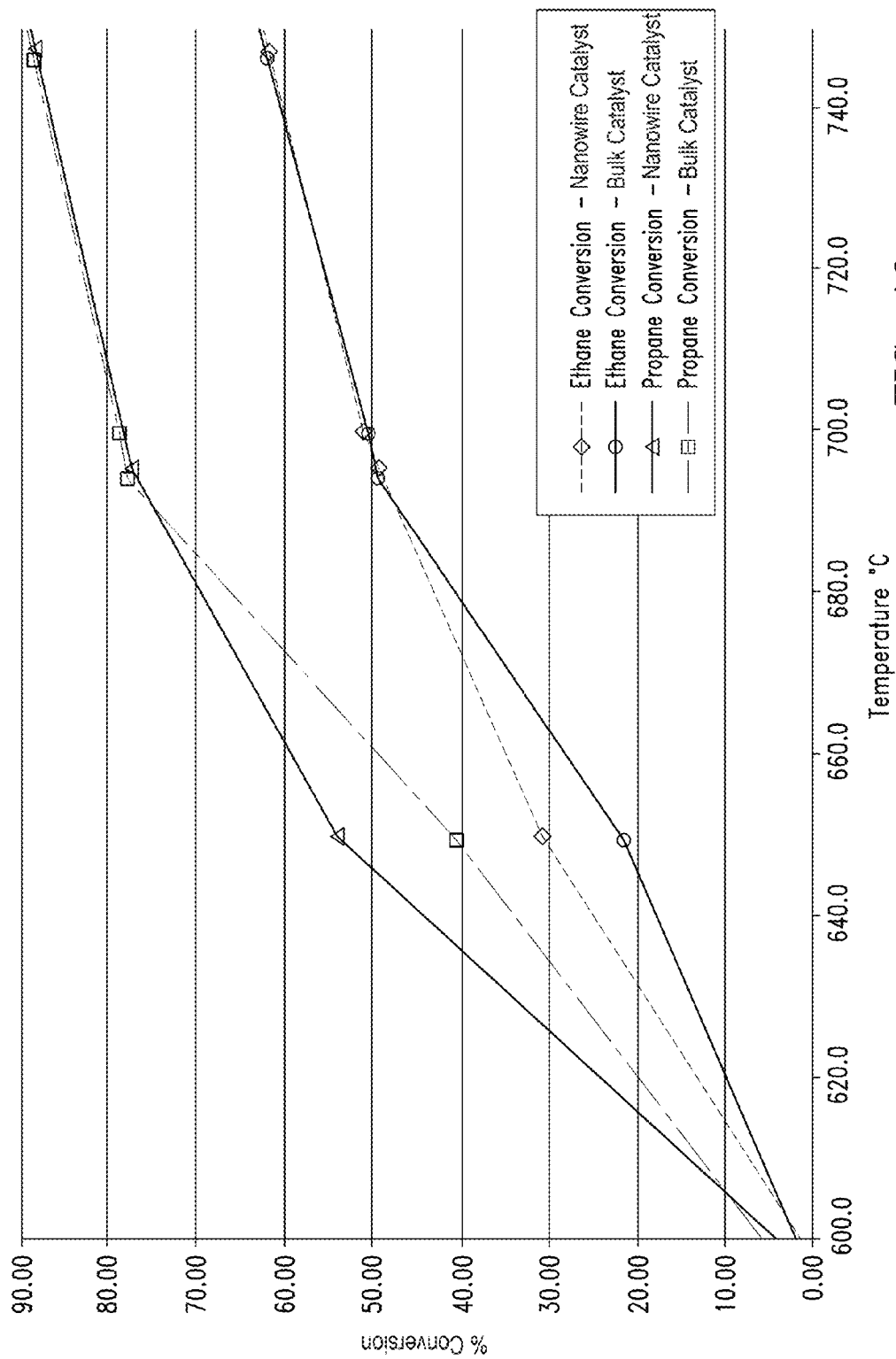
FIG. 19 is a graph comparing ethane and propane conversions in ODH reactions catalyzed by either Li doped MgO phage-based nanowires or Li doped MgO bulk catalyst.

As a point of comparison, 10 mg of bulk 1 wt % Li on MgO catalyst was diluted in the same manner and run through the exact flow and temperature protocol. The results of this experiment are shown in FIG. 19. As can be seen in FIG. 19, phage-based nanowires according to the present disclosure comprise better conversion of ethane and propane compared to a corresponding bulk catalyst.

Example 14

Synthesis of Sr Doped La$_2$O$_3$ Nanowires

Sr doped La$_2$O$_3$ nanowires were prepared according to the following non-template directed method.

A La(OH)$_3$ gel was prepared by adding 0.395 g of NH$_4$OH (25%) to 19.2 ml of water followed by addition of 2 ml of a 1 M solution of La(NO$_3$)$_3$. The solution was then mixed vigorously. The solution first gelled but the viscosity dropped with continuous agitation. The solution was then allowed to stand for a period of between 5 and 10 minutes. The solution was then centrifuged at 10,000 g for 5 minutes. The centrifuged gel was retrieved and washed with 30 ml of water and the centrifugation washing procedure was repeated.

To the washed gel was added 10.8 ml of water to suspend the solid. The suspension was then transferred to a hydrothermal bomb (20 ml volume, not stirred). The hydrothermal bomb was then loaded in a muffle furnace at 160° C. and the solution was allowed to stand under autogenous pressure at 160° C. for 16 hours.

The solids were then isolated by centrifugation at 10,000 g for 5 minutes, and wash with 10 ml of water to yield about 260 mg of solid (after drying for 1 h at 120° C. in a vacuum oven).

A 57 mg aliquot of nanowires was then mixed with 0.174 ml of a 0.1 M solution of Sr(NO$_3$)$_2$. This mixture was then stirred on a hot plate at 90° C. until a paste was formed.

The paste was then dried for 1 h at 120° C. in a vacuum oven and finally calcined in a muffle oven in air according to the following procedure: (1) load in the furnace at room temperature; (2) ramp to 200° C. with 3° C./min rate; (3) dwell for 120 min; (3) ramp to 400° C. with 3° C./min rate; (4) dwell for 120 min; (5) ramp to 500° C. with 3° C./min rate; and (6) dwell for 120 min. The calcined product was then ground to a fine powder.

Figure 20:
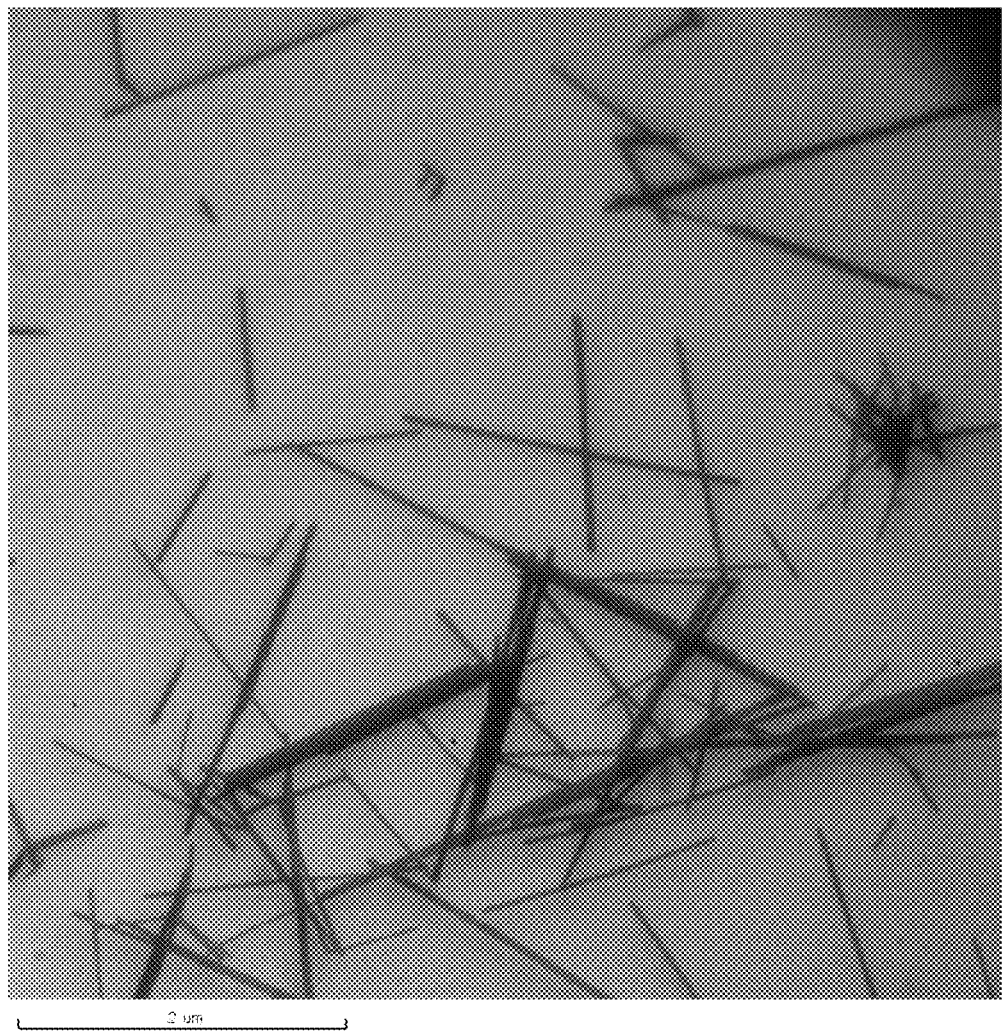
FIG. 20 is a TEM image showing $La_2O_3$ nanowires prepared under non-template-directed conditions.

FIG. 20 shows a TEM image of the nanowires obtained from this non-template directed method. As shown in FIG. 20, the nanowires comprise a ratio of effective length to actual length of about 1 (i.e., the nanowires comprise a "straight" morphology).

Example 15

Synthesis of La$_2$O$_3$ Nanowires

La(NO$_3$)$_3$.6 H$_2$O (10.825 g) is added to 250 mL distilled water and stirred until all solids are dissolved. Concentrated ammonium hydroxide (4.885 mL) is added to this mixture and stirred for at least one hour resulting in a white gel. This mixture is transferred equally to 5 centrifuge tubes and centrifuged for at least 15 minutes. The supernatant is discarded and each pellet is rinsed with water, centrifuged for at least 15 minutes and the supernatant is again discarded.

The resulting pellets are all combined, suspended in distilled water (125 mL) and heated at 105° C. for 24 hours. The lanthanum hydroxide is isolated by centrifugation and suspended in ethanol (20 mL). The ethanol supernatant is concentrated and the product is dried at 65° C. until all ethanol is removed.

The lanthanum hydroxide nanowires prepared above are calcined by heating at 100° C. for 30 min., 400° C. for 4 hours and then 550° C. for 4 hours to obtain the La$_2$O$_3$ nanowires.

Example 16

Preparation of Na$_{10}$MnW$_5$O$_{17}$ Nanowires 25 ml of concentrated reagent grade NH$_4$OH are dissolved in 25 ml of distilled water, and 1 ml of 0.001M aqueous solution of M13 bacteriophage is then added. 0.62 g of Mn(NO$_3$)$_2$, 1.01 g of NaCl and 2.00 g of WO$_3$ are then added to the mixture with stirring. The mixture is heated at a temperature of about 95° C. for 15 minutes. The mixture is then dried overnight at about 110° C. and calcined at about 400° C. for 3 hours.

Example 17

Preparation of Na$_{10}$MnW$_5$O$_{17}$ Nanowires 25 ml of concentrated reagent grade NH$_4$OH are dissolved in 25 ml of distilled water, and 1 ml of 0.001 M aqueous solution of M13 bacteriophage is then added. 1.01 g of NaCl and 2.00 g of WO$_3$ are then added to the mixture with stirring. The mixture is heated at a temperature of about 95° C. for 15 minutes. The mixture is then dried overnight at about 110° C. and calcined at about 400° C. for 3 hours. The resulting material is then suspended in 10 ml of distilled water and 0.62 g of Mn(NO$_3$)$_2$ is added to the mixture with stirring. The mixture is heated at a temperature of about 115° C. for 15 minutes. The mixture is then dried overnight at about 110° C. and calcined at about 400° C. for 3 hours.

Example 18

Preparation of Na$_{10}$MnW$_5$O$_{17}$/SiO$_2$ Nanowires

Nanowire material Na$_{10}$MnW$_5$O$_{17}$ (2.00 g), prepared as described in Example 16 above, is suspended in water, and about 221.20 g of a 40% by weight colloidal dispersion of SiO$_2$ (silica) is added while stirring. The mixture is heated at about 100° C. until near dryness. The mixture is then dried overnight at about 110° C. and heated under a stream of oxygen gas (i.e., calcined) at about 400° C. for 3 hours. The calcined product is cooled to room temperature and then ground to a 10-30 mesh size.

Example 19

Preparation of La$_2$O$_3$ Nanowires

Two identical syntheses were made in parallel. In each synthesis, 360 ml of 4 e12 pfu/ml solution of phage (SEQ ID NO: 3) were mixed in a 500 ml plastic bottle with 1.6 ml of 0.1 M LaCl3 aqueous solution and left incubating for at least 1 hour. After this incubation period, a slow multistep addition was conducted with 20 ml of 0.1 M LaCl3 solution and 40 ml of 0.3 M NH4OH. This addition was conducted in 24 hours and 100 steps. The reaction mixture was left stirred for at least another hour at room temperature. After that time the suspension was centrifuged in order to separate the solid phase from the liquid phase. The precipitated material was then re-suspended in 25 ml of ethanol. The ethanol suspensions from the two identical syntheses were combined and centrifuged in order to remove un-reacted species. The gel-like product remaining was then dried for 15 hours at 65° C. in an oven and then calcined in a muffle oven in air (load in the furnace at room temperature, ramp to 100° C. with 2° C./min rate, dwell for 30 min, ramp to 400° C. with 2° C./min rate, dwell for 240 min, ramp to 550° C. with 2° C./min rate, dwell for 240 min, cool to room temperature).

Example 20

Preparation of Mg/Na Doped La$_2$O$_3$ Nanowires

Two identical syntheses were made in parallel. In each synthesis, 360 ml of 4 e12 pfu solution of phage (SEQ ID NO: 3) were mixed in a 500 ml plastic bottle with 1.6 ml of 0.1 M LaCl$_3$ aqueous solution and left incubating for at least 1 hour. After this incubation period, a slow multistep addition was conducted with 20 ml of 0.1 M LaCl$_3$ solution and 40 ml of 0.3 M NH$_4$OH. This addition was conducted in 24 hours and 100 steps. The reaction mixture was left stirred for at least another hour at room temperature. After that time, the suspension was centrifuged in order to separate the solid phase from the liquid phase. The precipitated material was then resuspended in 25 ml of ethanol. The ethanol suspensions from the two identical syntheses were combined and centrifuged in order to remove un-reacted species. The gel-like product remaining was then dried for 15 hours at 65° C. in an oven.

The target doping level was 20 at % Mg and 5 at % Na at % refers to atomic percent). 182 mg of the dried product were suspended in 2.16 ml deionized water, 0.19 ml 1 M Mg(NO$_3$)$_2$ aqueous solution and 0.05 ml 1M NaNO$_3$ aqueous solution. The resulting slurry was stirred at room temperature for 1 hour, sonicated for 5 min, then dried at 120° C. in and oven until the powder was fully dried and finally calcined in a muffle oven in air (load in the furnace at room temperature, ramp to 100° C. with 2° C./min rate, dwell for 30 min, ramp to 400° C. with 2° C./min rate, dwell for 60 min, ramp to 550° C. with 2° C./min rate, dwell for 60 min, ramp to 650° C. with 2° C./min rate, dwell for 60 min, ramp to 750° C. with 2° C./min rate, dwell for 240 min, cool to room temperature).

Example 21

Oxidative Coupling of Methane Catalyzed by Mg/Na Doped La$_2$O$_3$ Nanowires 50 mg of Mg/Na-doped La$_2$O$_3$ nanowires catalyst from example 20 were placed into a reactor tube (4 mm ID diameter quartz tube with a 0.5 mm ID capillary downstream), which was then tested in an Altamira Benchcat 203. The gas flows were held constant at 46 sccm methane and 54 sccm air, which correspond to a $CH_4/O_2$ ratio of 4 and a feed gas-hour space velocity (GHSV) of about 130000/hour. The reactor temperature was varied from 400° C. to 450° C. in a 50° C. increment, from 450° C. to 550° C. in 25° C. increments and from 550° C. to 750° C. in 50° C. increments. The vent gases were analyzed with gas chromatography (GC) at each temperature level.

Figure 22:
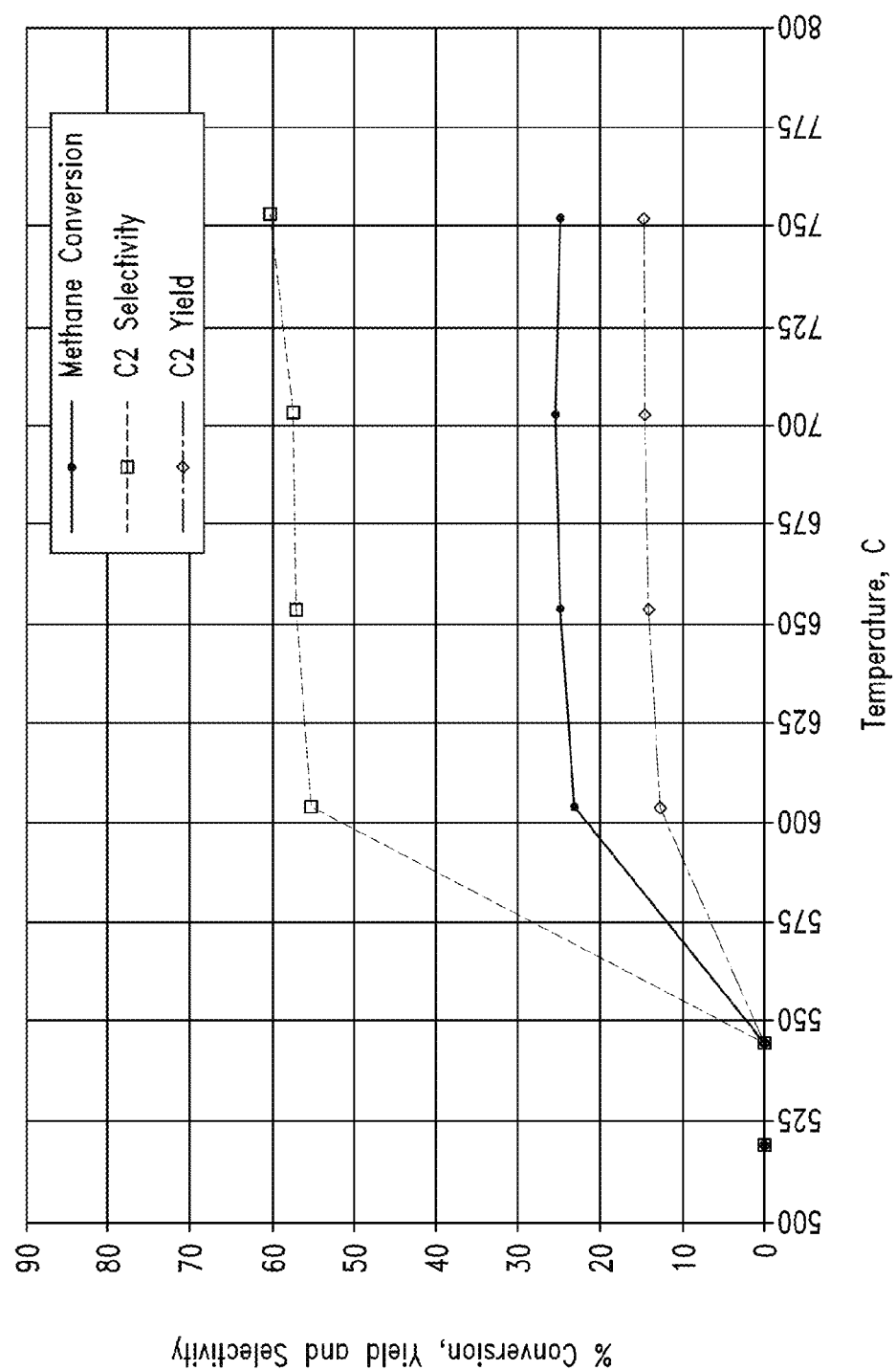
FIG. 22 shows methane conversion, C2 selectivity and C2 yield in a reaction catalyzed by representative nanowires.

FIG. 22 shows the onset of OCM between 550° C. and 600° C. The C2 selectivity, methane conversion and C2 yield at 650° C. were 57%, 25% and 14%, respectively.

In another example, 50 mg of Mg/Na-doped $La_2O_3$ nanowires catalyst from example 20 were placed into a reactor tube (4 mm ID diameter quartz tube with a 0.5 mm ID capillary downstream), which was then tested in an Altamira Benchcat 203. The gas flows were held constant at 46 sccm methane and 54 sccm air, which correspond to a feed gas-hour space velocity (GHSV) of about 130000 $h^{-1}$. The CH4/O2 ratio was 5.5. The reactor temperature was varied from 400° C. to 450° C. in a 50° C. increment, from 450° C. to 550° C. in a 25° C. increments and from 550° C. to 750° C. in 50° C. increments. The vent gases were analyzed with gas chromatography (GC) at each temperature level.

Figure 23:
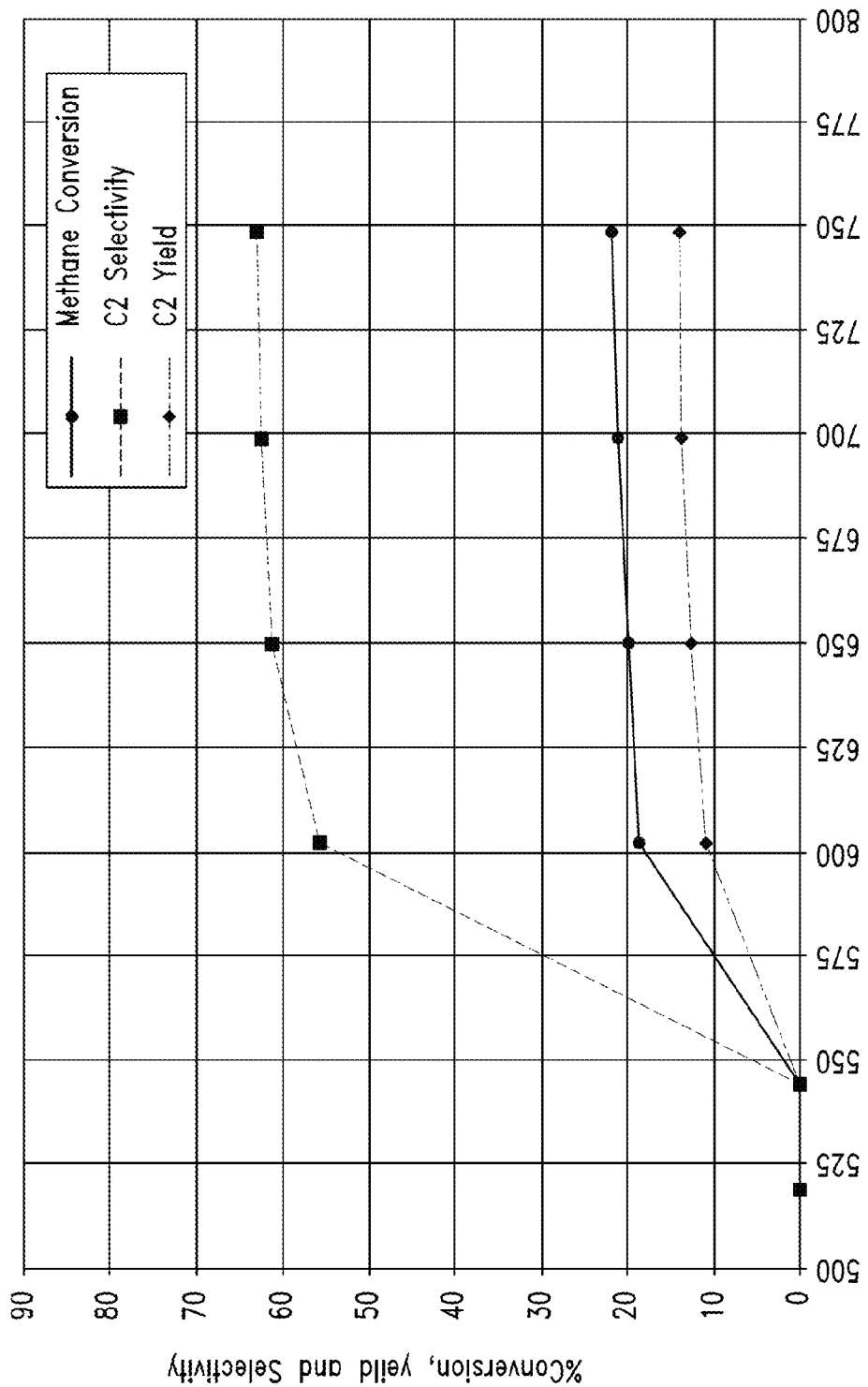
FIG. 23 shows methane conversion, C2 selectivity and C2 yield in a reaction catalyzed by representative nanowires.

FIG. 23 shows the onset of OCM between 550° C. and 600° C. The C2 selectivity, methane conversion and C2 yield at 650° C. were 62%, 20% and 12%, respectively.

Example 22

Nanowire Synthesis

Nanowires may be prepared by hydrothermal synthesis from metal hydroxide gels (made from metal salt+base). In some embodiments, this method is applicable to lanthanides, for example La, Nd, Pr, Sm, Eu, and lanthanide containing mixed oxides.

Alternatively, nanowires can be prepared by synthesis from metal hydroxide gel (made from metal salt+base) under reflux conditions. In some embodiments, this method is applicable to lanthanides, for example La, Nd, Pr, Sm, Eu, and lanthanide containing mixed oxides.

Alternatively, the gel can be aged at room temperature. Certain embodiments of this method are applicable for making magnesium hydroxychloride nanowires, which can be converted to magnesium hydroxide nanowires and eventually to MgO nanowires. In a related method, hydrothermal treatment of the gel instead of aging is used.

Nanowires may also be prepared by polyethyleneglycol assisted hydrothermal synthesis. For example, Mn containing nanowires may be prepared according to this method using methods known to those skilled in the art. Alternatively, hydrothermal synthesis directly from the oxide can be used.

Example 23

Preparation of Nanowires

Nanostructured catalyst materials can be prepared by a variety of starting materials. In certain embodiments, the rare earth oxides are attractive starting materials since they can be obtained at high purity and are less expensive than the rare earth salt precursors that are typically used in preparative synthesis work. Methods for making rare earth oxide nanowires and derivatives thereof are described below.

Method A: Lanthanide oxide starting material can be hydrothermally treated in the presence of ammonium halide to prepare rare earth oxide nanowires. The preparation is a simple one-pot procedure with high yield. For example, one gram of lanthanum oxide was placed in 10 mL of distilled water. Ammonium chloride (0.98 g) was added to the water, the mixture was placed in an autoclave, and the autoclave was placed in a 160 C oven for 18 h. The autoclave was taken out of the oven, cooled, and the product was isolated by filtration. Micron and submicron nanowires were observed in the TEM images of the product. This method could also be used to prepare mixed metal oxides, metal oxyhalides, metal oxynitrates, and metal sulfates.

Method B: Metal oxide nanowires can be prepared using a solid-state reaction of rare earth oxide or bismuth oxide in the presence of ammonium halide. The solid-state reaction is used to prepare the rare earth or bismuth oxyhalide. The metal oxyhalide is then placed in water at room temperature and the oxyhalide is slowly converted to metal oxide with nanowire/needle morphology. This method could also be used to prepare mixed metal oxides. For example: lanthanum oxide, bismuth oxide, and ammonium chloride were ground and fired in a ceramic dish to make the mixed lanthanum bismuth oxychloride. The metal oxychloride is then placed in water to form the mixed lanthanum bismuth oxide nanowires.

Example 24

Preparation of $MgO/Mn_2O_3$ Core/Shell Nanowires 19.7 ml of concentrated solution of phages (e.g., SEQ ID NO: 3 at a concentration of ~5E12 pfu/ml) were mixed in a 20 ml vial with 0.1 ml of 1 M LiOH aqueous solution and left incubating overnight (~15 h). 0.2 ml of 1 M $MgCl_2$ aqueous solution were then added using a pipette, and the mixture was mixed by gentle shaking. The reaction mixture was left incubating unstirred for 72 h. After the incubation time, the mixture was centrifuged and the supernatant decanted. The precipitated material was re-suspended in 5 ml of 0.001 M LiOH aqueous solution (pH=11), the mixture was centrifuged and the supernatant decanted.

19.8 ml of deionized water were added to the obtained $Mg(OH)_2$ nanowires. The mixture was left incubating for 1 h. After the incubation time, 0.2 ml of 1 M $MnCl_2$ aqueous solution were then added using a pipette and the mixture was mixed by gentle shaking. The reaction mixture was left incubating unstirred for 24 h. After the incubation time, the mixture was centrifuged and the supernatant decanted. The precipitated material was re-suspended in 3 ml of 0.001 M LiOH aqueous solution (pH=11), the mixture was centrifuged and the supernatant decanted. The precipitated material was finally re-suspended in 7 ml ethanol, the mixture was centrifuged and the supernatant decanted.

The obtained MnO(OH) coated $Mg(OH)_2$ nanowires were dried at 65° C. for 15 h in an oven. Finally, the dried product was calcined in a muffle furnace using a step recipe (load in the furnace at room temperature, ramp to 100° C. with 2° C./min rate, dwell for 60 min, ramp to 280° C. with 2° C./min rate, dwell for 60 min, ramp to 350° C. with 2° C./min rate, dwell for 60 min, ramp to 450° C. with 2° C./min rate, dwell for 60 min, ramp to 550° C. with 2° C./min rate, dwell for 60 min, cool to room temperature) to convert it to $MgO/Mn_2O_3$ core-shell nanowires.

Example 25

Preparation of $Mn_2O_3$ Nanowires 3.96 ml of concentrated solution of phages (e.g., SEQ ID NO: 3 at a concentration of ~5E12 pfu/ml) were mixed in a 8 ml vial with 0.04 ml of 1 M $MnCl_2$ aqueous solution and left incubating for 20 h. 0.02 ml of 1 M LiOH aqueous solution were then added using a pipette and the mixture was mixed by gentle shaking. The reaction mixture was left incubating unstirred for 72 h. After the incubation time, the mixture was centrifuged, and the supernatant was decanted. The precipitated material was re-suspended in 2 ml of 0.001 M LiOH aqueous solution (pH=11), the mixture was centrifuged and the supernatant decanted. The precipitated material was re-suspended in 2 ml ethanol, the mixture was centrifuged and the supernatant decanted. The obtained MnO(OH) nanowires were dried at 65° C. for 15 h in an oven. Finally, the dried product was calcined in a muffle furnace using a step recipe (load in the furnace at room temperature, ramp to 100° C. with 2° C./min rate, dwell for 60 min, ramp to 280° C. with 2° C./min rate, dwell for 60 min, ramp to 350° C. with 2° C./min rate, dwell for 60 min, ramp to 450° C. with 2° C./min rate, dwell for 60 min, ramp to 550° C. with 2° C./min rate, dwell for 60 min, cool to room temperature) to convert it to $Mn_2O_3$ nanowires.

Example 26

Preparation of $V_2O_5$ Nanowires 1.8 mg of $V_2O_5$ were dissolved in a 10 ml of a 2.5 wt % aqueous solution of HF. 1 ml of the $V_2O_5$/HF solution was mixed with 1 ml of concentrated solution of phages (e.g., SEQ ID NO: 3 at a concentration of ~5E12 pfu/ml) in a 15 ml plastic centrifugation tube and left incubating for 2 h. 1 ml of a saturated solution of boric acid (supernatant of nominally 1 M boric acid aqueous solution) were then added using a pipette and the mixture was mixed by gentle shaking. The reaction mixture was left incubating unstirred for 170 h. After the incubation time, the mixture was centrifuged, and the supernatant was decanted. The precipitated material was suspended in 2 ml ethanol, the mixture was centrifuged and the supernatant decanted. The obtained $V_2O_5$ nanowires were characterized by TEM.

Example 27

Synthesis of MgO Nanowires 12.5 ml of a 4M $MgCl_2$ aqueous solution were heated to 70° C. on a hotplate. 0.1 g of MgO (from Aldrich) were then slowly added, over a span of at least 5 minutes, to the solution while it was vigorously stirred. The mixture was kept stirring at 70° C. for 3 h and then cooled down overnight (~15 h) without stirring.

The obtained gel was transferred in a 25 ml hydrothermal bomb (Parr Bomb No. 4749). The hydrothermal bomb was then loaded in an oven at 120° C. and the solution was allowed to stand under autogenous pressure at 120° C. for 3 hours.

The product was centrifuged and the supernatant decanted. The precipitated product was suspended in about 50 ml ethanol and filtered over a 0.45 μm polypropylene hydrophilic filter using a Büchner funnel. Additional 200 ml ethanol were used to wash the product.

The obtained magnesium hydroxide chloride hydrate nanowires were suspended in 12 ml ethanol and 2.4 ml deionized water in a 20 ml vial. 1.6 ml of 5M NaOH aqueous solution were added and the vial was sealed with its cap. The mixture was then heated at 65° C. in an oven for 15 h.

The product was filtered over a 0.45 μm polypropylene hydrophilic filter using a Büchner funnel. About 250 ml ethanol were used to wash the product. The obtained $Mg(OH)_2$ nanowires were dried at 65° C. for 15 h in an oven. Finally, the dried product was calcined in a muffle furnace using a step recipe (load in the furnace at room temperature, ramp to 100° C. with 2° C./min rate, dwell for 60 min, ramp to 280° C. with 2° C./min rate, dwell for 60 min, ramp to 350° C. with 2° C./min rate, dwell for 60 min, ramp to 450° C. with 2° C./min rate, dwell for 60 min, cool to room temperature) to convert it to MgO nanowires.

Example 28

Synthesis of $Mg(OH)_2$ Nanowires 6.8 g of $MgCl_2.6H_2O$ were dissolved in 5 ml deionized water in a 20 ml vial. 0.4 g of MgO (from Aldrich) were then slowly added to the solution while it was vigorously stirred. The mixture was kept stirring at room temperature until it completely jellified (~2 h) and then it was left aging for 48 h without stirring.

The gel was transferred in a 50 ml centrifuge tube, which was then filled with deionized water and vigorously shaken until a homogenous suspension was obtained. The suspension was centrifuged and the supernatant decanted. The precipitated product was suspended in about 50 ml ethanol and filtered over a 0.45 μm polypropylene hydrophilic filter using a Büchner funnel. Additional 350 ml ethanol were used to wash the product.

The obtained magnesium hydroxide chloride hydrate nanowires were suspended in 24 ml ethanol in a 50 ml media bottle. The mixture was stirred for a few minutes, then 4.8 ml deionized water and 3.2 ml of 5M NaOH aqueous solution were added. The media bottle was sealed with its cap and the mixture was stirred for few more minutes. The mixture was then heated at 65° C. in an oven for 15 h.

The product was filtered over a 0.45 μm polypropylene hydrophilic filter using a Büchner funnel. About 400 ml ethanol were used to wash the product. The obtained $Mg(OH)_2$ nanowires were dried at 65° C. for 72 h in an oven and then additionally dried at 120° C. for 2 h in a vacuum oven. About 0.697 g of $Mg(OH)_2$ nanowires were obtained and the surface area of the nanowires was determined by BET (Brunauer, Emmett, Teller) measurement at 100.4 $m^2/g$.

Example 29

Synthesis of $MnO/Mn_2O_3$ Core/Shell Nanowires

This example describes a method for coating the $Mg(OH)_2$ nanowires from example 28 with MnO(OH).

Three almost identical syntheses were conducted in parallel. In each synthesis, the $Mg(OH)_2$ nanowires, prepared using the method described in example 28 but without the drying steps, were mixed with 250 ml deionized water in a 500 ml plastic bottle and stirred for 20 minutes. 2.4 ml of a 1M $MnCl_2$ solution were added to the first synthesis, 6 ml of a 1M $MnCl_2$ solution were added to the second synthesis and 9.6 ml of a 1M $MnCl_2$ solution were added to the third synthesis. The mixtures were stirred for 2 hours at room temperature. After this incubation period, a slow multistep addition was conducted with 1.2 ml, 3 ml and 4.8 ml of 0.1 M LiOH solution for the first, second and third synthesis, respectively. This addition was conducted in 2 hours and 20 steps. The reaction mixture was left stirred overnight (~15 h) at room temperature. After that time the suspensions were centrifuged in order to separate the solid phase from the liquid phase. The precipitated materials were then re-suspended in 50 ml of ethanol for each synthesis and filtered over a 0.45 μM polypropylene hydrophilic filter using a Büchner funnel. Additional 350 ml ethanol were used to wash each product of the three synthesis.

The obtained $Mg(OH)_2/MnO(OH)$ core/shell nanowires were characterized by TEM before being dried at 65° C. for 72 h in an oven and then additionally dried at 120° C. for 2 h in a vacuum oven. The yield for the three syntheses was 0.675 g, 0.653 g and 0.688 g, respectively. The surface area of the nanowires was determined by BET (Brunauer, Emmett, Teller) measurement at 94.6 $m^2/g$, 108.8 $m^2/g$ and 108.7 $m^2/g$, respectively.

The $Mg(OH)_2/MnO(OH)$ core/shell nanowires can be converted into $MgO/Mn_2O_3$ nanowires by calcining them in a muffle furnace using a step recipe (load in the furnace at room temperature, ramp to 100° C. with 2° C./min rate, dwell for 60 min, ramp to 280° C. with 2° C./min rate, dwell for 60 min, ramp to 350° C. with 2° C./min rate, dwell for 60 min, ramp to 450° C. with 2° C./min rate, dwell for 60 min, ramp to 550° C. with 2° C./min rate, dwell for 60 min, cool to room temperature).

Example 30

Preparation of $Nd_2O_3$, $Eu_2O_3$ and $Pr_2O_3$ Nanowires

Three syntheses were made in parallel. In each synthesis, 10 ml of a 2.5 e12 pfu/ml solution of phage (SEQ ID NO: 14) were mixed in a 60 ml glass vial with 25 μl of 0.08M $NdCl_3$, $EuCl_3$ or $PrCl_3$ aqueous solutions, respectively and left incubating for at least 1 hour. After this incubation period, a slow multistep addition was conducted with 630 μl of 0.08M $LaCl_3$, $EuCl_3$ or $PrCl_3$ aqueous solutions, respectively and 500 μl of 0.3M NH4OH. This addition was conducted in 33 hours and 60 steps. The reaction mixtures were left stirred for at least another 10 hour at room temperature. After that time the suspensions were centrifuged in order to separate the solid phase from the liquid phase. The precipitated material was then re-suspended in 4 ml of ethanol. The ethanol suspensions were centrifuged in order to finish removing un-reacted species. The gel-like product remaining was then dried for 1 hours at 65° C. in an oven and then calcined in a muffle oven in air (load in the furnace at room temperature, ramp to 100° C. with 2° C./min rate, dwell for 30 min, ramp to 500° C. with 2° C./min rate, dwell for 240 min, cool to room temperature). The obtained $Nd(OH)_3$, $Eu(OH)_3$ and $Pr(OH)_3$ nanowires were characterized by TEM before being dried.

Example 31

Preparation of $Ce_2O_3/La_2O_3$ Mixed Oxide Nanowires

In the synthesis, 15 ml of a 5 e12 pfu/ml solution of phage (SEQ ID NO: 3) were mixed in a 60 ml glass vial with 15 μl of 0.1M $La(NO_3)_3$ aqueous solution and left incubating for about 16 hour. After this incubation period, a slow multistep addition was conducted with 550 μl of 0.2M $Ce(NO_3)_3$ aqueous solution, 950 μl of 0.2M $La(NO_3)_3$ aqueous solution and 1500 μl of 0.4M $NH_4OH$. This addition was conducted in 39 hours and 60 steps. The reaction mixtures were left stirred for at least another 10 hours at room temperature. After that time the suspensions were centrifuged in order to separate the solid phase from the liquid phase. The precipitated material was then re-suspended in 4 ml of ethanol. The ethanol suspensions were centrifuged in order to finish removing un-reacted species. The gel-like product remaining was then dried for 1 hours at 65° C. in an oven and then calcined in a muffle oven in air (load in the furnace at room temperature, ramp to 100° C. with 2° C./min rate, dwell for 30 min, ramp to 500° C. with 2° C./min rate, dwell for 120 min, cool to room temperature).

Example 32

Synthesis of $Pr_2O_3/La_2O_3$ Mixed Oxide Nanowires 0.5 ml of 1M $Pr(NO_3)_3$ aqueous solution and 4.5 ml of 1M $La(NO_3)_3$ aqueous solution were mixed with 40 ml deionized water. Once well mixed, 5 ml of a 3M $NH_4OH$ aqueous solution were quickly injected in the mixture. A precipitate immediately formed. The suspension was kept stirring for another 10 minutes then transferred to centrifuge tubes and centrifuged in order to separate the solid phase from the liquid phase. The precipitated material was then re-suspended in 35 ml of deionized water. The solid fraction was separated again by centrifugation and the washing step was repeated one more time. The gel-like product remaining was then dispersed in deionized water and the suspension volume adjusted to 20 ml. The suspension was then transferred to a hydrothermal bomb and placed in an oven at 120° C. for 2 hours. The solids obtained after hydrothermal treatment were then separated by centrifugation and washed once with 35 ml of deionized water. The washed hydrothermally treated powder was then dried at 120° C. for 16 hours. The surface area, determine by BET, of the dried powder was about 41 $m^2/g$. Transmission electron microscopy was used to characterize the morphology of this sample further. The powder was constituted of large aspect ratio particles with about 30 nm wide by 0.5 to 2 μm length. The powder was calcined in three temperature steps at 200, 400 and 500° C. with 3° C./min ramp and 2 hours of dwell time at each step. The surface area of the $Pr_2O_3/La_2O_3$ mixed oxide nanowires was about 36 $m^2/g$.

Example 33

Synthesis of $MgO/Eu_2O_3$ Core/Shell Nanowires

In this example, $Mg(OH)_2$ nanowires are used as a support to grow a shell of $Eu(OH)_3$. $Mg(OH)_2$ nanowires, prepared according to the methods described in example 28 (wet product, before being dried) were used to prepare a suspension in deionized water with a concentration of 3 g/l of dried $Mg(OH)_2$. To 30 ml of the $Mg(OH)_2$ suspension, 3 ml of 0.1M $Eu(NO_3)_3$ aqueous solution and 3 ml of 0.3M $NH_4OH$ aqueous solution were added in a slow multistep addition. This addition was conducted in 48 hours and 360 steps. The solids were then separated using centrifugation. The powder is washed with 30 ml DI water and centrifuged again. An aliquot is retrieved prior to calcination for transmission electron miscopy evaluation of the sample morphology. The sample is mainly constituted of high aspect ratio wires with a rough surface. The general morphology of the support is preserved and no separate phase is observed.

The remaining of the powder was dried at 120° C. for 3 hours and calcined in three steps at 200, 400 and 500° C. with 2 hours at each step and a ramp rate of 3° C./min. The surface area, determined by BET, of the MgO/$Eu_2O_3$ core/shell nanowires is 209 m$^2$/g.

Example 34

Synthesis of $Y_2O_3$/$La_2O_3$ Mixed Oxide Nanowires 0.5 ml of 1M $Y(NO_3)_3$ aqueous solution and 4.5 ml of 1M $La(NO_3)_3$ aqueous solution were mixed with 40 ml deionized water. Once well mixed, 5 ml of a 3M NH4OH aqueous solution was quickly injected in the mixture. A precipitate immediately forms. The suspension was kept stirring for another 10 minutes then transferred to centrifuge tubes and centrifuged in order to separate the solid phase from the liquid phase. The precipitated material was then re-suspended in 35 ml deionized water. The solid fraction was separated again by centrifugation and the washing step was repeated one more time. The gel-like product remaining was then dispersed in deionized water and the suspension volume adjusted to 20 ml. The suspension was then transferred to a hydrothermal bomb and placed in an oven at 120° C. for 2 hours. The solids obtained after hydrothermal treatment were then separated by centrifugation and washed once with 35 ml of deionized water. The washed hydrothermally treated powder was then dried at 120° C. for 16 hours. The surface area, determined by BET, of the dried powder is about 20 m2/g. Transmission electron microscopy was used to characterize the morphology of this sample further. The powder was constituted of large aspect ratio particles with about 20 to 40 nm wide by 0.5 to 2 micron length. The $Y_2O_3$/$La_2O_3$ mixed oxide nanowires ware calcined in three temperature steps at 200, 400 and 500° C. with 3° C./min ramp and 2 hours of dwell time at each step.

Example 35

Synthesis of $La_2O_3$ Nanowires 1 g of $La_2O_3$ (13.1 mmol) and 0.92 g of $NH_4Cl$ (18.6 mmol) were placed in a 25 ml stainless steel autoclave with a Teflon liner (Parr Bomb No. 4749). 10 ml deionized water were then added to the dry reactants. The autoclave was sealed and placed in a 160° C. oven for 12 h. After 12 h, the autoclave was allowed to cool. The nanowires were washed several times with 10 mL of water to remove any excess $NH_4Cl$. The product was then dried in an oven for 15 hours at 65° C. in an oven and then calcined in a muffle oven in air (load in the furnace at room temperature, ramp to 100° C. with 2° C./min rate, dwell for 30 min, ramp to 400° C. with 2° C./min rate, dwell for 240 min, ramp to 550° C. with 2° C./min rate, dwell for 240 min, cool to room temperature.)

Example 36

Synthesis of $La_2O_3$/$Nd_2O_3$ Mixed Oxide Nanowires 0.5 g of $La_2O_3$ (1.5 mmol), 0.52 g of $Nd_2O_3$ (1.5 mmol), and 0.325 g of $NH_4Cl$ (6 mmol) were ground together using a mortar and pestle. Once the dry reactants were well mixed, the ground powder was placed in a ceramic crucible and then the crucible was transferred to a tube furnace. The tube furnace atmosphere was flushed with nitrogen for 0.5 h. The reactants were then calcined under nitrogen (25° C.-450° C., 2° C./min ramp, dwell 1 h; 450° C.-900° C.; 2° C./min ramp, 1 h hold, cool to room temperature.) The product (0.2 g) was placed in 10 mL of deionized water and stirred at room temperature for 24 h. The nanowires were then washed several times with deionized $H_2O$ and dried in an oven for 15 hours at 65° C. in an oven and then calcined in a muffle oven in air (load in the furnace at room temperature, ramp to 100° C. with 2° C./min rate, dwell for 30 min, ramp to 400° C. with 2° C./min rate, dwell for 240 min, ramp to 550° C. with 2° C./min rate, dwell for 240 min, cool to room temperature.)

Example 37

Oligomerization of Ethylene to Liquid Hydrocarbon Fuels with High Aromatics Content 0.1 g of the zeolite ZSM-5 is loaded into a fixed bed micro-reactor and heated at 400° C. for 2 h under nitrogen to activate the catalyst. The OCM effluent, containing ethylene and ethane, is reacted over the catalyst at 400° C. at a flow rate of 50 mL/min and GSHV=3000-10000 mL/(g h). The reaction products are separated into liquid and gas components using a cold trap. The gas and liquid components are analyzed by gas chromatography. C5-C10 hydrocarbon liquid fractions, such as xylene and isomers thereof, represent ≥90% of the liquid product ratio while the C11-C15 hydrocarbon fraction represents the remaining 10% of the product ratio.

Example 38

Oligomerization of Ethylene to Liquid Hydrocarbon Fuels with High Olefins Content 0.1 g of the zeolite ZSM-5 doped with nickel is loaded into a fixed bed micro-reactor and heated at 350° C. for 2 h under nitrogen to activate the catalyst. The OCM effluent, containing ethylene and ethane, is reacted over the catalyst at 250-400° C. temperature rage with GSHV=1000-10000 mL/(g h). The reaction products are separated into liquid and gas components using a cold trap. The gas and liquid components are analyzed by gas chromatography. $C_4$-$C_{10}$ olefin hydrocarbon liquid fractions, such as butene, hexane and octene represent ≥95% of the liquid product ratio while the $C_{12}$-$C_{18}$ hydrocarbon fraction represents the remaining 5% of the product ratio. Some trace amounts of odd numbered olefins are also possible in the product.

Example 39

Synthesis of $MnWO_4$ Nanowires 0.379 g of $Na_2WO_4$ (0.001 mol) was dissolved in 5 mL of deionized water. 0.197 g of $MnCl_2.6H2O$ (0.001 mol) was dissolved in 2 mL of deionized water. The two solutions were then mixed and a precipitate was observed immediately. The mixture was placed in a stainless steel autoclave with a Teflon liner (Parr Bomb No. 4749). 40 ml of deionized water was added to the reaction mixture and the pH was adjusted to 9.4 with NH4OH. The autoclave was sealed and placed in a 120° C. oven. The reaction was left to react for 18 h and then it was cooled to room temperature. The product was washed with deionized water and then dried in a 65° C. oven. The samples were calcined in a muffle oven in air (load in the furnace at room temperature, ramp to 400° C. with 5° C./min rate, dwell for 2 h, ramp to 850° C. with 5° C./min rate, dwell for 8 h, cool to room temperature).

Example 40

Preparation of Supported $MnWO_4$ Nanowire Catalysts

Supported $MnWO_4$ nanowires catalysts are prepared using the following general protocol. $MnWO_4$ nanowires are prepared using the method described in example 42. Manganese tungstate nanowires, support, and water are slurried for 6 h at room temperature. The manganese tungstate to support ratio is 2-10 wt %. The mixture is dried in a 65° C. oven and then calcined in a muffle oven in air: load in the furnace at room temperature, ramp to 400° C. with 5° C./min rate, dwell for 2 h, ramp to 850° C. with 5° C./min rate, dwell for 8 h, cool to room temperature. The following is a list of exemplary supports that may be used: $SiO_2$, $Al_2O_3$, $SiO_2$—$Al_2O_3$, $ZrO_2$, $TiO_2$, $HfO_2$, Silica-Aluminum Phosphate, and Aluminum Phosphate.

Example 41

OCM Catalyzed by $La_2O_3$ Nanowires 50 mg of $La_2O_3$ nanowires catalyst, prepared using the method described in example 19, were placed into a reactor tube (4 mm ID diameter quartz tube with a 0.5 mm ID capillary downstream), which was then tested in an Altamira Benchcat 203. The gas flows were held constant at 46 sccm methane and 54 sccm air, which correspond to a CH4/O2 ratio of 4 and a feed gas-hour space velocity (GHSV) of about 130000/hour. The reactor temperature was varied from 400° C. to 500° C. in a 100° C. increment and from 500° C. to 850° C. in 50° C. increments. The vent gases were analyzed with gas chromatography (GC) at each temperature level.

Figure 24:
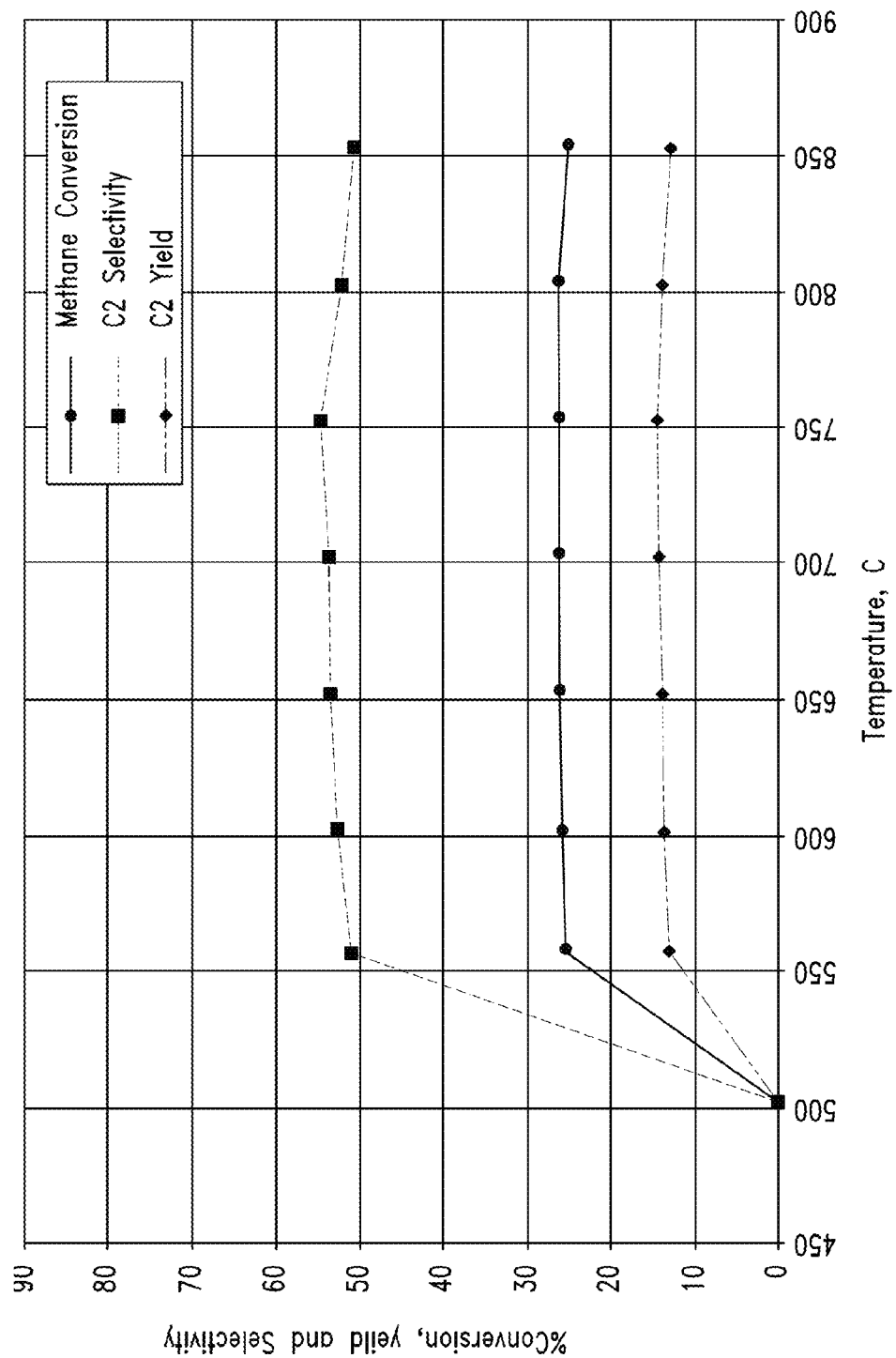
FIG. 24 is a graph showing methane conversion, C2 selectivity and C2 yield in a reaction catalyzed by representative nanowires.

FIG. 24 shows the onset of OCM between 500° C. and 550° C. The C2 selectivity, methane conversion and C2 yield at 650° C. were 54%, 27% and 14%, respectively.

Example 42

Synthesis of $La_2O_3$ Nanowires $La_2O_3$ (3.1 mmol) and $NH_4NO_3$ (other lanthanides and different ammonium salts, e.g., Cl or acetate and the like may also be used) (18.6 mmol) were placed in a stainless steel autoclave with a Teflon liner. Water (10 mL) was then added to the dry reactants. The autoclave was sealed and placed in a 160° C. oven for 12 h. After 12 h, the autoclave was allowed to cool (the ammonium acetate catalyzed reaction required 48 h). The nanowires were washed several times with 10 mL of water to remove any excess $NH_4NO_3$. The product was then dried in an oven for 15 hours at 65° C. and then calcined in a muffle oven in air (load in the furnace at room temperature, ramp to 100° C. with 2° C./min rate, dwell for 30 min, ramp to 400° C. with 2° C./min rate, dwell for 240 min, ramp to 550° C. with 2° C./min rate, dwell for 240 min, cool to room temperature.) Nanowire formation was confirmed by TEM. Calcination by microwave may also be used.

Example 43

Synthesis of $La_2O_3$ Nanowires $La_2O_3$ (1.02 g), $NH_4NO_3$ (1.64 g) and 20 mL of deionized water were added to a round bottom flask equipped with a stir-bar and a reflux condenser. The suspension was refluxed for 18 h. The product was washed with DI water and dried. The product was then calcined in a muffle oven according to the procedure described in Example 42. Nanowire formation was confirmed by TEM. Calcination by microwave may also be used.

Example 44

Purification of Bacteriophage M13 by TFF

In this example, both the microfiltration and the ultrafiltration steps were performed using TFF. A batch of M13 filamentous bacteriophage genetically engineered to express AEEEDP at the N-terminus of the mature pVIII protein (SEQ ID NO: 3) was amplified by incubation with *E. coli* bacteria. The concentration of the amplified solution was quantified by titration to be 7.7E11 pfu/mL. 890 mL of the solution was purified using the following parameters. For microfiltration, a 0.2 μm nylon flat sheet membrane cartridge was used. Prior to purification the membrane was cleaned and the normalized water flux was verified to be ≥85% of factory rating. Flow parameters of 550 L/hr/m$^2$ and transmembrane pressure at 15 psi were used. Prior to filtration the cell solution was recirculated for an hour at the same flow and pressure to equilibrate the membrane. Following this recirculation, the amplification culture was concentrated via TFF for ~4 hrs, until the retentate volume was 100 mL (~10 times less than original).

The retentate obtained above was diafiltered with approximately 2.5 volumes (270 mL) of Tris buffered saline pH 7.5 (TBS). The TBS filtrate was also collected with the permeate solution, containing the phage. The final yield of phage in the permeate was 2.3% as verified by titration (1007 mL at 1.5E10 pfu/mL). For the ultrafiltration and diafiltration steps a 100 kD polyethersulfone flat sheet membrane cartridge was used. Prior to purification the membrane was cleaned and the normalized water flux was verified to be ≥85% of factory rating. The phage solution clarified through TFF microfiltration as described above was combined with another batch similarly prepared. The combination resulted in a total of 1953 mL of solution of phage at a concentration of 4E9 pfu/mL. Flow parameters of approximately 1640 L/hr/m$^2$ and a transmembrane pressure of 7 psi were used. The retentate containing the phage product was concentrated 17 times and diafiltered with 10 volumes of deionized water. After sample collection, the system was rinsed through with a volume equivalent to the hold up volume (45 mL). The final yield of phage in the retentate was ~100% as verified by titration (113 mL, 6.8E10 pfu/mL).

Example 45

Purification of Bacteriophage M13 by Depth Filtration and TFF

In this example, instead of TFF microfiltration, depth filtration was used for the initial step to clarify the amplification phage (SEQ ID NO: 3) culture of bacterial cells, grown similarly as described in Example 44, of bacterial cells and cell debris. The second step to filter out media components and smaller contaminating bacterial cell particles such as proteins was performed with TFF ultrafiltration and diafiltration. 2660 mL of the amplification culture with an initial phage concentration of 1.2E12 pfu/mL was purified using the following parameters. Depth filtration was performed using a path containing two filters, a glass fiber cartridge with a nominal porosity rating of 1.2 µm, followed by a filter with double pleated polyethersulfone membranes, rated at 0.8 µm and 0.45 µm respectively. The filtration was performed at a constant pressure of 7 psi. The yield of phage in the filtrate was 86% (2500 mL 1.1E12 pfu/mL). For the ultrafiltration and diafiltration steps a 500 kD polyethersulfone flat sheet membrane cartridge was used. Prior to purification the membrane was cleaned and the normalized water flux was verified to be ≥85% of original. 2007 mL of phage purified by depth filtration above (1.1E12 pfu/mL) was purified. Flow parameters of approximately 2200 L/hr/m$^2$ and a transmembrane pressure of 7 psi were used. The solution was concentrated with the TFF 1 hr and 35 min until ~180 mL were remaining in the retentate (~10× concentration). The phage solution was then diafiltered with 2000 mL deionized water with recirculation for approximately one hour. The final volume collected was 156 mL at a concentration of 1.4E13 pfu/mL which corresponds to ~98% of starting phage material.

Example 46

Preparation of Catalytic Material Comprising Cordierite Honeycomb Ceramic Supported $Nd_2O_3$ Nanowires $Nd_2O_3$ nanowires were prepared in a manner analogous to Example 14 by substituting $La(NO_3)_3$ with $Nd(NO_3)_3$.

A 400 mg aliquot of $Nd_2O_3$ nanowires is mixed with 2 g of DI water and placed into a 5 ml glass vial containing 2 mm Yttria Stabilized Zirconia milling balls. The vial is placed on a shaker at 2000 RPM and agitated for 30 minutes. A thick slurry is obtained.

A ⅜ inch diameter core is cut along the channel direction into a 400 CPSI (channel per square inch) cordierite honeycomb monolith and cut in length so the core volume is approximately 1 ml.

The core is placed into a ⅜ inch tube, and the catalyst slurry is fed on top of the ceramic core and pushed with compressed air through the monolith channel. The excess slurry is captured into a 20 ml vial. The coated core is removed from the ⅜ inch tube and placed into a drying oven at 200° C. for 1 hour.

The coating step is repeated twice more time with the remaining slurry followed by drying at 200° C. and calcination at 500° C. for 4 hours. The catalyst amount deposited on the monolith channel walls is approximatively 50 mg and comprises very good adhesion to the ceramic wall.

Example 47

Preparation of Catalytic Material Comprising Silicon Carbide Ceramic Foam Supported $Nd_2O_3$ Nanowires $Nd_2O_3$ nanowires were prepared in a manner analogous to Example 14 by substituting $La(NO_3)_3$ with $Nd(NO_3)_3$.

A 400 mg aliquot of $Nd_2O_3$ nanowires is mixed with 2 g of DI water and placed into a 5 ml glass vial containing 2 mm Yttria Stabilized Zirconia milling balls. The vial is placed on a shaker at 2000 RPM and agitated for 30 minutes. A thick slurry is obtained.

A ⅜ inch diameter core is cut from a 65 PPI (Pore Per Inch) SiC foam and cut in length so the core volume is approximately 1 ml.

The core is placed into a ⅜ inch tube and the catalyst slurry is fed on top of the ceramic core and pushed with compressed air through the monolith channel. The excess slurry is captured into a 20 ml vial. The coated core is removed from the ⅜ inch tube and placed into a drying oven at 200° C. for 1 hour.

The coating step is repeated twice more time with the remaining slurry followed by drying at 200° C. and calcination at 500° C. for 4 hours. The catalyst amount deposited on the monolith channel walls is approximatively 60 mg and comprises very good adhesion to the ceramic mesh.

Example 48

Preparation of Catalytic Material Comprising Silicon Carbide and $Nd_2O_3$ Nanowires $Nd_2O_3$ nanowires were prepared in a manner analogous to Example 14 by substituting $La(NO_3)_3$ with $Nd(NO_3)_3$.

A 400 mg aliquot of $Nd_2O_3$ nanowires is dry blend mixed with 400 mg of 200-250 mesh SiC particles for 10 minutes or until the mixture appears homogeneous and wire clusters are no longer visible. The mixture is then placed into a ¼ inch die and pressed in 200 mg batches. The pressed pellets are then placed into an oven and calcined at 600° C. for 2 hours. The crush strength of the pellet obtained is comparable to the crush strength of a pellet made with only $Nd_2O_3$ nanowires.

Example 49

OCM Activity of Various Nanowire Catalysts

Exemplary nanowire catalysts comprising $La_2O_3$, $Nd_2O_3$ or $La_3NdO_6$ with one, two, three or four different dopants selected from Eu, Na, Sr, Ho, Tm, Zr, Ca, Mg, Sm, W, La, K, Ba, Zn, and Li, were prepared and tested for their OCM activity according to the general procedures described in the above examples. Each of the exemplary catalysts produced a C2 yield above 10%, a C2 selectivity above 50%, and a $CH_4$ conversion above 20%, when tested as OCM catalysts at 650° C. or lower at pressures ranging from 1 to 10 atm.

Example 50

Preparation of Sr Doped $La_2O_3$ Nanowires

Sr doped $La_2O_3$ nanowires are prepared according to the following method.

A 57 mg aliquot of $La_2O_3$ nanowires prepared as described herein is then mixed with 0.174 ml of a 0.1 M solution of $Sr(NO_3)_2$. This mixture is then stirred on a hot plate at 90° C. until a paste was formed.

The paste is then dried for 1 h at 120° C. in a vacuum oven and finally calcined in a muffle oven in air according to the following procedure: (1) load in the furnace at room temperature; (2) ramp to 200° C. with 3° C./min rate; (3) dwell for 120 min; (3) ramp to 400° C. with 3° C./min rate; (4) dwell for 120 min; (5) ramp to 500° C. with 3° C./min rate; and (6) dwell for 120 min. The calcined product is then ground to a fine powder.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, are incorporated herein by reference, in their entirety. Aspects of the embodiments can be modified, if necessary to employ concepts of the various patents, applications and publications to provide yet further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method for the preparation of ethane, ethylene or combinations thereof, the method comprising contacting a catalytic material with a gas comprising methane, wherein the catalytic material is in the form of a pressed pellet, extrudate or monolith and comprises:
   a) a plurality of catalytic nanowires, the catalytic nanowires comprising one or more doping elements; and
   b) a diluent or support selected from one or more alkaline earth metal compounds,
   and wherein the catalytic material has a C2+ yield above 5% when employed as catalytic material in the oxidative coupling of methane at an inlet temperature of 550° C. and an inlet pressure of about 2 atm in a fixed bed reactor with a gas-hour space velocity (GHSV) of at least about 20,000/hr.

2. The method of claim 1, wherein the catalytic materials is in the form of a pressure treated, pressed pellet and comprises no binder material.

3. The method of claim 1, wherein the catalytic material is in the form of a pressed pellet or extrudate and comprises pores greater than 20 nm in diameter.

4. The method of claim 1, wherein the alkaline earth metal compound is an alkaline earth metal oxide, alkaline earth metal carbonate, alkaline earth metal sulfate or alkaline earth metal phosphate.

5. The method of claim 1, wherein the alkaline earth metal compound is an alkaline earth metal carbonate, alkaline earth metal sulfate or alkaline earth metal phosphate.

6. The method of claim 1, wherein the alkaline earth metal compound is MgO, $MgCO_3$, $MgSO_4$, $Mg_3(PO_4)_2$, $MgAl_2O_4$, CaO, $CaCO_3$, $CaSO_4$, $Ca_3(PO_4)_2$, $CaAl_2O_4$, SrO, $SrCO_3$, $SrSO_4$, $Sr_3(PO_4)_2$, $SrAl_2O_4$, BaO, $BaCO_3$, $BaSO_4$, $Ba_3(PO_4)_2$, $BaAl_2O_4$ or combinations thereof.

7. The method of claim 1, wherein the alkaline earth metal compound is $MgCO_3$, $MgSO_4$, $Mg_3(PO_4)_2$, CaO, $CaCO_3$, $CaSO_4$, $Ca_3(PO_4)_2$, $CaAl_2O_4$, SrO, $SrCO_3$, $SrSO_4$, $Sr_3(PO_4)_2$, $SrAl_2O_4$, BaO, $BaCO_3$, $BaSO_4$, $Ba_3(PO_4)_2$, $BaAl_2O_4$ or combinations thereof.

8. The method of claim 1, wherein the alkaline earth metal compound is CaO, SrO, $MgCO_3$, $CaCO_3$, $SrCO_3$ or combinations thereof.

9. The method of claim 1, wherein the plurality of catalytic nanowires have a ratio of average effective length to average actual length of less than one and an average aspect ratio of greater than ten as measured by TEM in bright field mode at 5 keV, wherein the plurality of catalytic nanowires comprises one or more elements from any of Groups 1 through 7, lanthanides, actinides or combinations thereof.

10. The method of claim 1, wherein the plurality of catalytic nanowires comprises straight nanowires.

11. The method of claim 10, wherein the straight nanowires have a ratio of effective length to actual length equal to one.

12. The method of claim 1, wherein the plurality of catalytic nanowires comprises at least one nanowire selected from any one of Tables 1-12.

13. The method of claim 1, wherein the catalytic material has a C2 selectivity above 50% when employed as catalytic material in the oxidative coupling of methane at an inlet temperature of 550° C. and an inlet pressure of about 2 atm in a fixed bed reactor with a gas-hour space velocity (GHSV) of at least about 20,000/hr.

14. The method of claim 1, wherein the catalytic material has a $CH_4$ conversion above 20% when employed as catalytic material in the oxidative coupling of methane at an inlet temperature of 550° C. and an inlet pressure of about 2 atm in a fixed bed reactor with a gas-hour space velocity (GHSV) of at least about 20,000/hr.

15. The method of claim 1, wherein the catalytic material further comprises SiC or cordierite or combinations thereof.

16. The method of claim 1, wherein the catalytic material is contacted with the gas at a temperature less than 800° C.

17. The method of claim 1, wherein the catalytic material is contacted with the gas at a temperature less than 700° C.

18. The method of claim 1, having a conversion of methane to ethylene of greater than 10%.

19. The method of claim 1, having a yield of ethylene of greater than 10%.

20. The method of claim 1, having a conversion of methane of greater than 10%.

21. The method of claim 1, having a C2 yield of greater than 10%.

22. The method of claim 2, wherein the plurality of catalytic nanowires have a ratio of average effective length to average actual length of less than one and an average aspect ratio of greater than ten as measured by TEM in bright field mode at 5 keV, wherein the plurality of catalytic nanowires comprises one or more elements from any of Groups 1 through 7, lanthanides, actinides or combinations thereof.

23. The method of claim 2, wherein the plurality of catalytic nanowires comprises straight nanowires.

24. The method of claim 23, wherein the straight nanowires have a ratio of effective length to actual length equal to one.

25. The method of claim 2, wherein the plurality of catalytic nanowires comprises at least one nanowire selected from any one of Tables 1-12.

26. The method of claim 2, wherein the alkaline earth metal compound is an alkaline earth metal oxide, alkaline earth metal carbonate, alkaline earth metal sulfate or alkaline earth metal phosphate.

27. The method of claim 2, wherein the alkaline earth metal compound is MgO, $MgCO_3$, $MgSO_4$, $Mg_3(PO_4)_2$, $MgAl_2O_4$, CaO, $CaCO_3$, $CaSO_4$, $Ca_3(PO_4)_2$, $CaAl_2O_4$, SrO, $SrCO_3$, $SrSO_4$, $Sr_3(PO_4)_2$, $SrAl_2O_4$, BaO, $BaCO_3$, $BaSO_4$, $Ba_3(PO_4)_2$, $BaAl_2O_4$ or combinations thereof.

28. The method of claim 2, wherein the alkaline earth metal compound is MgO, CaO, SrO, $MgCO_3$, $CaCO_3$, $SrCO_3$ or combinations thereof.

29. The method of claim 2, wherein the catalytic material has a C2 selectivity above 50% when employed as catalytic material in the oxidative coupling of methane at an inlet temperature of 550° C. and an inlet pressure of about 2 atm in a fixed bed reactor with a gas-hour space velocity (GHSV) of at least about 20,000/hr.

30. The method of claim 2, wherein the catalytic material has a $CH_4$ conversion above 20% when employed as catalytic material in the oxidative coupling of methane at an inlet temperature of 550° C. and an inlet pressure of about 2 atm in a fixed bed reactor with a gas-hour space velocity (GHSV) of at least about 20,000/hr.

31. The method of claim 2, wherein the catalytic material further comprises SiC or cordierite or combinations thereof.

32. The method of claim 3, wherein the plurality of catalytic nanowires have a ratio of average effective length to average actual length of less than one and an average aspect ratio of greater than ten as measured by TEM in bright field mode at 5 keV, wherein the plurality of catalytic nanowires comprises one or more elements from any of Groups 1 through 7, lanthanides, actinides or combinations thereof.

33. The method of claim 3, wherein the plurality of catalytic nanowires comprises straight nanowires.

34. The method of claim 33, wherein the straight nanowires have a ratio of effective length to actual length equal to one.

35. The method of claim 3, wherein the plurality of catalytic nanowires comprises at least one nanowire selected from any one of Tables 1-12.

36. The method of claim 3, wherein the catalytic material has a C2 selectivity above 50% when employed as catalytic material in the oxidative coupling of methane at an inlet temperature of 550° C. and an inlet pressure of about 2 atm in a fixed bed reactor with a gas-hour space velocity (GHSV) of at least about 20,000/hr.

37. The method of claim 3, wherein the catalytic material has a $CH_4$ conversion above 20% when employed as catalytic material in the oxidative coupling of methane at an inlet temperature of 550° C. and an inlet pressure of about 2 atm in a fixed bed reactor with a gas-hour space velocity (GHSV) of at least about 20,000/hr.

38. The method of claim 3, wherein the alkaline earth metal compound is an alkaline earth metal oxide, alkaline earth metal carbonate, alkaline earth metal sulfate or alkaline earth metal phosphate.

39. The method of claim 3, wherein the alkaline earth metal compound is MgO, $MgCO_3$, $MgSO_4$, $Mg_3(PO_4)_2$, $MgAl_2O_4$, CaO, $CaCO_3$, $CaSO_4$, $Ca_3(PO_4)_2$, $CaAl_2O_4$, SrO, $SrCO_3$, $SrSO_4$, $Sr_3(PO_4)_2$, $SrAl_2O_4$, BaO, $BaCO_3$, $BaSO_4$, $Ba_3(PO_4)_2$, $BaAl_2O_4$ or combinations thereof.

40. The method of claim 3, wherein the alkaline earth metal compound is MgO, CaO, SrO, $MgCO_3$, $CaCO_3$, $SrCO_3$ or combinations thereof.

41. The method of claim 3, wherein the catalytic material further comprises SiC or cordierite or combinations thereof.

* * * * *